US010604547B2

(12) United States Patent
Burger et al.

(10) Patent No.: US 10,604,547 B2
(45) **Date of Patent: *Mar. 31, 2020**

(54) AMATOXIN DERIVATIVES AND CONJUGATES THEREOF AS INHIBITORS OF RNA POLYMERASE

(71) Applicant: NOVARTIS AG, Basel (CH)

(72) Inventors: Matthew T. Burger, Belmont, MA (US); Yunho Jin, San Diego, CA (US); Tetsuo Uno, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/574,500

(22) Filed: Sep. 18, 2019

(65) Prior Publication Data

US 2020/0024311 A1 Jan. 23, 2020

Related U.S. Application Data

(63) Continuation of application No. 16/098,289, filed as application No. PCT/IS2017/052577 on May 3, 2017, now Pat. No. 10,464,969.

(Continued)

(51) Int. Cl.
*C07K 7/64* (2006.01)
*A61P 35/00* (2006.01)
*A61K 47/68* (2017.01)

(52) U.S. Cl.
CPC ............ *C07K 7/64* (2013.01); *A61K 47/6831* (2017.08); *A61K 47/6863* (2017.08); *A61P 35/00* (2018.01)

(58) Field of Classification Search
None
See application file for complete search history.

(56) References Cited

U.S. PATENT DOCUMENTS 9,938,323 B2 4/2018 Grunewald et al.

FOREIGN PATENT DOCUMENTS

WO 2001018006 A1 3/2001
WO 2008086161 A1 7/2008

(Continued)

OTHER PUBLICATIONS

Lu, et al., "Improved Peak Detection and Deconvolution of Native Protein Complex Electrospray Mass Spectra", Molecular and Cellular Proteomics, , Aug., 2014, Supplement p. S45, vol. 13, No. 8, 11th International Symposium on Mass spectrometry, San Francisco, California, Aug. 17-21, 2014.

(Continued)

*Primary Examiner* — Karl J Puttlitz
(74) *Attorney, Agent, or Firm* — Daniel E. Raymond; Genomics Institute of the Novartis Research Foundation

(57) ABSTRACT

The invention disclosed herein relates to cytotoxic cyclic peptides of Formula (A), methods of inhibiting RNA polymerase with such cyclic peptides, immunoconjugates comprising such cyclic peptides (i.e Antibody Drug Conjugates), pharmaceutical compositions comprising such cyclic peptides immunoconjugates, compositions comprising such cyclic peptides immunoconjugates with a therapeutic co-agent and methods of treatment using such cyclic peptides immunoconjugates:

(Continued)

Formula (A)

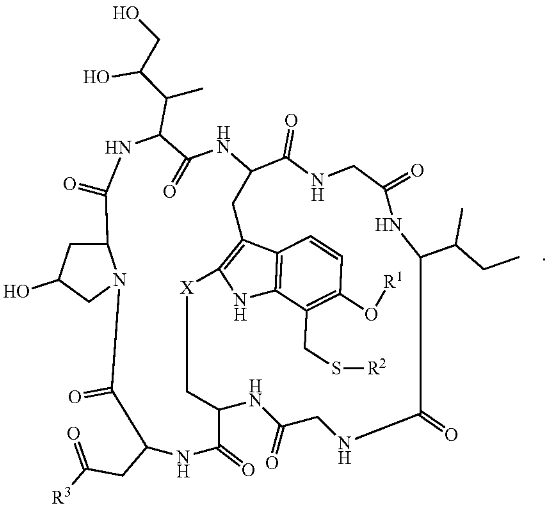

15 Claims, 2 Drawing Sheets

Specification includes a Sequence Listing.

Related U.S. Application Data

(60) Provisional application No. 62/332,117, filed on May 5, 2016.

(56) References Cited

FOREIGN PATENT DOCUMENTS

| | | | |
|---|---|---|---|
| WO | 2009114950 | A1 | 9/2009 |
| WO | 2010115629 | A2 | 10/2010 |
| WO | 2011014973 | A2 | 2/2011 |
| WO | 2012016186 | A1 | 2/2012 |
| WO | 2012041504 | A1 | 4/2012 |
| WO | 2012119787 | A1 | 9/2012 |
| WO | 2013104613 | A1 | 7/2013 |
| WO | 2014009025 | A1 | 1/2014 |
| WO | 2014043403 | * | 3/2014 |
| WO | 2014043403 | A1 | 3/2014 |
| WO | 2014135282 | A1 | 9/2014 |
| WO | 2014141094 | A1 | 9/2014 |
| WO | 2014151030 | A1 | 9/2014 |
| WO | 2017191579 | A1 | 11/2017 |
| WO | 2018116178 | A1 | 6/2018 |

OTHER PUBLICATIONS

Anderl, et al., "Antibody-Drug Conjugate Payloads", Methods in Molecular Biology, 2013, pp. 51-70, vol. 145, Springer Science & Business Media, LLC.

Adair, et al., "Antibody-drug conjugates—a perfect synergy", Expert Opin. Biol. Ther., 2012, pp. 1192-1206, vol. 12, No. 9, Informa UK, Ltd.

Senter, et al., The discovery and development of brentuximab vedotin for use in relapsed Hodgkin lymphoma and systemic anaplatic large cell lymphoma, nature biotechnology, 2012, pp. 631-637, vol. 30. No. 7, Nautre America, Inc.

Moldenhauer, et al., "Therapeutic Potential of Amanitin-Conjugated Anti-Epithelial Cell Adhesion Molecule Monocolonal Antibody Against Pancreatic Carcinoma", Journal of the National Cancer Institute, 2012, pp. 622-634, vol. 104, No. 8, Oxfor University Presss.

Jackson, et al., "Using the Lessons Learned From the Clinic to Improve the Preclinical Development of Antibody Drug Conjugates", Pharm. Res., Oct. 23, 2014, pp. 1-12, Springer.

Flygare, et al., "Antibody-Drug Conjugates for the Treatment of Cancer", Chem Biol Drug Des, 2013, pp. 113-121, vol. 81, John Wiley & Sons A/S.

Zhao, et al., "Synthesis of a Cytotoxic Amanitin for Biorthogonal Conjugation", ChemBioChem, 2015, pp. 1420-1425, vol. 16, Wiley-VCH Verlag GmbH & Co.

Liu, et al., "TP53 loss creates therapeutic vulnerability in colorectal cancer", Nature, Apr. 30, 2015, pp. 697-713, vol. 520, Macmillan Publishers Limited.

Li, et al., "An artificial receptor fabricated by target recognition determinant imprinting for selective capture of a-amanitin", Journal of Chromatography A, 2014, pp. 190-197, vol. 1324, Elsevier B.V.

* cited by examiner

SEQUENCE LISTING

<160> NUMBER OF SEQ ID NOS: 10

<210> SEQ ID NO 1
<211> LENGTH: 450
<212> TYPE: PRT
<213> ORGANISM: Artificial Sequence
<220> FEATURE:
<223> OTHER INFORMATION: anti-Her2 heavy chain wild-type

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: anti-Her2 light chain wild-type

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 331
<212> TYPE: PRT
<213> ORGANISM: Artificial Sequence
<220> FEATURE:
<223> OTHER INFORMATION: constant region of the heavy chain wild-type of anti-Her2

<400> SEQUENCE: 3

Ser Ala Ser Thr Lys Gly Pro Ser Val Phe Pro Leu Ala Pro Ser Ser
1 5 10 15

Lys Ser Thr Ser Gly Gly Thr Ala Ala Leu Gly Cys Leu Val Lys Asp
20 25 30

Tyr Phe Pro Glu Pro Val Thr Val Ser Trp Asn Ser Gly Ala Leu Thr
35 40 45

Ser Gly Val His Thr Phe Pro Ala Val Leu Gln Ser Ser Gly Leu Tyr
50 55 60

Ser Leu Ser Ser Val Val Thr Val Pro Ser Ser Ser Leu Gly Thr Gln
65 70 75 80

Thr Tyr Ile Cys Asn Val Asn His Lys Pro Ser Asn Thr Lys Val Asp
85 90 95

Lys Lys Val Glu Pro Lys Ser Cys Asp Lys Thr His Thr Cys Pro Pro
100 105 110

Cys Pro Ala Pro Glu Leu Leu Gly Gly Pro Ser Val Phe Leu Phe Pro
115 120 125

Pro Lys Pro Lys Asp Thr Leu Met Ile Ser Arg Thr Pro Glu Val Thr
130 135 140

Cys Val Val Val Asp Val Ser His Glu Asp Pro Glu Val Lys Phe Asn
145 150 155 160

Trp Tyr Val Asp Gly Val Glu Val His Asn Ala Lys Thr Lys Pro Arg
165 170 175

Glu Glu Gln Tyr Asn Ser Thr Tyr Arg Val Val Ser Val Leu Thr Val
180 185 190

Leu His Gln Asp Trp Leu Asn Gly Lys Glu Tyr Lys Cys Lys Val Ser
195 200 205

Asn Lys Ala Leu Pro Ala Pro Ile Glu Lys Thr Ile Ser Lys Ala Lys
210 215 220

Gly Gln Pro Arg Glu Pro Gln Val Tyr Thr Leu Pro Pro Ser Arg Glu
225 230 235 240

Glu Met Thr Lys Asn Gln Val Ser Leu Thr Cys Leu Val Lys Gly Phe
245 250 255

Tyr Pro Ser Asp Ile Ala Val Glu Trp Glu Ser Asn Gly Gln Pro Glu
260 265 270

Asn Asn Tyr Lys Thr Thr Pro Pro Val Leu Asp Ser Asp Gly Ser Phe
275 280 285

Phe Leu Tyr Ser Lys Leu Thr Val Asp Lys Ser Arg Trp Gln Gln Gly
290 295 300

Asn Val Phe Ser Cys Ser Val Met His Glu Ala Leu His Asn His Tyr
305 310 315 320

Thr Gln Lys Ser Leu Ser Leu Ser Pro Gly Lys
325 330

<210> SEQ ID NO 4
<211> LENGTH: 108
<212> TYPE: PRT
<213> ORGANISM: Artificial Sequence
<220> FEATURE:
<223> OTHER INFORMATION: constant region of the light chain wild-type of
anti-Her2

<400> SEQUENCE: 4

Lys Arg Thr Val Ala Ala Pro Ser Val Phe Ile Phe Pro Pro Ser Asp

```
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105


<210> SEQ ID NO 5
<211> LENGTH: 24
<212> TYPE: PRT
<213> ORGANISM: Artificial Sequence
<220> FEATURE:
<223> OTHER INFORMATION: signal sequence

<400> SEQUENCE: 5

Met Lys Thr Phe Ile Leu Leu Leu Trp Val Leu Leu Leu Trp Val Ile
1               5                   10                  15

Phe Leu Leu Pro Gly Ala Thr Ala
            20


<210> SEQ ID NO 6
<211> LENGTH: 450
<212> TYPE: PRT
<213> ORGANISM: Artificial Sequence
<220> FEATURE:
<223> OTHER INFORMATION: mutant heavy chain of anti-Her2-HC-E152C-S375C

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Cys Pro Val Thr Val Ser
145                 150                 155                 160

Trp Asn Ser Gly Ala Leu Thr Ser Gly Val His Thr Phe Pro Ala Val
                165                 170                 175
```

-continued

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Cys Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 7
<211> LENGTH: 38
<212> TYPE: DNA
<213> ORGANISM: Artificial Sequence
<220> FEATURE:
<223> OTHER INFORMATION: HC-E152C (sense)

<400> SEQUENCE: 7

ttcccttgtc ccgtgaccgt gtcctggaac agcggagc                              38


<210> SEQ ID NO 8
<211> LENGTH: 38
<212> TYPE: DNA
<213> ORGANISM: Artificial Sequence
<220> FEATURE:
<223> OTHER INFORMATION: HC-E152C (anti-sense)

<400> SEQUENCE: 8

cacgggacaa gggaagtagt ccttcaccag gcagccca                              38
```

-continued

```
<210> SEQ ID NO 9
<211> LENGTH: 38
<212> TYPE: DNA
<213> ORGANISM: Artificial Sequence
<220> FEATURE:
<223> OTHER INFORMATION: HC-S375C (sense)

<400> SEQUENCE: 9

ctacccctgc gacatcgccg tggagtggga gagcaacg                              38


<210> SEQ ID NO 10
<211> LENGTH: 38
<212> TYPE: DNA
<213> ORGANISM: Artificial Sequence
<220> FEATURE:
<223> OTHER INFORMATION: HC-S375C (anti-sense)

<400> SEQUENCE: 10

gatgtcgcag gggtagaagc ccttcaccag acaggtca                              38
```

AMATOXIN DERIVATIVES AND CONJUGATES THEREOF AS INHIBITORS OF RNA POLYMERASE

CROSS-REFERENCE TO RELATED APPLICATIONS

This application is a continuation of prior application Ser. No. 16/098,289, filed 1 Nov. 2018, which is a 371 U.S. national phase application of international application number PCT/IB2017/052577 filed 3 May 2017, which application claims the benefit of priority under 35 U.S.C. § 119(e) to U.S. Provisional Patent Application No. 62/332,117, filed 5 May 2016, the disclosures of which are incorporated herein by reference in their entirety and for all purposes.

FIELD OF THE INVENTION

The invention relates to amatoxins and conjugates of amatoxins to a target-binding moiety, e.g. an antibody, and the use of such conjugates to treat cancer.

BACKGROUND

Amatoxins are cyclic peptides comprised of eight amino acid units which can be prepared synthetically, or can be isolated from a variety of mushroom species, such as *Amanita phalloides* (green death cap mushroom), *Amanita bisporigera* (destroying angel), *Amanita ocreata* (destroying angel), *Amanita virosa* (destroying angel), *Amanita bisporigera* (fool's mushroom), *Lepiota brunneo-incamata* (deadly dapperling), *Conocybe filaris* and *Galerina marginata*.

There are currently ten known members of the Amatoxin Family: alpha-Amanitin, beta-Amanitin, gamma-Amanitin, epsilon-Amanitin, Amanullin, Amanullinic acid, Amaninamide, Amanin and Proamanullin. Different mushroom species contain varying amounts of different Amatoxin family members.

Amatoxins are potent and selective inhibitors of RNA polymerase II, a vital enzyme in the synthesis of messenger RNA (mRNA), microRNA, and small nuclear RNA (snRNA). By inhibiting the synthesis of mRNA, Amatoxins thereby stop cell metabolism by inhibiting transcription and protein biosynthesis, which results in cellular apoptosis. Consequently Amatoxins stop cell growth and proliferation.

Alpha-amanitin, is known to be an extremely potent inhibitor of eukaryotic RNA polymerase II (EC2.7.7.6) and to a lesser degree, RNA polymerase III, thereby inhibiting transcription and protein biosynthesis. Wieland (1983) Int. J. Pept. Protein Res. 22(3):257-276. Alpha-amanitin binds non-covalently to RNA polymerase II and dissociates slowly, making enzyme recovery unlikely.

The use of antibody-drug conjugates (ADCs) for the targeted delivery of cell proliferation inhibitors and/or cytotoxic agents to specific cells has been the focus of significant research. Antibody-Drug Conjugate, Methods in Molecular Biology, Vol. 1045, Editor L. Ducry, Humana Press (2013). ADCs include an antibody selected for its ability to bind to a cell targeted for therapeutic intervention, linked to a drug selected for its cytostatic or cytotoxic activity. Binding of the antibody to the targeted cell thereby delivers the drug to the site where its therapeutic effect is needed. Many antibodies that recognize and selectively bind to targeted cells, like cancer cells, have been disclosed for use in ADCs, and many methods for attaching payload (drug) compounds such as cytotoxins to antibodies have also been described. In spite of the extensive work on ADCs, though, only a few classes of cell proliferation inhibitors have been used extensively as ADC payloads. Even though the first ADC approved for use in humans in the U.S. was launched in 2000 (and later withdrawn from the market), a decade later only a few chemical classes of drug compounds (maytansinoids, auristatins, calicheamycins and duocarmycins) had reached clinical trials as payloads for ADCs. *Antibody-Drug Conjugates: the Next Generation of Moving Parts*, A. Lash, *Start-Up*, December 2011, 1-6.

The use of amatoxins as cytotoxic moieties in ADC's for tumour therapy was explored in 1981 (Davis & Preston, Science 1981, 213, 1385-1388) by coupling an anti-Thy 1.2 antibody to alpha-amanitin using a linker attached to the 7' position of the indole ring via diazotation. Morris & Venton (Morris & Venton, Int. J. Peptide Protein Res. 1983, 21 419-430) also demonstrated that substitution at the 7' position resulted in a derivative which maintained cytotoxic activity.

Patent application EP 1 859 811 A 1 (published Nov. 28, 2007) described the direct conjugation (i.e. without a linker structure) of albumin or a monoclonal antibody (HEA125, OKT3, or PA-1) to the gamma C-atom of amatoxin amino acid 1 of beta-amanitin. The inhibitory effect of these conjugates on the proliferation of breast cancer cells (MCF-7), Burkitt's lymphoma cells (Raji), and Tlymphoma cells (Jurkat) was shown. The use of linkers was suggested, however no such constructs were exemplified and no details regarding linker attachment sites on Amatoxins were provided.

Patent applications WO 2010/115629 and WO 2010/115630 (both published Oct. 14, 2010) describe conjugates, where antibodies, such as antiEpCAM antibodies such as humanized antibody huHEA125, are coupled to amatoxins via (i) the gamma C-atom of amatoxin amino acid 1, (ii) the 6' C-atom of amatoxin amino acid 4, or (iii) via the delta C-atom of amatoxin amino acid 3, in each case either directly or via a linker between the antibody and the amatoxins. The inhibitory effects of these conjugates on the proliferation of breast cancer cells (cell line MCF-7), pancreatic carcinoma (cell line Capan-1), colon cancer (cell line Colo205) and cholangiocarcinoma (cell line OZ) were shown.

Patent applications WO 2012/119787 (published Sep. 13, 2012) describes conjugating a target-binding moiety via a linker attached to the amatoxin indole nitrogen. The cytotoxic activity of such conjugates on a HER2-positive tumor cell line in vitro was disclosed.

Patent applications WO 2014/043403 (published Mar. 20, 2014) describes conjugating a target-binding moiety via a linker attached to the 7' position of the amatoxin indole. The cytotoxic activity of such conjugates on Herceptin and IgG1 in MDA-MB-468 cells was disclosed. Also, the cytotoxic activity of such conjugates on Herceptin in PC3, HCC-1954 and MDA-MB-46 cells was disclosed.

In view of the toxicity of amatoxins, particularly for liver cells, it is important that ADC's comprising a linked amatoxin remain highly stable in plasma prior to the release of the amatoxin after internalization into the target cells. In this regard, improvements of the conjugate stability may have drastic consequences for the therapeutic window and the safety of the amatoxin conjugates for therapeutic approaches. Thus, given the widely acknowledged value of ADCs as therapeutics for treating cancer, there remains a need for the stable delivery of potent RNA polymerase inhibitors to the target cells prior to internalization of the RNA polymerase inhibitors.

SUMMARY OF THE INVENTION

The invention provided herein includes cytotoxic cyclic peptides of formula (I), which are analogs of alpha-amanitin and beta-amanitin, and methods of using such cytotoxic cyclic peptides as the drug component of an antibody-drug conjugate (ADC). The present invention includes novel cytotoxic cyclic peptides and the use of such novel cytotoxic cyclic peptides as payloads for ADCs. The invention further includes methods and intermediates useful for incorporating such novel cytotoxic cyclic peptides into ADCs.

The invention further includes immunoconjugates comprising such cyclic peptides (i.e Antibody Drug Conjugates), pharmaceutical compositions comprising such cyclic peptides immunoconjugates and compositions comprising such cyclic peptides immunoconjugates with a therapeutic co-agent.

The invention further includes methods of inhibiting RNA polymerase using such immunoconjugates comprising such cyclic peptides and methods of treating cell proliferation diseases using such immunoconjugates comprising such cyclic peptides.

In one aspect the cytotoxic cyclic peptides of the invention, or stereoisomer and pharmaceutically acceptable salts thereof, have the structure of Formula (A)

Formula (A)

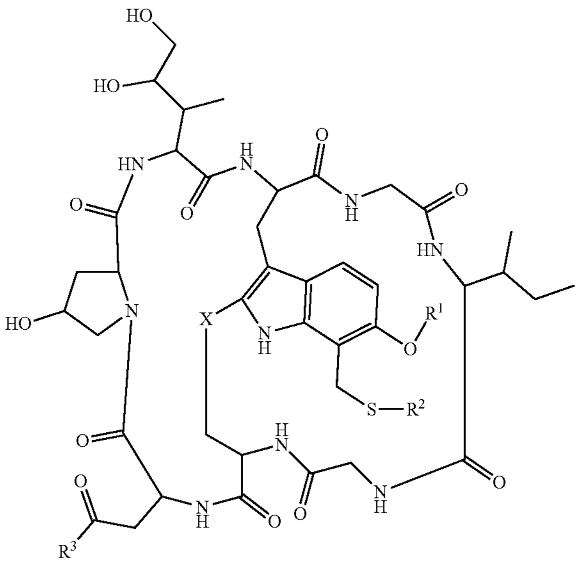

wherein:

X is $S({=}O)$, $S({=}O)_2$ or S; $R^1$ is H, $-CH_3$ or $-CD_3$; $R^2$ is $-L_1R^4$, $-L_2R^{14}$, $-L_2R^{24}$ or $-L_3R^{34}$;

$R^3$ is $-NH_2$ or $-OH$;

$L_1$ is $-((CH_2)_mO)_n(CH_2)_mX_3L_4-$ or $-((CH_2)_mO)_n(CH_2)_m X_4L_4-$;

$L_2$ is $-((CH_2)_mO)_n(CH_2)_m-$;

$L_3$ is $-((CH_2)_mO)_n(CH_2)_mX_3L_4-$, $-((CH_2)_mO)_n(CH_2)_m X_4L_4-$ or $-((CH_2)_mO)_n(CH_2)_m-$;

$L_4$ is $-((CH_2)_m-$ or $-((CH_2)_mNHC({=}O)X_1X_2C({=}O)(CH_2)_m-$;

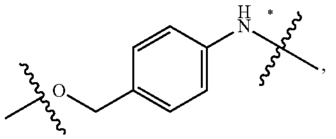
,
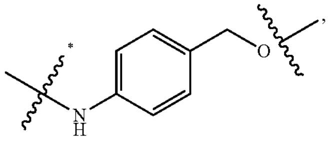
,
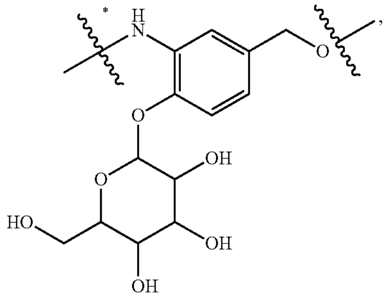
,
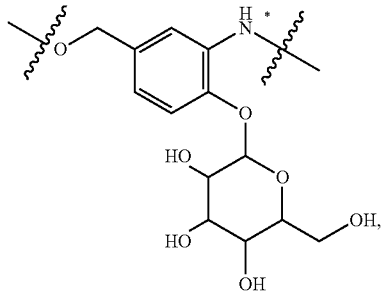
,
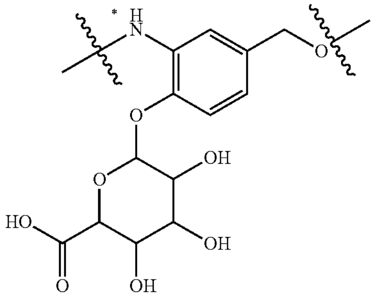
or
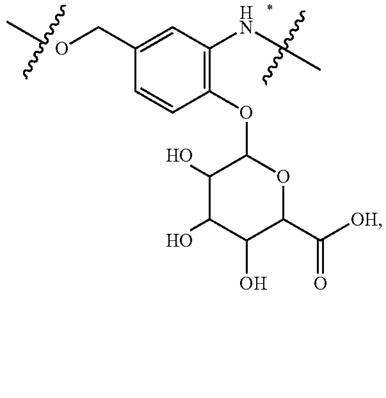
, where the * indicates attachment point to $X_2$;
$X_2$ is
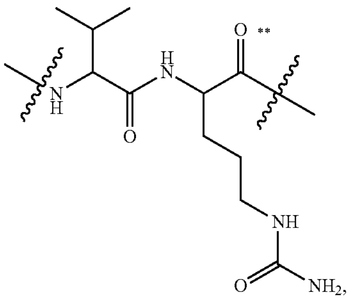
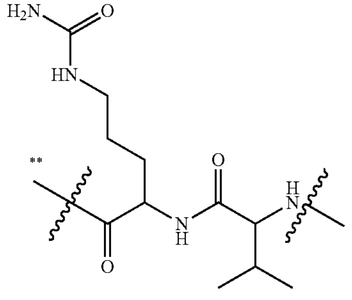
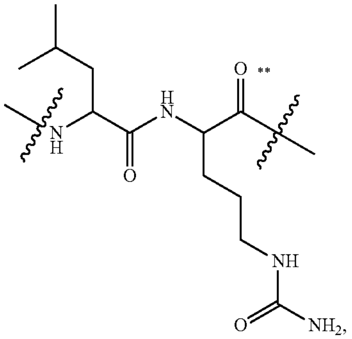
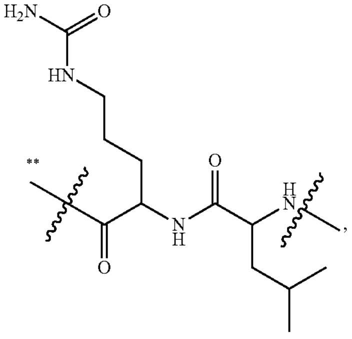
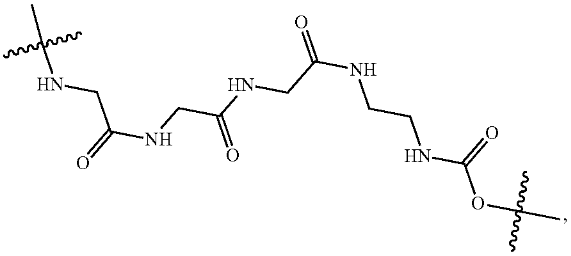
-continued
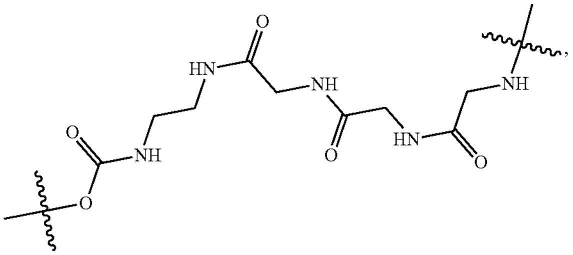
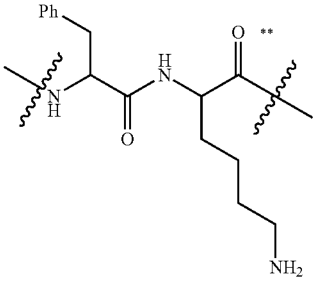
or
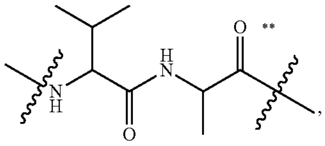
where the ** indicates attachment point to $X_1$;
$X_3$ is
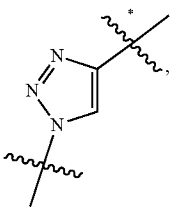
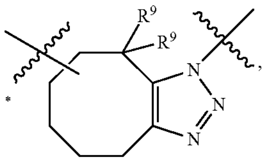
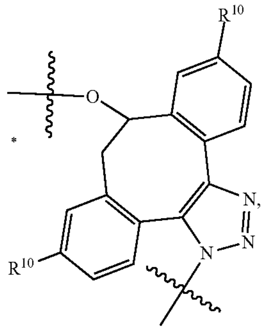
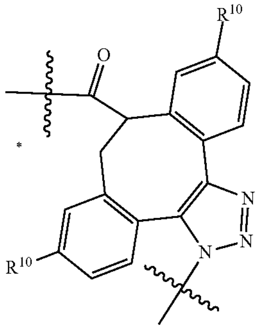
or -continued
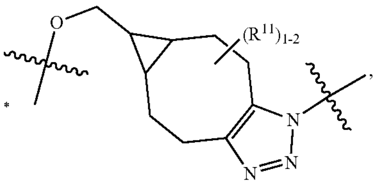
where the * indicates attachment point to $L_4$;
$X_4$ is
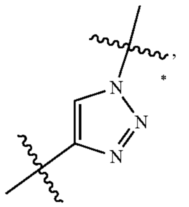,
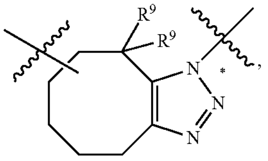,
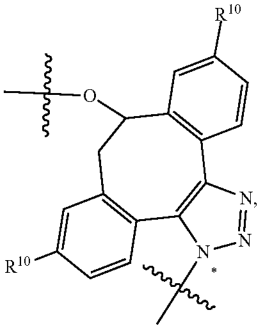
-continued
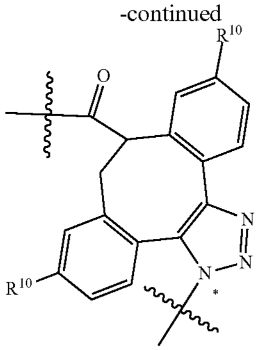
or
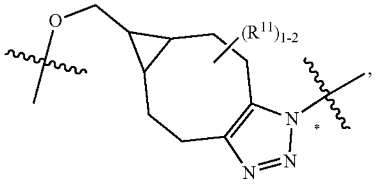,
where the * indicates attachment point to $L_4$;
$R^4$ is
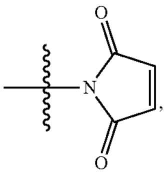 [SMILES: *N1C(=O)C=CC1=O],
$—N_3$, $—ONH_2$, $—NR_5C(═O)CH═CH_2$, SH, $—S(═O)_2(CH═CH_2)$, $—NR^5S(═O)_2(CH═CH_2)$, $—NR^5C(═O)CH_2Br$, $—NR^5C(═O)CH_2I$, $—NHC(═O)CH_2Br$, $—NHC(═O)CH_2I$, $—C(O)NHNH_2$,
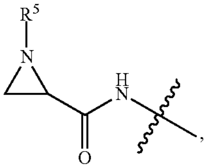, $—CO_2H$, $—NH_2$, 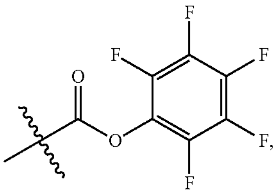,
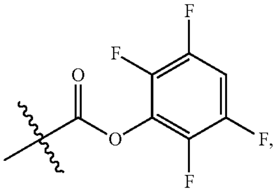, 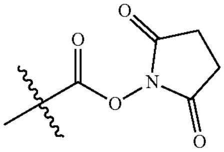, 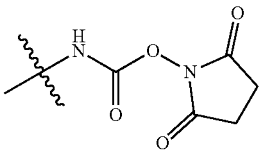,
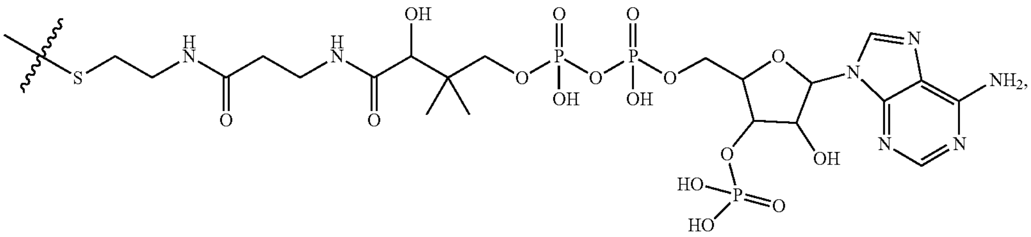, -continued
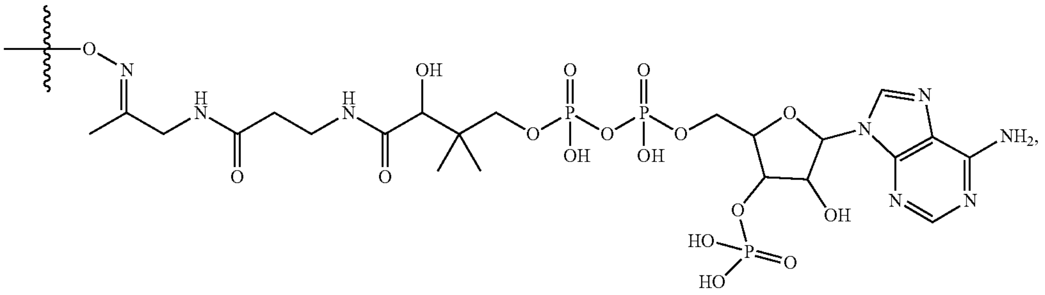
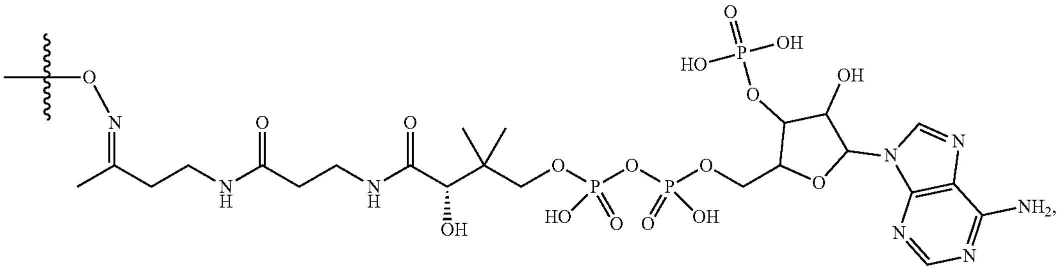
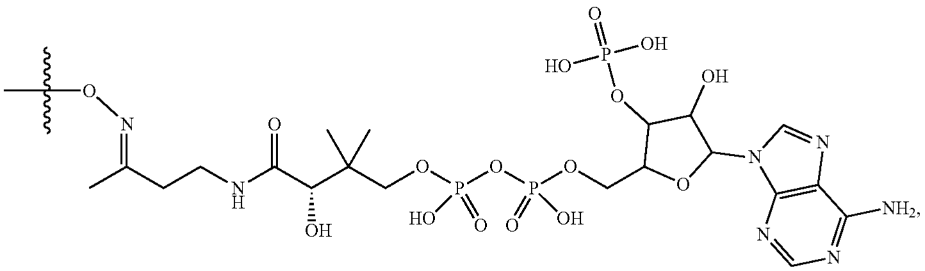
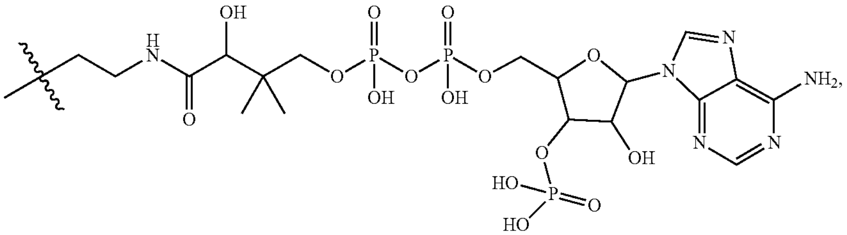
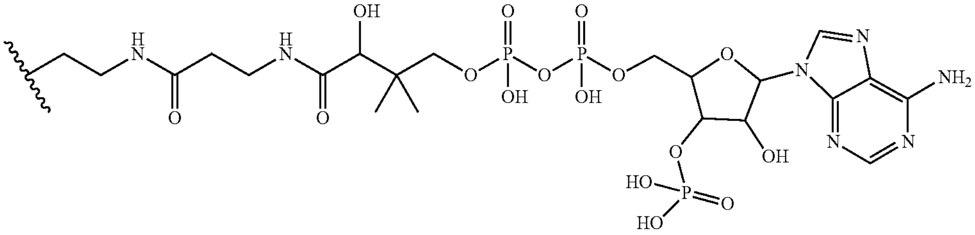
or
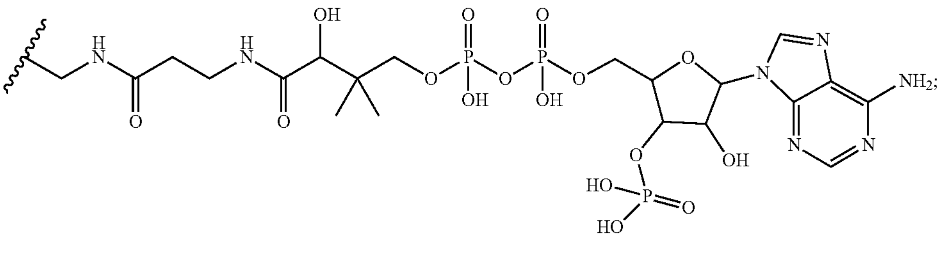

$R^{14}$ is

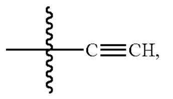
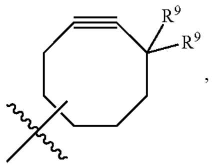
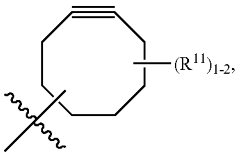
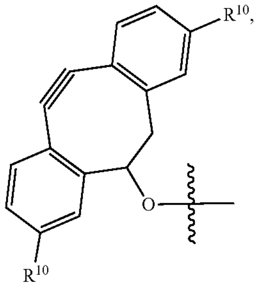
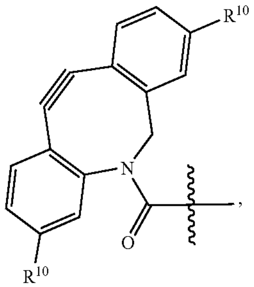
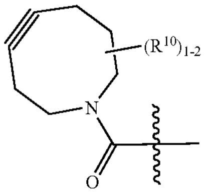
or
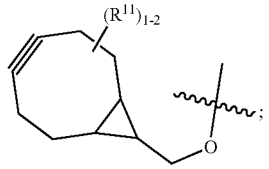

$R^{24}$ is, $-N_3$, $-ONH_2$, $-NR_5C(=O)CH=CH_2$, $-C(O)NHNH_2$, $-CO_2H$, $-NH_2$,

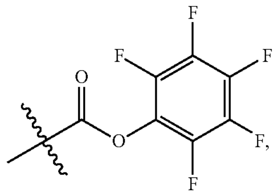
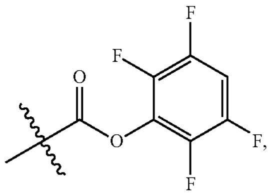
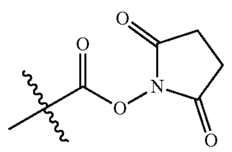
or
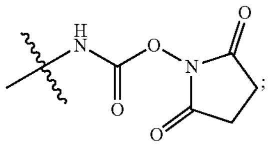

$R^{34}$ is

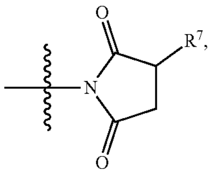
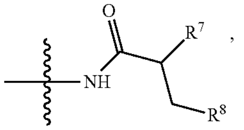
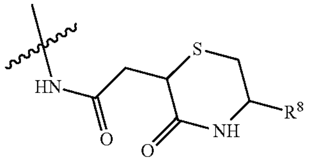

or $-NR^5C(=O)CH_2R^7$;

each $R^5$ is independently selected from H and $C_1$-$C_6$alkyl;

$R^7$ is $-S(CH_2)_nCHR^8NH_2$;

$R^8$ is $-C(=O)OR^5$;

each $R^9$ is independently selected from H, $C_1$-$C_6$alkyl, F, Cl, and —OH;

each $R^{10}$ is independently selected from H, $C_1$-$C_6$alkyl, F, Cl, $-NH_2$, $-OCH_3$, $-OCH_2CH_3$, $-N(CH_3)_2$, —CN, $-NO_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$ alkyl substituted with —C(=O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

In one aspect the cytotoxic cyclic peptides of the invention, or stereoisomer and pharmaceutically acceptable salts thereof, have the structure of Formula (I)

Formula (I)

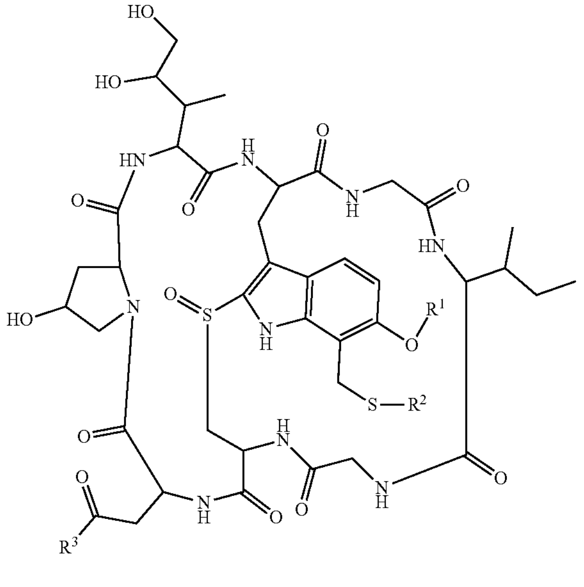

wherein:

$R^1$ is H, $-CH_3$ or $-CD_3$; $R^2$ is $-L_1R^4$, $-L_2R^{14}$, $-L_2R^{24}$ or $-L_3R^{34}$;

$R^3$ is —$NH_2$ or —OH;
$L_1$ is —$((CH_2)_mO)_n(CH_2)_mX_3L_4$- or —$((CH_2)_mO)_n(CH_2)_mX_4L_4$-;
$L_2$ is —$((CH_2)_mO)_n(CH_2)_m$—;
$L_3$ is —$((CH_2)_mO)_n(CH_2)_mX_3L_4$-, —$((CH_2)_mO)_n(CH_2)_mX_4L_4$- or —$((CH_2)_mO)_n(CH_2)_m$—;
$L_4$ is —$((CH_2)_m$— or —$((CH_2)_mNHC(=O)X_1X_2C(=O)(CH_2)_m$—;
$X_1$ is
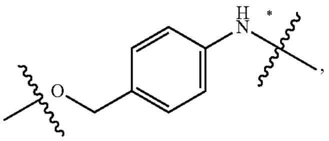
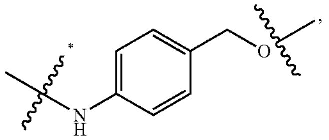
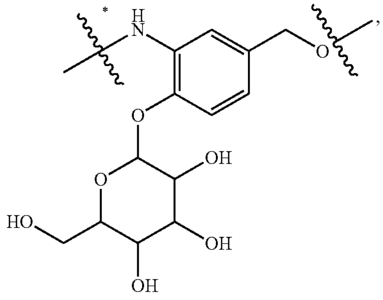
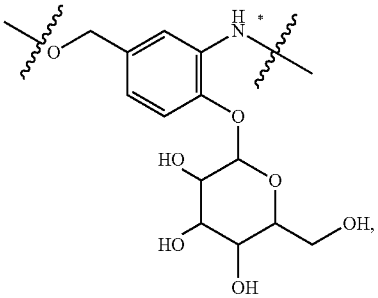
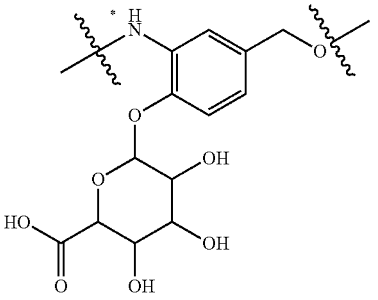
or
-continued
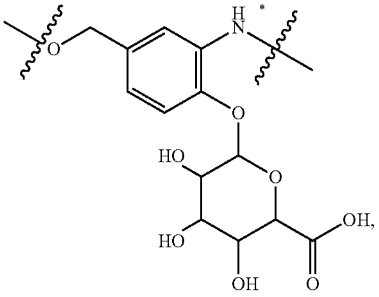
where the * indicates attachment point to $X_2$;
$X_2$ is
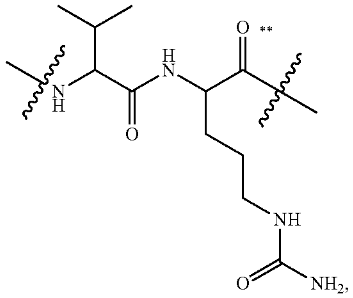
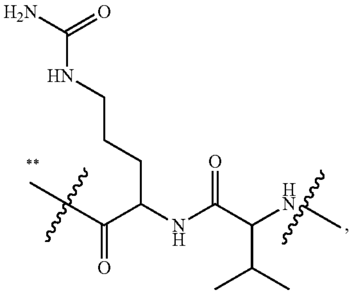
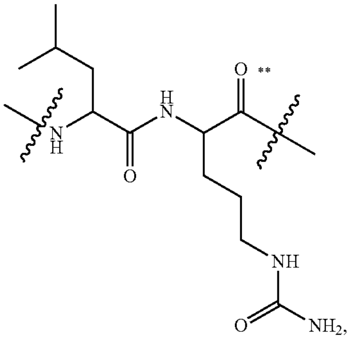
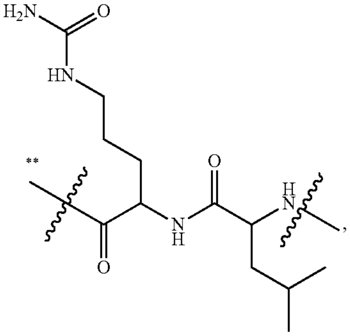

-continued
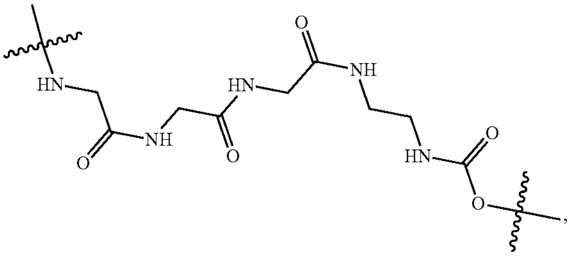
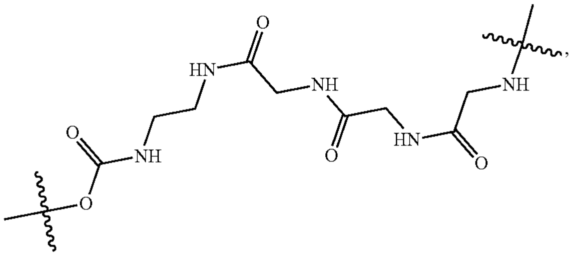
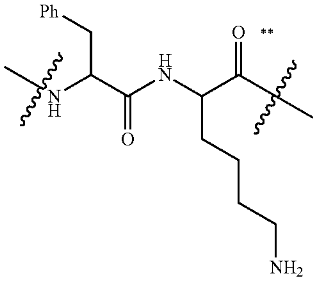
or
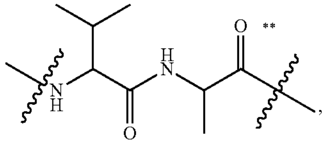
where the ** indicates attachment point to $X_1$; $X_3$ is
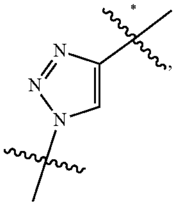
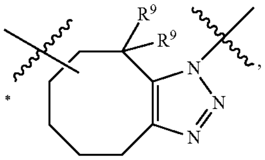
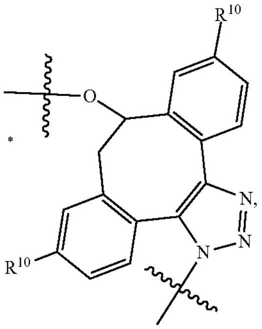
-continued
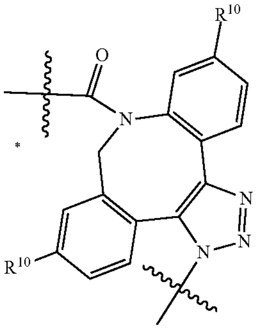
or
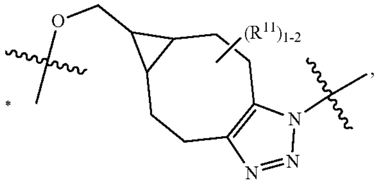
where the * indicates attachment point to $L_4$; $X_4$ is
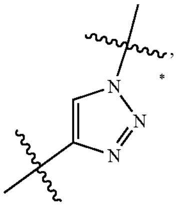
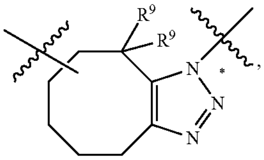
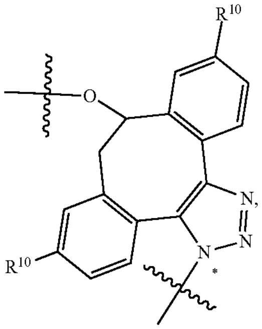
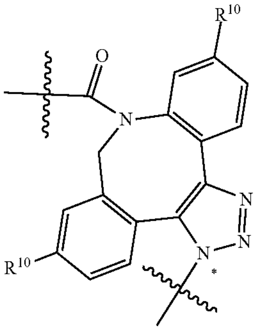
or -continued
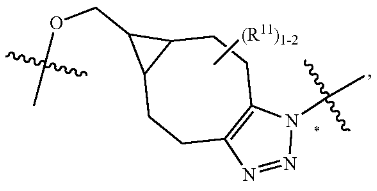
where the * indicates attachment point to $L_4$;
$R^4$ is
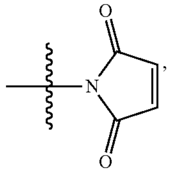 [SMILES: *N1C(=O)C=CC1=O]
$—N_3$, $—ONH_2$, $—NR_5C(═O)CH═CH_2$, SH, $—S(═O)_2(CH═CH_2)$, $—NR^5S(═O)_2(CH═CH_2)$, $—NR^5C(═O)CH_2Br$, $—NR^5C(═O)CH_2I$, $—NHC(═O)CH_2Br$, $—NHC(═O)CH_2I$, $—C(O)NHNH_2$,
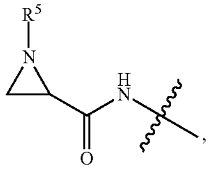
$—CO_2H$, $—NH_2$,
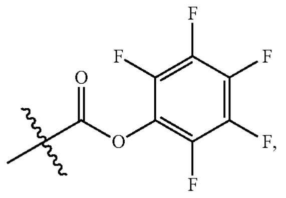
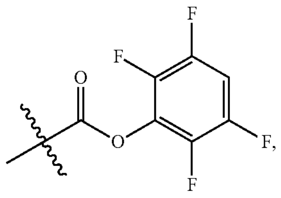
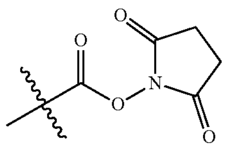
or
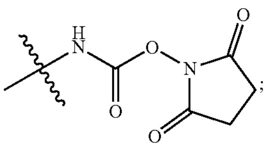
$R^{14}$ is
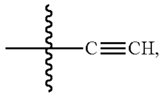
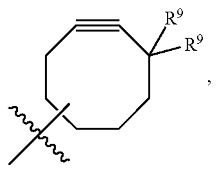
-continued
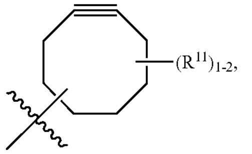
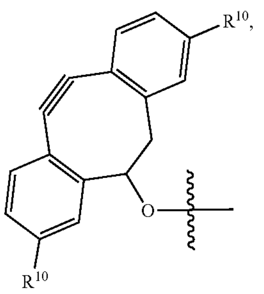
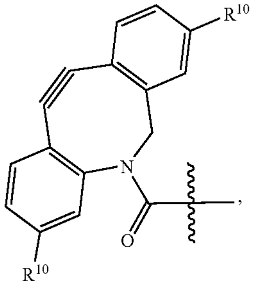
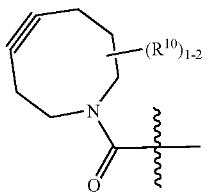
or
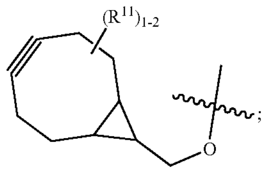
$R^{24}$ is, $—N_3$, $—ONH_2$, $—NR_5C(═O)CH═CH_2$, $—C(O)NHNH_2$, $—CO_2H$, $—NH_2$,
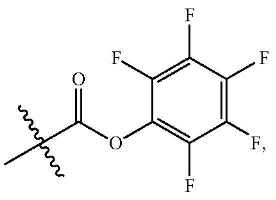
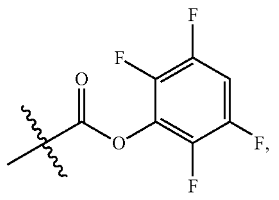
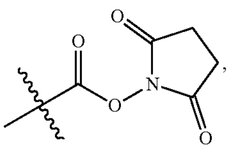
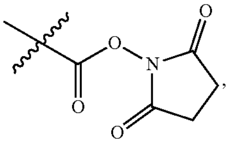
or
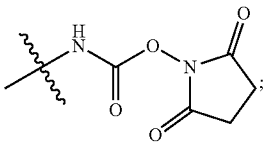
$R^{34}$ is
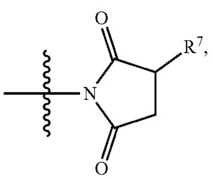
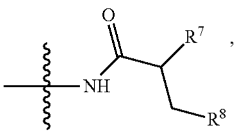

-continued

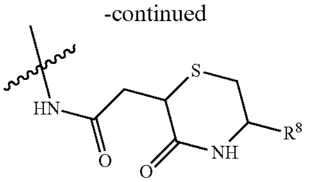

or $—NR^5C(=O)CH_2R^7$;

each $R^5$ is independently selected from H and $C_1$-$C_6$alkyl;

$R^7$ is $—S(CH_2)_nCHR^8NH_2$;

$R^8$ is $—C(=O)OR^5$;

each $R^9$ is independently selected from H, $C_1$-$C_6$alkyl, F, Cl, and —OH;

each $R^{10}$ is independently selected from H, $C_1$-$C_6$alkyl, F, Cl, $—NH_2$, $—OCH_3$, $—OCH_2CH_3$, $—N(CH_3)_2$, —CN, $—NO_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

In certain embodiments of this aspect of the cytotoxic cyclic peptides having the structure of Formula (A) and Formula (I), are cytotoxic cyclic peptides having the structure of Formula (Ia):

Formula (Ia)

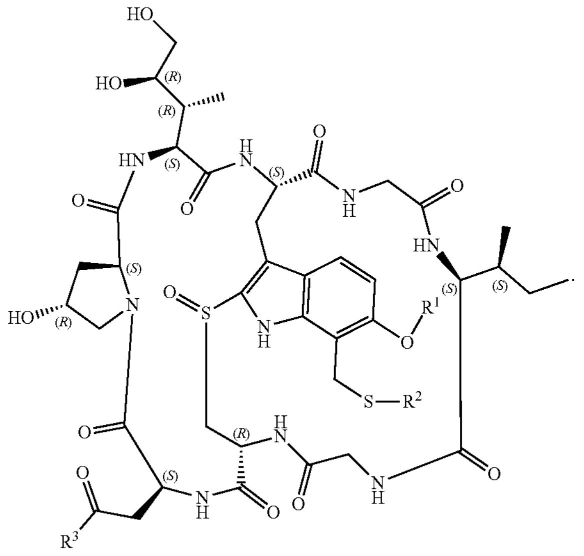

In certain embodiments of such cytotoxic cyclic peptides of Formula (A), Formula (I) and Formula (Ia):

$R^1$ is H, $—CH_3$ or $—CD_3$; $R^2$ is $-L_1R^4$, $-L_2R^{24}$ or $-L_3R^{34}$; $R^3$ is $—NH_2$ or —OH;

$L_1$ is $—((CH_2)_mO)_n(CH_2)_mX_3L_4$-;

$L_2$ is $—((CH_2)_mO)_n(CH_2)_m—$;

$L_3$ is $—((CH_2)_mO)_n(CH_2)_mX_3L_4$- or $—((CH_2)_mO)_n(CH_2)_m—$;

$L_4$ is $—((CH_2)_m—$ or $—((CH_2)_mNHC(=O)X_1X_2C(=O)(CH_2)_m—$;

$X_1$ is

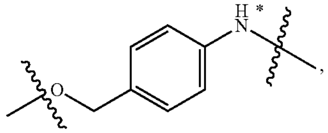

where the * indicates attachment point to $X_2$;

$X_2$ is

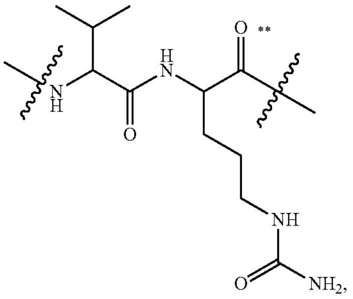

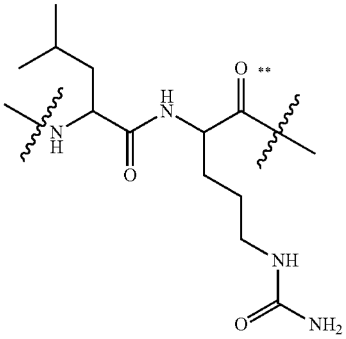

or

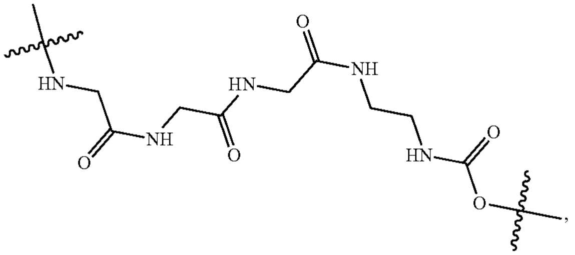

where the ** indicates attachment point to $X_1$;

$X_3$ is

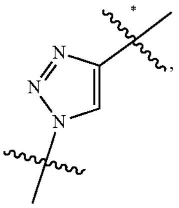 [SMILES: *c1cn(*)nn1]

where the * indicates attachment point to $L_4$;

$R^4$ is

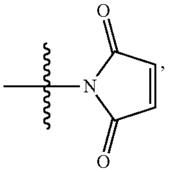 [SMILES: *N1C(=O)C=CC1=O]

$-N_3$ or $-ONH_2$;

$R^{24}$ is, $-N_3$ or $-ONH_2$;

$R^{34}$ is

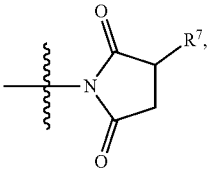

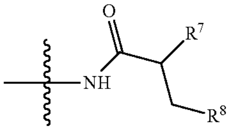

or

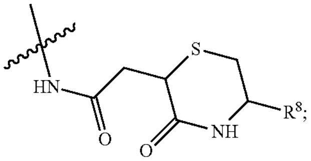

each $R^5$ is independently selected from H and $C_1$-$C_6$alkyl;

$R^7$ is $-S(CH_2)_nCHR^8NH_2$;

$R^8$ is $-C(=O)OR^5$;

each m is independently selected from 1, 2, 3, 4, 5, 6, 7, 8, 9 and 10;

each n is independently selected from 1, 2, 3, 4, 5, 6, 7, 8, 9, 10, 11, 12, 13 and 14.

In certain embodiments of such cytotoxic cyclic peptides of Formula (A), Formula (I) and Formula (Ia):

$R^1$ is H, $-CH_3$ or $-CD_3$; $R^2$ is $-L_1R^4$ or $-L_3R^{34}$; $R^3$ is $-NH_2$ or $-OH$;

$L_1$ is $-((CH_2)_mO)_n(CH_2)_mX_3L_4$-;

$L_3$ is $-((CH_2)_mO)_n(CH_2)_mX_3L_4$-;

$L_4$ is $-((CH_2)_m-$ or $-((CH_2)_mNHC(=O)X_1X_2C(=O)(CH_2)_m-$;

$X_1$ is

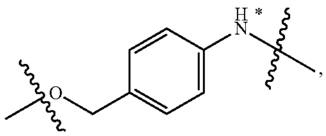

where the * indicates attachment point to $X_2$;

$X_2$ is

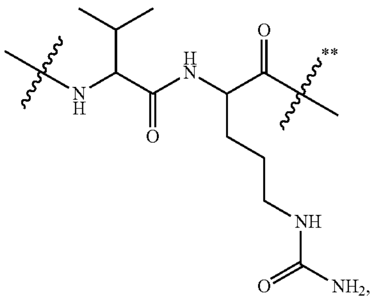

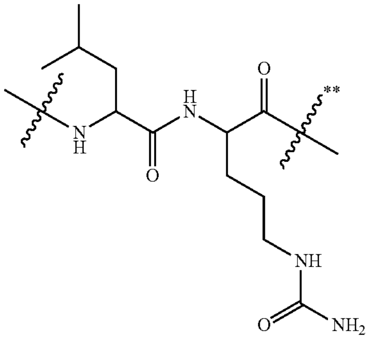

or

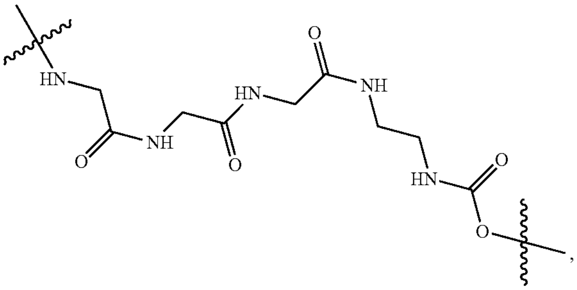

where the ** indicates attachment point to $X_1$;

$X_3$ is

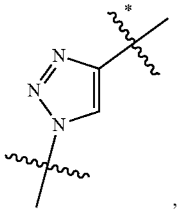 [SMILES: *c1cn(*)nn1]

where the * indicates attachment point to $L_4$;

$R^4$ is

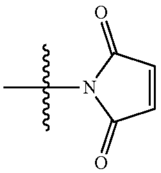 [SMILES: *N1C(=O)C=CC1=O]

or $-ONH_2$;

$R^{34}$ is
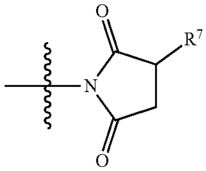
,
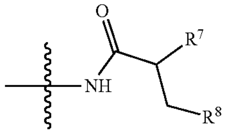
or
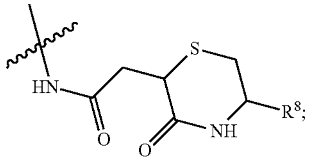
each $R^5$ is independently selected from H and $C_1$-$C_6$alkyl;
$R^7$ is —$S(CH_2)_mCHR^8NH_2$
;
$R^8$ is —$C(=O)OR^5$;
each m is independently selected from 1, 2, 3, 4, 5, 6, 7, 8, 9 and 10;
each n is independently selected from 1, 2, 3, 4, 5, 6, 7, 8, 9, 10, 11, 12, 13 and 14.
In preferred embodiments of any of the aforementioned cytotoxic cyclic peptides of Formula (A), Formula (I) and Formula (Ia): $R^2$ is
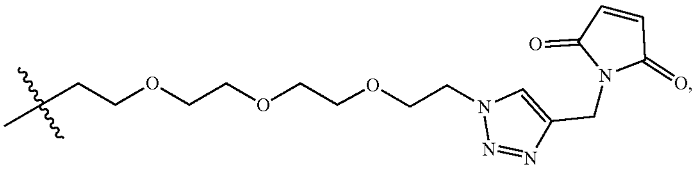
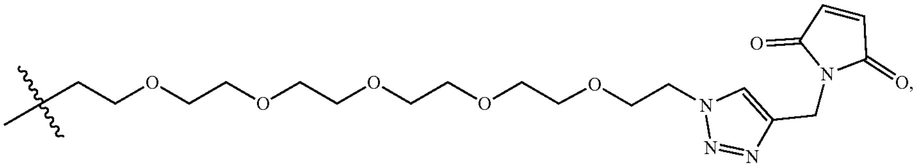
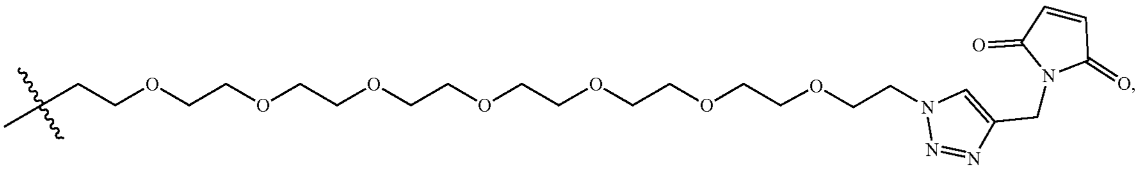
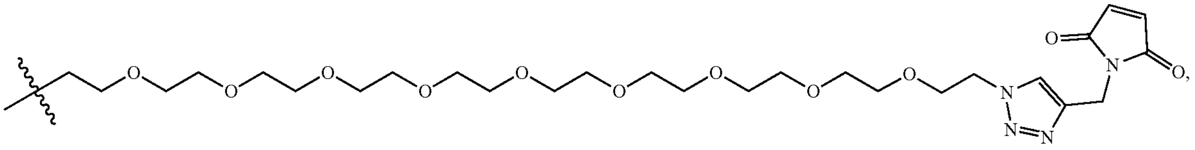
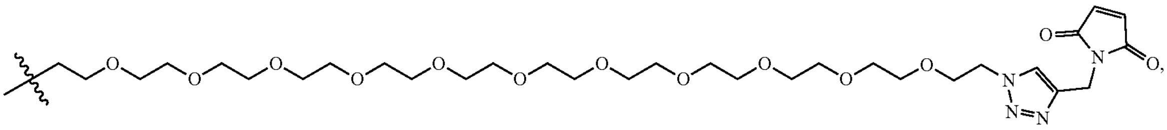
or
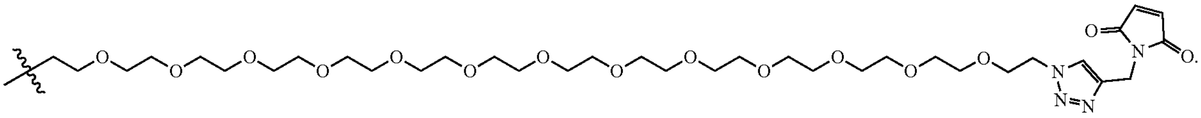

In preferred embodiments of any of the aforementioned cytotoxic cyclic peptides of Formula (A), Formula (I) and Formula (Ia): $R^2$ is
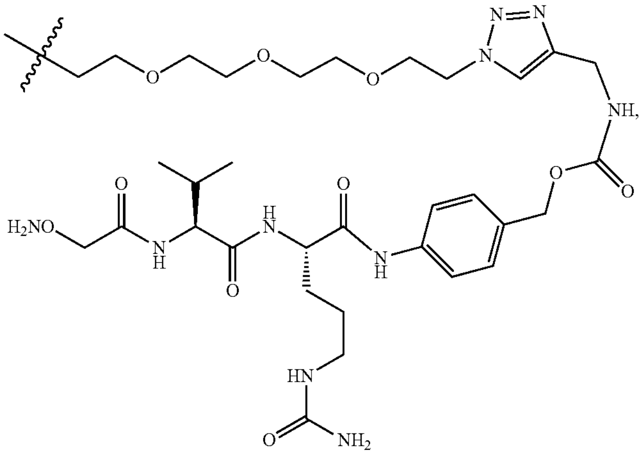
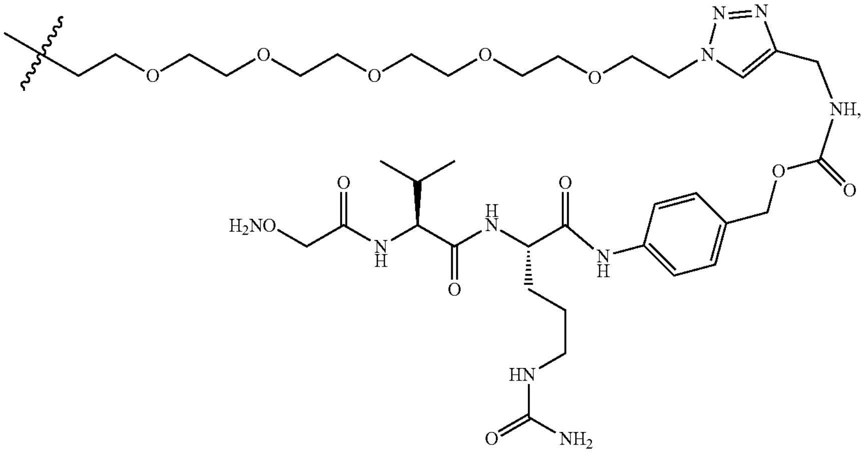
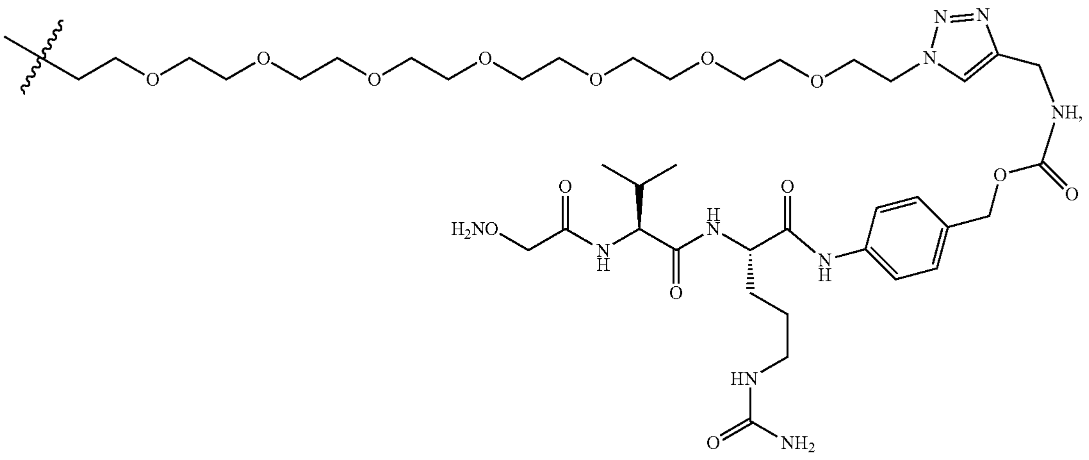

-continued
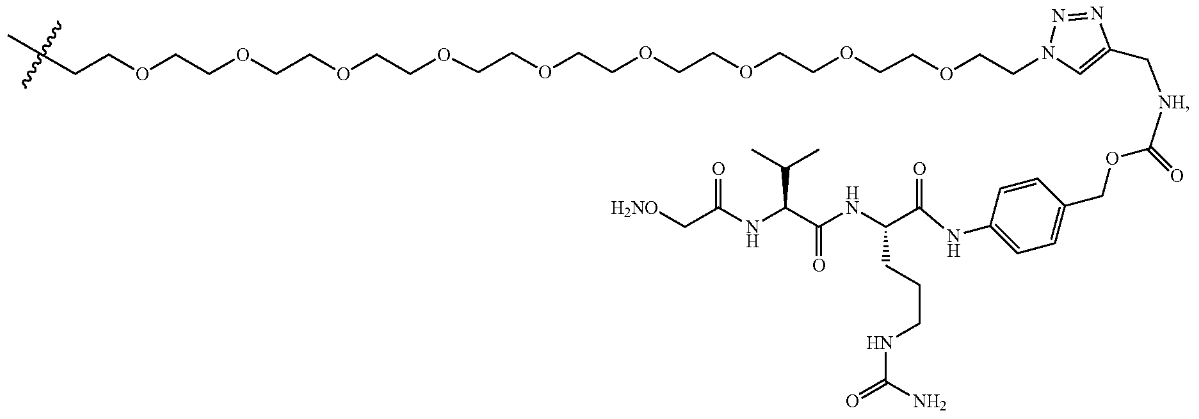
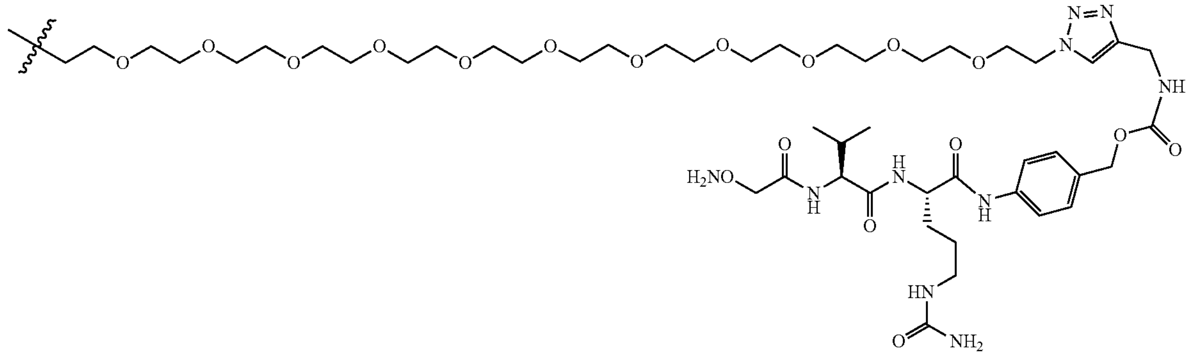
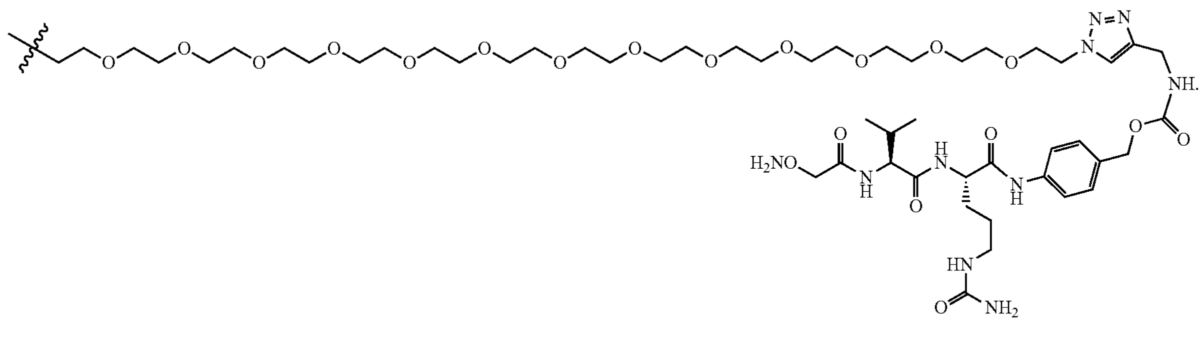

or
In preferred embodiments of any of the aforementioned cytotoxic cyclic peptides of Formula (A), Formula (I) and Formula (Ia):
$R^2$ is
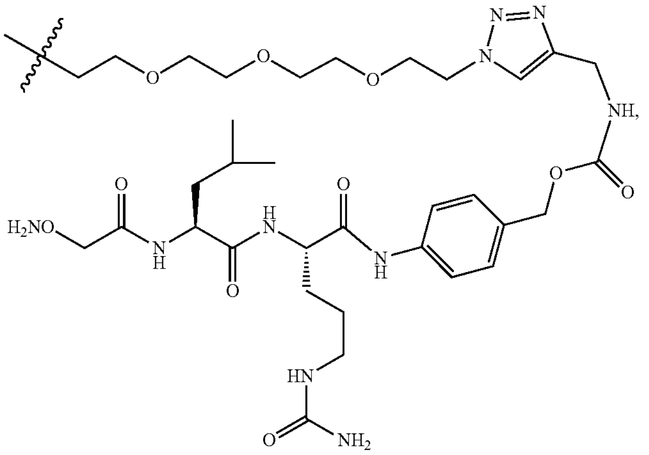
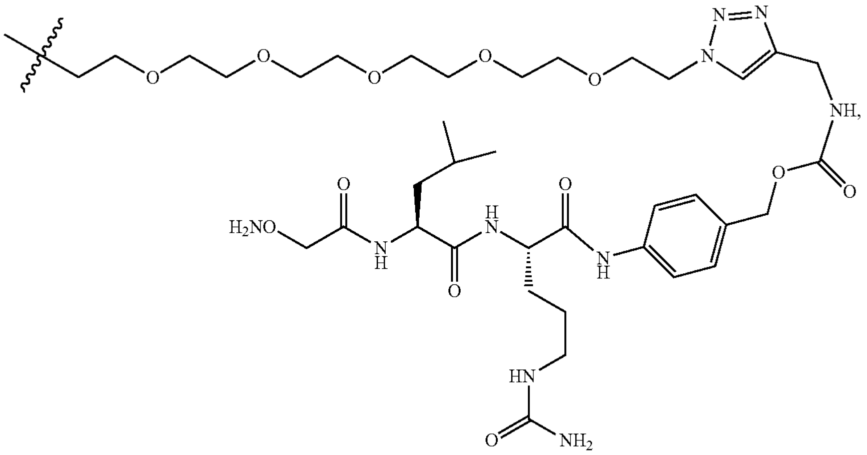
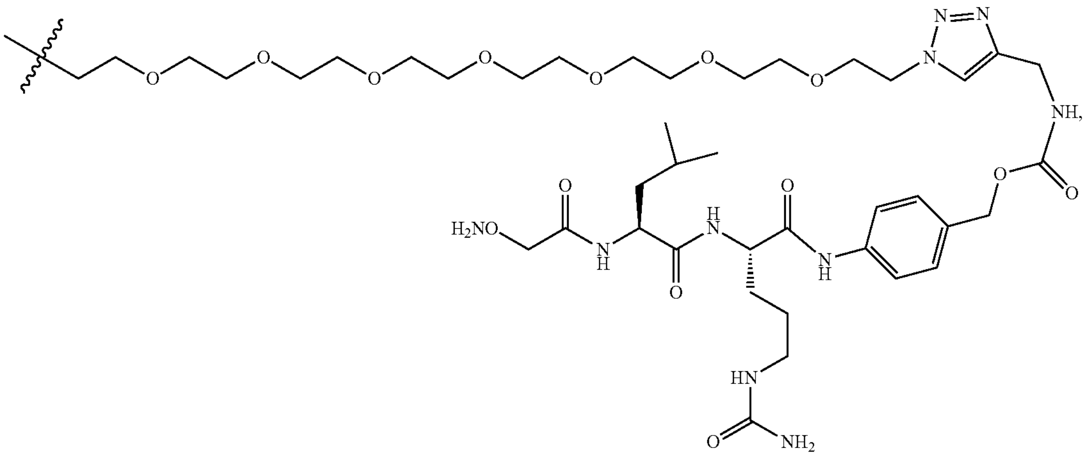

-continued
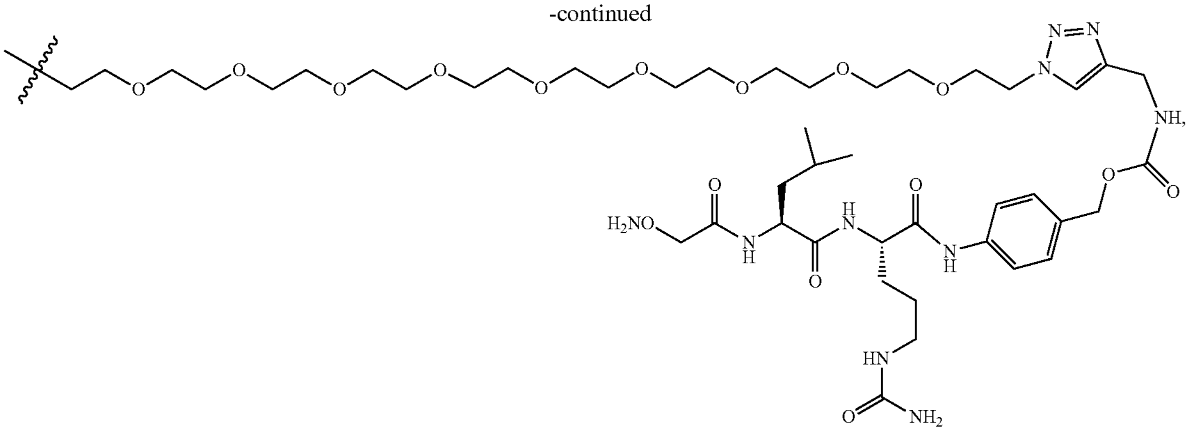
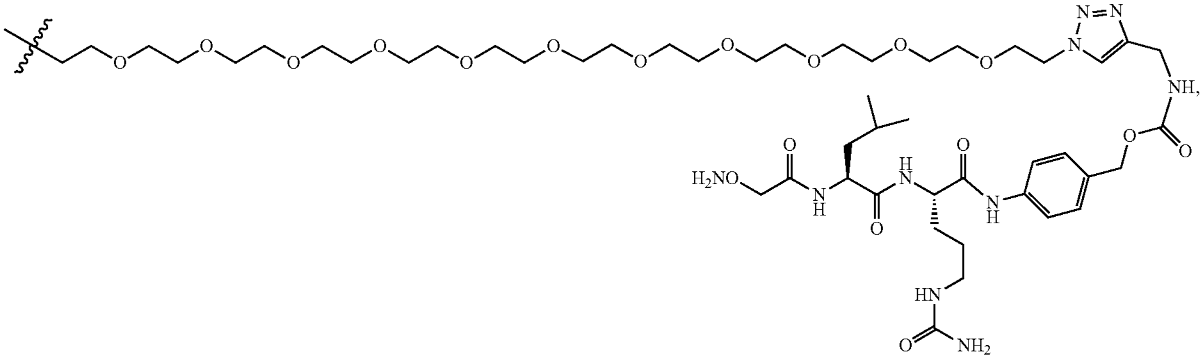
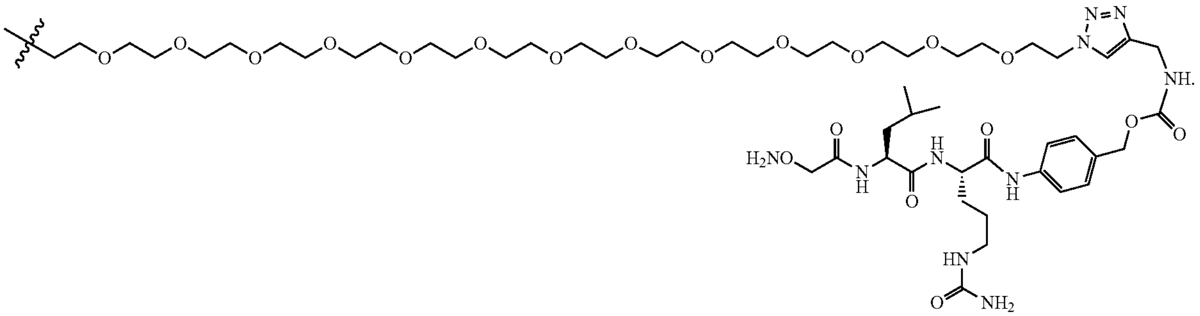
or
In preferred embodiments of any of the aforementioned cytotoxic cyclic peptides of Formula (A), Formula (I) and Formula (Ia):
$R^2$ is
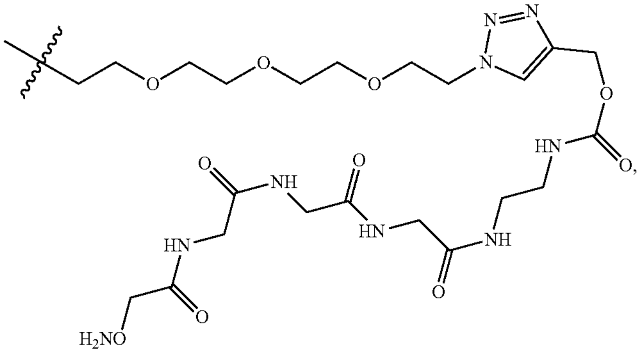

-continued
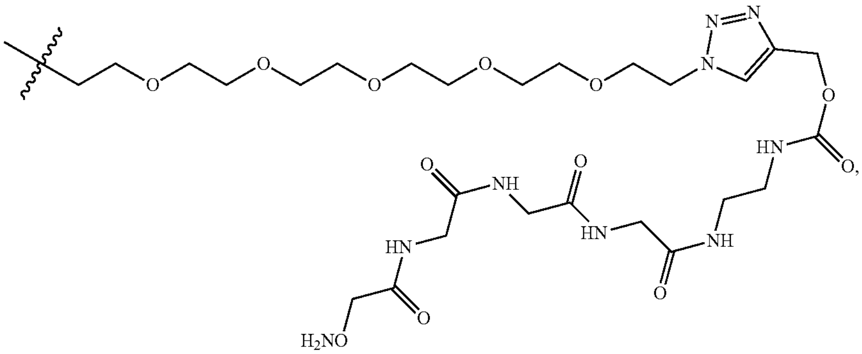
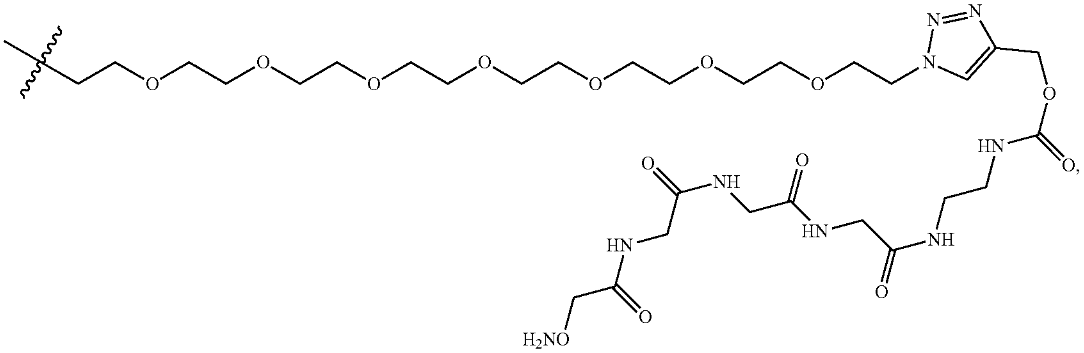
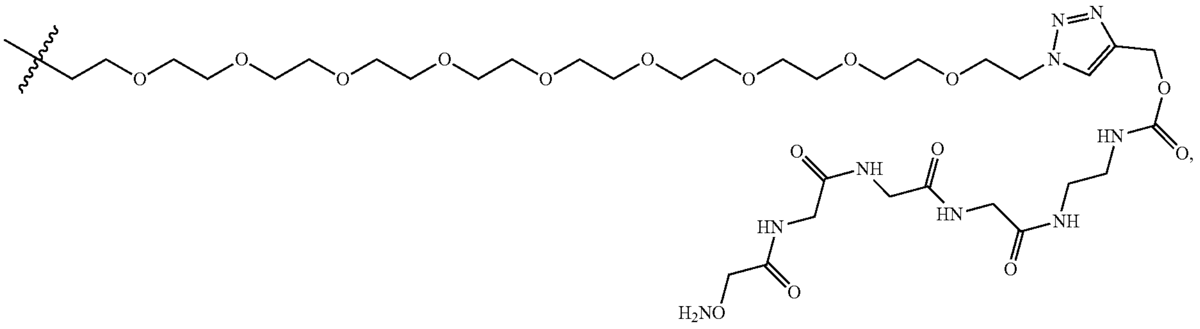
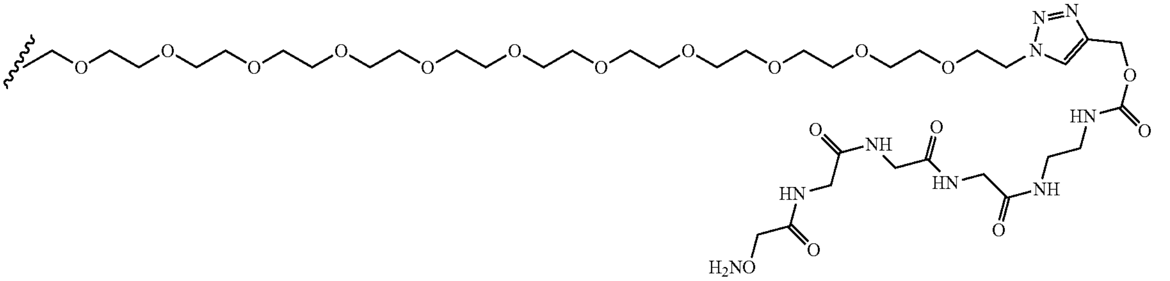
or
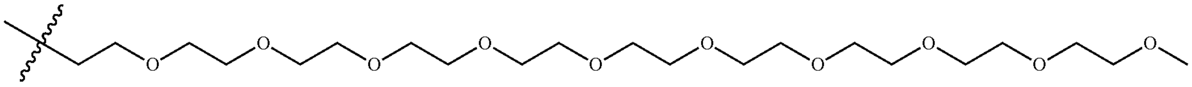

-continued

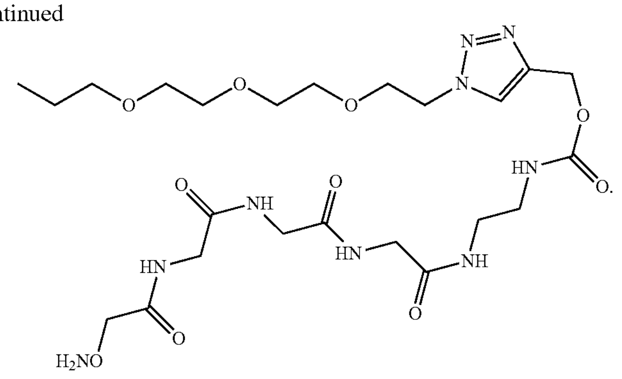

In certain embodiments of any of the aforementioned cytotoxic cyclic peptides of Formula (A), Formula (I) and Formula (Ia) $R^1$ is —$CH_3$, while in certain other embodiments of any of the aforementioned cytotoxic cyclic peptides of Formula (A), Formula (I) and Formula (Ia) $R^1$ is H. In other embodiments of any of the aforementioned cytotoxic cyclic peptides of Formula (A), Formula (I) and Formula (Ia) $R^1$ is —$CD_3$, In certain embodiments of any of the aforementioned cytotoxic cyclic peptides of Formula (A), Formula (I) and Formula (Ia) $R^3$ is —$NH_2$, while in certain other embodiments of any of the aforementioned cytotoxic cyclic peptides of Formula (A), Formula (I) and Formula (Ia) $R^3$ is —OH.

In certain embodiments of any of the aforementioned cytotoxic cyclic peptides of Formula (I) and Formula (Ia), the cytotoxic cyclic peptides of Formula (I) and Formula (Ia) is selected from:

6'O-methyl-7'C-(17-(4-((2,5-dioxo-2,5-dihydro-1H-pyrrol-1-yl)methyl)-1H-1,2,3-triazol-1-yl)-3,6,9,12,15-pentaoxaheptadecylthio)methyl-α-Amanitin;

7'C-((17-azido-3,6,9,12,15-pentaoxaheptadecanthio)methyl)-α-Amanitin;

6'O-methyl-7'C-((17-azido-3,6,9,12,15-pentaoxaheptadecanthio)methyl)-α-Amanitin;

6'O-methyl-7'C-((23-(4-((2,5-dioxo-2,5-dihydro-1H-pyrrol-1-yl)methyl)-1H-1,2,3-triazol-1-yl)-3,6,9,12,15,18,21-heptaoxatricosanthio)methyl)-α-Amanitin;

7'C-((23-azido-3,6,9,12,15,18,21-heptaoxatricosanthio)methyl)-α-Amanitin;

6'O-methyl-7'C-((23-azido-3,6,9,12,15,18,21-heptaoxatricosanthio)methyl)-α-Amanitin;

7'C-((23-(4-((2,5-dioxo-2,5-dihydro-1H-pyrrol-1-yl)methyl)-1H-1,2,3-triazol-1-yl)-3,6,9,12,15,18,21-heptaoxatricosanthio)methyl)-α-Amanitin;

6'O-methyl-7'C-((29-(4-((2,5-dioxo-2,5-dihydro-1H-pyrrol-1-yl)methyl)-1H-1,2,3-triazol-1-yl)-3,6,9,12,15,18,21,24,27-nonaoxanonacos anthio)methyl)-α-Amanitin;

7'C-((29-azido-3,6,9,12,15,18,21,24,27-nonaoxanonacos anthio)methyl)-α-Amanitin;

6'O-methyl-7'C-((29-azido-3,6,9,12,15,18,21,24,27-nonaoxanonacosanthio)methyl)-α-Amanitin;

7'C-((29-(4-((2,5-dioxo-2,5-dihydro-1H-pyrrol-1-yl)methyl)-1H-1,2,3-triazol-1-yl)-3,6,9,12,15,18,21,24,27-nonaoxanonacos anthio)methyl)-α-Amanitin;

6'O-methyl-7'C-((35-(4-((2,5-dioxo-2,5-dihydro-1H-pyrrol-1-yl)methyl)-1H-1,2,3-triazol-1-yl)-3,6,9,12,15,18,21,24,27,30,33-undecaoxapentatriacontanethio)methyl)-α-Amanitin;

7'C-((35-azido-3,6,9,12,15,18,21,24,27,30,33-undecaoxapentatriacontanethio)methyl)-α-Amanitin;

6'O-methyl-7'C-((35-azido-3,6,9,12,15,18,21,24,27,30,33-undecaoxapentatriacontanethio)methyl)-α-Amanitin;

7'C-((35-(4-((2,5-dioxo-2,5-dihydro-1H-pyrrol-1-yl)methyl)-1H-1,2,3-triazol-1-yl)-3,6,9,12,15,18,21,24,27,30,33-undecaoxapentatriacontanethio)methyl)-α-Amanitin;

6'O-methyl-7'C-((23-(4-(((((4-((S)-2-((S)-2-(2-(aminooxy)acetamido)-3-methylbutanamido)-5-ureidopentanamido)benzyl)oxy)carbonyl)amino)methyl)-1H-1,2,3-triazol-1-yl)-3,6,9,12,15,18,21-heptaoxatricosanyl)thio)methyl-α-Amanitin;

6'O-methyl-7'C-((23-(4-(((((4-((S)-2-((S)-2-(2-(aminooxy)acetamido)-4-methylpentanamido)-5-ureidopentanamido)benzyl)oxy)carbonyl)amino)methyl)-1H-1,2,3-triazol-1-yl)-3,6,9,12,15,18,21-heptaoxatricosanyl)thio)methyl-α-Amanitin;

6'O-methyl-7'C-((35-(4-(18-(aminooxy)-3,8,11,14,17-pentaoxo-2-oxa-4,7,10,13,16-pentaazaoctadecyl)-1H-1,2,3-triazol-1-yl)-3,6,9,12,15,18,21,24,27,30,33-undecaoxapentatriacontanyl)thio)methyl-s-Amanitin;

6'O-methyl-$d_3$-7'C-((((1-(4-maleimido-3,6,9,12,15,18,21-heptaoxatricosyl)-1H-1,2,3-triazol-4-yl)methyl)thio)methyl)-α-Amanitin, and 6'O-methyl-$d_3$-7'C-((23-azido-3,6,9,12,15,18,21-heptaoxatricosanthio)methyl)-α-Amanitin.

In certain embodiments of any of the aforementioned cytotoxic cyclic peptides of Formula (I) and Formula (Ia), the cytotoxic cyclic peptides of Formula (I) and Formula (Ia) is selected from:

6'O-methyl-7'C-(17-(4-((2,5-dioxo-2,5-dihydro-1H-pyrrol-1-yl)methyl)-1H-1,2,3-triazol-1-yl)-3,6,9,12,15-pentaoxaheptadecylthio)methyl-α-Amanitin;

6'O-methyl-7'C-((23-(4-((2,5-dioxo-2,5-dihydro-1H-pyrrol-1-yl)methyl)-1H-1,2,3-triazol-1-yl)-3,6,9,12,15,18,21-heptaoxatricosanthio)methyl)-α-Amanitin;

7'C-((23-(4-((2,5-dioxo-2,5-dihydro-1H-pyrrol-1-yl)methyl)-1H-1,2,3-triazol-1-yl)-3,6,9,12,15,18,21-heptaoxatricosanthio)methyl)-α-Amanitin;

6'O-methyl-7'C-((29-(4-((2,5-dioxo-2,5-dihydro-1H-pyrrol-1-yl)methyl)-1H-1,2,3-triazol-1-yl)-3,6,9,12,15,18,21,24,27-nonaoxanonacos anthio)methyl)-α-Amanitin;

7'C-((29-(4-((2,5-dioxo-2,5-dihydro-1H-pyrrol-1-yl)methyl)-1H-1,2,3-triazol-1-yl)-3,6,9,12,15,18,21,24,27-nonaoxanonacos anthio)methyl)-α-Amanitin;

6'O-methyl-7'C-((35-(4-((2,5-dioxo-2,5-dihydro-1H-pyrrol-1-yl)methyl)-1H-1,2,3-triazol-1-yl)-3,6,9,12,15,18,21,24,27,30,33-undecaoxapentatriacontanethio)methyl)-α-Amanitin;

7'C-((35-(4-((2,5-dioxo-2,5-dihydro-1H-pyrrol-1-yl)methyl)-1H-1,2,3-triazol-1-yl)-3,6,9,12,15,18,21,24,27,30,33-undecaoxapentatriacontanethio)methyl)-α-Amanitin;

6'O-methyl-7'C-((23-(4-(((((4-((S)-2-((S)-2-(2-(aminooxy)acetamido)-3-methylbutanamido)-5-ureidopentanamido)benzyl)oxy)carbonyl)amino)methyl)-1H-1,2,3-triazol-1-yl)-3,6,9,12,15,18,21-heptaoxatricosanyl)thio)methyl-α-Amanitin;

6'O-methyl-7'C-((23-(4-(((((4-((S)-2-((S)-2-(2-(aminooxy)acetamido)-4-methylpentanamido)-5-ureidopentanamido)benzyl)oxy)carbonyl)amino)methyl)-1H-1,2,3-triazol-1-yl)-3,6,9,12,15,18,21-heptaoxatricosanyl)thio)methyl-s-Amanitin;

6'O-methyl-7'C-((35-(4-(18-(aminooxy)-3,8,11,14,17-pentaoxo-2-oxa-4,7,10,13,16-pentaazaoctadecyl)-1H-1,2,3-triazol-1-yl)-3,6,9,12,15,18,21,24,27,30,33-undecaoxapentatriacontanyl)thio)methyl-α-Amanitin, and 6'O-methyl-$d_3$-7'C-((((1-(4-maleimido-3,6,9,12,15,18,21-heptaoxatricosyl)-1H-1,2,3-triazol-4-yl)methyl)thio)methyl)-α-Amanitin.

The present invention provides immunoconjugates, also referred to herein as ADCs, containing cytotoxic cyclic peptides linked to an antigen binding moiety, such as an antibody or antibody fragment. These conjugates comprising cytotoxic cyclic peptides are useful to treat cell proliferation disorders, particularly when the cytotoxic cyclic peptides are linked to an antibody that recognizes cancer cells and thus promotes delivery of the cytotoxic cyclic peptides to a cell targeted for attack. The immunoconjugates are especially useful for treating certain cancers as further detailed herein. Data provided herein demonstrate that these immunoconjugates are effective inhibitors of cell proliferation.

In one aspect of the immunoconjugates of the invention include immunoconjugates of Formula (B):

Formula (B)

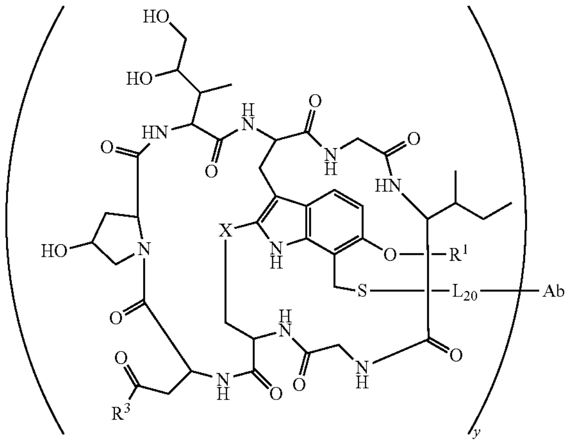

wherein:

X is S(=O), $S(=O)_2$ or S;

Ab represents an antigen binding moiety;

y is an integer from 1 to 16;

$R^1$ is H, $-CH_3$ or $-CD_3$; $R^3$ is $-NH_2$ or $-OH$;

$L_{20}$ is $-L_1R^{40}$;

$L_1$ is $-((CH_2)_mO)_n(CH_2)_mX_3L_4-$ or $-((CH_2)_mO)_n(CH_2)_mX_4L_4-$;

$L_4$ is $-((CH_2)_m-$ or $-((CH_2)_mNHC(=O)X_1X_2C(=O)(CH_2)_m-$;

$X_1$ is

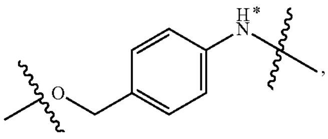
,

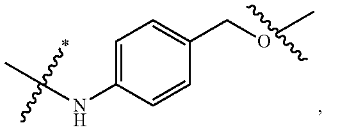
,

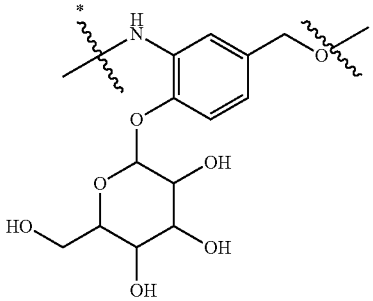
,

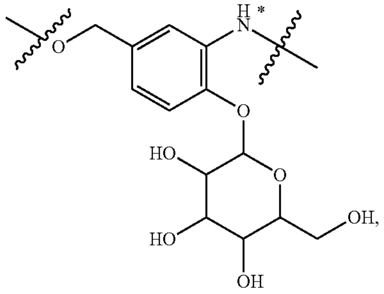

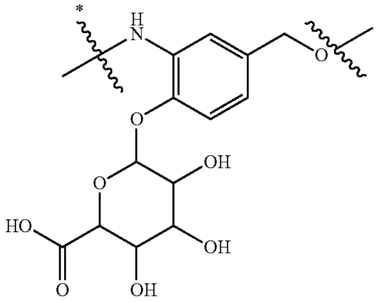
or

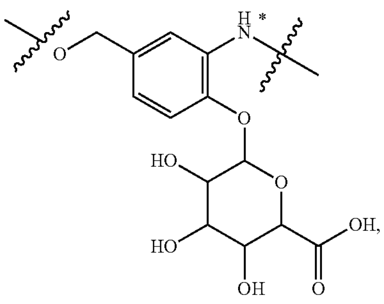

where the * indicated attachment point to $X_2$;

$X_2$ is
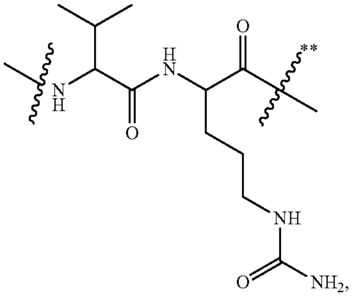
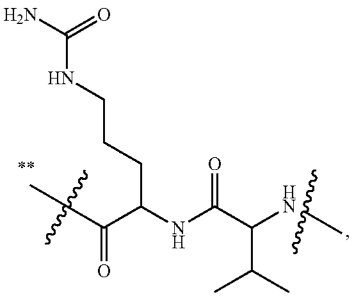
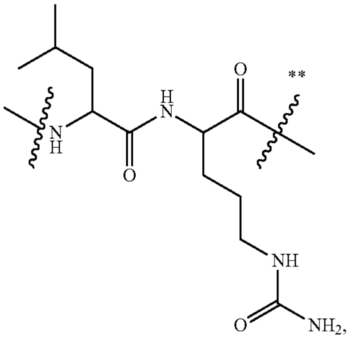
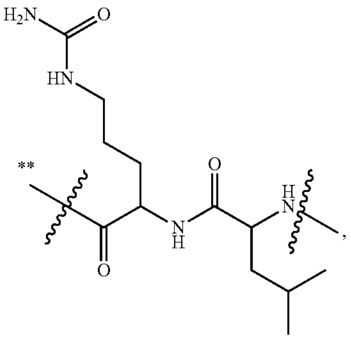
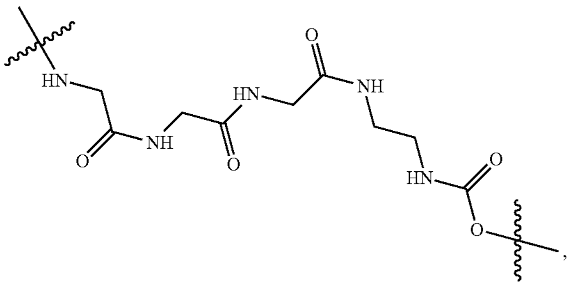
-continued
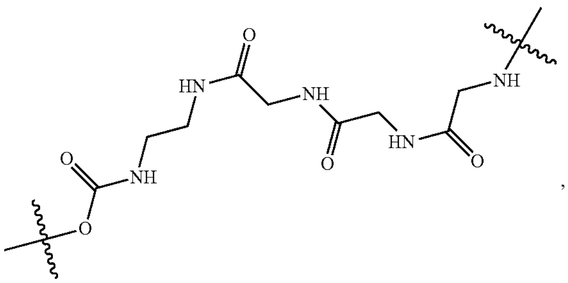
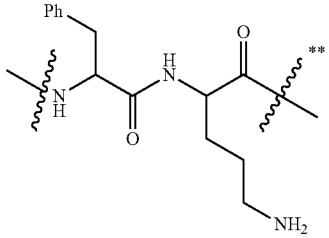
or
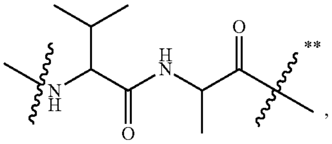
where the ** indicates attachment point to $X_1$;
$X_3$ is
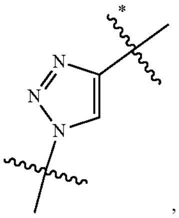
,
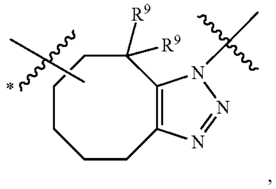
,
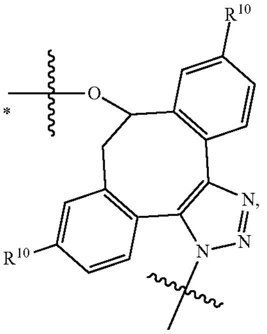
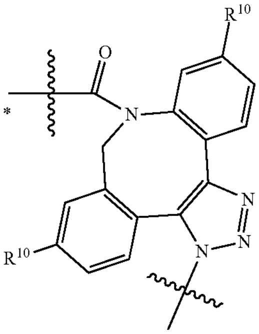
or
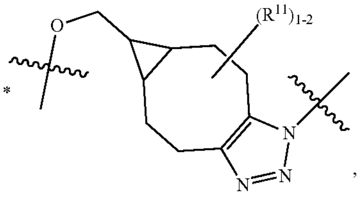
where the * indicates attachment point to $L_4$;

$X_4$ is
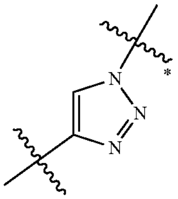
,
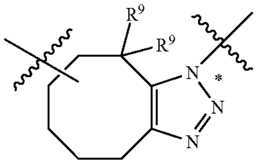
,
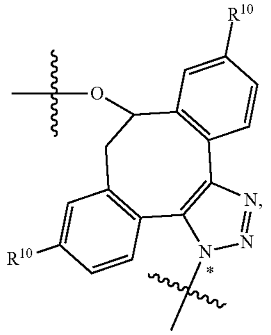
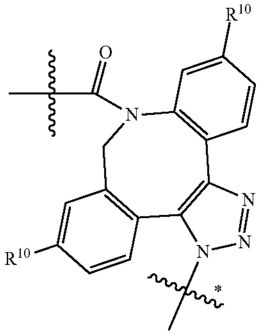
or
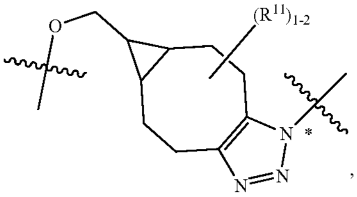
,
where the * indicates attachment point to $L_4$;
$R^{40}$ is
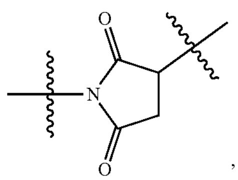
,
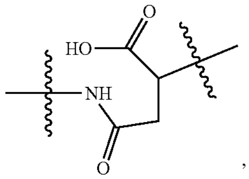
,
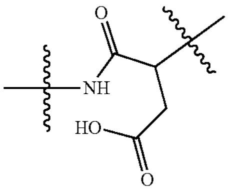
,
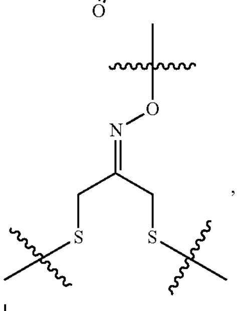
,
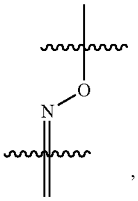
,
$-NR^5C(=O)CH_2-$, $-NHC(=O)CH_2-$, $-S(=O)_2CH_2CH_2-$, $-(CH_2)_2S(=O)_2CH_2CH_2-$, $-NR^5S(=O)_2CH_2CH_2$, $-NR^5C(=O)CH_2CH_2-$, $-NH-$, $-C(=O)-$, $-NHC(=O)-$, $-CH_2NHCH_2CH_2-$, $-NHCH_2CH_2-$, $-S-$,
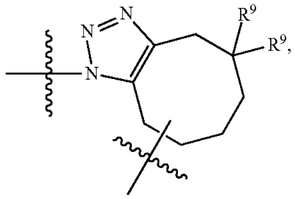
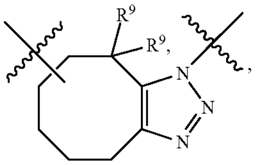
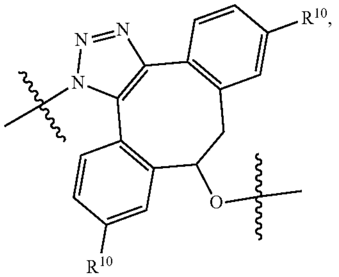
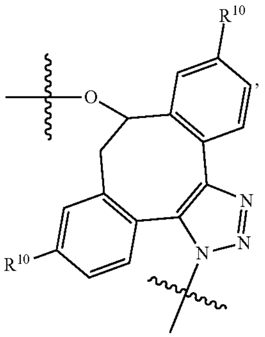
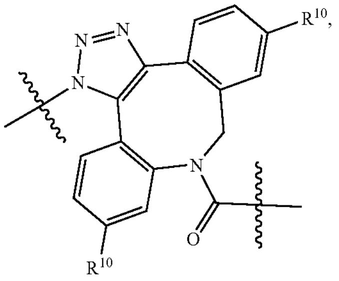
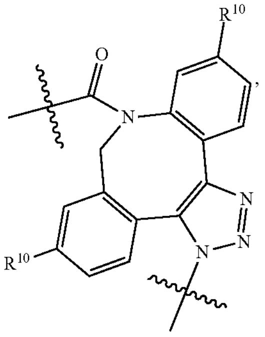

-continued

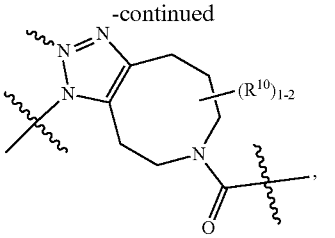

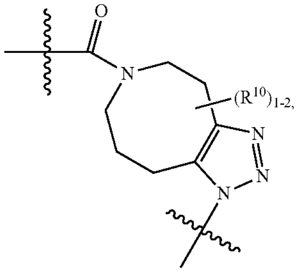

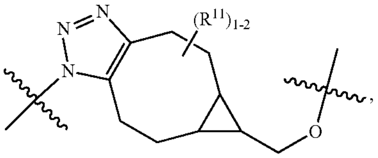

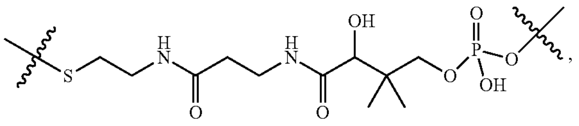

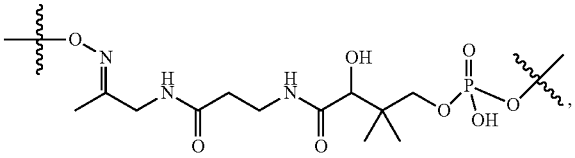

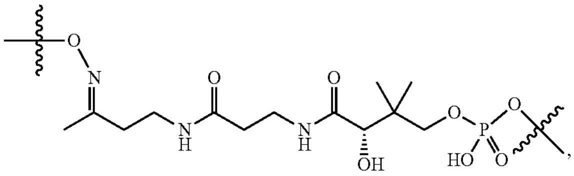

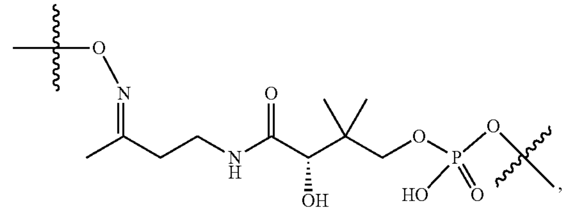

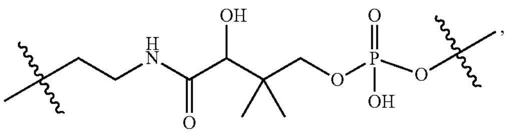

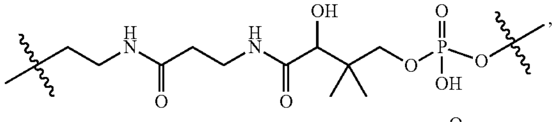

or

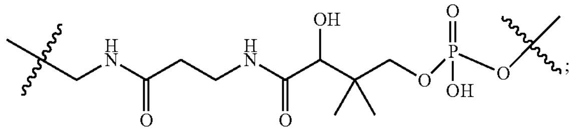

each $R^5$ is independently selected from H and $C_1$-$C_6$alkyl;

each $R^9$ is independently selected from H, $C_1$-$C_6$alkyl, F, Cl, and —OH;

each $R^{10}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{11}$ is independently selected from H, $C_{1-6}$alkyl, fluoro, benzyloxy substituted with —C(═O)OH, benzyl substituted with —C(═O)OH, $C_{1-4}$alkoxy substituted with —C(═O)OH and $C_{1-4}$alkyl substituted with —C(═O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

In one aspect of the immunoconjugates of the invention include immunoconjugates of Formula (II):

Formula (II)

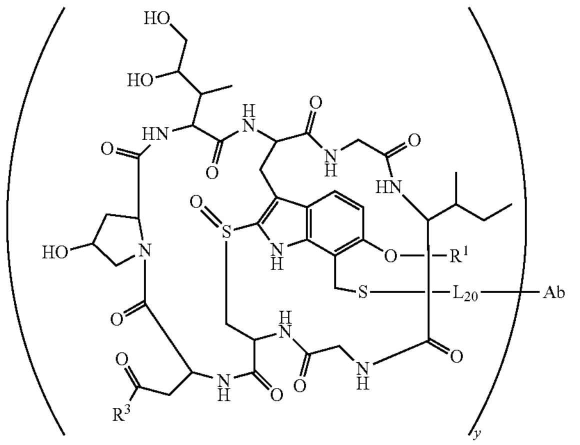

wherein:

Ab represents an antigen binding moiety;

y is an integer from 1 to 16;

$R^1$ is H, —$CH_3$ or —$CD_3$; $R^3$ is —$NH_2$ or —OH;

$L_{20}$ is -$L_1R^{40}$;

$L_1$ is —$((CH_2)_mO)_n(CH_2)_mX_3L_4$- or —$((CH_2)_mO)_n(CH_2)_mX_4L_4$-;

$L_4$ is —$((CH_2)_m$— or —$((CH_2)_mNHC(═O)X_1X_2C(═O)(CH_2)_m$—;

$X_1$ is

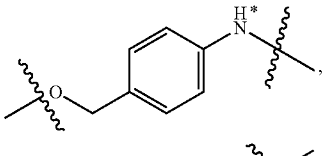

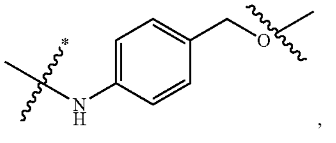

-continued
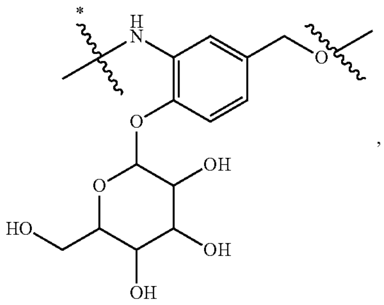
,
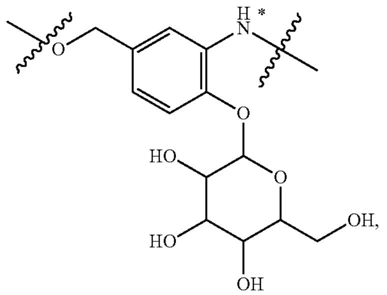
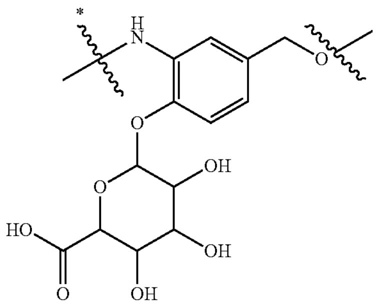
or
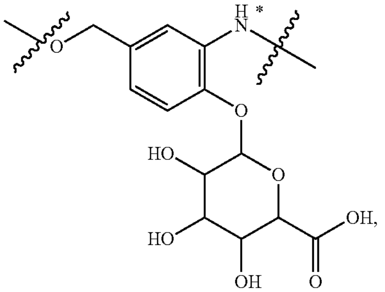
where the * indicates attachment point to $X_2$;
$X_2$ is
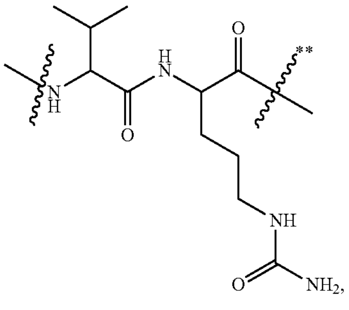
-continued
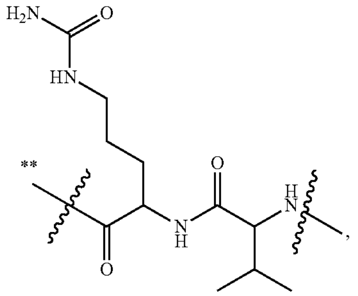
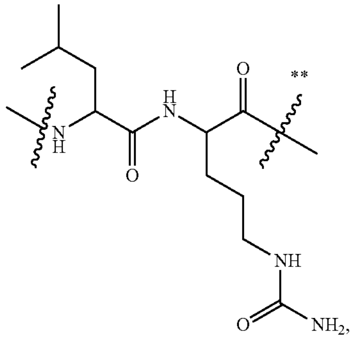
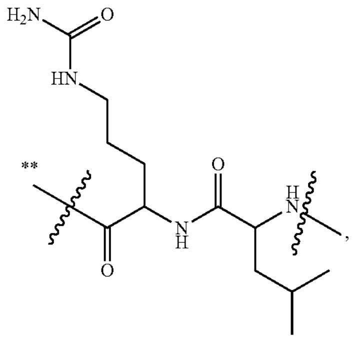
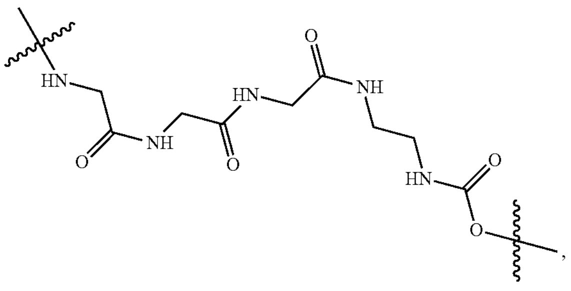
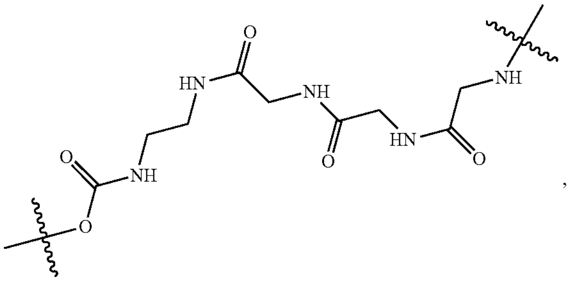
, -continued
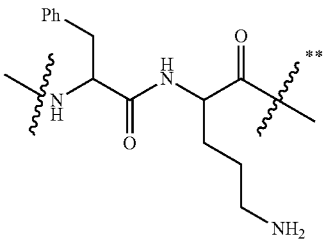
or
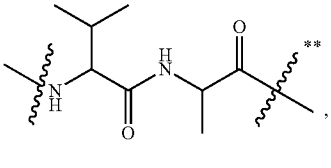
,
where the ** indicates attachment point to $X_1$;
$X_3$ is
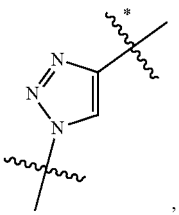
,
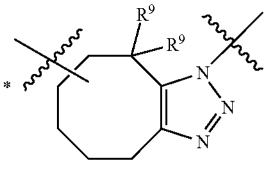
,
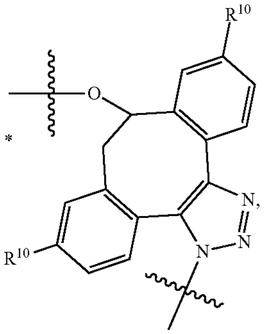
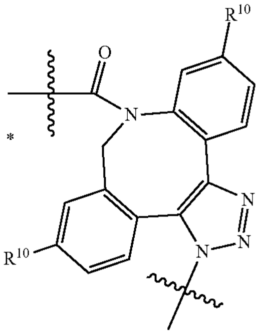
or
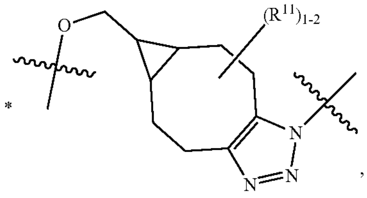
,
where the * indicates attachment point to $L_4$;
$X_4$ is
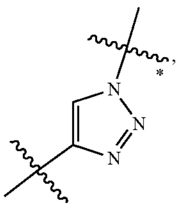
,
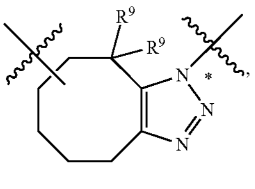
,
-continued
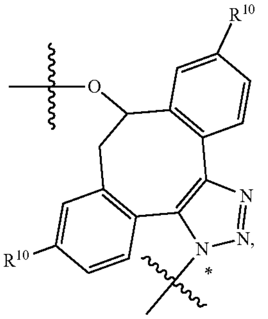
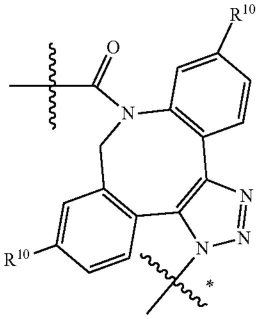
or
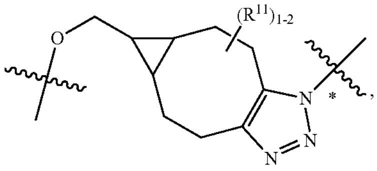
,
where the * indicates attachment point to $L_4$;
$R^{40}$ is
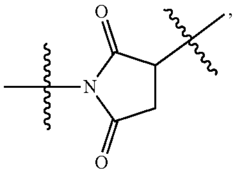
,
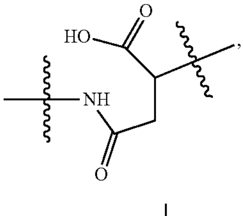
,
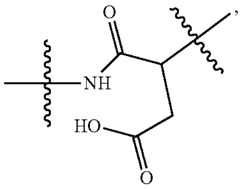
,
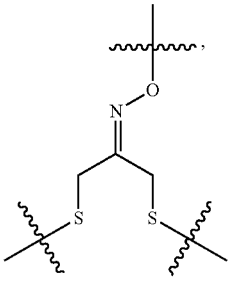
,
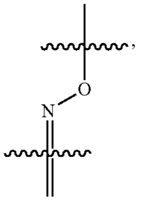
,
$-NR^5C(=O)CH_2-$, $-NHC(=O)CH_2-$, $-S(=O)_2CH_2CH_2-$, $-(CH_2)_2S(=O)_2CH_2CH_2-$, $-NR^5S(=O)_2$ $CH_2CH_2$, $-NR^5C(=O)CH_2CH_2-$, $-NH-$, $-C(=O)-$, $-NHC(=O)-$, $-CH_2NHCH_2CH_2-$, $-NHCH_2CH_2-$, $-S-$,

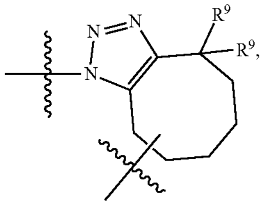

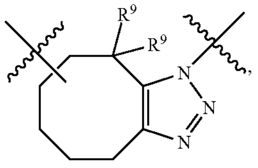

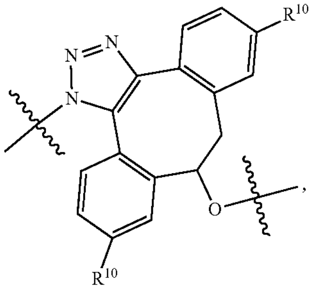

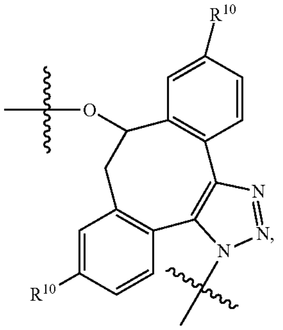

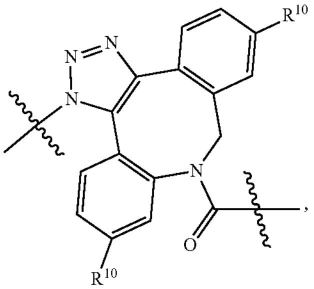

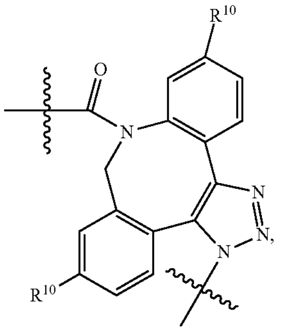

-continued

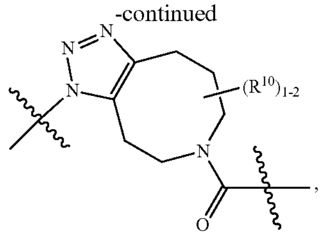

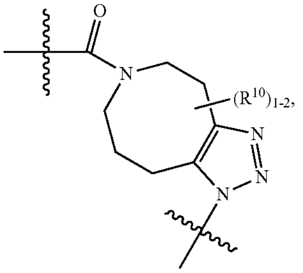

or

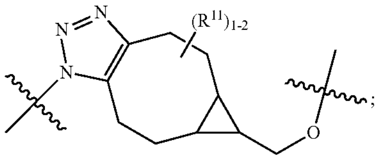

each $R^5$ is independently selected from H and $C_1$-$C_6$alkyl;

each $R^9$ is independently selected from H, $C_1$-$C_6$alkyl, F, Cl, and —OH;

each $R^{10}$ is independently selected from H, $C_1$-$C_6$alkyl, F, Cl, $-NH_2$, $-OCH_3$, $-OCH_2CH_3$, $-N(CH_3)_2$, —CN, $-NO_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

In certain embodiments of this aspect of immunoconjugates having the structure of Formula (II), are immunoconjugates having the structure of Formula (IIa):

Formula (IIa)

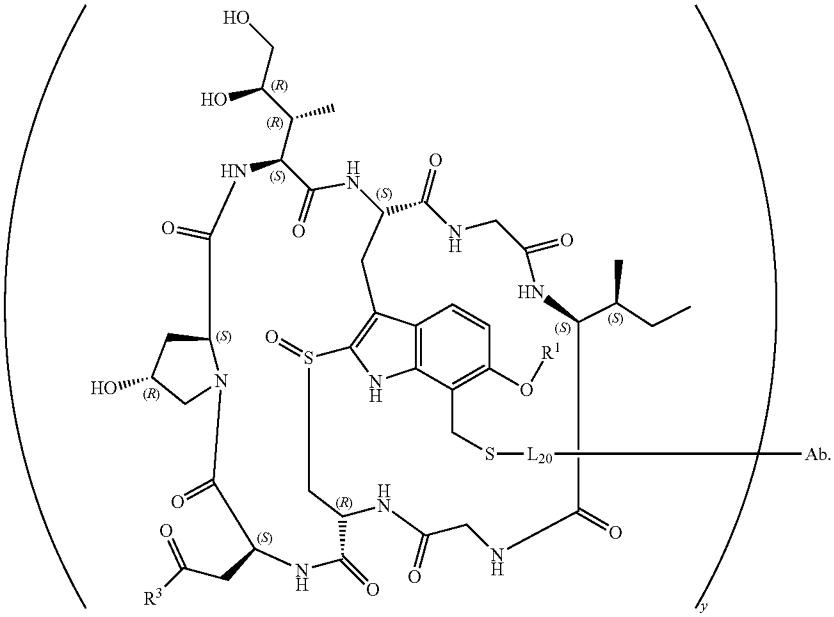

In certain embodiments of such immunoconjugates of Formula (B), Formula (II) and Formula (IIa):

Ab represents an antigen binding moiety;

y is an integer from 1 to 16;

$R^1$ is H, $-CH_3$ or $-CD_3$; $R^3$ is $-NH_2$ or $-OH$;

$L_{20}$ is $-L_1R^{40}$;

$L_1$ is $-((CH_2)_mO)_n(CH_2)_mX_3L_4-$;

$L_2$ is $-((CH_2)_mO)_n(CH_2)_m-$;

$L_3$ is $-((CH_2)_mO)_n(CH_2)_mX_3L_4-$ or $-((CH_2)_mO)_n(CH_2)_m-$;

$L_4$ is $-((CH_2)_m-$ or $-((CH_2)_mNHC(=O)X_1X_2C(=O)(CH_2)_m-$;

$X_1$ is

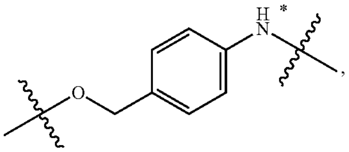 [SMILES: *Nc1ccc(CO*)cc1]

where the * indicates attachment point to $X_2$;

$X_2$ is

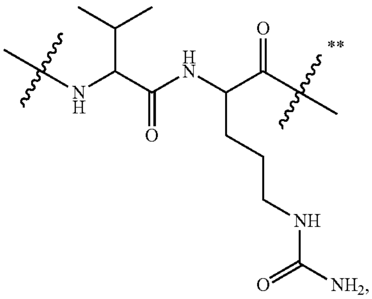

-continued

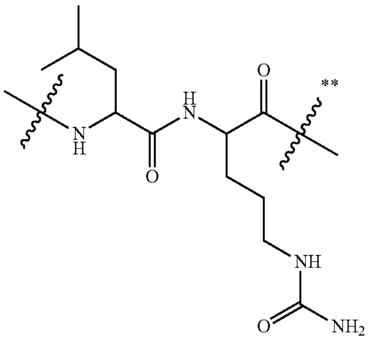

or

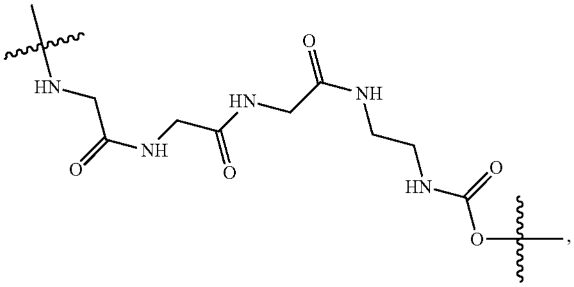

where the ** indicates attachment point to $X_1$;

$X_3$ is
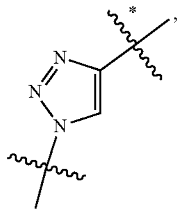 [SMILES: *c1cn(*)nn1]
where the * indicates attachment point to $L_4$;
$R^{40}$ is
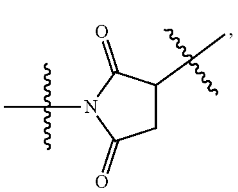
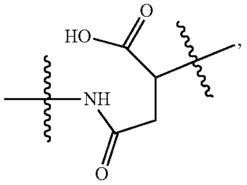
-continued
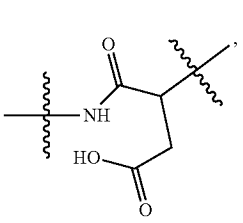
or
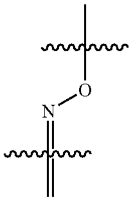
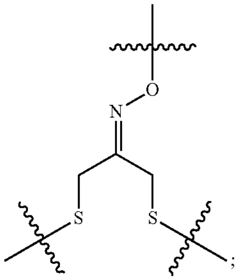
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.
In preferred embodiments of any of the aforementioned immunoconjugates of Formula (B), Formula (II) and Formula (IIa):
$L_{20}$ is
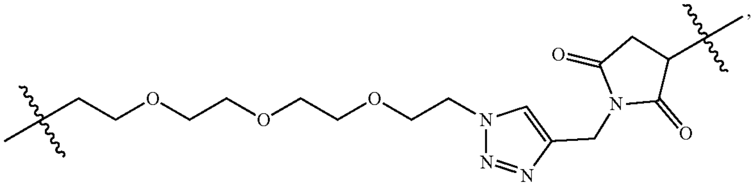
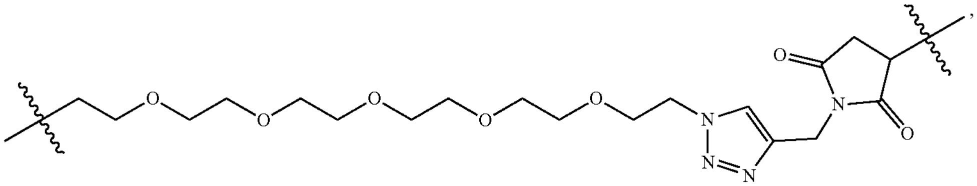
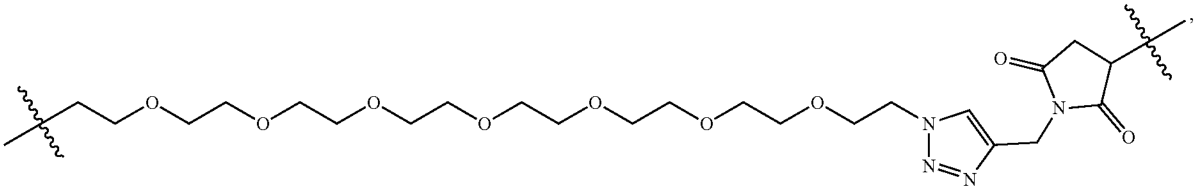
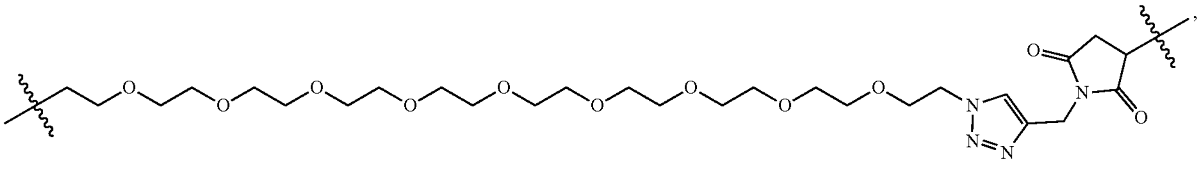

-continued
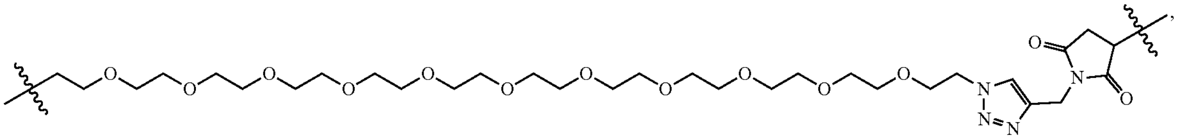
, or
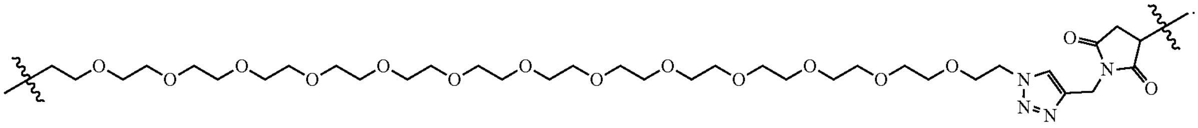
.
In preferred embodiments of any of the aforementioned immunoconjugates of Formula (B), Formula (II) and Formula (IIa):
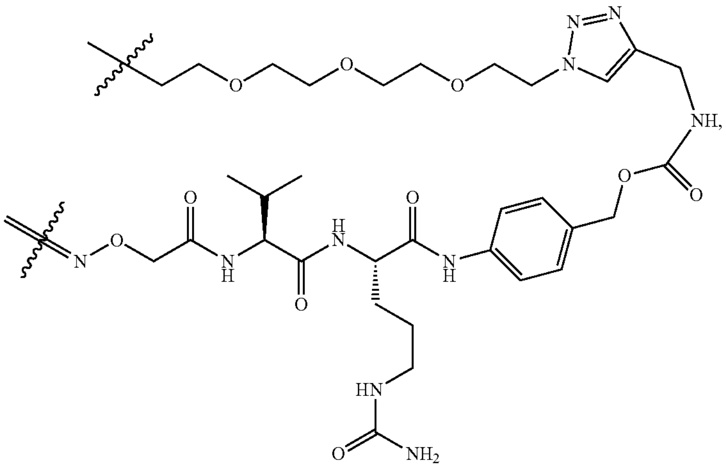
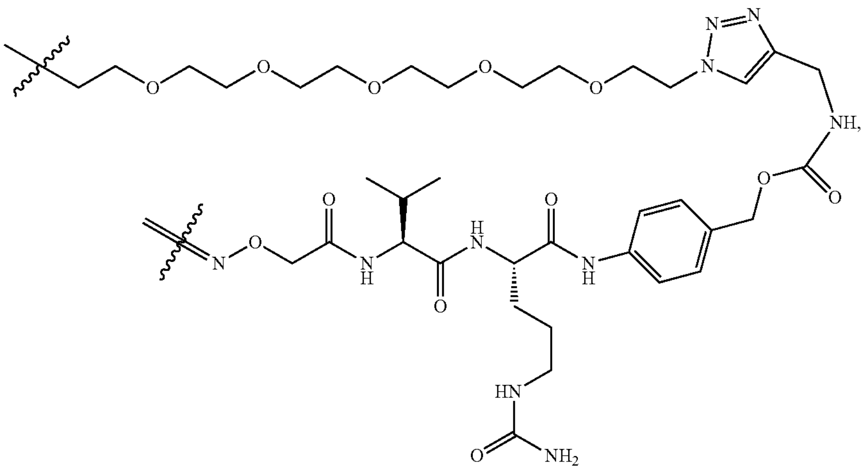

-continued
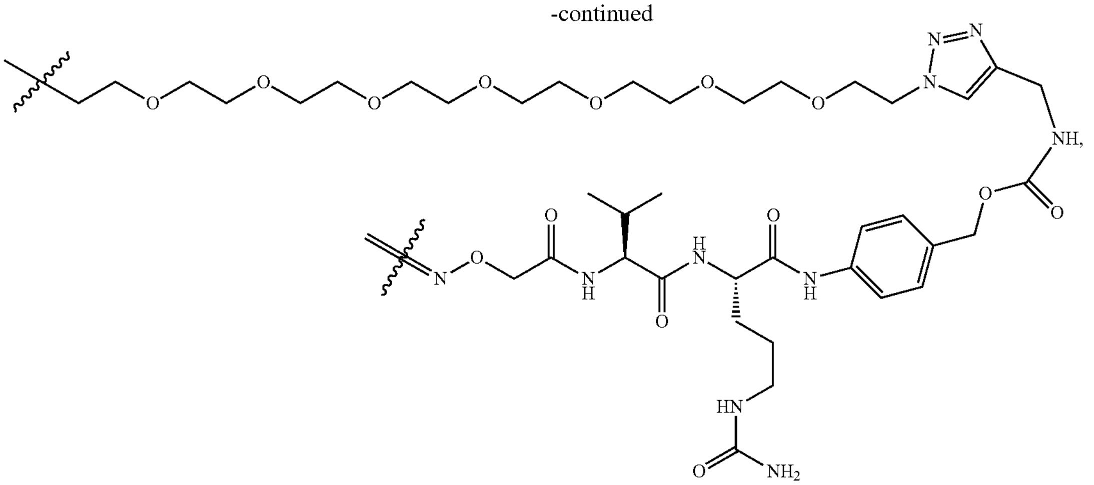
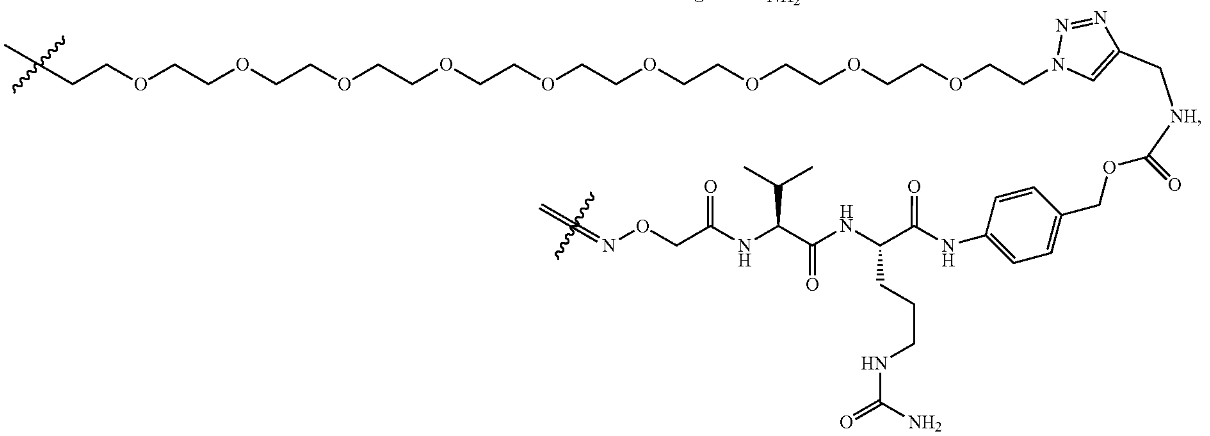
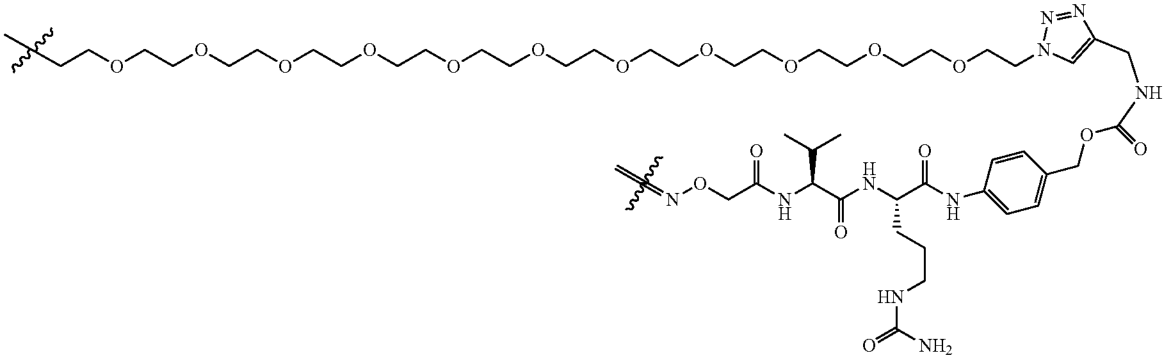
or
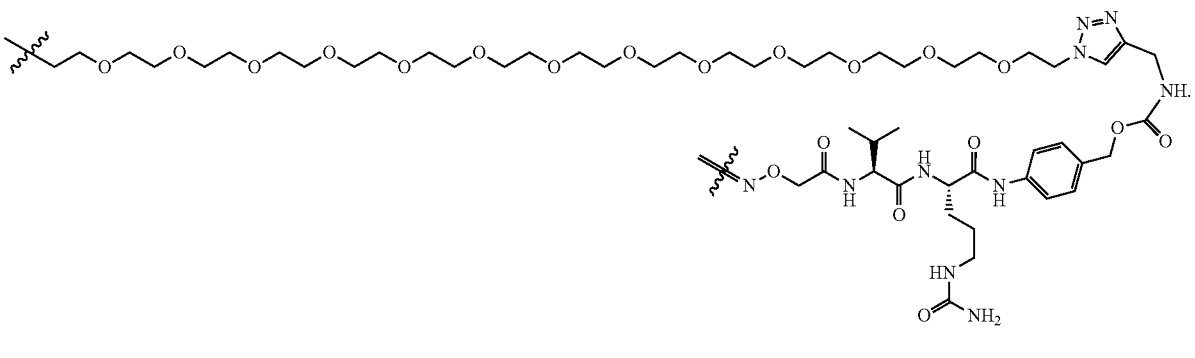

$L_{20}$ is
In preferred embodiments of any of the aforementioned immunoconjugates of Formula (B), Formula (II) and Formula (IIa):
$L_{20}$ is,
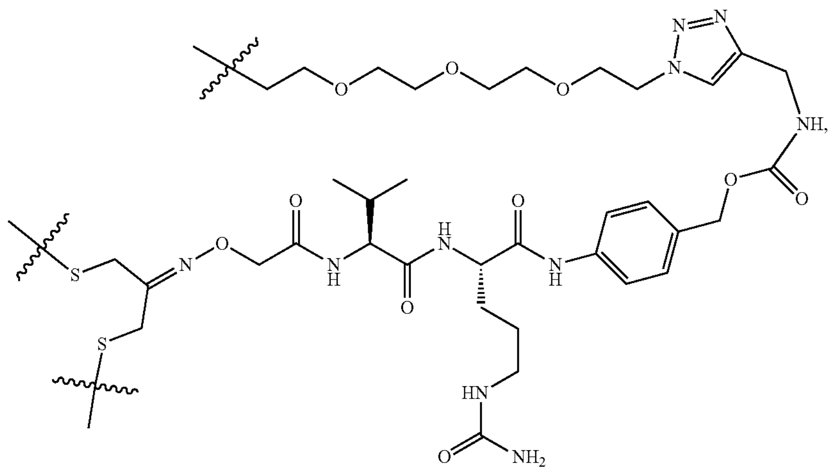
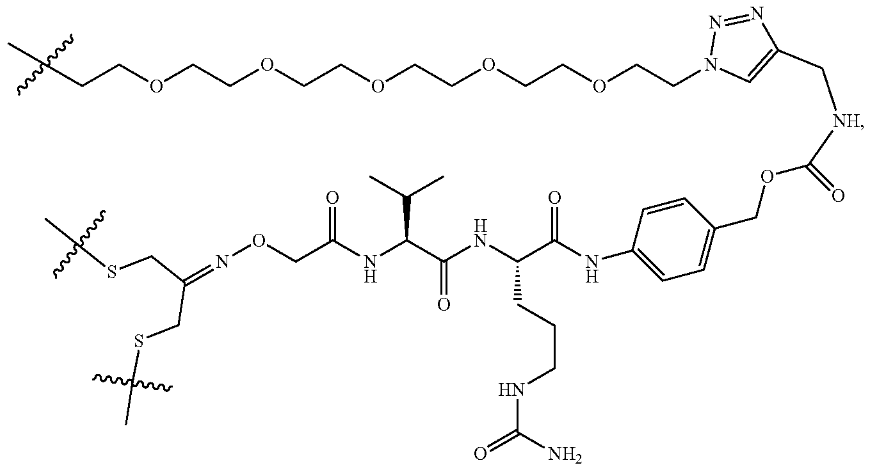
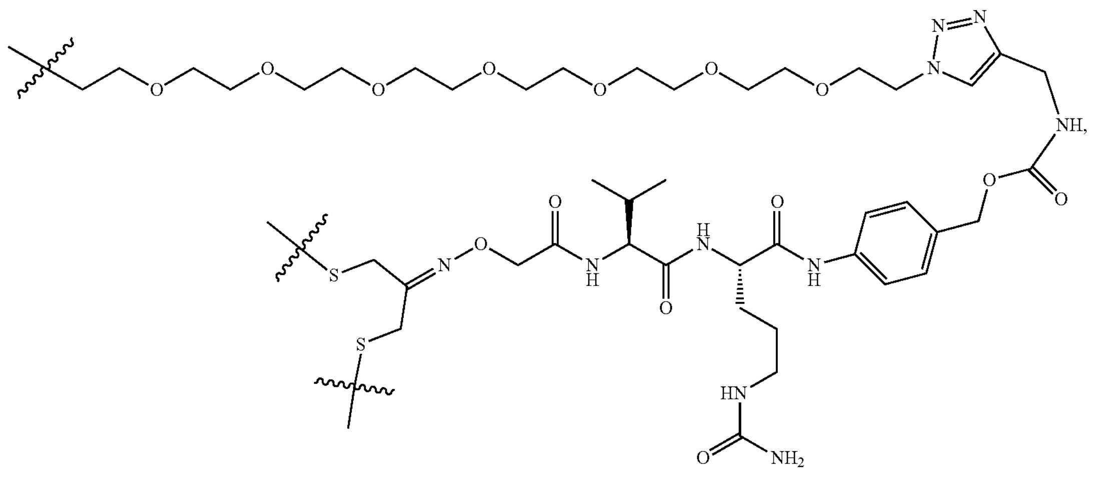

-continued
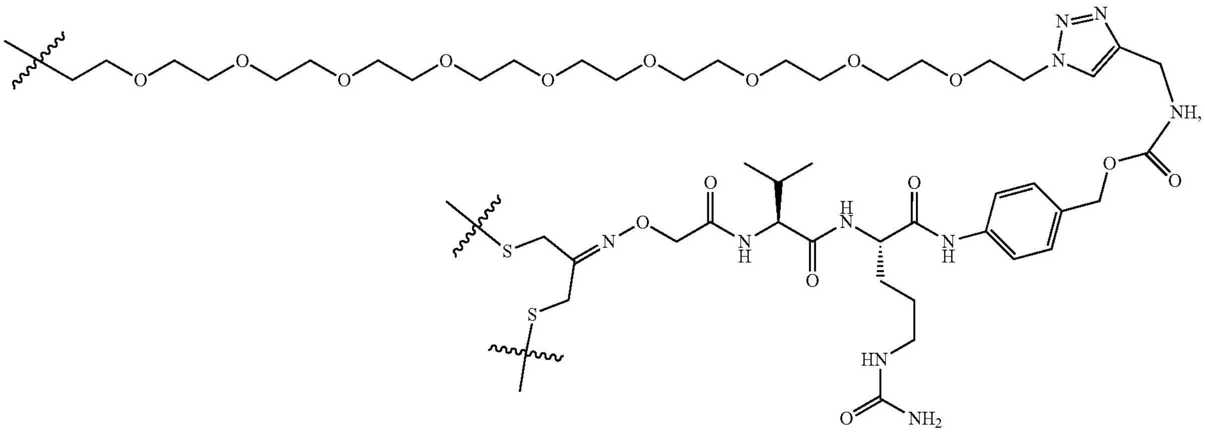
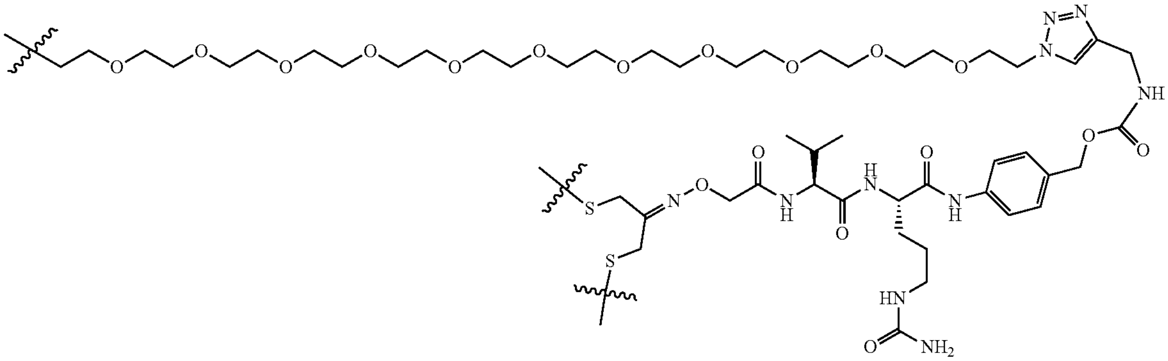
or
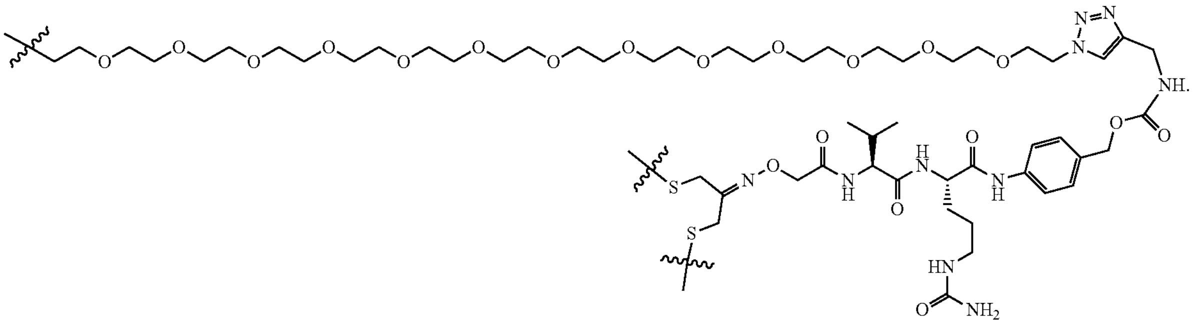

In preferred embodiments of any of the aforementioned immunoconjugates of Formula (B), Formula (II) and Formula (IIa):
$L_{20}$ is
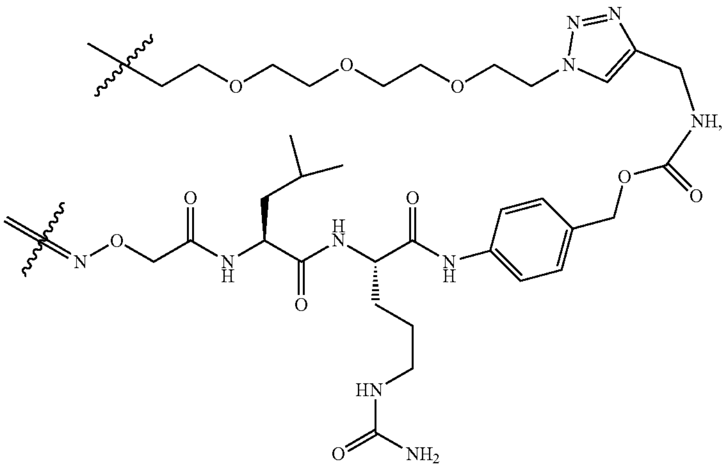
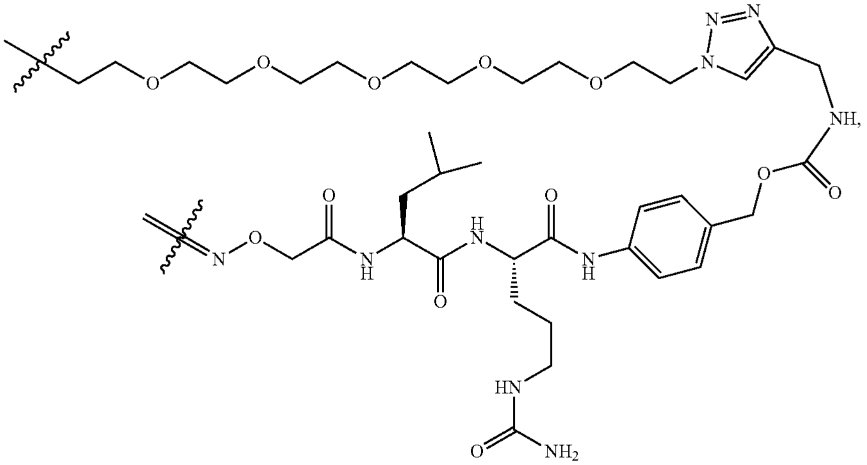
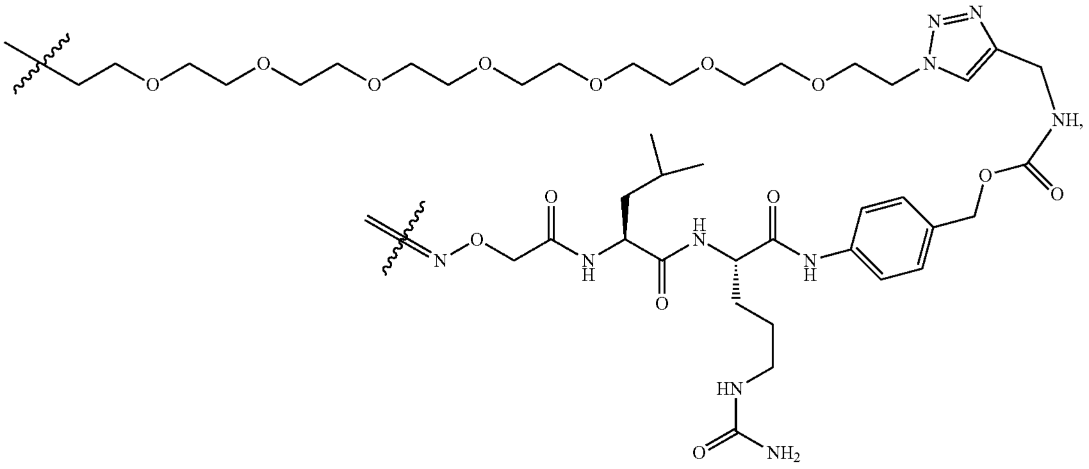

-continued
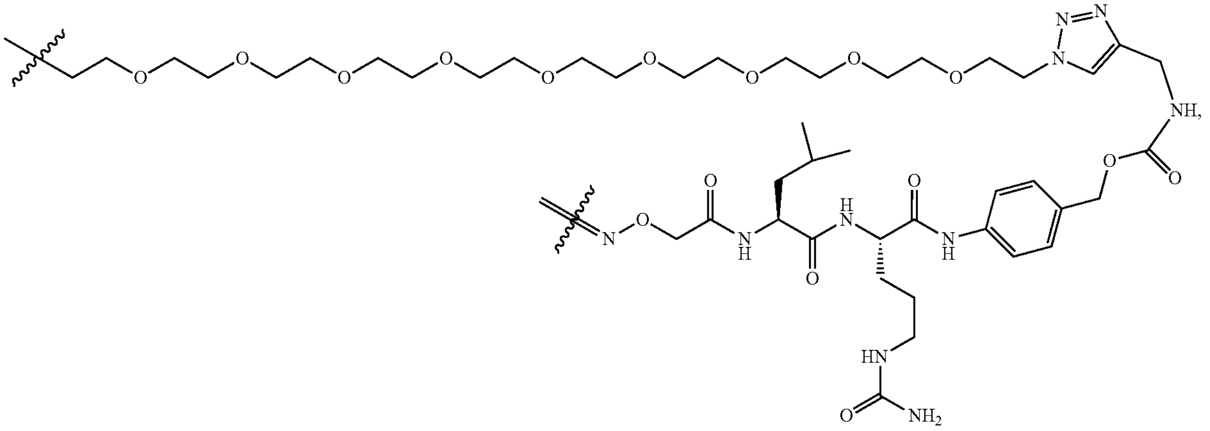
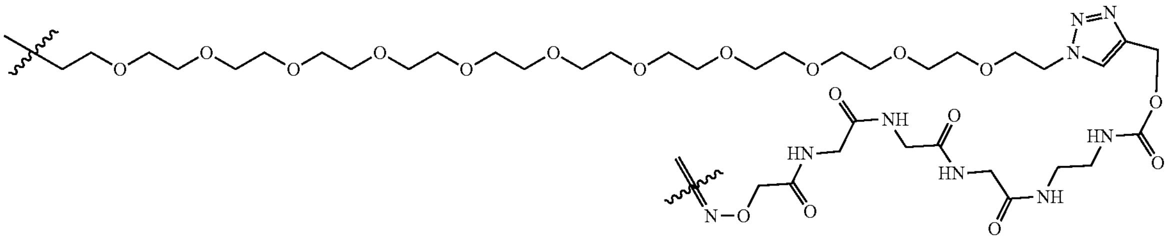
or
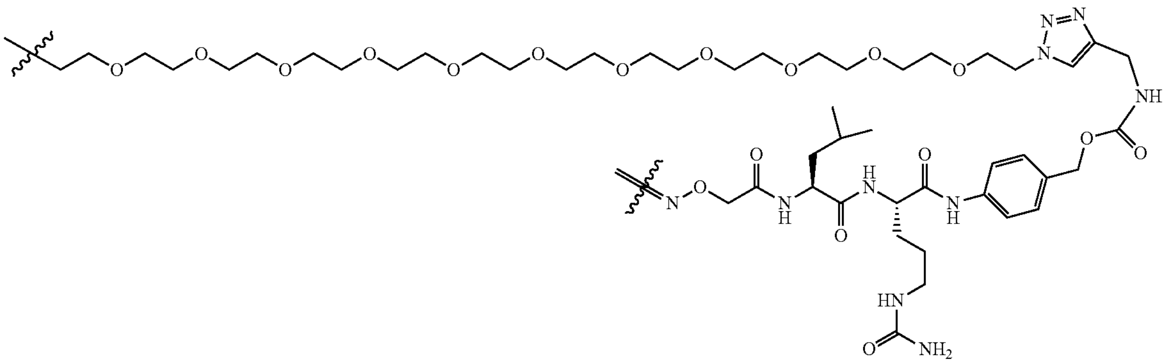
or
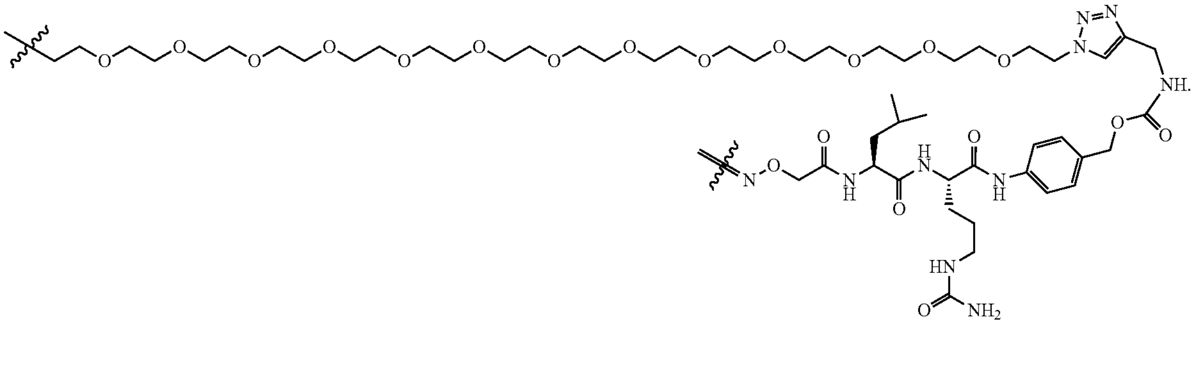

In preferred embodiments of any of the aforementioned immunoconjugates of Formula (B), Formula (II) and Formula (IIa):
$L_{20}$ is
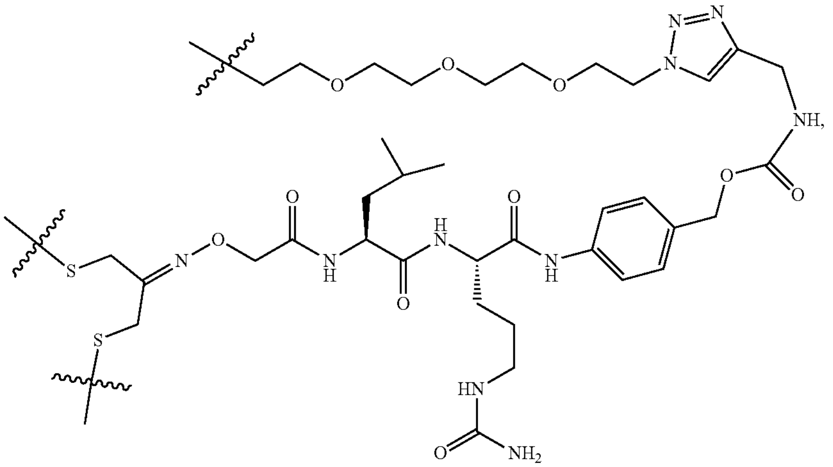
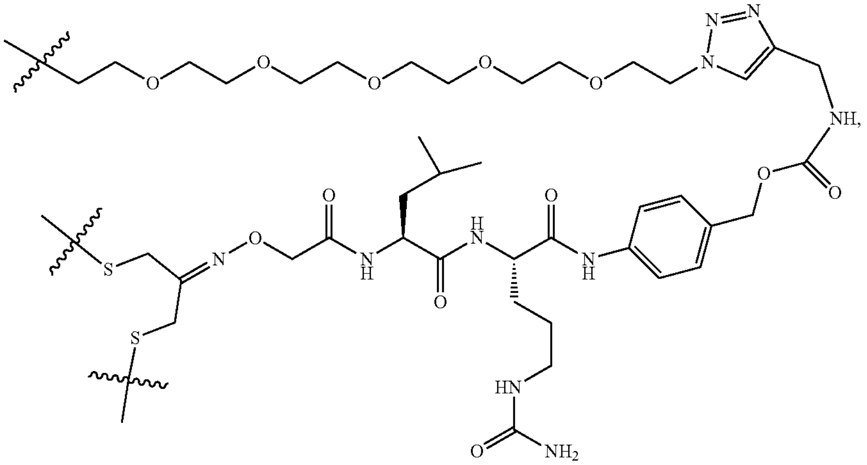
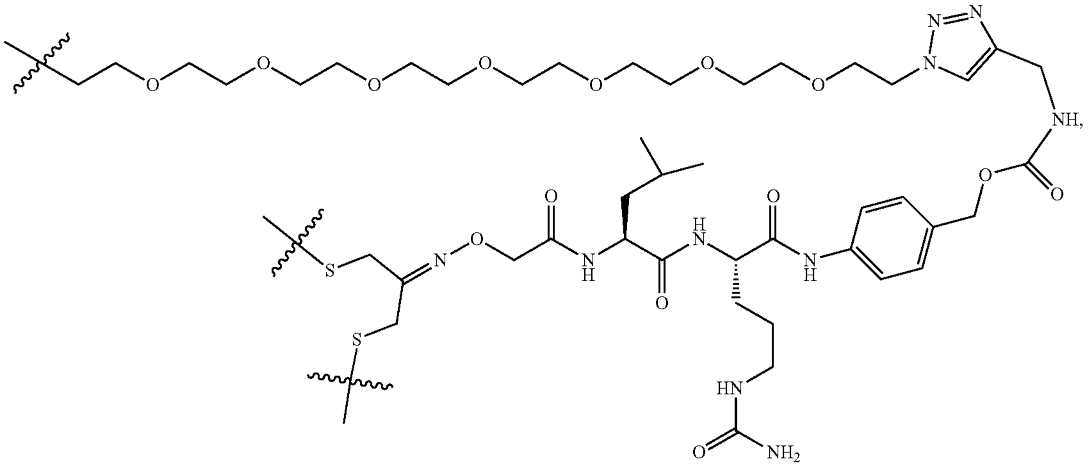

-continued
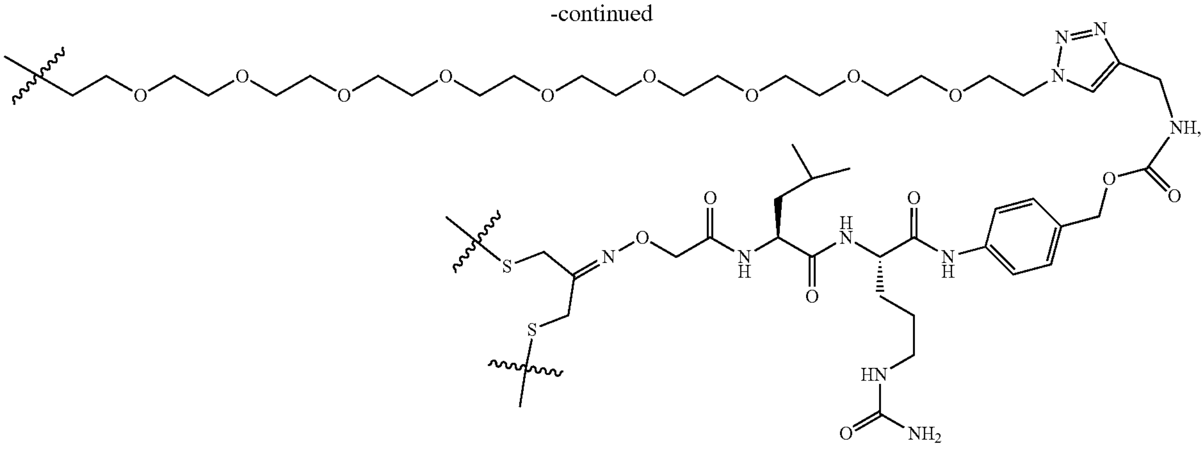
,
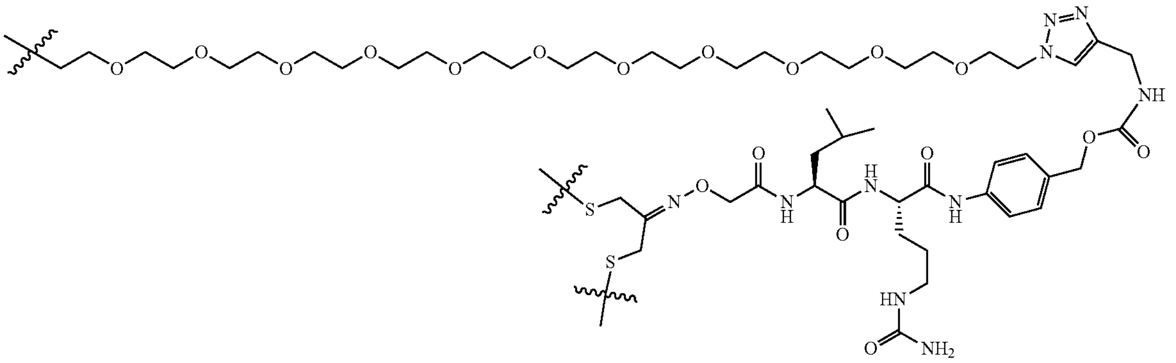
or
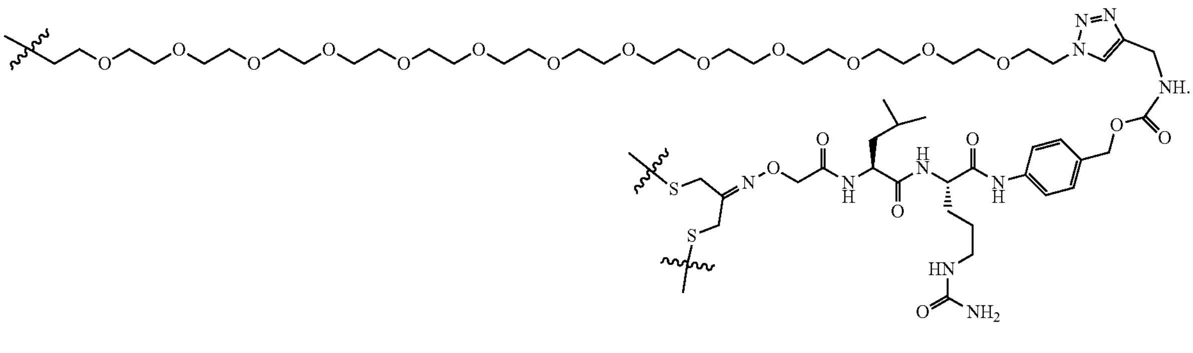
.
In preferred embodiments of any of the aforementioned immunoconjugates of Formula (B), Formula (II) and Formula (IIa):
$L_{20}$ is
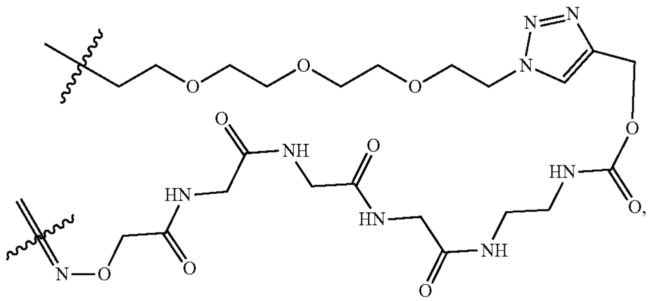
, -continued
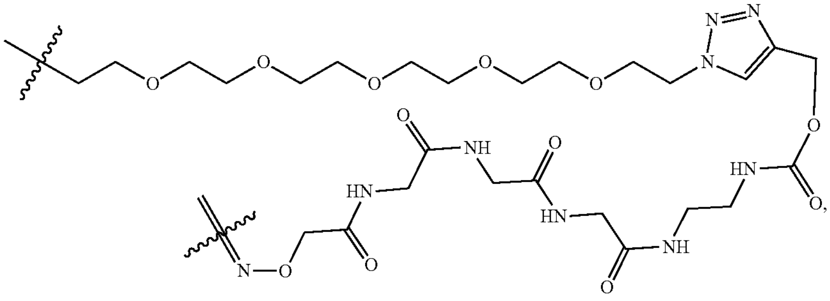
,
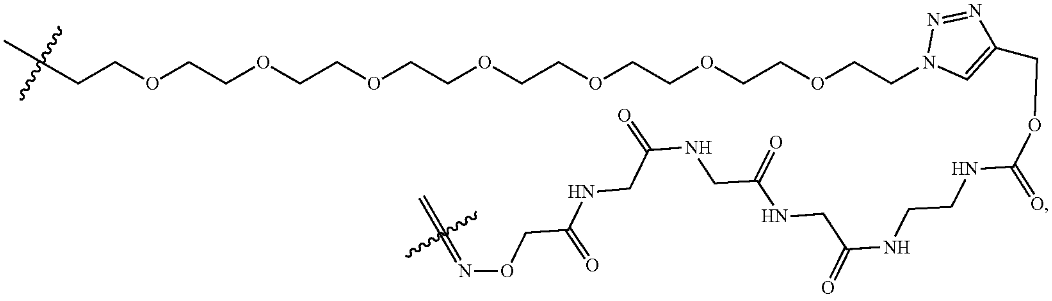
,
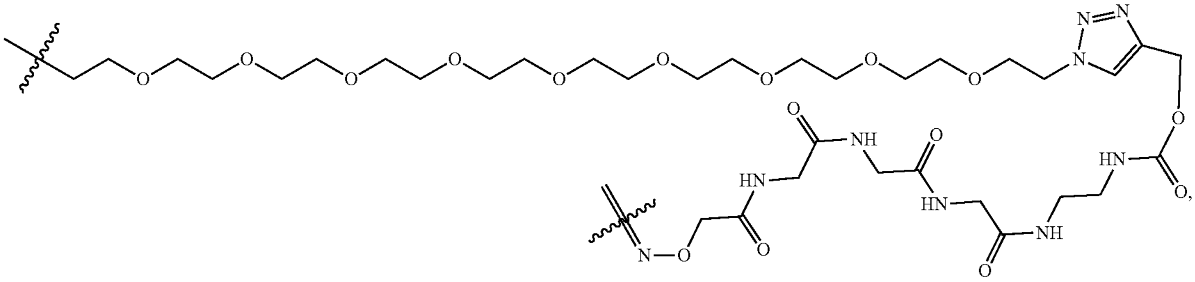
,
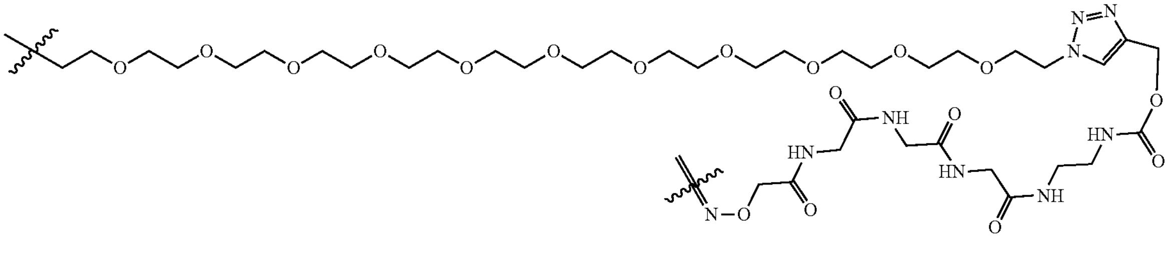
or
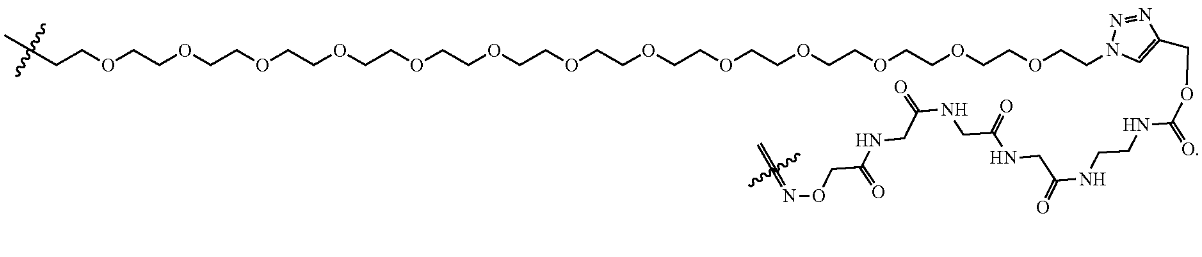
.

In preferred embodiments of any of the aforementioned immunoconjugates of Formula (B), Formula (II) and Formula (IIa):
$L_{20}$ is
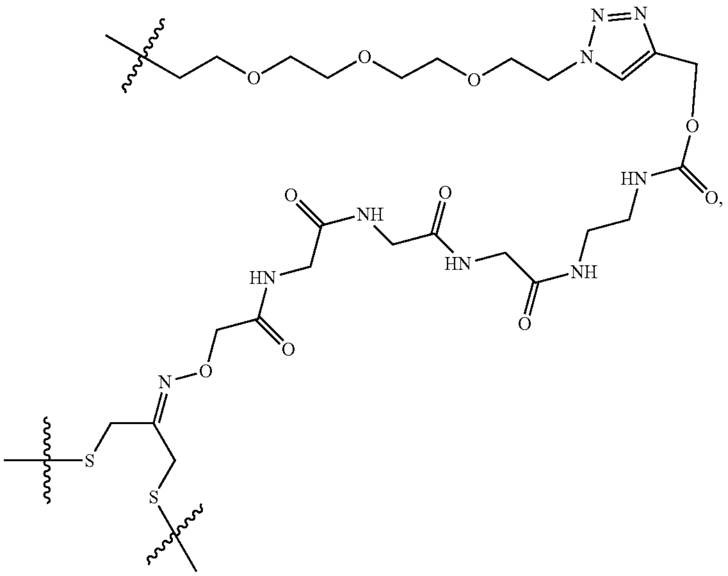
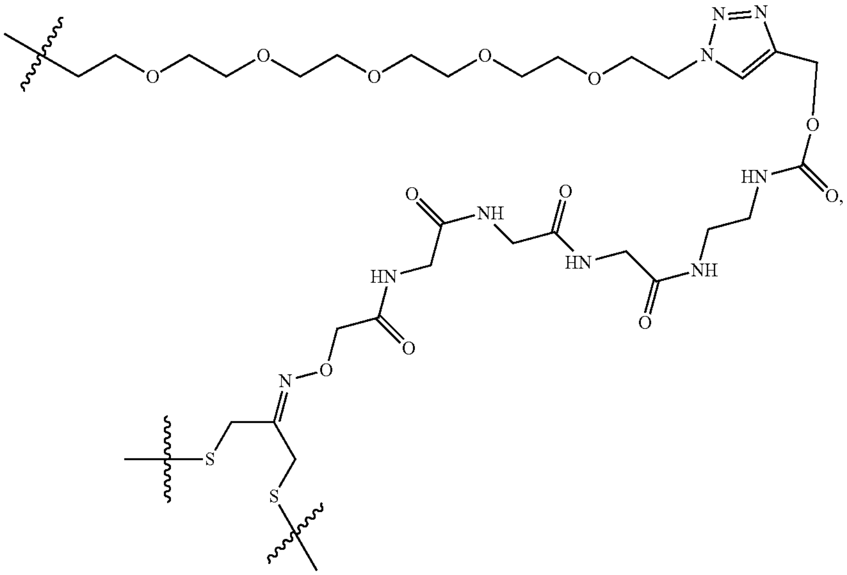

-continued
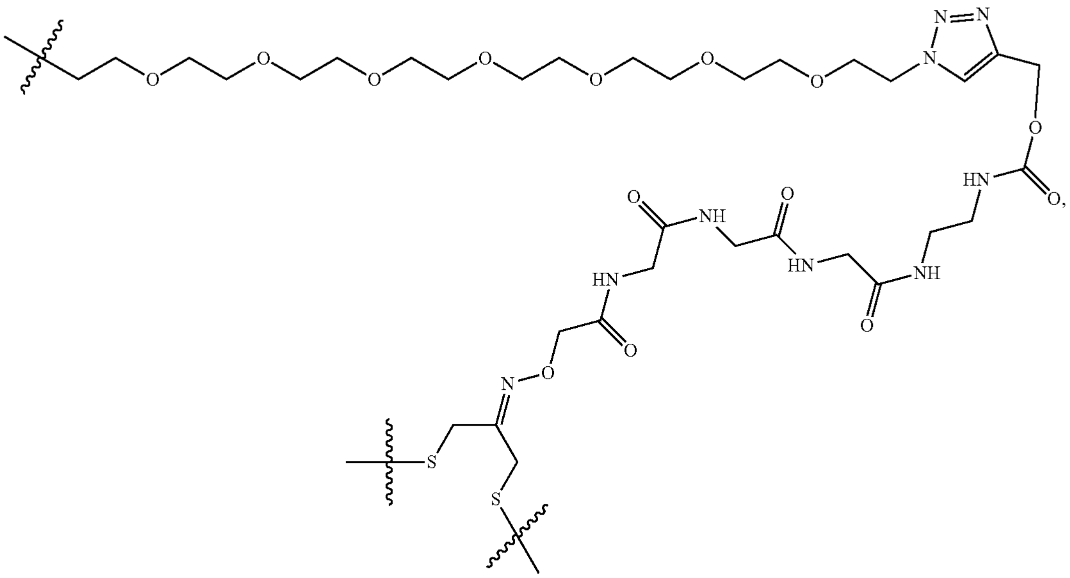
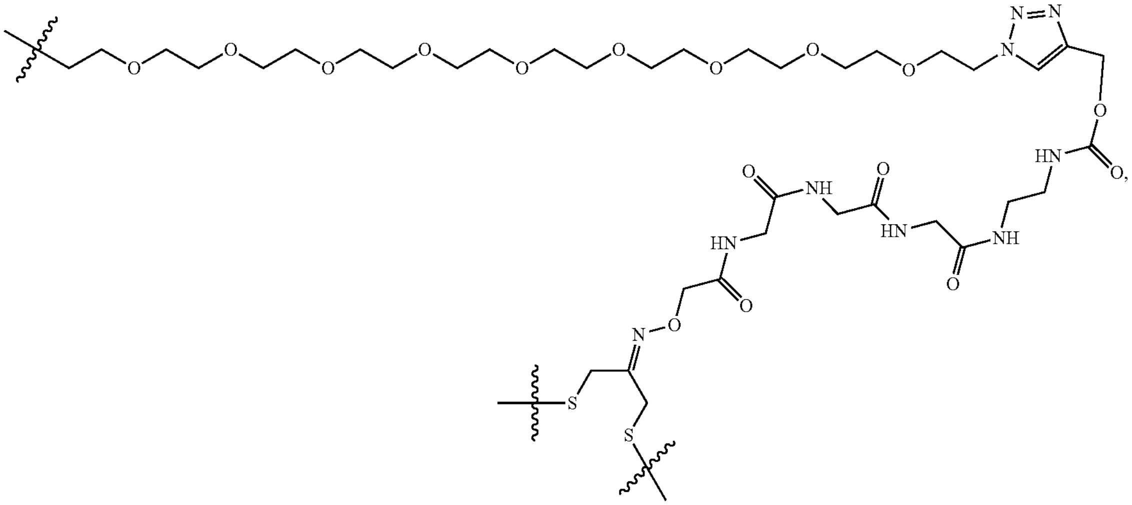
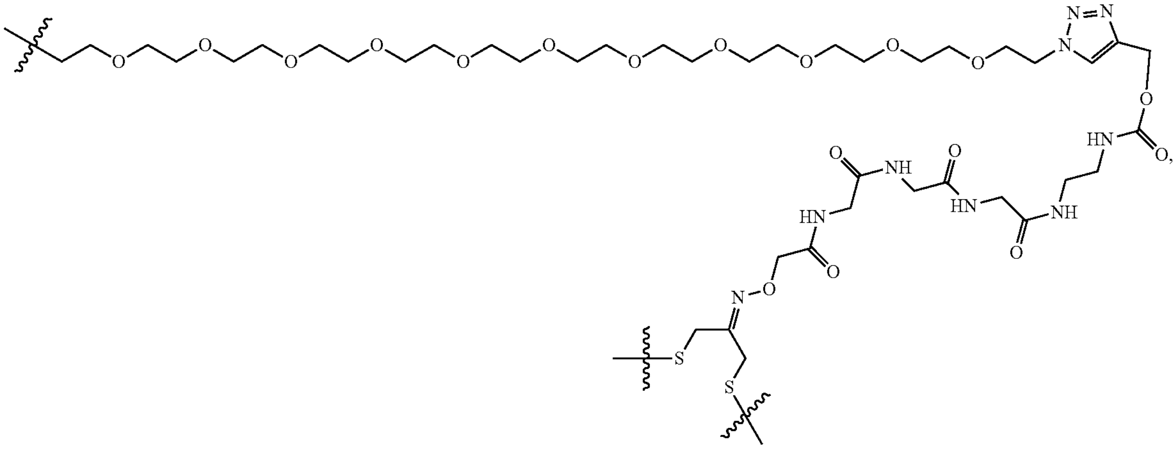
or

-continued

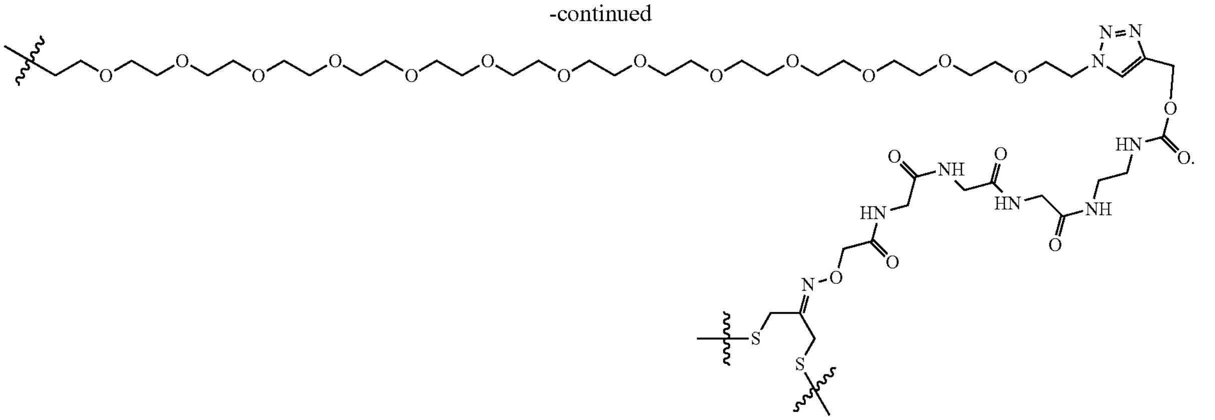

In certain embodiments of any of the aforementioned immunoconjugates of Formula (B), Formula (II) and Formula (IIa), $R^1$ is —$CH_3$, while in certain other embodiments of any of the aforementioned immunoconjugates of Formula (B), Formula (II) and Formula (IIa) $R^1$ is H. In other embodiments of any of the aforementioned immunoconjugates of Formula (B), Formula (II) and Formula (IIa), $R^1$ is —$CD_3$.

In certain embodiments of any of the aforementioned immunoconjugates of Formula (B), Formula (II) and Formula (IIa) $R^3$ is —$NH_2$, while in certain other embodiments of any of the aforementioned immunoconjugates of Formula (B), Formula (II) and Formula (IIa) $R^3$ is —OH.

The invention provides methods for making such immunoconjugates (ADCs) using cytotoxic cyclic peptides of Formula (A), Formula (I) or Formula (Ia) as the payload (drug) to be delivered. In such cytotoxic cyclic peptides the 7' position of the indole ring has been modified with a —$CH_2SH$ moiety which is further modified with linker component, $L_1$, and a reactive functional group, $R_4$, which facilitates connecting the cytotoxic cyclic peptide to the antibody or antigen binding fragment.

In another aspect, the invention provides pharmaceutical compositions comprising an immunoconjugate of Formula (B), Formula (II) or Formula (IIa), admixed with at least one pharmaceutically acceptable carrier or excipient, optionally admixed with two or more pharmaceutically acceptable carriers or excipients, and methods to use these compositions to treat cell proliferation disorders.

In another aspect, the invention provides a pharmaceutical composition comprising an immunoconjugate of Formula (B), Formula (II) or Formula (IIa) and one or more pharmaceutically acceptable carriers.

In another aspect, the invention provides a combination comprising a therapeutically effective amount of an immunoconjugate of Formula (B), Formula (II) or Formula (IIa) and one or more therapeutically active co-agents.

In another aspect, the invention provides a method to treat a condition characterized by excessive or undesired cell proliferation, which comprises administering to a subject in need thereof a therapeutically effective amount of an immunoconjugate of Formula (B), Formula (II) or Formula (IIa). The subject for treatment can be a mammal, and is preferably a human. Conditions treatable by the immunoconjugates and methods described herein include various forms of cancer, such as gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

In another aspect, the invention provides the use of an immunoconjugate of Formula (B), Formula (II) or Formula (IIa) in the manufacture of a medicament for the treatment of cancer, such as gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

In another aspect, the invention provides the use of an immunoconjugate of Formula (B), Formula (II) or Formula (IIa) as a medicament.

In another aspect, the invention provides a use of an immunoconjugate of Formula (B), Formula (II) or Formula (IIa) to treat cancer.

The invention includes all stereoisomers (including diastereoisomers and enantiomers), tautomers, and isotopically enriched versions thereof (including deuterium substitutions) of the compounds of Formula (A), Formula (I) and Formula (Ia) and immunoconjugates of Formula (B), Formula (II) and Formula (IIa). The invention also includes pharmaceutically acceptable salts of the compounds of Formula (A), Formula (I) and Formula (Ia) and immunoconjugates of Formula (B), Formula (II) and Formula (IIa).

X: Vehicle; Open Triangle: 2.5 mg/kg anti-Her2-HC-E152C-S375C-1; Open Circles: 2.5 mg/kg anti-Her2-HC-E152C-S375C-2 and Open Squares: 2.5 mg/kg anti-Her2-HC-E152C-S375C-6.

Figure 2:
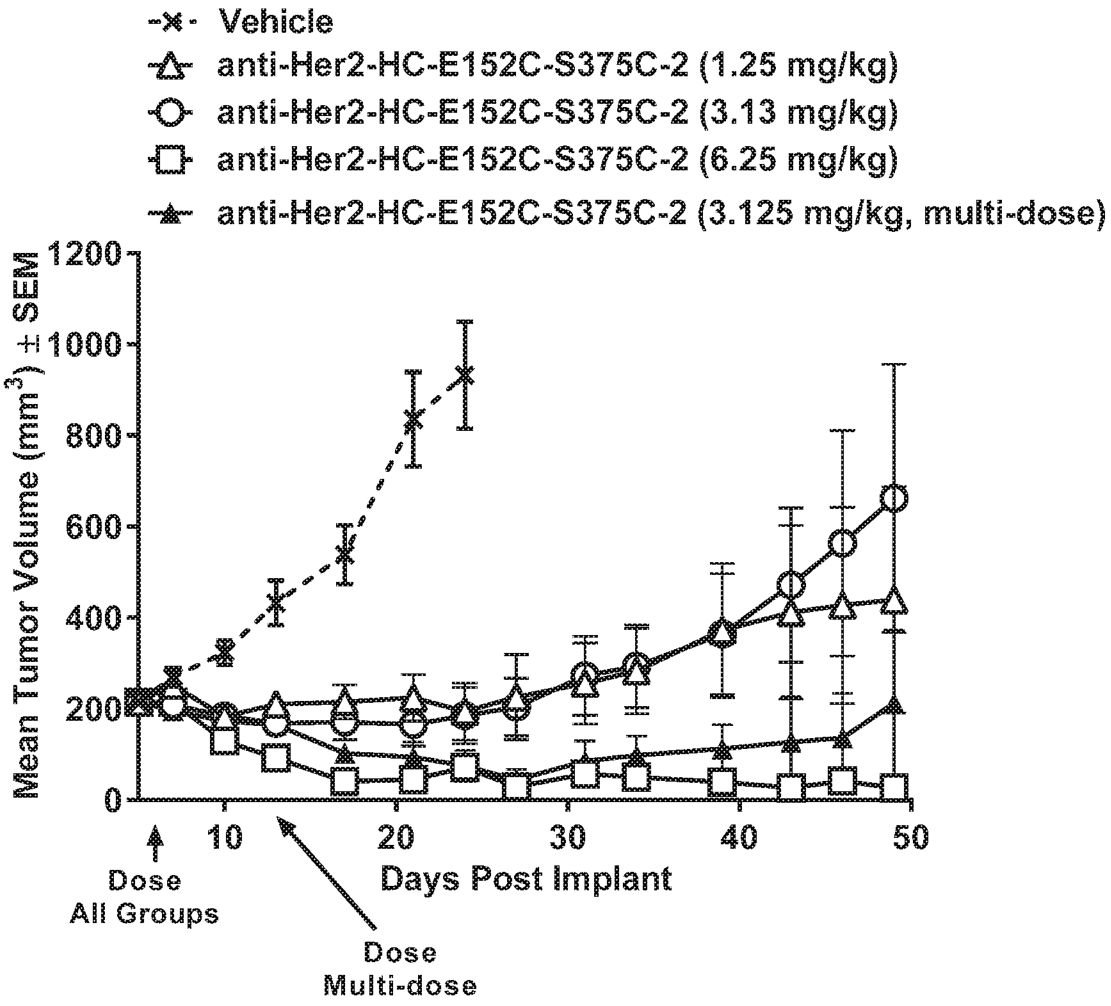

FIG. 2. Efficacy of anti-Her2-HC-E152C-S375C-2 in the NCI-N87 gastric model.

X: Vehicle; Open Triangle: 1.25 mg/kg anti-Her2-HC-E152C-S375C-2; Open Circles: 3.13 mg/kg anti-Her2-HC-E152C-S375C-2, Open Squares: 6.25 mg/kg anti-Her2-HC-E152C-S375C-2 and Filled Triangle: multi-dose 3.13 mg/kg anti-Her2-HC-E152C-S375C-2.

DETAILED DESCRIPTION

The following definitions apply unless otherwise expressly provided.

The term "amino acid" refers to canonical, synthetic, and unnatural amino acids, as well as amino acid analogs and amino acid mimetics that function in a manner similar to the canonical amino acids. Canonical amino acids are proteinogenous amino acids encoded by the genetic code and include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, as well as selenocysteine, pyrrolysine and pyrroline-carboxy-lysine. Amino acid analogs refer to compounds that have the same basic chemical structure as a canonical amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a canonical amino acid.

The term "antigen binding moiety" as used herein refers to a moiety capable of binding specifically to an antigen, and includes but is not limited to antibodies and antibody fragments.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hyper variability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and $C_L$ domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the invention may include amino acid residues not encoded by human sequences (e.g., mutations introduced by random or site-specific mutagenesis in vitro or by somatic mutation in vivo, or a substitution to promote stability or manufacturing).

The term "humanized" antibody, as used herein, refers to an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

The term "specifically binds" or "selectively binds," when used in the context of describing the interaction between an antigen (e.g., a protein or a glycan) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agents with a particular binding specificity bind to a particular antigen at least ten (10) times the background and do not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The terms "polypeptide" and "protein" are used interchangeably herein to refer to a polymer of amino acid residues. The terms apply to canonical amino acid polymers as well as to non-canonical amino acid polymers. Unless otherwise indicated, a particular polypeptide sequence also implicitly encompasses modified variants thereof.

The term "immunoconjugate" or "antibody-drug-conjugate" as used herein refers to the linkage of an antigen binding moiety such as an antibody or an antigen binding fragment thereof with an cytotoxic peptide of Formula (I). The linkage can be covalent bonds, or non-covalent interactions, and can include chelation. Various linkers, known in the art, can be employed in order to form the immunoconjugate.

The term "cytotoxin", or "cytotoxic agent" as used herein, refer to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein, refers to a chemical moiety that is or can be conjugated to an antibody or antigen binding fragment to form an immunoconjugate, and can include any moiety that is useful to attach to the antibody or antigen binding fragment. For example, "drug moiety" or "payload" includes, but is not limited to, the cytotoxic cyclic peptides described herein. The immunoconjugates of the invention comprise one or more cytotoxic cyclic peptides described herein as a payload, but may also include one or more other payloads. Other payloads include, for example, a drug moiety or payload can be an anti-cancer agent, an anti-inflammatory agent, an antifungal agent, an antibacterial agent, an anti-parasitic agent, an anti-viral agent, or an anesthetic agent. In certain embodiments a drug moiety is selected from an Eg5 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Suitable examples include calicheamycins such as gamma-calicheamycin; and maytansinoids such as DM1, DM3 and DM4. Methods for attaching each of these to a linker compatible with the antibodies and method of the invention are known in the art. See, e.g., Singh et al., (2009) Therapeutic Antibodies: Methods and Protocols, vol. 525, 445-457.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is to show a decline in growth rate of abnormal cells that arises during therapy or tumor size stability or reduction. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to at least partially alleviate, inhibit, prevent and/or ameliorate a condition, or a disorder or a disease.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

In certain embodiments, the modified immunoconjugates of the invention are described according to a "cytotoxic cyclic peptide-to-antibody" ratio of, e.g., 1, 2, 3, 4, 5, 6, 7, or 8, or 12 or 16; this ratio corresponds to "y" in Formula (II). While this ratio has an integer value for a specific conjugate molecule, it is understood that an average value is typically used to describe a sample containing many molecules, due to some degree of inhomogeneity within a sample of an immunoconjugate. The average loading for a sample of an immunoconjugate is referred to herein as the "drug to antibody ratio," or DAR. In some embodiments, the DAR is between about 1 and about 16, and typically is about 1, 2, 3, 4, 5, 6, 7, or 8. In some embodiments, at least 50% of a sample by weight is compound having the average DAR plus or minus 2, and preferably at least 50% of the sample is a product that contains the average DAR plus or minus 1.5. Preferred embodiments include immunoconjugates wherein the DAR is about 2 to about 8, e.g., about 2, about 3, about 4, about 5, about 6, about 7, or about 8. In these embodiments, a DAR of "about q" means the measured value for DAR is within ±20% of q, or preferably within ±10% of q.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms, unless otherwise stated, e.g., where a specific isomer is identified. Optically active (R)- and (S)-isomers may be prepared using chiral synthons or chiral reagents, or resolved using conventional techniques. If the compound contains a double bond, the substituent may be E or Z configuration. If the compound contains a di-substituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. "Substantially pure" or "substantially free of other isomers" as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The term "thiol-maleimide" as used herein refers to a group formed by reaction of a thiol with maleimide, having this general formula

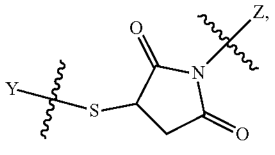

where Y and Z are groups to be connected via the thiol-maleimide linkage and can comprise linker components, antibodies or payloads.

"Cleavable" as used herein refers to a linker or linker component that connects two moieties by covalent connections, but breaks down to sever the covalent connection between the moieties under physiologically relevant conditions, typically a cleavable linker is severed in vivo more rapidly in an intracellular environment than when outside a cell, causing release of the payload to preferentially occur inside a targeted cell. Cleavage may be enzymatic or non-enzymatic, but generally releases a payload from an antibody without degrading the antibody. Cleavage may leave some portion of a linker or linker component attached to the payload, or it may release the payload without any residual part or component of the linker.

"Non-cleavable" as used herein refers to a linker or linker component that is not especially susceptible to breaking down under physiological conditions, e.g., it is at least as stable as the antibody or antigen binding fragment portion of the immunoconjugate. Such linkers are sometimes referred to as "stable", meaning they are sufficiently resistant to degradation to keep the payload connected to the antigen binding moiety Ab until Ab is itself at least partially degraded, i.e., the degradation of Ab precedes cleavage of the linker in vivo. Degradation of the antibody portion of an ADC having a stable or non-cleavable linker may leave some or all of the linker, and one or more amino acid groups from an antibody, attached to the payload or drug moiety that is delivered in vivo.

The terms "$C_1$-$C_4$alkyl" and "$C_1$-$C_6$alkyl", as used herein, refer to a fully saturated branched or straight chain hydrocarbon containing 1-4 carbon atoms or 1-6 carbon atoms, respectively. Non-limiting examples of "$C_1$-$C_4$alkyl" groups include methyl, ethyl, n-propyl, isopropyl, n-butyl, isobutyl, sec-butyl and tert-butyl. Non-limiting examples of "$C_1$-$C_6$alkyl" groups include methyl, ethyl, n-propyl, isopropyl, n-butyl, isobutyl, sec-butyl, tert-butyl, n-pentyl, isopentyl and hexyl.

The term "$C_1$-$C_4$alkoxy", as used herein, refer to the group —O—$C_1$-$C_4$alkyl, wherein the groups "$C_1$-$C_4$alkyl" is as defined herein. Non-limiting examples of "$C_1$-$C_4$alkoxy" groups include methoxy, ethoxy, n-propoxy, isopropoxy, n-butoxy, isobutoxy, sec-butoxy and tert-butoxy.

The immunoconjugate naming convention used herein is antibody-Compound Number, where Compound Number refers to the compound of Formula (A), Formula (I) or Formula Ia) used for conjugation to the particular antibody. By way of example, anti-Her2-HC-E152C-S375C-1 describes antibody anti-Her2-HC-E152C-S375C conjugated to Compound (1).

Cytotoxic Cyclic Peptides

The cytotoxic cyclic peptides of the invention, or stereoisomer thereof, and pharmaceutically acceptable salts thereof, are compounds having the structure of Formula (A):

Formula (A)

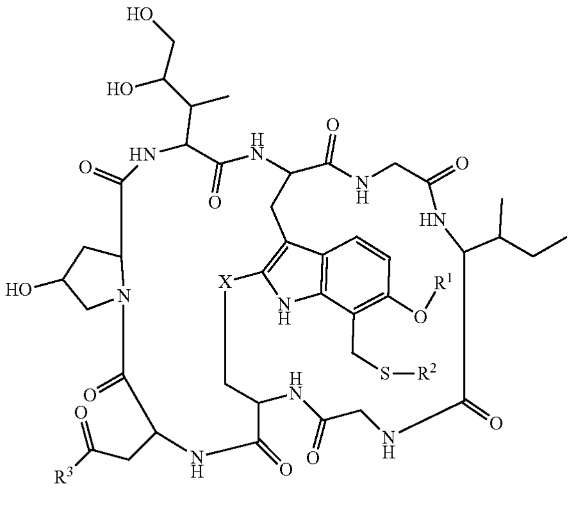

wherein:
X is S(=O), S(=O)$_2$ or S;
$R^1$ is H, —$CH_3$ or —$CD_3$; $R^2$ is -$L_1R^4$, -$L_2R^{14}$, -$L_2R^{24}$ or -$L_3R^{34}$; $R^3$ is —$NH_2$ or —OH;
$L_1$ is —$((CH_2)_mO)_n(CH_2)_mX_3L_4$- or —$((CH_2)_mO)_n(CH_2)_mX_4L_4$-;
$L_2$ is —$((CH_2)_mO)_n(CH_2)_m$—;
$L_3$ is —$((CH_2)_mO)_n(CH_2)_mX_3L_4$-, —$((CH_2)_mO)_n(CH_2)_mX_4L_4$- or —$((CH_2)_mO)_n(CH_2)_m$—;
$L_4$ is —$(CH_2)_m$— or —$(CH_2)_mNHC(=O)X_1X_2C(=O)(CH_2)_m$—;
$X_1$ is
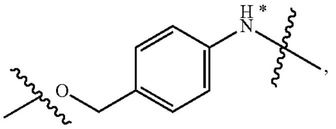
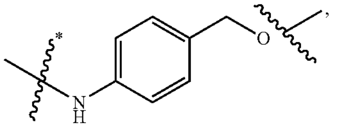
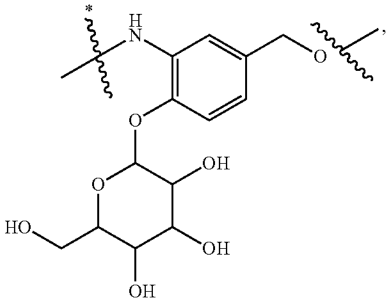
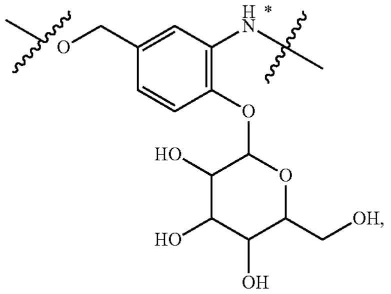
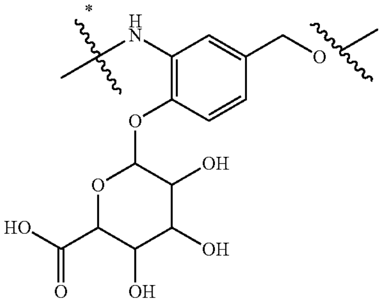
or
-continued
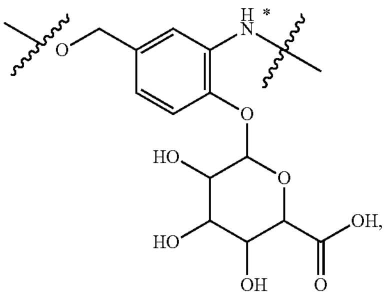
where the * indicates attachment point to $X_2$;
$X_2$ is
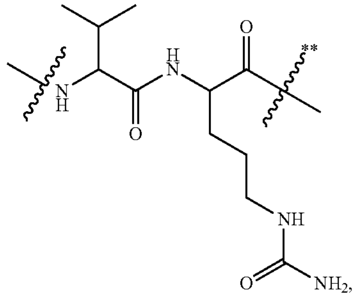
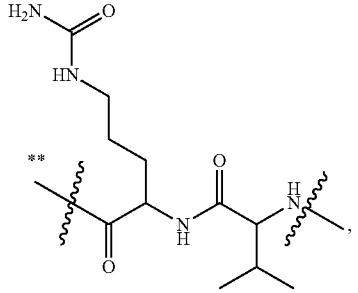
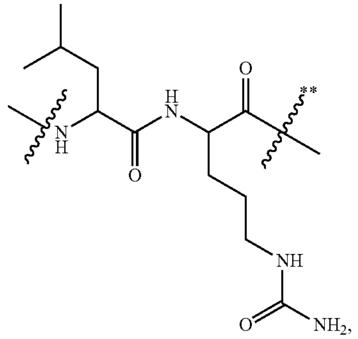
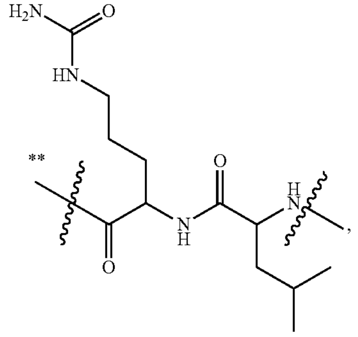

-continued
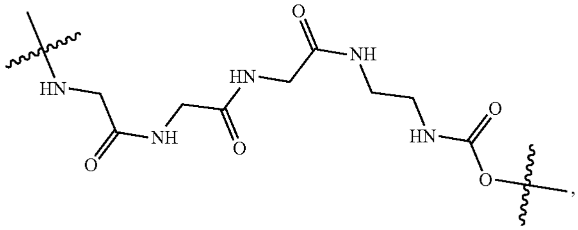
,
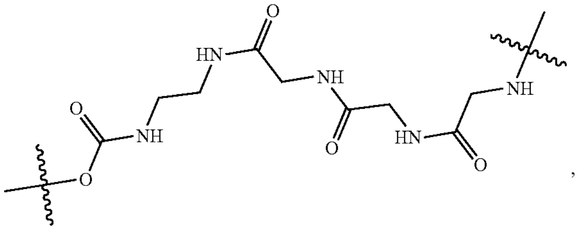
,
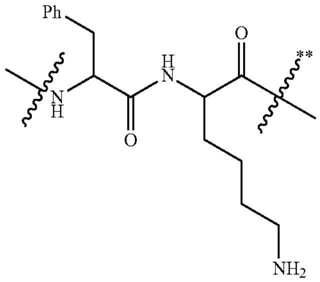
or
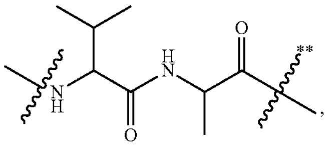
,
where the ** indicates attachment point to $X_1$;
$X_3$ is
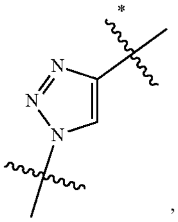
,
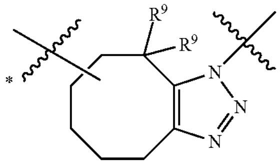
,
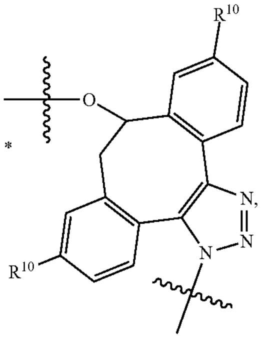
-continued
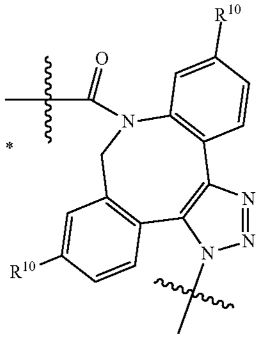
or
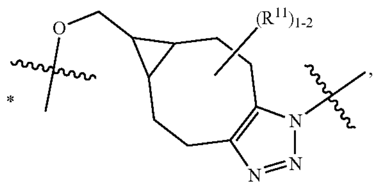
,
where the * indicates attachment point to $L_4$;
$X_4$ is
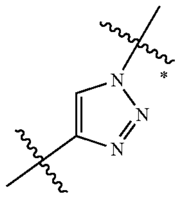
,
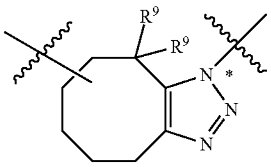
,
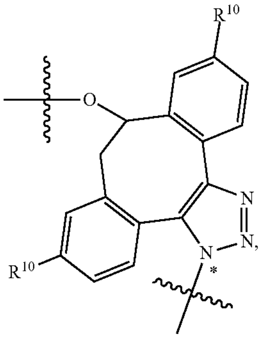
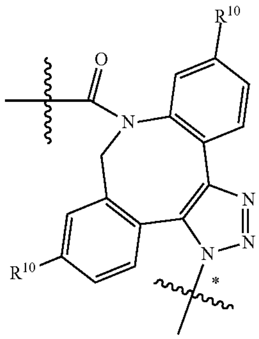
or -continued
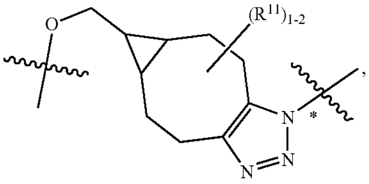
where the * indicates attachment point to $L_4$;
$R^4$ is
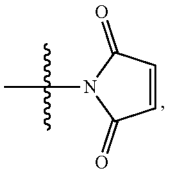 [SMILES: *N1C(=O)C=CC1=O]
—$N_3$, —$ONH_2$, —$NR_5C(=O)CH=CH_2$, SH, —$S(=O)_2(CH=CH_2)$, —$NR^5S(=O)_2(CH=CH_2)$, —$NR^5C(=O)CH_2Br$, —$NR^5C(=O)CH_2I$, —$NHC(=O)CH_2Br$, —$NHC(=O)CH_2I$, —$C(O)NHNH_2$,
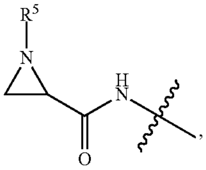
—$CO_2H$, —$NH_2$,
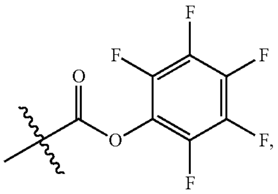
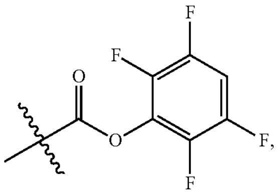
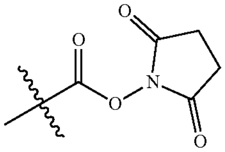
or
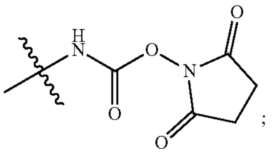
;
$R^{14}$ is
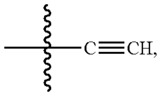
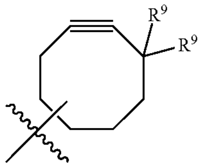
,
-continued
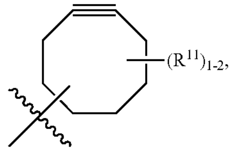
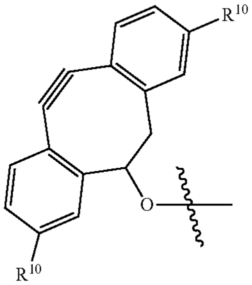
,
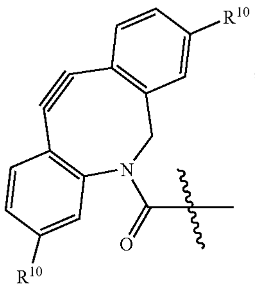
,
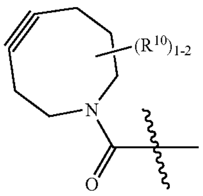
or
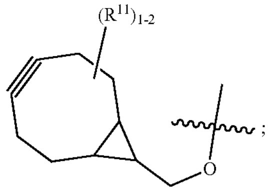
$R^{24}$ is, —$N_3$, —$ONH_2$, —$NR_5C(=O)CH=CH_2$, —$C(O)NHNH_2$, —$CO_2H$, —$NH_2$,
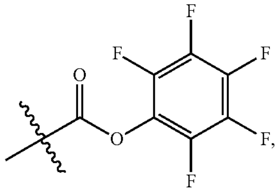
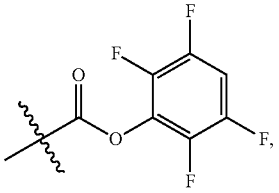
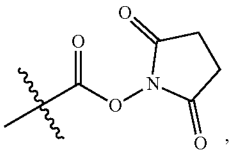
,
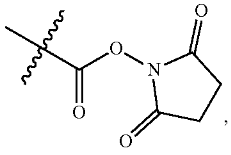
, or
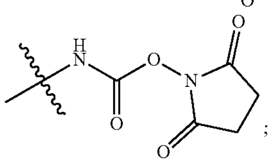
;
$R^{34}$ is
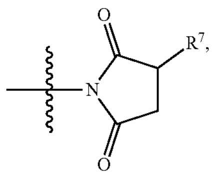
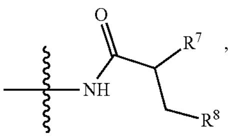
, -continued

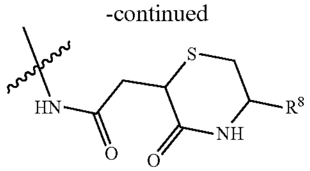

or $—NR^5C(=O)CH_2R^7$;

each $R^5$ is independently selected from H and $C_1$-$C_6$alkyl;

$R^7$ is $—S(CH_2)_nCHR^8NH_2$;

$R^8$ is $—C(=O)OR^5$;

each $R^9$ is independently selected from H, $C_1$-$C_6$alkyl, F, Cl, and —OH;

each $R^{10}$ is independently selected from H, $C_1$-$C_6$alkyl, F, Cl, $—NH_2$, $—OCH_3$, $—OCH_2CH_3$, $—N(CH_3)_2$, —CN, $—NO_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

Certain aspects and examples of the compounds of the invention are provided in the following listing of enumerated embodiments of the invention. It will be recognized that features specified in each embodiment may be combined with other specified features to provide further embodiments of the present invention.

Embodiment 1

A compound of Formula (I), or a pharmaceutically acceptable salt thereof,

Formula (I)

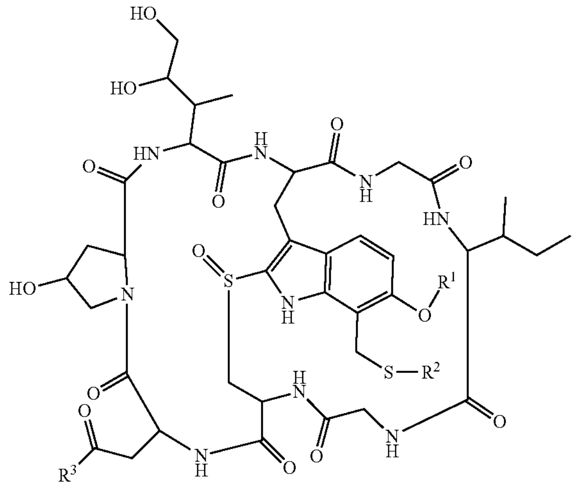

wherein:

$R^1$ is H, $—CH_3$ or $—CD_3$; $R^2$ is $-L_1R^4$, $-L_2R^{14}$, $-L_2R^{24}$ or $-L_3R^{34}$; $R^3$ is $—NH_2$ or —OH;

$L_1$ is $—((CH_2)_mO)_n(CH_2)_mX_3L_4$- or $—((CH_2)_mO)_n(CH_2)_mX_4L_4$-;

$L_2$ is $—((CH_2)_mO)_n(CH_2)_m—$;

$L_3$ is $—((CH_2)_mO)_n(CH_2)_mX_3L_4$-, $—((CH_2)_mO)_n(CH_2)_mX_4L_4$- or $—((CH_2)_mO)_n(CH_2)_m—$;

$L_4$ is $—((CH_2)_m—$ or $—((CH_2)_mNHC(=O)X_1X_2C(=O)(CH_2)_m—$;

$X_1$ is

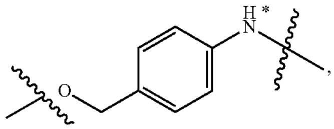

,

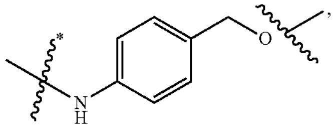

,

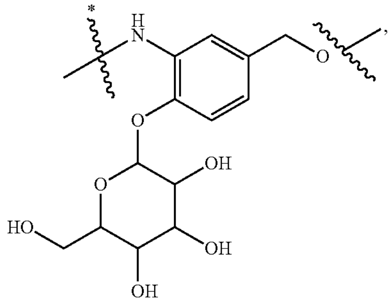

,

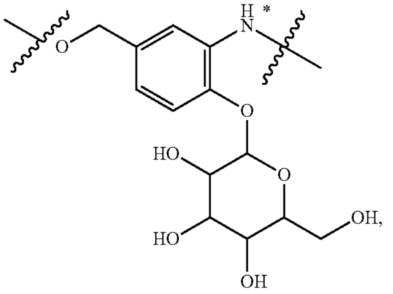

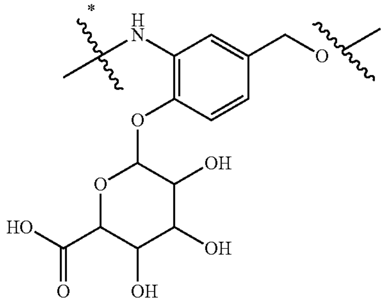

or

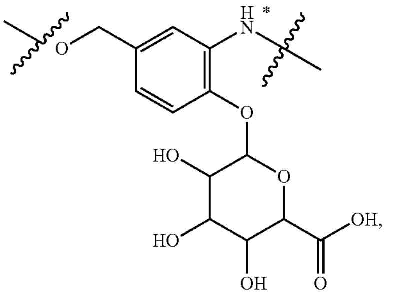

where the * indicates attachment point to $X_2$;

$X_2$ is
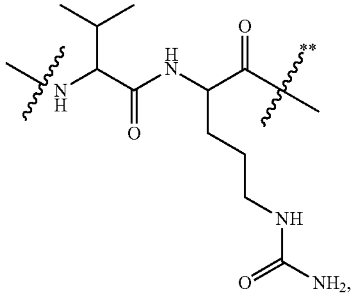
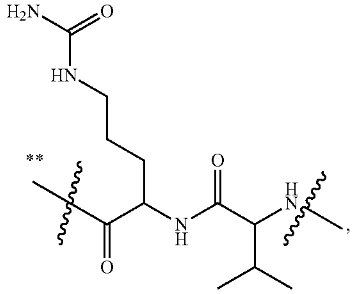
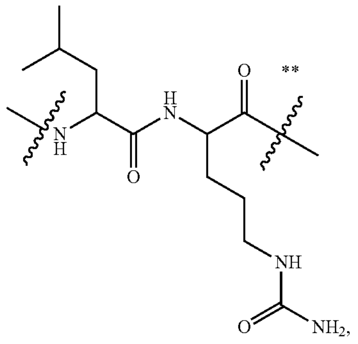
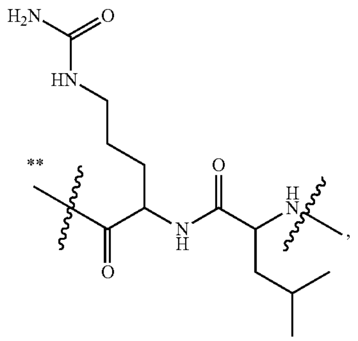
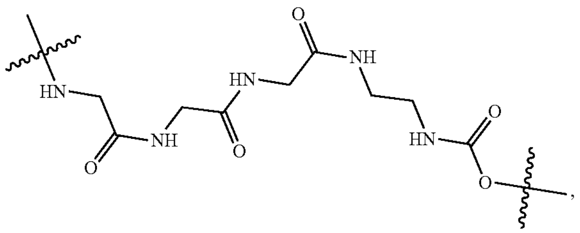
-continued
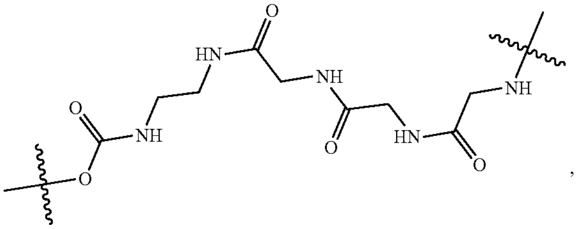
,
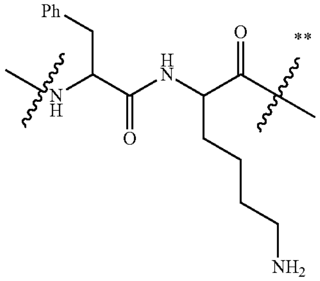
or
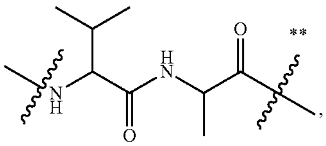
where the ** indicates attachment point to $X_1$;
$X_3$ is
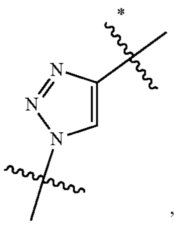
,
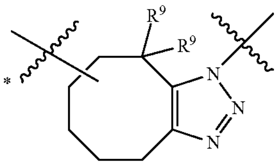
,
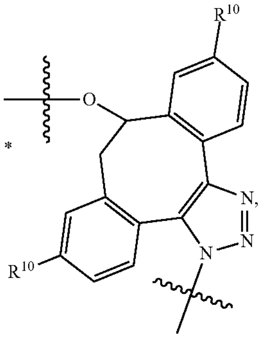
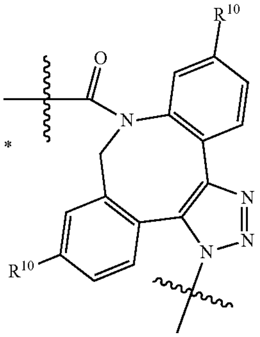
or -continued
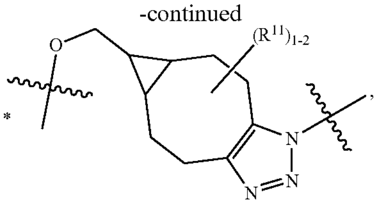
where the * indicates attachment point to $L_4$;
$X_4$ is
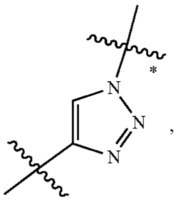
,
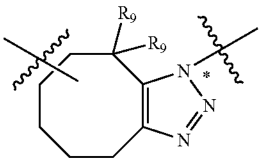
,
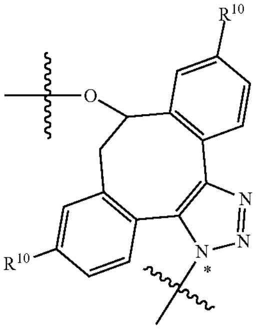
,
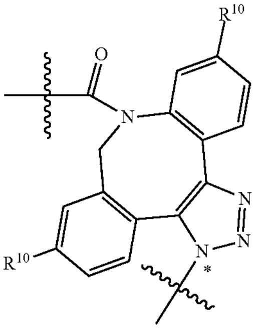
or
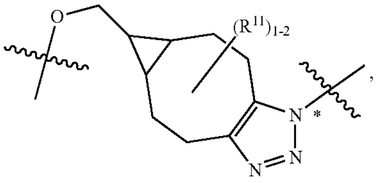
where the * indicates attachment point to $L_4$;
$R^4$ is
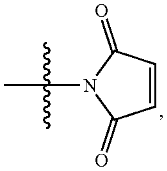 [SMILES: *N1C(=O)C=CC1=O]
—$N_3$, —$ONH_2$, —$NR_5C(=O)CH=CH_2$, SH, —$S(=O)_2(CH=CH_2)$, —$NR^5S(=O)_2(CH=CH_2)$, —$NR^5C(=O)CH_2Br$, —$NR^5C(=O)CH_2I$, —$NHC(=O)CH_2Br$, —$NHC(=O)CH_2I$, —C(O)$NHNH_2$,
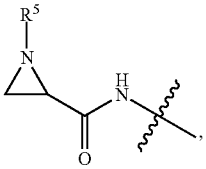
—$CO_2H$, —$NH_2$,
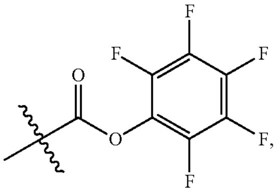
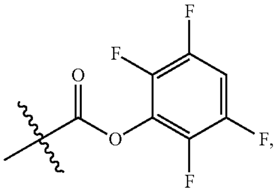
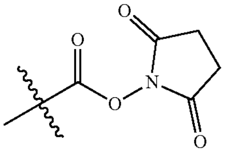
or
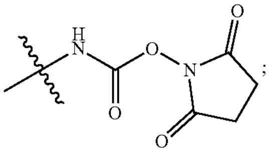
;
$R^{14}$ is
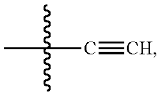
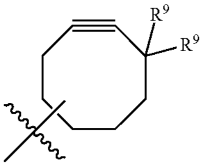
,
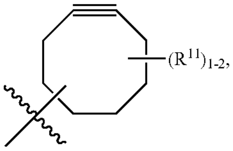
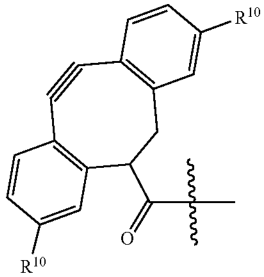
,
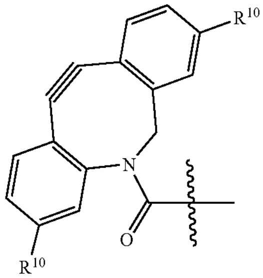
,
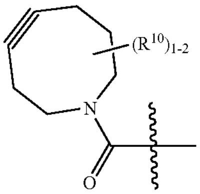
or
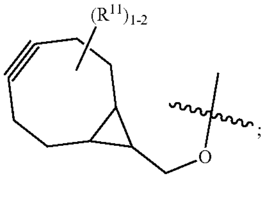
$R^{24}$ is, —$N_3$, —$ONH_2$, —$NR_5C(=O)CH=CH_2$, —C(O)$NHNH_2$, —$CO_2H$, —$NH_2$,

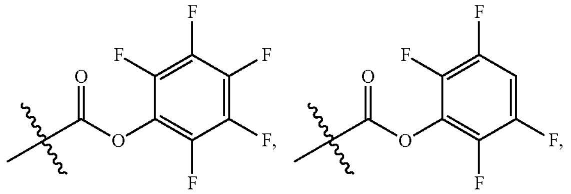

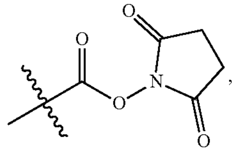

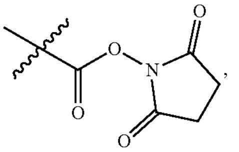

or

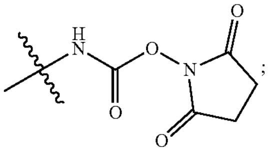

$R^{34}$ is

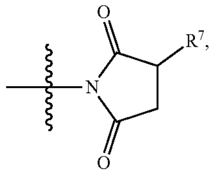

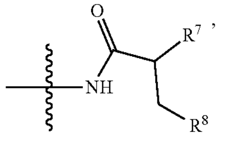

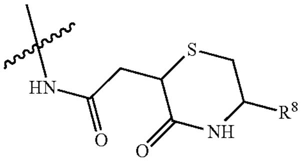

or $—NR^5C(═O)CH_2R^7$;

each $R^5$ is independently selected from H and $C_1$-$C_6$alkyl;

$R^7$ is $—S(CH_2)_nCHR^8NH_2$;

$R^8$ is $—C(═O)OR^5$;

each $R^9$ is independently selected from H, $C_1$-$C_6$alkyl, F, Cl, and —OH;

each $R^{10}$ is independently selected from H, $C_1$-$C_6$alkyl, F, Cl, $—NH_2$, $—OCH_3$, $—OCH_2CH_3$, $—N(CH_3)_2$, —CN, $—NO_2$ and —OH;

each $R^{11}$ is independently selected from H, $C_{1-6}$alkyl, fluoro, benzyloxy substituted with —C(═O)OH, benzyl substituted with —C(═O)OH, $C_{1-4}$alkoxy substituted with —C(═O)OH and $C_{1-4}$alkyl substituted with —C(═O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

Embodiment 2

A compound of Formula (Ia), or a pharmaceutically acceptable salt thereof,

Formula (Ia)

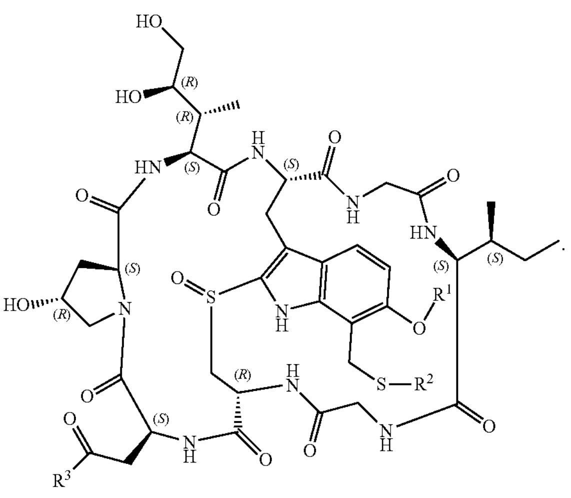

wherein:

$R^1$ is H, $—CH_3$ or $—CD_3$; $R^2$ is $-L_1R^4$, $-L_2R^{14}$, $-L_2R^{24}$ or $-L_3R^{34}$; $R^3$ is $—NH_2$ or —OH;

$L_1$ is $—((CH_2)_mO)_n(CH_2)_mX_3L_4$- or $—((CH_2)_mO)_n(CH_2)_mX_4L_4$-;

$L_2$ is $—((CH_2)_mO)_n(CH_2)_m—$;

$L_3$ is $—((CH_2)_mO)_n(CH_2)_mX_3L_4$-, $—((CH_2)_mO)_n(CH_2)_mX_4L_4$- or $—((CH_2)_mO)_n(CH_2)_m—$;

$L_4$ is $—(CH_2)_m—$ or $—((CH_2)_mNHC(═O)X_1X_2C(═O)(CH_2)_m—$;

$X_1$ is

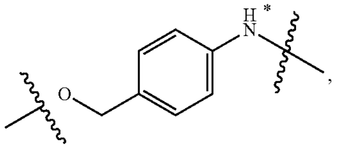

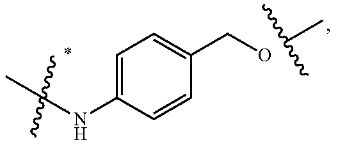

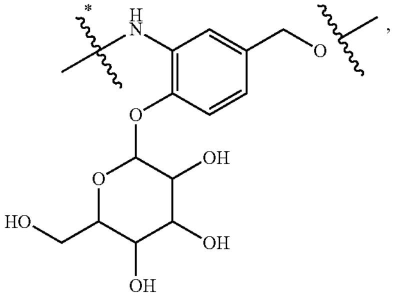

-continued
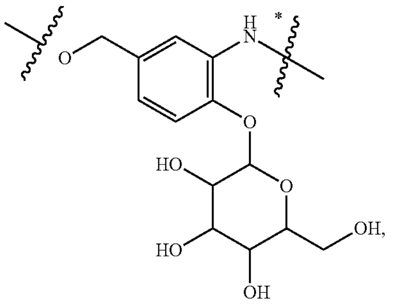
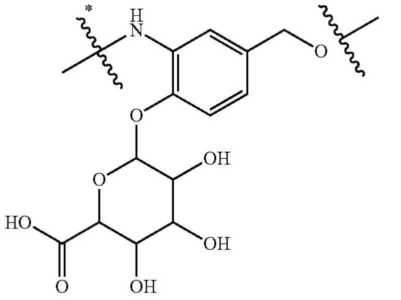
or
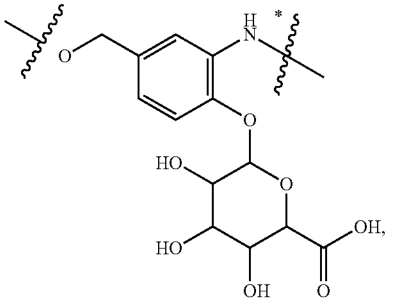
where the * indicates attachment point to $X_2$;
$X_2$ is
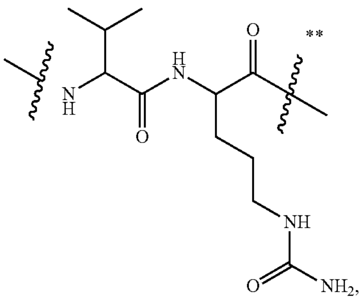
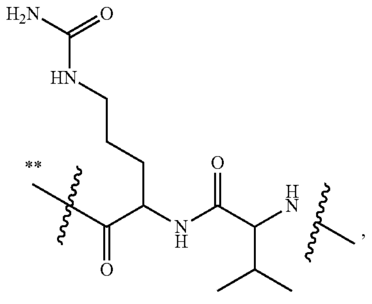
-continued
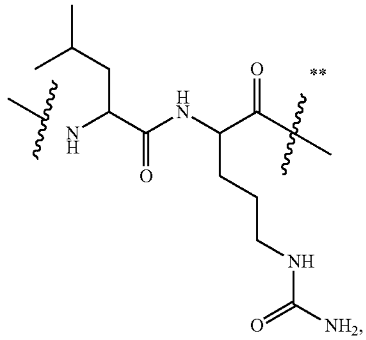
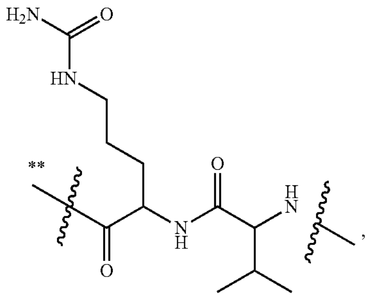
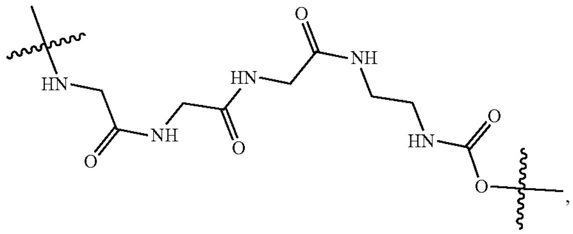
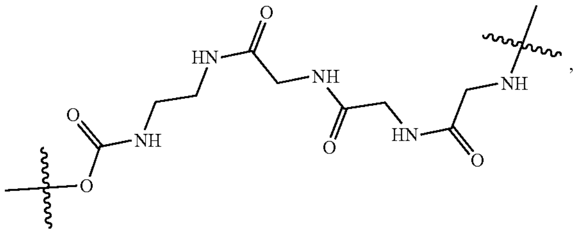
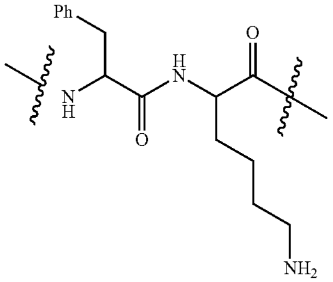
or
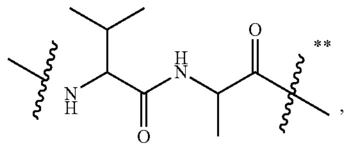
where the ** indicates attachment point to $X_1$;

$X_3$ is
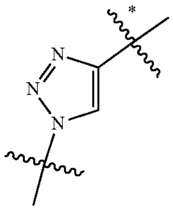
,
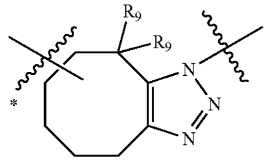
,
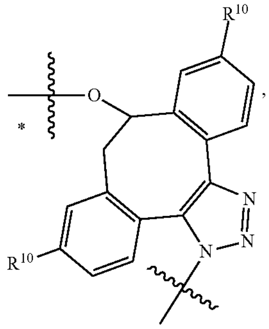
,
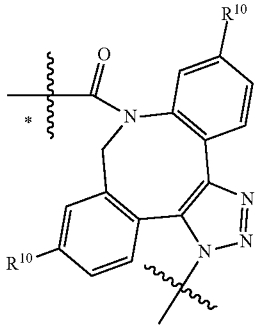
or
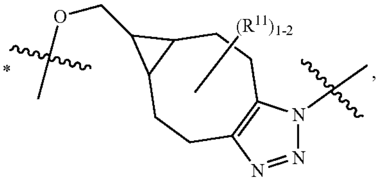
,
where the * indicates attachment point to $L_4$;
$X_4$ is
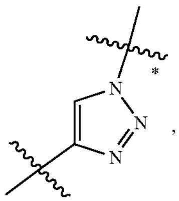
,
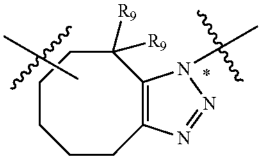
,
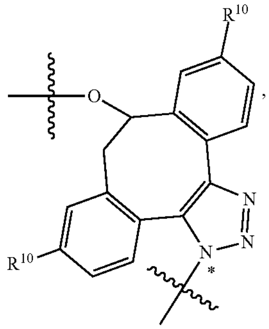
,
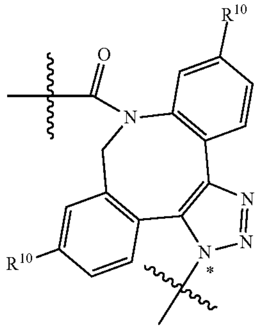
or
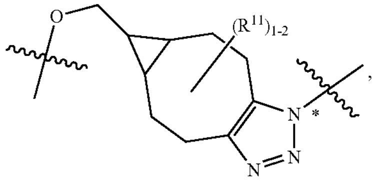
,
where the * indicated attachment to $L_4$;
$R^4$ is
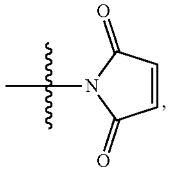 [SMILES: *N1C(=O)C=CC1=O]
,
$—N_3$, $—ONH_2$, $—NR_5C(=O)CH=CH_2$, SH, $—S(=O)_2(CH=CH_2)$, $—NR^5S(=O)_2(CH=CH_2)$, $—NR^5C(=O)CH_2Br$, $—NR^5C(=O)CH_2I$, $—NHC(=O)CH_2Br$, $—NHC(=O)CH_2I$, $—C(O)NHNH_2$,
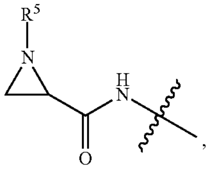
,
$—CO_2H$, $—NH_2$,
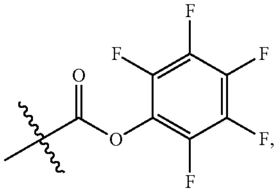
,
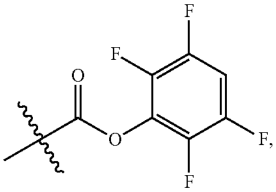
,
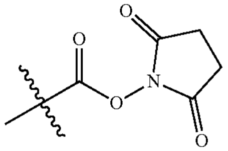
or
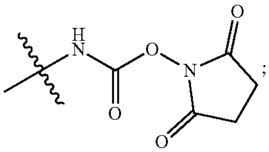
;
$R^{14}$ is
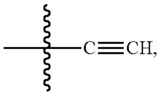
,
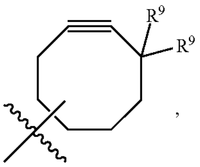
,
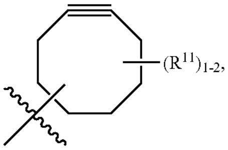
,
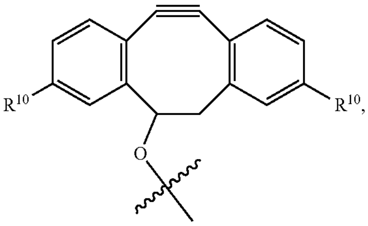
, -continued

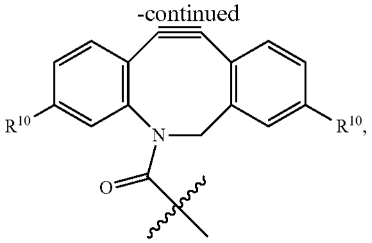

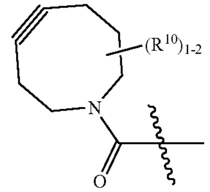

or

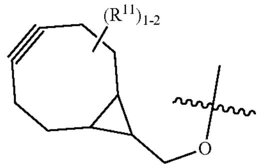

;

$R^{24}$ is, —$N_3$, —$ONH_2$, —$NR_5C(=O)CH=CH_2$, —C(O)$NHNH_2$, —$CO_2H$, —$NH_2$,

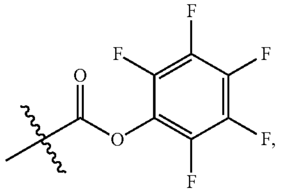

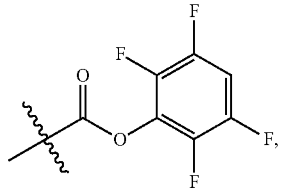

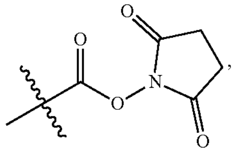

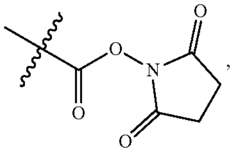

or

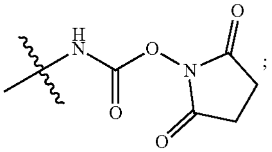

$R^{34}$ is

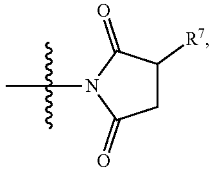

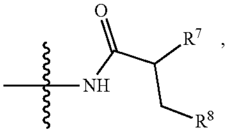

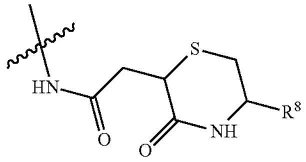

or —$NR^5C(=O)CH_2R^7$;

each $R^5$ is independently selected from H and $C_1$-$C_6$alkyl;

$R^7$ is —$S(CH_2)_nCHR^8NH_2$;

$R^8$ is —$C(=O)OR^5$;

each $R^9$ is independently selected from H, $C_1$-$C_6$alkyl, F, Cl, and —OH;

each $R^{10}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{11}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

Embodiment 3

The compounds of Formula (A), Formula (I) and Formula (Ia), or a pharmaceutically acceptable salt thereof, wherein $R^1$ is H, —$CH_3$ or —$CD_3$; $R^2$ is -$L_1R^4$, -$L_2R^{24}$ or -$L_3R^{34}$; $R^3$ is —$NH_2$ or —OH;

$L_1$ is —$((CH_2)_mO)_n(CH_2)_mX_3L_4$-;

$L_2$ is —$((CH_2)_mO)_n(CH_2)_m$—, $L_3$ is —$((CH_2)_mO)_n(CH_2)_mX_3L_4$- or —$((CH_2)_mO)_n(CH_2)_m$—;

$L_4$ is —$((CH_2)_m$— or —$((CH_2)_mNHC(=O)X_1X_2C(=O)(CH_2)_m$—;

$X_1$ is

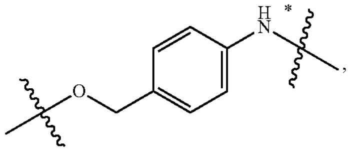 [SMILES: *Nc1ccc(CO*)cc1]

where the * indicates attachment point to $X_2$;

$X_2$ is

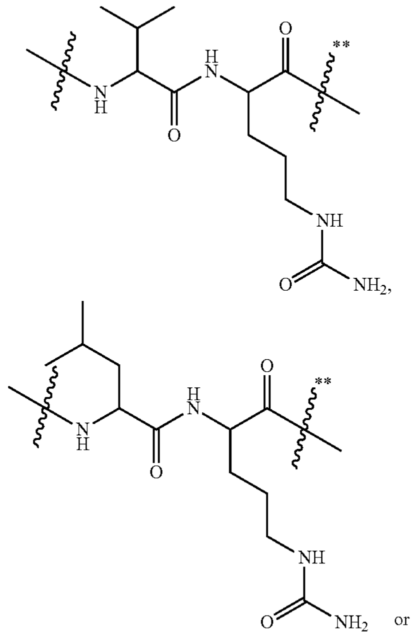

or

-continued

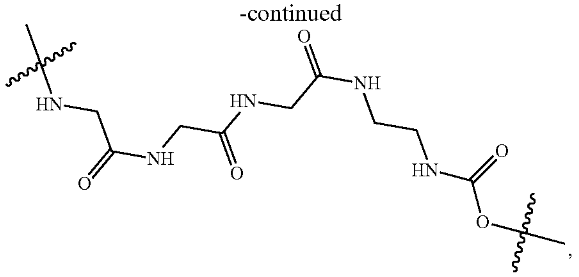

where the ** indicates attachment point to $X_1$;

$X_3$ is

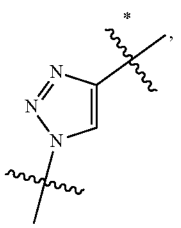 [SMILES: *c1cn(*)nn1]

where the * indicates attachment point to $L_4$;

$R^4$ is

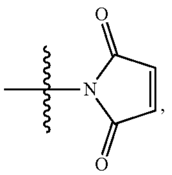

—$N_3$ or —$ONH_2$;

$R^{24}$ is —$N_3$ or —$ONH_2$;

$R^{34}$ is

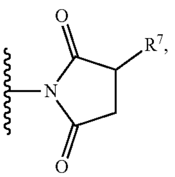

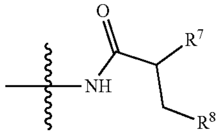

or

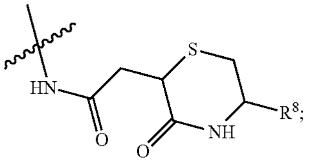

each $R^5$ is independently selected from H and $C_1$-$C_6$alkyl;

$R^7$ is —$S(CH_2)_nCHR^8NH_2$;

$R^8$ is —$C(=O)OR^5$;

each m is independently selected from 1, 2, 3, 4, 5, 6, 7, 8, 9 and 10;

each n is independently selected from 1, 2, 3, 4, 5, 6, 7, 8, 9, 10, 11, 12, 13 and 14.

Embodiment 4

The compounds of Formula (A), Formula (I) and Formula (Ia), or a pharmaceutically acceptable salt thereof, wherein $R^1$ is H, —$CH_3$ or —$CD_3$; $R^2$ is -$L_1R^4$ or -$L_3R^{34}$; $R^3$ is —$NH_2$ or —OH;

$L_1$ is —$((CH_2)_mO)_n(CH_2)_mX_3L_4$-;

$L_3$ is —$((CH_2)_mO)_n(CH_2)_mX_3L_4$-;

$L_4$ is —$((CH_2)_m$— or —$((CH_2)_mNHC(=O)X_1X_2C(=O)(CH_2)_m$—;

$X_1$ is

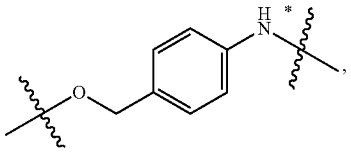 [SMILES: *Nc1ccc(CO*)cc1]

where the * indicates attachment point to $X_2$;

$X_2$ is

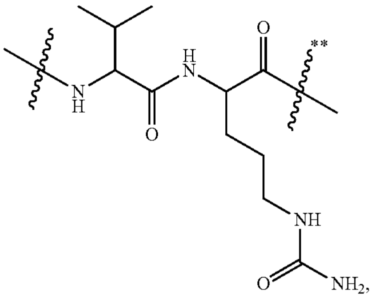

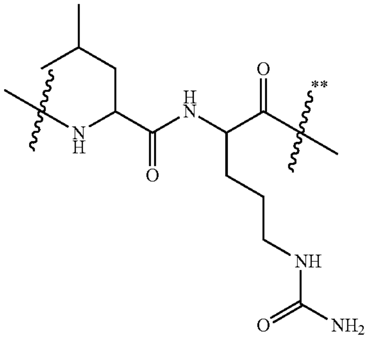

or

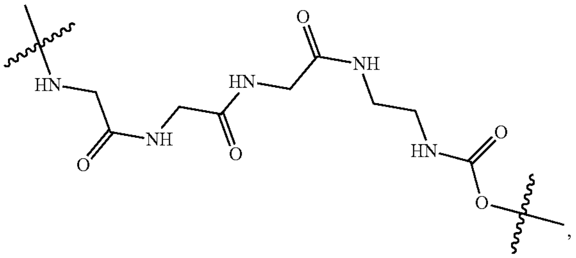

where the ** indicates attachment point to $X_1$;

$X_3$ is

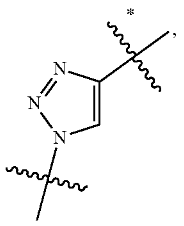 [SMILES: *c1cn(*)nn1]

where the * indicates attachment point to $L_4$;

$R^4$ is

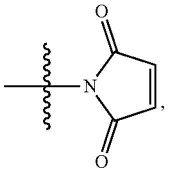

or —$ONH_2$;

$R^{34}$ is

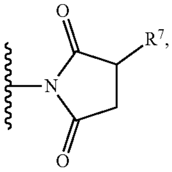

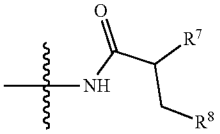

or

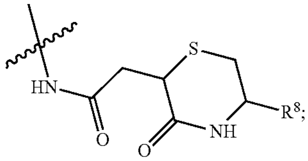

each $R^5$ is independently selected from H and $C_1$-$C_6$alkyl;

$R^7$ is —$S(CH_2)_nCHR^8NH_2$;

$R^8$ is —$C(=O)OR^5$;

each m is independently selected from 1, 2, 3, 4, 5, 6, 7, 8, 9 and 10;

each n is independently selected from 1, 2, 3, 4, 5, 6, 7, 8, 9, 10, 11, 12, 13 and 14.

Embodiment 5

The compounds of Formula (A), Formula (I) and Formula (Ia), or a pharmaceutically acceptable salt thereof, wherein $R^2$ is

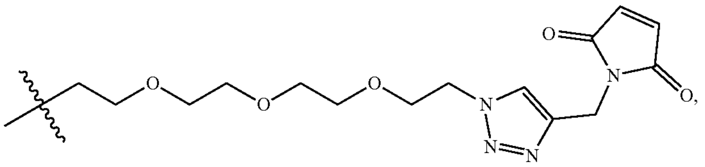

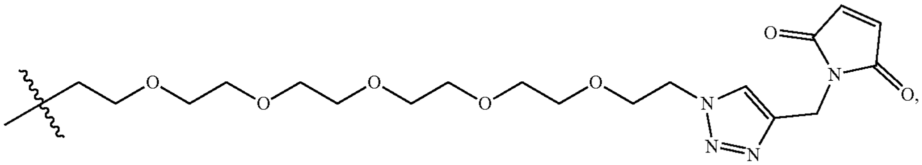

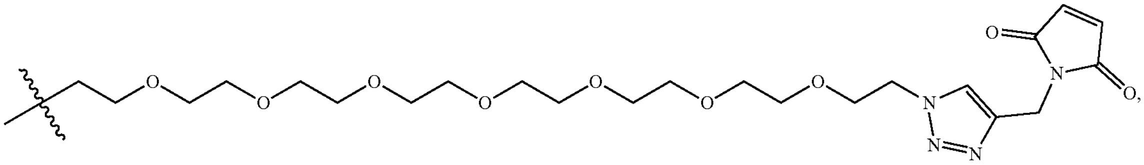

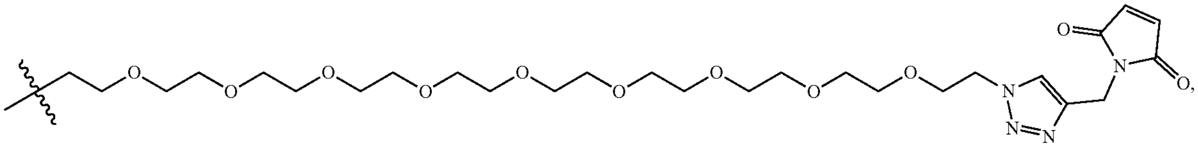

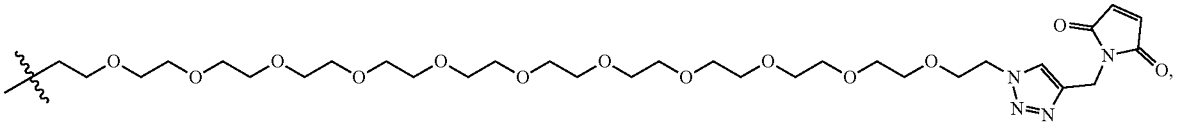

or

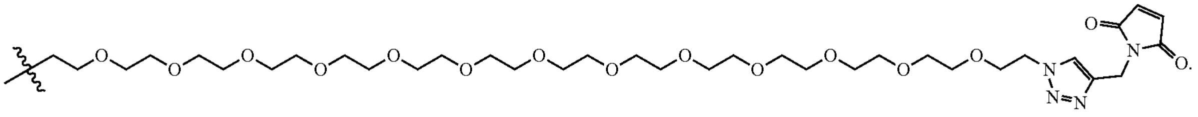

Embodiment 6
The compounds of Formula (A), Formula (I) and Formula (Ia), or a pharmaceutically acceptable salt thereof, wherein $R^2$ is
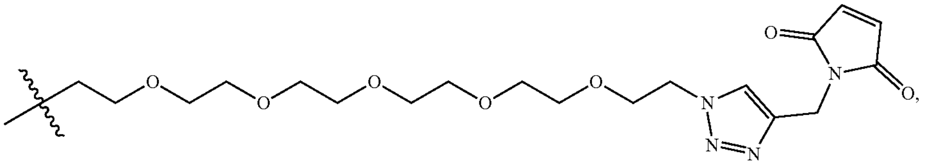
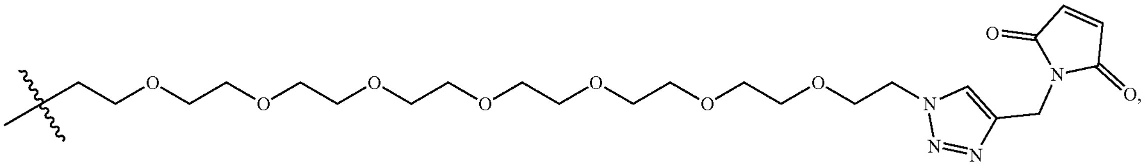
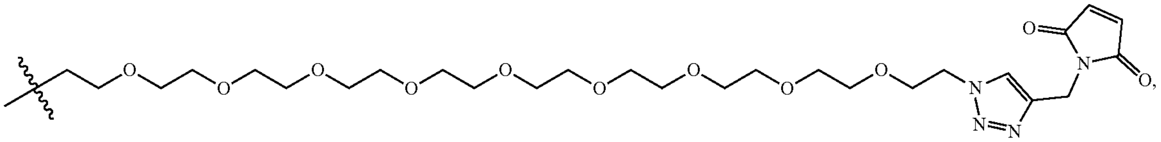
or
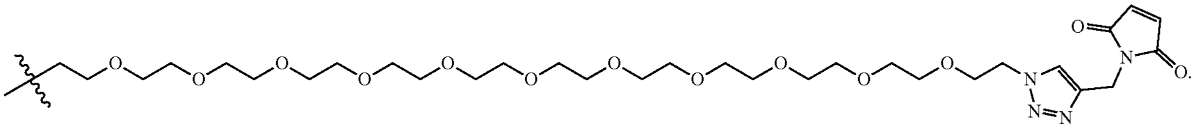
Embodiment 7
The compounds of Formula (A), Formula (I) and Formula (Ia), or a pharmaceutically acceptable salt thereof, wherein $R^2$ is
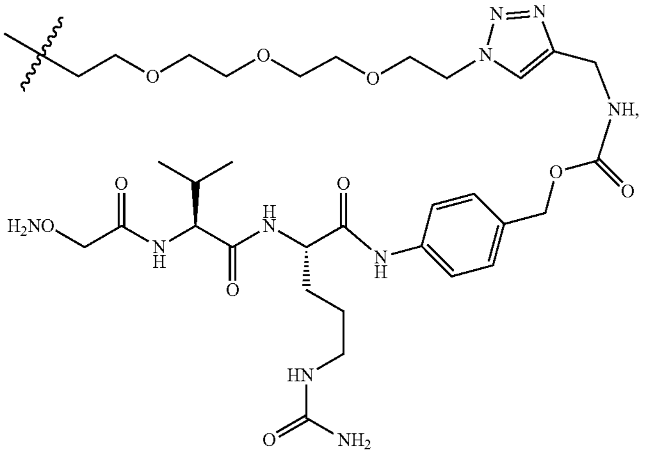

-continued
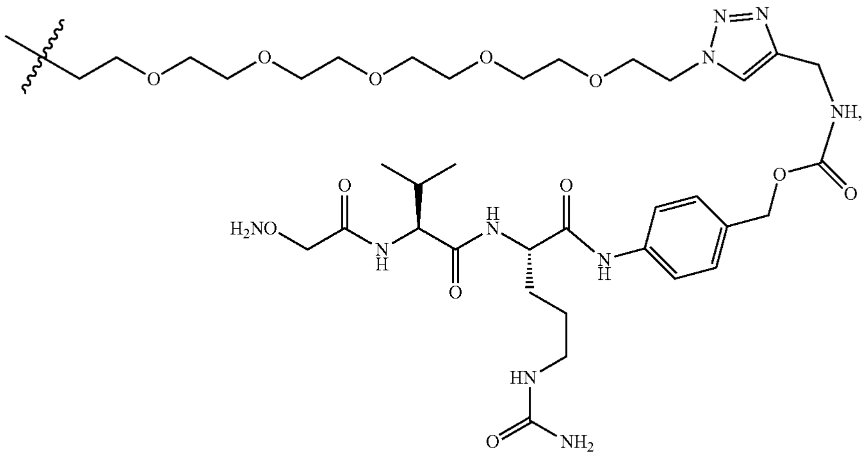
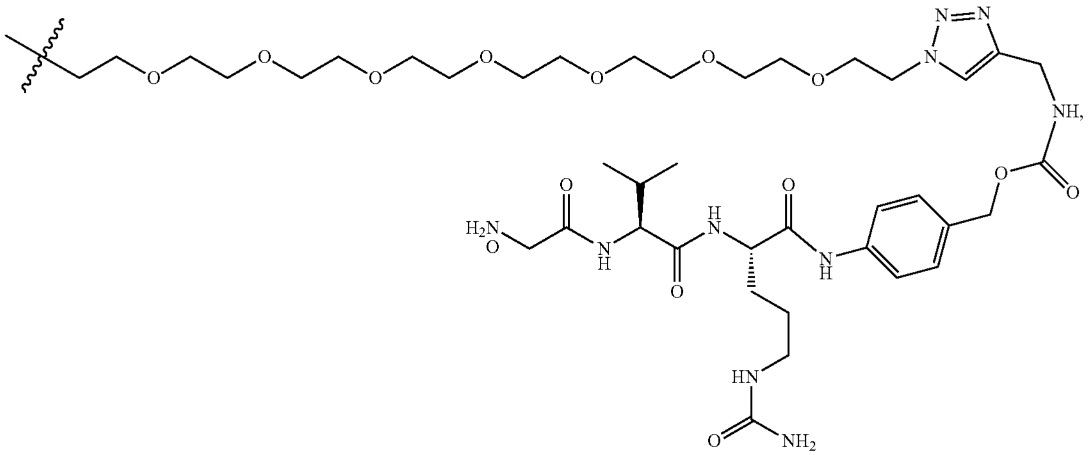
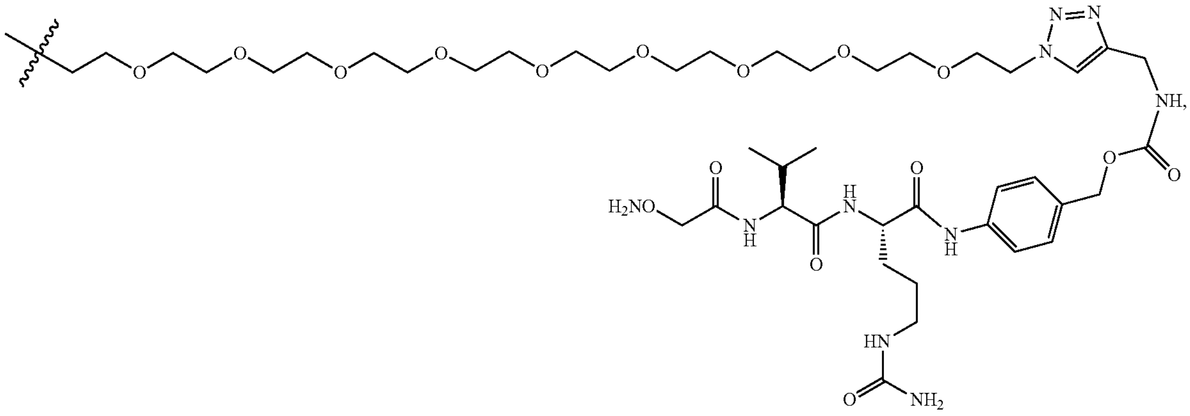
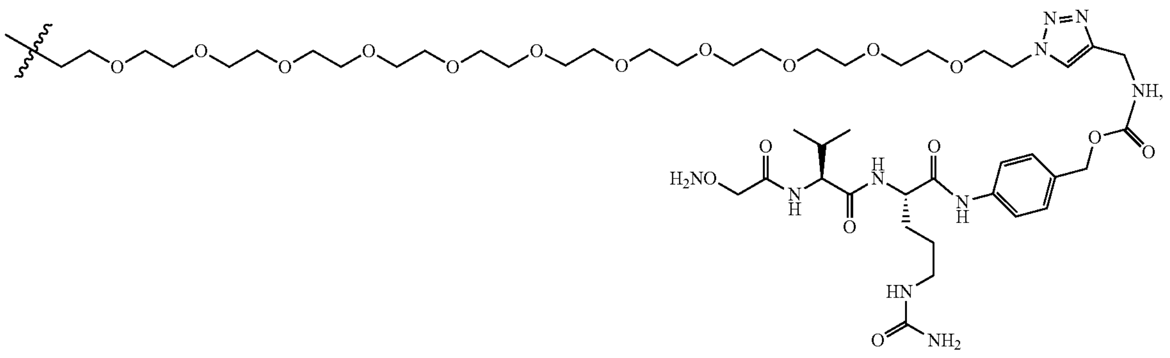
or

-continued
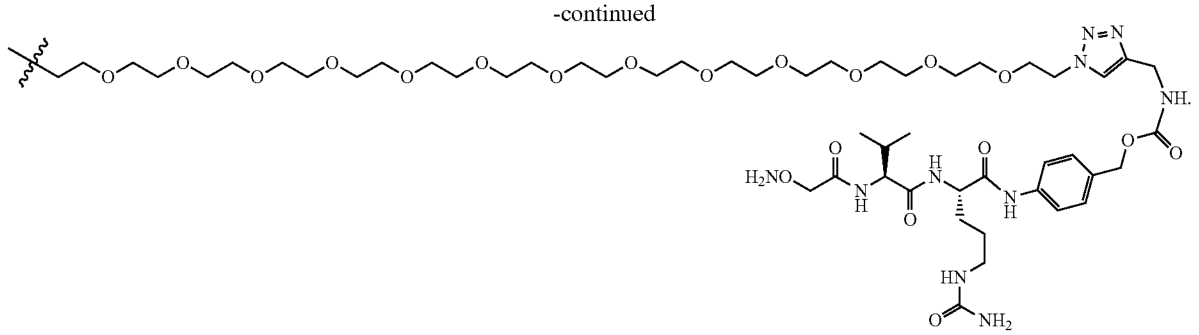
Embodiment 8
The compounds of Formula (A), Formula (I) and Formula (Ia), or a pharmaceutically acceptable salt thereof, wherein $R^2$ is $ONH_2$
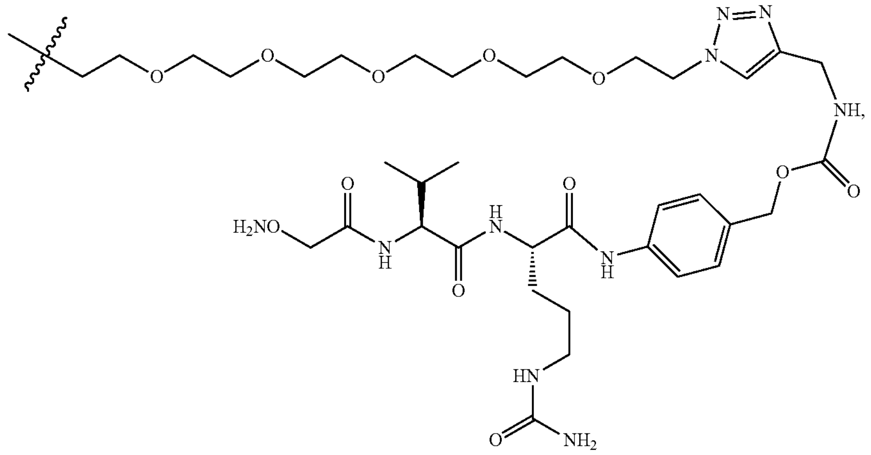
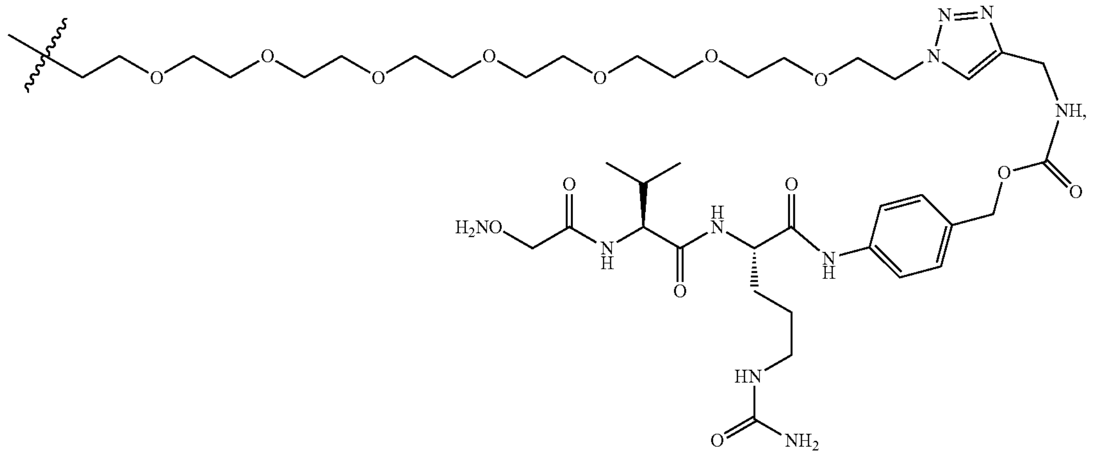

-continued
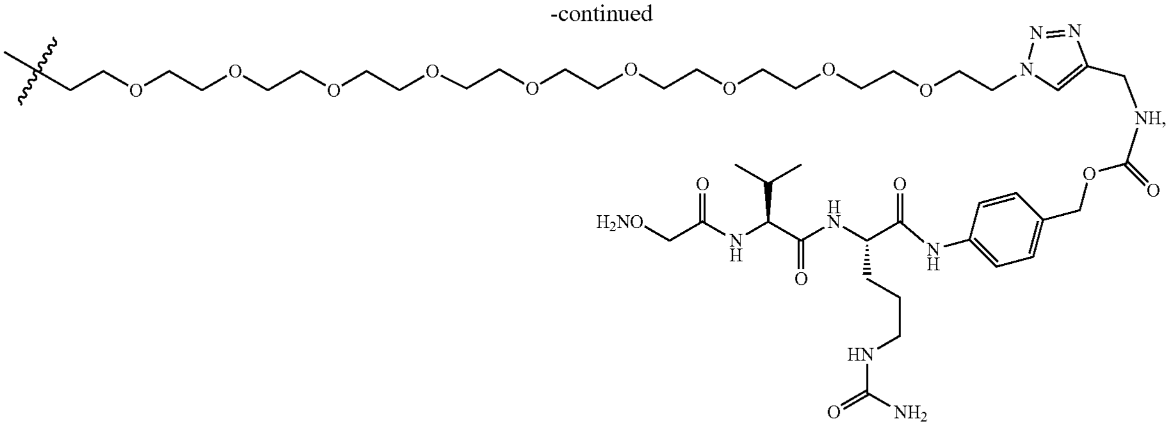
or
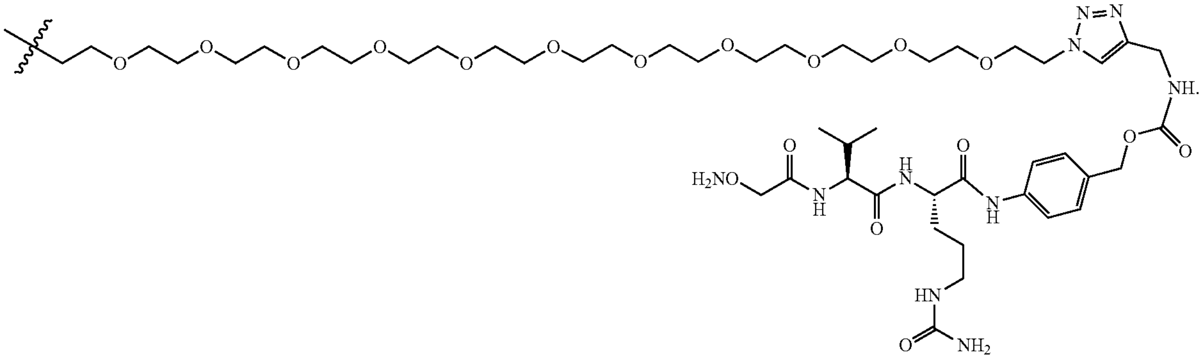
Embodiment 9
The compounds of Formula (A), Formula (I) and Formula (Ia), or a pharmaceutically acceptable salt thereof, wherein $R^2$ is
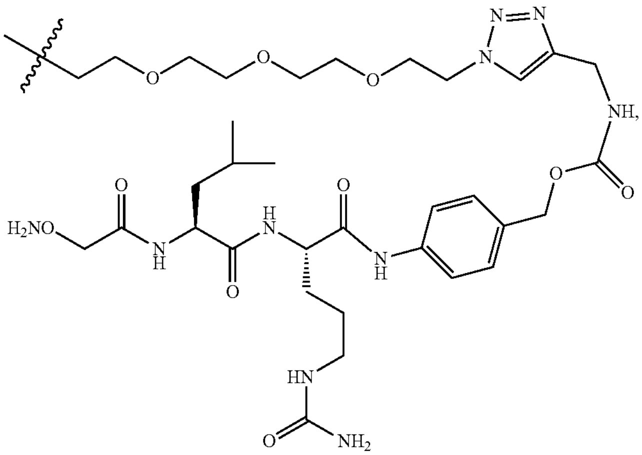

-continued
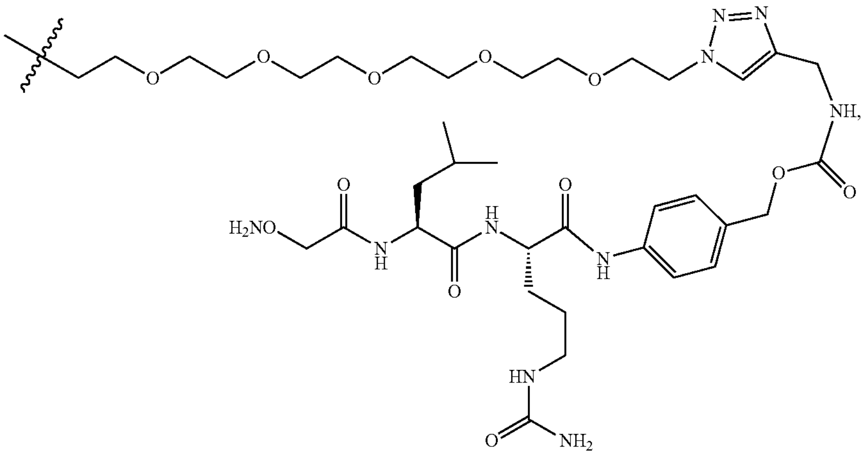
,
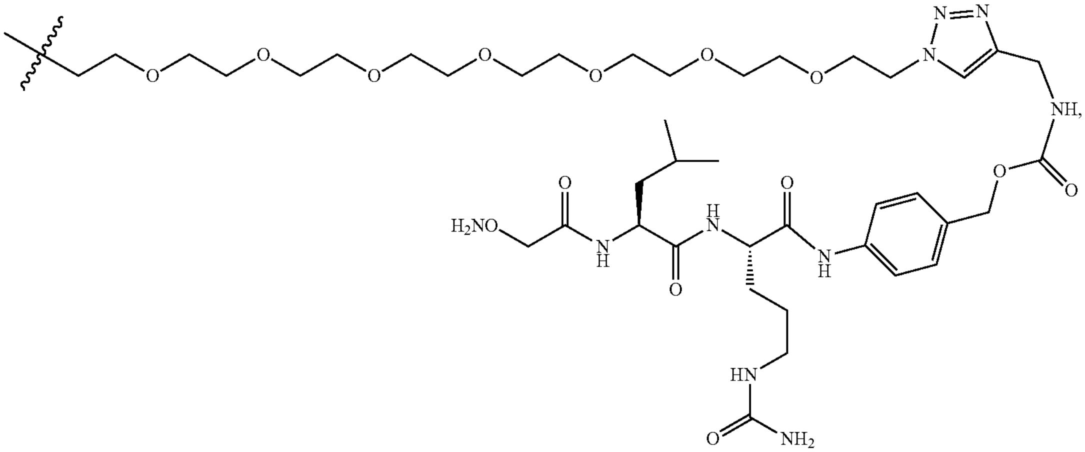
,
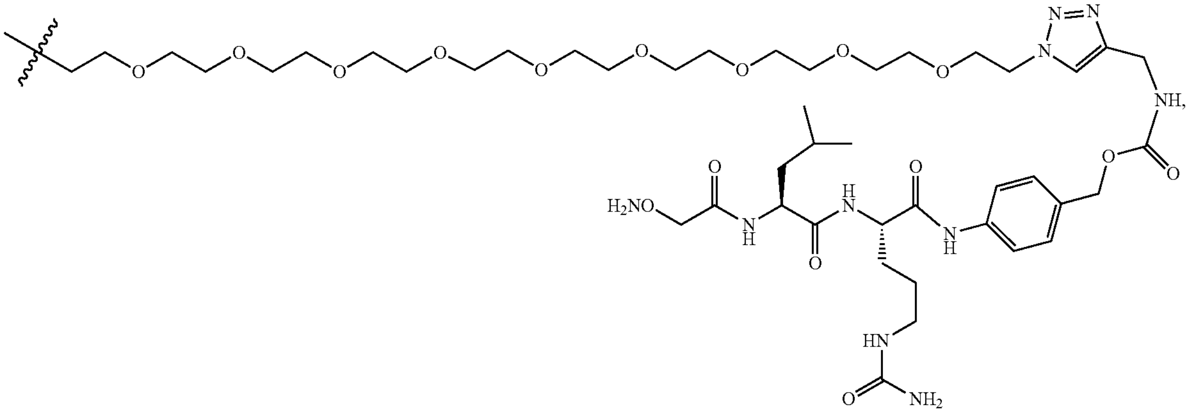
,
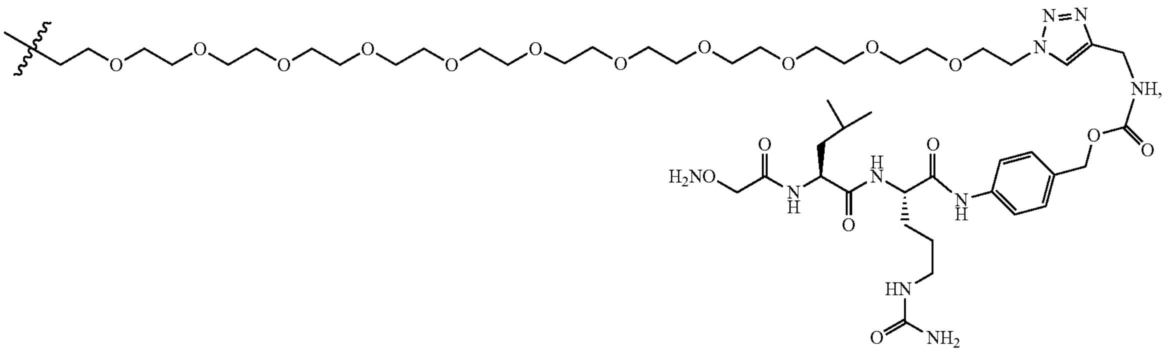
, or

-continued
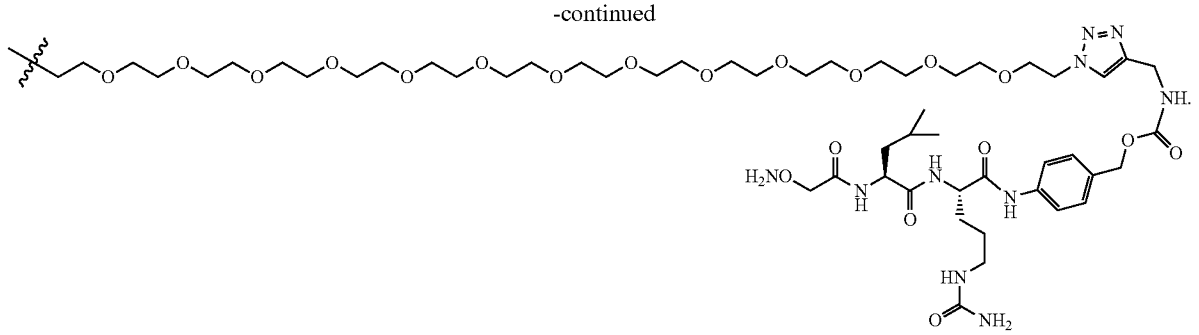
Embodiment 10
The compounds of Formula (A), Formula (I) and Formula (Ia), or a pharmaceutically acceptable salt thereof, wherein $R^2$ is
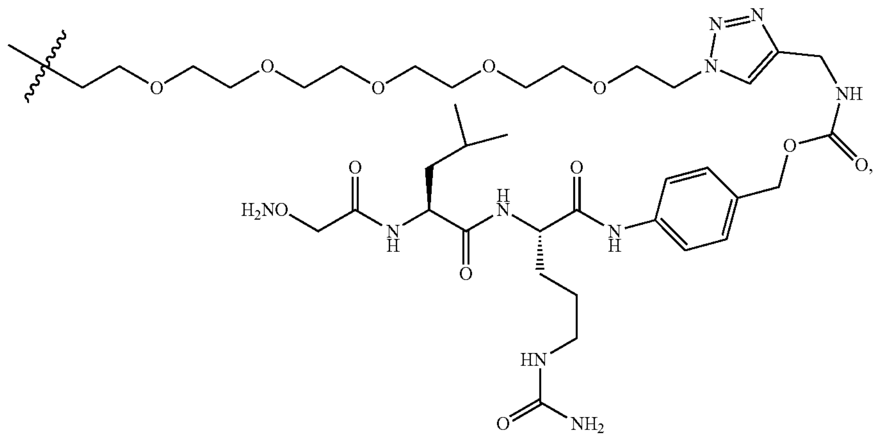
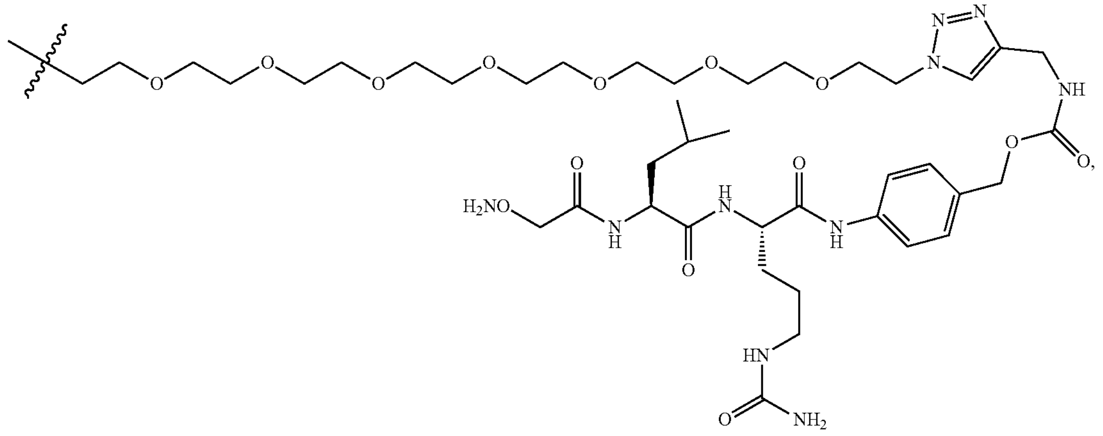

-continued
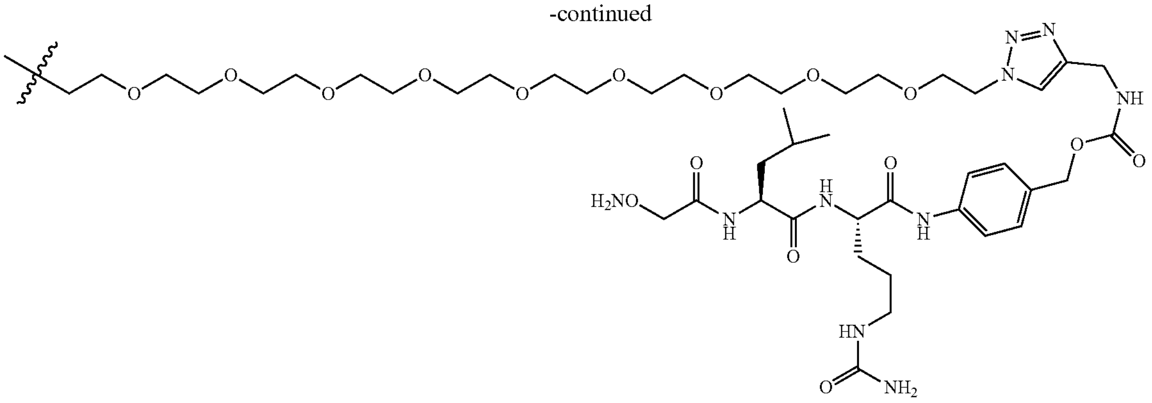
or
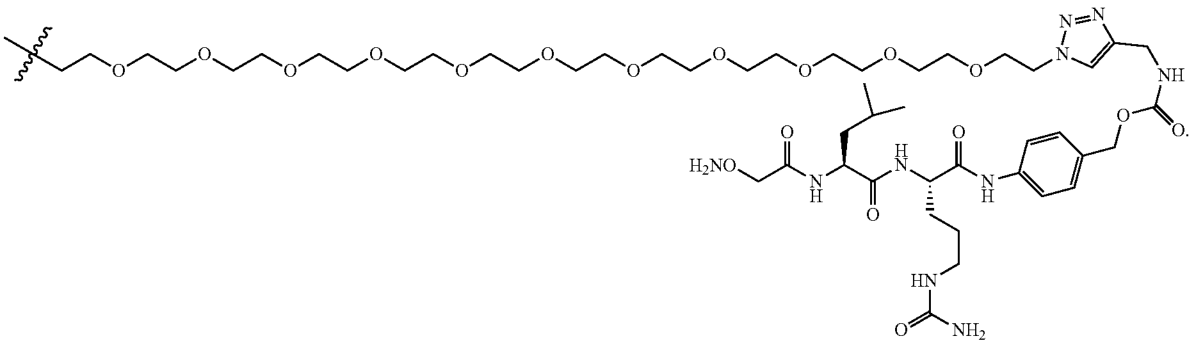
Embodiment 11
The compounds of Formula (A), Formula (I) and Formula (Ia), or a pharmaceutically acceptable salt thereof, wherein $R^2$ is
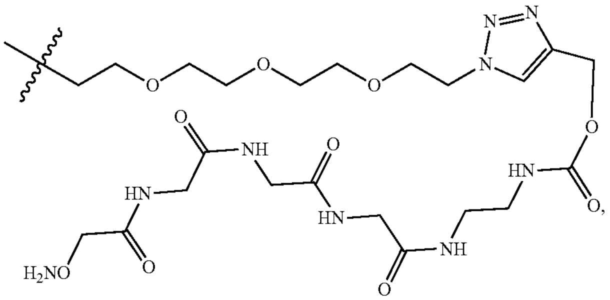
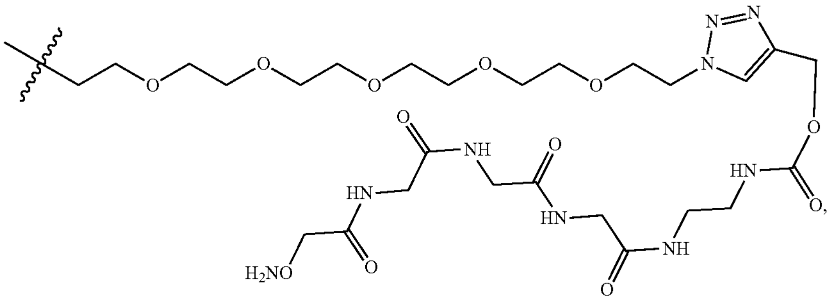

-continued
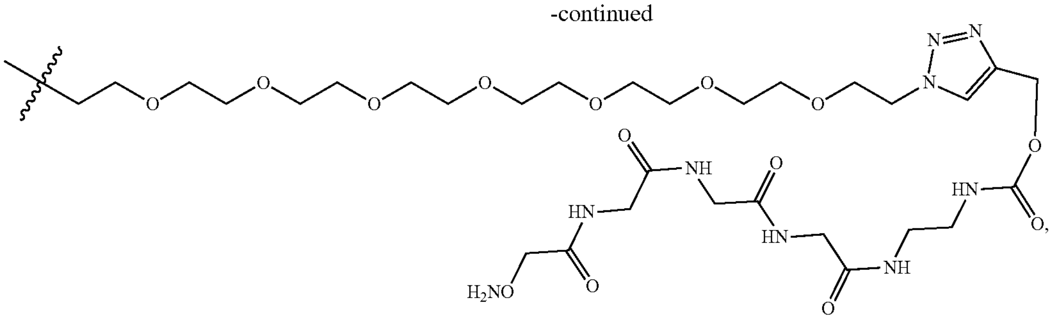
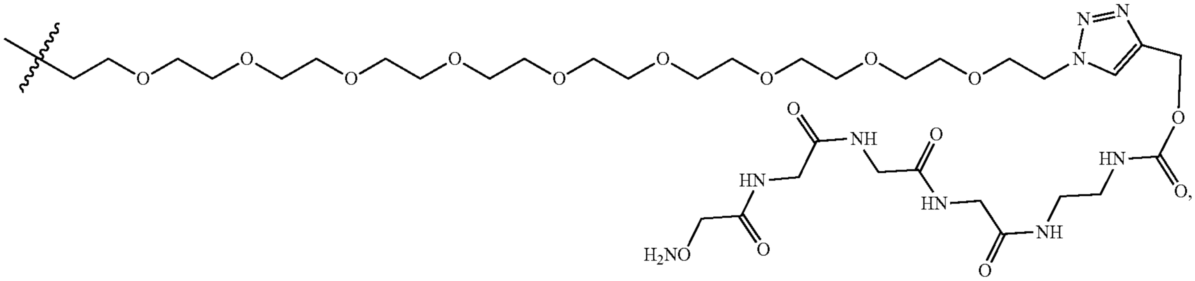
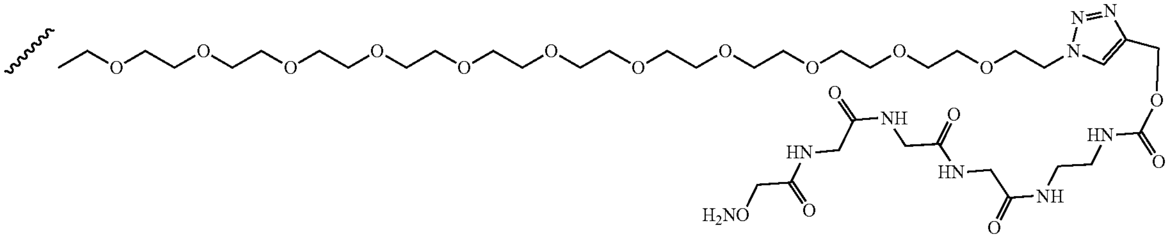
or
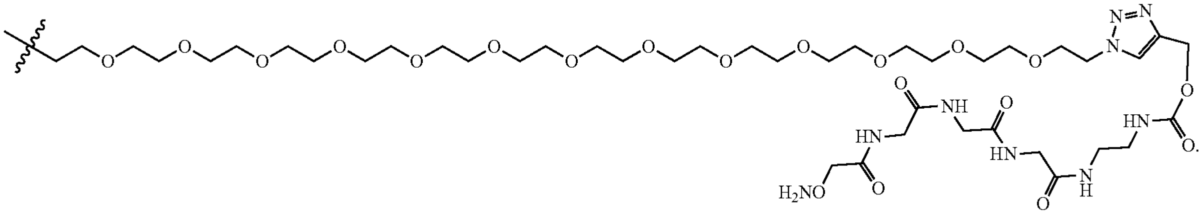
Embodiment 12
The compounds of Formula (A), Formula (I) and Formula (Ia), or a pharmaceutically acceptable salt thereof, wherein $R^2$ is
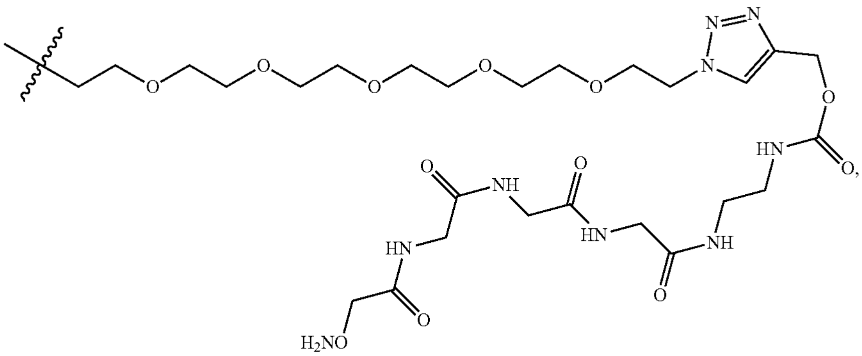

-continued
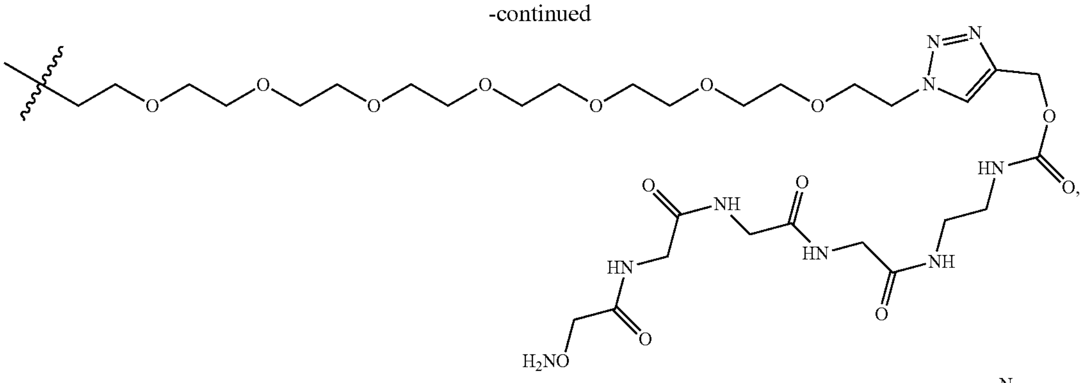
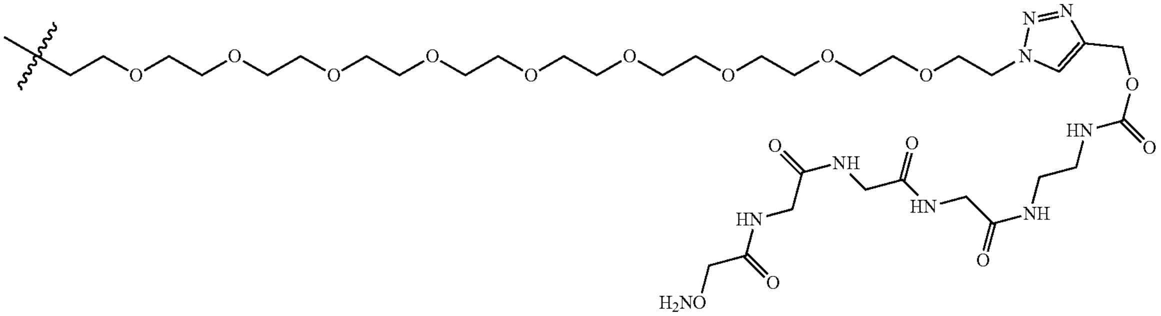
or
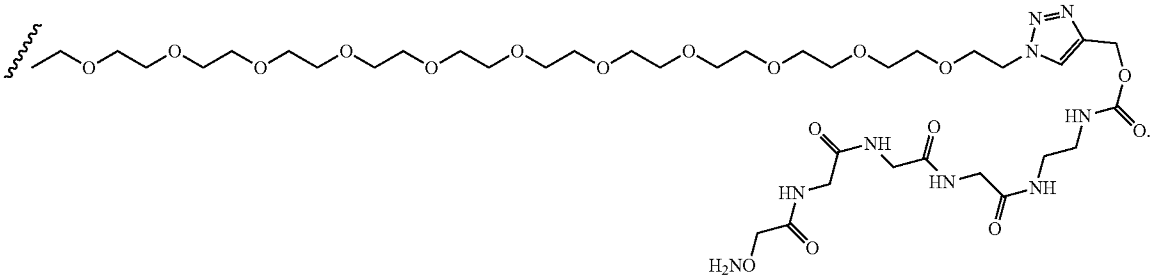
Embodiment 13
The compounds of Formula (A), Formula (I) and Formula (Ia), or a pharmaceutically acceptable salt thereof, wherein $R^2$ is
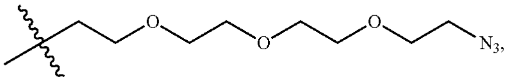
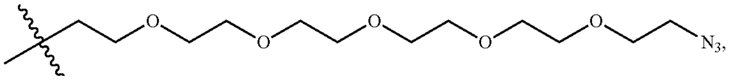
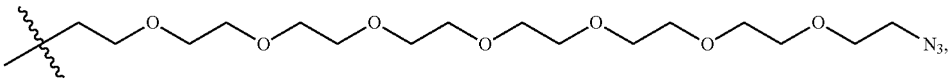
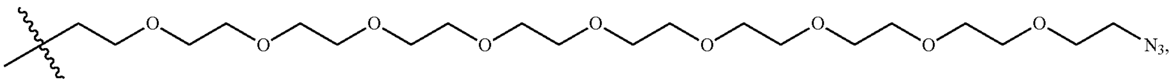
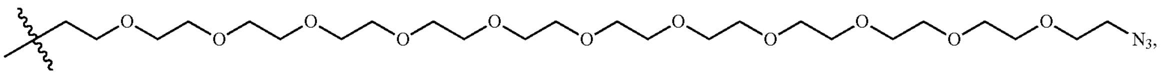
or
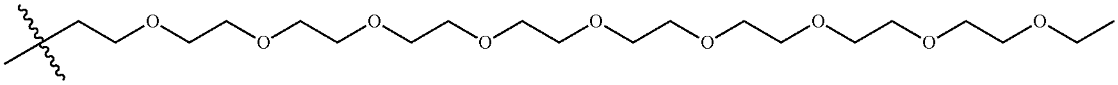

-continued
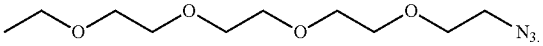
Embodiment 14
The compounds of Formula (A), Formula (I) and Formula (Ia), or a pharmaceutically acceptable salt thereof, wherein $R^2$ is
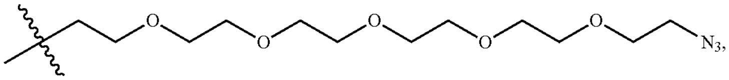
,
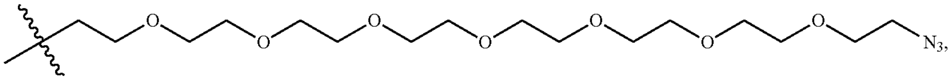
,
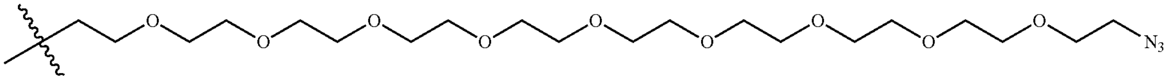
or
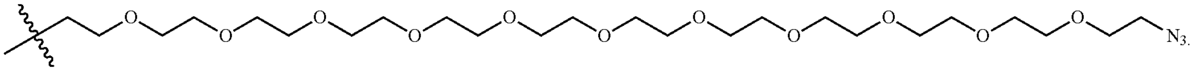
.
Embodiment 15
The compounds of Formula (A), Formula (I) and Formula (Ia), or a pharmaceutically acceptable salt thereof, wherein $R^2$ is
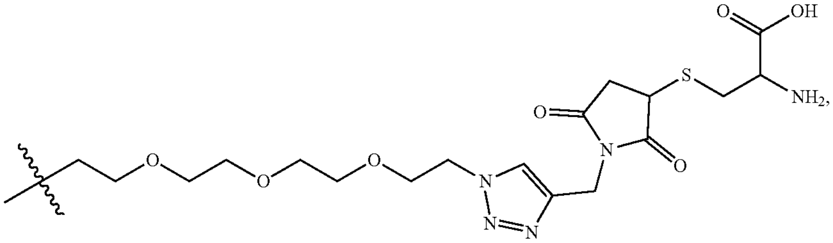
,
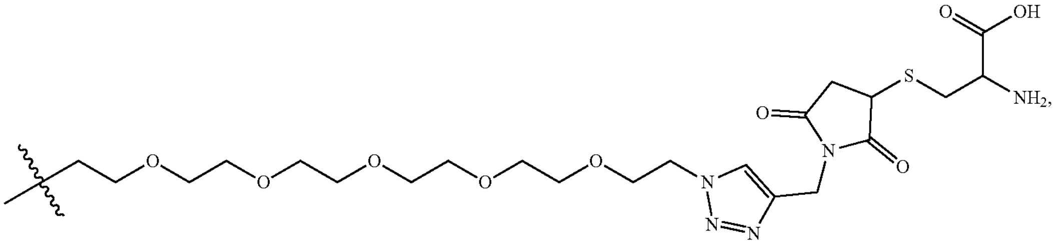
,
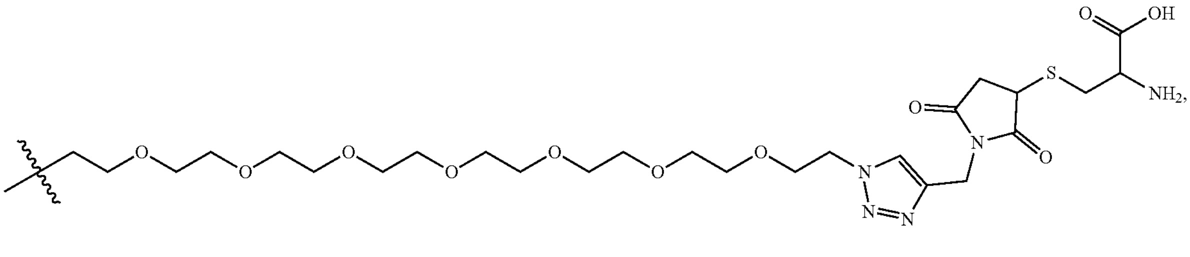
, -continued
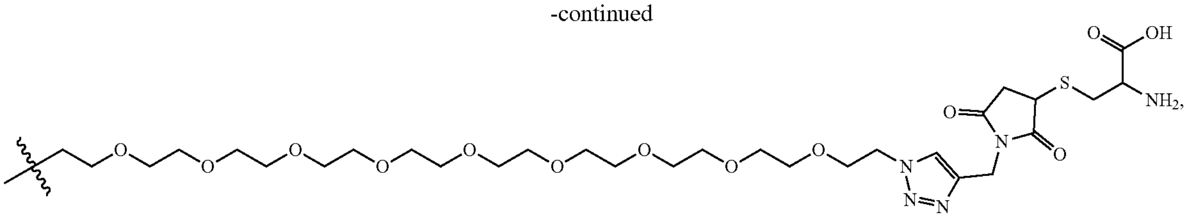
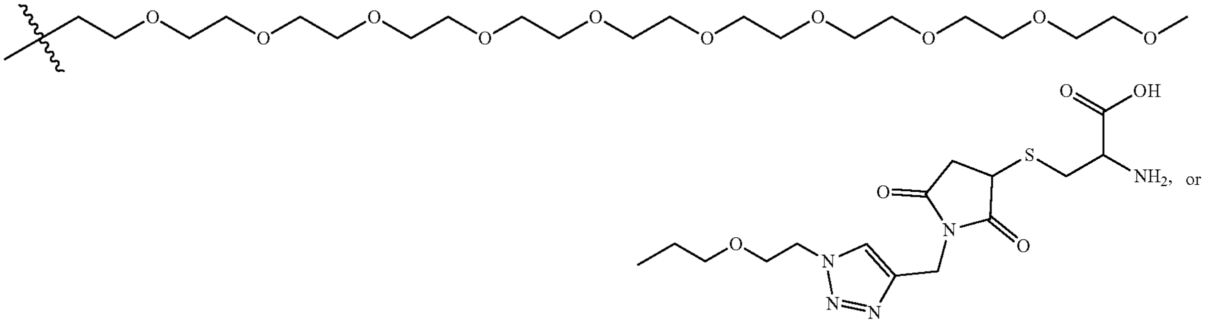
or
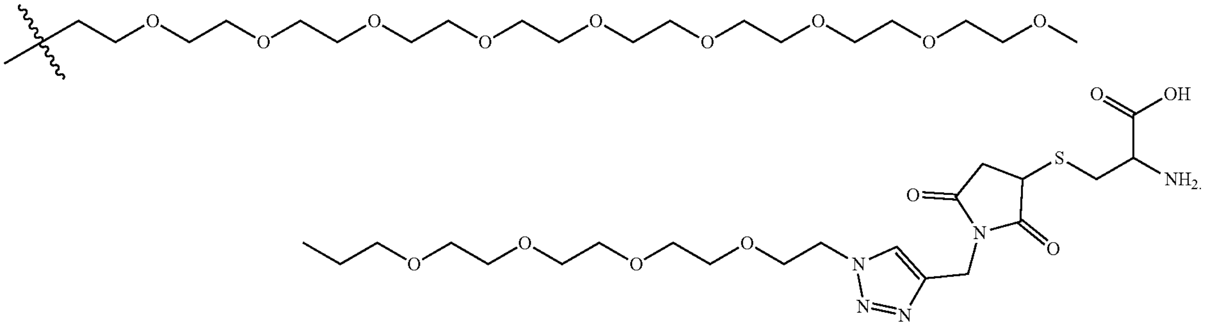
Embodiment 16
The compounds of Formula (A), Formula (I) and Formula (Ia), or a pharmaceutically acceptable salt thereof, wherein $R^2$ is
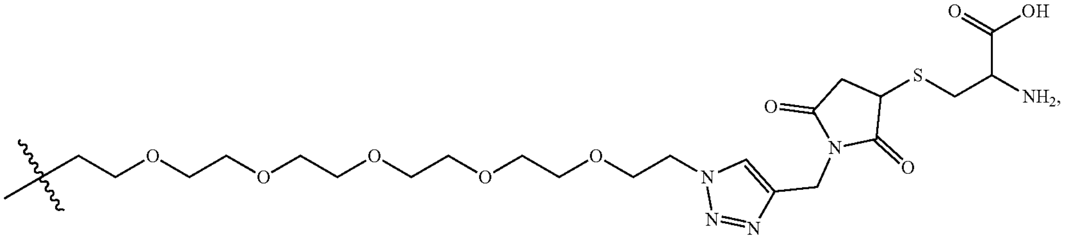
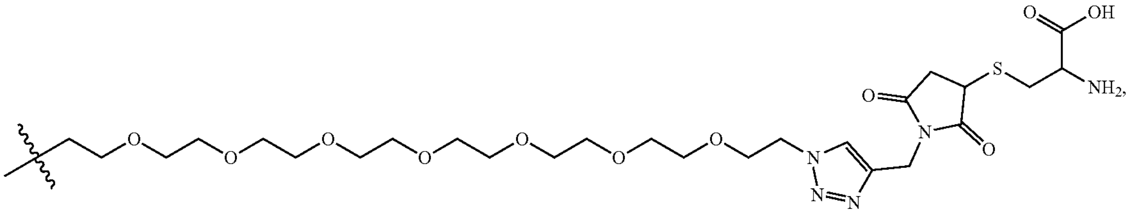
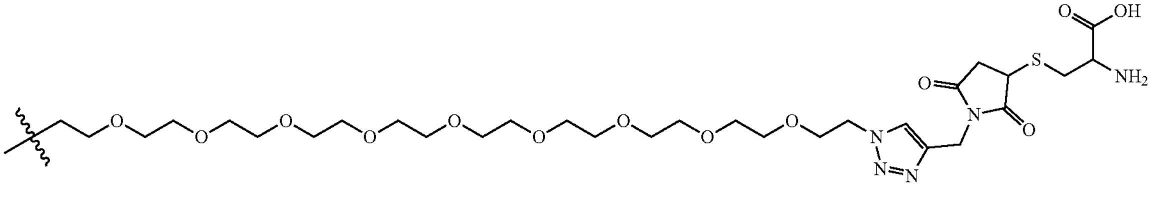
or -continued
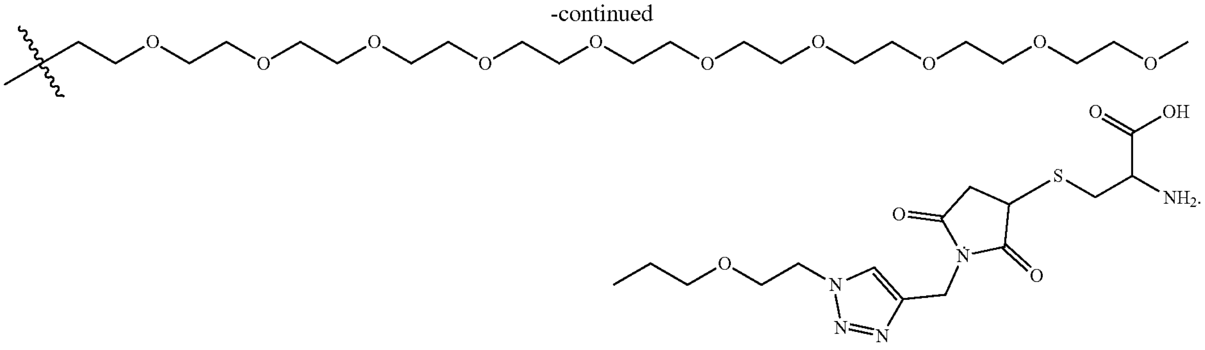
Embodiment 17
The compounds of Formula (A), Formula (I) and Formula (Ia), or a pharmaceutically acceptable salt thereof, wherein $R^2$ is
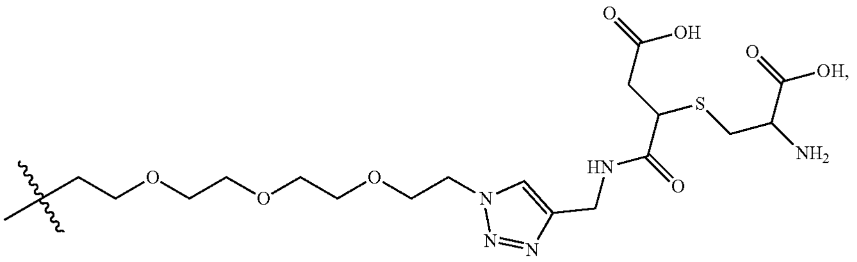
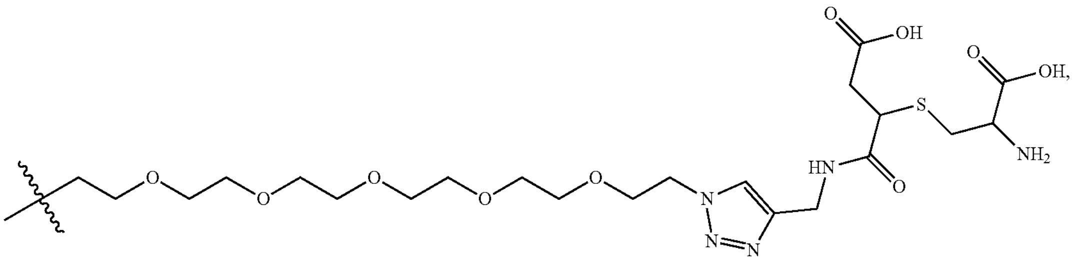
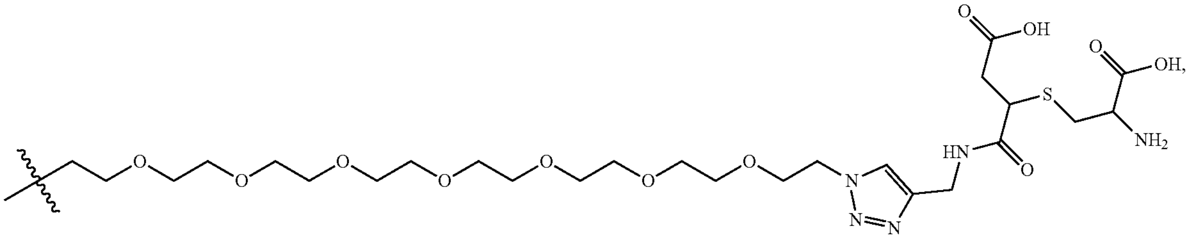
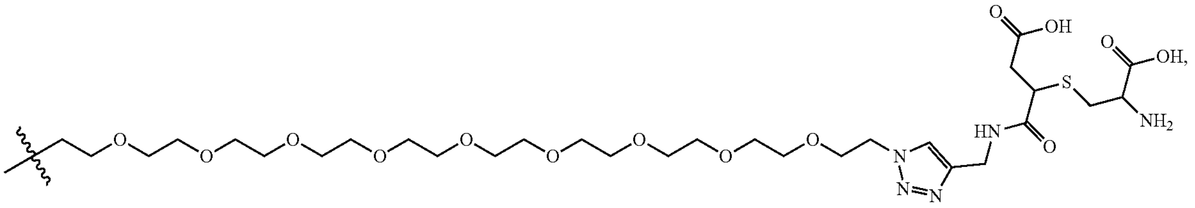
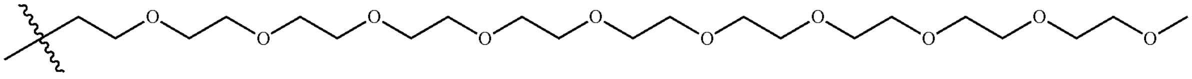

-continued
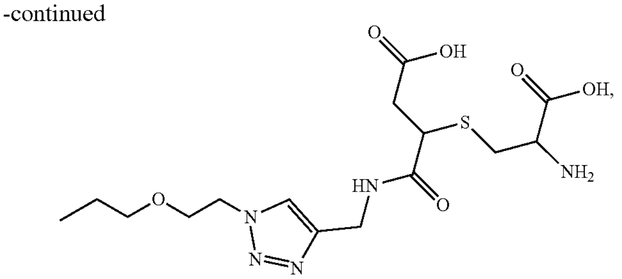
or
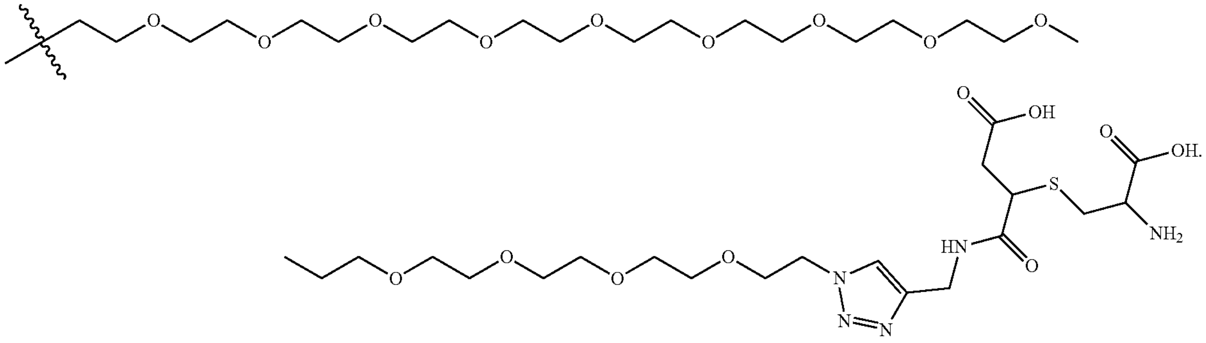
Embodiment 18
The compounds of Formula (A), Formula (I) and Formula (Ia), or a pharmaceutically acceptable salt thereof, wherein $R^2$ is
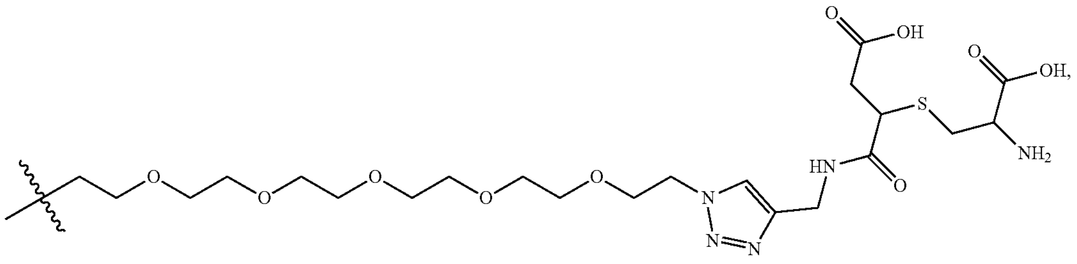
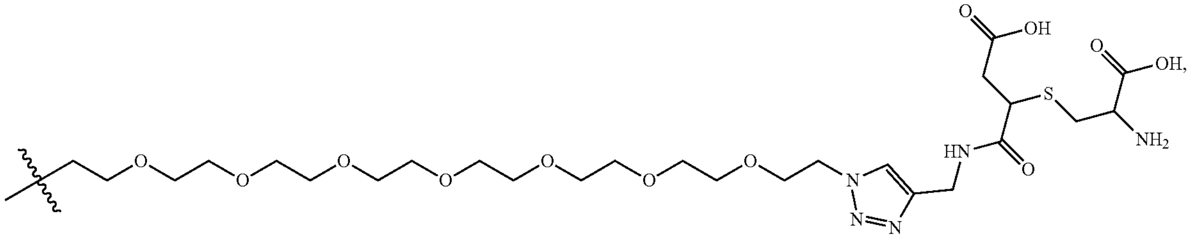
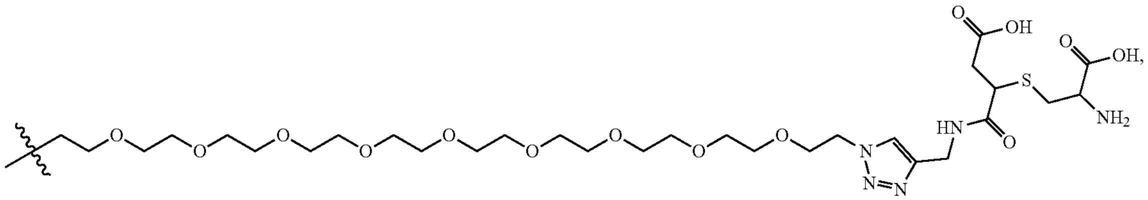
or
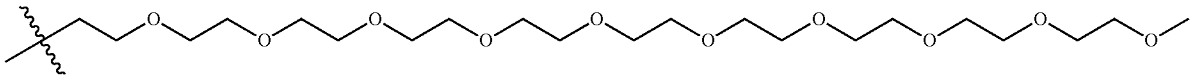

-continued
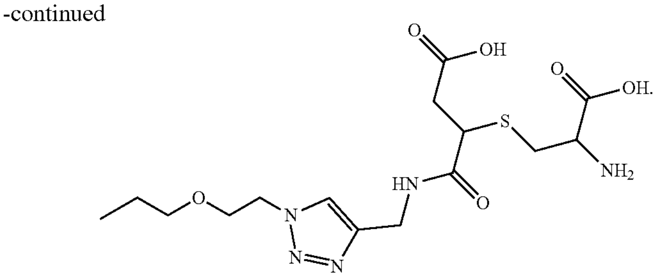
Embodiment 19
The compounds of Formula (A), Formula (I) and Formula (Ia), or a pharmaceutically acceptable salt thereof, wherein $R^2$ is
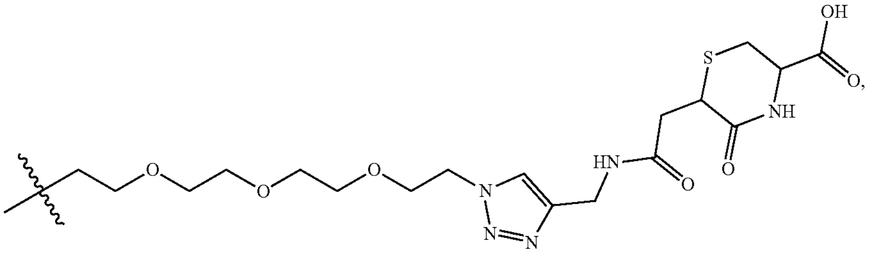
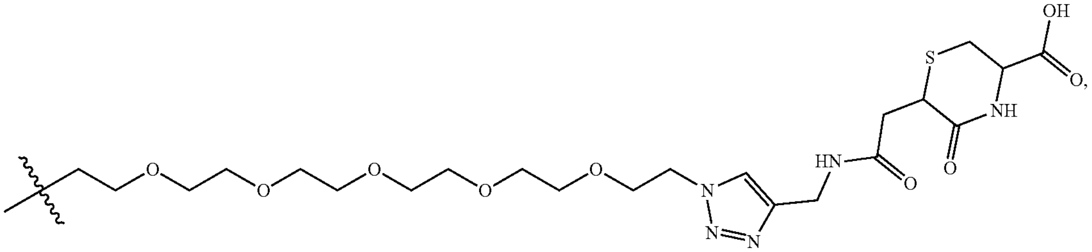
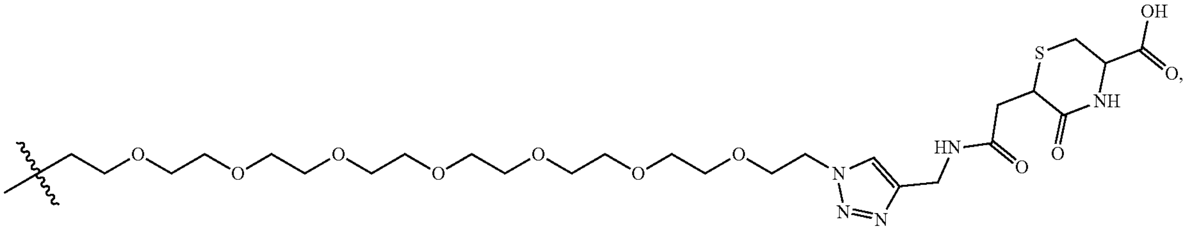
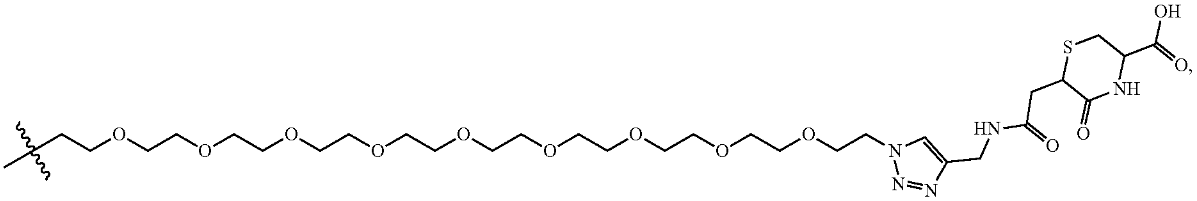
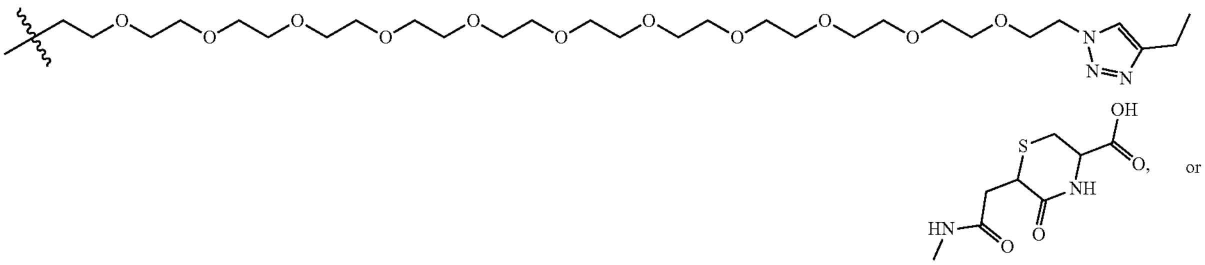
or -continued

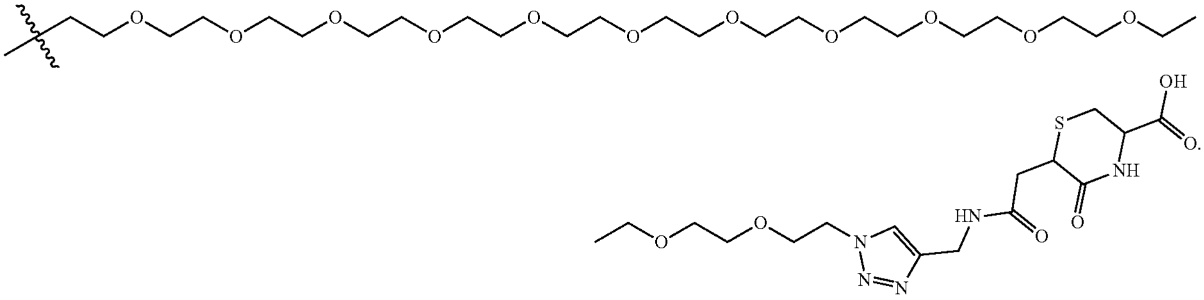

Embodiment 20

The compounds of Formula (A), Formula (I) and Formula (Ia), or a pharmaceutically acceptable salt thereof, wherein $R^2$ is

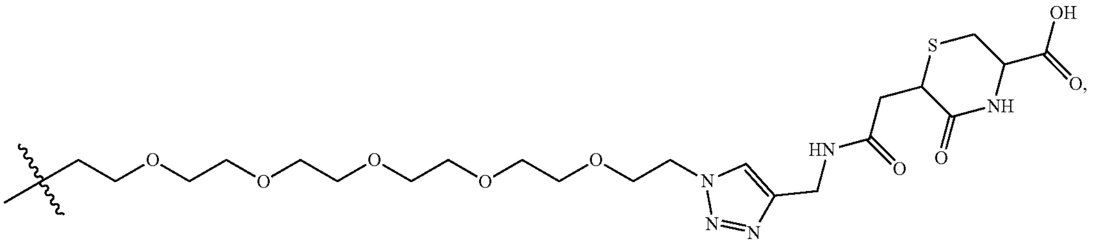

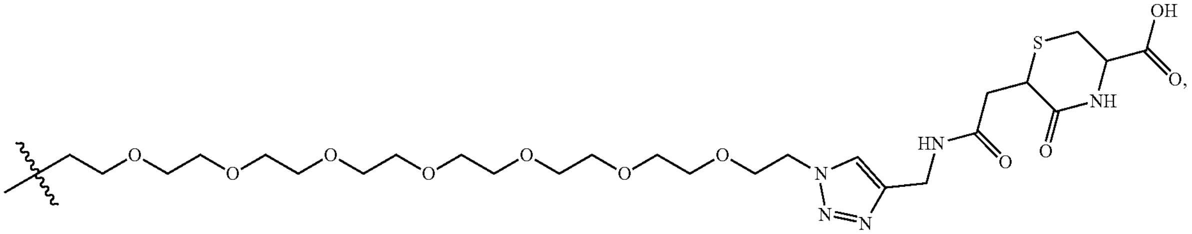

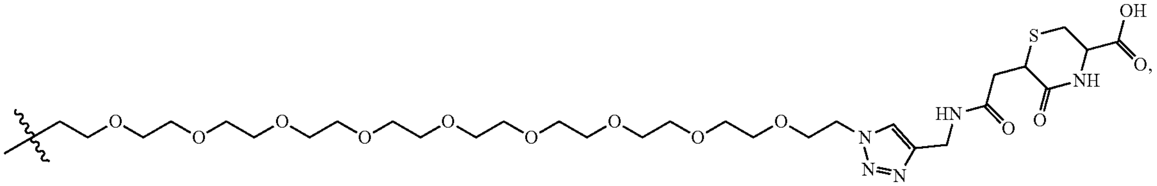

or

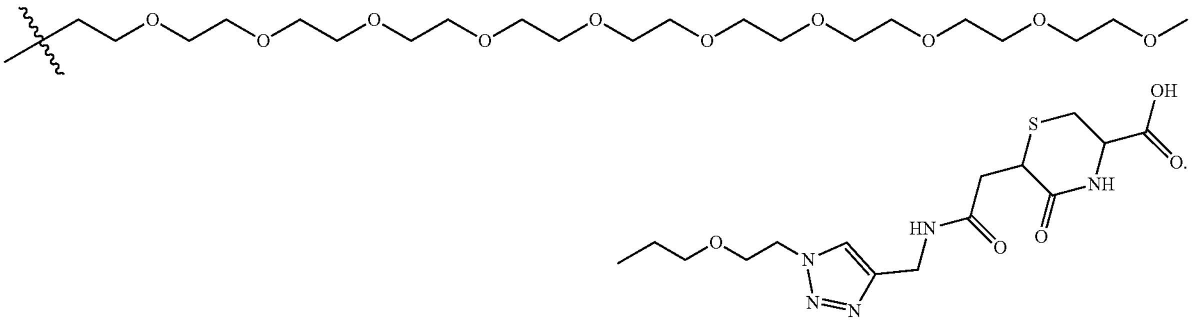

Embodiment 21

The compounds of Formula (A), Formula (I) and Formula (Ia), or a pharmaceutically acceptable salt thereof, wherein $R^1$ is —$CH_3$.

Embodiment 22

The compounds of Formula (A), Formula (I) and Formula (Ia), or a pharmaceutically acceptable salt thereof, wherein $R^1$ is —$CD_3$.

Embodiment 23

The compounds of Formula (A), Formula (I) and Formula (Ia), or a pharmaceutically acceptable salt thereof, wherein $R^1$ is H.

Embodiment 24

The compounds of Formula (A), Formula (I) and Formula (Ia), or a pharmaceutically acceptable salt thereof, wherein $R^3$ is —$NH_2$.

Embodiment 25

The compounds of Formula (A), Formula (I) and Formula (Ia), or a pharmaceutically acceptable salt thereof, wherein $R^3$ is —OH.

Embodiment 26

The compounds of Formula (A), Formula (I) and Formula (Ia), or a pharmaceutically acceptable salt thereof, wherein $R^2$ is $-L_1R^4$.

Embodiment 27

The compounds of Formula (A), Formula (I) and Formula (Ia), or a pharmaceutically acceptable salt thereof, wherein $R^2$ is $-L_2R^{14}$.

Embodiment 28

The compounds of Formula (A), Formula (I) and Formula (Ia), or a pharmaceutically acceptable salt thereof, wherein $R^2$ is $-L_2R^{24}$.

Embodiment 29

The compounds of Formula (A), Formula (I) and Formula (Ia), or a pharmaceutically acceptable salt thereof, wherein $R^2$ is or $-L_3R^{34}$.

Embodiment 30

The compounds of Formula (A), Formula (I) and Formula (Ia), or a pharmaceutically acceptable salt thereof, wherein $L_1$ is $-((CH_2)_mO)_n(CH_2)_mX_3L_4-$.

Embodiment 31

The compounds of Formula (A), Formula (I) and Formula (Ia), or a pharmaceutically acceptable salt thereof, wherein $L_1$ is $-((CH_2)_mO)_n(CH_2)_mX_4L_4-$.

Embodiment 32

The compounds of Formula (A), Formula (I) and Formula (Ia), or a pharmaceutically acceptable salt thereof, wherein $L_2$ is $-((CH_2)_mO)_n(CH_2)_m-$.

Embodiment 33

The compounds of Formula (A), Formula (I) and Formula (Ia), or a pharmaceutically acceptable salt thereof, wherein $L_3$ is $-((CH_2)_mO)_n(CH_2)_mX_3L_4-$.

Embodiment 34

The compounds of Formula (A), Formula (I) and Formula (Ia), or a pharmaceutically acceptable salt thereof, wherein $L_3$ is $-((CH_2)_mO)_n(CH_2)_mX_4L_4-$.

Embodiment 35

The compounds of Formula (A), Formula (I) and Formula (Ia), or a pharmaceutically acceptable salt thereof, wherein $L_3$ is or $-((CH_2)_mO)_n(CH_2)_m-$.

Embodiment 36

The compounds of Formula (A), Formula (I) and Formula (Ia), or a pharmaceutically acceptable salt thereof, wherein $L_4$ is $-((CH_2)_m-$.

Embodiment 37

The compounds of Formula (A), Formula (I) and Formula (Ia), or a pharmaceutically acceptable salt thereof, wherein $L_4-((CH_2)_mNHC(=O)X_1X_2C(=O)(CH_2)_m-$.

Embodiment 38

The compounds of Formula (A), Formula (I) and Formula (Ia), or a pharmaceutically acceptable salt thereof, wherein $X_1$ is

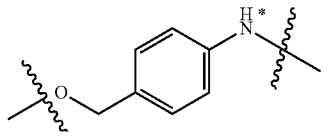

or

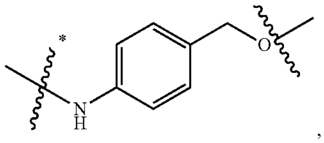

, where the * indicates attachment point to $X_2$.

Embodiment 39

The compounds of Formula (A), Formula (I) and Formula (Ia), or a pharmaceutically acceptable salt thereof, wherein $X_1$ is

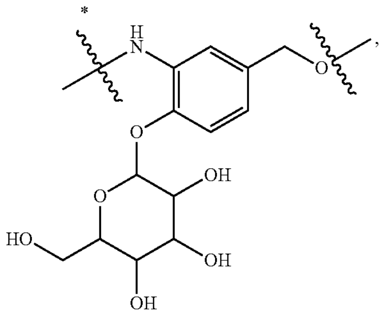

,

-continued

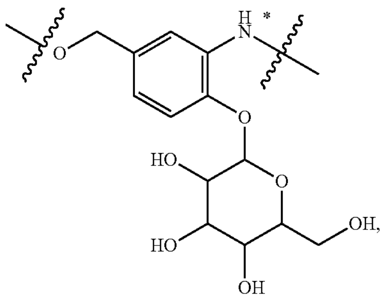

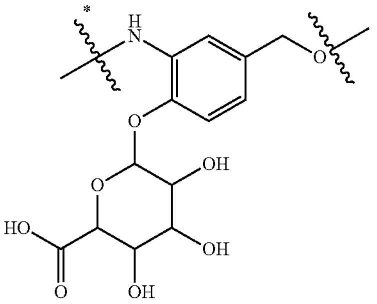

or

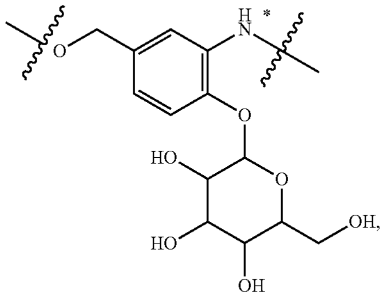

where the * indicates attachment point to $X_2$.

Embodiment 40

The compounds of Formula (A), Formula (I) and Formula (Ia), or a pharmaceutically acceptable salt thereof, wherein $X_2$ is

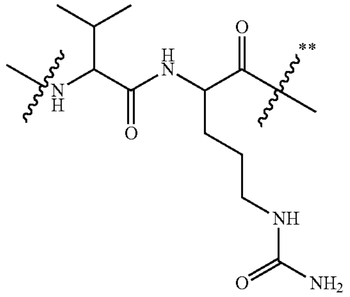

or

-continued

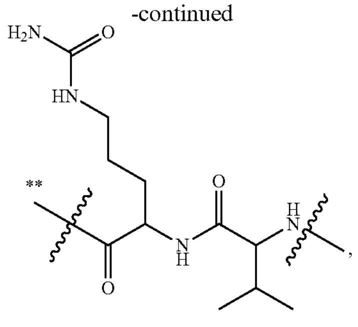

where the ** indicates attachment point to $X_1$.

Embodiment 41

The compounds of Formula (A), Formula (I) and Formula (Ia), or a pharmaceutically acceptable salt thereof, wherein $X_2$ is

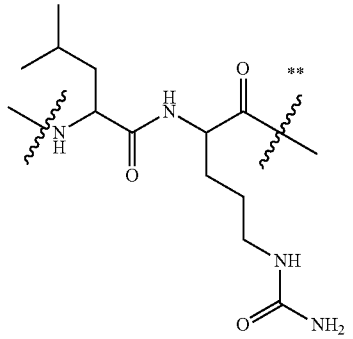

or

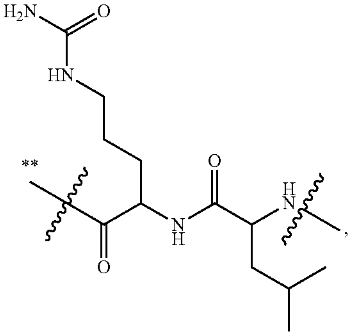

where the ** indicates attachment point to $X_1$.

Embodiment 42

The compounds of Formula (A), Formula (I) and Formula (Ia), or a pharmaceutically acceptable salt thereof, wherein $X_2$ is

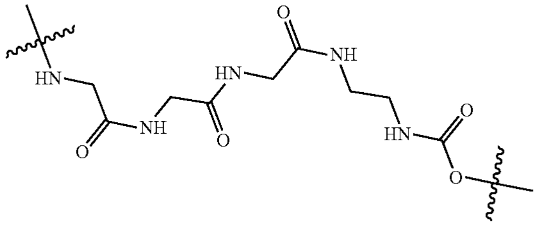

or

-continued

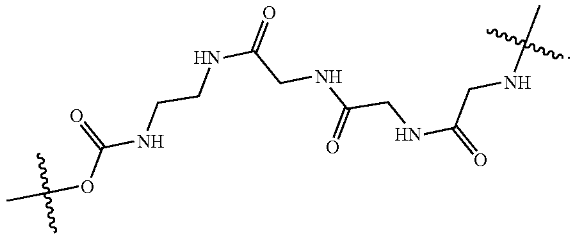

Embodiment 43

The compounds of Formula (A), Formula (I) and Formula (Ia), or a pharmaceutically acceptable salt thereof, wherein $X_2$ is

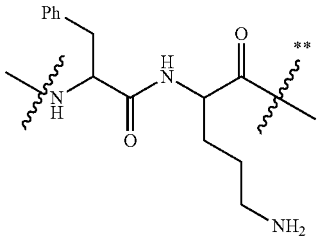

or

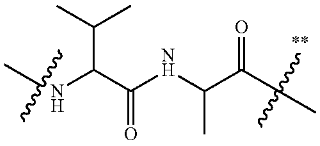

, where the ** indicates attachment point to $X_1$.

Embodiment 44

The compounds of Formula (A), Formula (I) and Formula (Ia), or a pharmaceutically acceptable salt thereof, wherein $X_3$ is

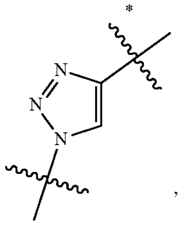 [SMILES: *c1cn(*)nn1]

, where the * indicates attachment point to $L_4$.

Embodiment 45

The compounds of Formula (A), Formula (I) and Formula (Ia), or a pharmaceutically acceptable salt thereof, wherein $X_3$ is

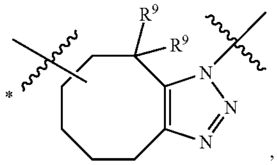

,

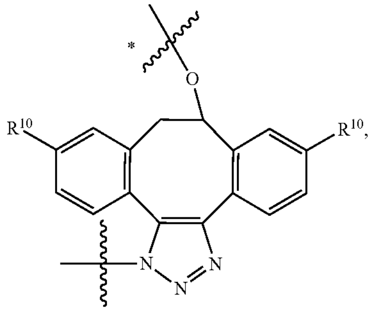

,

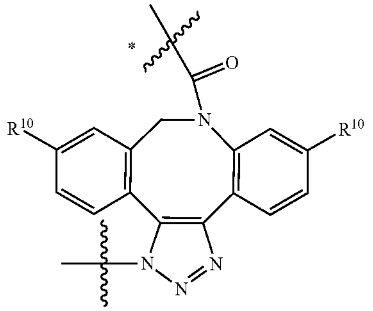

or

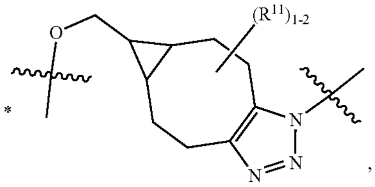

, where the * indicates attachment point to $L_4$.

Embodiment 46

The compounds of Formula (A), Formula (I) and Formula (Ia), or a pharmaceutically acceptable salt thereof, wherein $X_4$ is

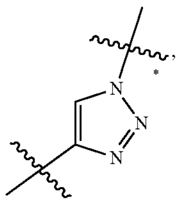 [SMILES: *c1cn(*)nn1]

where the * indicates attachment point to $L_4$.

Embodiment 47

The compounds of Formula (A), Formula (I) and Formula (Ia), or a pharmaceutically acceptable salt thereof, wherein $X_4$ is

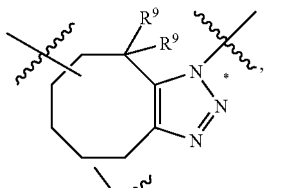

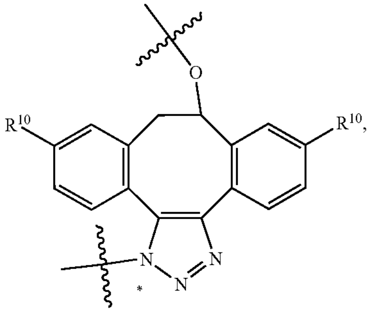

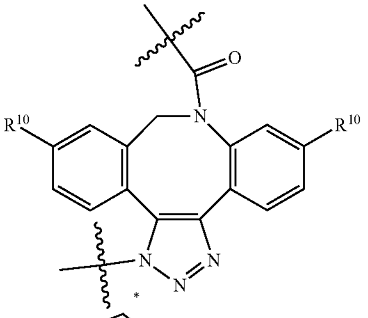

or

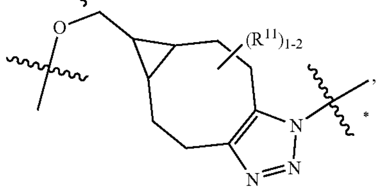

where the * indicates attachment point to $L_4$.

Embodiment 48

The compounds of Formula (A), Formula (I) and Formula (Ia), or a pharmaceutically acceptable salt thereof, wherein $R^4$ is

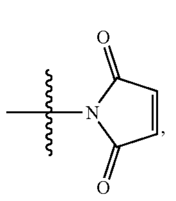

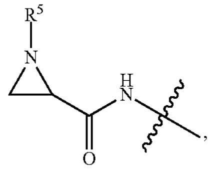

SH, $-S(=O)_2(CH=CH_2)$, $-NR^5S(=O)_2(CH=CH_2)$, $-NR^5C(=O)CH_2Br$, $-NR^5C(=O)CH_2I$, $-NHC(=O)CH_2Br$, or $-NHC(=O)CH_2I$.

Embodiment 49

The compounds of Formula (A), Formula (I) and Formula (Ia), or a pharmaceutically acceptable salt thereof, wherein $R^4$ is

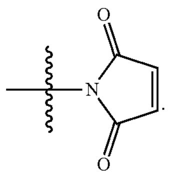

Embodiment 50

The compounds of Formula (A), Formula (I) and Formula (Ia), or a pharmaceutically acceptable salt thereof, wherein $R^4$ is $-ONH_2$.

Embodiment 51

The compounds of Formula (A), Formula (I) and Formula (Ia), or a pharmaceutically acceptable salt thereof, wherein $R^4$ is $-N_3$.

Embodiment 52

The compounds of Formula (A), Formula (I) and Formula (Ia), or a pharmaceutically acceptable salt thereof, wherein $R^4$ is

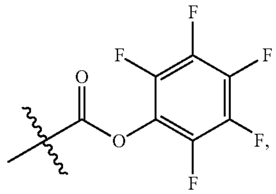

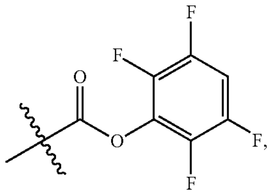

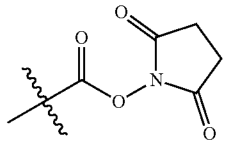

or

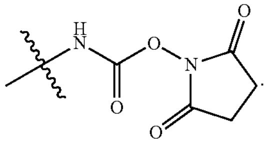

Embodiment 53

The compounds of Formula (A), Formula (I) and Formula (Ia), or a pharmaceutically acceptable salt thereof, wherein $R^4$ is $-NR_5C(=O)CH=CH_2$, $-C(O)NHNH_2$, $-CO_2H$ or $-NH_2$.

Embodiment 54

The compounds of Formula (A), Formula (I) and Formula (Ia), or a pharmaceutically acceptable salt thereof, wherein $R^{14}$ is

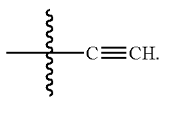 [SMILES: *C#C]

Embodiment 55

The compounds of Formula (A), Formula (I) and Formula (Ia), or a pharmaceutically acceptable salt thereof, wherein $R^{14}$ is

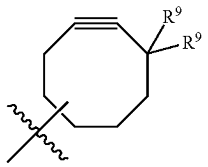
or
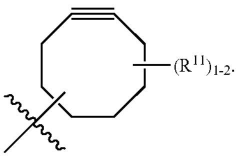

Embodiment 56

The compounds of Formula (A), Formula (I) and Formula (Ia), or a pharmaceutically acceptable salt thereof, wherein $R^{14}$ is

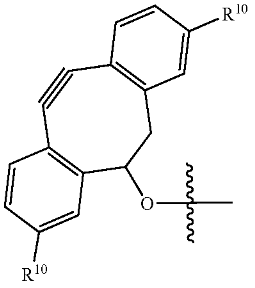
or
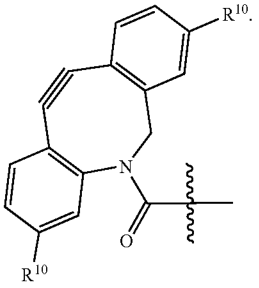

Embodiment 57

The compounds of Formula (A), Formula (I) and Formula (Ia), or a pharmaceutically acceptable salt thereof, wherein $R^{14}$ is

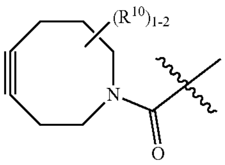
or
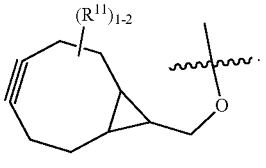

Embodiment 58

The compounds of Formula (A), Formula (I) and Formula (Ia), or a pharmaceutically acceptable salt thereof, wherein $R^{24}$ is, $—N_3$.

Embodiment 59

The compounds of Formula (A), Formula (I) and Formula (Ia), or a pharmaceutically acceptable salt thereof, wherein $R^{24}$ is, $—ONH_2$.

Embodiment 60

The compounds of Formula (A), Formula (I) and Formula (Ia), or a pharmaceutically acceptable salt thereof, wherein $R^{24}$ is

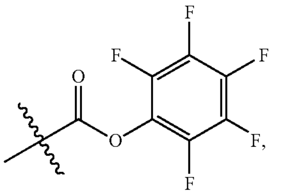
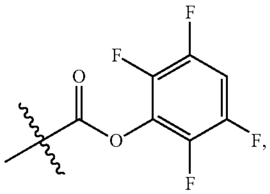
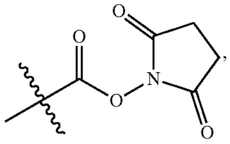
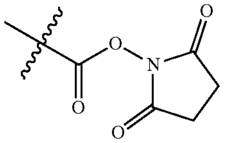
or
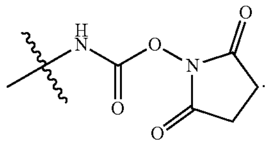

Embodiment 61

The compounds of Formula (A), Formula (I) and Formula (Ia), or a pharmaceutically acceptable salt thereof, wherein $R^{24}$ is $—NR_5C(=O)CH=CH_2$, $—C(O)NHNH_2$, $—CO_2H$ or $—NH_2$.

Embodiment 62

The compounds of Formula (A), Formula (I) and Formula (Ia), or a pharmaceutically acceptable salt thereof, wherein $R^{34}$ is

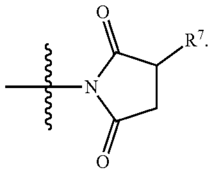

Embodiment 63

The compounds of Formula (A), Formula (I) and Formula (Ia), or a pharmaceutically acceptable salt thereof, wherein $R^{34}$ is

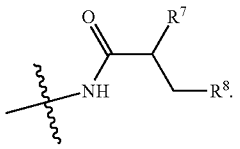

Embodiment 64

The compounds of Formula (A), Formula (I) and Formula (Ia), or a pharmaceutically acceptable salt thereof, wherein $R^{34}$ is

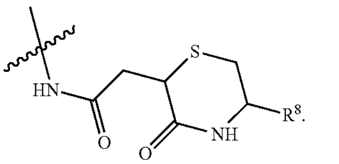

Embodiment 65

The compounds of Formula (A), Formula (I) and Formula (Ia), or a pharmaceutically acceptable salt thereof, wherein $R^{34}$ is $—NR^5C(=O)CH_2R^7$.

Embodiment 69

The compounds of Formula (A), Formula (I) and Formula (Ia), or a pharmaceutically acceptable salt thereof, wherein $R^8$ is $—C(=O)OR^5$.

Immunoconjungates

Immunoconjugates of the invention that comprise such cytotoxic cyclic peptides of the invention as a payload (drug) include conjugates of Formula (B):

Formula (B)

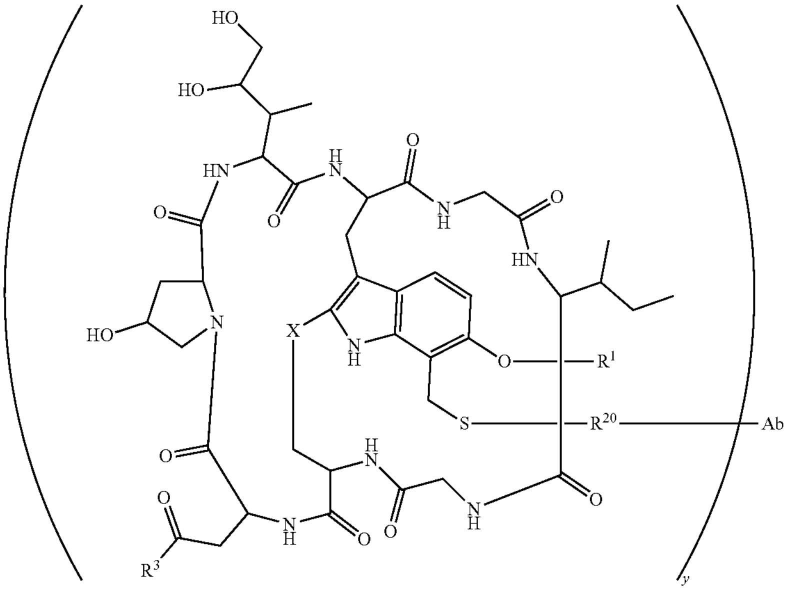

Embodiment 66

The compounds of Formula (A), Formula (I) and Formula (Ia), or a pharmaceutically acceptable salt thereof, wherein each $R^5$ is H.

Embodiment 67

The compounds of Formula (A), Formula (I) and Formula (Ia), or a pharmaceutically acceptable salt thereof, wherein each $R^5$ is $C_1$-$C_6$alkyl.

Embodiment 68

The compounds of Formula (A), Formula (I) and Formula (Ia), or a pharmaceutically acceptable salt thereof, wherein $R^7$ is $—S(CH_2)_nCHR^8NH_2$.

wherein:

X is S(=O), $S(=O)_2$ or S;

Ab represents an antigen binding moiety;

y is an integer from 1 to 16;

$R^1$ is H, $—CH_3$ or $—CD_3$;

$R^3$ is $—NH_2$ or —OH;

$L_{20}$ is $-L_1R^{40}$;

$L_1$ is $—((CH_2)_mO)_n(CH_2)_mX_3L_4$- or $—((CH_2)_mO)_n(CH_2)_mX_4L_4$-;

$L_4$ is $—((CH_2)_m—$ or $—((CH_2)_mNHC(=O)X_1X_2C(=O)(CH_2)_m—$;

$X_1$ is

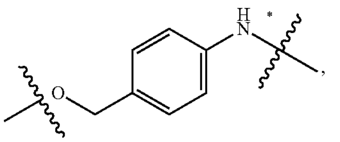

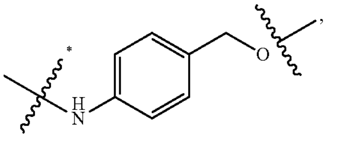

-continued
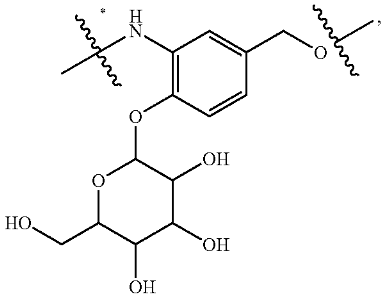
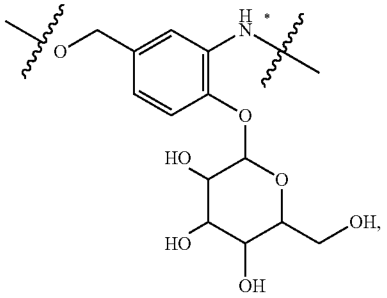
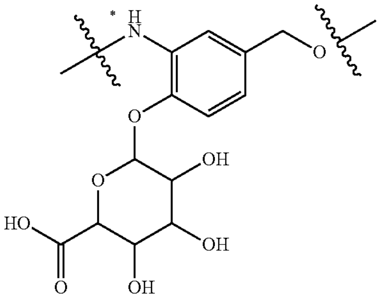
or
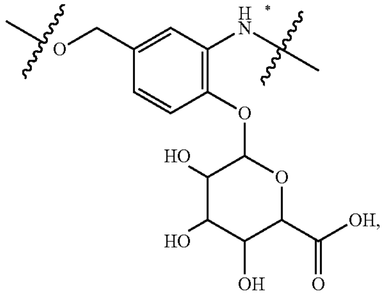
where the * indicates attachment point to $X_2$;
$X_2$ is
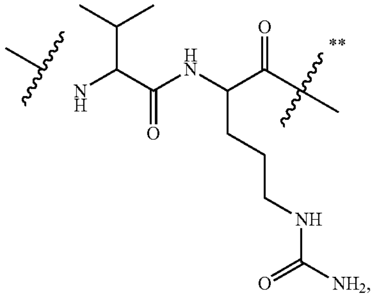
-continued
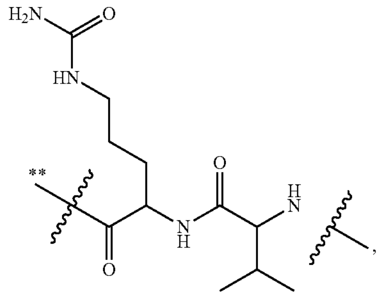
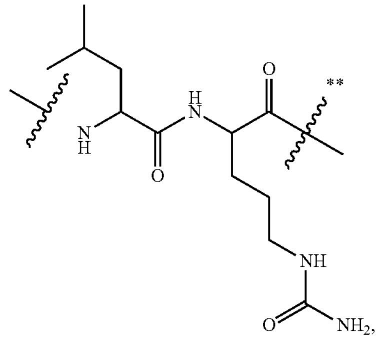
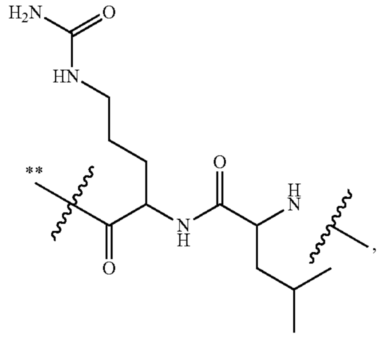
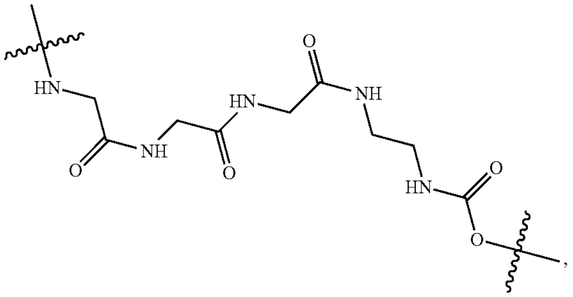
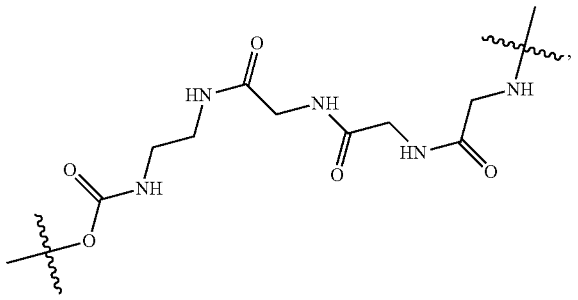

-continued
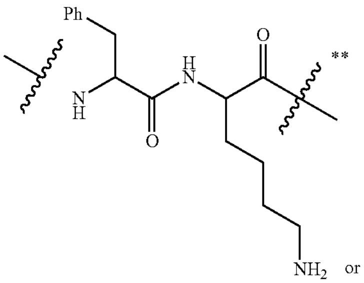
or
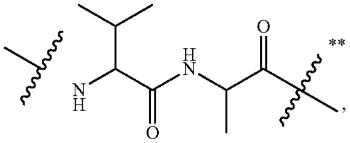
where the ** indicates attachment point to $X_1$;
$X_3$ is
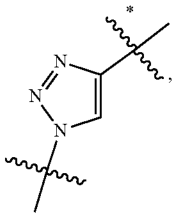
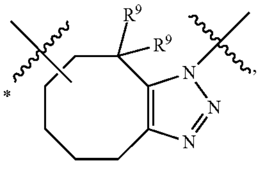
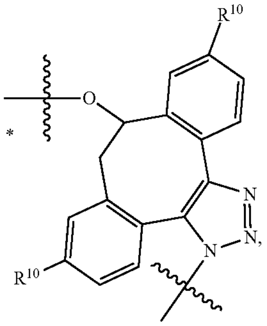
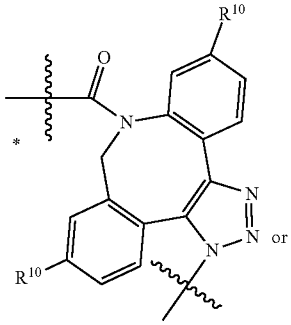
or
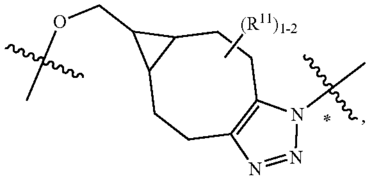
where the * indicates attachment point to $L_4$;
$X_4$ is
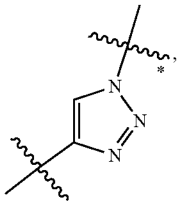
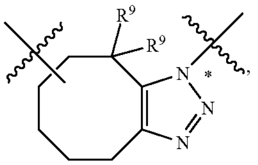
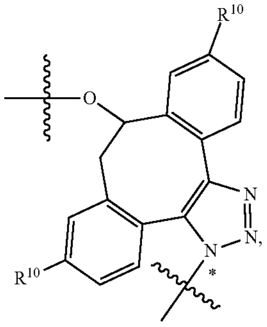
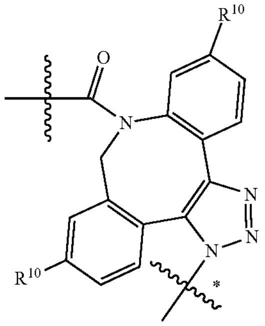
or
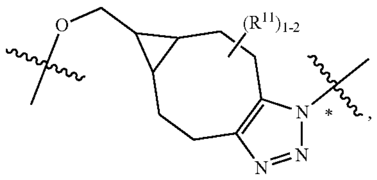
where the * indicates attachment point to $L_4$;
$R^{40}$ is
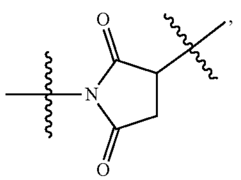
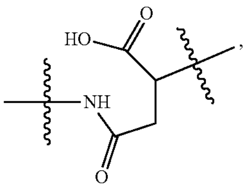

-continued

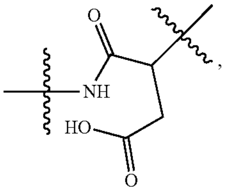

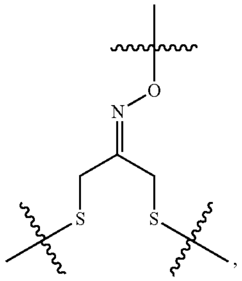

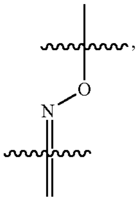

$-NR^5C(=O)CH_2-$, $-NHC(=O)CH_2-$, $-S(=O)_2CH_2CH_2-$, $-(CH_2)_2S(=O)_2CH_2CH_2-$, $-NR^5S(=O)_2CH_2CH_2$, $-NR^5C(=O)CH_2CH_2-$, $-NH-$, $-C(=O)-$, $-NHC(=O)-$, $-CH_2NHCH_2CH_2-$, $-NHCH_2CH_2-$, $-S-$

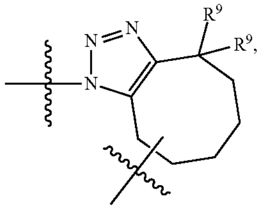

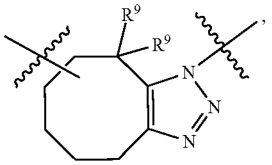

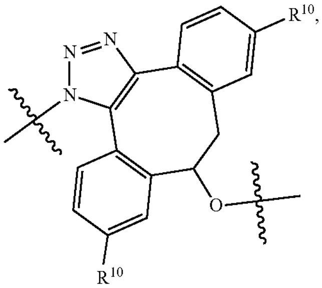

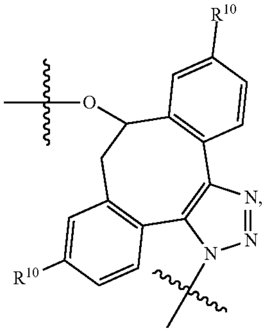

-continued

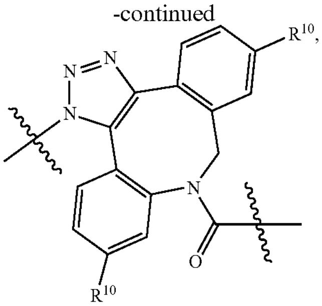

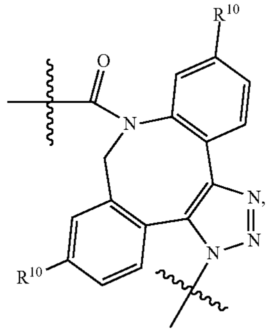

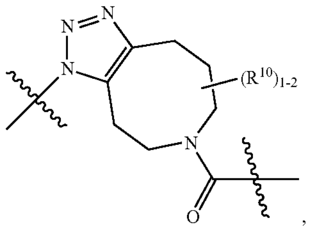

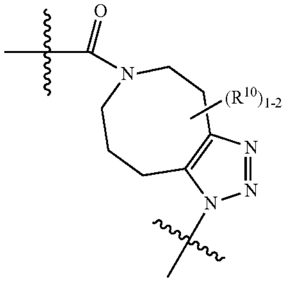

or

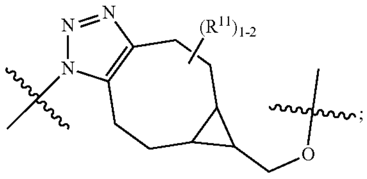

each $R^5$ is independently selected from H, and $C_1$-$C_6$alkyl;

each $R^9$ is independently selected from H, $C_1$-$C_6$alkyl, F, Cl, and —OH;

each $R^{10}$ is independently selected from H, $C_1$-$C_6$alkyl, F, Cl, $-NH_2$, $-OCH_3$, $-OCH_2CH_3$, $-N(CH_3)_2$, —CN, $-NO_2$ and —OH;

each $R^{11}$ is independently selected from H, $C_1$-$C_6$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

Certain aspects and examples of the immunoconjugates of the invention are provided in the following listing of enumerated embodiments of the invention. It will be recognized that features specified in each embodiment may be combined with other specified features to provide further embodiments of the present invention.

Embodiment 70

An immunoconjugates of Formula (II), wherein

Formula (II)

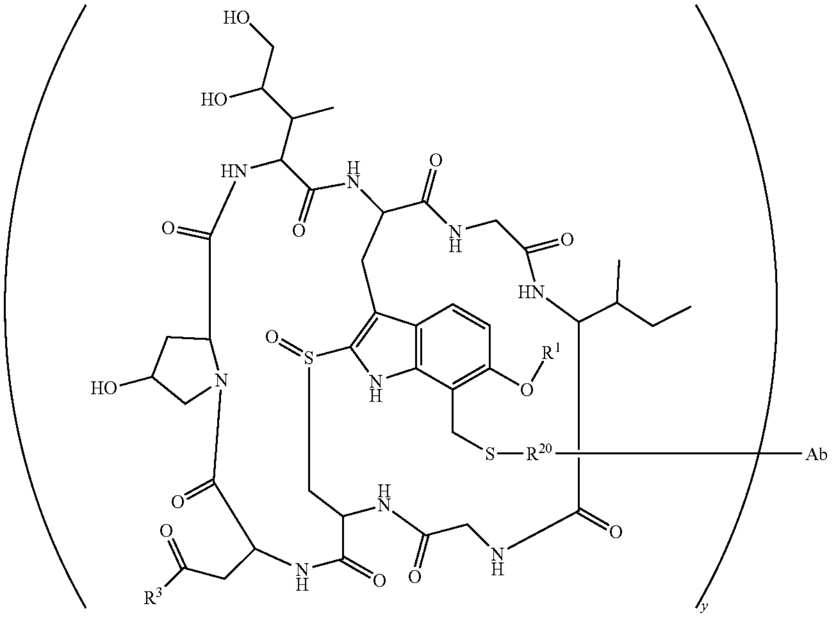

wherein:

Ab represents an antigen binding moiety;

y is an integer from 1 to 16;

$R^1$ is H, $-CH_3$ or $-CD_3$; $R^3$ is $-NH_2$ or $-OH$;

$L_{20}$ is $-L_1R^{40}$;

$L_1$ is $-((CH_2)_mO)_n(CH_2)_mX_3L_4-$ or $-((CH_2)_mO)_n(CH_2)_mX_4L_4-$;

$L_4$ is $-((CH_2)_m-$ or $-((CH_2)_mNHC(=O)X_1X_2C(=O)(CH_2)_m-$;

$X_1$ is

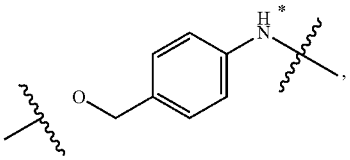

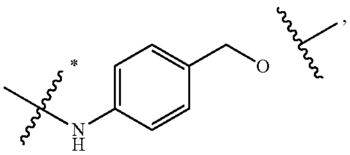

-continued

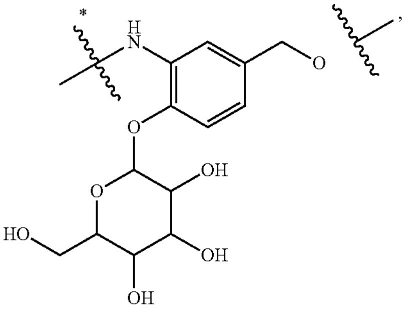

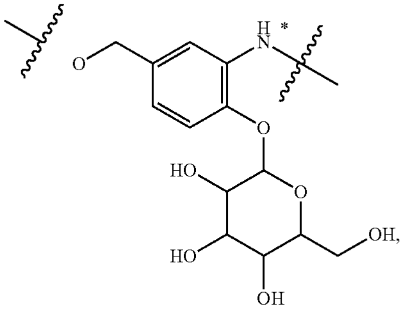

-continued
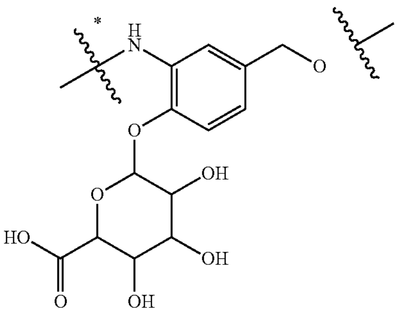
or
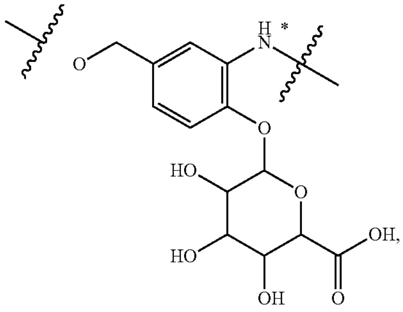
where the * indicates attachment point to $X_2$;
$X_2$ is
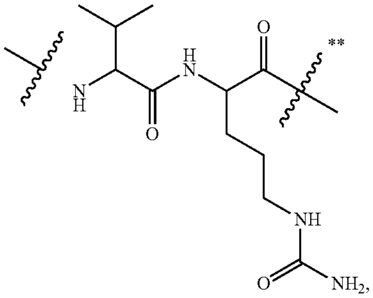
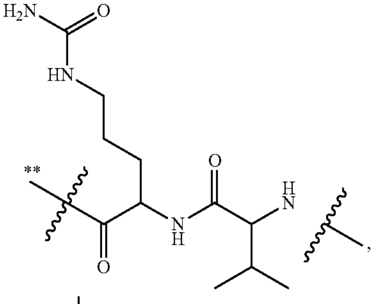
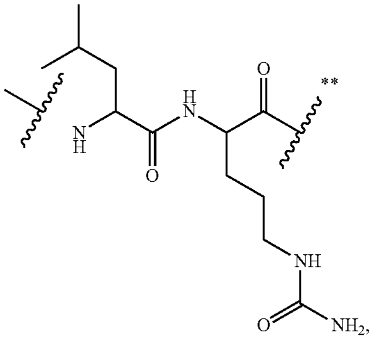
-continued
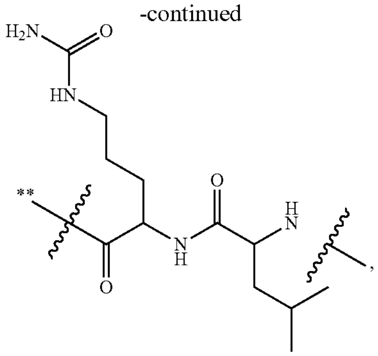
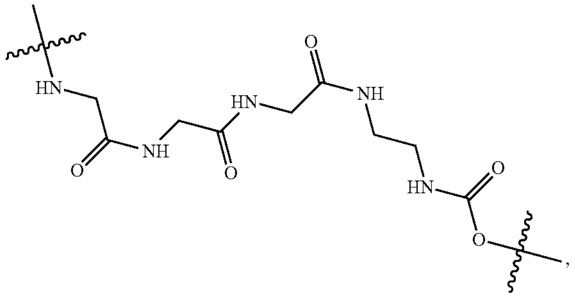
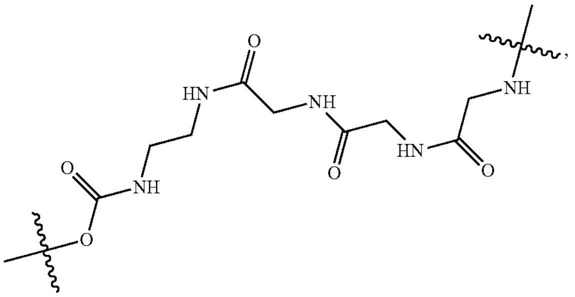
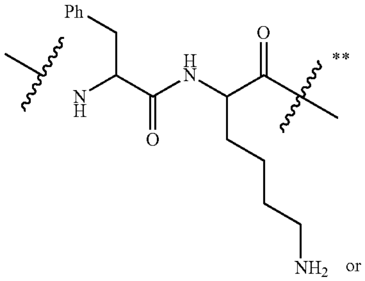
or
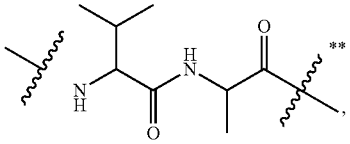
where the ** indicates attachment point to $X_1$;
$X_3$ is
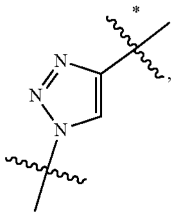
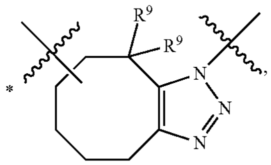

-continued
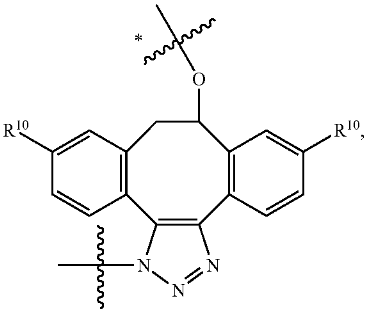
,
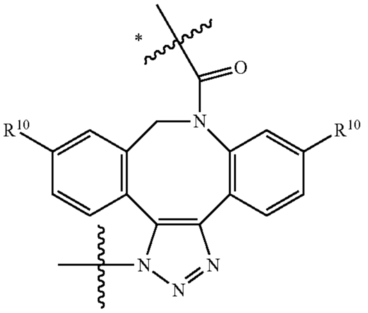
or
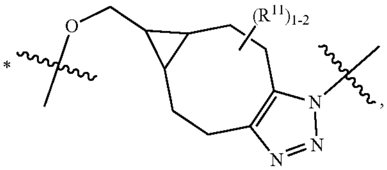
,
where the * indicates attachment point to $L_4$;
$X_4$ is
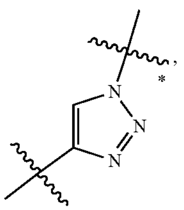
,
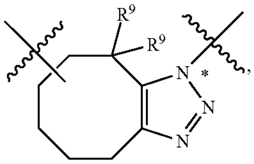
,
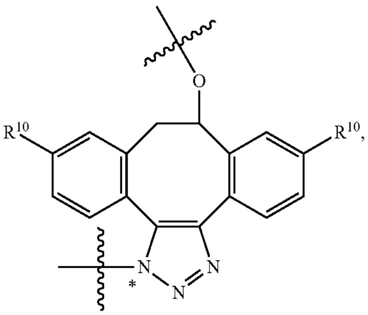
,
-continued
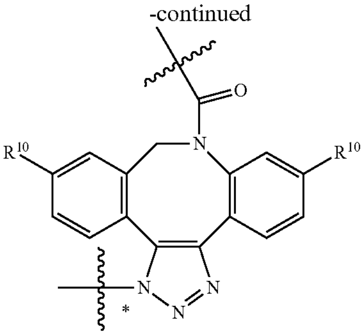
or
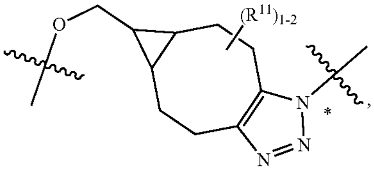
,
where the * indicates attachment point to $L_4$;
$R_{40}$ is
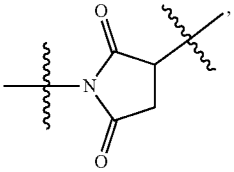
,
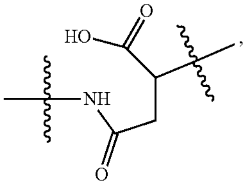
,
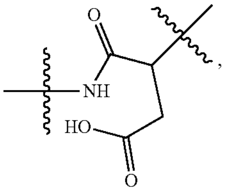
,
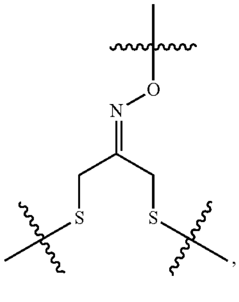
,
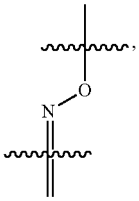
$-NR^5C(=O)CH_2-$, $-NHC(=O)CH_2-$, $-S(=O)_2CH_2CH_2-$, $-(CH_2)_2S(=O)_2CH_2CH_2-$, $-NR^5S(=O)_2CH_2CH_2$, $-NR^5C(=O)CH_2CH_2-$, $-NH-$, $-C(=O)-$, $-NHC(=O)-$, $-CH_2NHCH_2CH_2-$, $-NHCH_2CH_2-$, $-S-$,

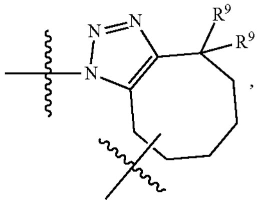

,

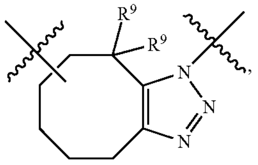

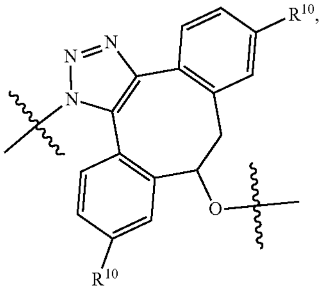

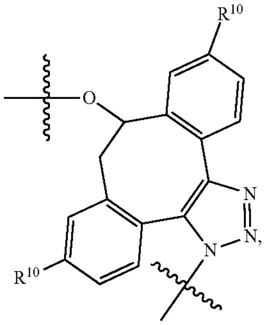

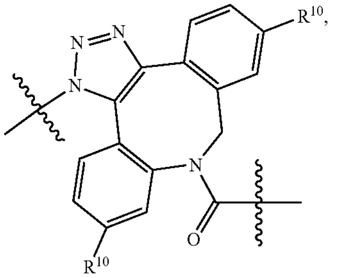

-continued

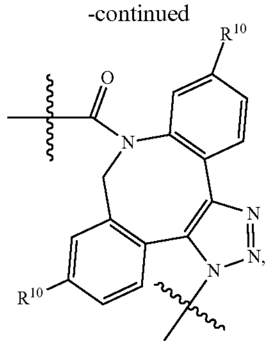

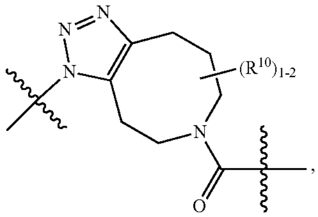

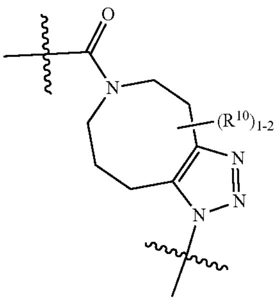

or

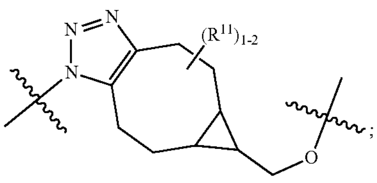

each $R^5$ is independently selected from H and $C_1$-$C_6$alkyl;

each $R^9$ is independently selected from H, $C_1$-$C_6$alkyl, F, Cl, and —OH;

each $R^{10}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{11}$ is independently selected from H, $C_1$-$C_6$alkyl, fluoro, benzyloxy substituted with —C(═O)OH, benzyl substituted with —C(═O)OH, $C_{1-4}$alkoxy substituted with —C(═O)OH and $C_{1-4}$alkyl substituted with —C(═O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

Embodiment 71
An immunoconjugates of Formula (IIa)
Formula (IIa)
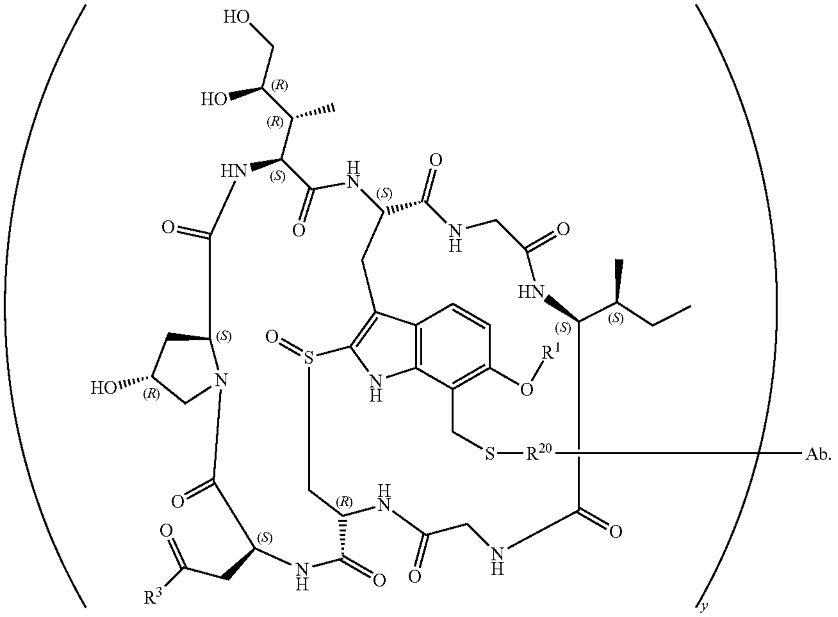
wherein:
Ab represents an antigen binding moiety;
y is an integer from 1 to 16;
$R^1$ is H, —$CH_3$ or —$CD_3$; $R^3$ is —$NH_2$ or —OH;
$L_{20}$ is -$L_1R^{40}$;
$L_1$ is —$((CH_2)_mO)_n(CH_2)_mX_3L_4$- or —$((CH_2)_mO)_n(CH_2)_mX_4L_4$-;
$L_4$ is —$((CH_2)_m$— or —$((CH_2)_mNHC(=O)X_1X_2C(=O)(CH_2)_m$—;
$X_1$ is
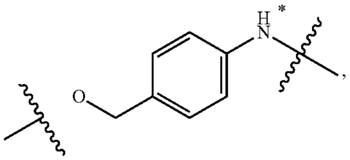,
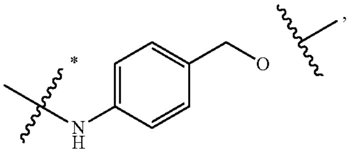,
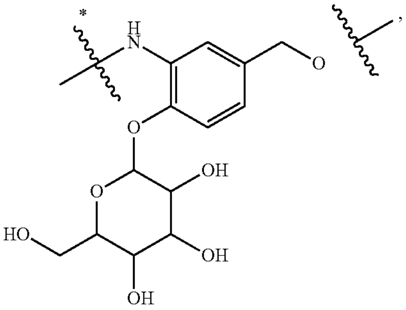,
-continued
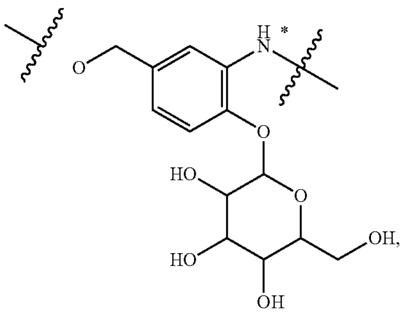,
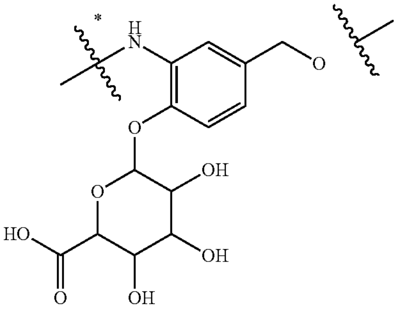
or -continued
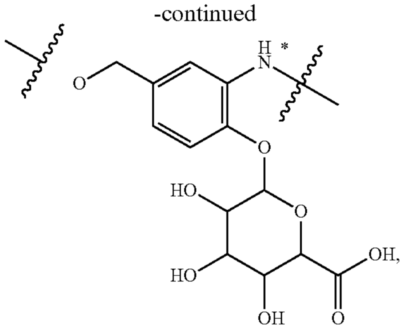
where the * indicates attachment point to $X_2$;
$X_2$ is
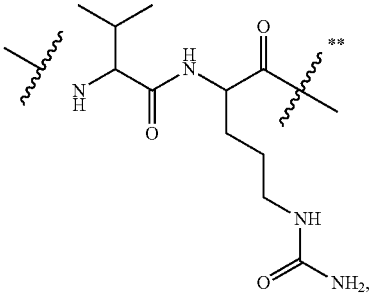
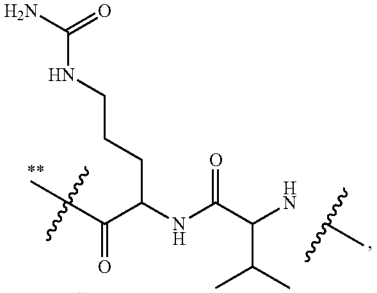
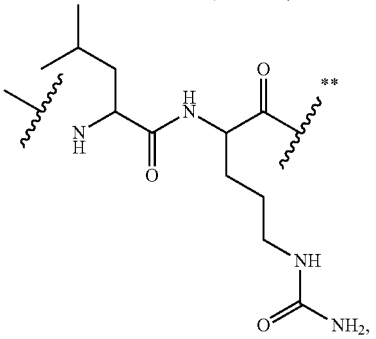
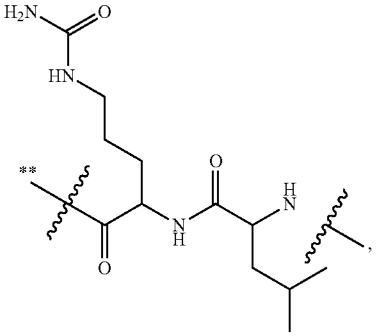
-continued
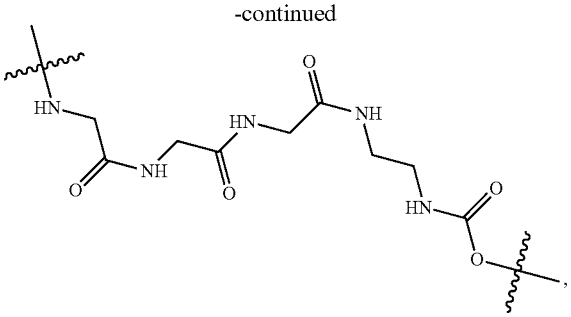
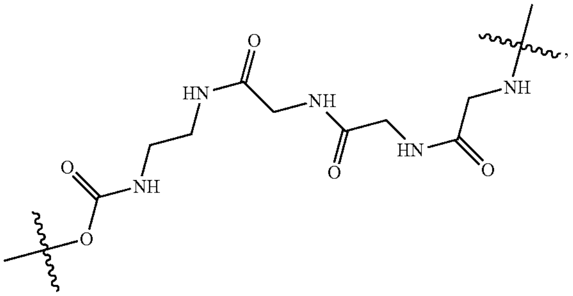
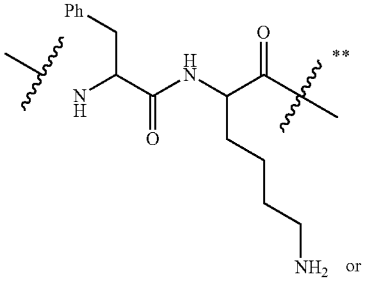
or
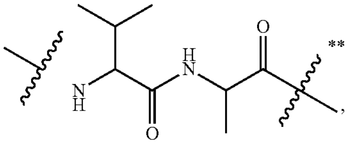
where the ** indicates attachment point to $X_1$;
$X_3$ is
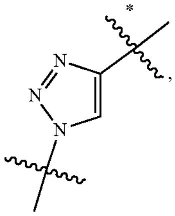
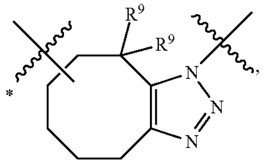
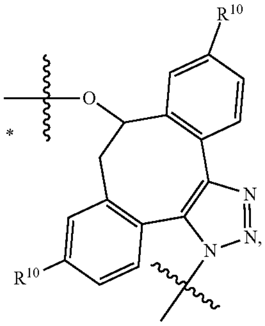

-continued
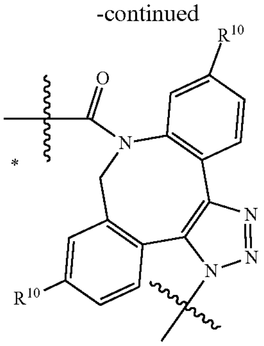 or
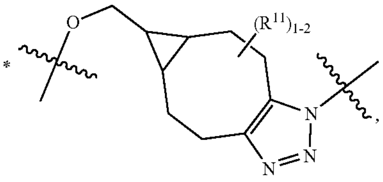
where the * indicates attachment point to $L_4$;
$X_4$ is
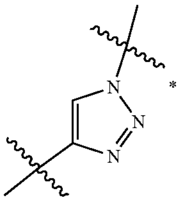,
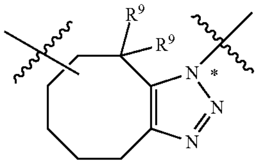,
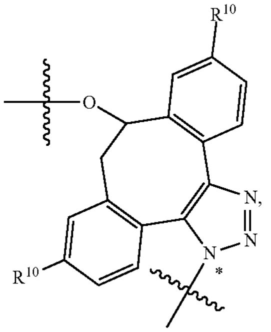
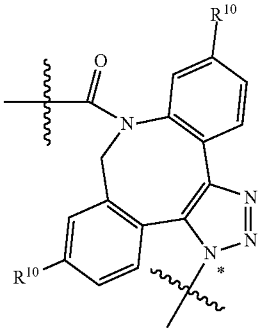 or
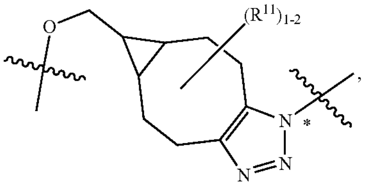
where the * indicates attachment point to $L_4$;
$R^{40}$ is
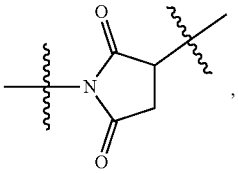,
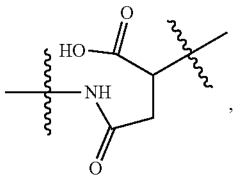,
-continued
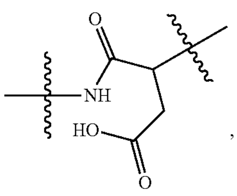,
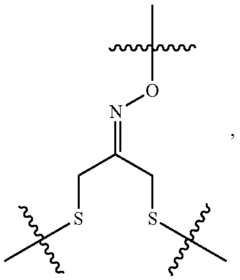,
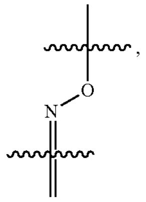
$—NR^5C(═O)CH_2—$, $—NHC(═O)CH_2—$, $—S(═O)_2CH_2CH_2—$, $—(CH_2)_2S(═O)_2CH_2CH_2—$, $—NR^5S(═O)_2CH_2CH_2$, $—NR^5C(═O)CH_2CH_2—$, $—NH—$, $—C(═O)—$, $—NHC(═O)—$, $—CH_2NHCH_2CH_2—$, $—NHCH_2CH_2—$, $—S—$,
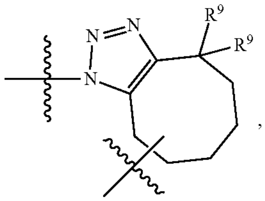,
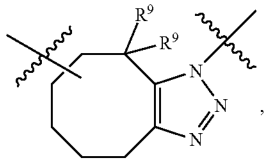,
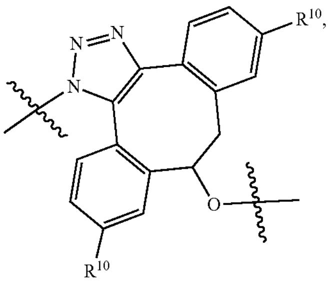
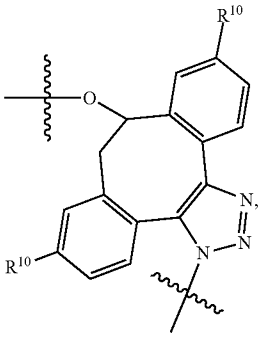

-continued

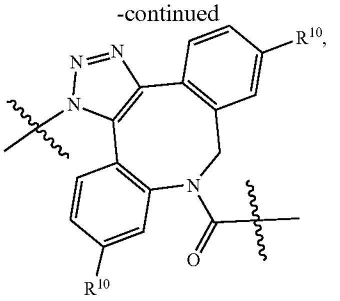

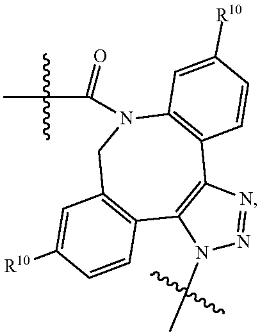

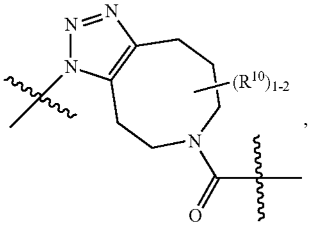
,

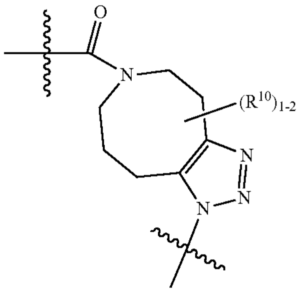

or

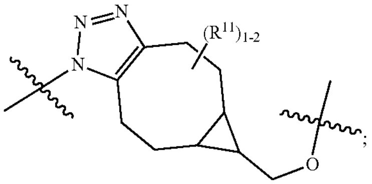

each $R^5$ is independently selected from H and $C_1$-$C_6$alkyl;

each $R^9$ is independently selected from H, $C_1$-$C_6$alkyl, F, Cl, and —OH;

each $R^{10}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{11}$ is independently selected from H, $C_{1-6}$alkyl, fluoro, benzyloxy substituted with —C(═O)OH, benzyl substituted with —C(═O)OH, $C_{1-4}$alkoxy substituted with —C(═O)OH and $C_{1-4}$alkyl substituted with —C(═O)OH;

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

Embodiment 72

The immunoconjugates of Formula (B), Formula (II) and Formula (IIa), wherein:

Ab represents an antigen binding moiety;

y is an integer from 1 to 16;

$R^1$ is H, —$CH_3$ or —$CD_3$;

$R^3$ is —$NH_2$ or —OH;

$L_{20}$ is -$L_1R^{40}$;

$L_1$ is —$((CH_2)_mO)_n(CH_2)_mX_3L_4$-;

$L_2$ is —$((CH_2)_mO)_n(CH_2)_m$—;

$L_3$ is —$((CH_2)_mO)_n(CH_2)_mX_3L_4$- or —$((CH_2)_mO)_n(CH_2)_m$—;

$L_4$ is —$(CH_2)_m$— or —$(CH_2)_m$NHC(═O)$X_1X_2$C(═O)$(CH_2)_m$—;

$X_1$ is

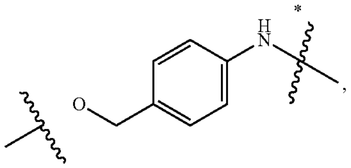

where the * indicates attachment point to $X_2$;

$X_2$ is

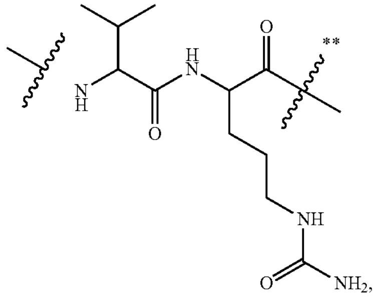

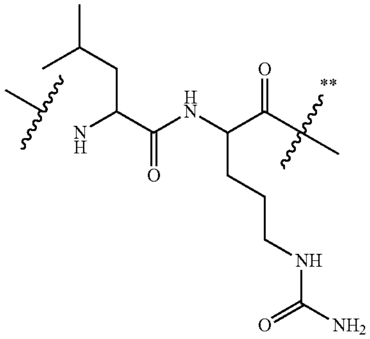

or

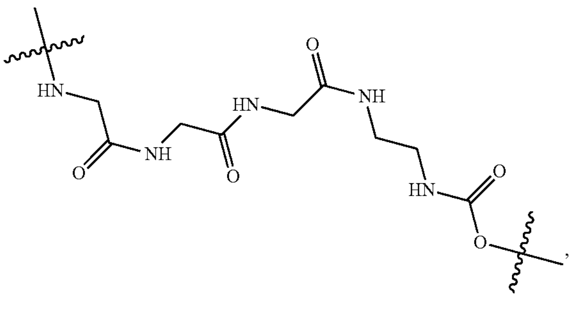

where the ** indicates attachment point to $X_1$;

$X_3$ is
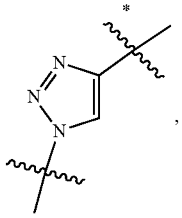 [SMILES: *c1cn(*)nn1]
,
where the * indicates attachment point to $L_4$;
$R^{40}$ is
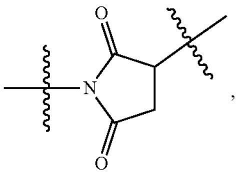
,
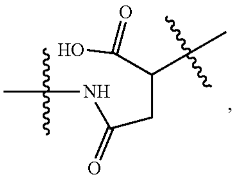
,
-continued
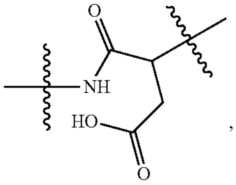
,
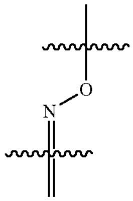
or
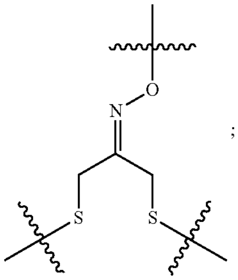
;
each m is independently selected from 1, 2, 3, 4, 5, 6, 7, 8, 9 and 10, and
each n is independently selected from 1, 2, 3, 4, 5, 6, 7, 8, 9, 10, 11, 12, 13 and 14.
Embodiment 73
The immunoconjugates of Formula (B), Formula (II) and Formula (IIa), wherein $L_{20}$ is
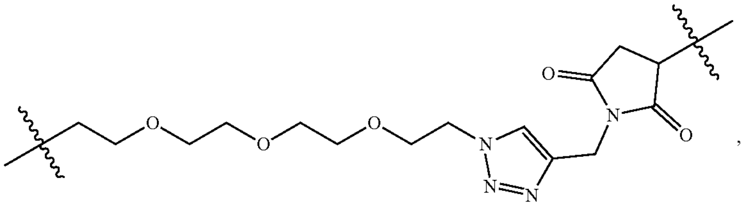
,
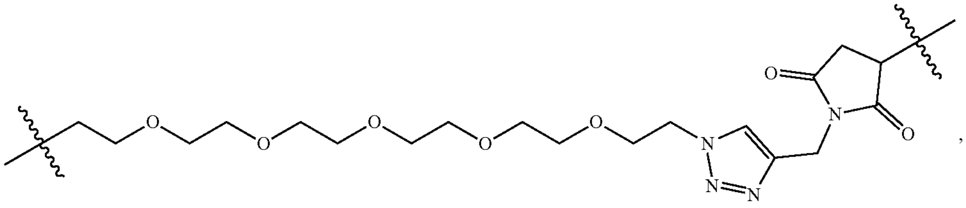
,
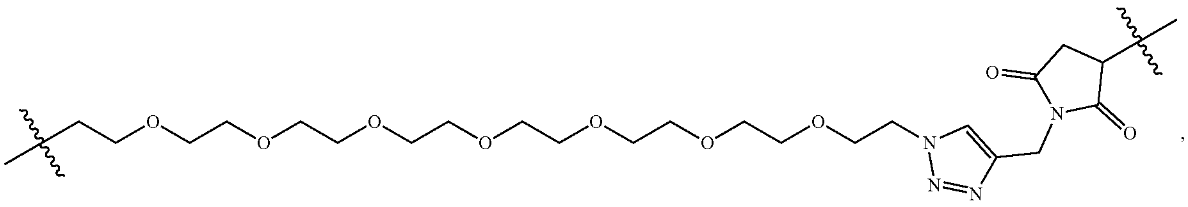
,
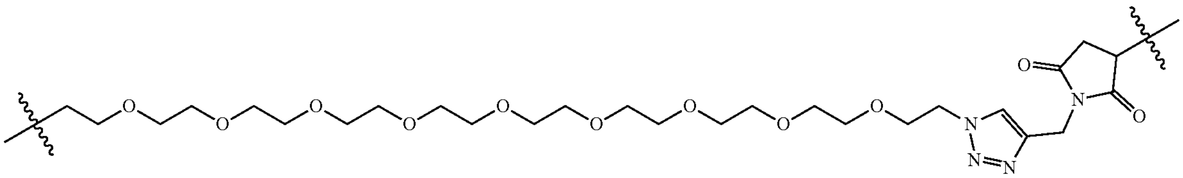
, -continued
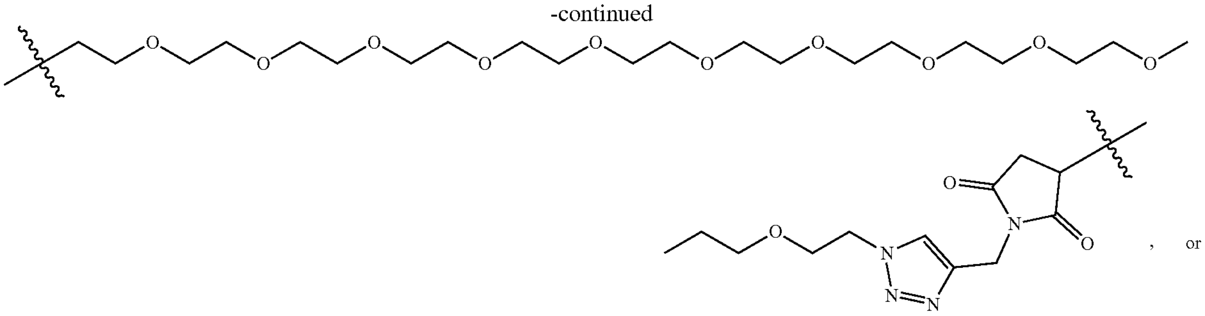
, or
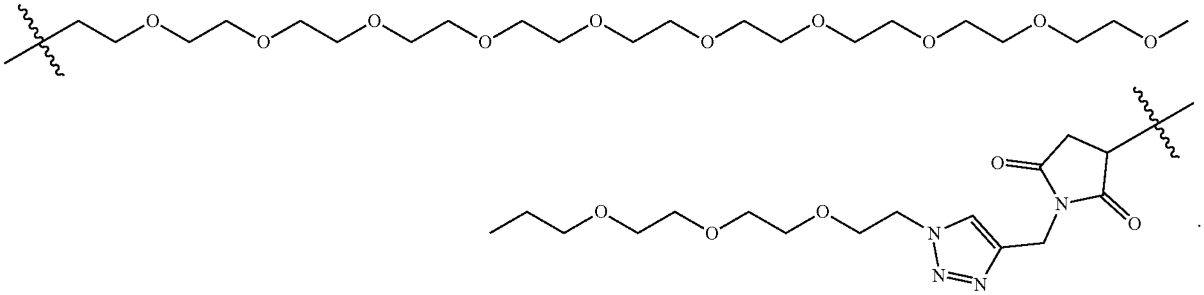
.
Embodiment 74
The immunoconjugates of Formula (B), Formula (II) and Formula (IIa), wherein $L_{20}$ is
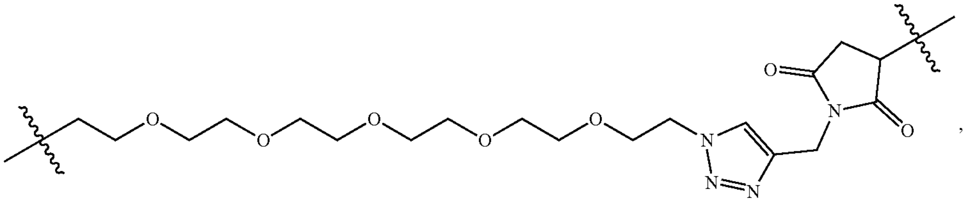
,
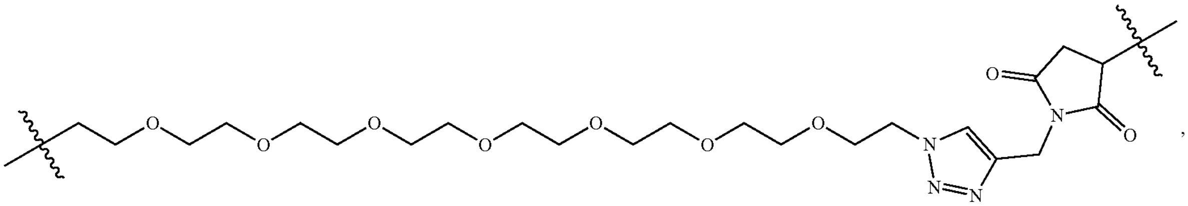
,
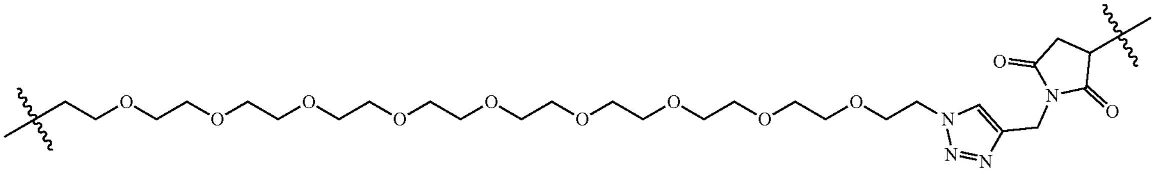
or
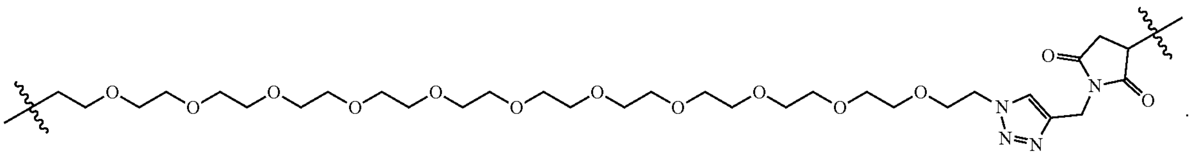
.

Embodiment 75
The immunoconjugates of Formula (B), Formula (II) and Formula (IIa), wherein $L_{20}$ is
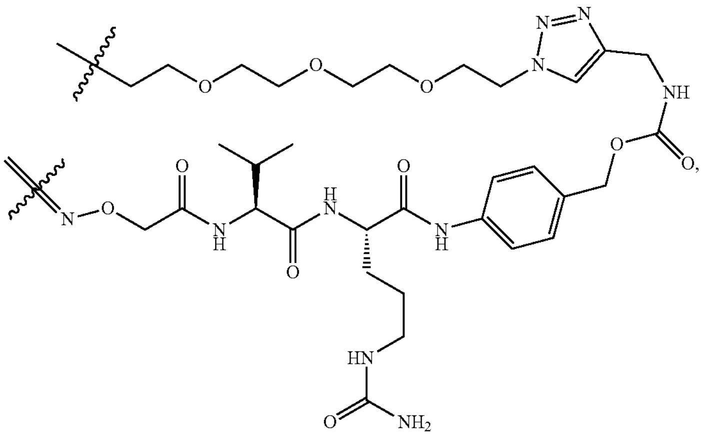
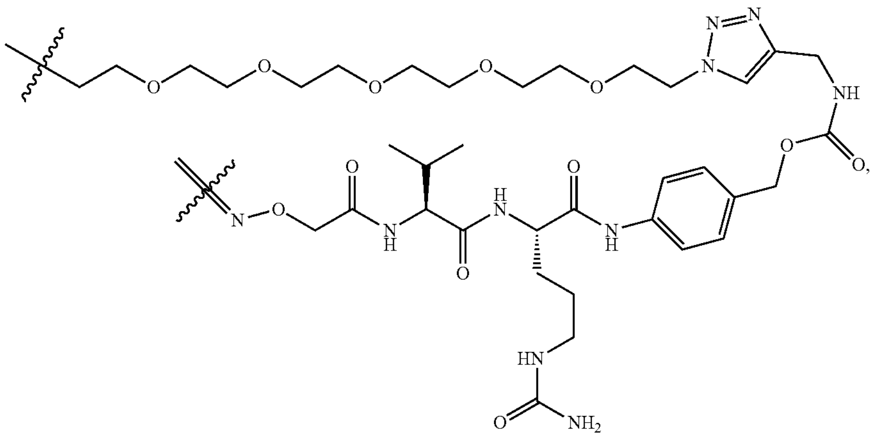
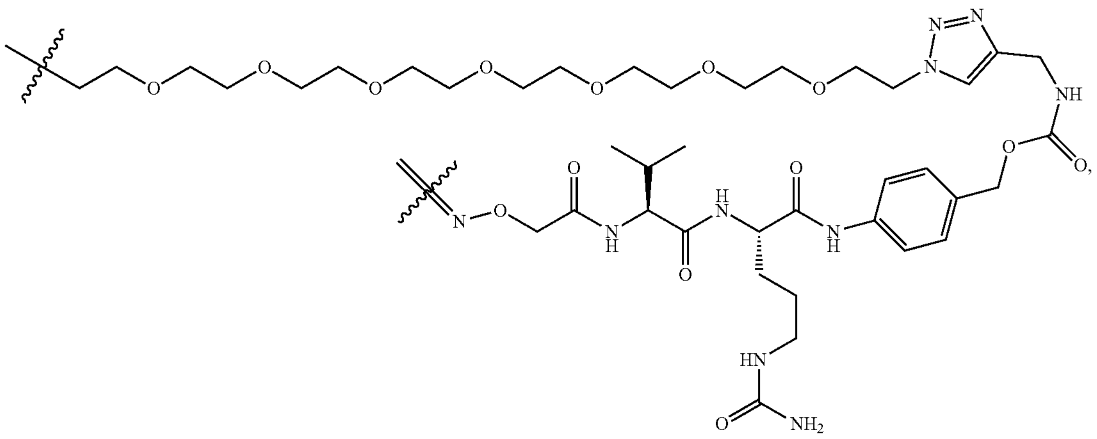

-continued
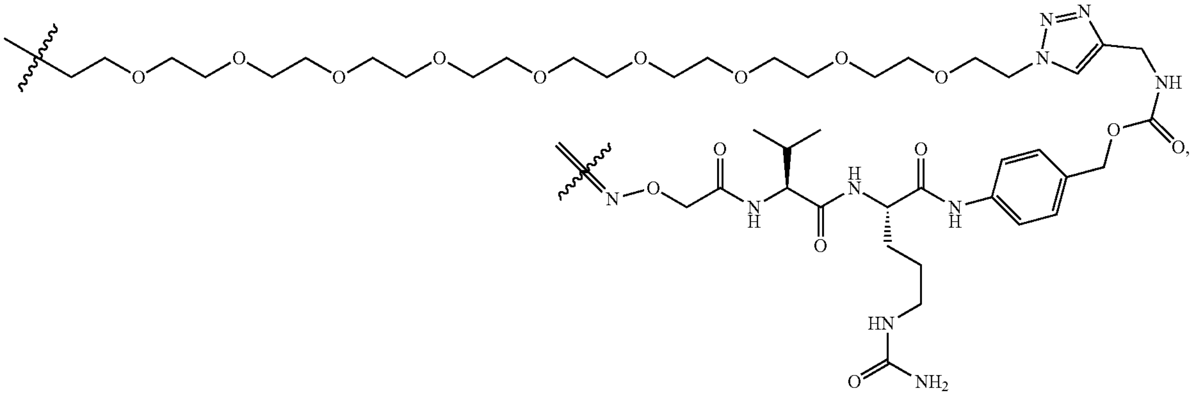
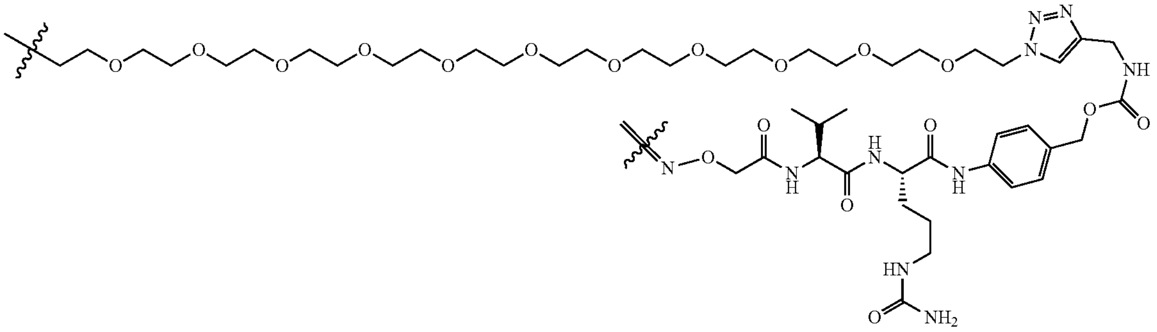
or
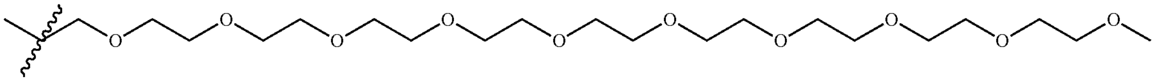
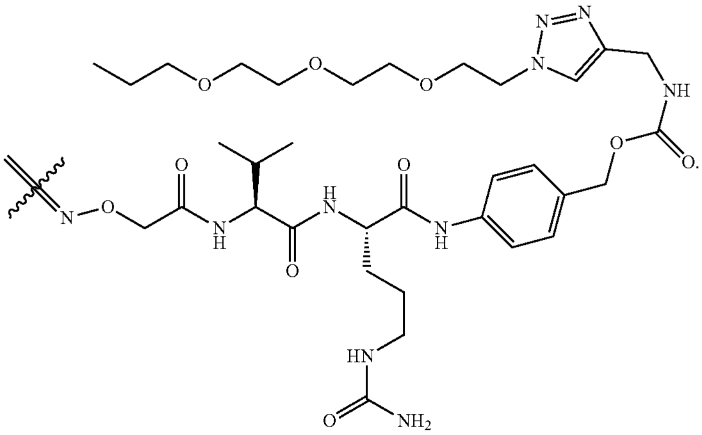

Embodiment 76
The immunoconjugates of Formula (B), Formula (II) and Formula (IIa), wherein $L_{20}$ is
Embodiment 77
The immunoconjugates of Formula (B), Formula (II) and Formula (IIa), wherein $L_{20}$ is
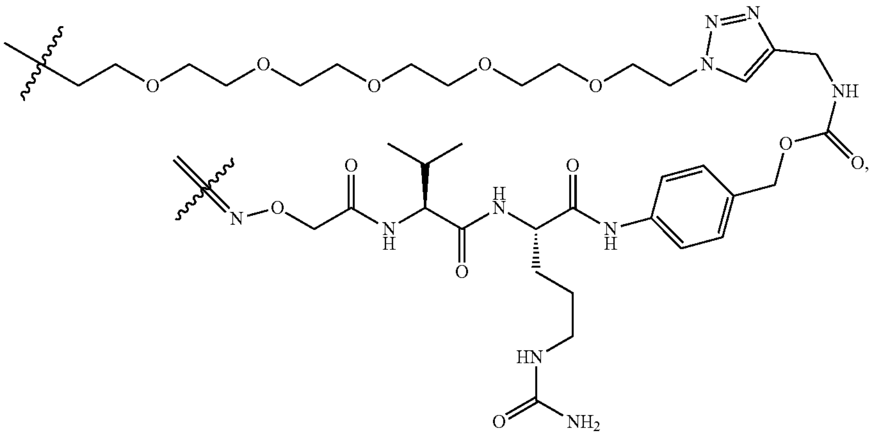
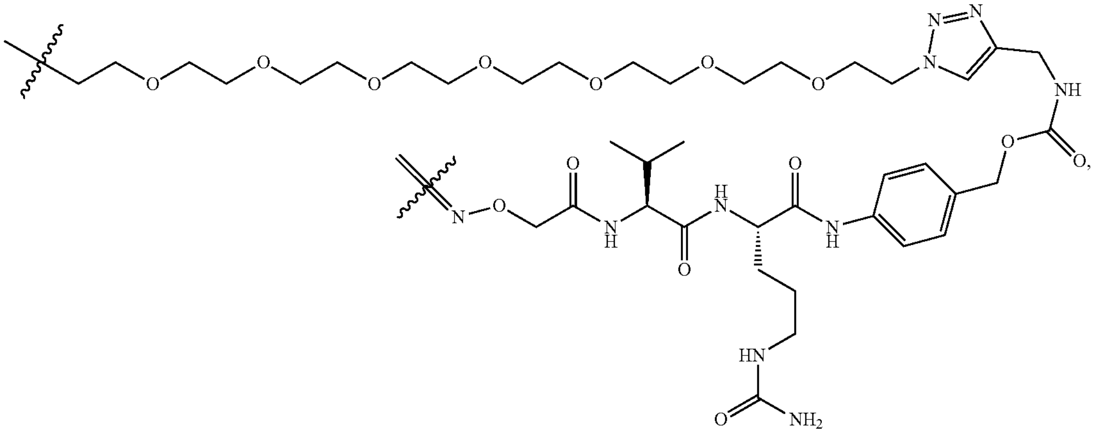
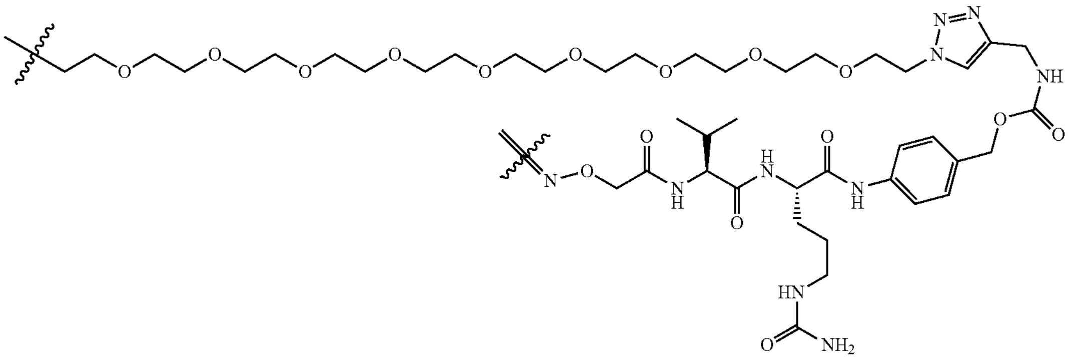
or
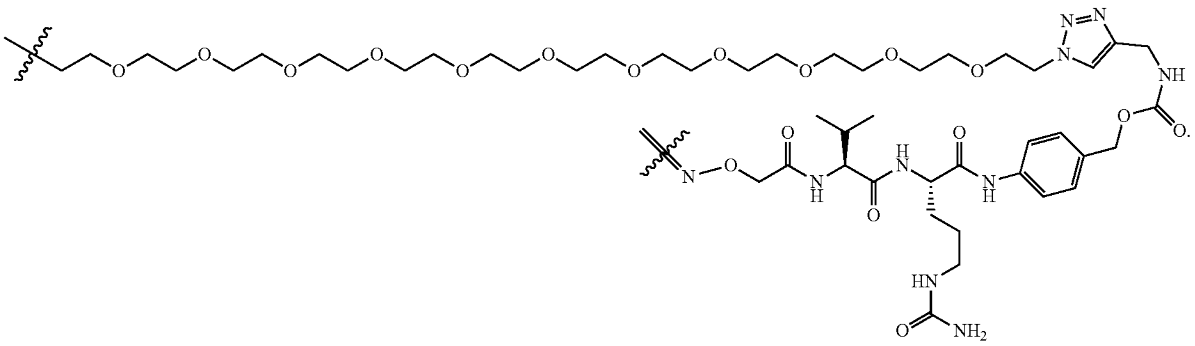 [SMILES: *CCOCCOCCOCCOCCOCCOCCOCCOCCOCCOCCOCCn1cc(CNC(=O)OCc2ccc(NC(=O)[C@H](CCCNC(N)=O)NC(=O)[C@@H](NC(=O)CON=*)C(C)C)cc2)nn1]

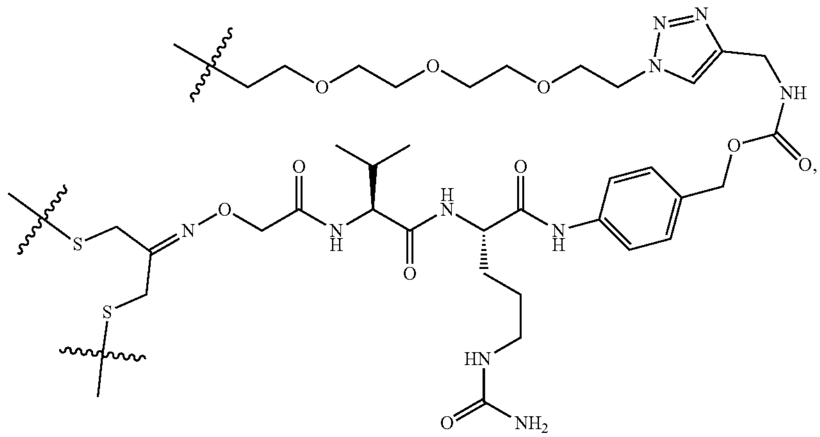
,
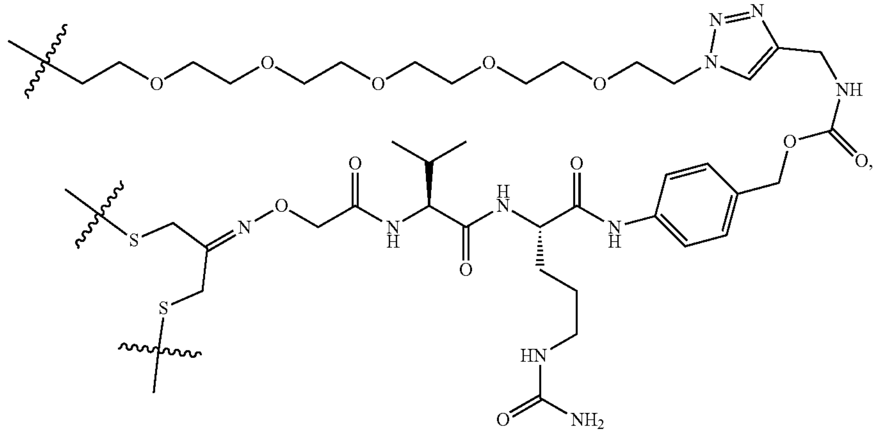
,
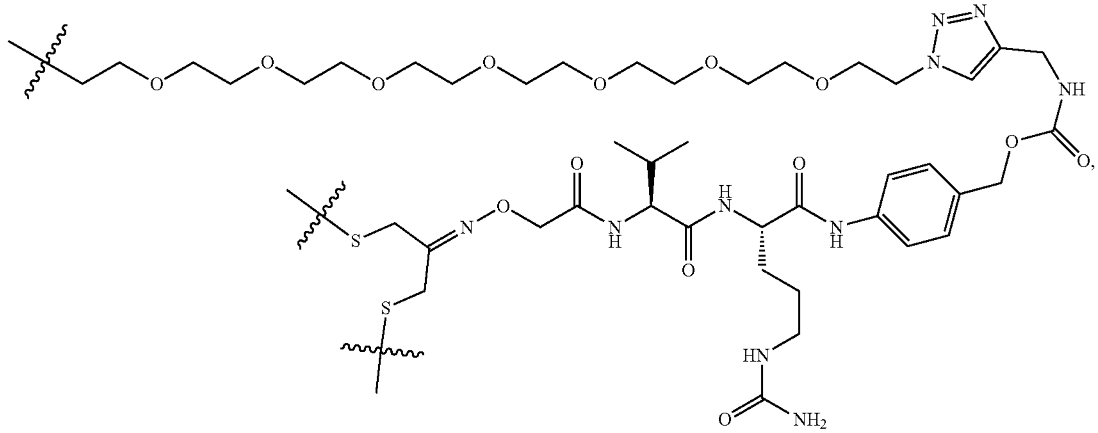
,
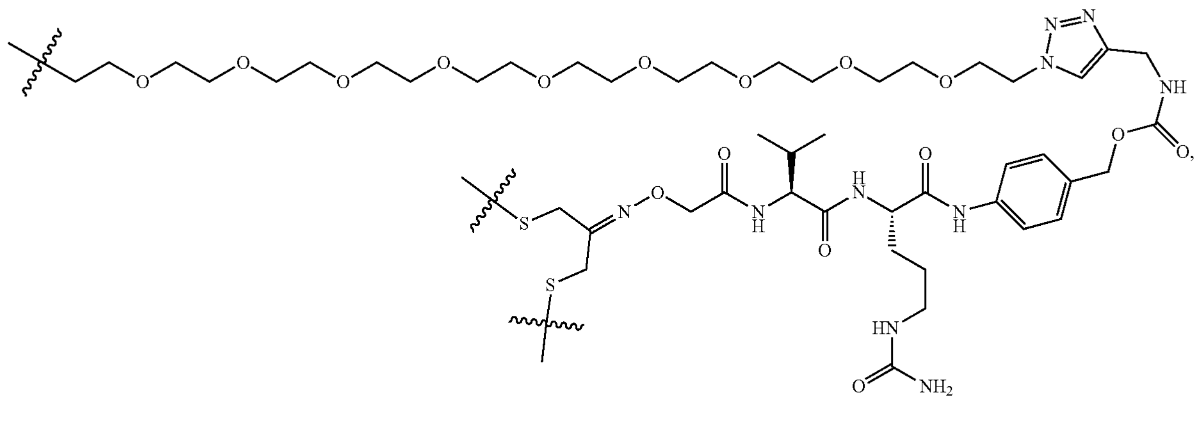
,

-continued
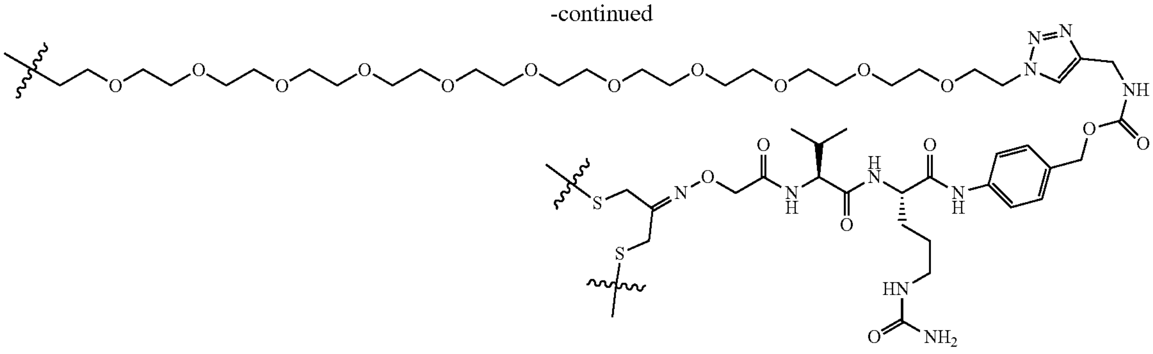
or
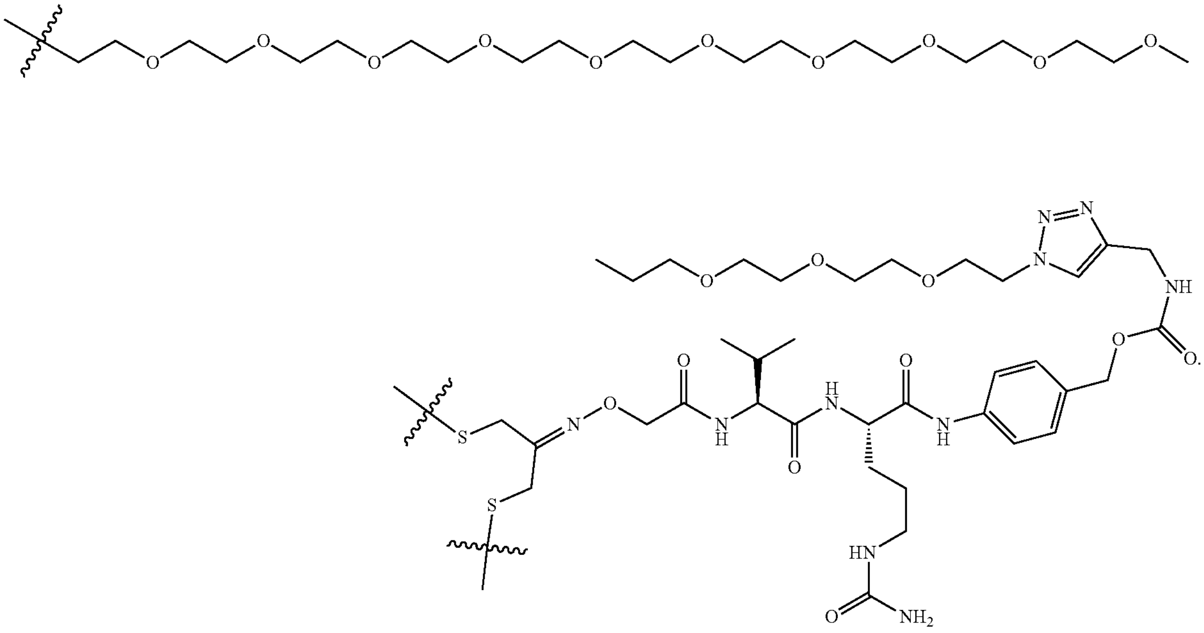
Embodiment 78
The immunoconjugates of Formula (B), Formula (II) and Formula (IIa), wherein $L_{20}$ is
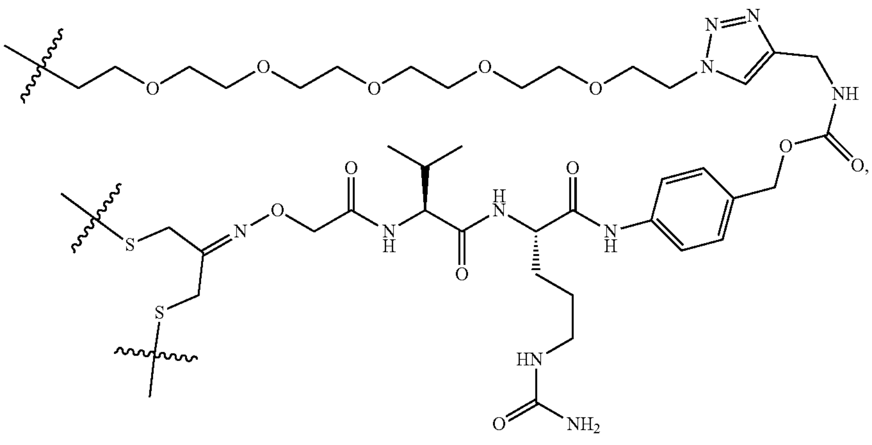

-continued
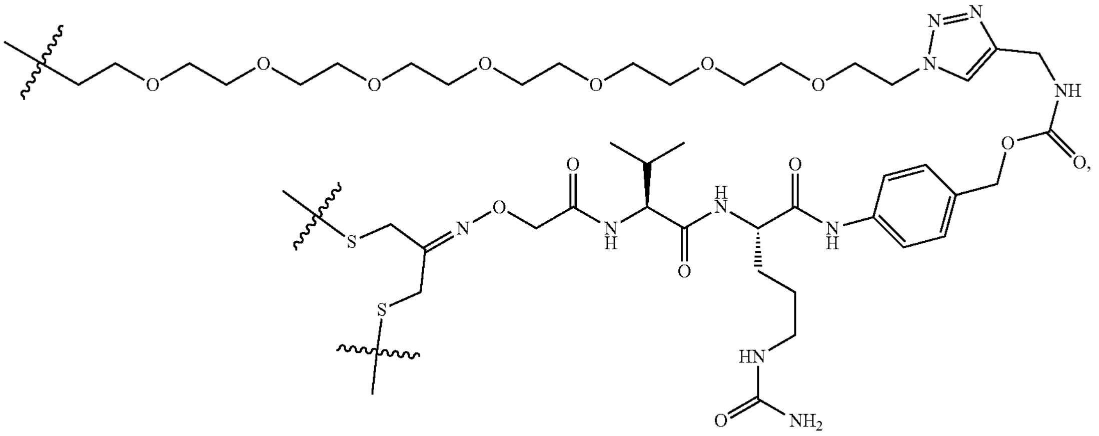
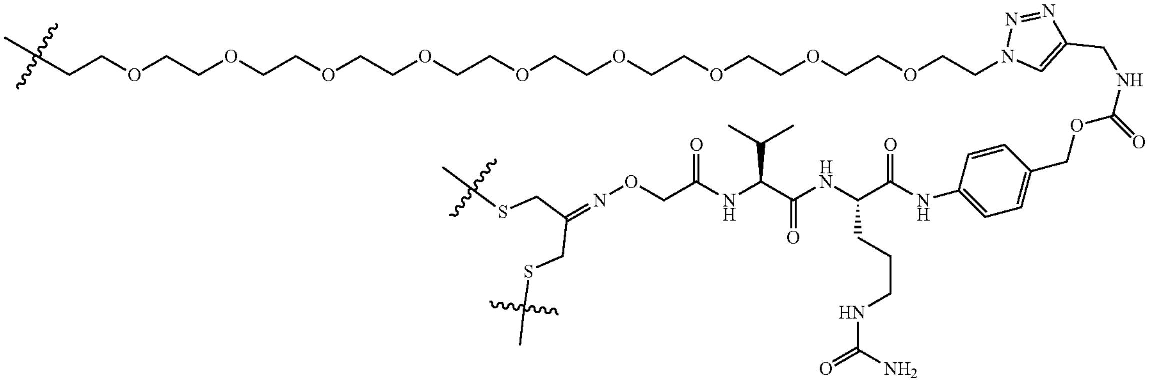
or
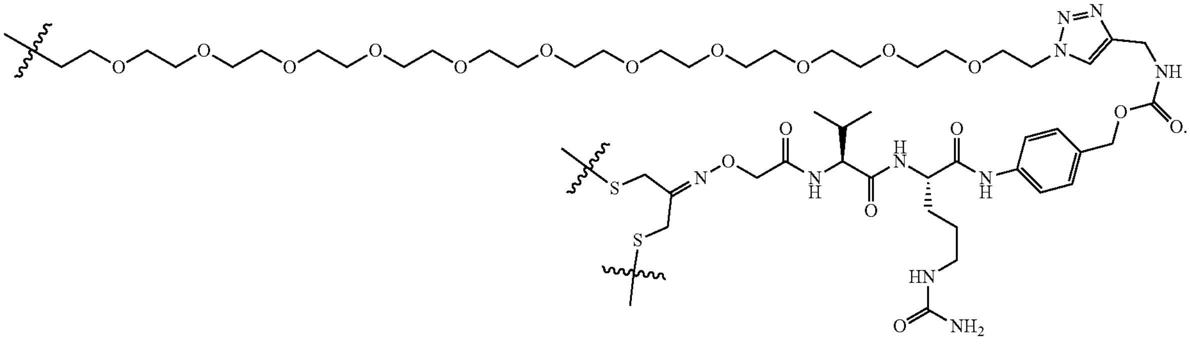 [SMILES: *CCOCCOCCOCCOCCOCCOCCOCCOCCOCCOCCOCCn1cc(CNC(=O)OCc2ccc(NC(=O)[C@H](CCCNC(N)=O)NC(=O)[C@@H](NC(=O)CON=C(CS*)CS*)C(C)C)cc2)nn1]

Embodiment 79
The immunoconjugates of Formula (B), Formula (II) and Formula (IIa), wherein $L_{20}$ is
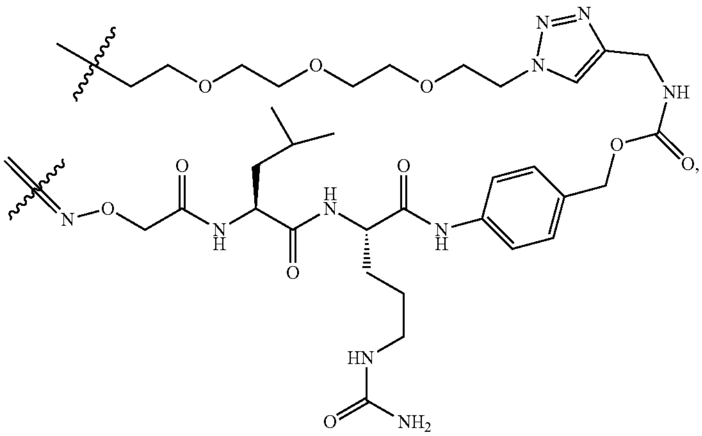
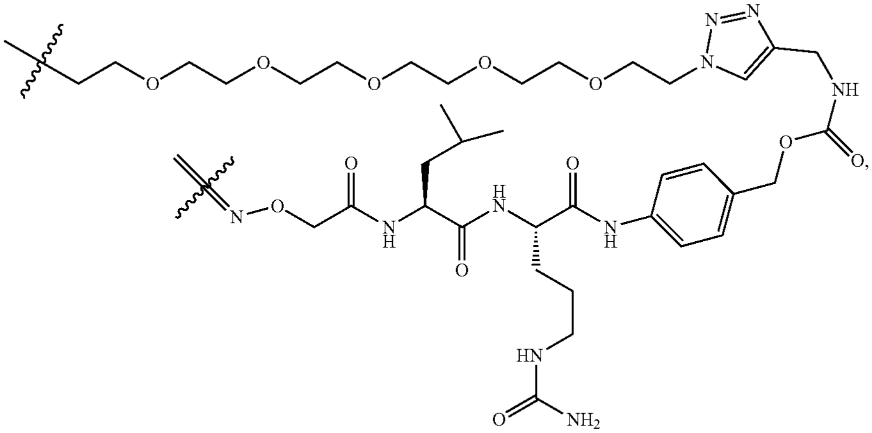
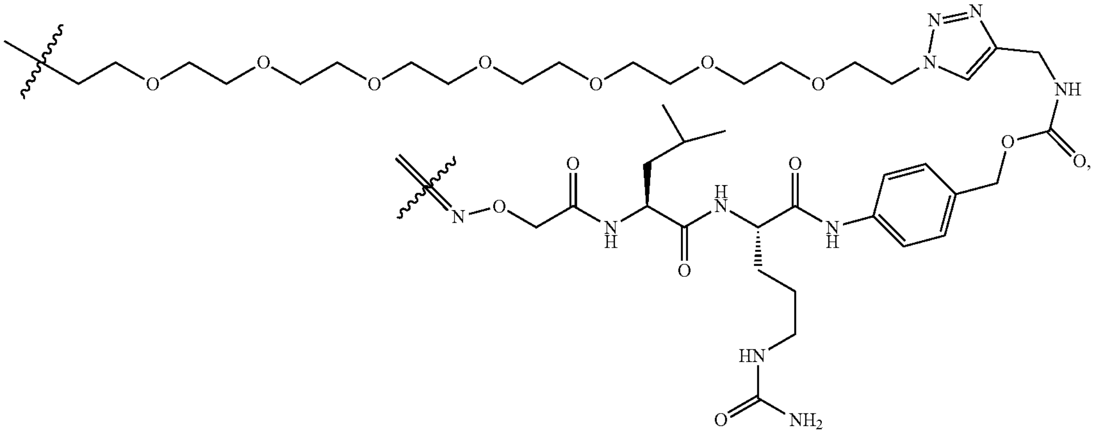

-continued
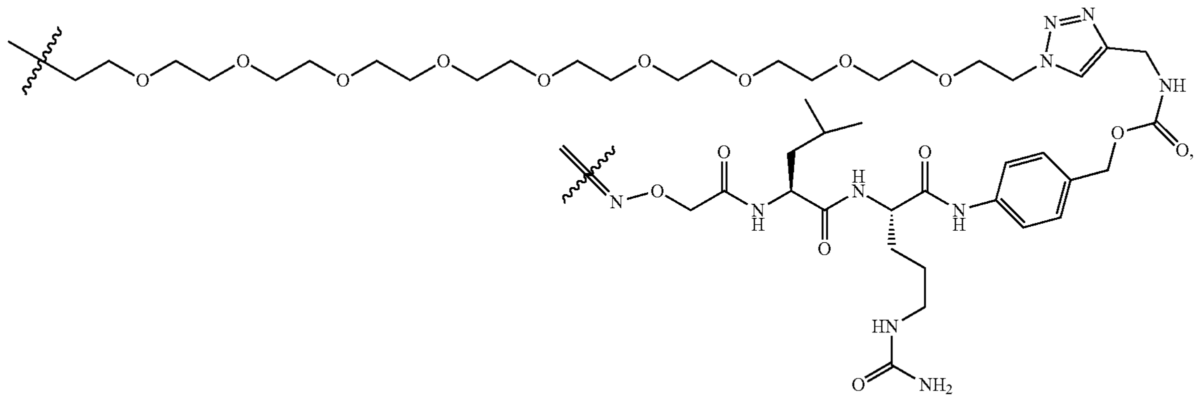
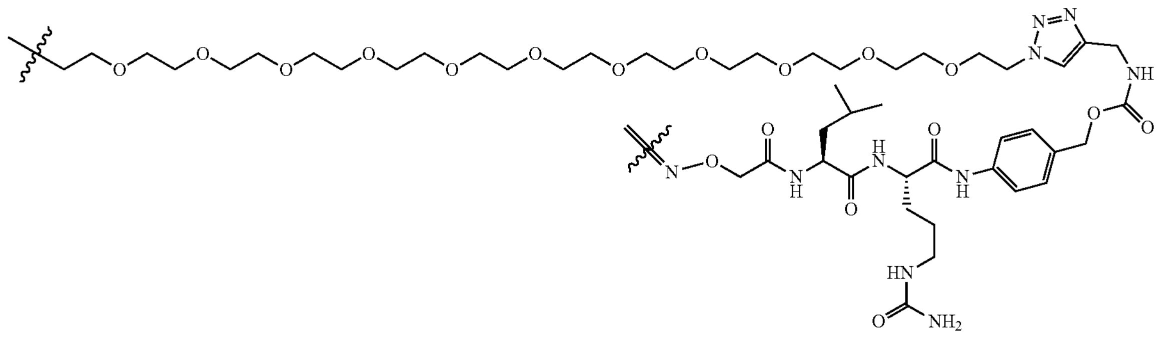
or
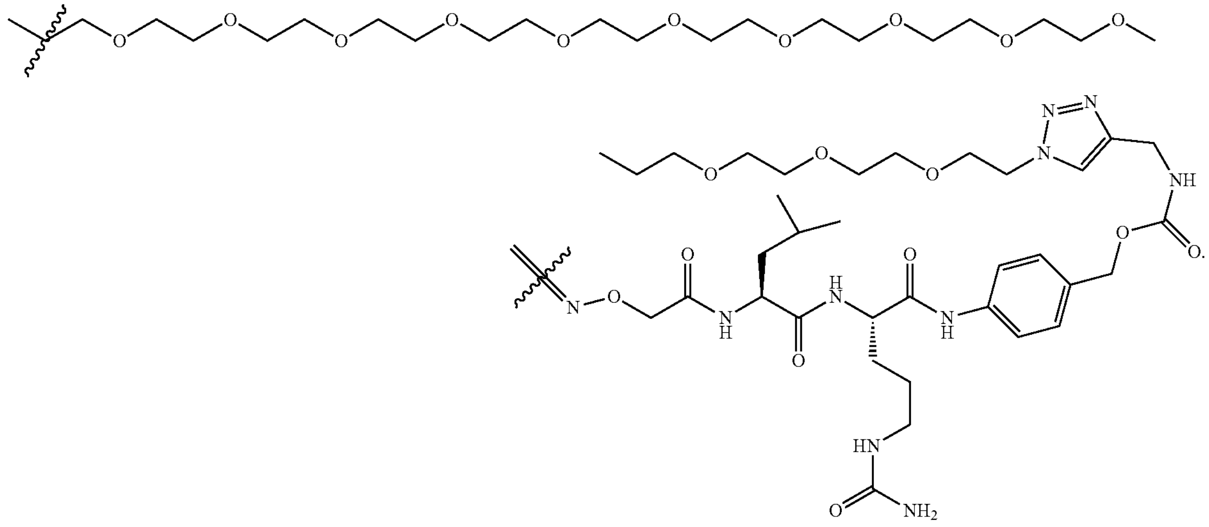

Embodiment 80
The immunoconjugates of Formula (B), Formula (II) and Formula (IIa), wherein $L_{20}$ is $NH_2$
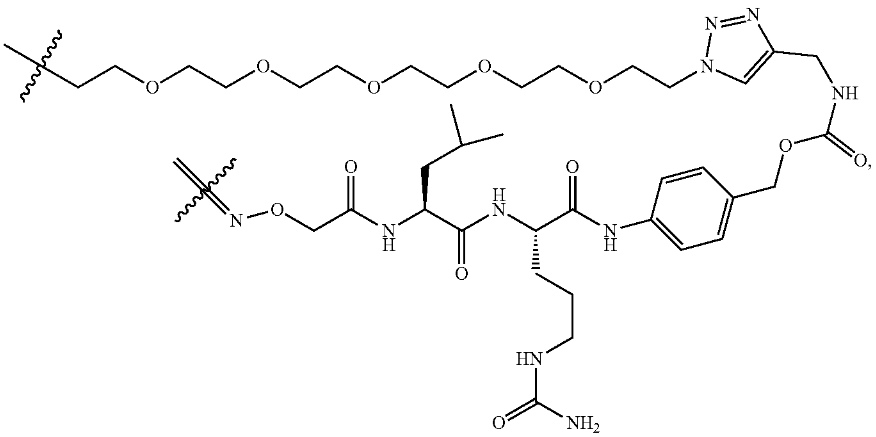
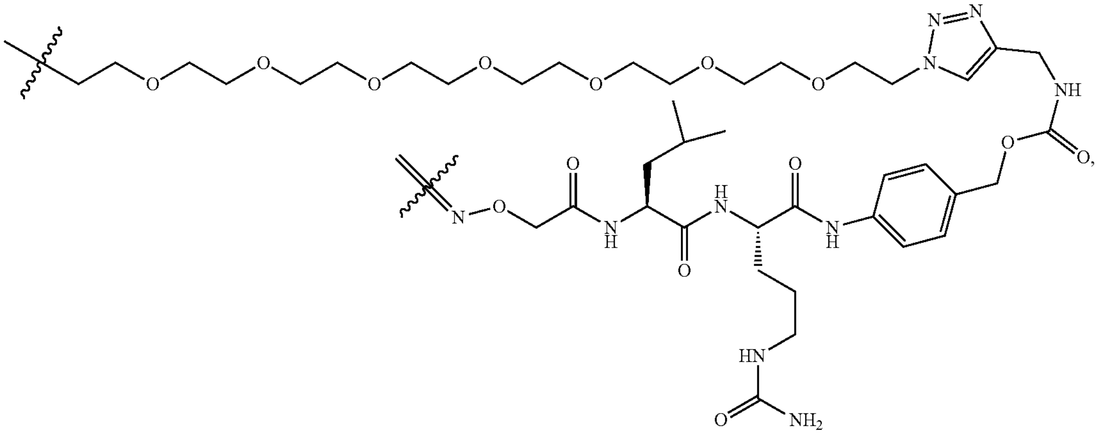
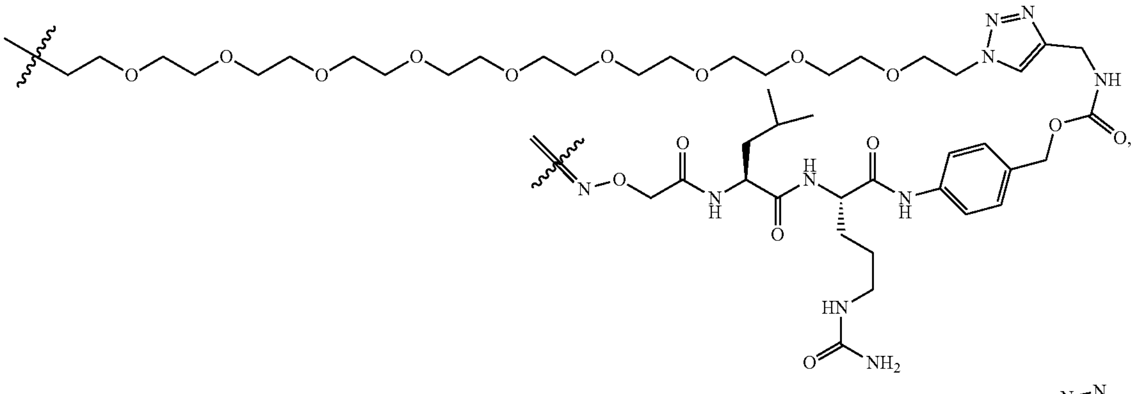
or
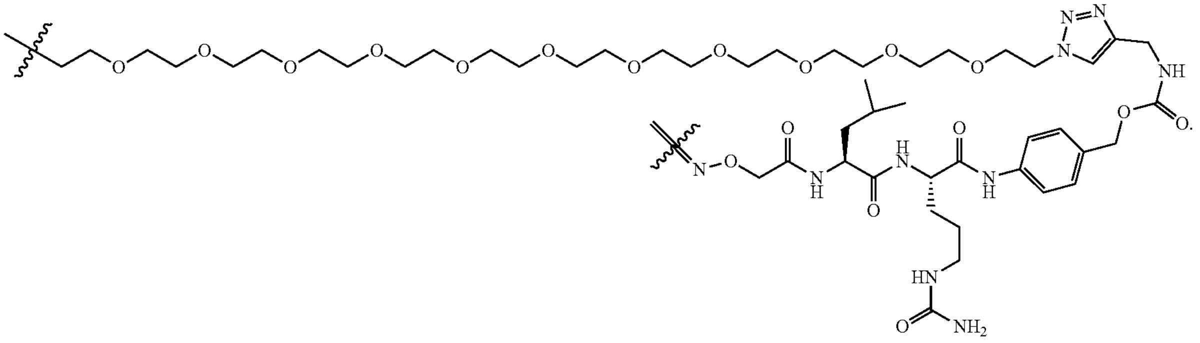

Embodiment 81
The immunoconjugates of Formula (B), Formula (II) and Formula (IIa), wherein $L_{20}$ is
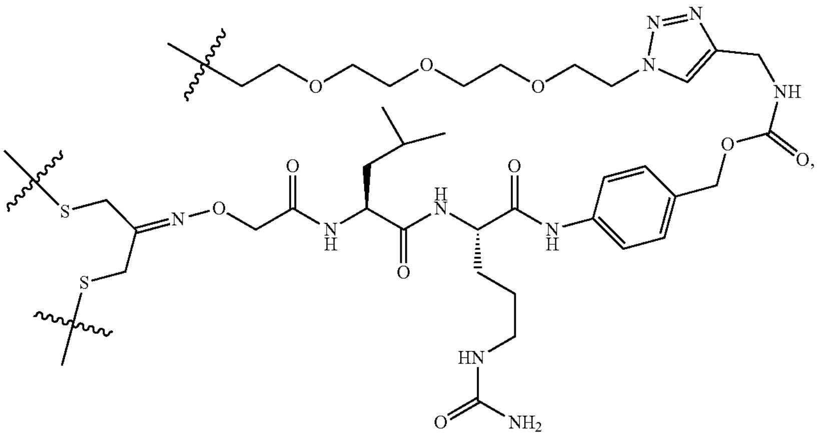
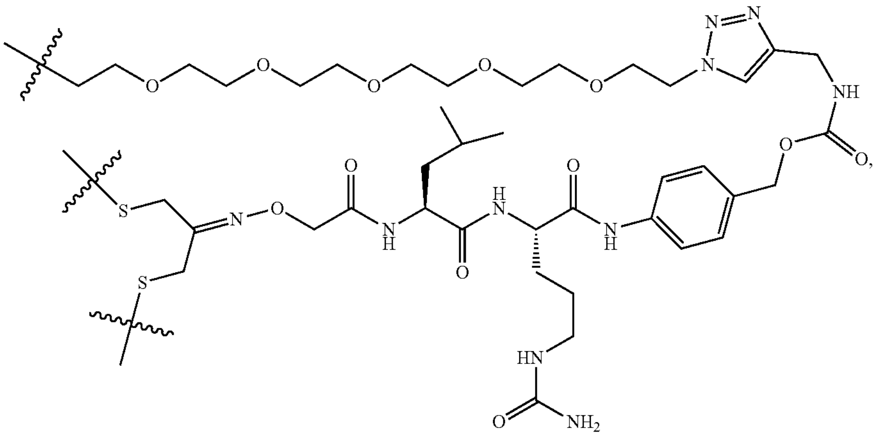
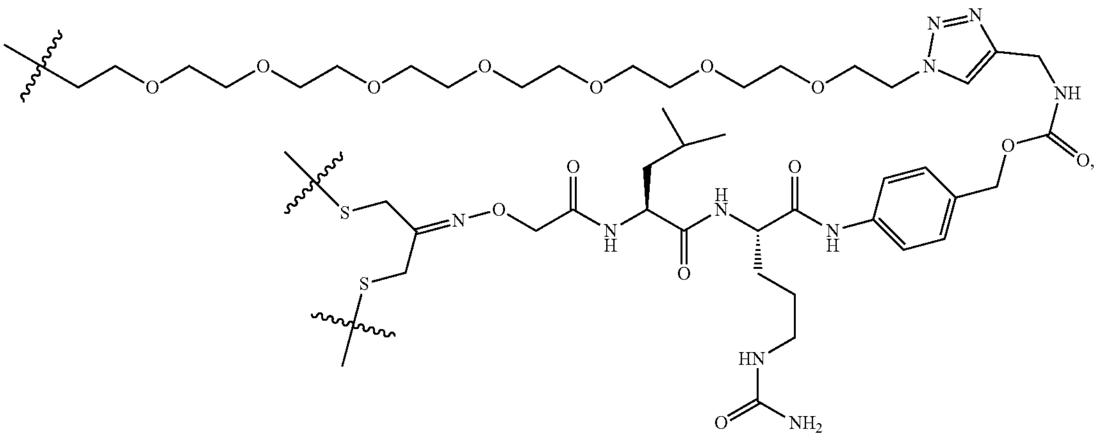

-continued
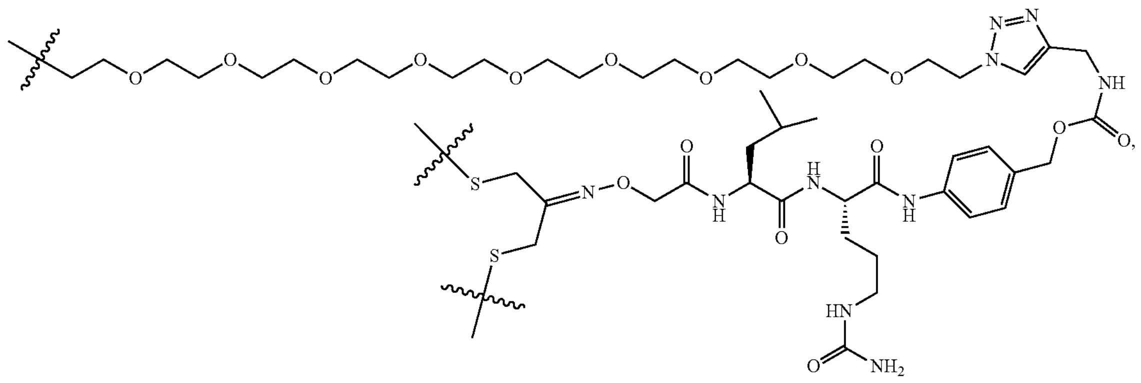
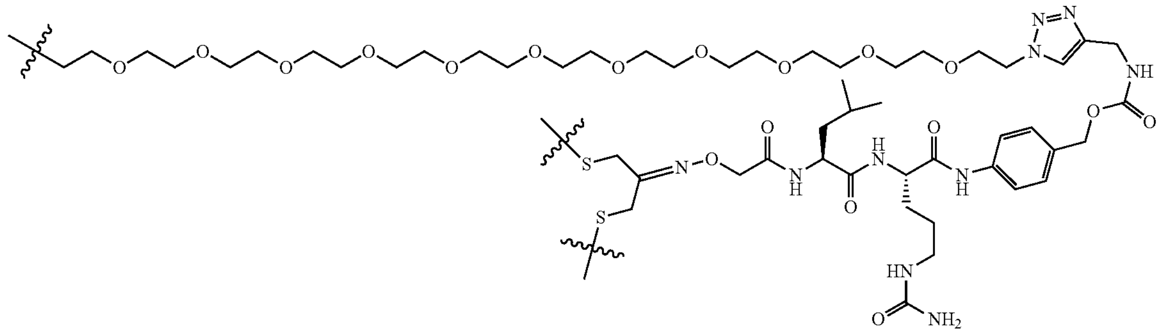
or
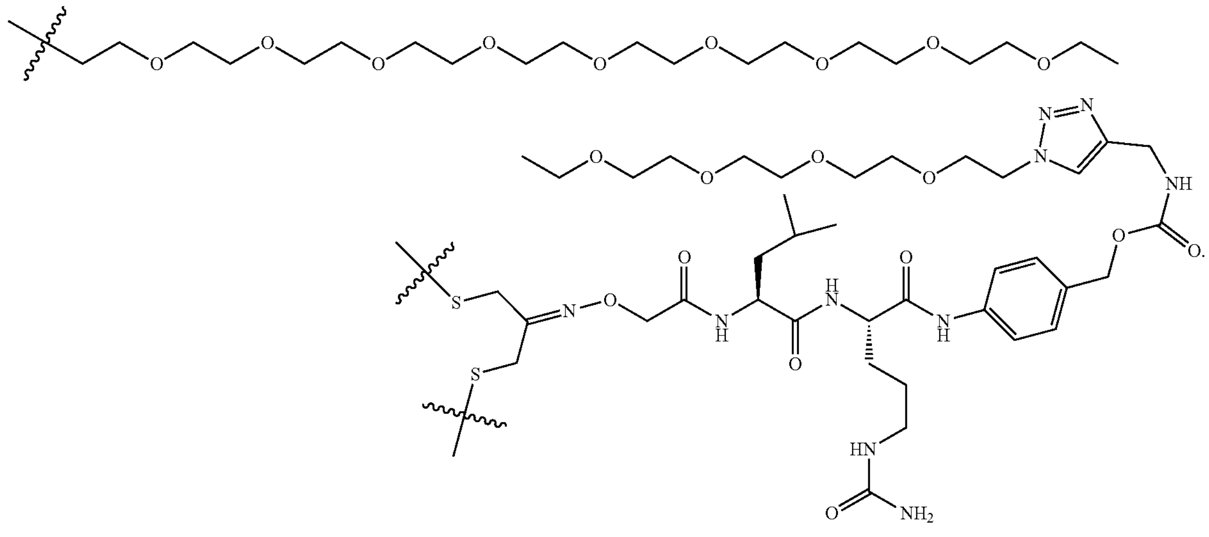

Embodiment 82
The immunoconjugates of Formula (B), Formula (II) and Formula (IIa), wherein $L_{20}$ is
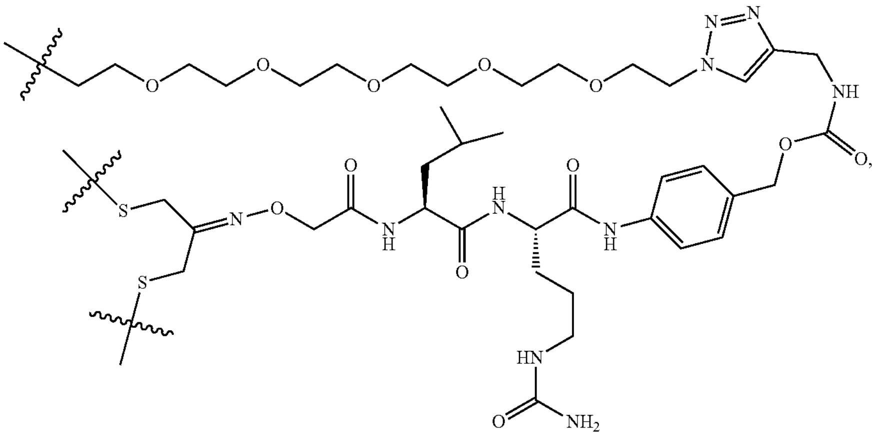
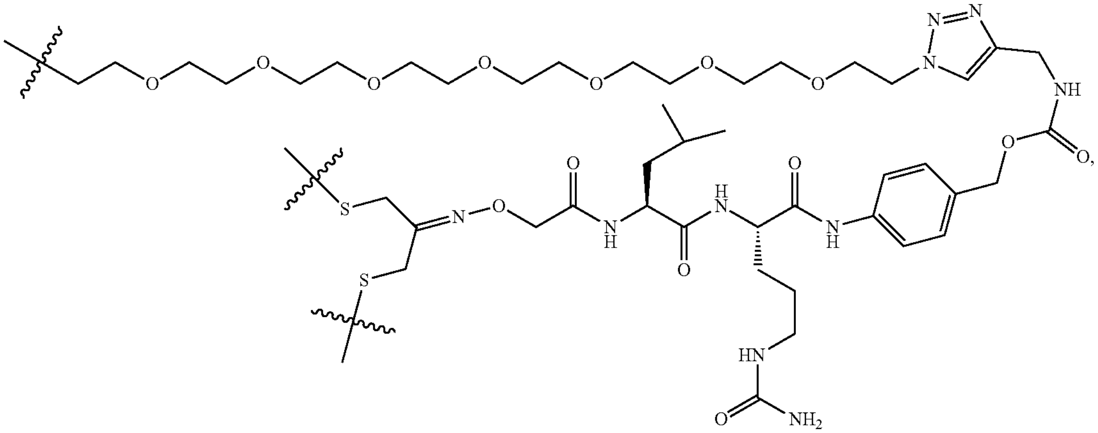
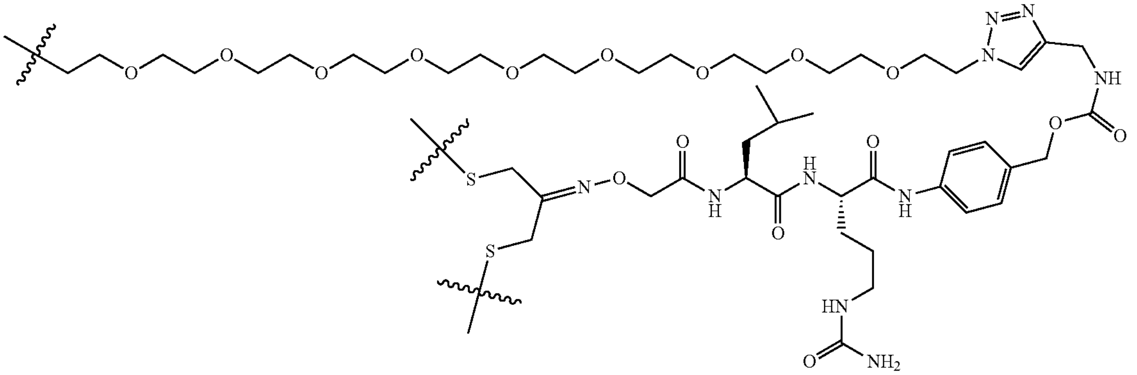
or
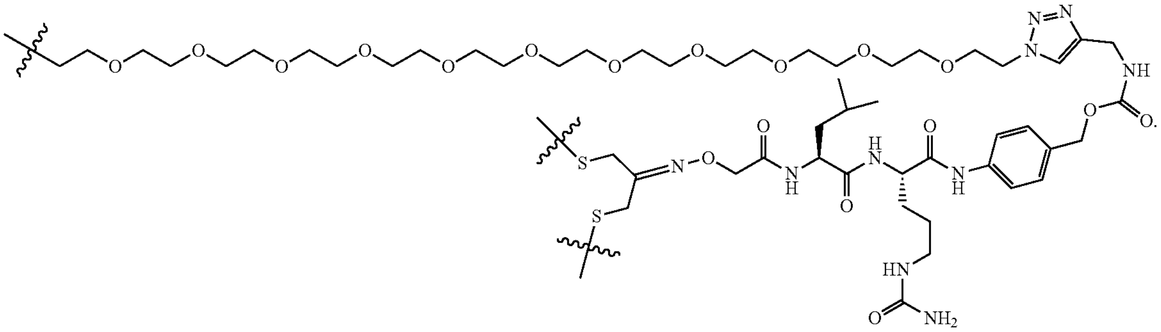

Embodiment 83
The immunoconjugates of Formula (B), Formula (II) and Formula (IIa), wherein $L_{20}$ is
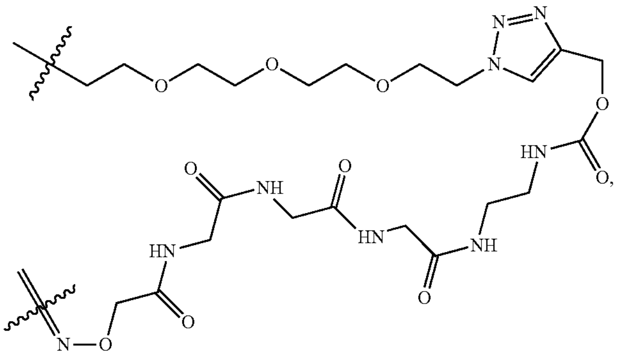
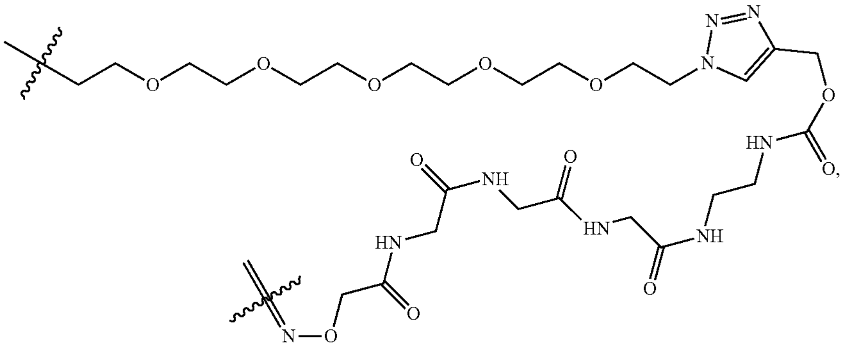
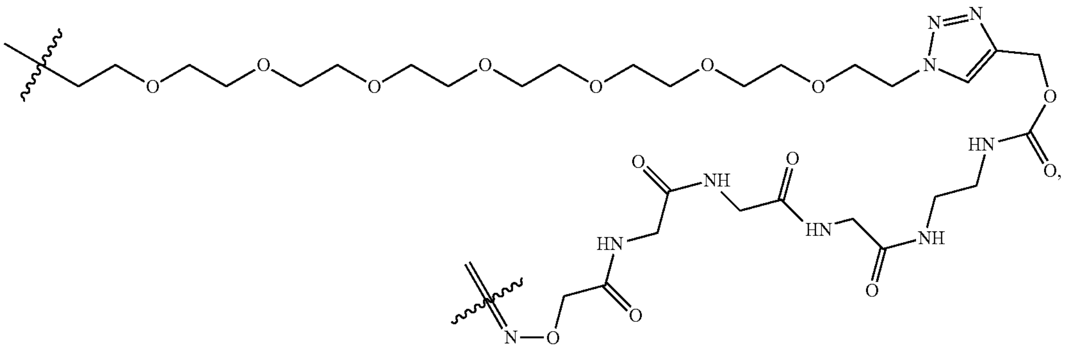
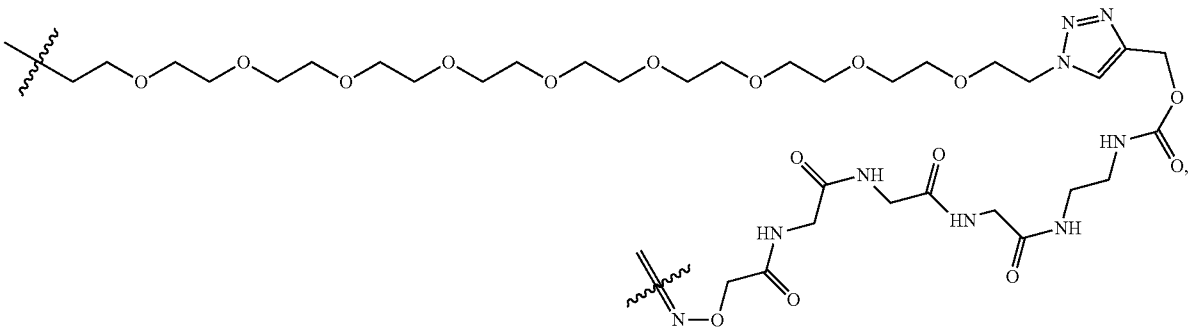

-continued
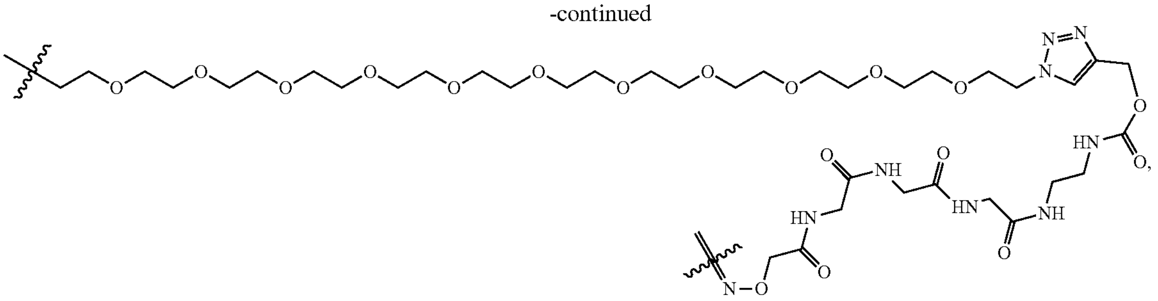
or
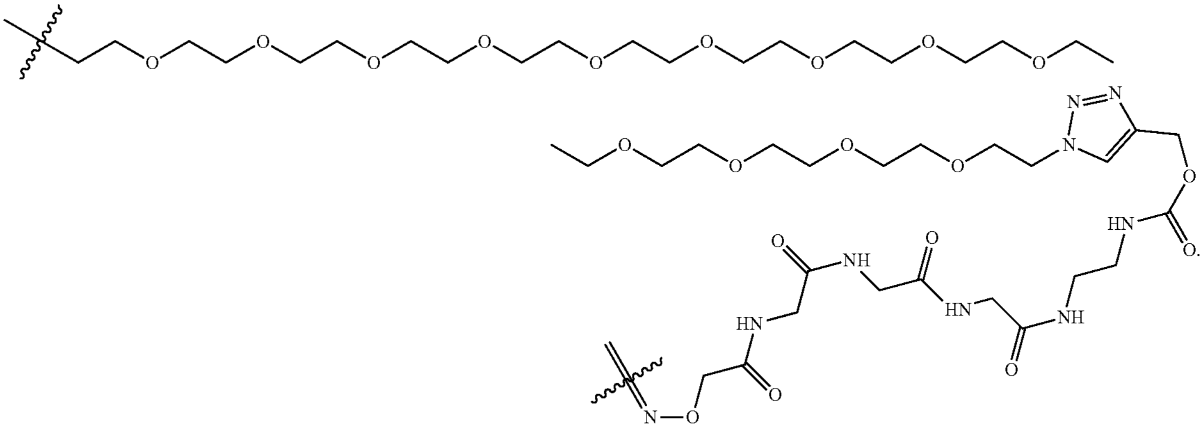
Embodiment 84
The immunoconjugates of Formula (B), Formula (II) and Formula (IIa), wherein $L_{20}$ is
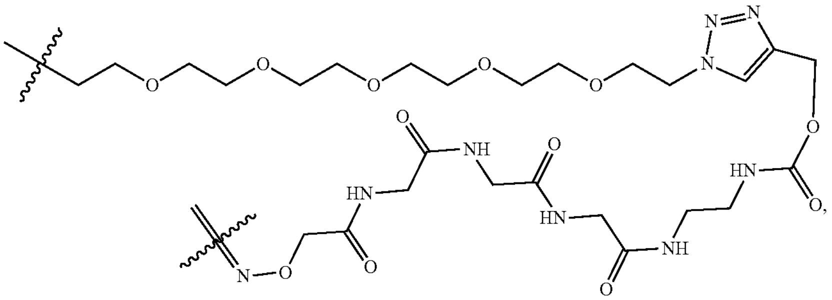
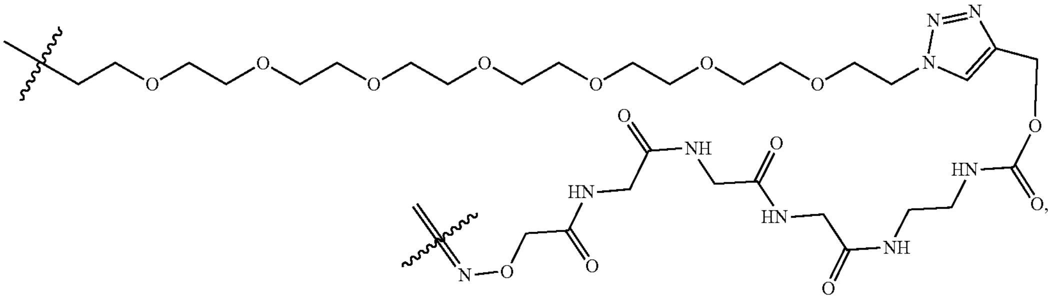

-continued
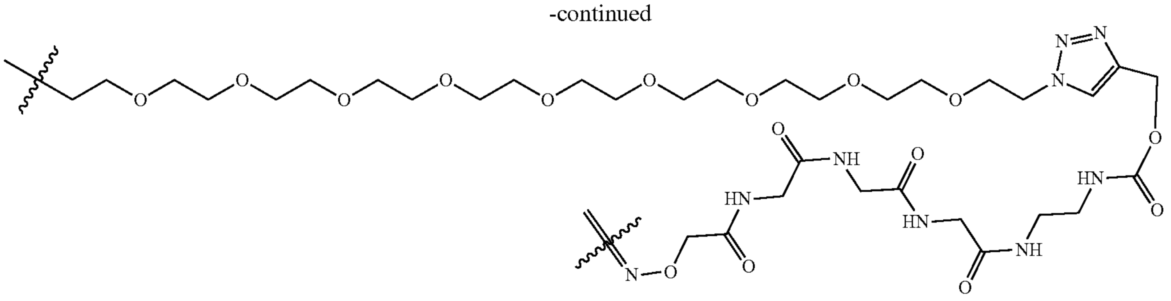
or
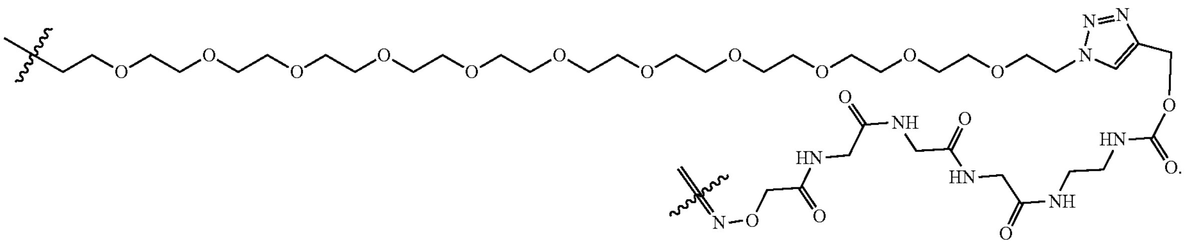
Embodiment 85
The immunoconjugates of Formula (B), Formula (II) and Formula (IIa), wherein $L_{20}$ is
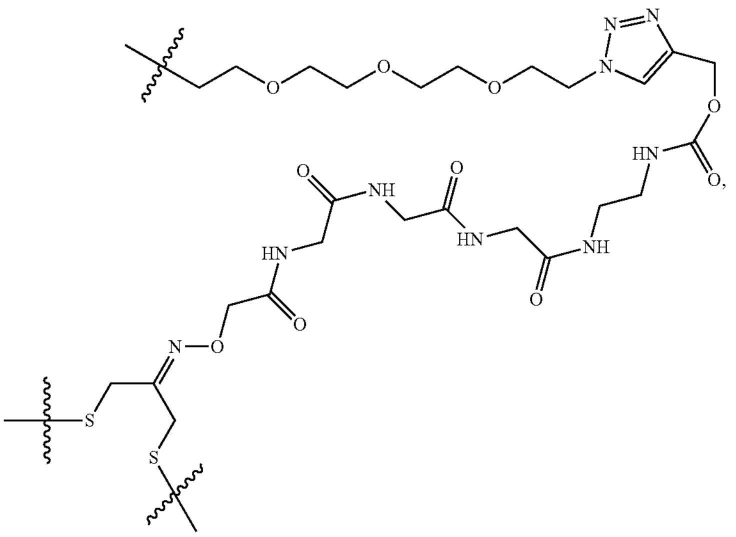

-continued
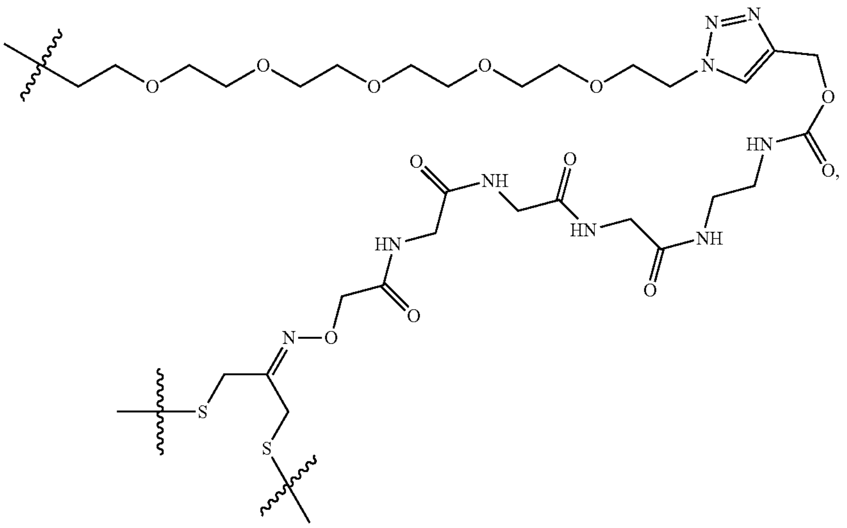
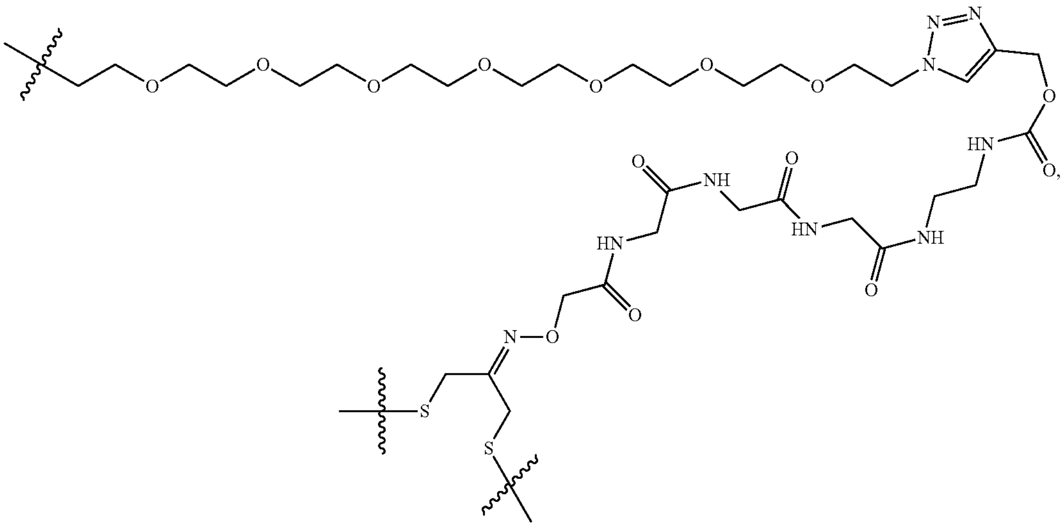
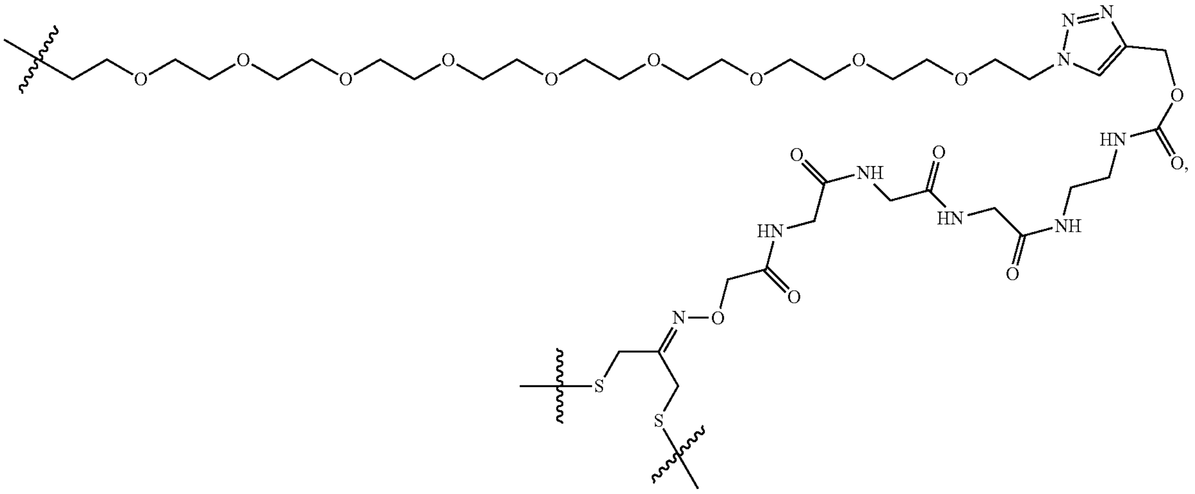

-continued
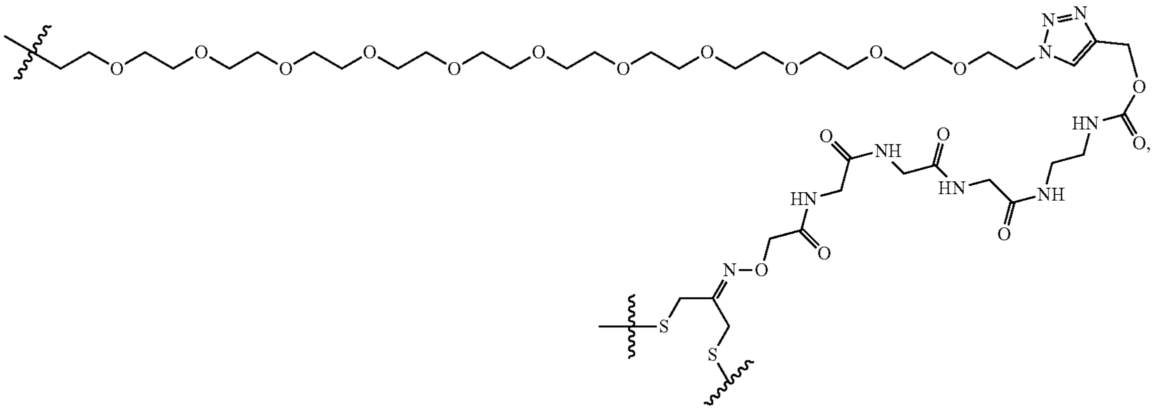
, or
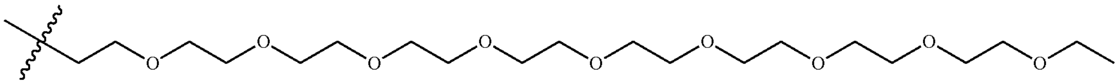
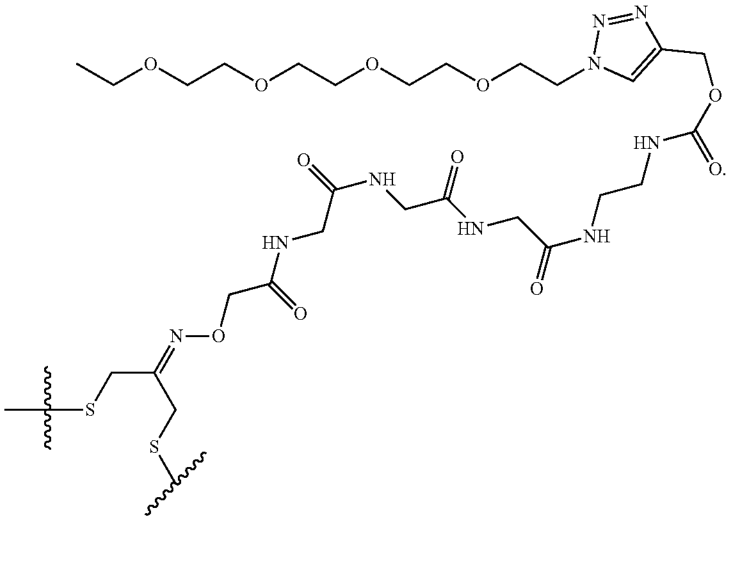
.

Embodiment 86
The immunoconjugates of Formula (B), Formula (II) and Formula (IIa), wherein $L_{20}$ is
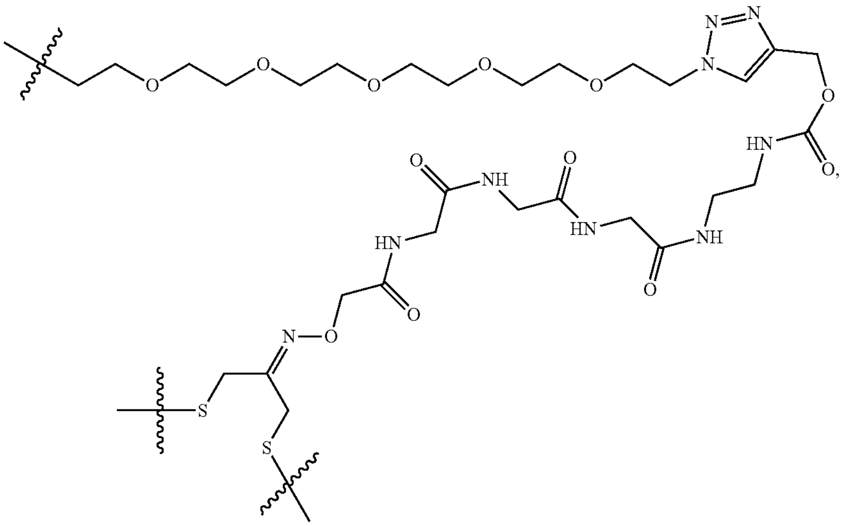
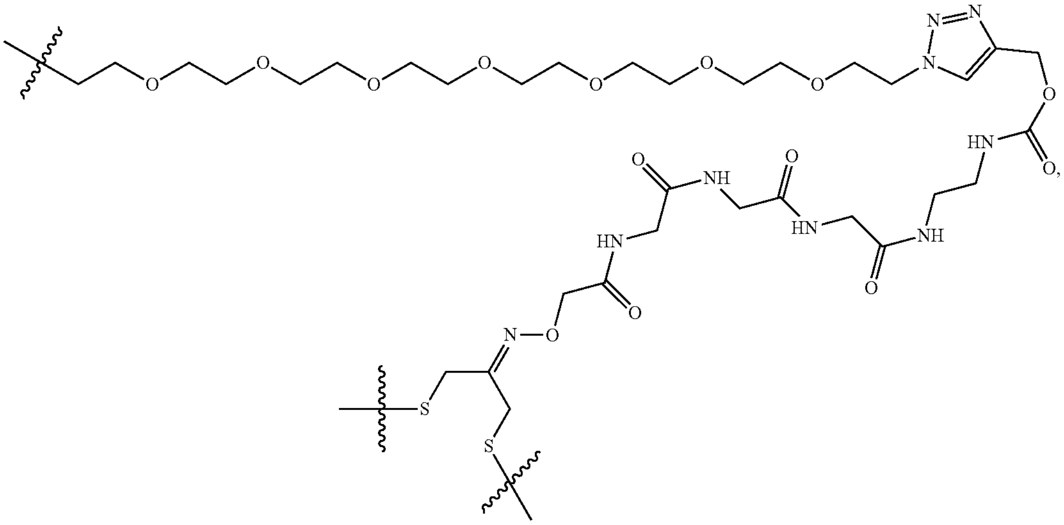
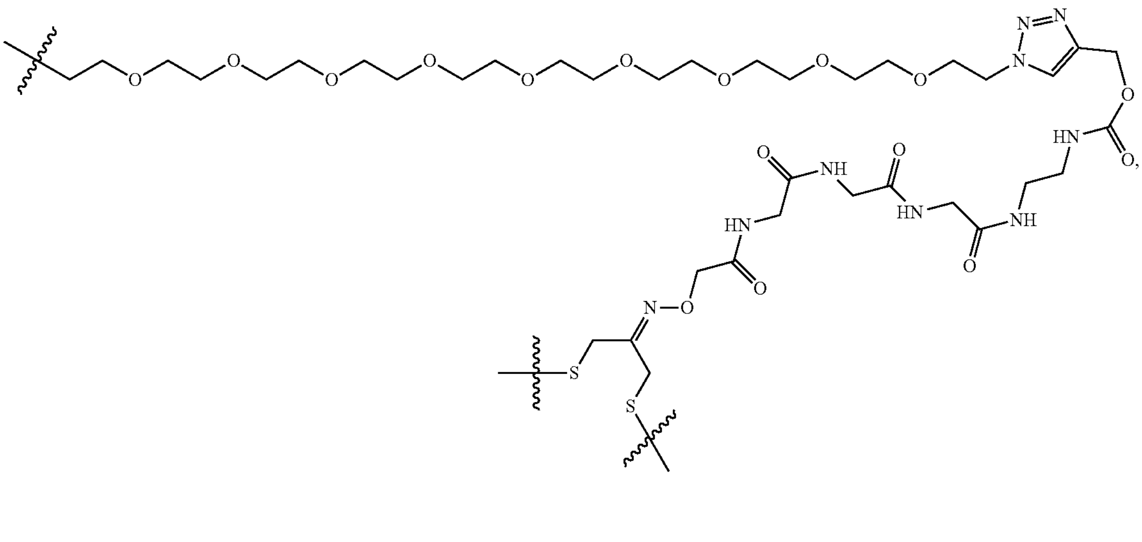
or -continued
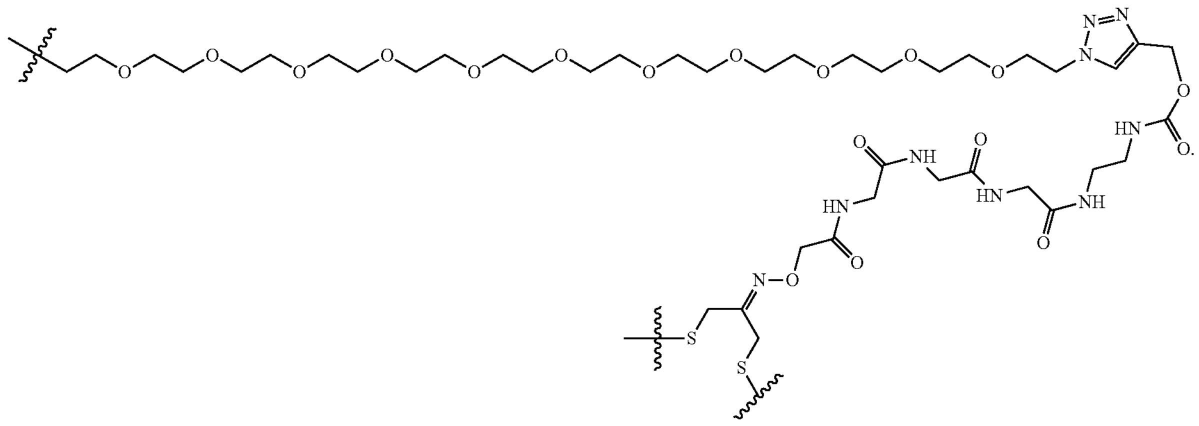 [SMILES: *CCOCCOCCOCCOCCOCCOCCOCCOCCOCCOCCOCCn1cc(COC(=O)NCCNC(=O)CNC(=O)CNC(=O)CNC(=O)CON=C(CS*)CS*)nn1]
Embodiment 87
The immunoconjugates of Formula (B), Formula (II) and Formula (IIa), selected from:
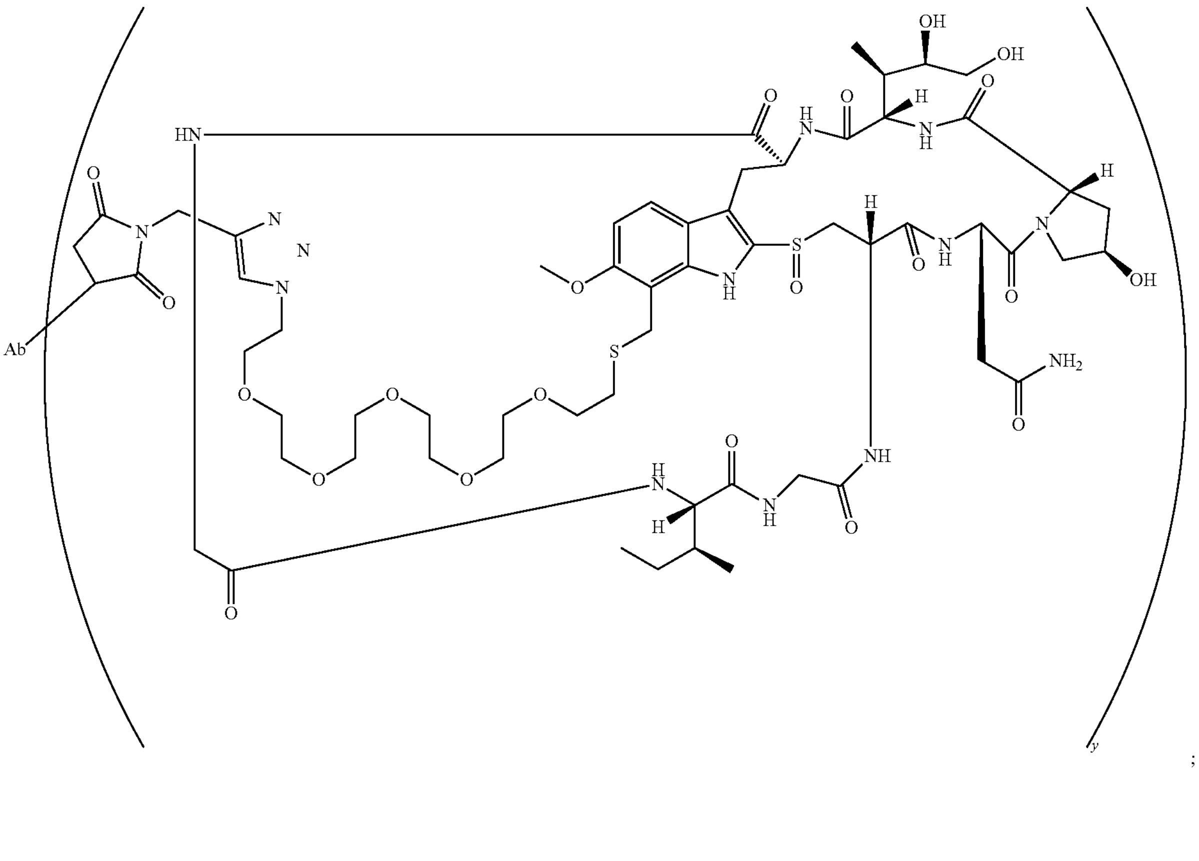
;

-continued
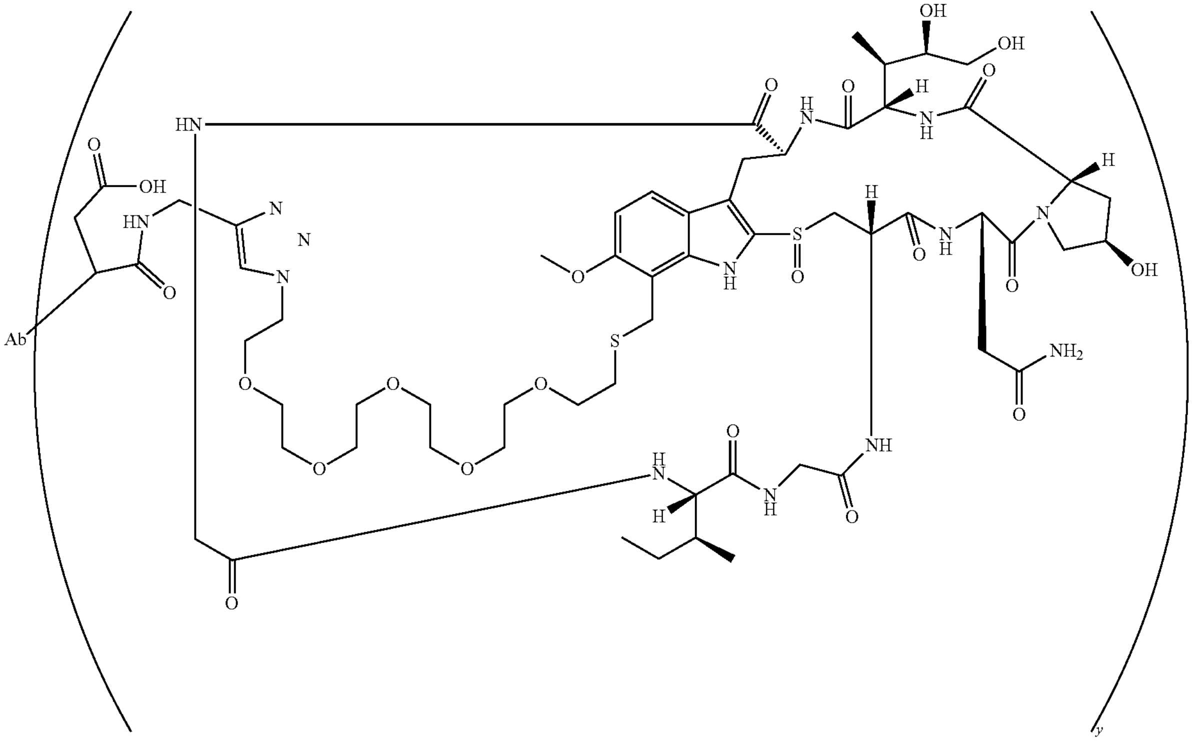
;
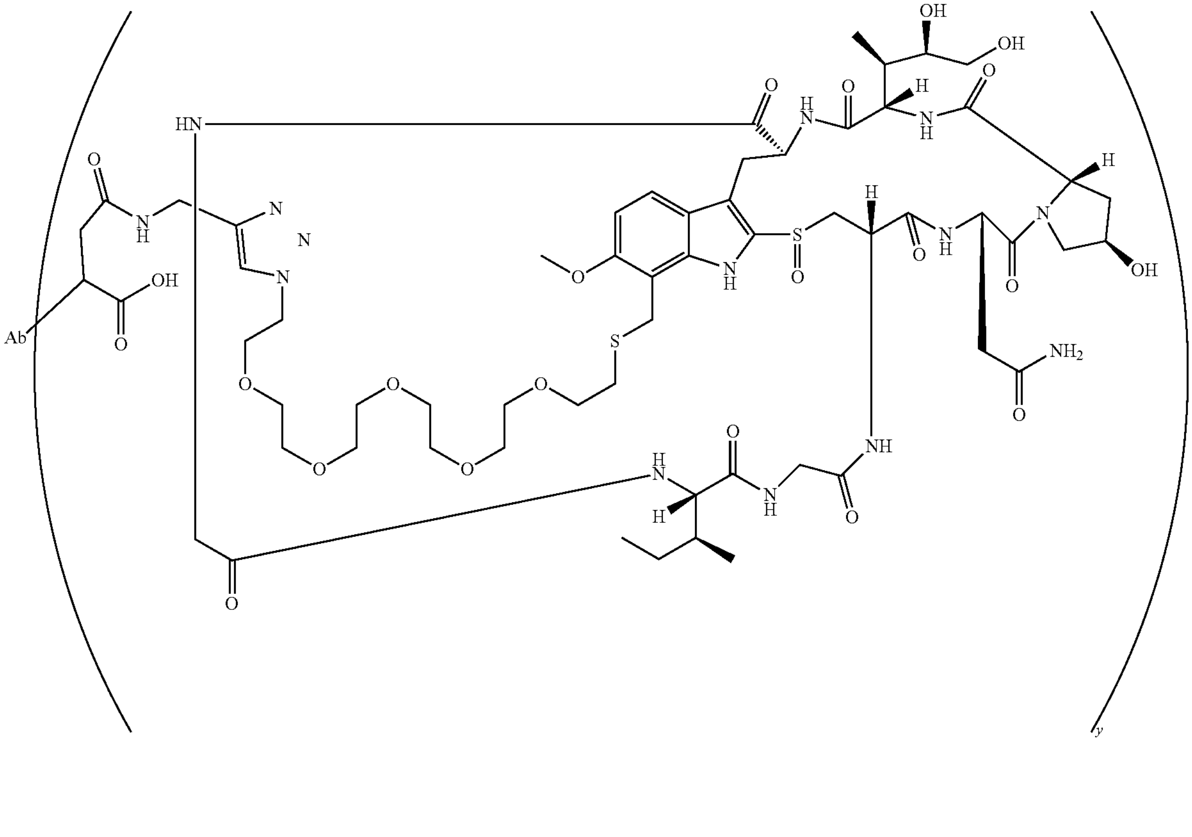
;

-continued
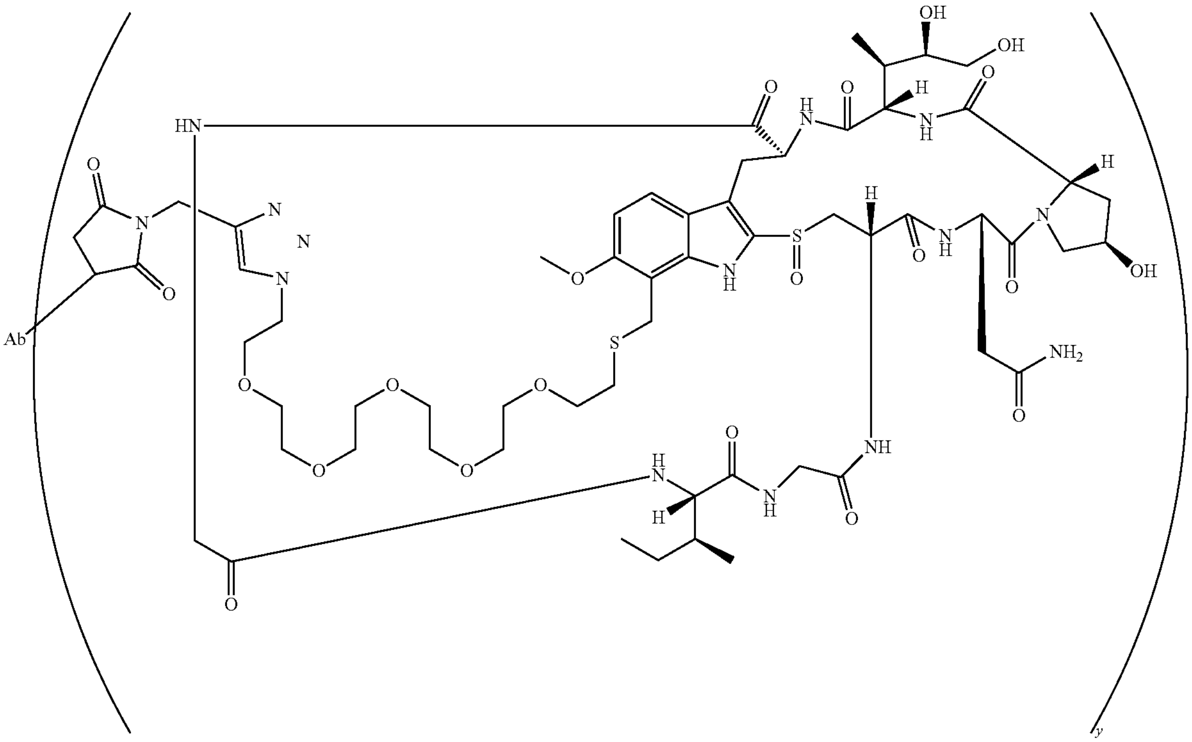
;
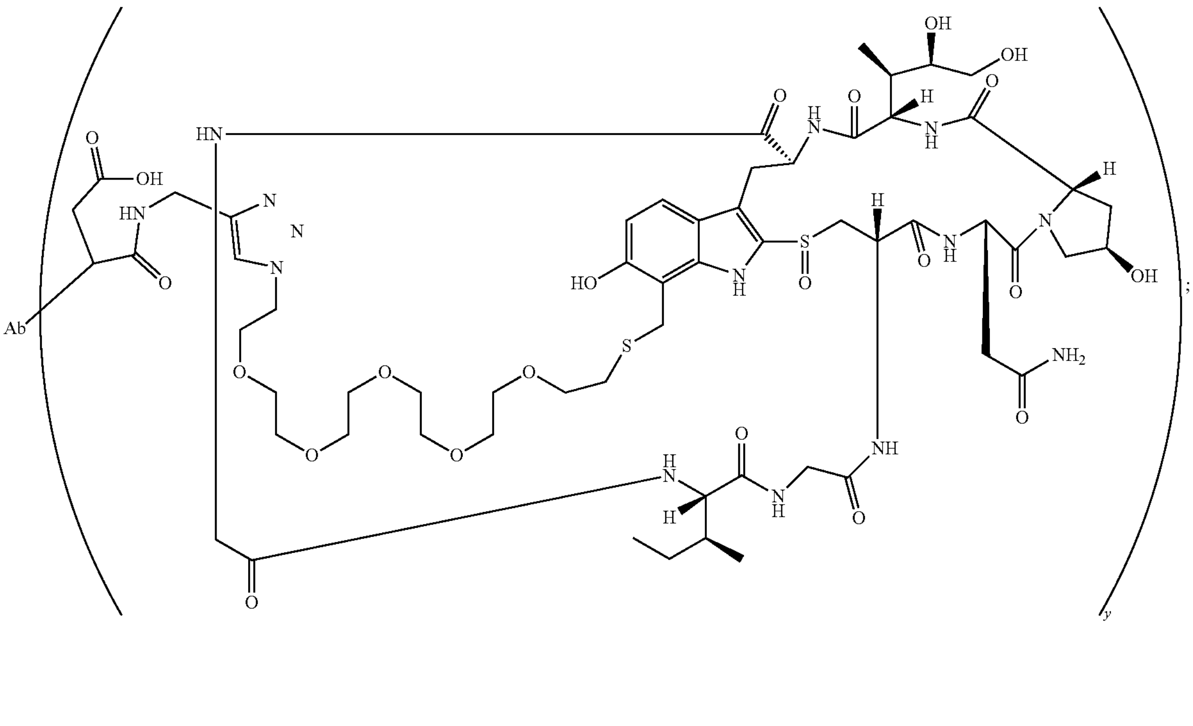
;

-continued
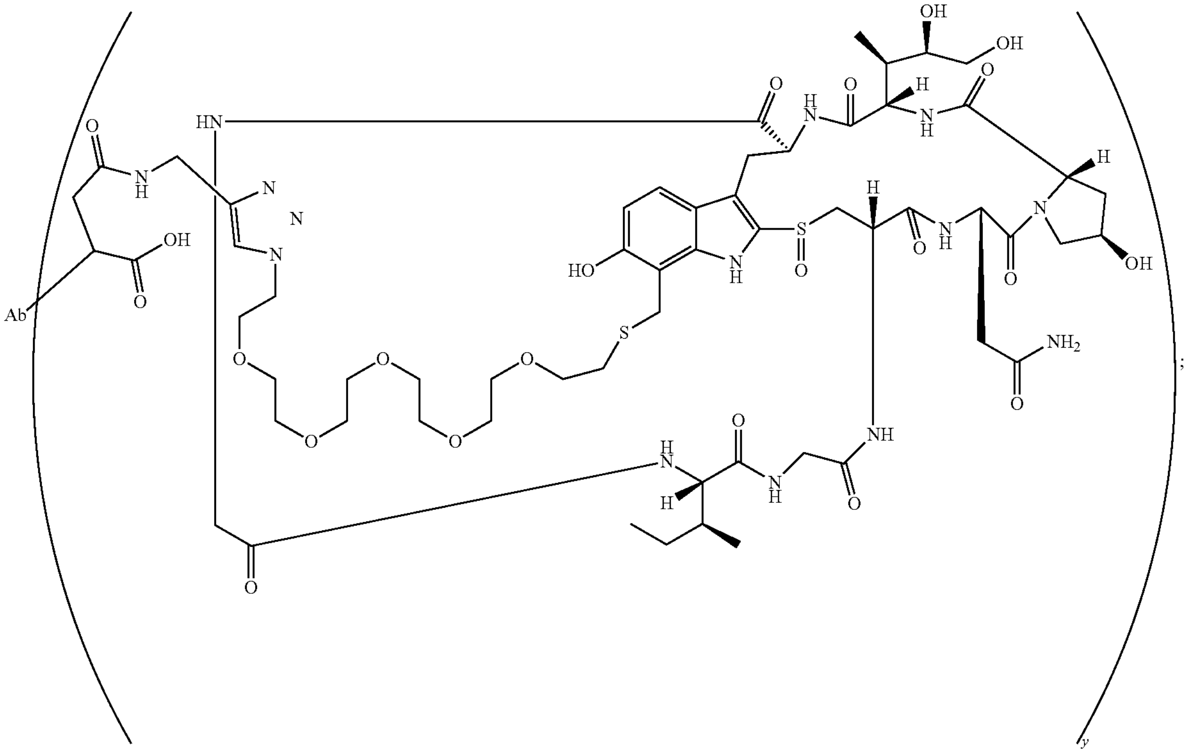
;
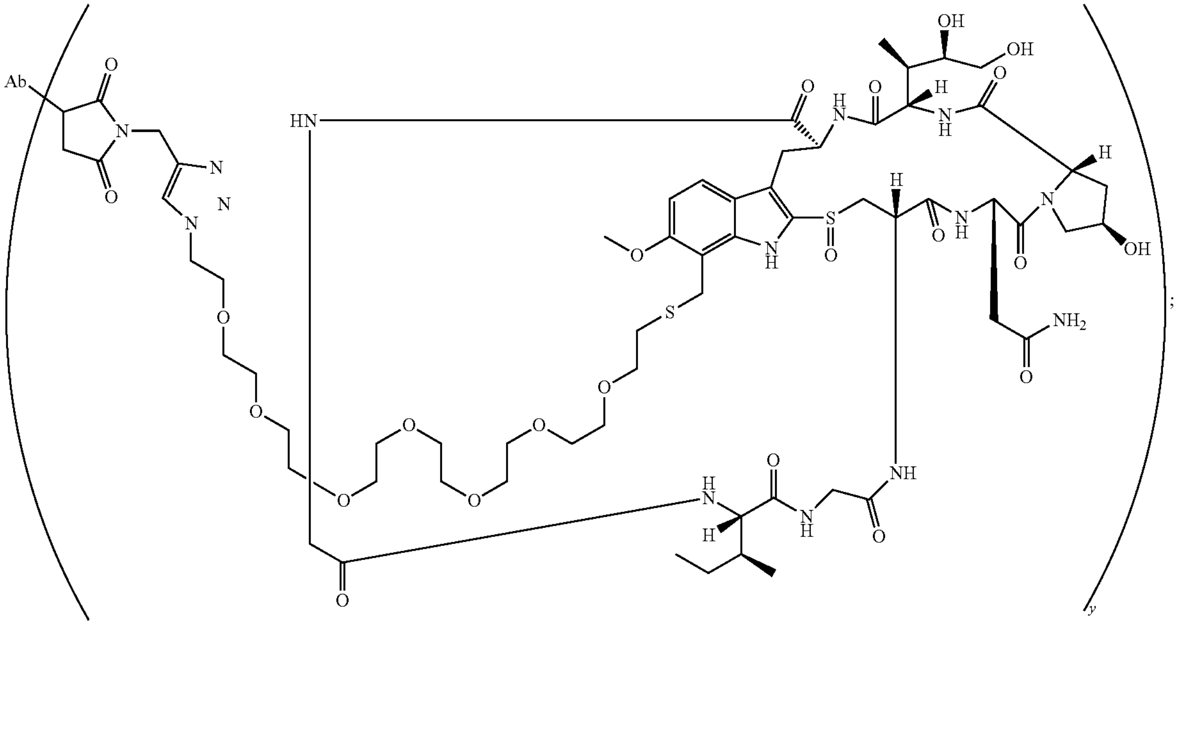
;

-continued
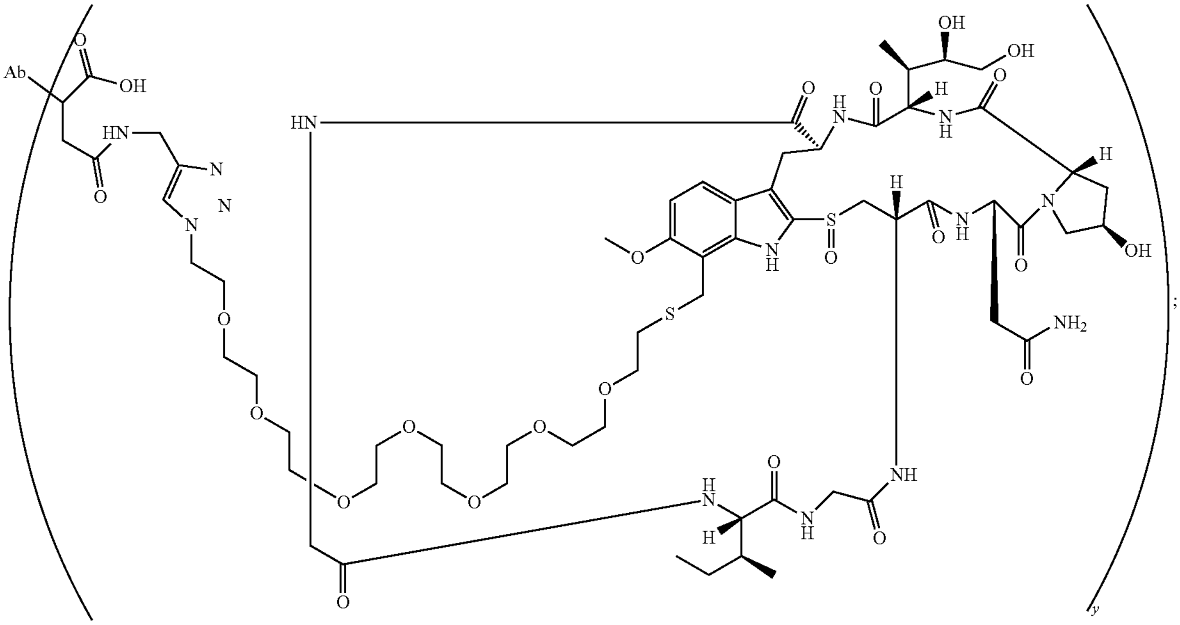
;
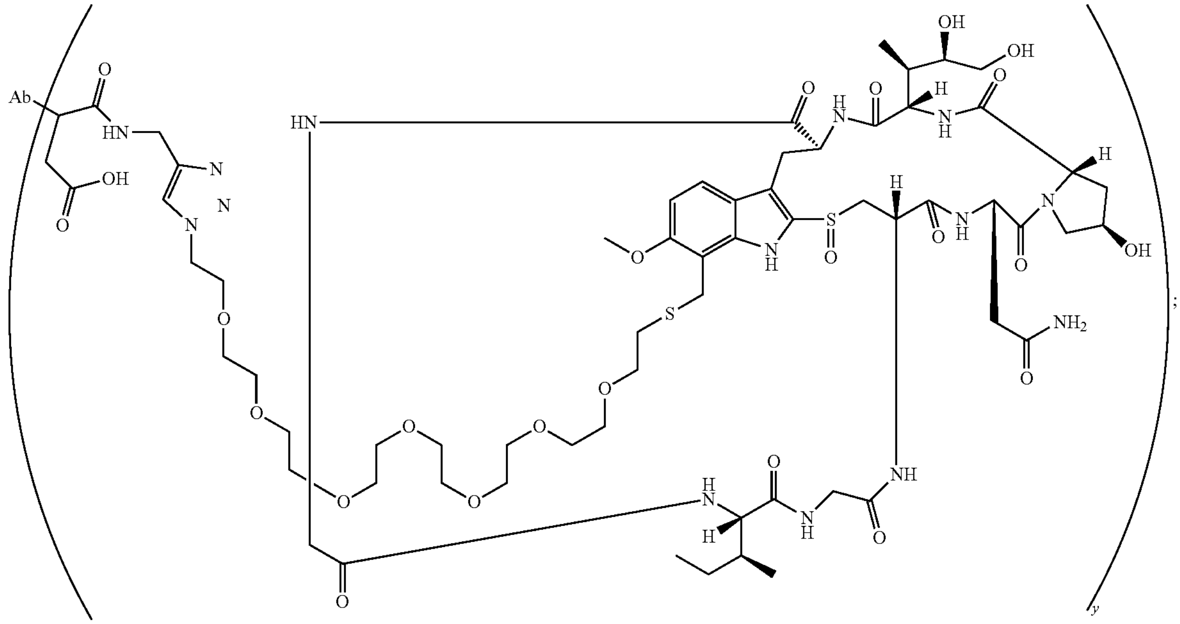
;

-continued
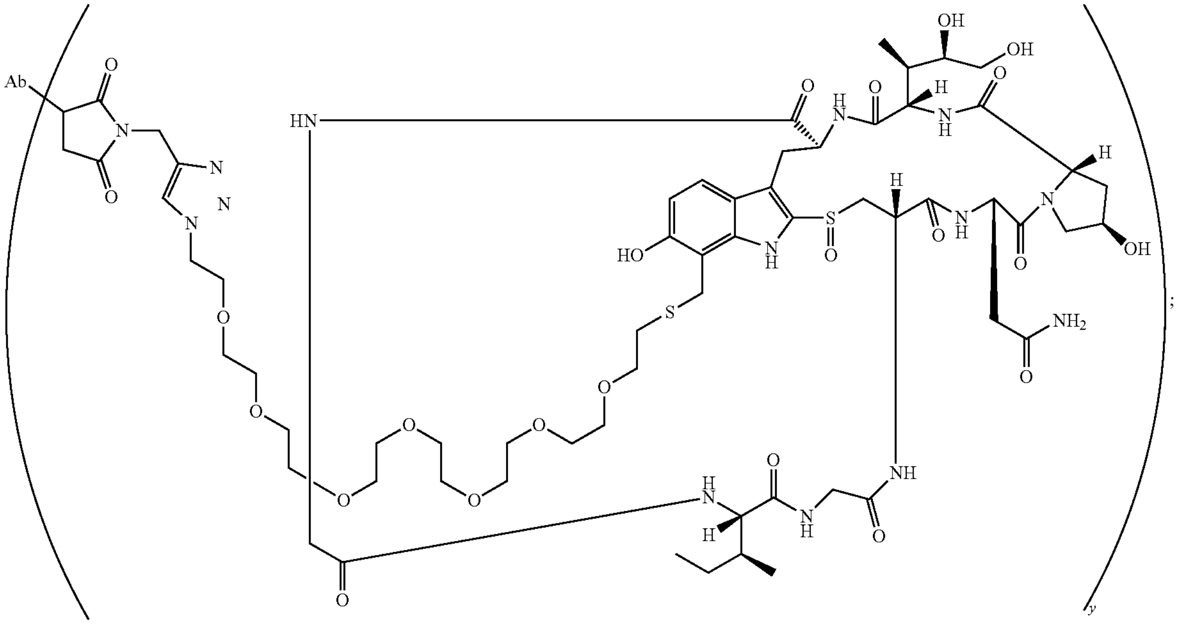
;
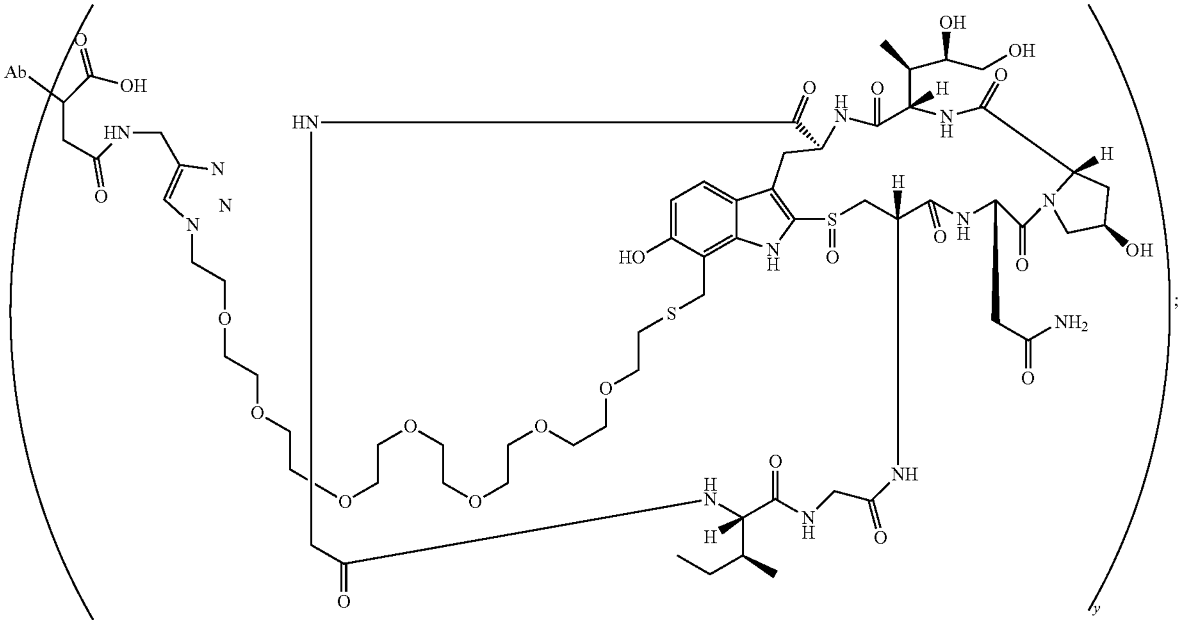
;

-continued
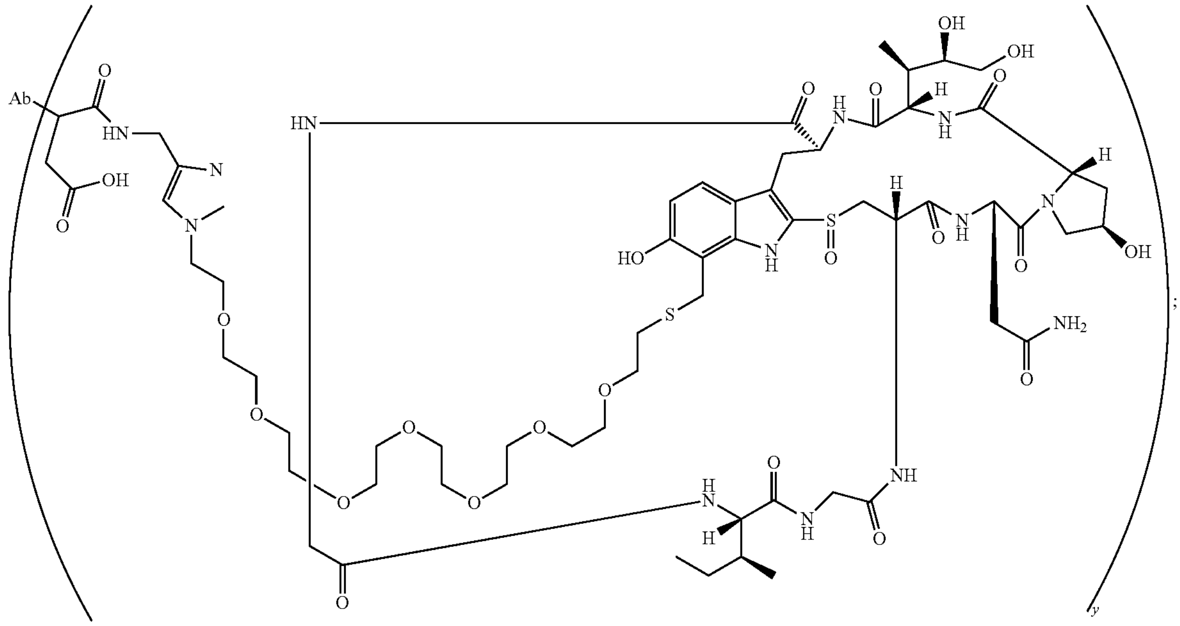
;
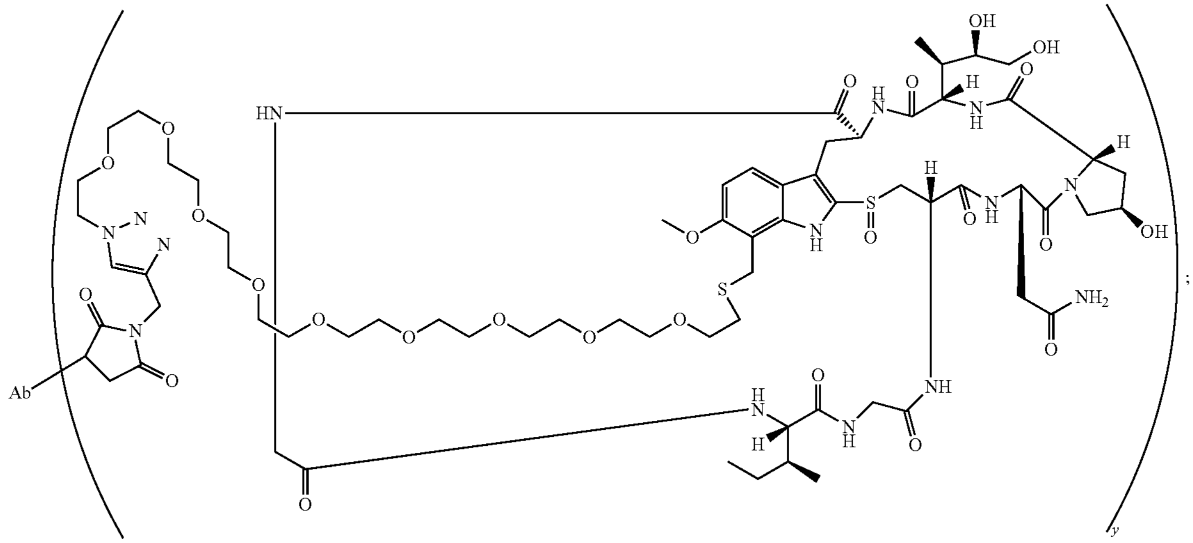
;
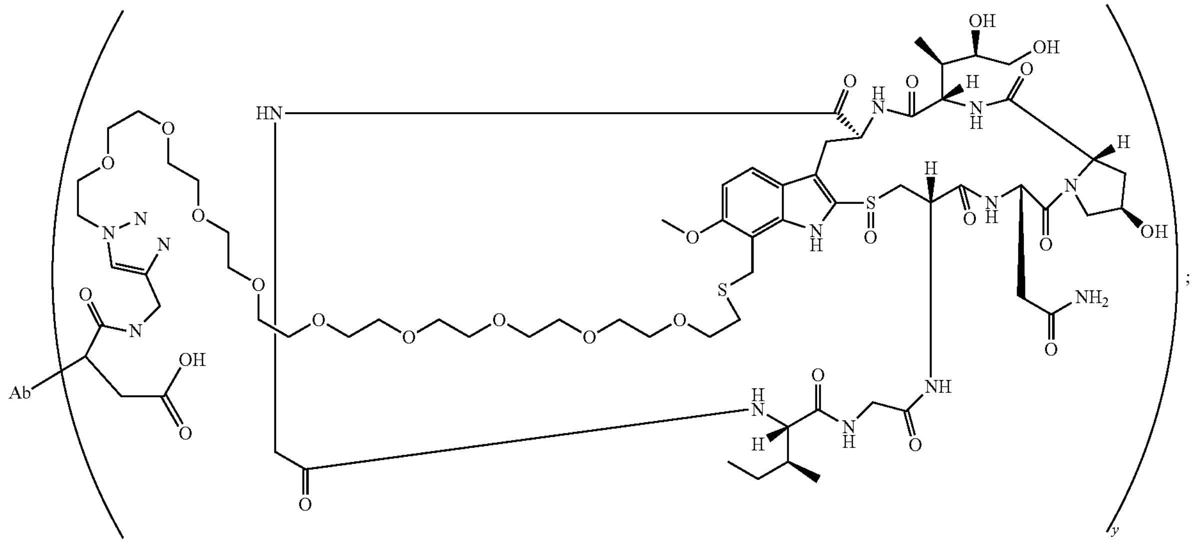
;

-continued
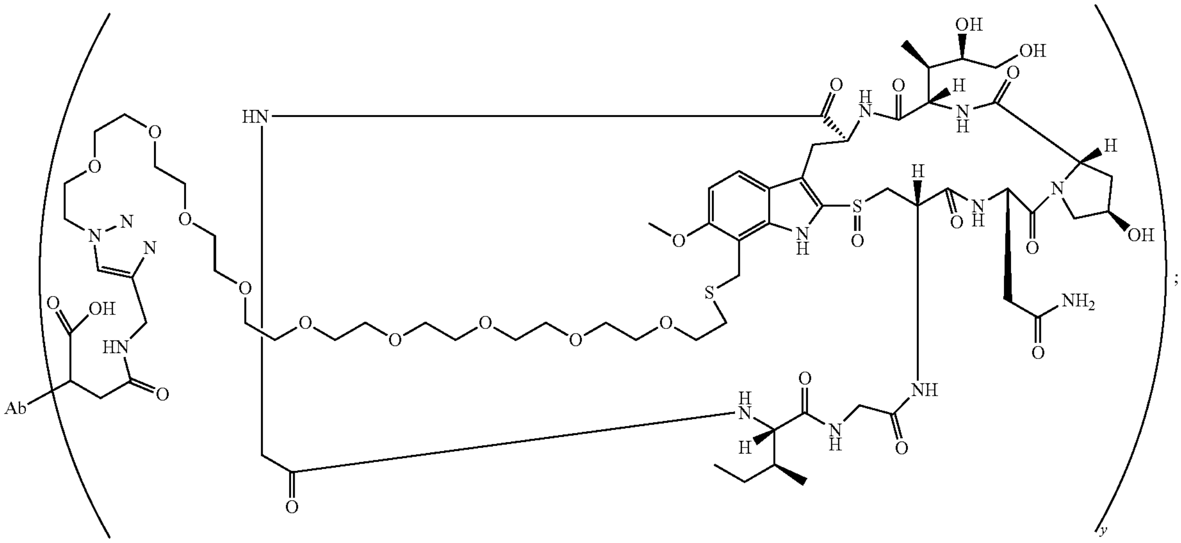
;
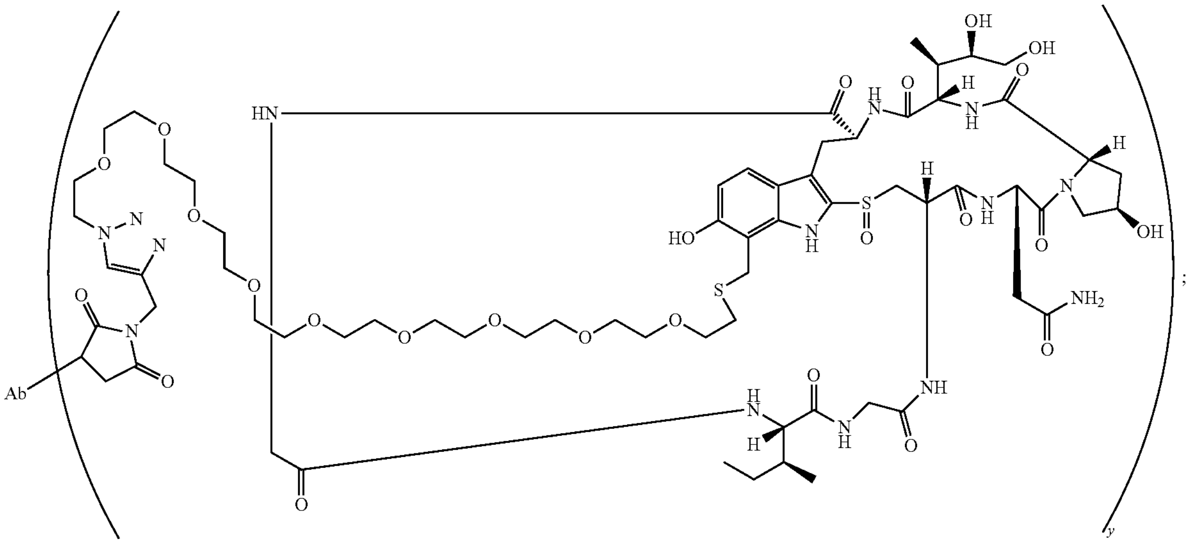
;
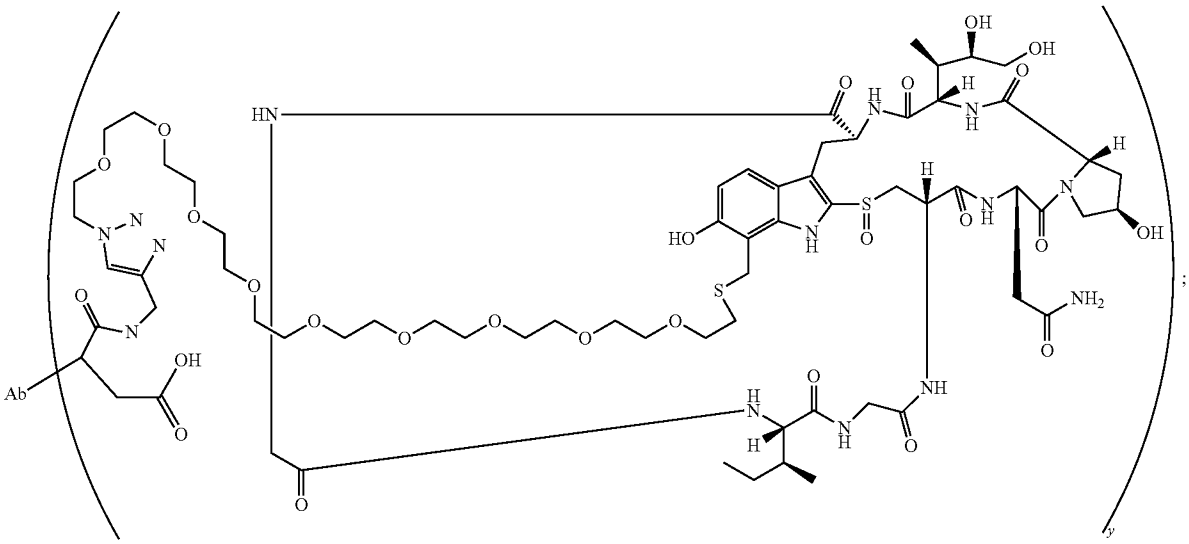
;

-continued
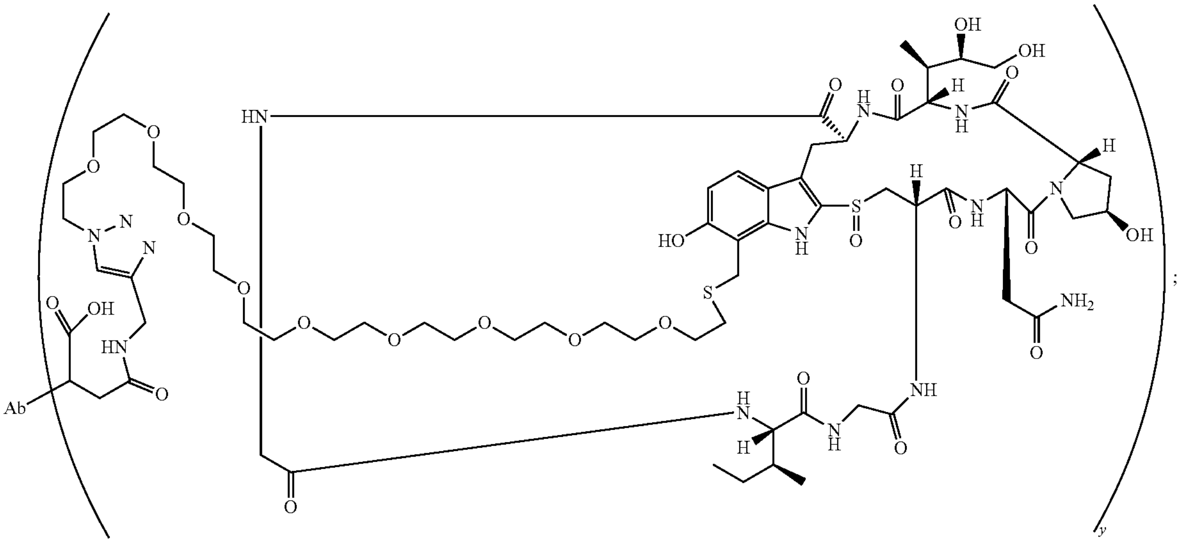
;
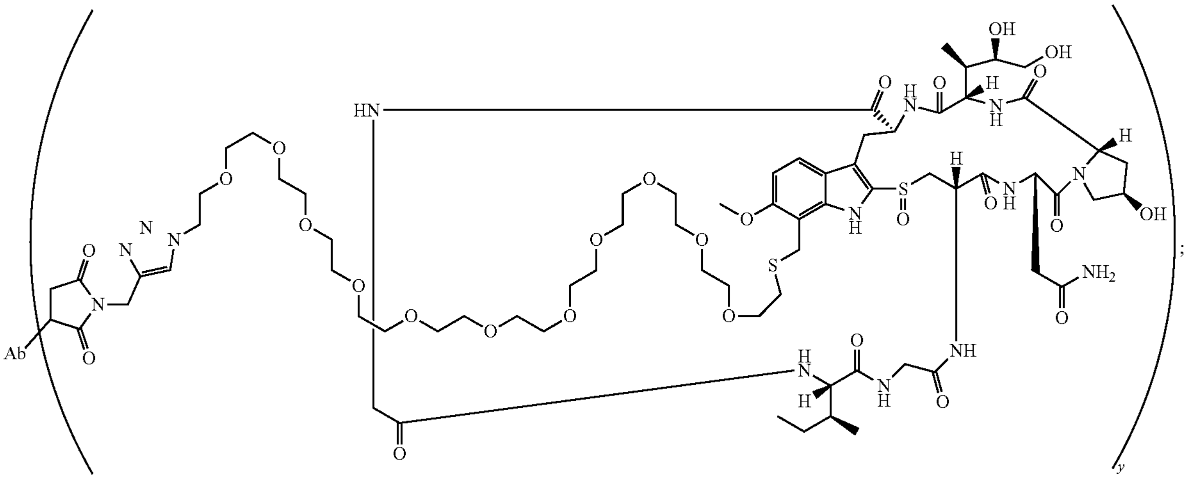
;
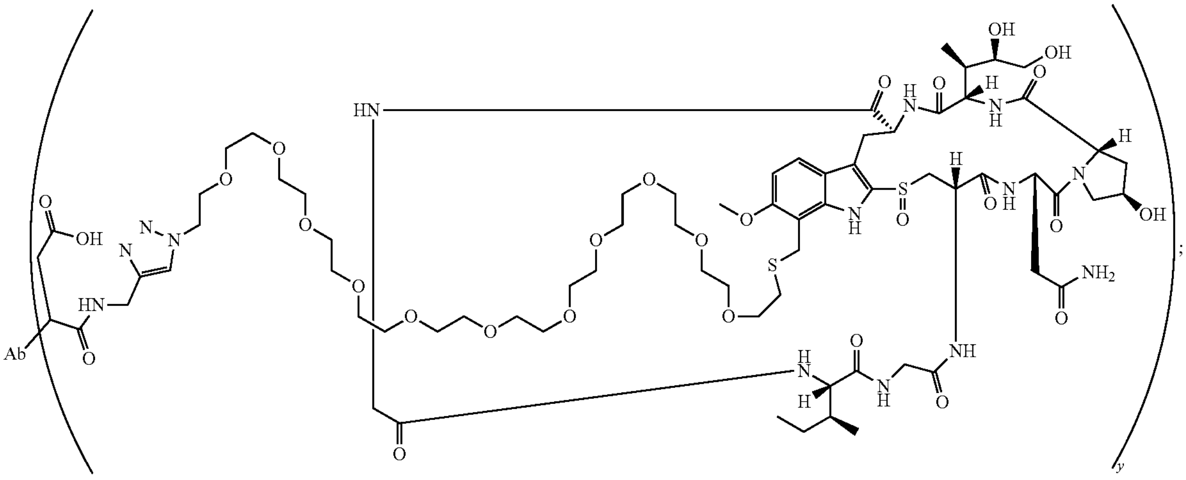
;

-continued
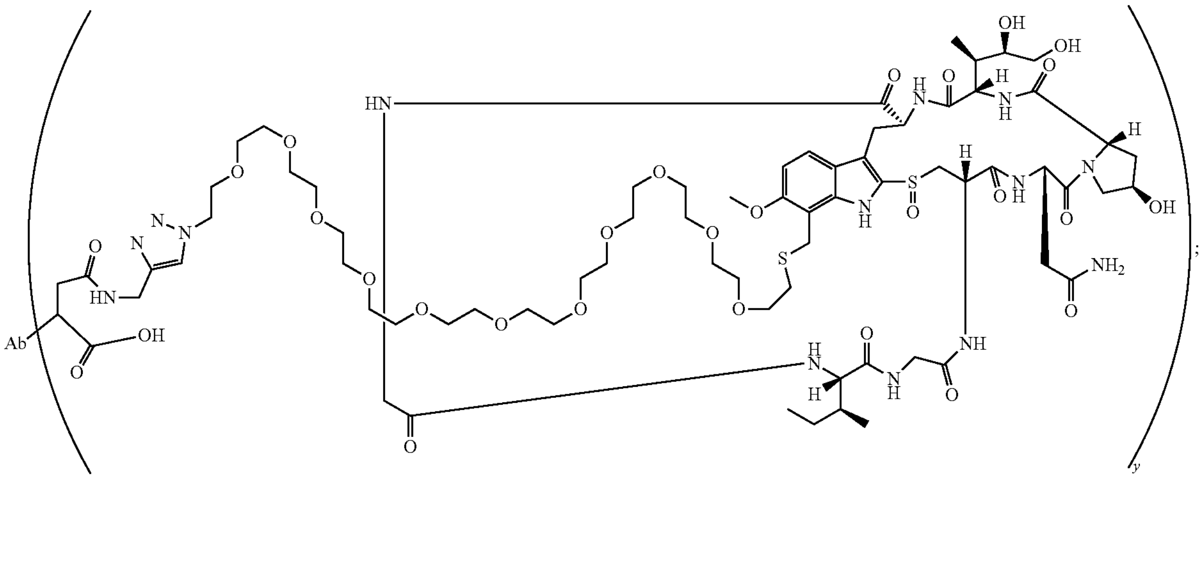
;
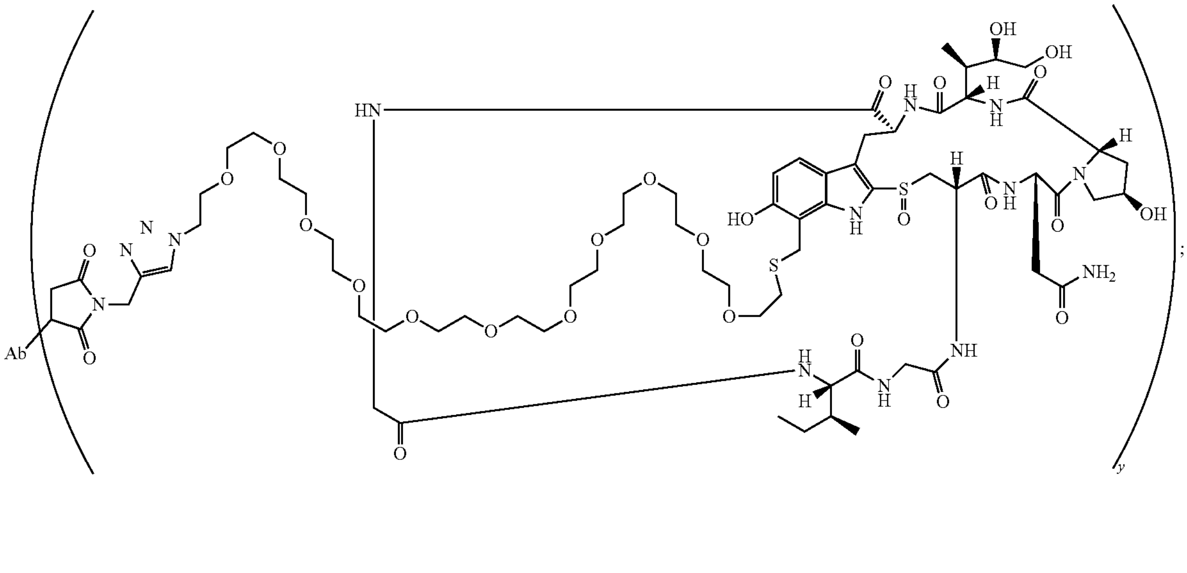
;
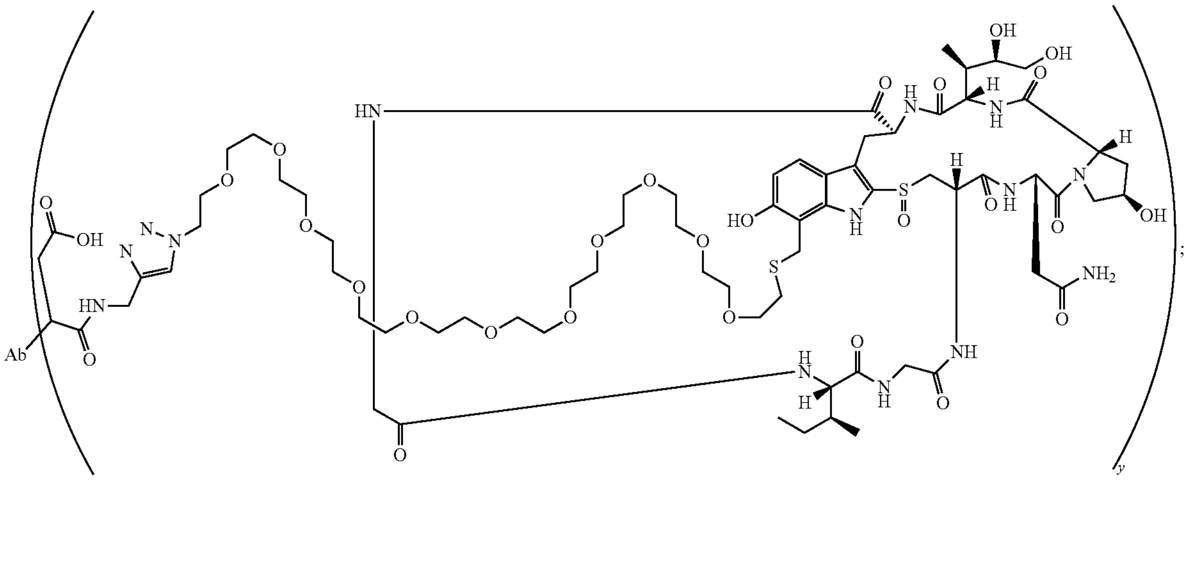
;

-continued
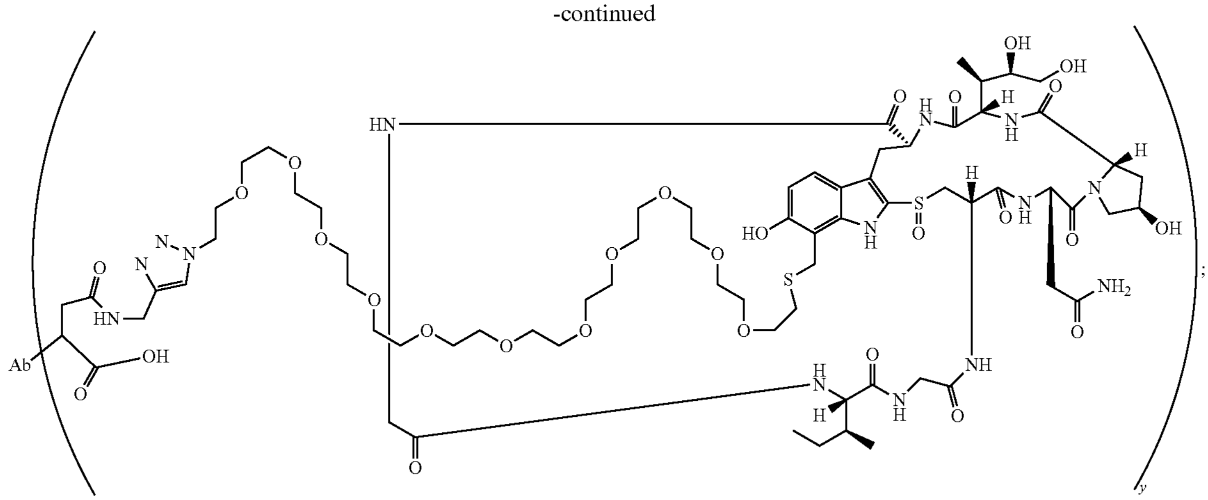
;
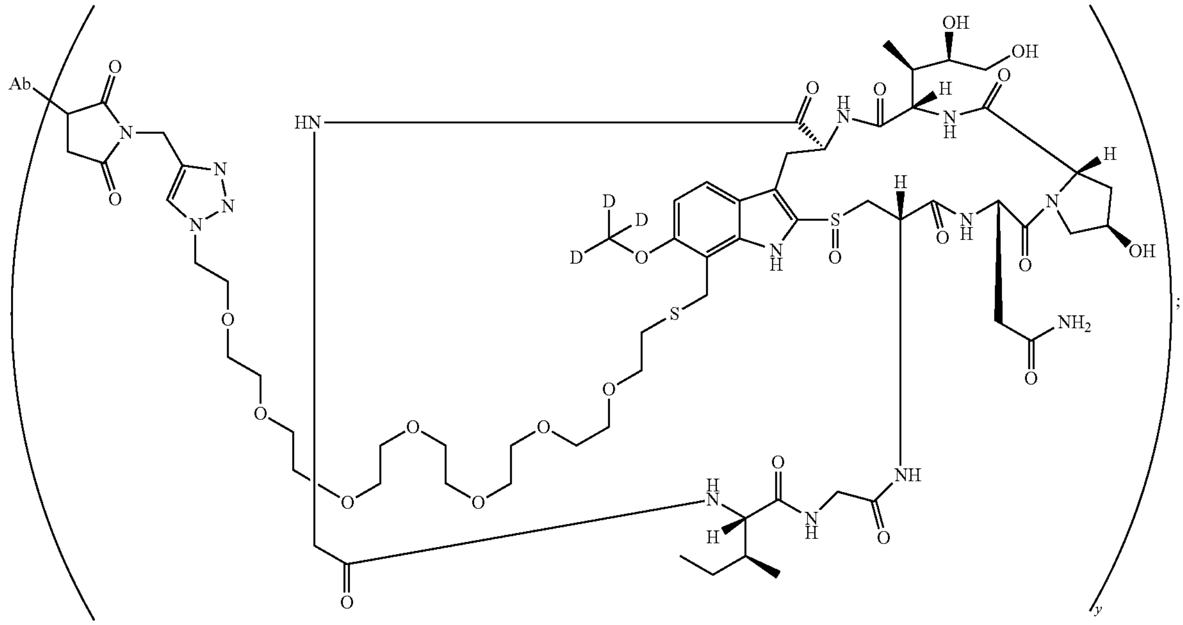
;
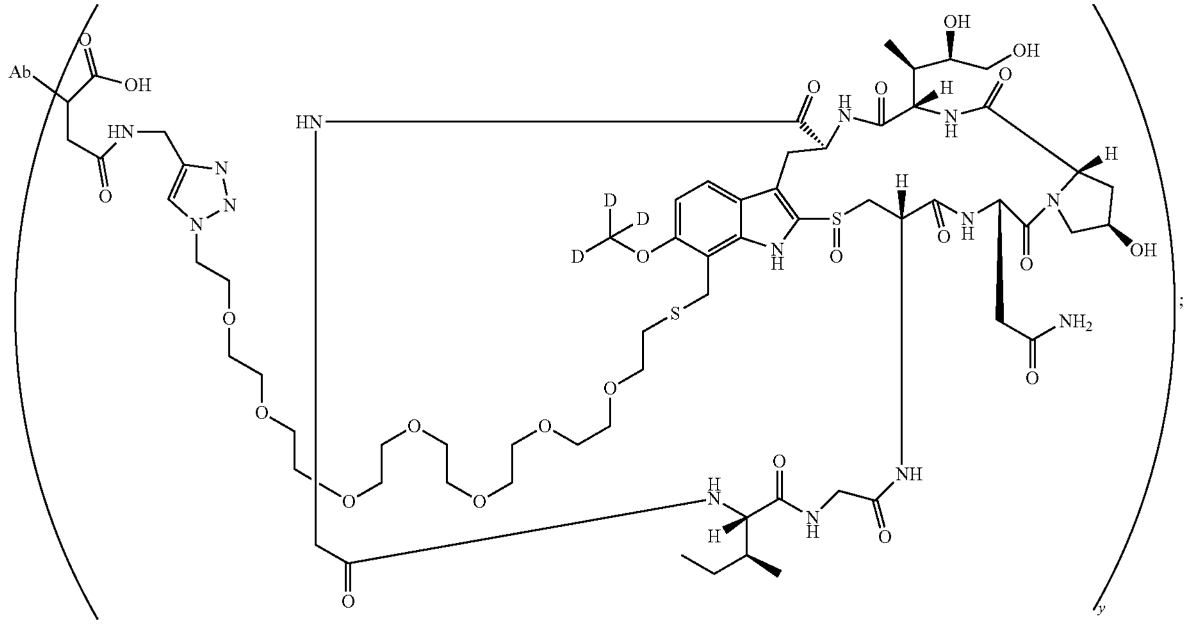
;

-continued
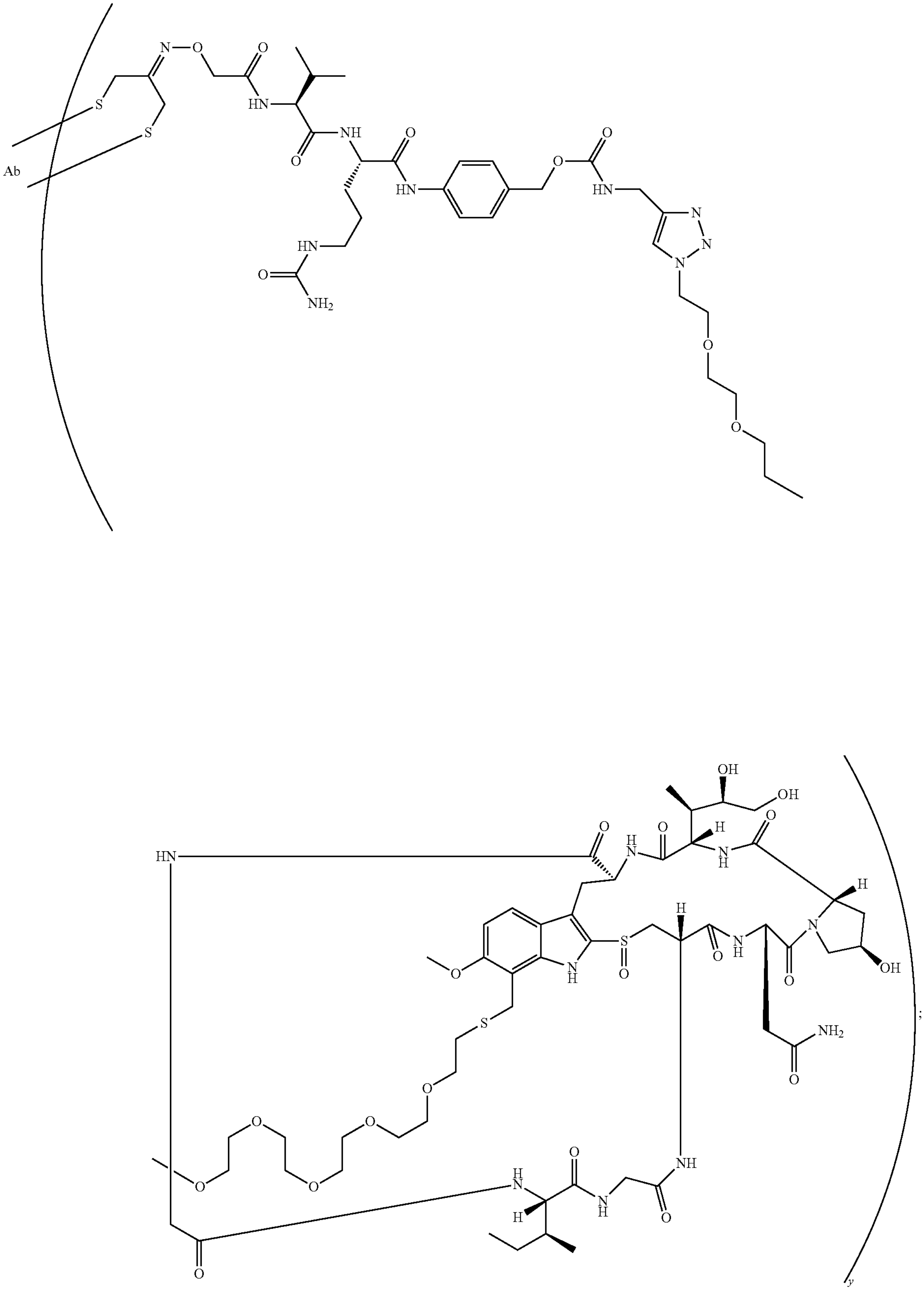
;

-continued
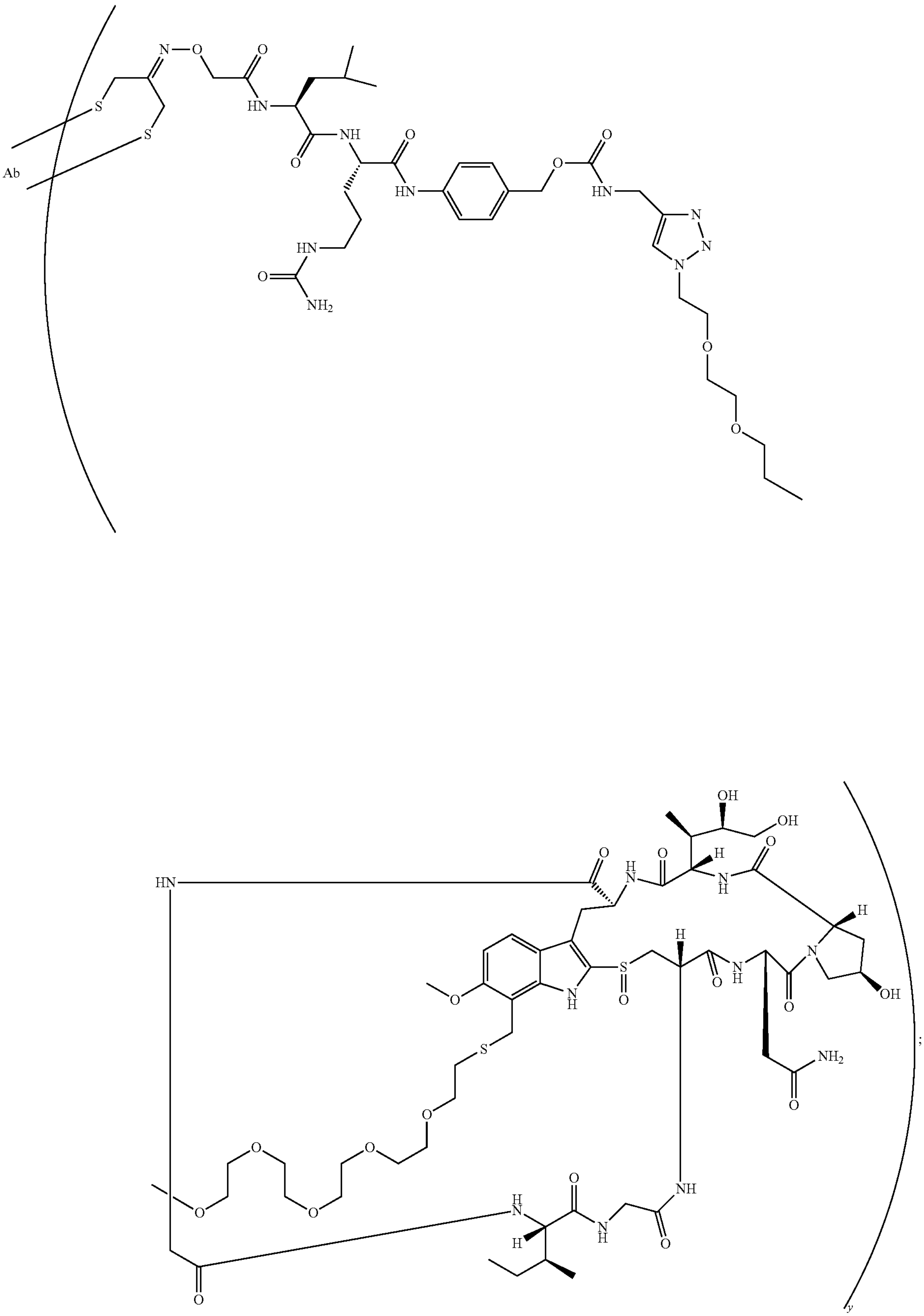
;

-continued
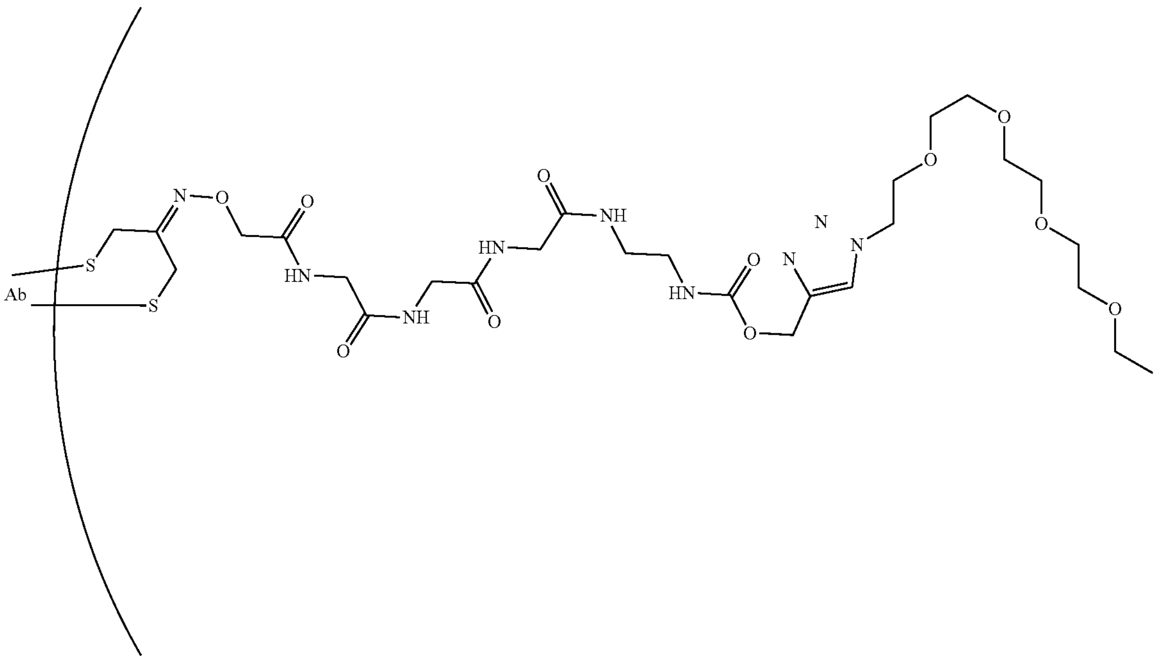
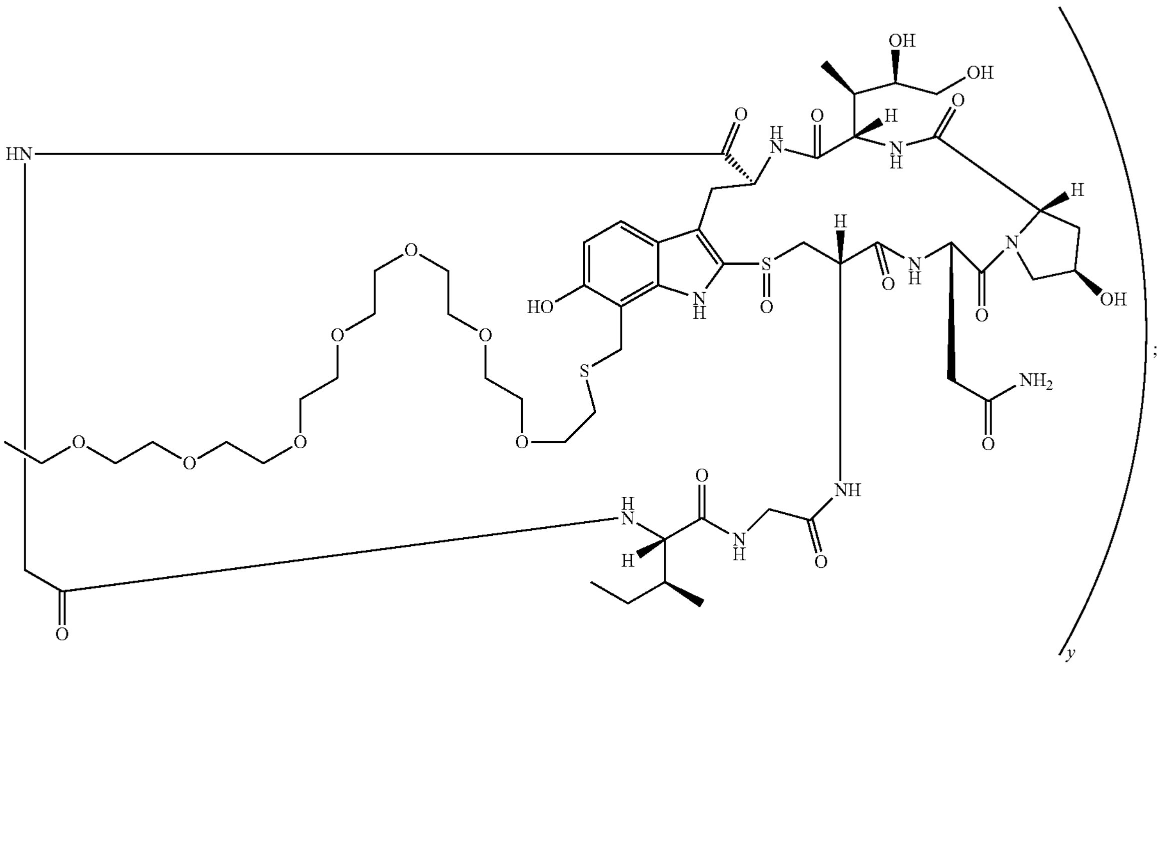
;

-continued
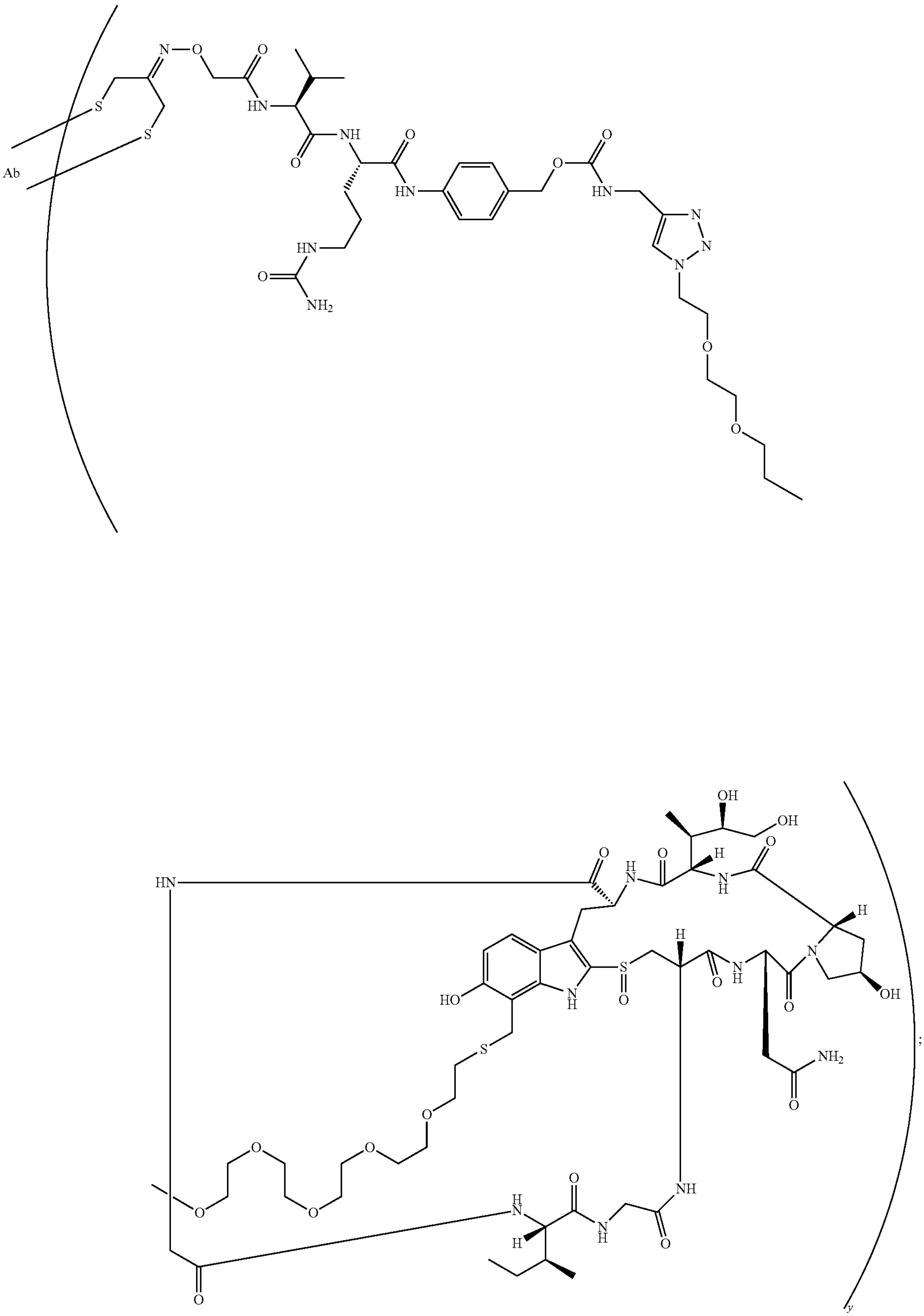
;

-continued
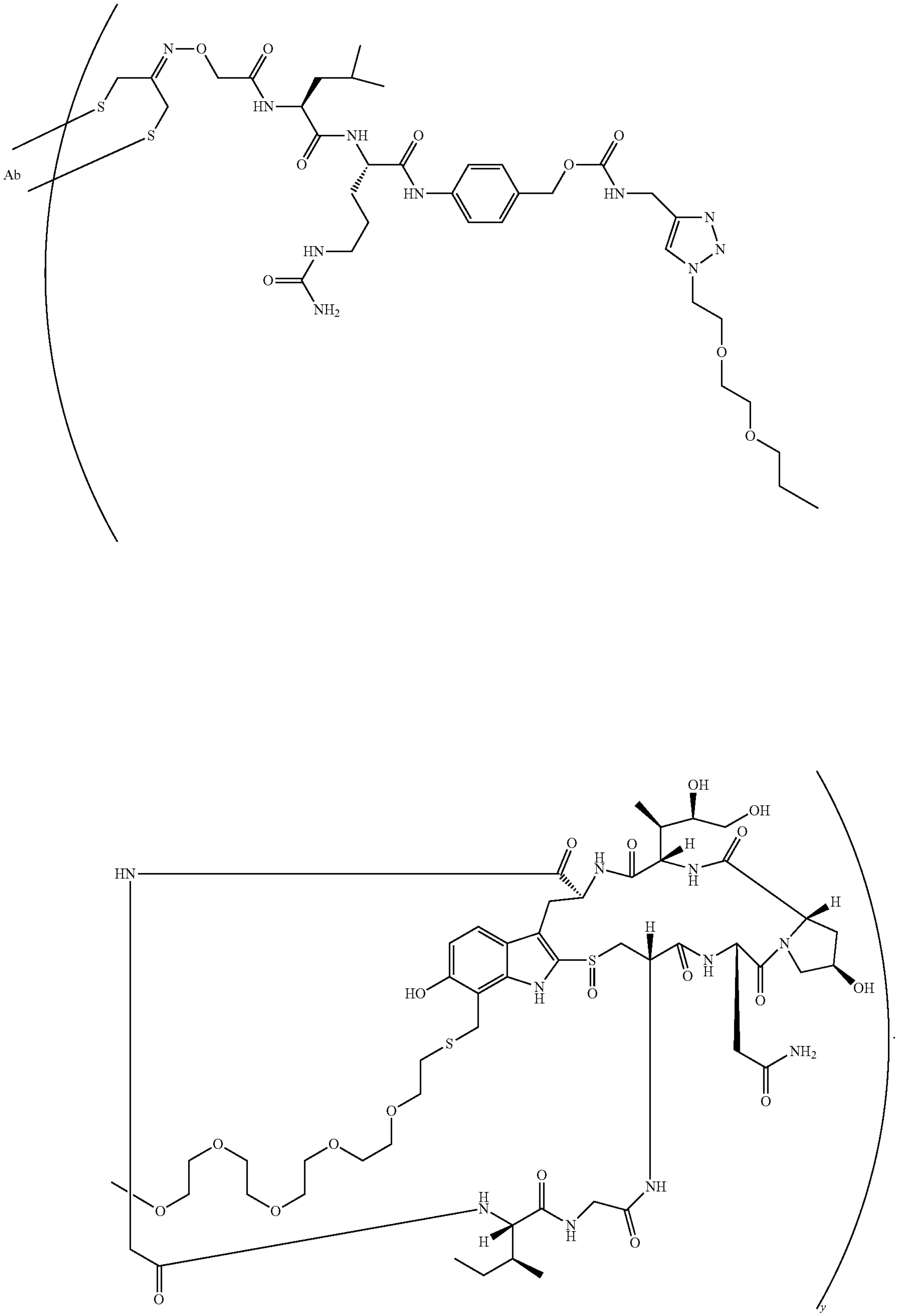
. and

-continued

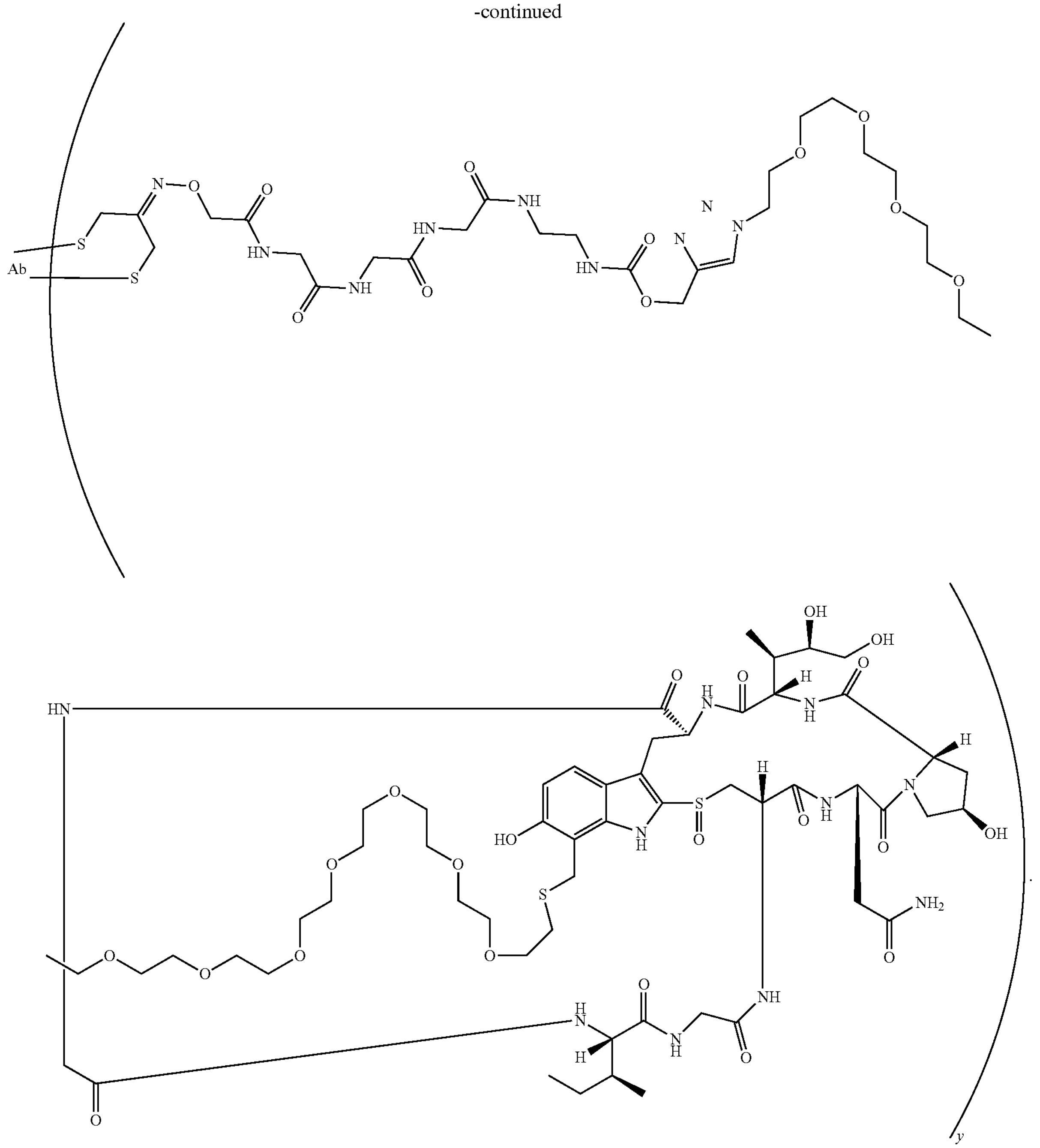

Embodiment 88

The immunoconjugates of Formula (B), Formula (II) and Formula (IIa) wherein $R^3$ is —$CH_3$.

Embodiment 89

The immunoconjugates of Formula (B), Formula (II) and Formula (IIa) wherein $R^3$ is —$CD_3$.

Embodiment 90

The immunoconjugates of Formula (B), Formula (II) and Formula (IIa) wherein $R^1$ is —H.

Embodiment 91

The immunoconjugates of Formula (B), Formula (II) and Formula (IIa) wherein $R^3$ is —$NH_2$.

Embodiment 92

The immunoconjugates of Formula (B), Formula (II) and Formula (IIa) wherein $R^3$ is —OH.

Embodiment 93

The immunoconjugates of Formula (B), Formula (II) and Formula (IIa) wherein $L_{20}$ is -$L_1R^{40}$.

Embodiment 94

The immunoconjugates of Formula (B), Formula (II) and Formula (IIa) wherein $L_1$ is $—((CH_2)_mO)_n(CH_2)_mX_3L_4$-.

Embodiment 95

The immunoconjugates of Formula (B), Formula (II) and Formula (IIa) wherein $L_1$ is $—((CH_2)_mO)_n(CH_2)_mX_4L_4$-.

Embodiment 96

The immunoconjugates of Formula (B), Formula (II) and Formula (IIa) wherein $L_4$ is $—((CH_2)_m—$.

Embodiment 97

The immunoconjugates of Formula (B), Formula (II) and Formula (IIa) wherein $L_4$-$((CH_2)_mNHC(=O)X_1X_2C(=O)(CH_2)_m—$.

Embodiment 98

The immunoconjugates of Formula (B), Formula (II) and Formula (IIa) wherein $X_1$ is

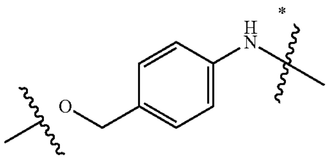

or

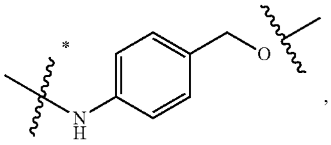

, where the * indicates attachment point to $X_2$.

Embodiment 99

The immunoconjugates of Formula (B), Formula (II) and Formula (IIa) wherein $X_1$ is

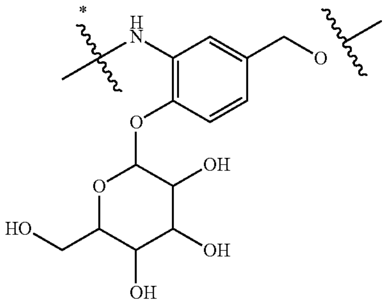

,

-continued

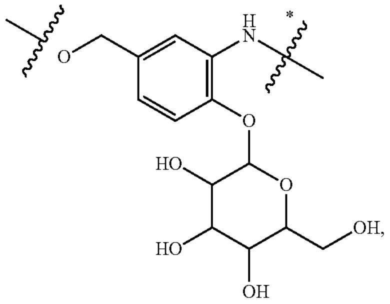

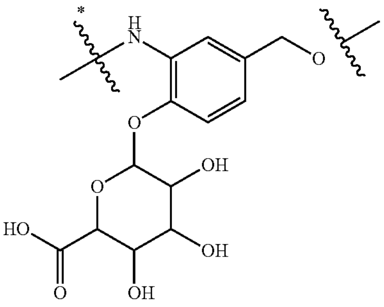

or

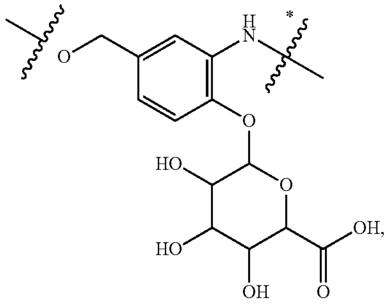

where the * indicates attachment point to $X_2$.

Embodiment 100

The immunoconjugates of Formula (B), Formula (II) and Formula (IIa) wherein $X_2$ is

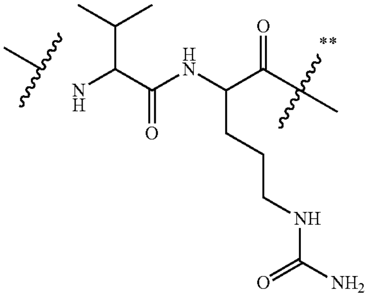

or

-continued

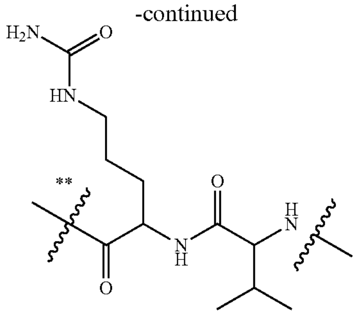

, where the ** indicates attachment point to $X_1$.

Embodiment 101

The immunoconjugates of Formula (B), Formula (II) and Formula (IIa) wherein $X_2$ is

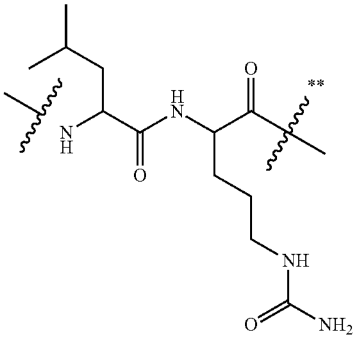

or

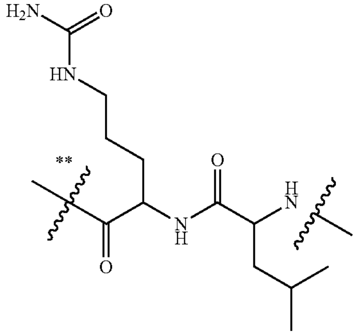

, where the ** indicates attachment point to $X_1$.

Embodiment 102

The immunoconjugates of Formula (B), Formula (II) and Formula (IIa) wherein $X_2$ is

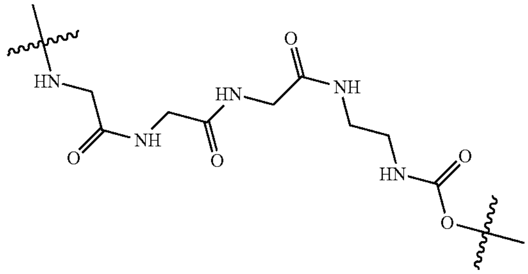

or

-continued

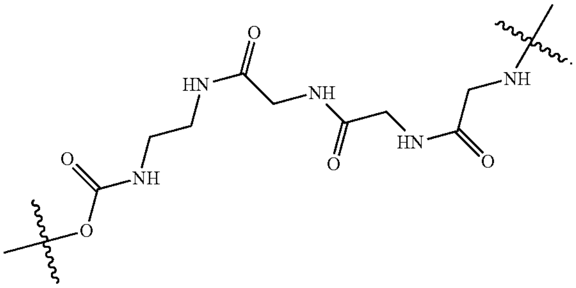

Embodiment 103

The immunoconjugates of Formula (B), Formula (II) and Formula (IIa) wherein $X_2$ is

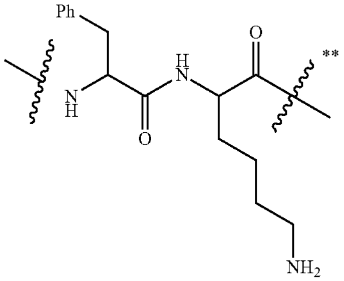

or

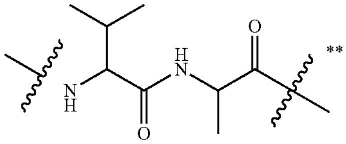

, where the ** indicates attachment point to $X_1$.

Embodiment 104

The immunoconjugates of Formula (B), Formula (II) and Formula (IIa) wherein $X_3$ is

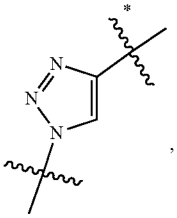 [SMILES: *c1cn(*)nn1]

, where the * indicates attachment point to $L_4$.

Embodiment 105

The immunoconjugates of Formula (B), Formula (II) and Formula (IIa) wherein $X_3$ is

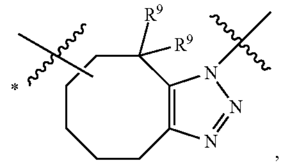
,

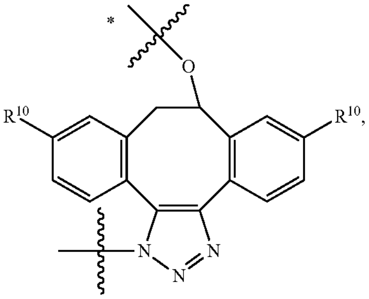

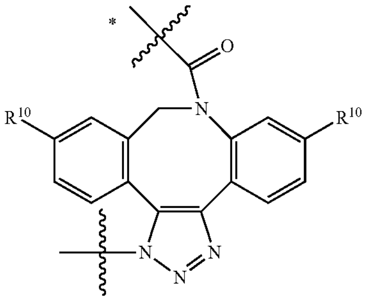
or

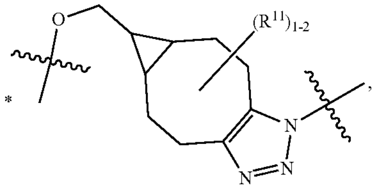
, where the * indicates attachment point to $L_4$.

Embodiment 106

The immunoconjugates of Formula (B), Formula (II) and Formula (IIa) wherein $X_4$ is

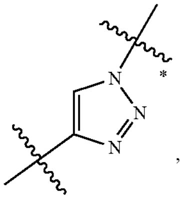 [SMILES: *c1cn(*)nn1]
, where the * indicates attachment point to $L_4$.

Embodiment 107

The immunoconjugates of Formula (B), Formula (II) and Formula (IIa) wherein $X_4$ is

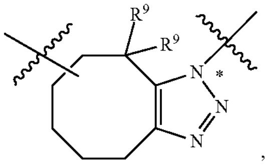
,

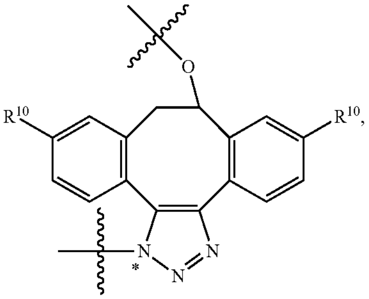

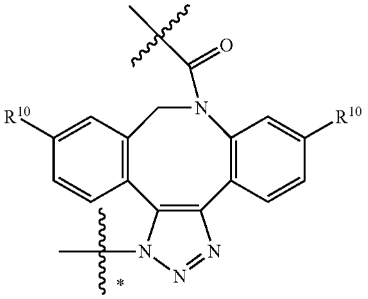
or

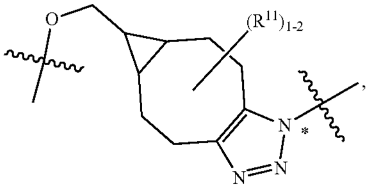
, where the * indicates attachment point to $L_4$.

Embodiment 107

The immunoconjugates of Formula (B), Formula (II) and Formula (IIa) wherein $R^{40}$ is

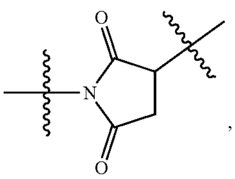
,
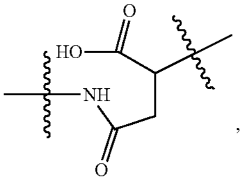
,

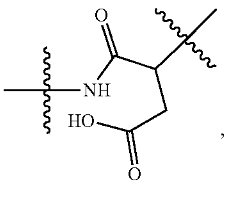
,
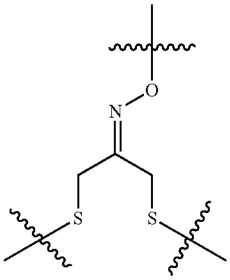
or

-continued

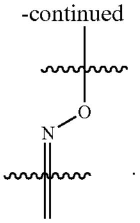

.

Embodiment 108

The immunoconjugates of Formula (B), Formula (II) and Formula (IIa) wherein $R^{40}$ is

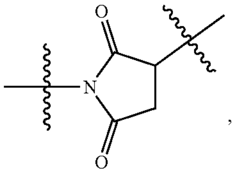

,

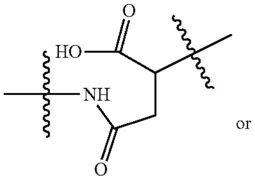

or

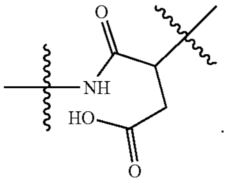

.

Embodiment 109

The immunoconjugates of Formula (B), Formula (II) and Formula (IIa) wherein $R^{40}$ is,

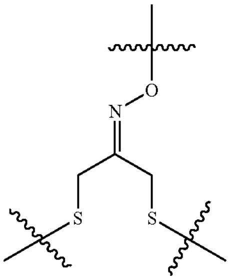

or

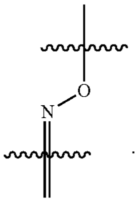

.

Embodiment 110

The immunoconjugates of Formula (B), Formula (II) and Formula (IIa) wherein $R^{40}$ is $-NR^5C(=O)CH_2-$, $-NHC(=O)CH_2-$, $-S(=O)_2CH_2CH_2-$, $-(CH_2)_2S(=O)_2CH_2CH_2-$, $-NR^5S(=O)_2CH_2CH_2$, $-NR^5C(=O)CH_2CH_2-$, $-NH-$, $-C(=O)-$, $-NHC(=O)-$, $-CH_2NHCH_2CH_2-$, $-NHCH_2CH_2-$ or $-S-$.

Embodiment 111

The immunoconjugates of Formula (B), Formula (II) and Formula (IIa) wherein $R^{40}$ is

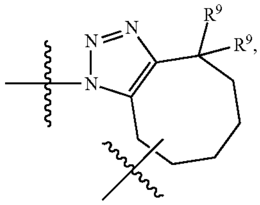

,

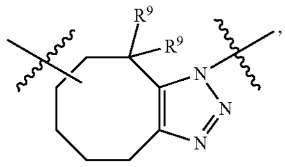

,

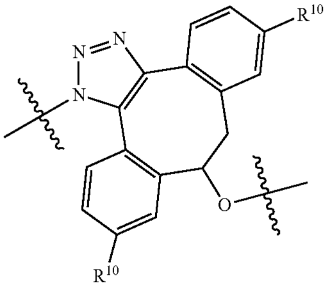

,

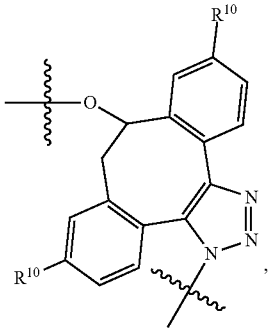

,

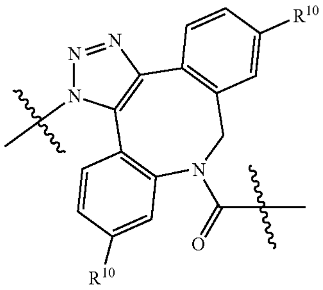

,

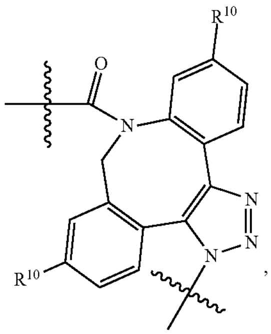

,

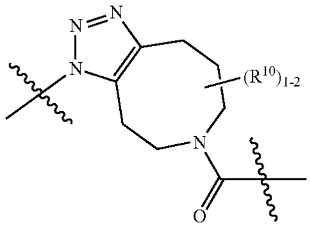

,

-continued

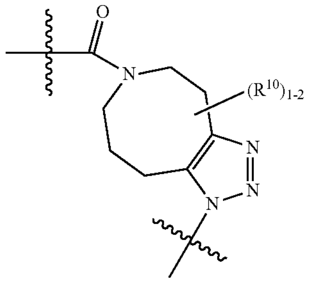

or

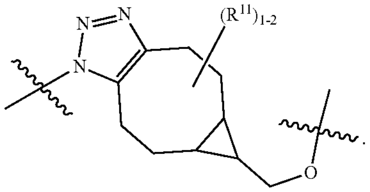

Embodiment 112

The immunoconjugates of Formula (B), Formula (II) and Formula (IIa) wherein each $R^5$ is H.

Embodiment 113

The immunoconjugates of Formula (B), Formula (II) and Formula (IIa) wherein each $R^5$ is $C_1$-$C_6$alkyl.

Embodiment 114

The compounds of Formula (A), Formula (I) and Formula (Ia) and the immunoconjugates of Formula (B), Formula (II) and Formula (IIa) wherein each m is independently selected from 1, 2, 3, 4, 5 and 6.

Embodiment 115

The compounds of Formula (A), Formula (I) and Formula (Ia) and the immunoconjugates of Formula (B), Formula (II) and Formula (IIa) wherein each m is independently selected from 1, 2, 3, 4 and 5.

Embodiment 116

The compounds of Formula (A), Formula (I) and Formula (Ia) and the immunoconjugates of Formula (B), Formula (II) and Formula (IIa) wherein each m is independently selected from 1, 2, 3 and 4.

Embodiment 117

The compounds of Formula (A), Formula (I) and Formula (Ia) and the immunoconjugates of Formula (B), Formula (II) and Formula (IIa) wherein each m is independently selected from 1, 2 and 3.

Embodiment 118

The compounds of Formula (A), Formula (I) and Formula (Ia) and the immunoconjugates of Formula (B), Formula (II) and Formula (IIa) wherein each m is independently selected from 1 and 2.

Embodiment 119

The compounds of Formula (A), Formula (I) and Formula (Ia) and the immunoconjugates of Formula (B), Formula (II) and Formula (IIa) wherein each n is independently selected from 1, 2, 3, 4, 5, 6, 7, 8, 9, 10, 11 and 12.

Embodiment 120

The compounds of Formula (A), Formula (I) and Formula (Ia) and the immunoconjugates of Formula (B), Formula (II) and Formula (IIa) wherein each n is independently selected from 1, 2, 3, 4, 5, 6, 7, 8, 9, 10 and 11.

Embodiment 121

The compounds of Formula (A), Formula (I) and Formula (Ia) and the immunoconjugates of Formula (B), Formula (II) and Formula (IIa) wherein each n is independently selected from 1, 2, 3, 4, 5, 6, 7, 8, 9, 10, 11, 12, 13 and 14.

Embodiment 122

The compounds of Formula (A), Formula (I) and Formula (Ia) and the immunoconjugates of Formula (B), Formula (II) and Formula (IIa) wherein each n is independently selected from 1, 2, 3, 4, 5, 6, 7, 8 and 9.

Embodiment 123

The compounds of Formula (A), Formula (I) and Formula (Ia) and the immunoconjugates of Formula (B), Formula (II) and Formula (IIa) wherein each n is independently selected from 1, 2, 3, 4, 5, 6, 7 and 8.

Embodiment 124

The compounds of Formula (A), Formula (I) and Formula (Ia) and the immunoconjugates of Formula (B), Formula (II) and Formula (IIa) wherein each n is independently selected from 1, 2, 3, 4, 5, 6 and 7.

Embodiment 125

The compounds of Formula (A), Formula (I) and Formula (Ia) and the immunoconjugates of Formula (B), Formula (II) and Formula (IIa) wherein each n is independently selected from 1, 2, 3, 4, 5 and 6.

Embodiment 126

The compounds of Formula (A), Formula (I) and Formula (Ia) and the immunoconjugates of Formula (B), Formula (II) and Formula (IIa) wherein each n is independently selected from 1, 2, 3, 4 and 5.

Embodiment 127

The compounds of Formula (A), Formula (I) and Formula (Ia) and the immunoconjugates of Formula (B), Formula (II) and Formula (IIa) wherein each n is independently selected from 1, 2, 3 and 4.

Embodiment 128

The compounds of Formula (A), Formula (I) and Formula (Ia) and the immunoconjugates of Formula (B), Formula (II) and Formula (IIa) wherein each n is independently selected from 1, 2 and 3.

Embodiment 129

The compounds of Formula (A), Formula (I) and Formula (Ia) and the immunoconjugates of Formula (B), Formula (II) and Formula (IIa) wherein each n is independently selected from 1 and 2.

Embodiment 130

The compounds of Formula (A), Formula (I) and Formula (Ia) and the immunoconjugates of Formula (B), Formula (II) and Formula (IIa) wherein y is 1, 2, 3, 4, 5, 6, 7, 8, 9, 10, 11 or 12.

Embodiment 131

The compounds of Formula (A), Formula (I) and Formula (Ia) and the immunoconjugates of Formula (B), Formula (II) and Formula (IIa) wherein y is 1, 2, 3, 4, 5, 6, 7, 8, 9, 10 or 11.

Embodiment 132

The compounds of Formula (A), Formula (I) and Formula (Ia) and the immunoconjugates of Formula (B), Formula (II) and Formula (IIa) wherein y is 1, 2, 3, 4, 5, 6, 7, 8, 9 or 10.

Embodiment 133

The compounds of Formula (A), Formula (I) and Formula (Ia) and the immunoconjugates of Formula (B), Formula (II) and Formula (IIa) wherein y is 1, 2, 3, 4, 5, 6, 7, 8 or 9.

Embodiment 134

The compounds of Formula (A), Formula (I) and Formula (Ia) and the immunoconjugates of Formula (B), Formula (II) and Formula (IIa) wherein y is 1, 2, 3, 4, 5, 6, 7 and 8.

Embodiment 135

The compounds of Formula (A), Formula (I) and Formula (Ia) and the immunoconjugates of Formula (B), Formula (II) and Formula (IIa) wherein y is 1, 2, 3, 4, 5, 6 or 7.

Embodiment 136

The compounds of Formula (A), Formula (I) and Formula (Ia) and the immunoconjugates of Formula (B), Formula (II) and Formula (IIa) wherein y is 1, 2, 3, 4, 5 or 6.

Embodiment 137

The compounds of Formula (A), Formula (I) and Formula (Ia) and the immunoconjugates of Formula (B), Formula (II) and Formula (IIa) wherein y is 1, 2, 3, 4 or 5.

Embodiment 138

The compounds of Formula (A), Formula (I) and Formula (Ia) and the immunoconjugates of Formula (B), Formula (II) and Formula (IIa) wherein y is 1, 2, 3 or 4.

Embodiment 139

The compounds of Formula (A), Formula (I) and Formula (Ia) and the immunoconjugates of Formula (B), Formula (II) and Formula (IIa) wherein y is 1, 2 or 3.

Embodiment 140

The compounds of Formula (A), Formula (I) and Formula (Ia) and the immunoconjugates of Formula (B), Formula (II) and Formula (IIa) wherein y is 1 or 2.

In the immunoconjugates of Formula (B), Formula (II) or Formula (IIa), unless otherwise described, Ab can be any antigen binding moiety, and is preferably an antigen or antigen fragment that recognizes a cell surface marker such as those described herein that is characteristic of a targeted cell, such as a cancer cell. In addition, in the immunoconjugates of Formula (B), Formula (II) or Formula (IIa), unless otherwise described, Ab can be any antigen binding moiety, typically one that recognizes an antigen characteristic of cells to be targeted for pharmaceutical intervention, such as cancer cells. Many suitable antigens are well known in the art; specific ones of special interest are described herein. Typically, Ab is an antibody, which may be isolated or constructed, and may be natural or modified (engineered), or an antibody fragment that retains antigen binding activity similar to the antibody.

The invention provides immunoconjugates comprising one or more cytotoxic cyclic peptides linked to an antigen-binding moiety, such as an antibody or antibody fragment. Preferred immunoconjugates of the invention are those of Formula (II) or Formula (IIa) as described herein.

Non-limiting examples of immunoconjugates of Formula (B), Formula (II) or Formula (IIa) are given in Tables 4 and 5. However, immunoconjugates of Formula (B), Formula (II) or Formula (IIa) can also include variations thereof having another antigen binding moiety instead of anti-Her2 antibody, particularly such conjugates where anti-Her2 antibody is replaced by an antibody selected from the following list: anti-estrogen receptor antibody, anti-progesterone receptor antibody, anti-p53 antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD1-antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD39 antibody, anti-CD41 antibody, anti-LCA/CD45 antibody, anti-CD45RO antibody, anti-CD45RA antibody, anti-CD71 antibody, anti-CD95/Fas antibody, anti-CD99 antibody, anti-CD100 antibody, anti-S-100 antibody, anti-CD106 antibody, anti-ubiquitin antibody, anti-c-myc antibody, anti-cytokeratin antibody, anti-lambda light chains antibody, anti-melanosomes antibody, anti-prostate specific antigen antibody, anti-tau antigen antibody, anti-fibrin antibody, anti-keratins antibody, and anti-Tn-antigen antibody.

Linkers

The cytotoxic cyclic peptides provided herein for use as payloads in immunoconjugate (ADC) of Formula (B), Formula (II) and Formula (IIa) are attached to an antigen binding moiety via the linker, $L_{20}$, where $L_{20}$ is $-L_1R^{40}$—. Furthermore, the linker, $-L_1R^{40}$—, is attached to the cytotoxic cyclic peptides of the invention via an —$CH_2S$— group, where the $CH_2S$— has been attached to the 7' position of the amatoxin indole and where the $-L_1$-component of the linker, -$L_1R^{40}$—, is attached to the sulphur of the —$CH_2S$— group. The linker, $L_{20}$, can be attached to the antigen binding moiety at any suitable available position on the antigen binding moiety: typically the linker is attached to an available amino nitrogen atom (i.e., a primary or secondary amine, rather than an amide) or a hydroxylic oxygen atom, or to an available sulfhydryl, such as on a cysteine.

The linker, -$L_1$-, of compounds of Formula (A), Formula (I), and Formula (Ia) and of immunoconjugates of Formula (B), Formula (II) and Formula (IIa) can be cleavable or non-cleavable. Cleavable linkers, such as those containing a hydrazone, a disulfide, the dipeptide Val-Cit, Ile-Cit and ones containing a glucuronidase-cleavable p-aminobenzyloxycarbonyl moiety, are well known in the art, and can be used. See, e.g., Ducry, et al., *Bioconjugate Chem., vol.* 21, 5-13 (2010). For the immunoconjugates of comprising a cleavable linker, the linker is substantially stable in vivo until the immunoconjugate binds to or enters a cell, at which point either intracellular enzymes or intracellular chemical conditions (pH, reduction capacity) cleave the linker to free the cytotoxic peptide.

Alternatively, non-cleavable linkers can be used in compounds of Formula (A), Formula (I) and Formula (Ia) and in the immunoconjugates of Formula (B), Formula (II) and Formula (IIa). Non-cleavable linkers lack structural components designed to degrade in cells, and thus their structures can vary substantially. See, e.g., Ducry, et al., *Bioconjugate Chem., vol.* 21, 5-13 (2010). These immunoconjugates are believed to enter a targeted cell and undergo proteolytic degradation of the antibody rather than linker decomposition; thus at least a portion, or all, of the linker and even some of the antibody or antibody fragment may remain attached to the payload.

The linker component, -$L_1$-, of compounds of Formula (A), Formula (I), and Formula (Ia) and immunoconjugates of Formula (B), Formula (II) and Formula (IIa) is selected from $—((CH_2)_mO)_n(CH_2)_mX_3L_4$- or $—((CH_2)_mO)_n(CH_2)_mX_4L_4$-, where $X_3$, $X_4$, $L_4$, m and n are as defined herein.

The linker component, -$L_1$-, can comprise thiol-maleimide groups, thioethers, amides, and esters; groups that are easily cleaved in vivo under conditions found in, on or around targeted cells, such as disulfides, hydrazones, dipeptides like Val-Cit and Ile-Cit, substituted benzyloxycarbonyl groups, and the like; spacers to orient the payload in a suitable position relative to the antigen binding moiety, such as phenyl, heteroaryl, cycloalkyl or heterocyclyl rings, and alkylene chains; and/or pharmacokinetic property-enhancing groups, such as alkylene substituted with one or more polar groups (carboxy, sulfonate, hydroxyl, amine, amino acid, saccharide), and alkylene chains containing one or more —NH— or —O— in place of methylene group(s), such as glycol ethers $(—CH_2CH_2O—)_p$ where p is 1-14, which may enhance solubility or reduce intermolecular aggregation, for example.

The linker, -$L_{20}$- can comprise chemical moieties that are readily formed by reaction between two reactive groups. Non-limiting examples of such chemical moieties are given in Table 1.

In preferred embodiments, linker, -$L_{20}$-, of immunoconjugates of Formula (B), Formula (II) and Formula (IIa) includes a group formed upon reaction of a reactive functional group with one of the amino acid side chains commonly used for conjugation, e.g., the thiol of cysteine, the free —$NH_2$ of lysine, or a

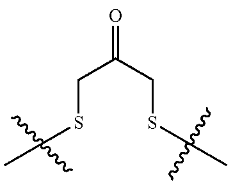 [SMILES: *SCC(=O)CS*]

group formed from a disulfide bridge. Such groups formed by reaction with a cysteine residue of the antigen binding moiety include, but are not limited to,

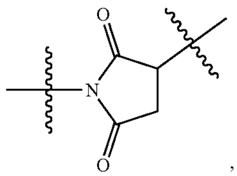,
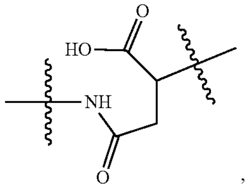,
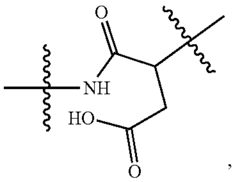,
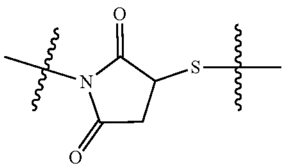,
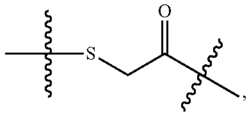,
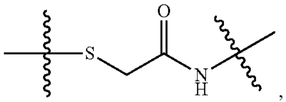,
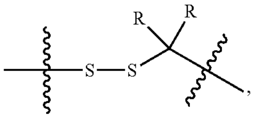,
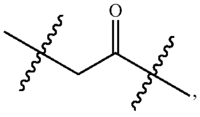,
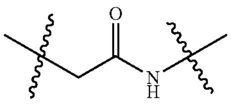
and
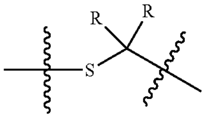, where each R is independently H or $C_{1-4}$ alkyl (preferably methyl). Such groups formed by reaction with the —$NH_2$ of a lysine residue of the antigen binding moiety, where each p is 1-14, and each R is independently H or $C_{1-4}$ alkyl (preferably methyl) include, but are not limited to,

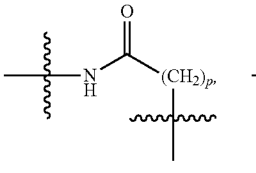
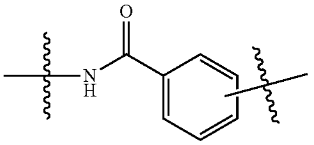,
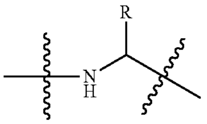
and
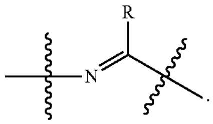.

Such a group formed upon reaction of

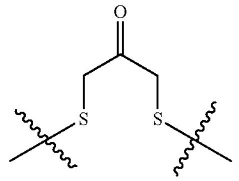 [SMILES: *SCC(=O)CS*]

and a compound of Formula (I) or Formula (Ia) which contains an hydroxylamine is

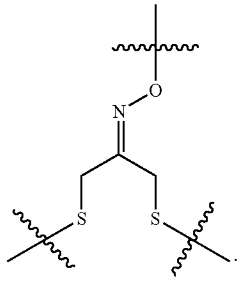 [SMILES: *ON=C(CS*)CS*]

In the most preferred embodiments, an immunoconjugate of Formula (B), Formula (II) or Formula (IIa) comprises Ab, an antibody or antibody fragment having antigen-binding activity, where the linker $-L_1R^{40}$ is attached to Ab at a cysteine sulfur atom of Ab. The resulting linkage formed by reaction with a cysteine residue of the antigen binding moiety is

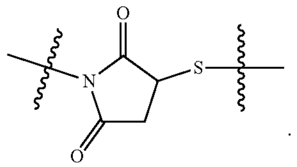 [SMILES: *SC1CC(=O)N(*)C1=O]

In such embodiments the $R^{40}$ of linkers $-L_1R^{40}$ is

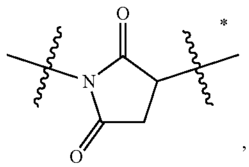

,

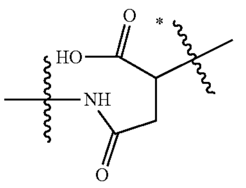

or

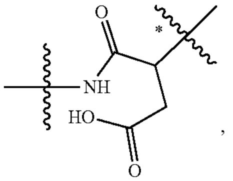

, and the * indicates the point of attachment to the cysteine sulfur atom.

Other reactive groups used for reaction with a cysteine sulfur group and the resulting group formed are given in Table 1.

In the other preferred embodiments, an immunoconjugate of Formula (II) or Formula (IIa) comprises Ab, an antibody or antibody fragment having antigen-binding activity, where the linker $-L_1R^{40}$ is attached to Ab via a bridged disulfide in Ab. The resulting linkage formed is

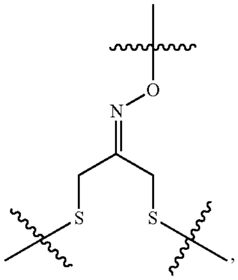 [SMILES: *ON=C(CS*)CS*]

and the $R^{40}$ of linkers $-L_1R^{40}$ is

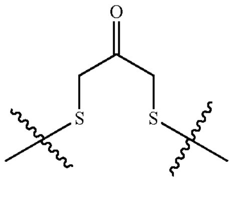

or

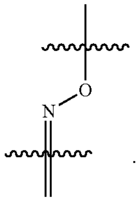

.

In other embodiments, an immunoconjugate of Formula (B), Formula (II) or Formula (IIa) comprises Ab, an antibody or antibody fragment having antigen-binding activity, where the linker $-L_1R^{40}$ is attached to Ab at a free $-NH_2$ of a lysine residue.

By way of example, one general reaction scheme for the formation of immunoconjugates of Formula (II) is shown in Scheme 5 below:

Scheme 5

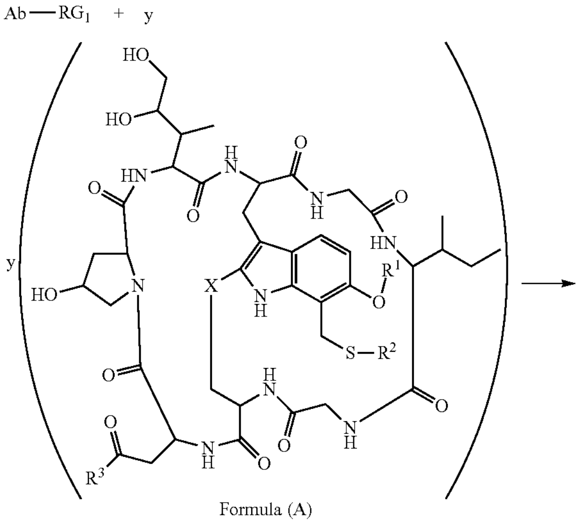

Formula (A)

-continued

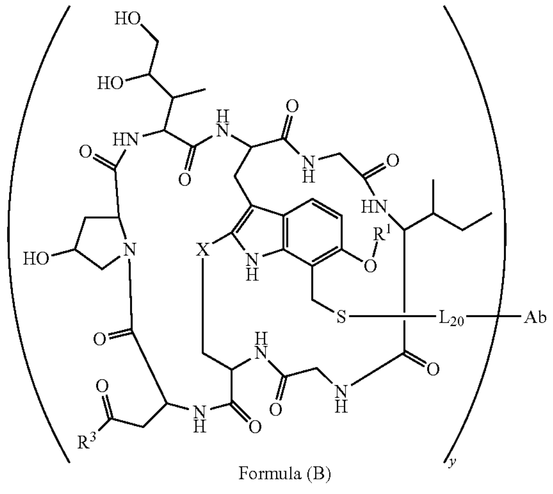

Formula (B)

-continued

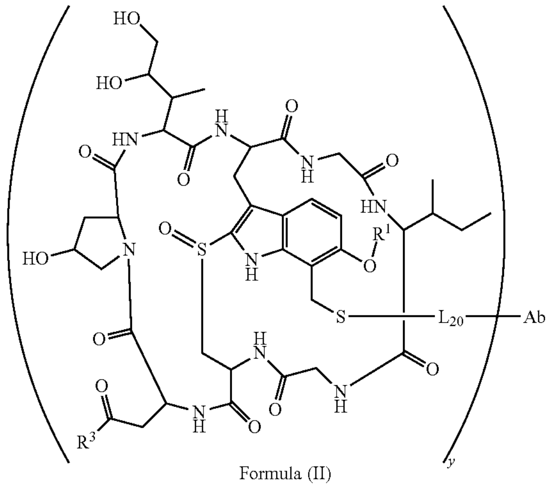

Formula (II)

where $RG_1$ is a reactive group 1 from Table 1 and $R^2$ is $-L_1R^4$, where $R^4$ is as defined herein or is a reactive group 2 from Table 1. $L_{20}$ is $-L_1R^{40}$ and $R^{40}$ is as defined herein or is the chemical moiety as seen in Table 1. X, $R^1$, $R^3$, and Ab are as defined herein.

where $RG_1$ is a reactive group 1 from Table 1 and $R^2$ is $-L_1R^4$, where $R^4$ is as defined herein or is a reactive group 2 from Table 1. $L_{20}$ is $-L_1R^{40}$ and $R^{40}$ is as defined herein or is the chemical moiety as seen in Table 1. $R^1$, $R^3$, and Ab are as defined herein.

By way of example, one general reaction scheme for the formation of immunoconjugates of Formula (II) is shown in Scheme 6 below:

Another general reaction scheme for the formation of immunoconjugates of Formula (II) is shown in Scheme 7 below:

Scheme 6

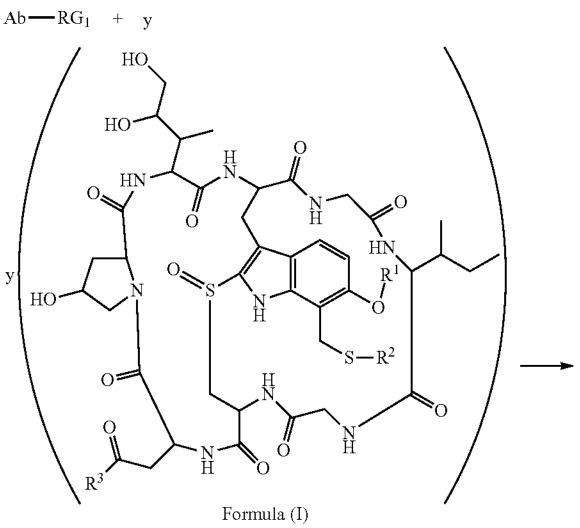

Formula (I)

Scheme 7

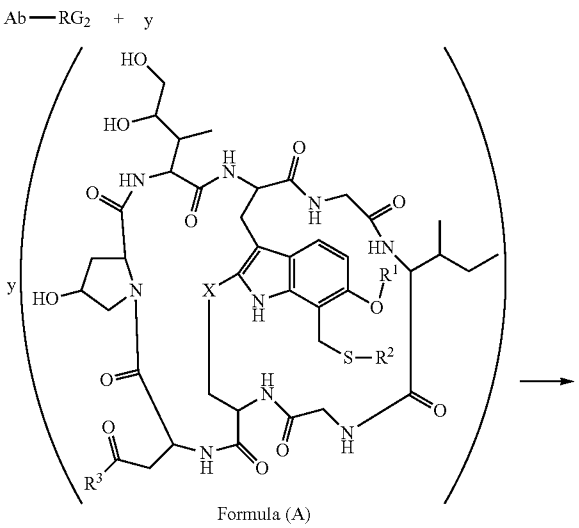

Formula (A)

-continued

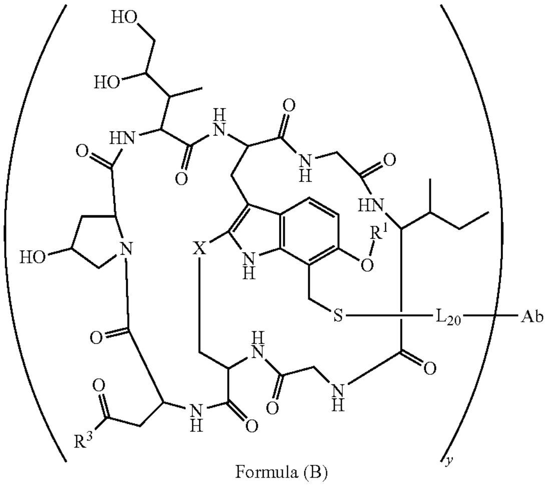

Formula (B)

where $RG_2$ is a reactive group 2 from Table 1 and $R^2$ is $-L_1R^4$, where $R^4$ is as defined herein or is a reactive group 1 from Table 1. $L_{20}$ is $-L_1R^{40}$ and $R^{40}$ is as defined herein or is the chemical moiety as seen in Table 1. X, $R^1$, $R^3$, and Ab are as defined herein.

Another general reaction scheme for the formation of immunoconjugates of Formula (II) is shown in Scheme 8 below:

Scheme 8

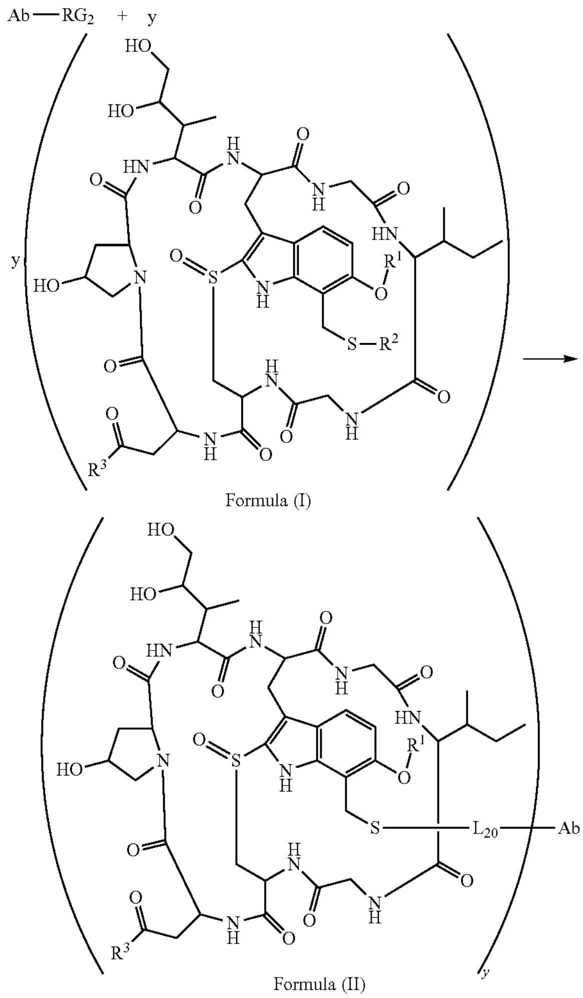

Formula (I)

Formula (II)

where $RG_2$ is a reactive group 2 from Table 1 and $R^2$ is $-L_1R^4$, where $R^4$ is as defined herein or is a reactive group 1 from Table 1. $L_{20}$ is $-L_1R^{40}$ and $R^{40}$ is as defined herein or is the chemical moiety as seen in Table 1. $R^1$, $R^3$, and Ab are as defined herein.

TABLE 1

| Reactive Group 1 | Reactive Group 2 | Chemical Moiety |
|---|---|---|
| a thiol | a thiol | —S—S— |
| a thiol | a maleimide | 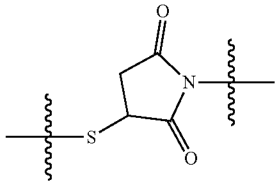 [SMILES: *SC1CC(=O)N(*)C1=O] |
| a thiol | a haloacetamide | 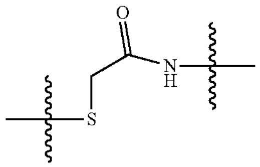 [SMILES: *NC(=O)CS*] |

TABLE 1-continued
| Reactive Group 1 | Reactive Group 2 | Chemical Moiety |
|---|---|---|
| an azide | an alkyne | 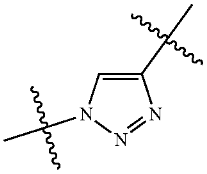 or 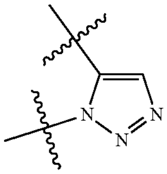 |
| an alkyne | an azide | +get,218 |
| a cyclooctyne | azide | 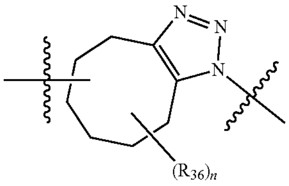 or 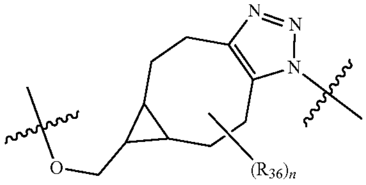 or 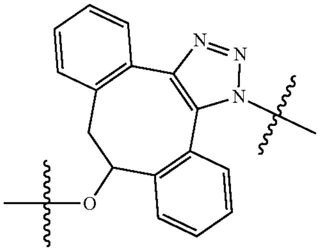 |
| an aldehyde | a hydroxylamine | 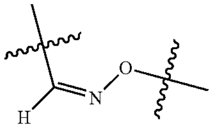 [SMILES: */C=N\O*] |
| an aldehyde | a hydrazine | 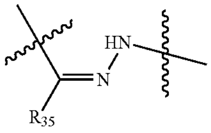 |
| an aldehyde | $NH_2$—NH—C(=O)— | 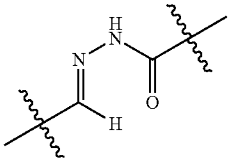 [SMILES: */C=N/NC(*)=O] |
| a ketone | a hydroxylamine | 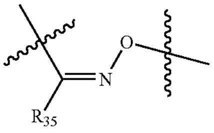 |

TABLE 1-continued
| Reactive Group 1 | Reactive Group 2 | Chemical Moiety |
|---|---|---|
| a ketone | a hydrazine | 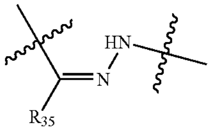 |
| a ketone | $NH_2$—NH—C(═O)— | 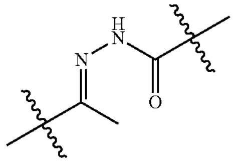 [SMILES: *C(=O)N/N=C(/*)C] |
| a hydroxylamine | an aldehyde | 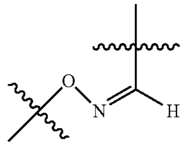 [SMILES: */C=N\O*] |
| a hydroxylamine | a ketone | 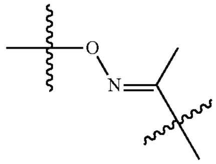 [SMILES: *O/N=C(/*)C] |
| a hydrazine | an aldehyde | 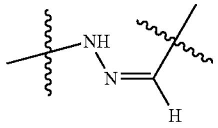 [SMILES: */C=N\N*] |
| a hydrazine | a ketone | 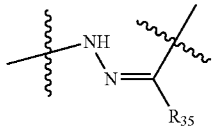 |
| $NH_2$—NH—C(═O)— | an aldehyde | 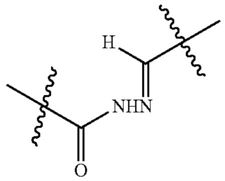 |
| $NH_2$—NH—C(═O)— | a ketone | 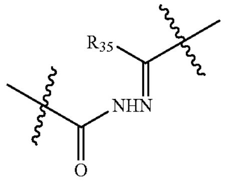 |
| a haloacetamide | a thiol | 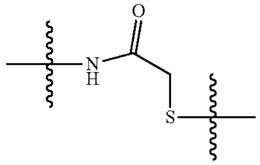 [SMILES: *NC(=O)CS*] |

TABLE 1-continued

| Reactive Group 1 | Reactive Group 2 | Chemical Moiety |
| --- | --- | --- |
| a maleimide | a thiol | 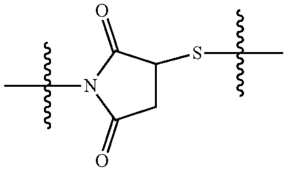 [SMILES: *SC1CC(=O)N(*)C1=O] |
| a vinyl sulfone | a thiol | 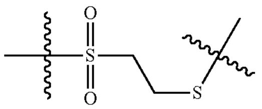 [SMILES: *SCCS(*)(=O)=O] |
| a thiol | a vinyl sulfone | 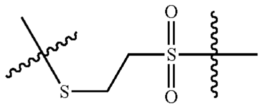 [SMILES: *SCCS(*)(=O)=O] |
| an aziridine | a thiol | 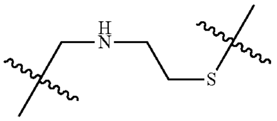 or 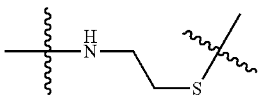 |
| a thiol | an aziridine | 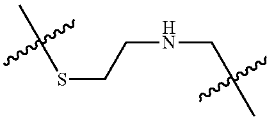 or 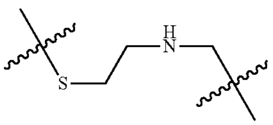 |
| 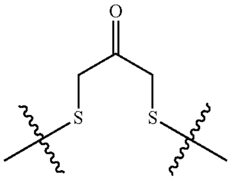 [SMILES: *SCC(=O)CS*] | hydroxylamine | 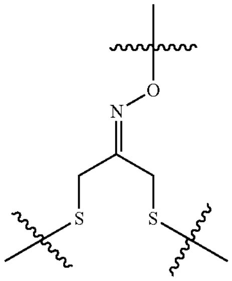 [SMILES: *ON=C(CS*)CS*] |

where: $R^{35}$ in Table 1 is H, $C_{1-6}$alkyl, phenyl or $C_{1-4}$alkyl substituted with 1 to 3 —OH groups; each $R^{36}$ in Table 1 is independently selected from H, $C_{1-6}$alkyl, fluoro, benzyloxy substituted with —C(═O)OH, benzyl substituted with —C(═O)OH, $C_{1-4}$alkoxy substituted with —C(═O)OH and $C_{1-4}$alkyl substituted with —C(═O)OH In another aspect, the present invention provides a pharmaceutical composition comprising an immunoconjugate of Formula (B), Formula (II) or Formula (IIa) of the present invention and at least one pharmaceutically acceptable carrier. The pharmaceutical composition can be formulated for particular routes of administration such as intravenous administration, parenteral administration, and the like.

The immunoconjugates of the invention are typically formulated as solutions or suspensions in aqueous buffer and/or isotonic aqueous solution. They are typically administered parenterally, either by injection or by infusion. Methods for their formulation and administration are similar to those for formulation and administration of other biologic-based pharmaceuticals such as antibody therapeutics, and are known to those of skill in the art.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

The immunoconjugates comprising a compound of formula (I), as demonstrated herein, exhibit substantial activity on targeted cells in vitro and on tumors in vivo, as demonstrated by potent growth inhibition of xenograft tumors representing different human cancers. Thus the immunoconjugates of Formula (B), Formula (II) or Formula (IIa) of the invention, comprising a payload of Formula (A), Formula (I), and subformulae thereof, linked to an antigen binding moiety such as an antibody, are also useful to treat cancers, such as gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

An embodiment of the invention provides conjugation of a compound of Formula (A), Formula (I) or Formula (Ia) to an antigen binding moiety and thereby forming an immunoconjugate of Formula (B), Formula (II) or Formula (IIa), as described herein.

The immunoconjugates of Formula (B), Formula (II) or Formula (IIa) of the invention, which comprise a compound of Formula (A), Formula (I) or Formula (Ia), are particularly useful for treating cancers known in the art to be inhibited by toxins which inhibit RNA polymerase, and those tumor types demonstrated herein to be susceptible to inhibition by the compounds and conjugates of the invention. Suitable indications for treatment include, but are not limited to, gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma. The immunoconjugates of the invention comprising a compound of Formula (I), or subformulae thereof, are particularly useful in therapy. In a further embodiment, the therapy is for a disease which may be treated by anti-mitotic toxins. In another embodiment, the compounds of the invention are useful to treat cancers, including but not limited to gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

The methods typically comprise administering an effective amount of an immunoconjugate of Formula (B), Formula (II) or Formula (IIa) of the invention as described herein or a pharmaceutical composition comprising such immunoconjugates to a subject in need of such treatment. The immunoconjugate may be administered by any suitable method such as those described herein, and the administration may be repeated at intervals selected by a treating physician.

Thus, as a further embodiment, the present invention provides the use of a immunoconjugate of Formula (B), Formula (II) or Formula (IIa) for the manufacture of a medicament. In a further embodiment, the medicament is for treatment of a disease which may be treated by the inhibition of RNA polymerase. In another embodiment, the disease is selected from gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

The pharmaceutical composition or combination of the present invention can be in unit dosage of about 1-1000 mg of active ingredient(s) for a subject of about 50-100 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-12}$ molar concentrations. A therapeutically effective amount in vivo may range depending on the route of administration, between about 0.1-500 mg/kg, or between about 1-100 mg/kg.

An immunoconjugate of Formula (B), Formula (II) or Formula (IIa), of the present invention may be administered either simultaneously with, or before or after, one or more therapeutic co-agent(s). An immunoconjugate of Formula (B), Formula (II) or Formula (IIa), of the present invention may be administered separately, by the same or different route of administration, or together in the same pharmaceutical composition as the co-agent(s).

In one embodiment, the invention provides a product comprising immunoconjugate of Formula (B), Formula (II) or Formula (IIa), and at least one other therapeutic co-agent as a combined preparation for simultaneous, separate or sequential use in therapy. In one embodiment, the therapy is the treatment of a disease or condition such as cancer with an anti-mitotic toxin. Products provided as a combined preparation include a composition comprising an immunoconjugate of Formula (B), Formula (II) or Formula (IIa), and the other therapeutic co-agent(s) together in the same pharmaceutical composition, or the immunoconjugate of Formula (B), Formula (II) or Formula (IIa), and the other therapeutic co-agent(s) in separate form, e.g. in the form of a kit.

In one embodiment, the invention provides a pharmaceutical composition comprising an immunoconjugate of Formula (B), Formula (II) or Formula (IIa), and another therapeutic co-agent(s). Optionally, the pharmaceutical composition may comprise a pharmaceutically acceptable carrier, as described above.

Suitable co-agents for use with the immunoconjugates of the invention include other anti-cancer agents, anti-allergic agents, anti-nausea agents (or anti-emetics), pain relievers, anti-inflammatory agents, cytoprotective agents, and combinations thereof.

Specific co-agents considered for use in combination with the compounds and conjugates disclosed herein include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In one embodiment, the invention provides a kit comprising two or more separate pharmaceutical compositions, at least one of which contains an immunoconjugate of Formula (B), Formula (II) or Formula (IIa). In one embodiment, the kit comprises means for separately retaining said compositions, such as a container, divided bottle, or divided foil packet In the combination therapies of the invention, the immunoconjugate of Formula (B), Formula (II) or Formula (IIa) of the invention and the other therapeutic co-agent may be manufactured and/or formulated by the same or different manufacturers. Moreover, the immunoconjugate of Formula (B), Formula (II) or Formula (IIa) of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

The invention also provides an immunoconjugate of Formula (B), Formula (II) or Formula (IIa), for use in a method of treating a disease or condition with a cytotoxic peptide. The invention also provides an immunoconjugate of Formula (B), Formula (II) or Formula (IIa) for use in a method of treating a disease or condition with a cytotoxic peptide, wherein the immunoconjugate of Formula (B), Formula (II) or Formula (IIa) is prepared for administration with another therapeutic agent. The invention also provides an immunoconjugate of Formula (B), Formula (II) or Formula (IIa) for use in a method of treating a disease or condition with cytotoxic peptide, wherein the immunoconjugate of Formula (B), Formula (II) or Formula (IIa), is administered to the a subject in need of such treatment. The invention also provides another therapeutic co-agent for use in a method of treating a disease or condition with a cytotoxic peptide, wherein the other therapeutic co-agent is prepared for administration with an immunoconjugate of Formula (B), Formula (II) or Formula (IIa). The invention also provides an immunoconjugate of Formula (B), Formula (II) or Formula (IIa) for use in a method of treating a disease or condition with an toxin which inhibits RNA Polymerase, wherein the immunoconjugate of Formula (B), Formula (II) or Formula (IIa), is administered with another therapeutic co-agent.

The invention also provides the use of an immunoconjugate of Formula (B), Formula (II) or Formula (IIa), for treating a disease or condition with a cytotoxic peptide, wherein the patient has previously (e.g. within 24 h) been treated with another therapeutic agent. The invention also provides the use of another therapeutic agent for treating a disease or condition with an anti-mitotic toxin, wherein the patient has previously (e.g. within 24 h) been treated with an immunoconjugate of Formula (B), Formula (II) or Formula (IIa).

The invention also provides an immunoconjugate of Formula (B), Formula (II) or Formula (IIa) for use in a method of treating a disease or condition with a toxin which inhibits RNA polymerase, wherein the immunoconjugate of Formula (B), Formula (II) or Formula (IIa), is administered to the a subject in need of such treatment. The invention also provides an immunoconjugate of Formula (B), Formula (II) or Formula (IIa), for use in a method of treating a disease or condition with a toxin which inhibits RNA polymerase. The invention also provides an immunoconjugate of Formula (B), Formula (II) or Formula (IIa) for use in a method of treating a disease or condition with a toxin which inhibits RNA polymerase, wherein the immunoconjugate of Formula (B), Formula (II) or Formula (IIa) is prepared for administration with another therapeutic agent. The invention also provides another therapeutic co-agent for use in a method of treating a disease or condition with a toxin which inhibits RNA polymerase, wherein the other therapeutic co-agent is prepared for administration with an immunoconjugate of Formula (B), Formula (II) or Formula (IIa). The invention also provides an immunoconjugate of Formula (B), Formula (II) or Formula (IIa) for use in a method of treating a disease or condition with a toxin which inhibits RNA polymerase, wherein the immunoconjugate of Formula (B), Formula (II) or Formula (IIa) is administered with another therapeutic co-agent. The invention also provides another therapeutic co-agent for use in a method of treating a disease or condition with a toxin which inhibits RNA polymerase, wherein the other therapeutic co-agent is administered with an immunoconjugate of Formula (B), Formula (II) or Formula (IIa).

The invention also provides the use of an immunoconjugate of Formula (B), Formula (II) or Formula (IIa), for treating a disease or condition with a toxin which inhibits RNA polymerase, wherein the patient has previously (e.g. within 24 h) been treated with another therapeutic agent. The invention also provides the use of another therapeutic agent for treating a disease or condition with an anti-mitotic toxin, wherein the patient has previously (e.g. within 24 h) been treated with an immunoconjugate of Formula (B), Formula (II) or Formula (IIa).

Synthetic Methods

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (see e.g., Houben-Weyl 4th Ed. 1952, *Methods of Organic Synthesis, Thieme, Volume* 21). Further, the compounds of the present invention can be produced by organic synthesis methods known to one of ordinary skill in the art in view of the following examples.

Illustrative examples of synthetic approaches to the compound of Formula (A), Formula (I) and Formula (Ia) are provided in the following general Scheme 1, Scheme 2, Scheme 3 and Scheme 4.

In Scheme 1, a Thiol-Mannich reaction is used to couple an $L_2N_3$ group to the 7 position of the indole of an Amanitin (α or β) via formation of a methylene linked thio ether. Subsequent reaction with the alkyne,

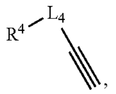

results in the formation of certain compounds Formula (A), Formula (I) and Formula (Ia):

Scheme 1

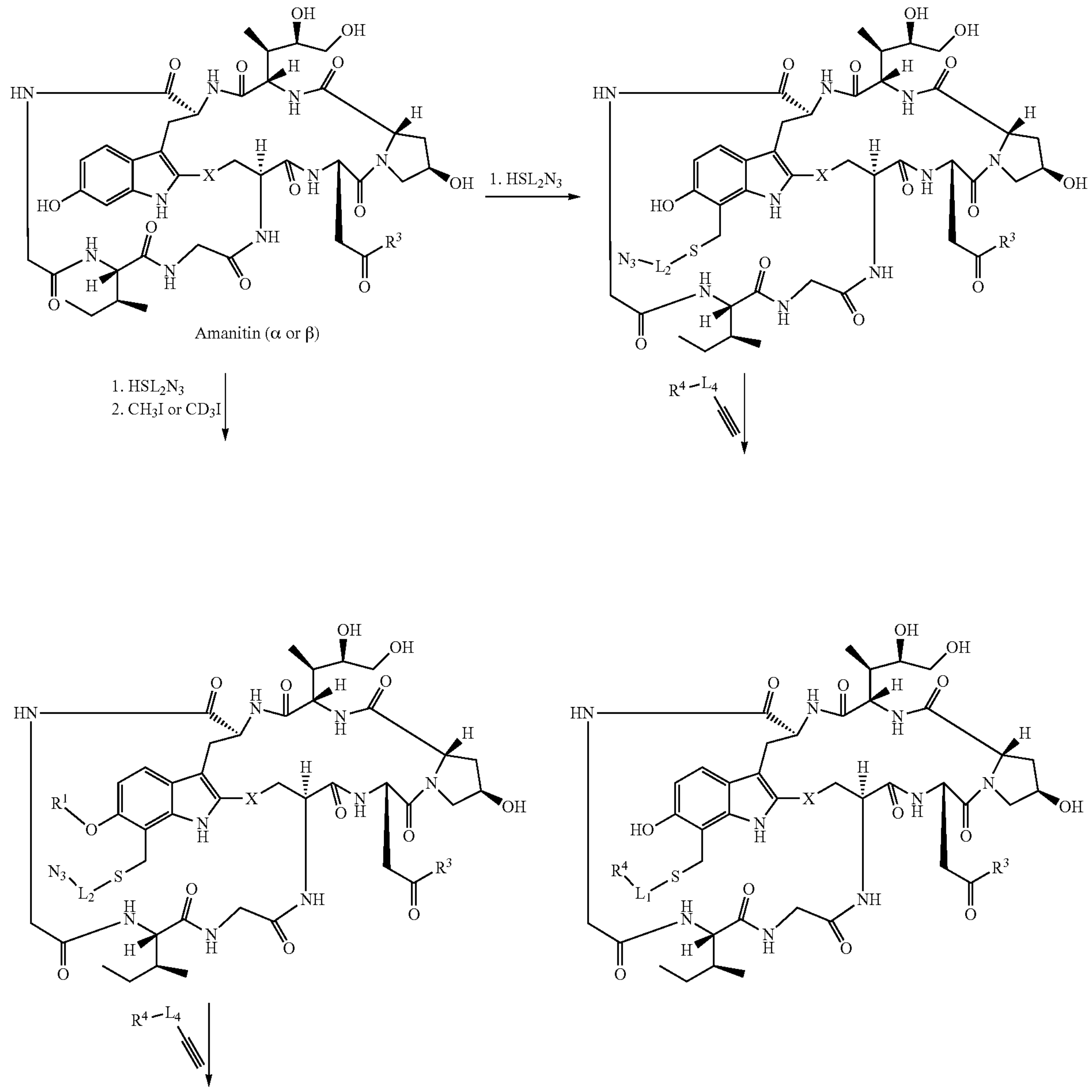

-continued

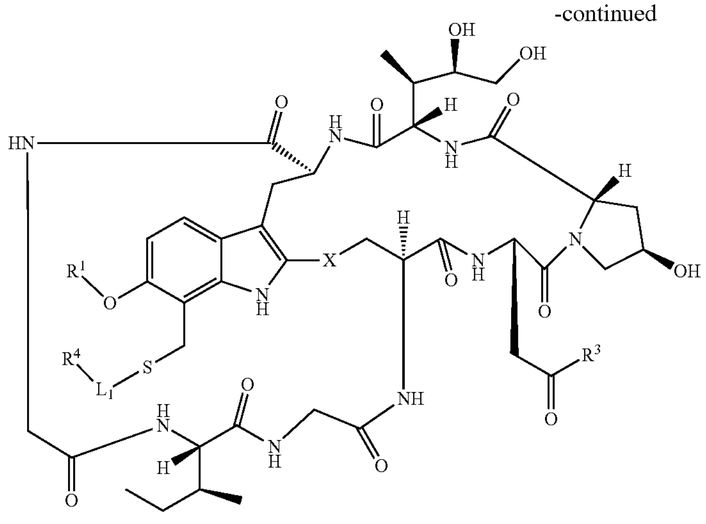

where: X is $S(=O)$, $S(=O)_2$ or S; $R^1$ is $-CH_3$ or $-CD_3$; $L_1$ is $-((CH_2)_mO)_n(CH_2)_mX_3L_4$-, $L_2$ is $-((CH_2)_mO)_n(CH_2)_m-$ and $L_4$ is $-((CH_2)_m-$ or $-((CH_2)_mNHC(=O)X_1X_2C(=O)(CH_2)_m-$;

$R^4$ is

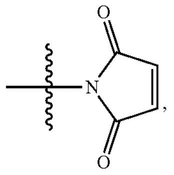 [SMILES: *N1C(=O)C=CC1=O]

$-ONH_2$, SH, $-NR_5C(=O)CH=CH_2$, $-S(=O)_2(CH=CH_2)$, $-NR^5S(=O)_2(CH=CH_2)$, $-NR^5C(=O)CH_2Br$, $-NR^5C(=O)CH_2I$, $-NHC(=O)CH_2Br$, $-NHC(=O)CH_2I$, $-C(O)NHNH_2$, $CO_2H$, $-NH_2$,

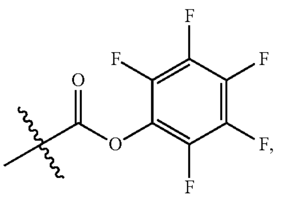

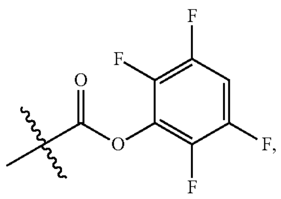

-continued

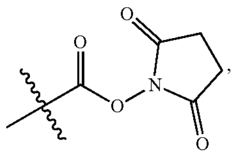

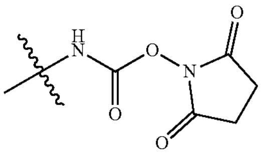

or

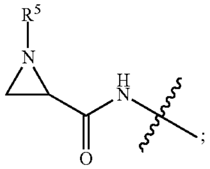

and $X_1$, $X_2$ and $X_3$ are as defined herein.

In Scheme 2, a Thiol-Mannich reaction is used to couple an alkyne containing group, $L_2R^{14}$ to the 7 position of the indole of an Amanitin (α or β) via formation of a methylene linked thio ether. Subsequent reaction with the azide containing group,

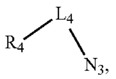

results in the formation of certain compounds Formula (A), Formula (I) and Formula (Ia):

Scheme 2
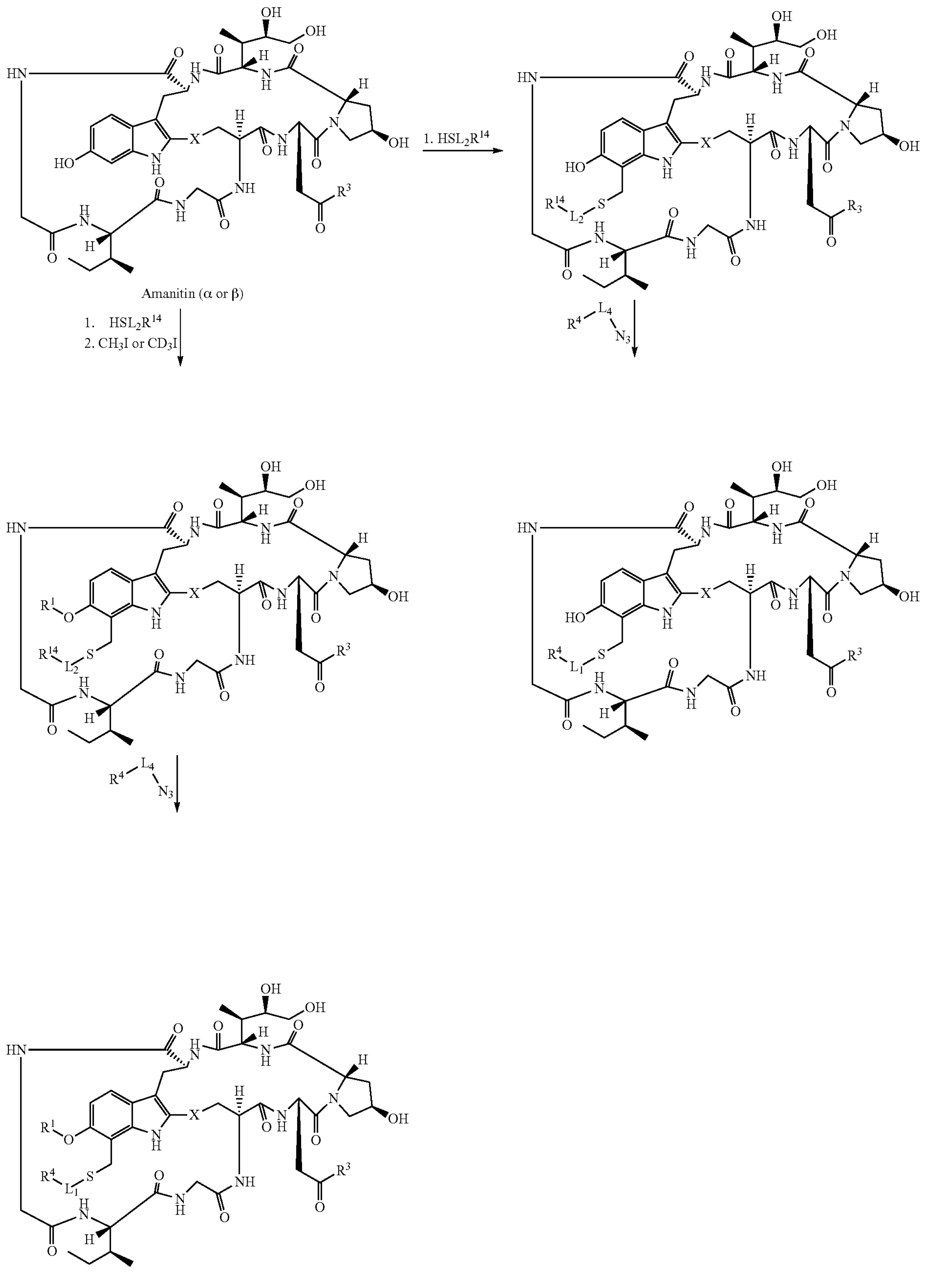

where: X is S(=O), S(=O)$_2$ or S; R$^1$ is —CH$_3$ or —CD$_3$; L$_1$ is —((CH$_2$)$_m$O)$_n$(CH$_2$)$_m$X$_4$L$_4$-, L$_2$ is —((CH$_2$)$_m$O)$_n$(CH$_2$)$_m$— and L$_4$ is —((CH$_2$)$_m$— or —((CH$_2$)$_m$NHC(=O)X$_1$X$_2$C(=O)(CH$_2$)$_m$—;

R$^4$ is

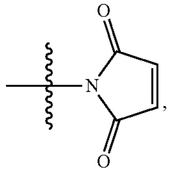

—ONH$_2$, SH, —NR$_5$C(=O)CH=CH$_2$, —S(=O)$_2$(CH=CH$_2$), —NR$^5$S(=O)$_2$(CH=CH$_2$), —NR$^5$C(=O)CH$_2$Br, —NR$^5$C(=O)CH$_2$I, —NHC(=O)CH$_2$Br, —NHC(=O)CH$_2$I, —C(O)NHNH$_2$, CO$_2$H, —NH$_2$,

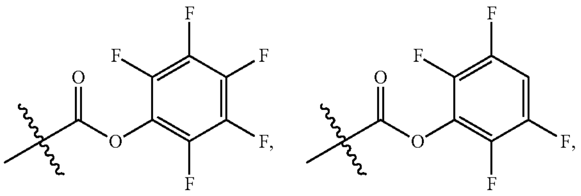

-continued

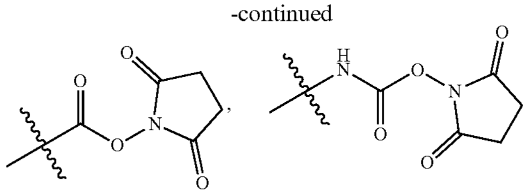

or

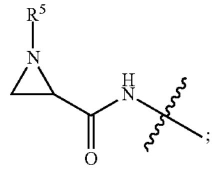

and X$_1$, X$_2$, X$_3$ and X$_4$ and R$^{14}$ are as defined herein.

In Scheme 3, a Thiol-Mannich reaction is used to couple an L$_2$R$^{24}$ group to the 7 position of the indole of an Amanitin (α or β) via formation of a methylene linked thio ether which results in the formation of certain compounds Formula (A), Formula (I) and Formula (Ia).

where: X is S(=O), S(=O)$_2$ or S; R$^1$ is —CH$_3$ or —CD$_3$; L$_2$ is —((CH$_2$)$_m$O)$_n$(CH$_2$)$_m$—; and R$^{24}$ is, —N$_3$, —ONH$_2$, —CO$_2$H, Scheme 3

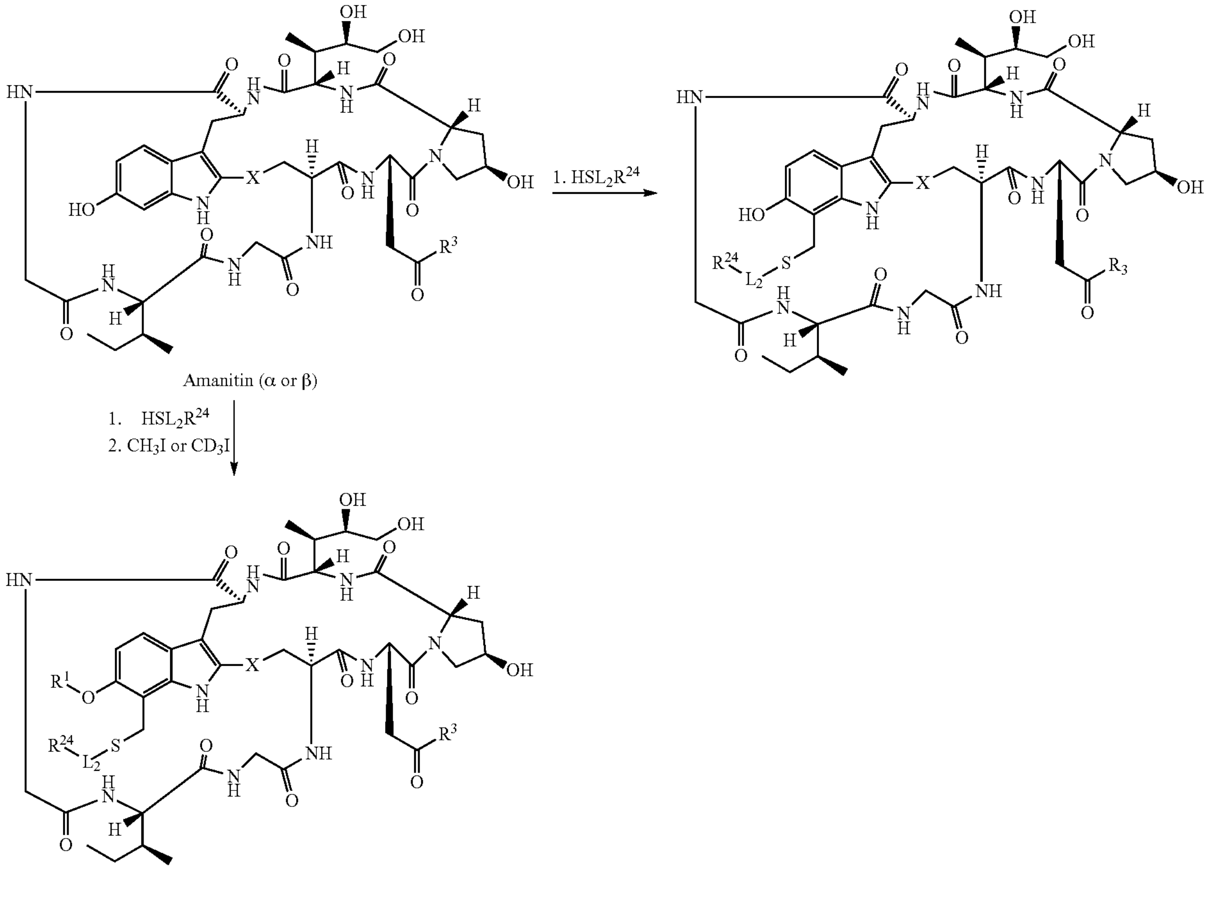

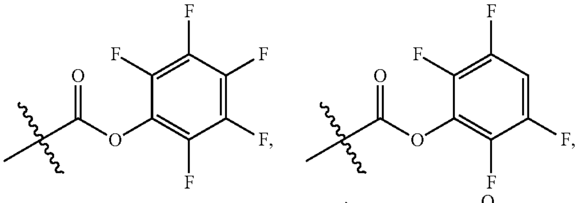

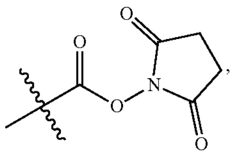

,

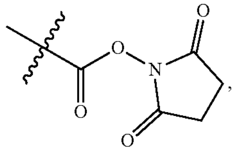

, or

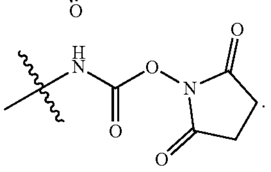

.

In Scheme 4, a Thiol-Mannich reaction is used to couple a $L_2R_{prot}^{24}$ group to the 7 position of the indole of an Amanitin (α or β) via formation of a methylene linked thio ether. Subsequent deprotection results in the formation of certain compounds Formula (A), Formula (I) and Formula (Ia).

where: X is S(═O), S(═O)$_2$ or S; $R^1$ is —$CH_3$ or —$CD_3$;

$L_2$ is —$((CH_2)_mO)_n(CH_2)_m$—;

$R^{24}$ prot is a protected amine where Prot is an amine protecting group including, but not limited to, —C(═O)OC$(CH_3)_3$(i.e.Boc) and $R^{24}$ is —$NH_2$.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

The following examples are intended to illustrate the invention and are not to be construed as being limitations thereon. Temperatures are given in degrees Celsius. Room temperature (rt) is 20 to 21° C. If not mentioned otherwise, all evaporations are performed under reduced pressure, typically between about 1 mm Hg and 100 mm Hg (=1-133 mbar). Abbreviations used are those conventional in the art. All reactions were carried out under nitrogen using commercial grade anhydrous solvents without any further distillation. Reagents were used as commercial grade without further purification. Thin layer chromatography was carried out using TLC silica gel plates. Column chromatography was carried out using an ISCO Combiflash Rf system, using flash grade prepacked Redisep® columns.

Scheme 4

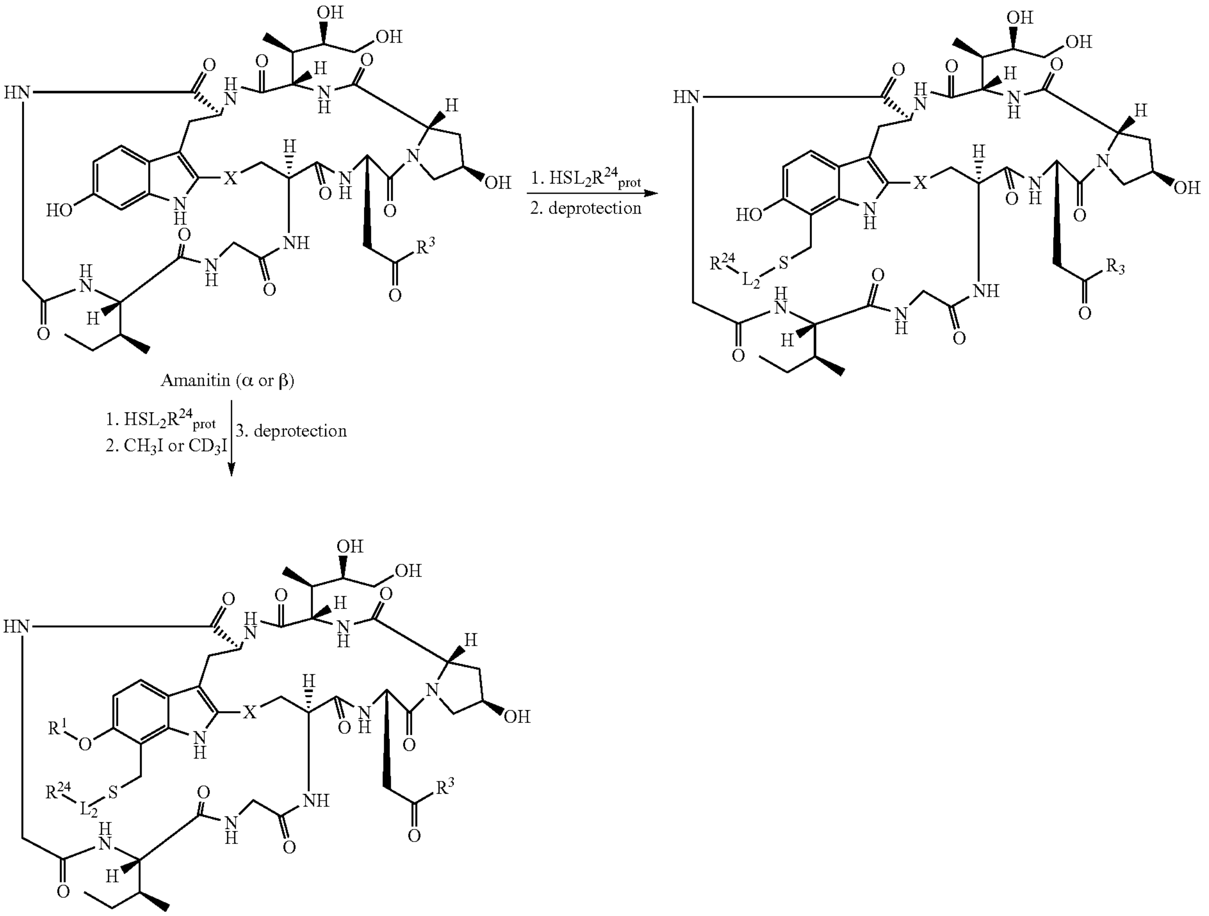

Preparative HPLC was performed on Waters Autopurification system using the following conditions: Column Sunfire C18 30×100 mm, 5μ, gradient elution with $CH_3CN$ in water+0.05% TFA-$CH_3CN$ at 30 ml/min.

After chromatography purification fractions containing desired product of appropriate purity were combined and concentrated to obtain desired products.

Analytical Methods

Unless otherwise indicated, the following HPLC and HPLC/MS methods were used in the preparation of Intermediates and Examples.

LC/MS analysis was performed on an Agilent 1200 sl/6140 system.

Column: Waters Acquity HSS T3 C18, 50×2.0, 1.8 um

Mobile Phase: A) $H_2O$+0.05% TFA; B: acetonitrile+0.035% TFA

Pump Method:

| Time | A % | B % | Flow (mL/min) |
|---|---|---|---|
| 0 | 90 | 10 | 0.9 |
| 1.35 | 0 | 100 | 0.9 |
| 1.36 | 0 | 100 | 0.9 |

-continued

| Time | A % | B % | Flow (mL/min) |
|---|---|---|---|
| 1.95 | 0 | 100 | 0.9 |
| 1.96 | 90 | 10 | 0.9 |
| 2.0 | 90 | 10 | 0.9 |

Detection: UV Diode Array at 190 nm-400 nm
MS Scan: 200-1350 amu
ELSD: 60 C.

Ms Parameters:

| Polarity | Positive |
|---|---|
| Drying Gas | 12 |
| Nebulizer Pressure | 50 |
| Drying Gas Temperature | 350 |
| Capillary Voltage | 3000 |

Synthetic Procedure for Intermediates

Synthesis of 17-azido-3,6,9,12,15-pentaoxaheptadecane-1-thiol (i-1)

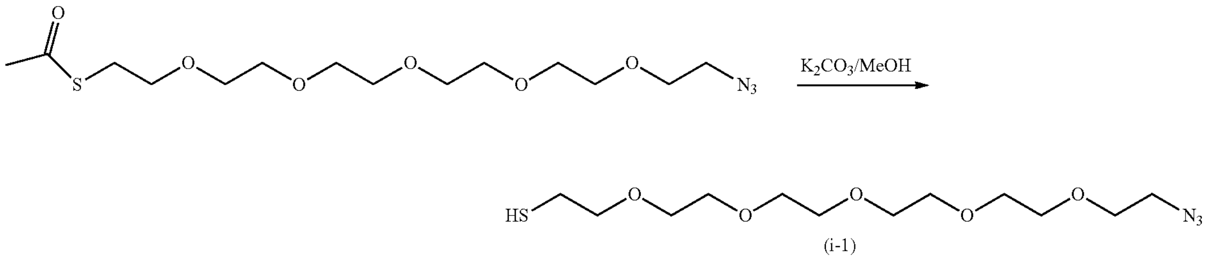

(i-1)

Using a 40 mL vial, potassium carbonate (7 mg, 0.06 mmol) was added to S-(17-azido-3,6,9,12,15-pentaoxaheptadecyl) ethanethioate (100 mg, 0.577 mmol) in MeOH (20 mL) and the reaction mixture was stirred at rt for 1 h. The reaction mixture was then filtered over celite pad and concentrated. The residue was dissolved in EtOAc (100 mL), washed with 0.1N HCl solution (50 mL) and brine (50 mL), dried over $Na_2SO4$, filtered and concentrated. The residue was purified by ISCO purification on 24 g of silica gel and concentrated to give 17-azido-3,6,9,12,15-pentaoxaheptadecane-1-thiol (i-1). $^1H$ NMR ($CDCl_3$): δ 3.69-3.60 (m, 20H), 3.41-3.38 (m, 2H), 2.73-2.67 (m, 2H), 1.60 (t, 1H). LRMS [M+H]=324.1.

Synthesis of 23-azido-3,6,9,12,15,18,21-heptaoxatricosane-1-thiol (i-2)

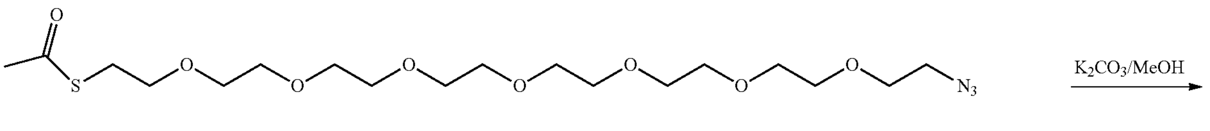

-continued

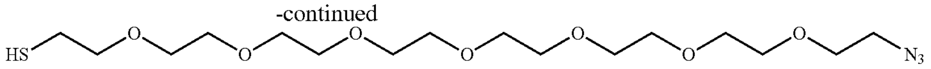

(i-2)

Using a 40 mL vial, potassium carbonate (7 mg, 0.06 mmol) was added to S-(23-azido-3,6,9,12,15,18,21-heptaoxatricosyl) ethanethioate (100 mg, 0.577 mmol) in MeOH (20 mL) and the reaction mixture was stirred at rt for 1 h. The reaction mixture was then filtered over celite pad and concentrated. The residue was dissolved in EtOAc (100 mL), washed with 0.1N HCl solution (50 mL) and brine (50 mL), dried over $Na_2SO4$, filtered and concentrated. The residue was purified by ISCO purification on 24 g of silica gel and concentrated to give 23-azido-3,6,9,12,15,18,21-heptaoxatricosane-1-thiol (i-2). $^1H$ NMR ($CDCl_3$): δ 3.69-3.60 (m, 28H), 3.40-3.38 (m, 2H), 2.72-2.67 (m, 2H), 1.60 (t, 1H). LRMS [M+Na]=434.2.

Synthesis of 29-azido-3,6,9,12,15,18,21,24,27-nonaoxanonacosane-1-thiol (i-3)

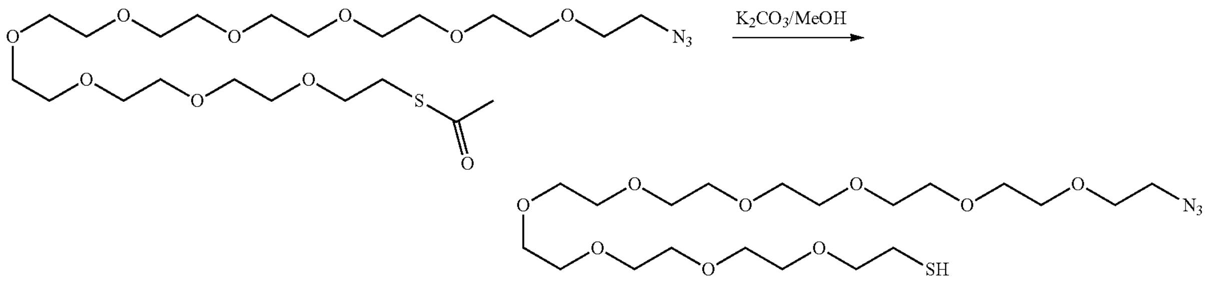

(i-3)

Using a 40 mL vial, potassium carbonate (7 mg, 0.06 mmol) was added to S-(29-azido-3,6,9,12,15,18,21,24,27-nonaoxanonacosyl) ethanethioate (100 mg, 0.577 mmol) in MeOH (20 mL) and the reaction mixture was stirred at rt for 1 h. The reaction mixture was then filtered over celite pad and concentrated. The residue was dissolved in EtOAc (100 mL), washed with 0.1N HCl solution (50 mL) and brine (50 mL), dried over $Na_2SO4$, filtered and concentrated. The residue was purified by ISCO purification on 24 g of silica gel and concentrated to give 29-azido-3,6,9,12,15,18,21,24,27-nonaoxanonacosane-1-thiol (i-3). $^1H$ NMR ($CDCl_3$): δ 3.69-3.60 (m, 44H), 3.40-3.38 (m, 2H), 2.72-2.67 (m, 2H), 1.59 (t, 1H). LRMS [M+23]=610.3.

Synthesis of 35-azido-3,6,9,12,15,18,21,24,27,30,33-undecaoxapentatriacontane-1-thiol (i-4)

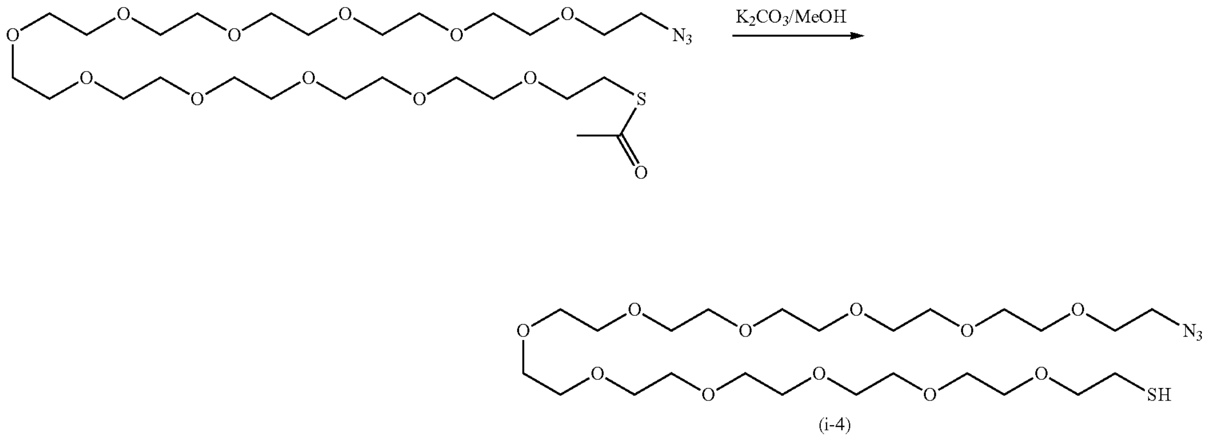

(i-4)

Using a 40 mL vial, potassium carbonate (7 mg, 0.06 mmol) was added to S-(35-azido-3,6,9,12,15,18,21,24,27,30,33-undecaoxapentatriacontyl) ethanethioate (100 mg, 0.577 mmol) in MeOH (20 mL) and the reaction mixture was stirred at rt for 1 h. The reaction mixture was then filtered over celite pad and concentrated. The residue was dissolved in EtOAc (100 mL), washed with 0.1N HCl solution (50 mL) and brine (50 mL), dried over $Na_2SO4$, filtered and concentrated. The residue was purified by ISCO purification on 24 g of silica gel and concentrated to give 35-azido-3,6,9,12,15,18,21,24,27,30,33-undecaoxapentatriacontane-1-thiol (i-4). $^1H$ NMR ($CDCl_3$): δ 3.69-3.60 (m, 36H), 3.40-3.38 (m, 2H), 2.72-2.67 (m, 2H), 1.59 (t, 1H). LRMS [M-$N_2$]=472.3.

Synthesis of 6-(4-((2,5-dioxo-2,5-dihydro-1H-pyrrol-1-yl)methyl)cyclohexanecarboxamido) hexanoic acid (i-5)

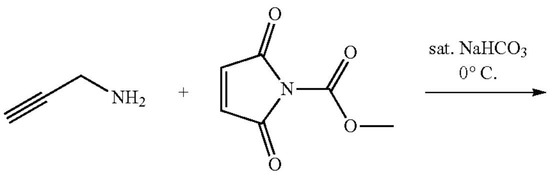

-continued

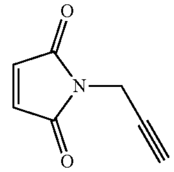

(i-5)

Using a 40 mL vial, a solution of prop-2-yn-1-amine (500 mg, 9.08 mmol) in 15 mL of sat. aqueous $NaHCO_3$ was cooled to 0° C. with ice bath and then methyl 2,5-dioxo-2,5-dihydro-1H-pyrrole-1-carboxylate (1.27 g, 8.17 mmol) was added. The reaction mixture was then stirred at the same temperature for 4 h and then extracted with 50 mL of $CH_2Cl_2$ three times. The combined organic layers were dried over $Na_2SO4$, concentrated, purified by ISCO (24 g, silica gel) and concentrated to give 1-(prop-2-yn-1-yl)-1H-pyrrole-2,5-dione (i-5). 1H-NMR (CDCl3, 400 MHz) δ 6.76 (s, 2H), 4.29 (d, 2H, J=2.8 Hz), 2.21 (t, 1H, J=2.8 Hz).

Synthesis of tert-butyl (2-(((S)-3-methyl-1-oxo-1-(((S)-1-oxo-1-((4-(((prop-2-yn-1-ylcarbamoyl)oxy)methyl)phenyl)amino)-5-ureidopentan-2-yl)amino)butan-2-yl)amino)-2-oxoethoxy)carbamate (i-6)

(i-6)

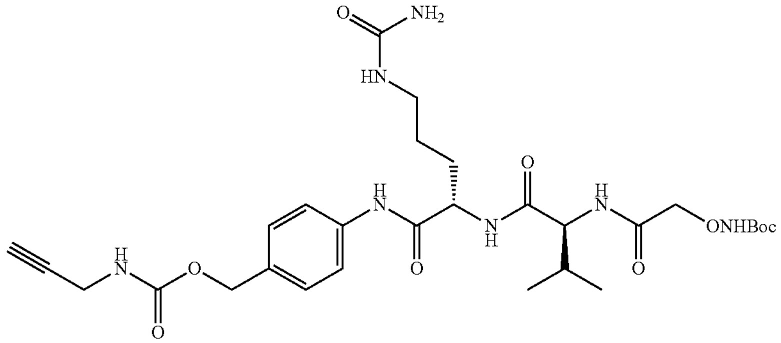

To a solution of (S)-2-((S)-2-amino-3-methylbutanamido)-N-(4-(hydroxymethyl)phenyl)-5-ureidopentanamide (152 mg, 0.4 mmol, CAS #159857-79-1) and 2,5-dioxopyrrolidin-1-yl 2-(((tert-butoxycarbonyl)amino)oxy)acetate (127 mg, 0.44 mmol) in 2:1 $CH_2Cl_2$/MeOH (6 mL) was added DIEA (77 uL, 0.44 mmol). After stirring for 2 hours additional 2,5-dioxopyrrolidin-1-yl 2-(((tert-butoxycarbonyl)amino)oxy)acetate (40 mg, 0.1 mmol) was added. After stirring for 16 hours the reaction was directly purified by ISCO $SiO_2$ chromatography (eluting with 5-30% MeOH/$CH_2Cl_2$) to yield tert-butyl (2-(((S)-1-(((S)-1-((4-(hydroxymethyl)phenyl)amino)-1-oxo-5-ureidopentan-2-yl)amino)-3-methyl-1-oxobutan-2-yl)amino)-2-oxoethoxy)carbamate (MH+=553.2).

To a solution of tert-butyl (2-(((S)-1-(((S)-1-((4-(hydroxymethyl)phenyl)amino)-1-oxo-5-ureidopentan-2-yl)amino)-3-methyl-1-oxobutan-2-yl)amino)-2-oxoethoxy)carbamate (152 mg, 0.275 mmol) in DMF (1.5 mL) was added DIEA (0.144 mL, 0.825 mmol) followed by bis(4-nitrophenyl) carbonate (84 mg, 0.275 mmol). After stirring for 23 hours, additional bis(4-nitrophenyl) carbonate (70 mg, 0.23 mmol) was added. After stirring for an additional 24 hours the reaction was diluted with DMSO (3 mL) and was directly purified by RP-HPLC. After lyophilization tert-butyl (2-(((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)amino)-2-oxoethoxy)carbamate (MH+=718.3) was obtained.

To a solution of tert-butyl (2-(((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)amino)-2-oxoethoxy)carbamate (40 mg, 0.056 mmol) in DMF (0.5 mL) was added propargyl amine (0.0107 mL, 0.167 mmol). After standing for 16 hours the solution was diluted with DMSO (1 mL) and was purified by RP-HPLC to yield after lyophilization tert-butyl (2-(((S)-3-methyl-1-oxo-1-(((S)-1-oxo-1-((4-(((prop-2-yn-1-ylcarbamoyl)oxy)methyl)phenyl)amino)-5-ureidopentan-2-yl)amino)butan-2-yl)amino)-2-oxoethoxy)carbamate (i-6) (MH+=634.2).

Synthesis of tert-butyl (2-(((S)-4-methyl-1-oxo-1-(((S)-1-oxo-1-((4-(((prop-2-yn-1-ylcarbamoyl)oxy)methyl)phenyl)amino)-5-ureidopentan-2-yl)amino)pentan-2-yl)amino)-2-oxoethoxy)carbamate (i-7)

1.65 mmol) in 2:1 $CH_2Cl_2$/MeOH (8 mL) was added DIEA (0.289 mL, 1.65 mmol). After stirring for 60 hours additional 2,5-dioxopyrrolidin-1-yl 2-(((tert-butoxycarbonyl)amino)oxy)acetate (120 mg, 0.3 mmol) was added. After stirring for 16 hours the reaction was directly purified by ISCO $SiO_2$ chromatography (eluting with 5-30% MeOH/$CH_2Cl_2$) to yield tert-butyl (2-(((S)-1-(((S)-1-((4-(hydroxymethyl)phenyl)amino)-1-oxo-5-ureidopentan-2-yl)amino)-4-methyl-1-oxopentan-2-yl)amino)-2-oxoethoxy)carbamate (MH+=567.2).

To a solution of tert-butyl (2-(((S)-1-(((S)-1-((4-(hydroxymethyl)phenyl)amino)-1-oxo-5-ureidopentan-2-yl)amino)-4-methyl-1-oxopentan-2-yl)amino)-2-oxoethoxy)carbamate (506 mg, 0.89 mmol) in DMF (5 mL) was added DIEA (0.187 mL, 1.07 mmol) followed by bis(4-nitrophenyl) carbonate (408 mg, 1.34 mmol). After stirring for 16 hours the reaction was diluted with DMSO (9 mL) and was directly purified by RP-HPLC. The product fractions were added to an equal volume of EtOAc and $NaHCO_{3(solid)}$ (200 mg) was added. The material was mixed, separated, washed with $NaCl_{(sat.)}$, dried over $MgSO_4$, filtered and concentrated to yield tert-butyl (2-(((S)-4-methyl-1-(((S)-1-((4-((((4-nitrophenoxy)carbonyl)oxy)methyl)phenyl)amino)-1-oxo-5-

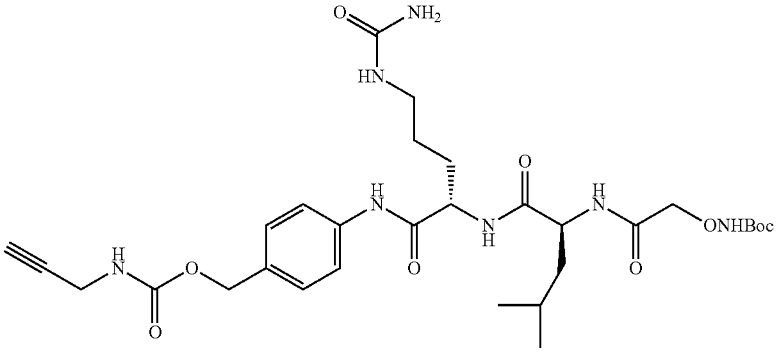

(i-7)

To a suspension of 10% DeGussa type Pd—C (0.579 g, 0.544 mmol) in MeOH was added benzyl ((S)-1-(((S)-1-((4-(hydroxymethyl)phenyl)amino)-1-oxo-5-ureidopentan-2-yl)amino)-4-methyl-1-oxopentan-2-yl)carbamate (2.87 g, 5.44 mmol, CAS #448963-30-2) and 2N ammonia in MeOH (2.72 mL, 5.44 mmol). The mixture was charged with $H_2$ (1 atm) and was stirred for 16 hours. The reaction mixture was filtered through a pad of celite, rinsed with EtOH and concentrated to yield (S)-2-amino-N—((S)-1-((4-(hydroxymethyl)phenyl)amino)-1-oxo-5-ureidopentan-2-yl)-4-methylpentanamide (MH+=394.3).

To a solution of (S)-2-amino-N—((S)-1-((4-(hydroxymethyl)phenyl)amino)-1-oxo-5-ureidopentan-2-yl)-4-methylpentanamide (500 mg, 1.27 mmol) and 2,5-dioxopyrrolidin-1-yl 2-(((tert-butoxycarbonyl)amino)oxy)acetate (476 mg, ureidopentan-2-yl)amino)-1-oxopentan-2-yl)amino)-2-oxoethoxy)carbamate (MH+=732.3).

To a solution of tert-butyl (2-(((S)-4-methyl-1-(((S)-1-((4-((((4-nitrophenoxy)carbonyl)oxy)methyl)phenyl)amino)-1-oxo-5-ureidopentan-2-yl)amino)-1-oxopentan-2-yl)amino)-2-oxoethoxy)carbamate (52.5 mg, 0.072 mmol) in DMF (0.75 mL) was added propargyl amine (0.025 mL, 0.395 mmol). After standing for 2 hours the solution was diluted with DMSO (2 mL) and was purified by RP-HPLC to yield after lyophilization tert-butyl (2-(((S)-4-methyl-1-oxo-1-(((S)-1-oxo-1-((4-(((prop-2-yn-1-ylcarbamoyl)oxy)methyl)phenyl)amino)-5-ureidopentan-2-yl)amino)pentan-2-yl)amino)-2-oxoethoxy)carbamate (i-7) (MH+=648.3).

Synthesis of tert-butyl ((2,5,8,11,16-pentaoxo-17-oxa-3,6,9,12,15-pentaazaicos-19-yn-1-yl)oxy)carbamate (i-8)

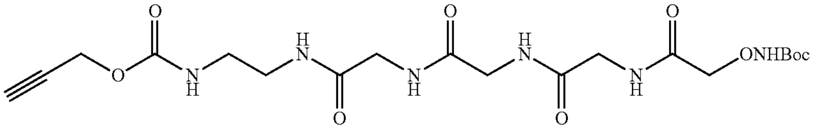
(i-8)

To a solution of N-BocTriGlycine (1.0 g, 3.46 mmol), (9H-fluoren-9-yl)methyl (2-aminoethyl)carbamate hydrochloride (1.32 g, 4.15 mmol), 3H-[1,2,3]triazolo[4,5-b]pyridin-3-ol (0.565 g, 4.15 mmol) in 2:1 $CH_2Cl_2$/MeOH (30 mL) was added DIEA (0.724 mL, 4.15 mmol) followed by EDC (0.765 g, 4.15 mmol). After stirring for 48 hours the reaction solution was directly purified by $SiO_2$ chromatography (0-10% MeOH/$CH_2Cl_2$) to yield tert-butyl (1-(9H-fluoren-9-yl)-3,8,11,14-tetraoxo-2-oxa-4,7,10,13-tetraazapentadecan-15-yl)carbamate (MH+=554.3).

tert-butyl (1-(9H-fluoren-9-yl)-3,8,11,14-tetraoxo-2-oxa-4,7,10,13-tetraazapentadecan-15-yl)carbamate (1 gram, 1.81 mmol) was treated with 25% TFA/$CH_2Cl_2$ (20 mL) for 1.5 hours at which time the volatiles were removed in vacuo. The residue was dissolved in $CH_2Cl_2$ (20 mL) and to about 0.905 mmoles was add DIEA (0.788 mL, 4.51 mmol) and 2,5-dioxopyrrolidin-1-yl 2-(((tert-butoxycarbonyl)amino)oxy)acetate (295 mg, 1.08 mmol). After stirring for 21 hours MeOH (5 mL) was added to make the solution homogeneous and the reaction was directly purified by ISCO $SiO_2$ chromatography (eluting with 0-30% MeOH/$CH_2Cl_2$) to yield (9H-fluoren-9-yl)methyl (2,2-dimethyl-4,8,11,14,17-pentaoxo-3,6-dioxa-5,9,12,15,18-pentaazaicosan-20-yl)carbamate (MH+=627.3). To a 1:1 MeOH/$CH_2Cl_2$ (60 mL) solution of (9H-fluoren-9-yl)methyl (2,2-dimethyl-4,8,11,14,17-pentaoxo-3,6-dioxa-5,9,12,15,18-pentaazaicosan-20-yl)carbamate (assumed 0.90 mmol) was added 2N dimethylamine in MeOH (13.55 mL, 27.1 mmol). After standing for 16 hours the volatiles were removed in vacuo, the residue was dissolved in DMSO (7 mL) and was purified by RP-HPLC to yield after lyophilization tert-butyl ((14-amino-2,5,8,11-tetraoxo-3,6,9,12-tetraazatetradecyl)oxy) carbamate (M H+=405.2) as the TFA salt.

To a solution of tert-butyl ((14-amino-2,5,8,11-tetraoxo-3,6,9,12-tetraazatetradecyl)oxy)carbamate (83.2 mg, 0.16 mmol) and 4-nitrophenyl prop-2-yn-1-yl carbonate (49.7 mg, 0.225 mmol, CAS #228111-40-8) in DMF (0.85 mL) was added DIEA (0.084 mL, 0.481 mmol). After standing for 1.5 hours the solution was diluted with DMSO (2 mL) and was purified by RP-HPLC to yield after lyophilization tert-butyl ((2,5,8,11,16-pentaoxo-17-oxa-3,6,9,12,15-pentaazaicos-19-yn-1-yl)oxy)carbamate (i-8) (MH+=487.1).

Synthetic Procedure for Non-Linked Amatoxins

Example 1: Synthesis of 6'O-methyl-7'C-(17-(4-((2,5-dioxo-2,5-dihydro-1H-pyrrol-1-yl)methyl)-1H-1,2,3-triazol-1-yl)-3,6,9,12,15-pentaoxaheptadecylthio)methyl-α-Amanitin (1), 7'C-((17-azido-3,6,9,12,15-pentaoxaheptadecanthio)methyl)-α-Amanitin (A-1) and 6'O-methyl-7'C-((17-azido-3,6,9,12,15-pentaoxahepta decanthio)methyl)-α-Amanitin (A-2)

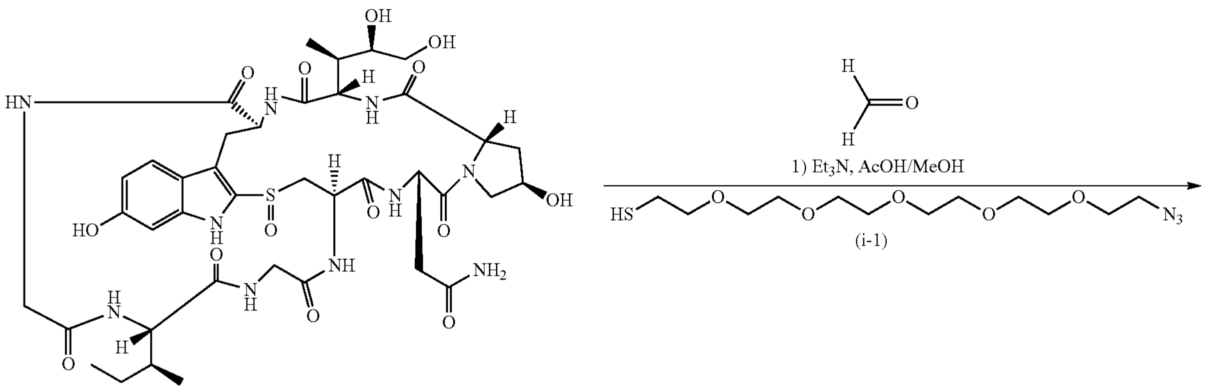

(A)
(i-1)

-continued

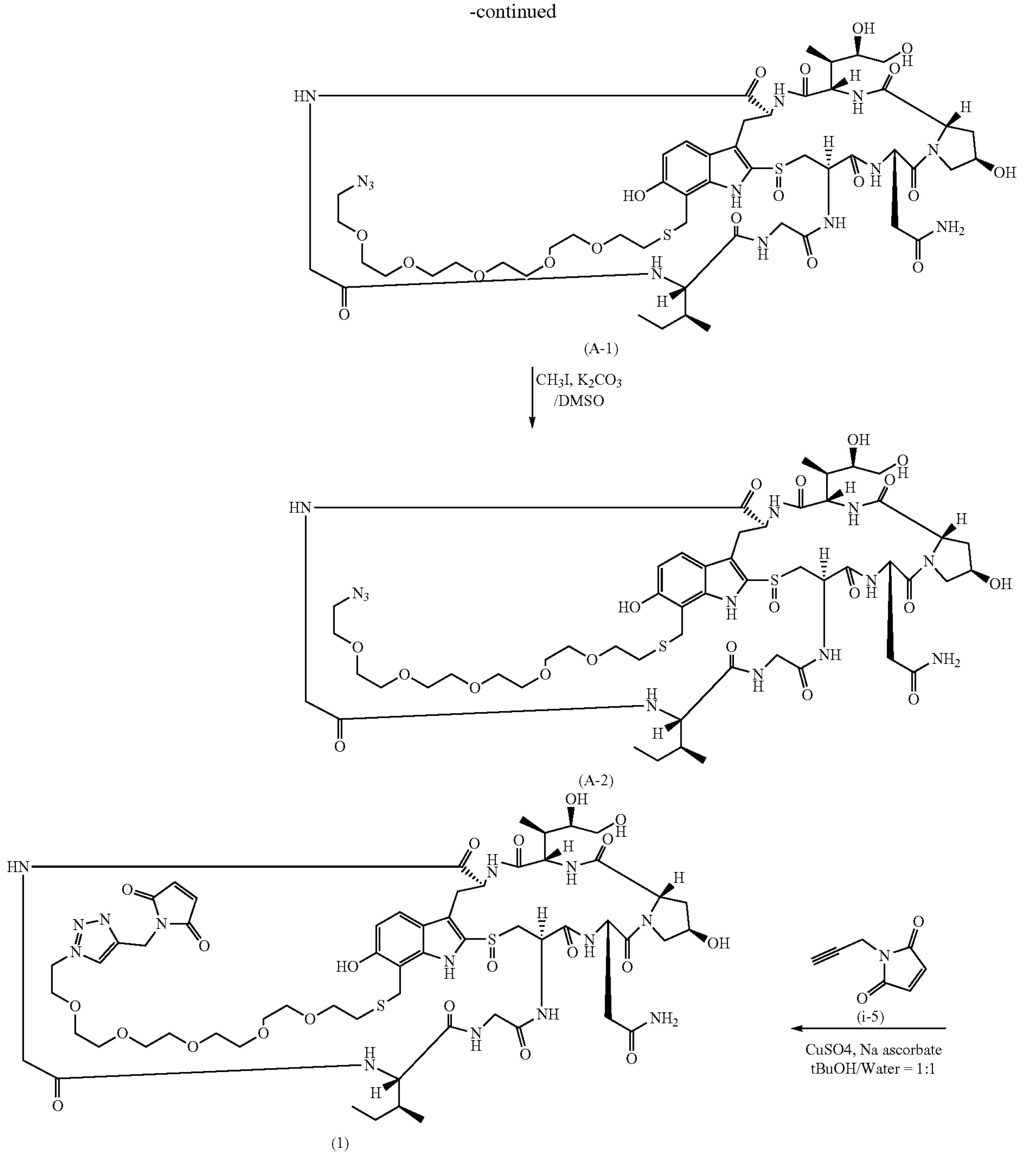

Step 1: Synthesis of Compound (A-1)

Formaldehyde (0.035 mL, 0.44 mmol) and 17-azido-3,6,9,12,15-pentaoxaheptadecane-1-thiol (i-1) (35 mg, 0.11 mmol) were added to a solution of α-Amanitin (A) (20 mg, 0.022 mmol) in MeOH (2 mL). Triethylamine (1.2 mL, 8.7 mmol) and acetic acid (0.25 mL, 4.4 mmol) were added to the reaction mixture and flushed with $N_2$ gas three times. The reaction mixture was stirred at 40° C. for 2 days. After concentration in vacuo, the residue was then purified by HPLC and lyophilized to give Compound (A-1). MS (m+1) =1254.4, HPLC Peak RT=0.819 min, 1H-NMR (MeOD, 500 MHz) δ 10.68 (s, 1H), 8.83 (m, 1H), 8.63 (d, 1H, J=2.5 Hz), 8.50 (d, 1H, J=10.5 Hz), 8.49 (s, 1H), 8.36 (s, 1H), 8.18 (d, 1H, J=8.5 Hz), 8.05 (d, 1H, J=10.0 Hz), 7.94 (d, 1H, J=9.0 Hz), 7.69 (s, 1H), 7.54 (d, 1H, J=8.5 Hz), 6.75 (d, 1H, J=9.0 Hz), 5.30 (m, 1H), 5.17 (m, 1H), 4.79 (bs, 1H), 4.67 (dd, 1H, J=5.5 and 10.0 Hz), 4.56 (m, 2H), 4.34 (dd, 1H, J=9.0 and 18.5 Hz), 4.18 (m, 1H), 4.16 (d, 1H, J=13.0 Hz), 4.10 (d, 1H, J=13.5 Hz), 3.96 (m, 1H), 3.33~3.79 (m, 50H), 3.12 (m, 1H), 2.96 (m, 1H), 2.62 (m, 2H), 2.46 (m, 2H), 2.05 (m, 1H), 1.65 (m, 2H), 1.21 (m, 1H), 0.99 (d, 3H, J=7.0 Hz), 0.90 (m, 6H).

Step 2: Synthesis of Compound (A-2)

Compound (A-1) (14.0 mg, 0.011 mmol) and DMSO (1 mL) were treated with methyliodide (0.0007 mL) and K2CO3 (1.5 mg) at rt and stirred at rt for 1 h. Additional methyliodide (0.0007 mL) and K2CO3 (1.5 mg) were added at rt and stirred at rt for 2 h. Additional methyliodide (0.0007 mL) and K2CO3 (1.5 mg) at rt and stirred at rt for 2 h, again. The reaction mixture was then purified by RP-C18 ISCO and lyophilized to give Compound (A-2). MS (m+1) =1268.3, HPLC Peak RT=0.873 min, 1H-NMR (MeOD, 500 MHz) δ 10.76 (s, 1H), 8.83 (m, 1H), 8.64 (d, 1H, J=2.5 Hz), 8.52 (d, 1H, J=10.5 Hz), 8.48 (d, 1H, J=3.5 Hz), 8.36 (s, 1H), 8.18 (d, 1H, J=8.0 Hz), 8.05 (d, 1H, J=10.0 Hz), 7.96 (d, 1H, J=9.0 Hz), 7.70 (d, 1H, J=9.0 Hz), 7.69 (s, 1H), 6.98 (d, 1H, J=9.0 Hz), 5.34 (m, 1H), 5.18 (m, 1H), 4.79 (bs, 1H), 4.67 (dd, 1H, J=5.5 and 9.5 Hz), 4.57 (m, 2H), 4.34 (dd, 1H, J=9.0 and 18.5 Hz), 4.10~4.20 (m, 3H), 3.97 (m, 1H), 3.92 (s, 3H), 3.45~3.79 (m, 34H), 3.43 (q, 1H, J=7.5 Hz), 3.37 (t, 2H, J=5.0 Hz), 3.11 (m, 1H), 2.96 (m, 1H), 2.60 (m, 2H), 2.44 (m, 2H), 2.06 (m, 1H), 1.65 (m, 2H), 1.20 (m, 1H), 0.99 (d, 3H, J=7.0 Hz), 0.90 (m, 6H).

Step 3: Synthesis of Compound (1)

Compound (A-2) (8 mg, 0.006 mmol) and Compound (i-5) (2 mg, 0.012 mmol) were added to t-butanol (0.5 mL) and the reaction mixture was flushed with $N_2$ gas five times. L-Ascorbic acid sodium salt (1 mg, 0.006 mmol), $CuSO_4$ (0.2 mg, 0.0012 mmol) and 0.5 mL of $H_2O$ were then added. The reaction mixture was flushed with $N_2$ gas five times and stirred at rt for 4 h, and then purified by RP-C18 ISCO to give Compound (1). MS (m+2/2)=702.4, HPLC Peak RT=0.818 min, 1H-NMR (MeOD, 500 MHz) δ 10.75 (s, 1H), 8.83 (m, 1H), 8.64 (d, 1H, J=2.0 Hz), 8.51 (d, 1H, J=10.0 Hz), 8.47 (d, 1H, J=3.5 Hz), 8.17 (d, 1H, J=8.5 Hz), 8.05 (d, 1H, J=10.0 Hz), 7.95 (d, 1H, J=9.0 Hz), 7.93 (s, 1H), 7.68 (d, 1H, J=9.0 Hz), 6.97 (d, 1H, J=9.0 Hz), 6.83 (s, 2H), 5.34 (m, 1H), 5.17 (m, 1H), 4.79 (bs, 1H), 4.75 (s, 2H), 4.68 (dd, 1H, J=5.0 and 9.5 Hz), 4.56 (m, 2H), 4.49 (dd, 1H, J=5.0 and 5.5 Hz), 4.34 (dd, 1H, J=9.0 and 18.5 Hz), 4.09~4.19 (m, 3H), 3.97 (m, 1H), 3.91 (s, 3H), 3.39~3.82 (m, 30H), 3.10 (m, 1H), 2.94 (m, 1H), 2.59 (m, 2H), 2.41 (m, 2H), 2.06 (m, 1H), 1.63 (m, 2H), 1.20 (m, 1H), 0.99 (d, 3H, J=7.0 Hz), 0.91 (m, 6H).

Example 2: Synthesis of 6'O-methyl-7'C-((23-(4-((2,5-dioxo-2,5-dihydro-1H-pyrrol-1-yl)methyl)-1H-1,2,3-triazol-1-yl)-3,6,9,12,15,18,21-heptaoxatricosanthio)methyl)-α-Amanitin (2), 7'C-((23-azido-3,6,9,12,15,18,21-heptaoxatricosanthio)methyl)-α-Amanitin (A-3) and 6'O-methyl-7'C-((23-azido-3,6,9,12,15,18,21-heptaoxatricosanthio)methyl)-α-Amanitin (A4)

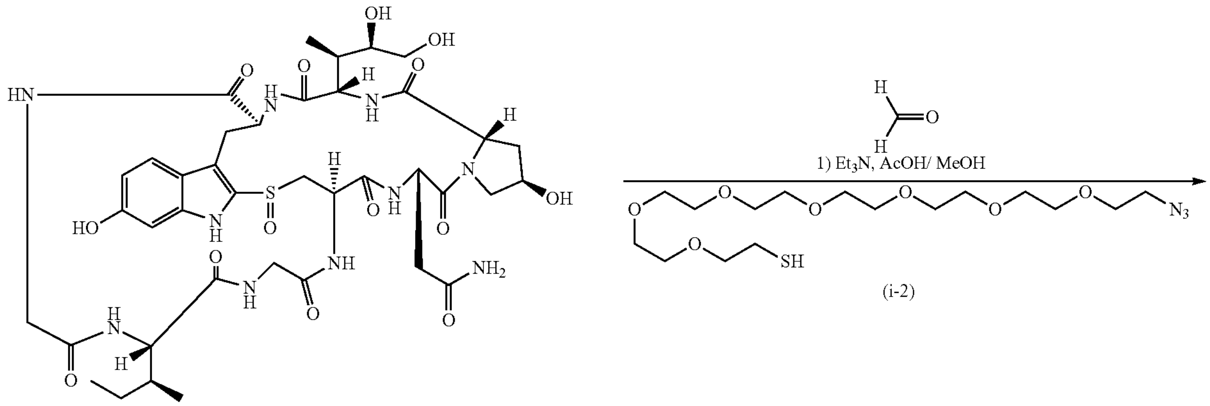

(A)

(i-2)

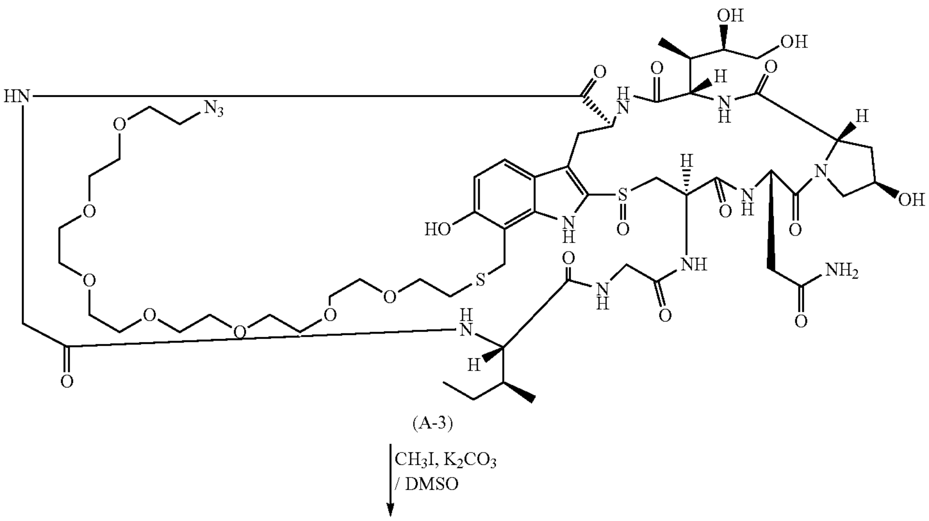

(A-3)

-continued

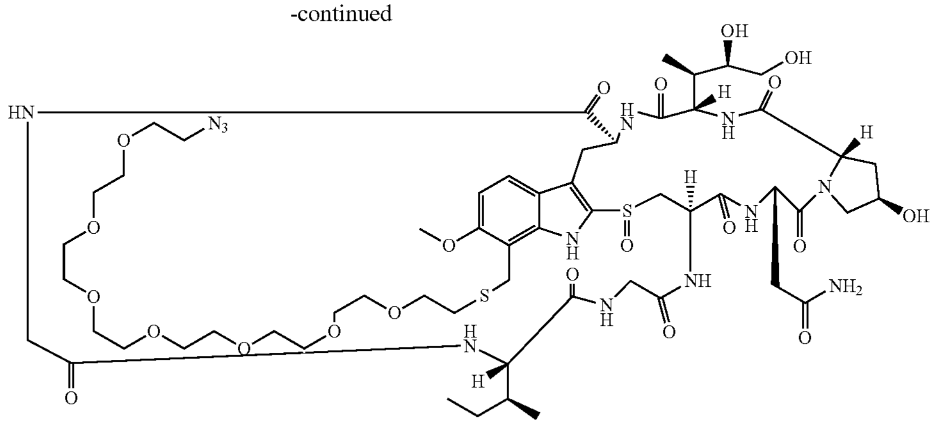

(A-4)

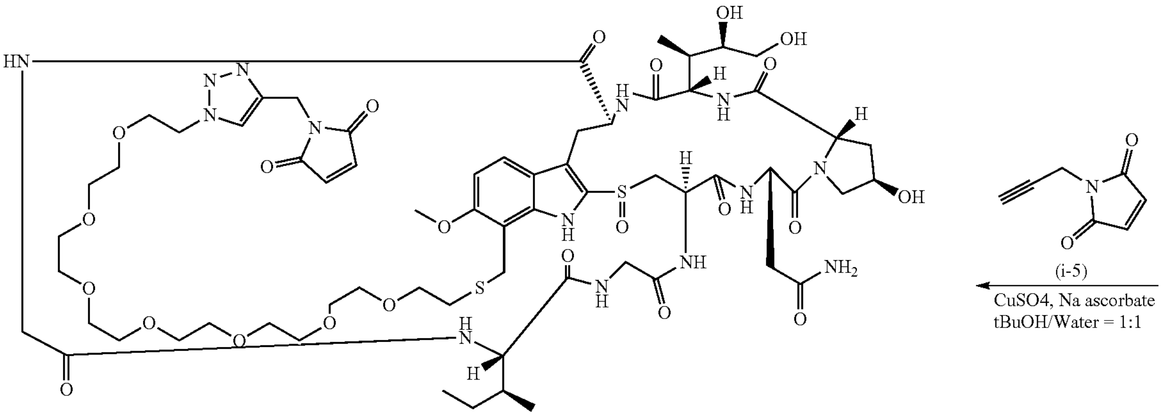

(2)

Step 1: Synthesis of Compound (A-3)

Compound (A-3) was prepared using the method described for Compound (A-1), except Compound (i-2) was used in place of Compound (i-1). MS (m+1)=1342.4, HPLC Peak RT=0.834 min, 1H-NMR (MeOD, 500 MHz) δ 10.65 (s, 1H), 8.81 (m, 1H), 8.59 (d, 1H, J=2.0 Hz), 8.45 (m, 2H), 8.33 (s, 1H), 8.14 (d, 1H, J=10.5 Hz), 8.00 (d, 1H, J=12.0 Hz), 7.90 (d, 1H, J=11.0 Hz), 7.67 (s, 1H), 7.48 (d, 1H, J=11.0 Hz), 6.69 (d, 1H, J=10.5 Hz), 5.25 (m, 1H), 5.12 (m, 1H), 4.74 (bs, 1H), 4.61 (dd, 1H, J=6.5 and 12.0 Hz), 4.51 (m, 2H), 4.29 (dd, 1H, J=10.5 and 23.0 Hz), 4.09 (m, 3H), 3.92 (m, 1H), 3.38~3.73 (m, 43H), 3.29 (m, 2H), 3.21 (m, 1H), 3.06 (m, 1H), 3.12 (m, 1H), 2.91 (m, 1H), 2.56 (m, 2H), 2.39 (m, 2H), 2.00 (m, 1H), 1.60 (m, 2H), 1.15 (m, 1H), 0.94 (d, 3H, J=9.0 Hz), 0.85 (m, 6H).

Step 2: Synthesis of Compound (A-27)

Compound (A-4) was prepared using the method described for Compound (A-2), except Compound (A-3) was used in place of Compound (A-1). MS (m+2/2)=679.0, HPLC Peak RT=0.887 min, 1H-NMR (MeOD, 500 MHz) δ 10.75 (s, 1H), 8.83 (m, 1H), 8.64 (d, 1H, J=2.0 Hz), 8.52 (d, 1H, J=10.0 Hz), 8.47 (d, 1H, J=3.5 Hz), 8.36 (s, 1H), 8.18 (d, 1H, J=8.5 Hz), 8.05 (d, 1H, J=9.5 Hz), 7.96 (d, 1H, J=9.0 Hz), 7.70 (d, 1H, J=9.0 Hz), 7.69 (s, 1H), 6.98 (d, 1H, J=9.0 Hz), 5.33 (m, 1H), 5.18 (m, 1H), 4.80 (bs, 1H), 4.68 (dd, 1H, J=5.5 and 9.5 Hz), 4.56 (m, 2H), 4.35 (dd, 1H, J=9.0 and 18.5 Hz), 4.10~4.21 (m, 3H), 3.97 (m, 1H), 3.92 (s, 3H), 3.45~3.79 (m, 42H), 3.35~3.44 (m, 3H), 3.11 (m, 1H), 2.96 (m, 1H), 2.61 (m, 2H), 2.44 (m, 2H), 2.06 (m, 1H), 1.65 (m, 2H), 1.21 (m, 1H), 0.99 (d, 3H, J=7.0 Hz), 0.90 (m, 6H).

Step 3: Synthesis of Compound (2)

Compound (2) was prepared using the method described for Compound (1), except Compound (A-4) was used in place of Compound (A-2). MS (m+2/2)=746.5, HPLC Peak RT=0.850 min, 1H-NMR (MeOD, 500 MHz) δ 10.74 (s, 1H), 8.83 (m, 1H), 8.63 (d, 1H, J=2.0 Hz), 8.51 (d, 1H, J=10.0 Hz), 8.47 (d, 1H, J=3.5 Hz), 8.36 (s, 1H), 8.17 (d, 1H, J=8.5 Hz), 8.04 (d, 1H, J=10.0 Hz), 7.96 (d, 1H, J=9.5 Hz), 7.94 (s, 1H), 7.69 (d, 1H, J=9.0 Hz), 6.97 (d, 1H, J=9.0 Hz), 6.83 (s, 2H), 5.34 (m, 1H), 5.17 (m, 1H), 4.79 (bs, 1H), 4.75 (s, 2H), 4.68 (dd, 1H, J=5.0 and 9.5 Hz), 4.56 (m, 2H), 4.52 (t, 1H, J=5.0 Hz), 4.34 (dd, 1H, J=9.0 and 18.5 Hz), 4.08~4.20 (m, 3H), 3.97 (m, 1H), 3.91 (s, 3H), 3.39~3.78 (m, 38H), 3.10 (m, 1H), 2.94 (dd, 1H, J=14.0 and 15.0 Hz), 2.61 (m, 2H), 2.41 (m, 2H), 2.05 (m, 1H), 1.57~1.68 (m, 2H), 1.20 (m, 1H), 0.99 (d, 3H, J=7.0 Hz), 0.91 (m, 6H).

Example 3: Synthesis of 7'C-((23-(4-((2,5-dioxo-2,5-dihydro-1H-pyrrol-1-yl)methyl)-1H-1,2,3-triazol-1-yl)-3,6,9,12,15,18,21-heptaoxatricosanthio)methyl)-α-Amanitin (3)

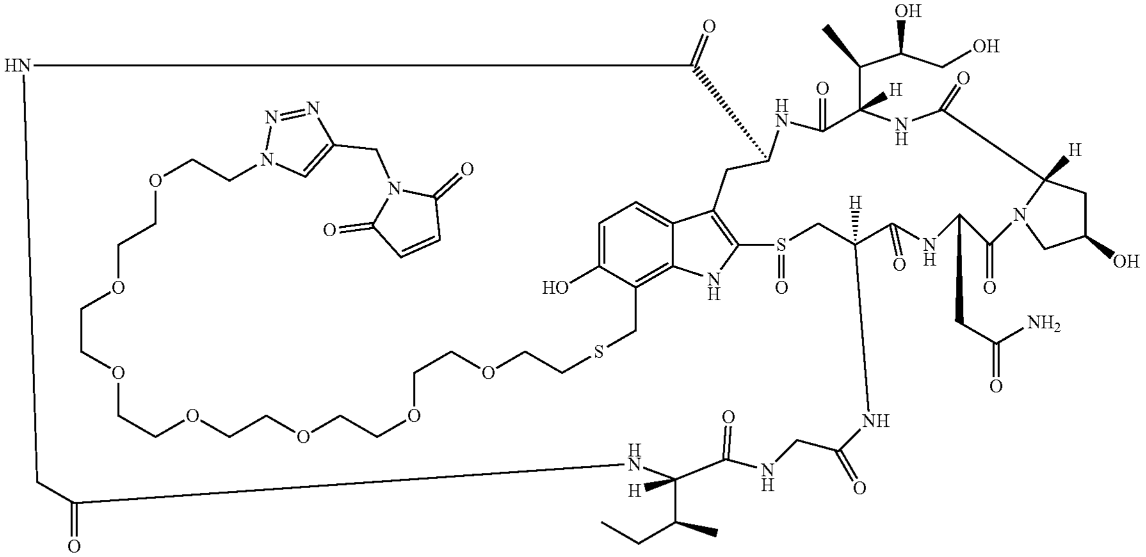

(3)

Compound (3) was prepared using the method described for Compound (2), except Compound (A-3) was used in place of Compound (A-4). MS (m+2/2)=739.4, HPLC Peak RT=0.794 min, 1H-NMR (MeOD, 500 MHz) δ 10.65 (s, 1H), 8.83 (m, 1H), 8.63 (d, 1H, J=2.0 Hz), 8.50 (d, 1H, J=10.5 Hz), 8.47 (d, 1H, J=4.0 Hz), 8.16 (d, 1H, J=8.0 Hz), 8.05 (d, 1H, J=9.5 Hz), 7.94 (s, 1H), 7.93 (d, 1H, J=7.0 Hz), 7.53 (d, 1H, J=8.5 Hz), 6.85 (s, 2H), 6.74 (d, 1H, J=8.5 Hz), 5.32 (m, 1H), 5.17 (m, 1H), 4.80 (bs, 1H), 4.76 (s, 2H), 4.67 (dd, 1H, J=5.5 and 10.0 Hz), 4.56 (m, 2H), 4.52 (dd, 1H, J=5.0 and 5.5 Hz), 4.34 (dd, 1H, J=8.5 and 18.5 Hz), 4.07~4.20 (m, 3H), 3.98 (m, 1H), 3.84 (t, 2H, J=5.0 Hz), 3.45~3.78 (m, 38H), 3.40 (dd, 1H, J=8.0 and 15.0 Hz), 3.26 (t, 1H, J=13.5 Hz), 3.11 (dd, 1H, J=4.0 and 16.0 Hz), 2.95 (dd, 1H, J=12.0 and 15.0 Hz), 2.63 (m, 2H), 2.47 (m, 2H), 2.06 (m, 1H), 1.57~1.68 (m, 2H), 1.21 (m, 1H), 0.99 (d, 3H, J=7.0 Hz), 0.91 (m, 6H).

Example 4: Synthesis of 6'O-methyl-7'C-((29-(4-((2,5-dioxo-2,5-dihydro-1H-pyrrol-1-yl)methyl)-1H-1,2,3-triazol-1-yl)-3,6,9,12,15,18,21,24,27-nonaoxanonacos anthio)methyl)-α-Amanitin (4), 7'C-((29-azido-3,6,9,12,15,18,21,24,27-nonaoxanonacos anthio)methyl)-α-Amanitin (A-5) and 6'O-methyl-7'C-((29-azido-3,6,9,12,15,18,21,24,27-nonaoxanonacosanthio)methyl)-α-Amanitin (A-6)

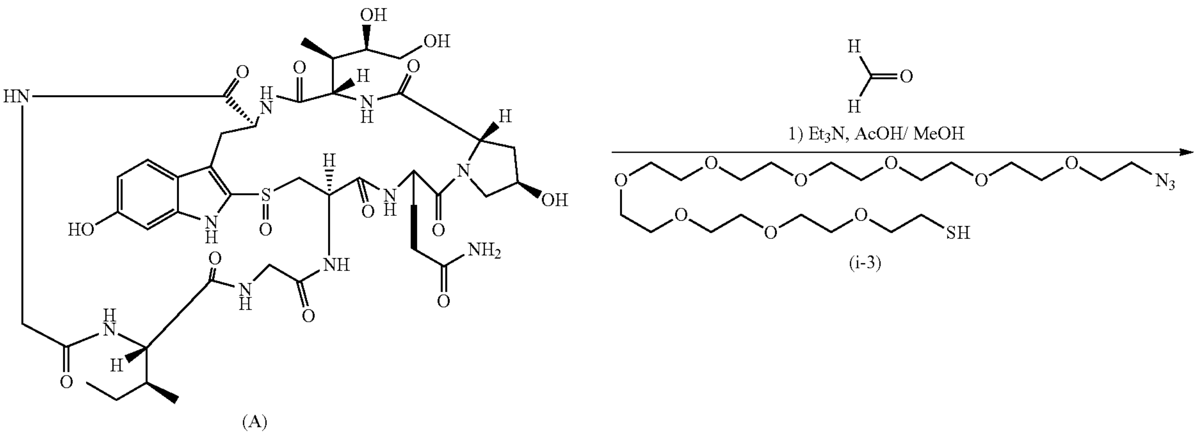

(A)

-continued

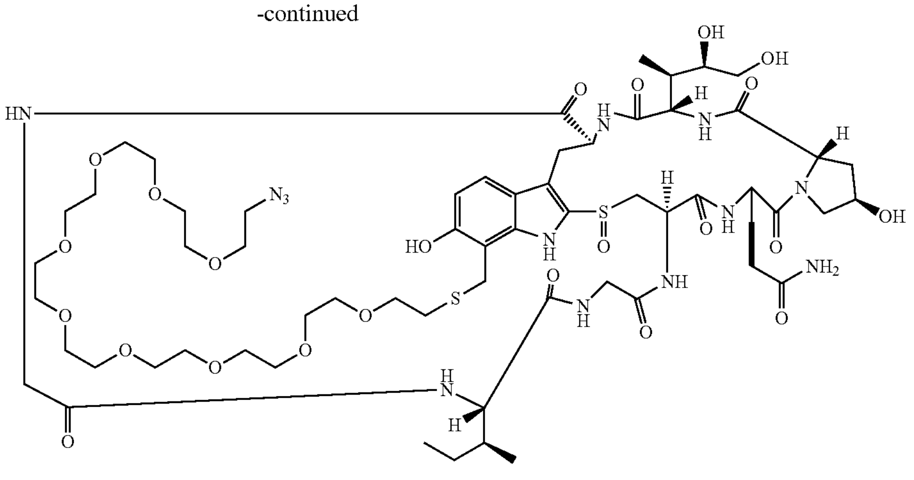

(A-5)

CH3I, K2CO3
/ DMSO

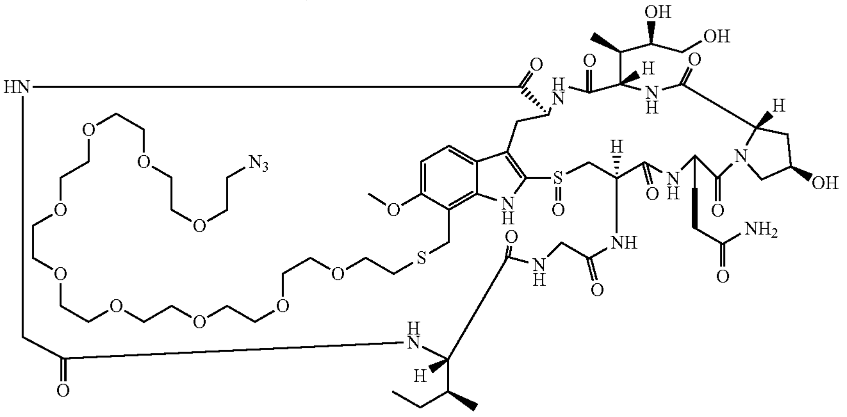

(A-6)

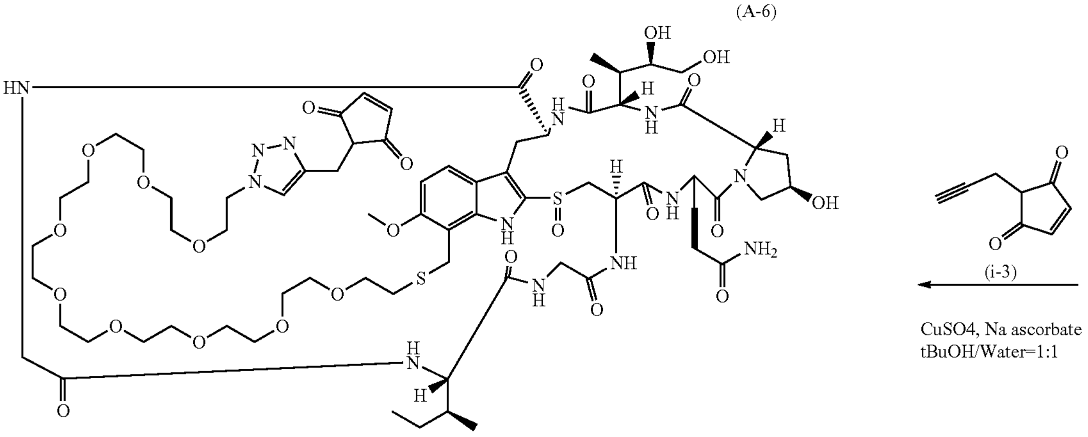

(4)

Step 1: Synthesis of Compound (A-28)

Compound (A-5) was prepared using the method described for Compound (A-1), except Compound (i-3) was used in place of Compound (i-1). MS (m+2/2)=715.9, HPLC Peak RT=0.879 min, 1H-NMR (MeOD, 500 MHz) δ 10.67 (s, 1H), 8.82 (m, 1H), 8.63 (d, 1H, J=2.5 Hz), 8.51 (d, 1H, J=10.5 Hz), 8.48 (d, 1H, J=8.0 Hz), 8.17 (d, 1H, J=8.0 Hz), 8.05 (d, 1H, J=9.5 Hz), 7.94 (d, 1H, J=9.0 Hz), 7.54 (d, 1H, J=9.0 Hz), 6.75 (d, 1H, J=9.0 Hz), 5.31 (m, 1H), 5.17 (m, 1H), 4.74 (bs, 1H), 4.80 (s, 1H), 4.67 (dd, 1H, J=5.5 and 10.0 Hz), 4.56 (m, 2H), 4.35 (dd, 1H, J=8.5 and 18.5 Hz), 4.19 (dd, 1H, J=8.0 and 17.5 Hz), 4.13 (dd, 2H, J=13.5 and 32.5 Hz), 3.97 (dd, 1H, J=3.0 and 11.0 Hz), 3.43~3.78 (m, 48H), 3.37 (m, 3H), 3.26 (t, 1H, J=13.5 Hz), 3.11 (dd, 1H, J=3.5 and 16.0 Hz), 2.95 (dd, 1H, J=12.0 and 15.0 Hz), 2.63 (m, 2H), 2.45 (m, 2H), 2.06 (m, 1H), 1.63 (m, 2H), 1.19 (m, 1H), 0.99 (d, 3H, J=7.0 Hz), 0.90 (m, 6H).

Step 2: Synthesis of Compound (A-6)

Compound (A-6) was prepared using the method described for Compound (A-2), except Compound (A-5) was used in place of Compound (A-1). MS (m+2/2)=722.9, HPLC Peak RT=0.911 min, 1H-NMR (MeOD, 500 MHz) δ 10.77 (s, 1H), 8.82 (m, 1H), 8.63 (d, 1H, J=2.0 Hz), 8.51 (d, 1H, J=10.0 Hz), 8.48 (d, 1H, J=4.0 Hz), 8.36 (s, 1H), 8.18 (d, 1H, J=8.0 Hz), 8.05 (d, 1H, J=10.0 Hz), 7.96 (d, 1H, J=9.0 Hz), 7.70 (d, 1H, J=8.5 Hz), 6.98 (d, 1H, J=9.0 Hz), 5.34 (m, 1H), 5.19 (m, 1H), 4.78 (bs, 1H), 4.68 (dd, 1H, J=5.5 and 10.0 Hz), 4.58 (m, 2H), 4.35 (dd, 1H, J=9.0 and 18.0 Hz), 4.10~4.21 (m, 3H), 3.97 (m, 1H), 3.92 (s, 3H), 3.45~3.79 (m, 48H), 3.37 (t, 2H, J=5.5 Hz), 3.25 (m, 1H), 3.13 (m, 1H), 2.96 (dd, 1H, J=12.0 and 15.0 Hz), 2.61 (m, 2H), 2.44 (m, 2H), 2.08 (m, 1H), 1.63 (m, 2H), 1.21 (m, 1H), 0.99 (d, 3H, J=7.0 Hz), 0.90 (m, 6H).

Step 3: Synthesis of Compound (4)

Compound (4) was prepared using the method described for Compound (1), except Compound (A-6) was used in place of Compound (A-2). MS (m+2/2)=790.5, HPLC Peak RT=0.847 min, 1H-NMR (MeOD, 500 MHz) δ 10.75 (s, 1H), 8.83 (m, 1H), 8.64 (d, 1H, J=2.0 Hz), 8.51 (d, 1H, J=10.5 Hz), 8.47 (d, 1H, J=3.5 Hz), 8.18 (d, 1H, J=7.5 Hz), 8.04 (d, 1H, J=10.0 Hz), 7.96 (d, 1H, J=8.0 Hz), 7.94 (s, 1H), 7.69 (d, 1H, J=8.5 Hz), 6.98 (d, 1H, J=9.0 Hz), 6.85 (s, 2H), 5.34 (m, 1H), 5.17 (m, 1H), 4.79 (bs, 1H), 4.76 (s, 2H), 4.68 (dd, 1H, J=5.0 and 9.5 Hz), 4.56 (m, 5H), 4.34 (m, 1H), 4.09~4.20 (m, 3H), 3.97 (m, 1H), 3.91 (s, 3H), 3.85 (t, 2H, J=5.5 Hz), 3.39~3.70 (m, 54H), 3.10 (m, 1H), 2.96 (dd, 1H, J=12.0 and 15.0 Hz), 2.61 (m, 2H), 2.41 (m, 2H), 2.06 (m, 1H), 1.57~1.68 (m, 2H), 1.20 (m, 1H), 0.99 (d, 3H, J=7.0 Hz), 0.91 (m, 6H).

Example 5: Synthesis of 7'C-((29-(4-((2,5-dioxo-2,5-dihydro-1H-pyrrol-1-yl)methyl)-1H-1,2,3-triazol-1-yl)-3,6,9,12,15,18,21,24,27-nonaoxanonacosanthio)methyl)-α-Amanitin (5)

(5)

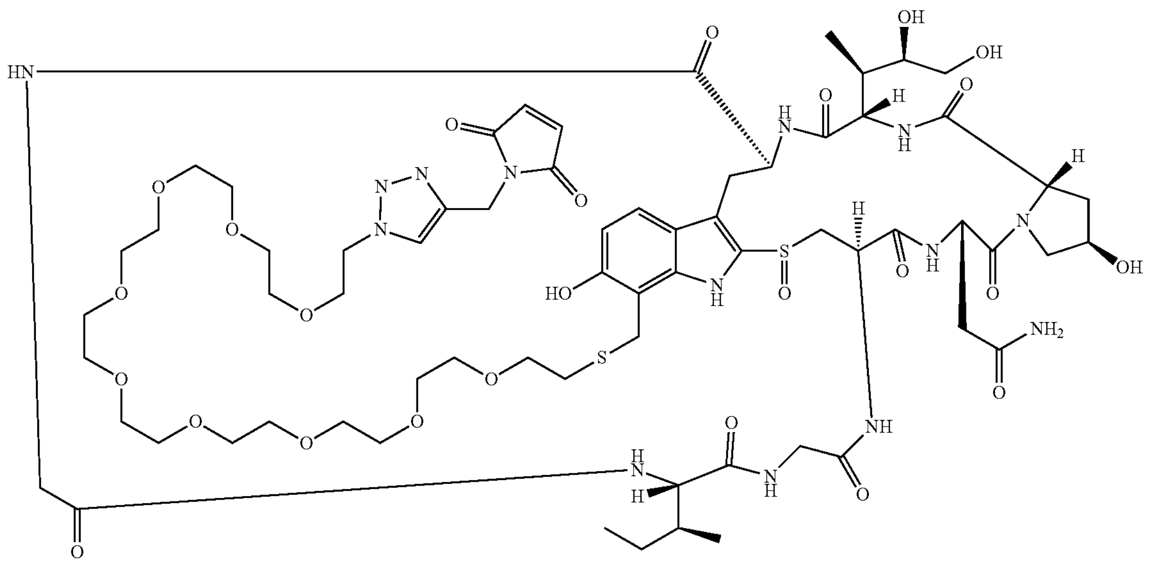

Compound (5) was prepared using the method described for Compound (2), except Compound (A-5) was used in place of Compound (A-4). MS (m+2/2)=783.5, HPLC Peak RT=0.799 min, 1H-NMR (MeOD, 500 MHz) δ 10.65 (s, 1H), 8.83 (m, 1H), 8.63 (d, 1H, J=2.5 Hz), 8.50 (d, 1H, J=10.5 Hz), 8.47 (d, 1H, J=3.5 Hz), 8.17 (d, 1H, J=8.5 Hz), 8.05 (d, 1H, J=10.0 Hz), 7.94 (s, 1H), 7.93 (d, 1H, J=8.5 Hz), 7.53 (d, 1H, J=9.0 Hz), 6.86 (s, 2H), 6.74 (d, 1H, J=9.0 Hz), 5.32 (m, 1H), 5.17 (m, 1H), 4.80 (bs, 1H), 4.76 (s, 2H), 4.67 (dd, 1H, J=5.0 and 9.5 Hz), 4.52~4.58 (m, 4H), 4.34 (dd, 1H, J=8.5 and 18.0 Hz), 4.17 (m, 1H), 4.12 (dd, 2H, J=13.0 and 35.0 Hz), 3.97 (dd, 1H, J=3.5 and 11.5 Hz), 3.86 (t, 2H, J=5.0 Hz), 3.45~3.78 (m, 50H), 3.40 (dd, 1H, J=8.0 and 15.0 Hz), 3.26 (t, 1H, J=13.0 Hz), 3.12 (dd, 1H, J=4.0 and 16.0 Hz), 2.95 (dd, 1H, J=12.0 and 15.0 Hz), 2.63 (m, 2H), 2.47 (m, 2H), 2.06 (m, 1H), 1.59~1.70 (m, 2H), 1.21 (m, 1H), 0.99 (d, 3H, J=7.0 Hz), 0.91 (m, 6H).

Example 6: Synthesis of 6'O-methyl-7'C-((35-(4-((2,5-dioxo-2,5-dihydro-1H-pyrrol-1-yl)methyl)-1H-1,2,3-triazol-1-yl)-3,6,9,12,15,18,21,24,27,30,33-undecaoxapentatriacontanethio)methyl)-α-Amanitin (6), 7'C-((35-azido-3,6,9,12,15,18,21,24,27,30,33-undecaoxapentatriacontanethio)methyl)-α-Amanitin (A-7) and 6'O-methyl-7'C-((35-azido-3,6,9,12,15,18,21,24,27,30,33-undecaoxapentatriacontanethio)methyl)-α-Amanitin (A-8)
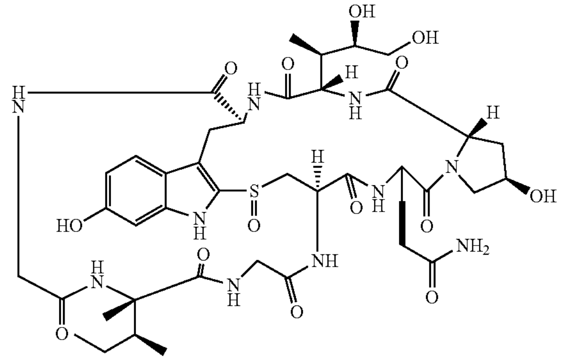
(A)
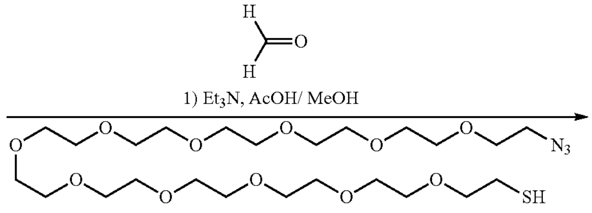
(i-4)
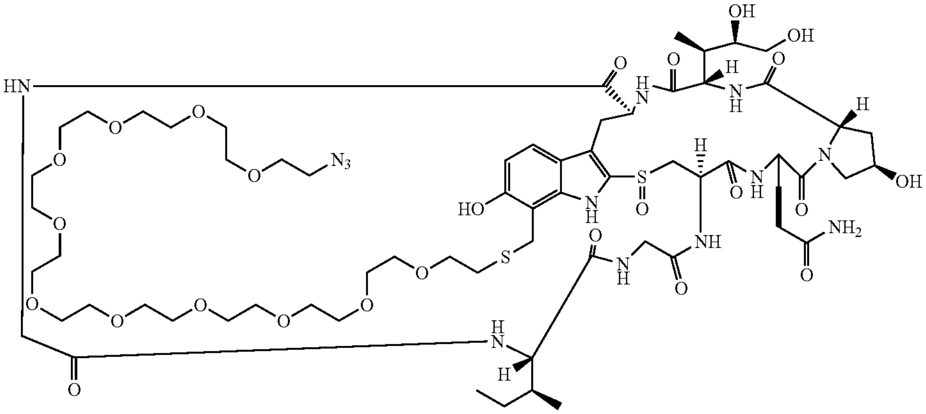
(A-7)

-continued

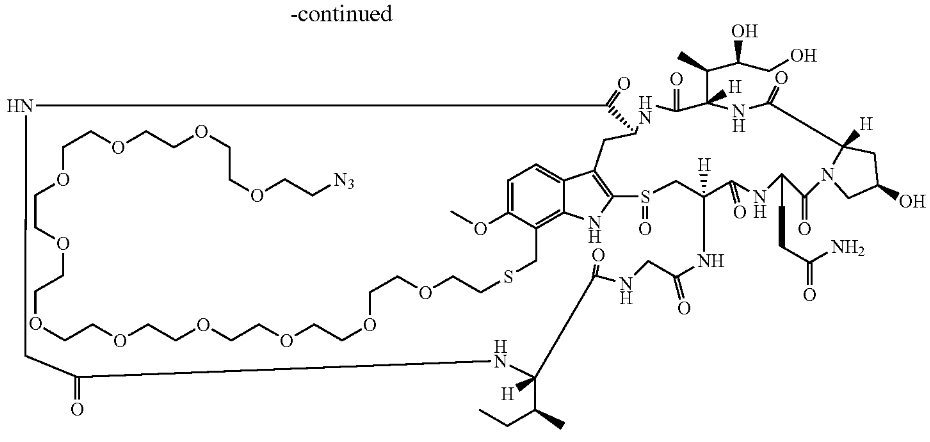

(A-8)

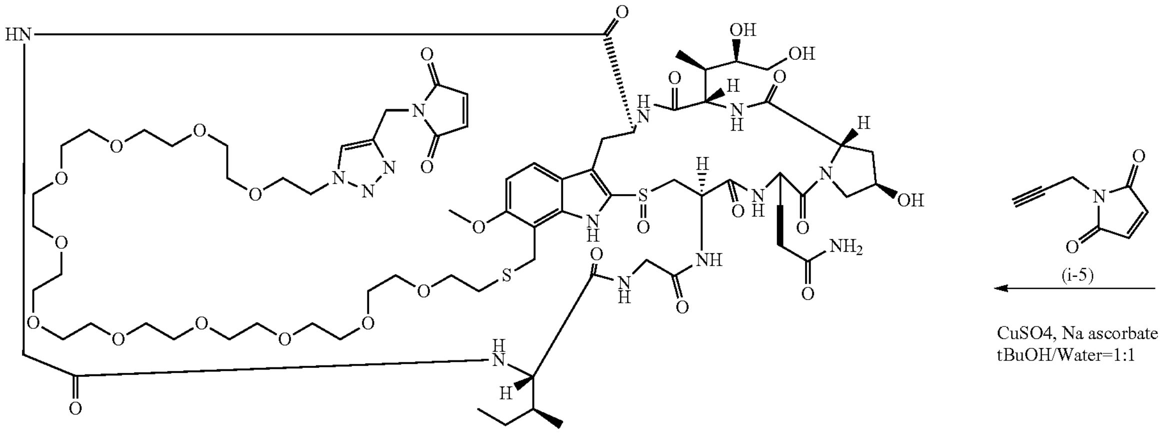

(6)

Step 1 Synthesis of Compound (A-7)

Compound (A-7) was prepared using the method described for Compound (A-1), except Compound (i-4) was used in place of Compound (i-1). MS (m+2/2)=760.0, HPLC Peak RT=0.889 min, 1H-NMR (MeOD, 500 MHz) δ 10.67 (s, 1H), 8.82 (m, 1H), 8.63 (d, 1H, J=2.5 Hz), 8.51 (d, 1H, J=10.5 Hz), 8.48 (d, 1H, J=8.5 Hz), 8.36 (s, 1H), 8.17 (d, 1H, J=8.5 Hz), 8.05 (d, 1H, J=9.5 Hz), 7.94 (d, 1H, J=9.0 Hz), 7.68 (s, 1H), 7.54 (d, 1H, J=8.5 Hz), 6.75 (d, 1H, J=8.5 Hz), 5.31 (m, 1H), 5.18 (m, 1H), 4.79 (bs, 1H), 4.67 (dd, 1H, J=5.0 and 9.5 Hz), 4.56 (m, 2H), 4.35 (dd, 1H, J=9.0 and 18.5 Hz), 4.19 (m, 1H), 4.13 (dd, 2H, J=13.5 and 32.5 Hz), 3.98 (dd, 1H, J=3.0 and 11.0 Hz), 3.47~3.78 (m, 68H), 3.39 (m, 3H), 3.26 (t, 1H, J=13.5 Hz), 3.12 (m, 1H), 2.95 (m, 1H), 2.65 (m, 2H), 2.45 (m, 2H), 2.06 (m, 1H), 1.63 (m, 2H), 1.19 (m, 1H), 0.99 (d, 3H, J=7.0 Hz), 0.90 (m, 6H).

Step 2: Synthesis of Compound (A-8)

Compound (A-8) was prepared using the method described for Compound (A-2), except Compound (A-7) was used in place of Compound (A-1). MS (m+2/2)=767.0, HPLC Peak RT=0.915 min, 1H-NMR (MeOD, 500 MHz) δ 10.76 (s, 1H), 8.83 (m, 1H), 8.64 (d, 1H, J=2.0 Hz), 8.52 (d, 1H, J=10.5 Hz), 8.47 (d, 1H, J=3.0 Hz), 8.36 (s, 1H), 8.18 (d, 1H, J=8.5 Hz), 8.04 (d, 1H, J=9.5 Hz), 7.96 (d, 1H, J=9.0 Hz), 7.70 (d, 1H, J=8.5 Hz), 6.98 (d, 1H, J=8.5 Hz), 5.34 (m, 1H), 5.19 (m, 1H), 4.80 (bs, 1H), 4.68 (dd, 1H, J=5.5 and 10.0 Hz), 4.56 (m, 2H), 4.35 (dd, 1H, J=9.0 and 18.5 Hz), 4.10~4.21 (m, 3H), 3.98 (m, 1H), 3.92 (s, 3H), 3.45~3.78 (m, 64H), 3.39 (m, 2H), 3.26 (m, 1H), 3.13 (m, 1H), 2.96 (dd, 1H, J=12.0 and 15.0 Hz), 2.61 (m, 2H), 2.44 (m, 2H), 2.06 (m, 1H), 1.63 (m, 2H), 1.21 (m, 1H), 0.99 (d, 3H, J=7.0 Hz), 0.90 (m, 6H).

Step 3: Synthesis of Compound (6)

Compound (6) was prepared using the method described for Compound (1), except Compound (A-8) was used in place of Compound (A-2). MS (m+2/2)=834.5, HPLC Peak RT=0.882 min, 1H-NMR (MeOD, 500 MHz) δ 10.74 (s, 1H), 8.83 (m, 1H), 8.64 (d, 1H, J=2.0 Hz), 8.52 (d, 1H, J=10.5 Hz), 8.46 (d, 1H, J=3.5 Hz), 8.35 (s, 1H), 8.18 (d, 1H, J=8.5 Hz), 8.04 (d, 1H, J=10.0 Hz), 7.96 (d, 1H, J=9.0 Hz), 7.94 (s, 1H), 7.69 (d, 1H, J=9.0 Hz), 6.98 (d, 1H, J=9.0 Hz), 6.85 (s, 2H), 5.33 (m, 1H), 5.17 (m, 1H), 4.79 (bs, 1H), 4.76 (s, 2H), 4.68 (dd, 1H, J=5.0 and 9.5 Hz), 4.56 (m, 5H), 4.34 (m, 1H), 4.09~4.20 (m, 3H), 3.97 (m, 1H), 3.91 (s, 3H), 3.86 (t, 2H, J=5.0 Hz), 3.39~3.70 (m, 68H), 3.25 (m, 1H), 3.10 (m, 1H), 2.96 (dd, 1H, J=12.0 and 15.0 Hz), 2.62 (m, 2H), 2.41 (m, 2H), 2.05 (m, 1H), 1.57~1.68 (m, 2H), 1.20 (m, 1H), 0.99 (d, 3H, J=7.0 Hz), 0.90 (m, 6H).

Example 7: Synthesis of 7'C-((35-(4-((2,5-dioxo-2,5-dihydro-1H-pyrrol-1-yl)methyl)-1H-1,2,3-triazol-1-yl)-3,6,9,12,15,18,21,24,27,30,33-undecaoxapentatriacontanethio)methyl)-α-Amanitin (7)

(7)

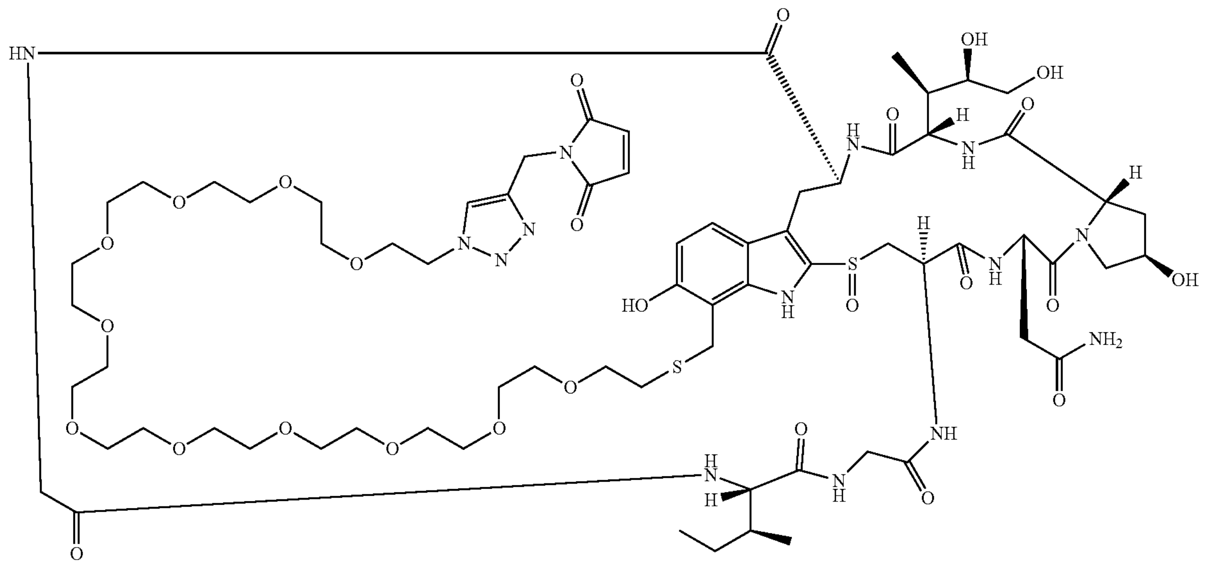

Compound (7) was prepared using the method described for Compound (2), except Compound (A-7) was used in place of Compound (A-4). MS (m+2/2)=827.5, HPLC Peak RT=0.830 min, 1H-NMR (MeOD, 500 MHz) δ 8.81 (m, 1H), 8.63 (d, 1H, J=2.0 Hz), 8.50 (d, 1H, J=10.5 Hz), 8.47 (d, 1H, J=4.0 Hz), 8.17 (d, 1H, J=8.0 Hz), 8.05 (d, 1H, J=10.0 Hz), 7.94 (s, 1H), 7.93 (d, 1H, J=9.0 Hz), 7.53 (d, 1H, J=8.5 Hz), 6.86 (s, 2H), 6.75 (d, 1H, J=8.5 Hz), 5.31 (m, 1H), 5.17 (m, 1H), 4.80 (bs, 1H), 4.77 (s, 2H), 4.67 (dd, 1H, J=5.0 and 9.5 Hz), 4.52~4.58 (m, 4H), 4.34 (dd, 1H, J=8.5 and 18.0 Hz), 4.17 (m, 1H), 4.12 (dd, 2H, J=13.5 and 34.5 Hz), 3.97 (m, 1H), 3.86 (t, 2H, J=5.0 Hz), 3.46~3.78 (m, 54H), 3.40 (dd, 1H, J=8.0 and 15.0 Hz), 3.26 (t, 1H, J=13.0 Hz), 3.12 (dd, 1H, J=4.0 and 16.0 Hz), 2.95 (m, 1H), 2.63 (m, 2H), 2.47 (m, 2H), 2.04 (m, 1H), 1.59~1.70 (m, 2H), 1.21 (m, 1H), 0.99 (d, 3H, J=7.0 Hz), 0.91 (m, 6H).

Example 8: Synthesis of 6'O-methyl-7'C-((23-(4-(((((4-((S)-2-((S)-2-(2-(aminooxy)acetamido)-3-methylbutanamido)-5-ureidopentanamido)benzyl)oxy)carbonyl)amino)methyl)-1H-1,2,3-triazol-1-yl)-3,6,9,12,15,18,21-heptaoxatricosanyl)thio)methyl-α-Amanitin (8)

(8)
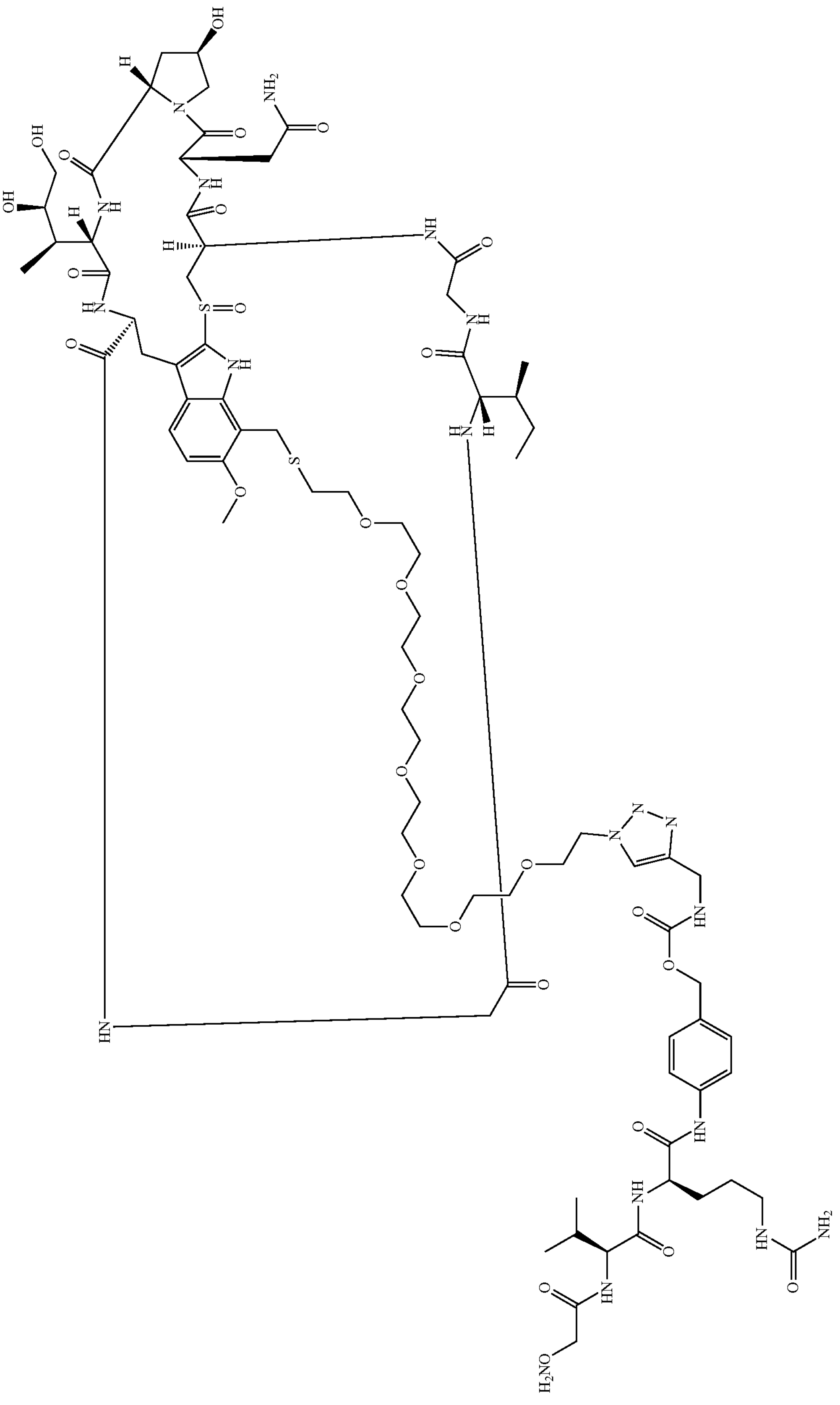

A solution of 6'O-methyl-7'C-((23-azido-3,6,9,12,15,18,21-heptaoxatricosanthio)methyl)-α-Amanitin (A-4) (15 mg, 0.011 mmol) in t-BuOH (1.5 mL) was added to tert-butyl (2-(((S)-3-methyl-1-oxo-1-(((S)-1-oxo-1-((4-(((prop-2-yn-1-ylcarbamoyl)oxy)methyl)phenyl)amino)-5-ureidopentan-2-yl)amino)butan-2-yl)amino)-2-oxoethoxy)carbamate (i-6) (9.8 mg, 0.015 mmol). The solution was degassed and purged with $N_2$ three times. To the degassed solution was added sodium abscorbate (0.94 mL of a 2.35 mg/mL solution, 2.2 mg, 0.011 mmol) and copper (II) sulfate pentahydrate (0.522 mL of a 1 mg/mL solution, 0.552 mg, 0.002 mmol). The solution was again degassed and purged with $N_2$ three times at which time the reaction stirred for 6 hours. Additional sodium abscorbate (0.94 mL of a 2.35 mg/mL solution, 2.2 mg, 0.011 mmol) and copper (II) sulfate pentahydrate (0.522 mL of a 1 mg/mL solution, 0.552 mg, 0.002 mmol) was added. After stirring for an additional 2 hours the reaction mixture was purified directly by RP-HPLC to yield the N-Boc protected 6'O-methyl-7'C-((23-(4-(((((4-((S)-2-((S)-2-(2-(aminooxy)acetamido)-3-methylbutanamido)-5-ureidopentanamido)benzyl)oxy)carbonyl)amino)methyl)-1H-1,2,3-triazol-1-yl)-3,6,9,12,15,18,21-heptaoxatricosanyl)thio)methyl-α-Amanitin (M+2H/2=995.7 and HRMS+$H^+$=1989.8987). The Boc group was removed by treating with 25% TFA/$CH_2Cl_2$ (1.5 mL) for 30 minutes. At this time EtOH (0.07 mL) was added, the volatiles were removed in vacuo, the residue was dissolved in DMSO (1 mL) and was purified by RP-HPLC to yield after lyophilization 6'O-methyl-7'C-((23-(4-(((((4-((S)-2-((S)-2-(2-(aminooxy)acetamido)-3-methylbutanamido)-5-ureidopentanamido)benzyl)oxy)carbonyl)amino)methyl)-1H-1,2,3-triazol-1-yl)-3,6,9,12,15,18,21-heptaoxatricosanyl)thio)methyl-α-Amanitin (8) as a TFA salt (M+2H+/2=945.3 and HRMS+$H^+$=1889.7903). The material was dissolved in DMSO (0.041 mL) to yield a 150 mg/mL solution for use in conjugation reactions.

Example 9: Synthesis of 6'O-methyl-7'C-((23-(4-(((((4-((S)-2-((S)-2-(2-(aminooxy)acetamido)-4-methylpentanamido)-5-ureidopentanamido)benzyl)oxy)carbonyl)amino)methyl)-1H-1,2,3-triazol-1-yl)-3,6,9,12,15,18,21-heptaoxatricosanyl)thio)methyl-α-Amanitin (9)

(9)
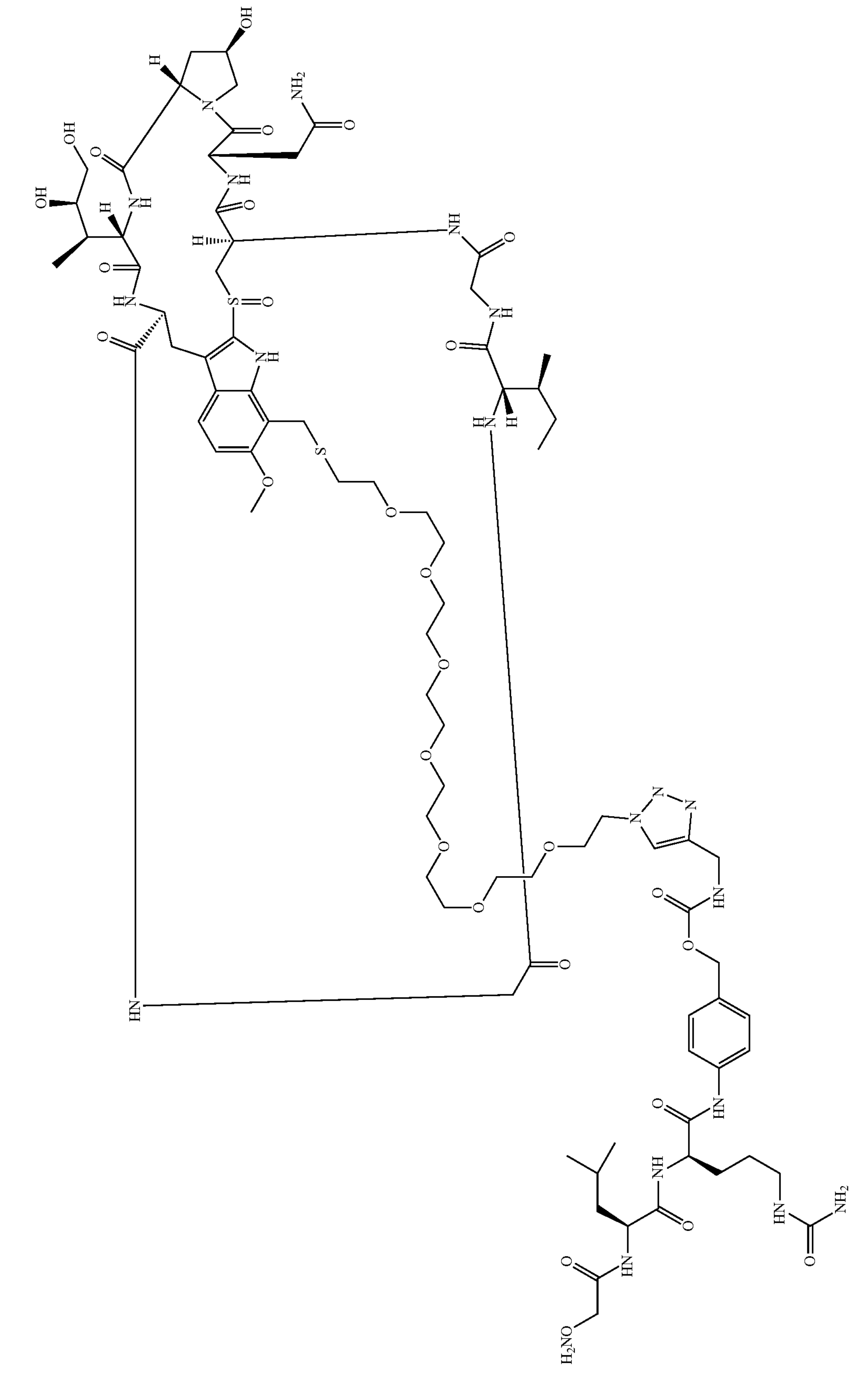

A solution of 6'O-methyl-7'C-((23-azido-3,6,9,12,15,18,21-heptoaoxatricosanthio)methyl)-α-Amanitin (A-4)(15 mg, 0.011 mmol) in BuOH (1.5 mL) was added to tert-butyl (2-(((S)-4-methyl-1-oxo-1-(((S)-1-oxo-1-((4-(((prop-2-yn-1-ylcarbamoyl)oxy)methyl)phenyl)amino)-5-ureidopentan-2-yl)amino)pentan-2-yl)amino)-2-oxoethoxy)carbamate (i-7) (14.3 mg, 0.022 mmol). The solution was degassed and purged with $N_2$ three times. To the degassed solution was added sodium abscorbate (0.94 mL of a 2.35 mg/mL solution, 2.2 mg, 0.011 mmol) and copper (II) sulfate pentahydrate (0.522 mL of a 1 mg/mL solution, 0.552 mg, 0.002 mmol). The solution was again degassed and purged with $N_2$ three times at which time the reaction stirred for 6 hours. Additional sodium abscorbate (0.94 mL of a 2.35 mg/mL solution, 2.2 mg, 0.011 mmol) and copper (II) sulfate pentahydrate (0.522 mL of a 1 mg/mL solution, 0.552 mg, 0.002 mmol) was added. After stirring for an additional 2 hours the reaction mixture was purified directly by RP-HPLC to yield the N-Boc-Aminooxy$CH_2$CO-Ile-Cit-PABA-CONH$CH_2$triazole-PEG8-thiomethyl-(a)-Amanitin (M+2H/2=1002.7 and HRMS+$H^+$=2003.9119). The Boc group was removed by treating with 25% TFA/$CH_2Cl_2$ (1.5 mL) for 30 minutes. At this time EtOH (0.07 mL) was added, the volatiles were removed in vacuo, the residue was dissolved in DMSO (1 mL) and was purified by RP-HPLC to yield after lyophilization Aminooxy$CH_2$CO-Ile-Cit-PABA-CONH$CH_2$triazole-PEG8-thiomethyl-(a)-Amanitin (9) as a TFA salt (M+2H+/2=952.5 and HRMS+$H^+$=1903.7821). The material was dissolved in DMSO (0.030 mL) to yield a 150 mg/mL solution for use in conjugation reactions.

Example 10: Synthesis of 6'O-methyl-7'C-((35-(4-(18-(aminooxy)-3,8,11,14,17-pentaoxo-2-oxa-4,7,10,13,16-pentaazaoctadecyl)-1H-1,2,3-triazol-1-yl)-3,6,9,12,15,18,21,24,27,30,33-undecaoxapentatriacontanyl)thio)methyl-α-Amanitin (10)

(10)
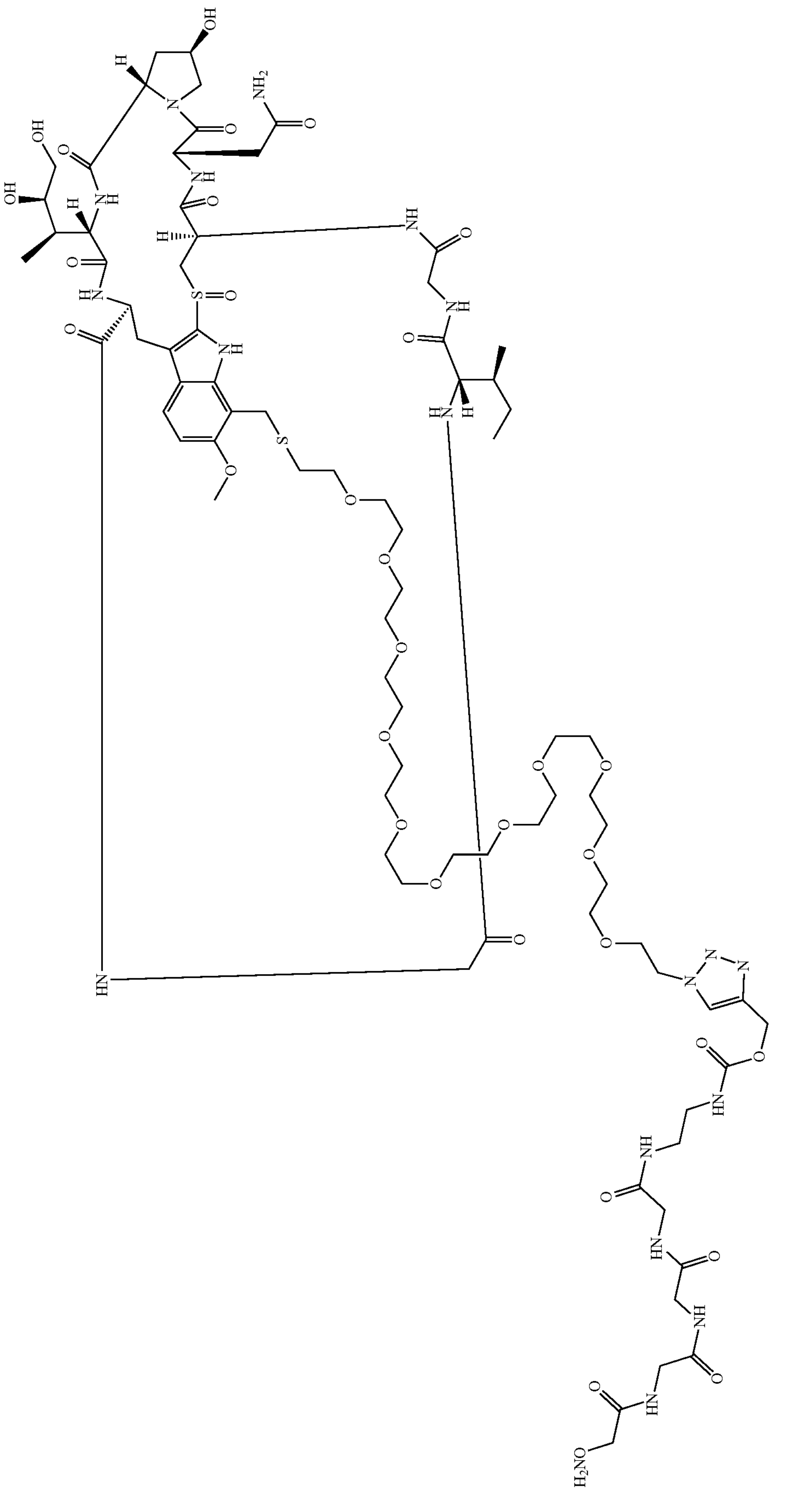

A solution of 6'O-methyl-7'C-((35-azido-3,6,9,12,15,18,21,24,27,30,33-undecaoxapentatriacontanethio)methyl)-α-Amanitin (A-8) (7.9 mg, 0.005 mmol) in t-BuOH (0.7 mL) was added to tert-butyl ((2,5,8,11,16-pentaoxo-17-oxa-3,6,9,12,15-pentaazaicos-19-yn-1-yl)oxy)carbamate (i-8) (5 mg, 0.010 mmol). The solution was degassed and purged with $N_2$ three times. To the degassed solution was added sodium abscorbate (0.44 mL of a 2.35 mg/mL solution, 1.0 mg, 0.005 mmol) and copper (II) sulfate pentahydrate (0.257 mL of a 1 mg/mL solution, 0.257 mg, 0.001 mmol). The solution was again degassed and purged with $N_2$ three times. After stirring for 6 hours the reaction mixture was purified directly by RP-HPLC to yield the N-Boc protected 6'O-methyl-7'C-((35-(4-(18-(aminooxy)-3,8,11,14,17-pentaoxo-2-oxa-4,7,10,13,16-pentaazaoctadecyl)-1H-1,2,3-triazol-1-yl)-3,6,9,12,15,18,21,24,27,30,33-undecaoxapentatriacontanyl)thio)methyl-α-Amanitin (M+2H/2=1009.7 and HRMS+$H^+$=2018.8899). The Boc group was removed by treating with 25% TFA/$CH_2Cl_2$ (0.6 mL) for 30 minutes. At this time EtOH (0.04 mL) was added, the volatiles were removed in vacuo, the residue was dissolved in DMSO (1 mL) and was purified by RP-HPLC to yield after lyophilization 6'O-methyl-7'C-((35-(4-(18-(aminooxy)-3,8,11,14,17-pentaoxo-2-oxa-4,7,10,13,16-pentaazaoctadecyl)-1H-1,2,3-triazol-1-yl)-3,6,9,12,15,18,21,24,27,30,33-undecaoxapentatriacontanyl)thio)methyl-α-Amanitin (10) as a TFA salt (M+2H+/2=960.2 and HRMS+$H^+$=1918.8431). The material was dissolved in DMSO (0.010 mL) to yield a 150 mg/mL solution for use in conjugation reactions.

Example 11: Synthesis of 6'O-methyl-$d_3$-7'C-((((1-(4-maleimido-3,6,9,12,15,18,21-heptaoxatricosyl)-1H-1,2,3-triazol-4-yl)methyl)thio)methyl)-α-Amanitin (11) and Compound 6'O-methyl-$d_3$-7'C-((23-azido-3,6,9,12,15,18,21-heptaoxatricosanthio)methyl)-α-Amanitin (A-9)

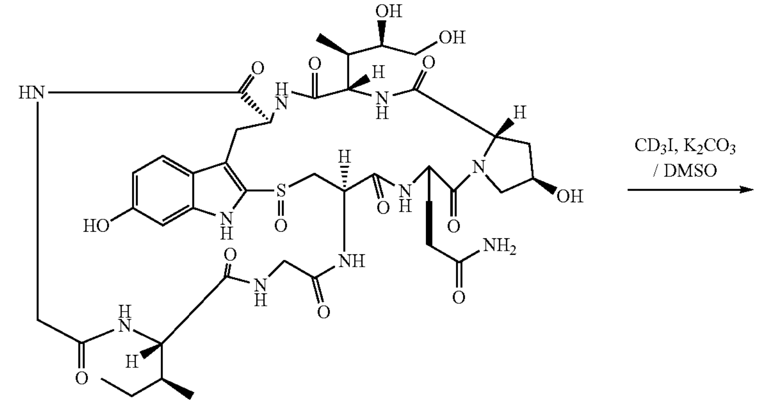

(A-1)

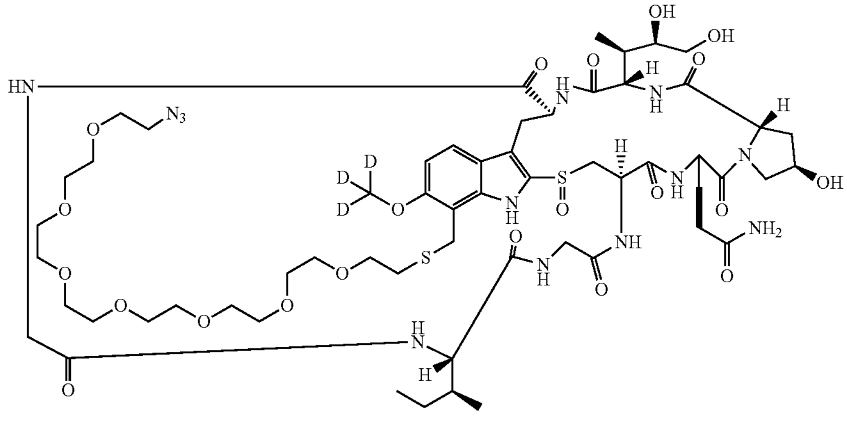

(A-9)

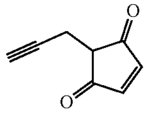

(i-3)

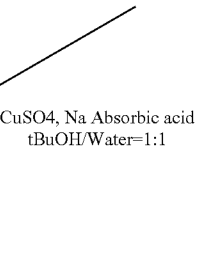

-continued

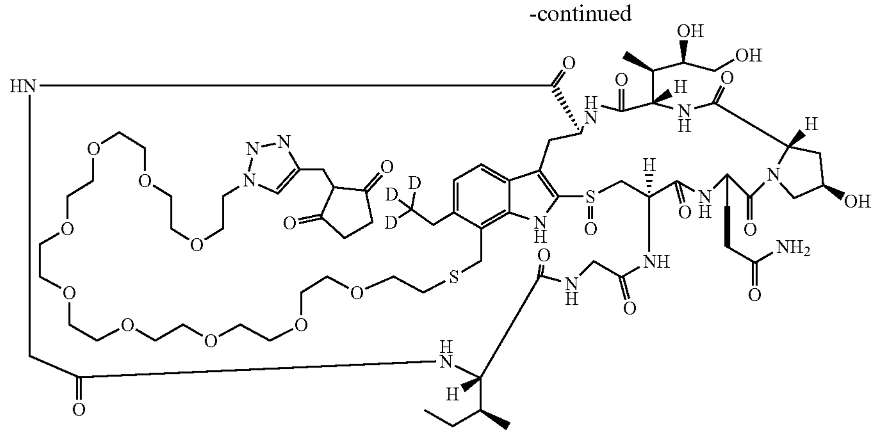

(11)

Step 1: Synthesis of Compound (A-9)

Compound (A-9) was prepared using the method described for Compound (A-2), except methyliodide-$d_3$ was used in place of methyliodide. MS (m+2/2)=680.4, HPLC Peak RT=0.969 min, 1H-NMR (MeOD, 500 MHz) δ 10.80 (s, 1H), 8.86 (m, 1H), 8.67 (d, 1H, J=2.0 Hz), 8.53 (m, 2H), 8.40 (s, 1H), 8.17 (m, 1H), 8.09 (d, 1H, J=12.0 Hz), 7.98 (d, 1H, J=11.0 Hz), 7.73 (d, 1H, J=11.0 Hz), 7.01 (d, 1H, J=10.5 Hz), 5.37 (m, 1H), 5.22 (m, 1H), 4.97 (bs, 1H), 4.71 (m, 1H), 4.59 (m, 2H), 4.38 (dd, 1H, J=10.5 and 23.0 Hz), 4.18 (m, 3H), 4.01 (m, 1H), 3.38~3.79 (m, 43H), 3.17 (m, 1H), 2.99 (m, 1H), 2.63 (m, 2H), 2.49 (m, 2H), 2.08 (m, 1H), 1.66 (m, 2H), 1.02 (d, 3H, J=9.0 Hz), 0.94 (m, 6H).

Step 2: Synthesis of Compound (11)

Compound (11) was prepared using the method described for Compound (1), except Compound (A-9) was used in place of Compound (A-2). MS (m+2/2)=748.0, HPLC Peak RT=0.901 min, 1H-NMR (MeOD, 500 MHz) δ 10.78 (s, 1H), 8.85 (m, 1H), 8.67 (d, 1H, J=2.0 Hz), 8.54 (d, 1H, J=10.0 Hz), 8.50 (d, 1H, J=3.5 Hz), 8.39 (s, 1H), 8.20 (d, 1H, J=8.5 Hz), 8.08 (d, 1H, J=10.0 Hz), 7.98 (d, 1H, J=9.5 Hz), 7.97 (s, 1H), 7.72 (d, 1H, J=9.0 Hz), 7.00 (d, 1H, J=9.0 Hz), 6.88 (s, 2H), 5.36 (m, 1H), 5.21 (m, 1H), 4.83 (bs, 1H), 4.79 (s, 2H), 4.71 (dd, 1H, J=5.0 and 9.5 Hz), 4.59 (m, 2H), 4.55 (t, 1H, J=5.0 Hz), 4.38 (dd, 1H, J=9.0 and 18.5 Hz), 4.08~4.20 (m, 3H), 4.01 (m, 1H), 3.39~3.88 (m, 38H), 3.15 (m, 1H), 2.99 (dd, 1H, J=14.0 and 15.0 Hz), 2.63 (m, 2H), 2.49 (m, 2H), 2.09 (m, 1H), 1.57~1.69 (m, 2H), 1.23 (m, 1H), 1.02 (d, 3H, J=7.0 Hz), 0.94 (m, 6H).

Antigen-Binding Moieties

The antigen-binding moiety (Ab) in Formula (B), Formula (II) or Formula (IIa) can be any moiety that selectively binds to a targeted cell type. In some aspects, Ab is an antibody or antibody fragment (e.g. antigen binding fragment of an antibody) that specifically binds to an antigen predominantly or preferentially found on the surface of cancer cells, e.g., a tumor-associated antigen. In some aspects, Ab is an antibody or antibody fragment (e.g., antigen binding fragment) that specifically binds to a cell surface receptor protein or other cell surface molecules, a cell survival regulatory factor, a cell proliferation regulatory factor, a molecules associated with (for e.g., known or suspected to contribute functionally to) tissue development or differentiation, a lymphokine, a cytokine, a molecule involved in cell cycle regulation, a molecule involved in vasculogenesis or a molecule associated with (for e.g., known or suspected to contribute functionally to) angiogenesis. A tumor-associated antigen may be a cluster differentiation factor (i.e., a CD protein). In some aspects of the invention, the antigen binding moiety of the invention specifically binds to one antigen. In some aspects of the invention, the antigen binding moiety of the invention specifically binds to two or more antigens described herein, for example, the antigen binding moiety of the invention is a bispecific or multispecific antibody or antigen binding fragment thereof.

Exemplary antibodies or antigen binding fragments include but are not limited to anti-estrogen receptor antibody, anti-progesterone receptor antibody, anti-p53 antibody, anti-HER-2 antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD1-antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD39 antibody, anti-CD41 antibody, anti-LCA/CD45 antibody, anti-CD45RO antibody, anti-CD45RA antibody, anti-CD71 antibody, anti-CD95/Fas antibody, anti-CD99 antibody, anti-CD100 antibody, anti-S—100 antibody, anti-CD106 antibody, anti-ubiquitin antibody, anti-c-myc antibody, anti-cytokeratin antibody, anti-lambda light chains antibody, anti-melanosomes antibody, anti-prostate specific antigen antibody, anti-tau antigen antibody, anti-fibrin antibody, anti-keratins antibody, and anti-Tn-antigen antibody.

The antigen binding moiety of the antibody-drug conjugates (ADC) of Formula (B), Formula (II) or Formula (IIa) specifically binds to a receptor encoded by an ErbB gene. The antigen binding moiety may bind specifically to an ErbB receptor selected from EGFR, HER2, HER3 and HER4. The antigen binding moiety may be an antibody that will specifically bind to the extracellular domain (ECD) of the HER2 receptor and inhibit the growth of tumor cells which overexpress HER2 receptor. The antibody may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (trastuzumab). The antibody may be an antibody fragment, e.g. a Fab fragment.

Antigen-binding moieties in Formula (B), Formula (II) or Formula (IIa) include, but are not limited to, antibodies or antibody fragments (e.g., antigen binding fragments) against cell surface receptors and tumor-associated antigens. Such tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Antibodies and antibody fragments (e.g., antigen binding fragment) useful for the immunoconjugates of the invention include modified or engineered antibodies, such as an antibody modified to introduce a cysteine residue (Junutula J R, Raab H, Clark S, Bhakta S, Leipold D D, Weir S, Chen Y, Simpson M, Tsai S P, Dennis M S, Lu Y et al.: Nat Biotechnol 2008, 26:925-932), or other reactive amino acid, including Pcl, pyrrolysine and non-natural amino acids, in place of at least one amino acid of the native sequence, thus providing a reactive site on the antibody or antigen binding fragment for conjugation to a cytotoxic peptide of Formula (A), Formula (I) or Formula (Ia). For example, the antibodies or antibody fragments can be modified to incorporate Pcl or pyrrolysine (W. Ou et al. (2011) PNAS 108 (26), 10437-10442) or unnatural amino acids (J. Y. Axup, K. M. Bajjuri, M. Ritland, B. M. Hutchins, C. H. Kim, S. A. Kazane, R. Halder, J. S. Forsyth, A. F. Santidrian, K. Stafin, Y. Lu et al. Proc Natl Acad Sci USA, 109 (2012), pp. 16101-16106; for review, see C. C. Liu and P. G. Schultz (2010) Annu Rev Biochem 79, 413-444; C. H. Kim, J. Y. Axup, P. G. Schultz (2013) Curr Opin Chem Biol. 17, 412-419) as sites for conjugation to a drug. Similarly, peptide tags for enzymatic conjugation methods can be introduced into an antibody (Strop P. et al. Chem Biol. 2013, 20(2):161-7; Rabuka D., Curr Opin Chem Biol. 2010 December; 14(6):790-6; Rabuka D, et al., Nat Protoc. 2012, 7(6):1052-67). One other example is the use of 4'-phosphopantetheinyl transferases (PPTase) for the conjugation of Co-enzyme A analogs to peptide tags such as S6, A1 and ybbR tags (Site-Specific Labeling Methods and Molecules Produced Thereby, WO20130184514). Methods for conjugating such modified or engineered antibodies with payloads or linker-payload combinations are known in the art.

Antigen-binding moieties (e.g., antibodies and antigen binding fragments) useful in the invention may also have other modifications or be conjugated to other moieties, such as but not limited to polyethylene glycol tags, albumin, and other fusion polypeptide.

The antibodies used in the examples herein have the heavy chain and light chain sequences listed in Table 2. Some of these antibodies were engineered to contain cysteine residues for site-specific conjugation with cytotoxic cyclic peptides of the invention. The examples herein illustrate that these engineered antibodies are suitable antibody for use in the immunoconjugates of Formula (B), Formula (II) or Formula (IIa). In addition, non-engineered antibodies can also be used for the preparation of the immunoconjugates of Formula (B), Formula (II) or Formula (IIa) through traditional methods (Carter P J, Senter P D, Antibody-drug conjugates for cancer therapy, *Cancer J.* 2008, 14(3):154-69; J. E. Stefano, M. Busch, L. Hou, A. Park, and D. A. Gianolio, p. 145-171, and M.-P. Brun and L. Gauzy-Lazo, p. 173-187 in Antibody-Drug Conjugate, Methods in Molecular Biology, Vol. 1045, Editor L. Ducry, Humana Press, 2013).

TABLE 2

| Amino acid sequences of example antibodies |
|---|
| (anti-Her2 heavy chain wild-type;<br>CDR sequences underlined) SEQ ID NO: 1<br>EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLVK<br>DYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKP<br>KDTLMISRTPEVTCWVDVSHEDPEVKFNWYVDGVEVHNAKTKPREEQYNS<br>TYRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPVL<br>DSDGSFFLYSKLTVDKSRWQQGNVFSCSVMHEALHNHYTQKSLSLSPGK |
| (anti-Her2 light chain wild-type;<br>CDR sequences underlined) SEQ ID NO: 2<br>DIQMTQSPSSLSASVGDRVTITCRASQDVNTAVAWYQQKPGKAPKLLIYS<br>ASFLYSGVPSRFSGSRSGTDFTLTISSLQPEDFATYYCQQHYTTPPTFGQ<br>GTKVEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGEC |
| (constant region of the heavy<br>chain wild-type of anti-Her2) SEQ ID NO: 3<br>SASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKVE<br>PKSCDKTHTCPPCPAPELLGGPSVFLFPPKPKDTLMISRTPEVTCVWDVS<br>HEDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLTC<br>LVKGFYPSDIAVEWESNGQPENNYKTTPPVLDSDGSFFLYSKLTVDKSRW<br>QQGNVFSCSVMHEALHNHYTQKSLSLSPGK |
| (constant region of the light<br>chain wild-type of anti-Her2) SEQ ID NO: 4<br>KRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVT<br>KSFNRGEC |
| (signal sequence) SEQ ID NO: 5<br>MKTFILLLWVLLLWVIFLLPGATA |
| (Full length sequence of the<br>mutant heavy chain of<br>anti-Her2-HC-E152C-S375C,<br>CDR sequences underlined) SEQ ID NO: 6<br>EVQLVESGGGLVQPGGSLRLSCAASGFNIKDTYIHWVRQAPGKGLEWVAR<br>IYPTNGYTRYADSVKGRFTISADTSKNTAYLQMNSLRAEDTAVYYCSRWG<br>GDGFYAMDYWGQGTLVTVSSASTKGPSVFPLAPSSKSTSGGTAALGCLVK<br>DYFPCPVTVSWNSGALTSGVHTFPAVLQSSGLYSLSSVVTVPSSSLGTQT<br>YICNVNHKPSNTKVDKRVEPKSCDKTHTCPPCPAPELLGGPSVFLFPPKP<br>KDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQ<br>VYTLPPSREEMTKNQVSLTCLVKGFYPCDIAVEWESNGQPENNYKTTPPV<br>LDSDGSFFLYSKLTVDKSRWQQGNVFSCSVMHEALHNHYTQKSLSLSPGK |

SEQ ID NO:1 and SEQ ID NO:2 are the full length amino acid sequence of wild-type anti-Her2 antibody heavy chain (HC) and light chain (LC), respectively. SEQ ID NO:3, and SEQ ID NO:4 are the amino acid sequences of the constant regions for the HC and LC, respectively of anti-Her2 antibody. SEQ ID NO:5 is the signal peptide used. Mutant Cys residue are shown in bold and are underlined in the sequences of corresponding mutant chains. CDR sequences are underlined in SEQ ID NO:1 and SEQ ID NO:2. SEQ ID NO:6 is the full length amino acid sequence of the heavy chain double cysteine mutant HC-E152C and HC-S375C of anti-Her2.

Antibody Production

The antibodies and antibody fragments (e.g., antigen binding fragments) of the invention can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementary determining regions as described herein.

The polynucleotide sequences can be produced by de novo solid-phase DNA synthesis or by PCR mutagenesis of an existing sequence (e.g., sequences as described in the examples below) encoding an antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., *Meth. Enzymol.* 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., *Nucleic Acids Res.* 19:967, 1991; and Eckert et al., *PCR Methods and Applications* 1:17, 1991.

Also provided in the invention are expression vectors and host cells for producing the antibodies or antibody fragments described above. Various expression vectors can be employed to express the polynucleotides encoding the antibody chains or binding fragments of the invention. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., *Nat Genet* 15:345, 1997). For example, nonviral vectors useful for expression of the polynucleotides and polypeptides in mammalian (e.g., human) cells include pThioHis A, B & C, pcDNA3.1/His, pEBVHis A, B & C (Life Tech., San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Smith, *Annu. Rev. Microbiol.* 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an antibody chain or fragment of the invention. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an antibody chain or fragment of the invention. These elements typically include an ATG initiation codon and adjacent ribosome binding site or other sequences. In addition, the efficiency of expression may be enhanced by the inclusion of enhancers appropriate to the cell system in use (see, e.g., Scharf et al., *Results Probl. Cell Differ.* 20:125, 1994; and Bittner et al., *Meth. Enzymol.,* 153:516, 1987). For example, the SV40 enhancer or CMV enhancer may be used to increase expression in mammalian host cells.

The expression vectors may also provide a secretion signal sequence position to form a fusion protein with polypeptides encoded by inserted antibody sequences. More often, the inserted antibody sequences are linked to a signal sequences before inclusion in the vector. Vectors to be used to receive sequences encoding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the antibody chains of the invention can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters may be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express the antibodies or antibody fragments of the invention. Insect cells in combination with baculovirus vectors can also be used.

In one aspect, mammalian host cells are used to express and produce the antibodies and antibody fragments of the present invention. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987.

Expression vectors for mammalian host cells can include expression control sequences, such as an origin of replication, a promoter, and an enhancer (see, e.g., Queen et al., *Immunol. Rev.* 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Example 12: Cloning of Anti-Her2 Cys Mutant Antibodies for Conjugation Studies DNA oligonucleotides encoding variable regions of heavy and light chains of an anti-Her2 antibody (Carter P, Presta L, Gorman C M, Ridgway J B, Henner D, Wong W L, Rowland A M, Kotts C, Carver M E, Shepard H M. (1992) Proc. Natl. Acad. Sci. USA, 89, 4285-4289, Humanization of an anti-p185her2 antibody for human Cancer therapy) were chemically synthesized and cloned into two mammalian expression vectors, pOG-HC and pOG-LC that contain the constant regions of human IgG1 and human kappa light chain, resulting in two wild-type constructs, pOG-anti-Her2 antibody HC and pOG-anti-Her2 antibody LC, respectively. The amino acid sequences of the constant regions are shown in Table 2 with the mutated Cys in bold and underlined.

In these vectors, the expression of antibody heavy and light chain in mammalian cells is driven by a CMV promoter. The vectors encode a synthetic 24 amino acid signal sequence, MKTFILLLWVLLLWVIFLLPGATA (SEQ ID NO:5), at the N-terminal of heavy chain and light chain to guide their secretion from mammalian cells. The signal sequence has been validated to be efficient in directing protein secretion in hundreds of mammalian proteins in 293 Freestyle™ cells (Gonzalez R, Jennings L L, Knuth M, Orth A P, Klock H E, Ou W, Feuerhelm J, Hull M V, Koesema E, Wang Y, Zhang J, Wu C, Cho C Y, Su Al, Batalov S, Chen H, Johnson K, Laffitte B, Nguyen D G, Snyder E Y, Schultz P G, Harris J L, Lesley S A. (2010) Proc Natl Acad Sci USA. 107:3552-7). Oligonucleotide directed mutagenesis was employed to prepare mutant constructs of anti-Her2 antibodies listed in Table 2. The sense and anti-sense primers (Table 3) that correspond to mutation sites in the constant regions of human IgG heavy chain and human kappa light chain were chemically synthesized. PCR reactions were performed using PfuUltra II Fusion HS DNA Polymerase (Stratagene) with pOG-anti-Her2 antibody HC and pOG-anti-Her2 antibody LC as the templates. The PCR products were confirmed on agarose gels, and treated with DPN I followed by transformation in DH5a cells (Klock et al., (2009) *Methods Mol Biol.* 498:91-103).

The sequences of wild-type and the Cys mutant constructs were confirmed by DNA sequencing. The full-length amino acid sequence of wild-type anti-Her2 antibody heavy chain is shown as SEQ ID NO:1 and that of light chain is shown as SEQ ID NO:2 (Table 2). The amino acid sequence of the HC-E152C-S375C double mutant constructs of anti-Her2 antibody is shown in Table 2 with the Cys mutation site in bold and underlined (SEQ ID NO:6). Amino acid residues in human IgG1 heavy chain and human kappa light chain are numbered according to the Eu numbering system (Edelman et al, (1969) *Proc Natl Acad Sci USA,* 63:78-85). The anti-Her-HC-E152C-S375C antibodies were further cloned into vectors containing antibiotic selection markers for selection of stably transfected cell clones in media containing corresponding antibiotics.

TABLE 3

DNA sequences of mutation primers used to clone Cys mutant antibodies.

| | | | |
|---|---|---|---|
| HC-E152C | Sense | TTCCCTTGTCCCGTGACCG TGTCCTGGAACAGCGGAGC | SEQ ID NO: 7 |
| | Anti-sense | CACGGGACAAGGGAAGTAG TCCTTCACCAGGCAGCCCA | SEQ ID NO: 8 |
| HC-5375C | Sense | CTACCCCTGCGACATCGCC GTGGAGTGGGAGAGCAACG | SEQ ID NO: 9 |
| | Anti-sense | GATGTCGCAGGGGTAGAAG CCCTTCACCAGACAGGTCA | SEQ ID NO: 10 |

Example 13: Preparation of Antibodies

Antibodies were expressed in 293 Freestyle™ cells by co-transfecting heavy chain and light chain plasmids using transient transfection method as described previously (Meissner, et al., *Biotechnol Bioeng.* 75:197-203 (2001)). The DNA plasmids used in co-transfection were prepared using Qiagen plasmid preparation kit according to manufacturer's protocol. 293 Freestyle™ cells were cultured in suspension in Freestyle™ expression media (Invitrogen) at 37° C. under 5% $CO_2$. On the day before transfection, cells were split to $0.7\times10^6$ cells/mL into fresh media. On the day of transfection, the cell density typically reached $1.5\times10^6$ cells/mL. The cells were transfected with a mixture of heavy chain and light chain plasmids at the ratio of 1:1 using the PEI method (Meissner et al., 2001 supra). The transfected cells were further cultured for five days. The media from the culture was harvested by centrifugation of the culture at 2000×g for 20 min and filtered through 0.2 micrometer filters. The expressed antibodies were purified from the filtered media using Protein A-Sepharose™ (GE Healthcare Life Sciences). IgG antibodies were eluted from the Protein A-Sepharose™ column using a pH 3.0 elution buffer. Eluted IgG solutions were immediately neutralized with 1 M Tris-HCl (pH 8.0) followed by a buffer exchange to PBS.

Expression constructs for anti-Her2-HC-E152C-S375C antibodies were also transfected into CHO cells. Following standard protocols, cells stably expressing anti-Her-HC-E152C-S375C were then selected using antibiotics. All anti-Her2 antibody constructs expressed in the selected CHO cell clones were purified by Protein A-Sepharose chromatography as described above.

Example 14: Preparation of Antibody Drug Conjugates Using Engineered Cys Mutant Antibodies Numerous methods for conjugating linker-payloads to antigen binding moieties are known in the art (reviewed in for example: Antibody-Drug Conjugate, Methods in Molecular Biology, Vol. 1045, Editor L. Ducry, Humana Press (2013)). In this example, compounds described in the invention comprising a linker were conjugated to cysteine residues engineered into an antibody as described in Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925-932. As way of example, conjugation of the cytotoxic peptides of the invention is illustrated for only a small set of Cys antibody mutants but it is anticipated that the cytotoxic peptides can be conjugated to most if not all possible Cys antibody mutants.

Because engineered Cys in antibodies expressed in mammalian cells are modified by adducts (disulfides) such as glutathione (GSH) and/or cysteine during their biosynthesis (Chen et al. 2009), the modified Cys in the product as initially expressed is unreactive to thiol reactive reagents such as maleimido or bromo- or iodo-acetamide groups. To conjugate the engineered cysteine after expression, the glutathione or cysteine adducts need to be removed by reducing these disulfides, which generally entails reducing also the native disulfides in the expressed antibody. This can be accomplished by first exposing the antibody to a reducing agent such as dithiothreitol (DTT) followed by a procedure that allows for the re-oxidation of all native disulfide bonds of the antibody to restore and/or stabilize the functional antibody structure. Accordingly, in order to reduce all native disulfide bonds and the disulfide bound between the cysteine or GSH adducts of the engineered cysteine residue, freshly prepared DTT was added to Cys engineered antibodies to a final concentration of 10 mM. Anti-Her2-HC-E152C-S375C is used as an example of Cys engineered antibodies that can be used with the cytotoxic peptides of the invention. After incubation with DTT at 37° C. for 1 h, the mixtures were dialyzed at 4° C. against PBS for three days with daily buffer exchange to remove DTT and re-oxidize the native disulfide bonds. An alternative method is to remove the reducing reagents through a desalting column such as Sephadex G-25 after the protein is reduced. 1 mM oxidized ascorbate (dehydro-ascorbic acid) is added to the desalted samples and the re-oxidation incubations are carried out for 20 h. Both methods produce similar results. However, attempts to follow the re-oxidation protocols previously described in the literature using $CuSO_4$ resulted in protein precipitation (Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925). All examples herein use the dialysis protocol described above. Reoxidation restores intra-chain disulfides, while the dialysis removes cysteines and glutathiones initially connected to the engineered cysteine(s) of the antibody.

After re-oxidation, the antibody was conjugated with cytotoxic peptides comprising a linker and a reactive moiety. By way of example, cytotoxic peptides having a linked maleimide moiety (10 molar equivalents relative to the antibody) were added to re-oxidized anti-Her2 Cys engineered antibodies in PBS buffer (pH 7.2). The incubations were carried out for 1 h. Conjugation of payload compounds to antibodies was determined by MS as described herein.

Conjugation efficiency of various cytotoxic peptides having a linked maleimide to anti-Her2 Cys engineered antibodies varied depending on the solubility of the cytotoxic peptides used but most reactions resulted in more than 80% conjugate (Table 4). To evaluate the aggregation state, the resulting ADCs were analyzed by size exclusion chromatography (Agilent Bio SEC3, 300 Å, 7.8×150 mm) at a flow rate of 1 mL/min in PBS. The most ADC preparations contained more than 95% monomeric material. All ADC preparations contained less than 8% dimeric and oligomeric material (Table 4).

The conjugates were also characterized in terms of average loading of a cytotoxic peptide to the antibody binding moiety, generally referred to as drug to antibody ratio (DAR). The DAR value is extrapolated from LC-MS analysis. LC/MS allows quantitation of the average number of molecules of payload (drug) attached to an antibody in an ADC. For LC-MS analysis, ADCs are typically reduced and deglycosylated. LC separates heavy chain (HC) and light chain (LC) of the reduced antibody according to the number of linker-payload groups per chain. Mass spectral data enables identification of the component species in the mixture, e.g., LC, LC+1 drug, LC+2 drugs, HC, HC+1 drug, HC+2 drugs, etc. From the average loading on the LC and HC chains, the average DAR can be calculated for an ADC. The DAR for a given conjugate represents the average number of drug (payload) molecules attached to a typical antibody containing two light chains and two heavy chains. Antibody constructs containing four Cys mutations per antibody molecule were produced by introducing two Cys mutations at two sites in the heavy chain of anti-Her2, resulting in a DAR of 4. As way of example, anti-Her2-HC-E152C-S375C antibody was conjugated to compounds 1, 2 and 6. Selected properties of these double mutant ADCs are shown in Table 4.

The maleimide-activated linker-payloads of the invention can also be used in conjugation reactions with partially reduced non-engineered antibodies. In this case, attachment occurs at the native cysteines of an antibody.

While the immunoconjugates of Formula (B), Formula (II) or Formula (IIa) disclosed in Table 4 were obtained by conjugating anti-Her2 Cys mutant antibodies with certain cytotoxic cyclic peptides of Formula (A), Formula (I) or Formula (Ia) having a linked maleimide moiety, other linker-payload combinations of the invention may be made using methods know in the art, including conjugation to cysteine residues of non-engineered antibodies (Table 5).

All example ADCs were tested for in vitro cell killing potency as described in Examples 16 and 17.

TABLE 4

Properties of various anti-Her2-HC-E152C-S375C ADCs

| ADC[a] | Conjugation efficiency[b] (%) | Oligomer[c] (%) | DAR[d] |
|---|---|---|---|
| anti-Her2-HC-E152C-S375C-1 | 95 | 1 | 3.8 |
| anti-Her2-HC-E152C-S375C-2 | 95 | 1 | 3.8 |
| anti-Her2-HC-E152C-S375C-3 | 95 | 1 | 3.8 |

[a]Name consists of a description of the Cys engineered antibody and a description of the compound used in the chemical conjugation step.
[b]Conjugation efficiency was measured by MS and describes the percentage of antibody converted to ADC.
[c]Aggregation was measured by analytical size exclusion chromatography. Percent oligomer includes dimeric and oligomeric species.
[d]Drug-to-antibody ratio according to MS.

Example 15: Preparation of Antibody Drug Conjugates Using 1,3-Dichloropropan-2-One to Reconnect Native Disulfide Bonds of Non-Engineered Antibodies In an alternative method, inter- and intra-chain disulfides bonds of the antibody are first reduced and then chemically reconnected through a reaction with 1,3-dichloropropan-2-one. In the process, the four native interchain disulfide bonds in an antibody are replaced by a three carbon "ketone bridge". The ketone group can then specifically be conjugated with a cytotoxic drug in the second step, by reaction with a hydroxyl amine linked to the cytotoxic drug. The resulting ADC has up to four drugs attached specifically at the location of the four native, interchain disulfide bonds of the antibody.

In one example antiHer2 (SEQ ID NO:1) was conjugated to a compound (8) in two steps:

Step 1: Reduction of native disulfide bridges and re-bridging using 1,3-dichloropropan-2-one TCEP-HCl (41.4 μg, 0.144 μmol) was added to a solution of antiHer2 (SEQ ID NO:1) (1770 μg, 0.012 μmol, 147 μL in 0.25 M Tris pH 7.4) and 1,3-dichloropropan-2-one (193 μg, 1.443 μmol) at 4° C. The resulting mixture was kept at 4° C. for 4 h. The reaction mixture was then desalted using a Zeba spin column 7K MWCO (0.5 mL) with PBS (pH 7.4) as the eluting buffer for 4 times to give the modified antibody 20507: 144483 Da (after deglycosylation by PNGase F (New England Biolabs)). ESI (Eluent A: water+0.1% Formic acid, Eluent B: Acetonitrile+0.04% Formic acid. Gradient: from 3 to 80% B in 2 min—Flow 1.0 mL/min. Column: Proswift Monolith 4.6*50 mm 40° C.).

Step 2—Conjugation of the Cytotoxic Drug:

Into a solution of ketone modified Anti-Her2 (0.097 mL of 17.67 mg/mL solution in PBS buffer, 1.71 mg, 0.012 μmol) was added compound (8) (0.0077 mL of a 150 mg/mL solution in DMSO, 1.16 mg, 0.58 μmol) and then 3,5 diaminobenzoic acid (0.0026 mL of a 200 mg/mL solution in $H_2O$, 0.53 mg, 3.46 μmol) at room temperature, which was then agitated for 15 h. The resulting mixture was passed three times through a 0.5 mL Zeba™ spin column eluting with PBS pH7.2. Successful modification of ketones was confirmed by analysis with PNGase F (New England Biolab), Endoproteinase Lys-C(Roche) and non reducing/reducing SDS PAGE (4-12% Bis-Tris Gel with colloidal blue staining) performed with samples taken from the reaction solution.

Similarly conjugation of compound (9) and compound (10) was achieved. Some properties of the resulting ADCs are given in Table 5.

TABLE 5

Properties of various non-engineered anti-Her2 ADCs

| ADC[a] | DAR[d] | LCMS: MH+ |
|---|---|---|
| Anti-Her2-8 | 3.8 | 155940 |
| Anti-Her2-9 | 3.9 | 155996 |
| Anti-Her2-10 | 2.1 | 156220 |

[a]Name consists of a antibody and a description of the compound used in the chemical conjugation step.
[d]Drug-to-antibody ratio according to MS.

Example 16: Cell Proliferation Assays to Measure In Vitro Cell Killing Potency of ADCs Cells that naturally express target antigens or cell lines engineered to express target antigens are frequently used to assay the activity and potency of ADCs. For evaluation of the cell killing potency of anti-Her2 antibody ADCs in vitro, four endogenous cell lines, NCI-N87, SK-BR-3, JimT-1 and HCC1954 cells were employed (Clinchy B, Gazdar A, Rabinovsky R, Yefenof E, Gordon B, Vitetta E S. Breast Cancer Res Treat. (2000) 61:217-228). High levels of Her2 are endogenously expressed in HCC1954 (~$5\times10^5$ copies/cell), SKBR-3 ($5.4\times10^5$ copies/cell) and NCI-N87 ($2.7\times10^5$ copies/cell) cell lines while JimT-1 cells express human Her2 at a medium level (~$8\times10^4$ copies/cell). A375 cells express a low level of Her2 and were also used for evaluation of the cell killing potency of anti-Her2 antibody ADCs in vitro.

An ADC should kill cells in an antigen-dependent manner, meaning that only cells that express sufficient antigen in the cell surface but not cells lacking the antigen will be killed. To measure antigen-dependent cell killing, cell proliferation assays were conducted with Cell-Titer-Glo™ (Promega) five days after different cell types were incubated with various concentrations of ADCs (Riss et al., (2004) Assay Drug Dev. Technol. 2:51-62). In some studies, the cell based assays are high throughput and conducted on an automated system (Melnick et al., (2006) Proc Natl Acad Sci USA. 103:3153-3158).

Anti-Her2 amanitin ADCs prepared with compounds of Formula (A), Formula (I) or Formula (Ia) disclosed in the invention and conjugated site-specifically to anti-Her2 Cys engineered antibodies (see Table 4) were assayed in the aforementioned four cell lines to evaluate their cytotoxicity (see Table 6). The ADCs specifically killed HCC1954, JimT-1, NCI-87, and SK-BR-3, the four cell lines with high levels of Her2 expression, but not A375 cells that express a low level of Her2 (Table 6).

TABLE 6

| ADC potency in in vitro cell killing assay: $IC_{50}$ of anti-Her2 ADCs in HCC1954, JimT-1, NCI-87, SK-BR-3 and A375 cell proliferation assays. | | | | | |
|---|---|---|---|---|---|
| | $IC_{50}$ (nM)[b] | | | | |
| ADC name[a] | HCC1954 | JimT-1 | NCI-N87 | SK-BR-3 | A375 |
| anti-Her2-HC-E1520-S3750-1 | 4.4E−02 | 4.2E−02 | 3.5E−02 | 3.9E−02 | 67 |
| anti-Her2-HC-E152C-S3750-2 | 1.4E−02 | 1.3E−02 | 1.0E−02 | 1.2E−02 | 67 |
| anti-Her2-HC-E152C-S3750-6 | 1.2E−01 | 1.2E−01 | 1.1E−01 | 8.7E−02 | 67 |

[a]Name consists of a description of the mutated antibody and a description of the compound(s) used in the chemical conjugation step.
[b]The highest concentration used in the assay was 67 nM. $IC_{50}$ values of 67 nM indicate inactivity of the ADC in the assay.

Example 17: Cellular Activity of Anti-Her2 Amanitin ADCs in an In Vitro Cytotoxicity Assay The cellular activity of a series of anti-Her2 amanitin ADCs in a panel of cancer cell lines was evaluated. This panel comprised four cancer cell lines featuring endogenous expression of HER2 (MDA-MB-453, KPL4, JimT-1 and NCI-N87), the HER2-negative cell line MDA-MB-231, as well as an engineered clone of MDA-MB-231 featuring exogenous over-expression of HER2, here forth called MDA-MB-231-HER2(+). Six anti-Her2 amanitin ADCs were generated as described in Examples 14 and 15: anti-Her2-HC-E152C-S375C-1, anti-Her2-HC-E152C-S375C-2, anti-Her2-HC-E152C-S375C-6, anti-Her2-8, anti-Her2-9 and anti-Her2-10.

The cell lines were acquired and cultured as follows: MDA-MB-453 (ATCC; RPMI-1640 (Lonza 12-702F)+10% FBS), KPL4 (Kawasaki Medical School, Kurashiki, Japan), JIMT1 (DSMZ (Deutsche Sammlung von Mikroorganismen und Zellkulturen; DMEM (Lonza 12-604)+10% FBS)); NCI-N87 (ATCC; RPMI-1640 (Lonza 12-702F)+10% FBS) and MDA-MB-231 (ATCC; RPMI-1640 (Lonza 12-702F)+10% FBS). All cell culture was performed at 37° C. in a humidified incubator. To generate the MDA-MB-231-HER2 (+) cell line featuring exogenous Her2-overexpression, MDA-MB-231 breast cancer cells were stably transduced with a lentiviral construct (pLenti 6.3 (Invitrogen); driven by a cytomegalovirus enhancer-promoter) encoding a mutant form of the Her2 antigen (NM_004448; codon K753M), lacking kinase activity and therefore non-oncogenic but still recognized by the anti-Her2 antibody. A Her2-overexpressing line, MDA-MB-231-HER2(+), was isolated by fluorescence-activated cell sorting and selection with blasticidin. MDA-MB-231-HER2(+) and parental MDA-MB-231-HER2(−) cultures were maintained by passage in RPMI-1640 growth medium, supplemented with 10% (v/v) fetal bovine serum.

In vitro cytotoxicity assay: Cells in culture were trypsinized, counted and diluted in medium to a concentration of $1\times10^5$ cells/ml. 1000 cells/well were transferred to 384-well plates (Corning Costar #3707, Corning, Tewksbury, Mass.). ADC stock solutions were prepared in 1.4 ml Matrix tubes (Thermo, #3790, Rockford, Ill.). A 20-point, 1:3 serial dilution was prepared in a 384-well deep-well plate (Brandtech Scientific Inc #701355, Essex, CT) and 25 μl were transferred per assay plate (triplicates) to yield a highest starting concentration of the ADC of 33 nM. For controls, wells with cells only (=100% viability control) were prepared. Plates were incubated for 120 h at 37° C. and 5% $CO_2$. Cellular activity of the ADCs was determined using CellTiter-Glo® reagent (Promega # G7571, Madison, Wis.) according to the manufacturer's instructions. Viability was normalized to the cells-only control, the data were plotted using Tibco Spotfire (Tibco Software Inc, Palo Alto, Calif.) and inflection point ($IC_{50}$) and Amax were derived from exporting the curve fit parameters of a logistical regression fit of the data.

Treatment of the cells with the anti-Her2 amanitin ADCs resulted in target-dependent cellular cytotoxicity (Table 7) as evidenced by activity at sub-nanomolar concentrations in HER2-positive cell lines, but not in the HER2-negative wild-type MDA-MB-231 cell line.

TABLE 7

| Anti-Her2 amanitin DAR 4 ADC potency in in vitro cell killing assay | | | | | | |
|---|---|---|---|---|---|---|
| ADC Name[a] | MDA-MB-231 HER2 (+) | MDA-MB-231 HER2 (−) | MDA-MB-453 | JimT-1 | KPL4 | NCI-N87 |
| | Inflection point: $IC_{50}$ (nM) | | | | | |
| anti-Her2-HC-E152C-S375C-1 | 1.63E−04 | >33 | 7.44E−06 | 6.03E−04 | 4.02E−06 | 1.79E−05 |
| anti-Her2-HC-E152C-S375C-2 | 1.36E−04 | >33 | 1.83E−05 | 1.40E−03 | 1.33E−05 | 3.82E−05 |
| anti-Her2-HC-E152C-S375C-6 | 1.79E−04 | >33 | 5.58E−05 | 1.61E−03 | 3.64E−05 | 4.43E−05 |
| anti-Her2-8 | N.D. | N.D. | <6.81E−06 | >1.34E−01 | N.D. | <6.81E−06 |
| anti-Her2-9 | N.D. | N.D. | <6.55E−06 | >1.29E−01 | N.D. | <6.55E−06 |
| anti-Her2-10 | N.D. | N.D. | <6.81E−06 | >1.34E−01 | N.D. | <6.81E−06 |
| | Amax % inhibition | | | | | |
| anti-Her2-HC-E152C-S375C-1 | 94 | 21 | 89 | 75 | 86 | 94 |
| anti-Her2-HC-E152C-S375C-2 | 91 | 17 | 87 | 74 | 83 | 94 |
| anti-Her2-HC-E152C-S375C-6 | 93 | 16 | 85 | 70 | 86 | 93 |
| anti-Her2-8 | N.D. | N.D. | 98 | 7 | N.D. | 89 |
| anti-Her2-9 | N.D. | N.D. | 98 | 8 | N.D. | 87 |
| anti-Her2-10 | N.D. | N.D. | 97 | 7 | N.D. | 82 |

[a]Name consists of a description of the mutated antibody and a description of the compound(s) used in the chemical conjugation step.
N.D.: Not Determined In addition to the evaluation of the cellular activity of a series of anti-Her2 amanitin ADCs in a panel of cancer cell lines, the cellular activity of anti-Her2 amanitin ADCs was also evaluated in an in vitro colony formation assay using the MDA-MB-231-HER2(+) and NCI-N87 cells lines. Specifically, cells from both cell lines were either untreated or were treated with a dilution series of anti-Her2-HC-E152C-S375C-1, anti-Her2-HC-E152C-S375C-2 or anti-Her2-HC-E152C-S375C-6. Maximal activity for the anti-Her2 amanitin ADCs across the dilution points in the MDA-MB-231-HER2(+) cell line and a concentration-dependent inhibition of colony formation in NCI-N87 were observed.

In vitro colony formation assay: Cells in culture were trypsinized, counted and plated into 12-well plates (Corning, # CLS3513, Corning, Tewksbury, Mass.) at 5000 cells per well. Following incubation of cells overnight, the ADCs were diluted into cell culture media to yield 10× concentration stocks for final concentrations of 1 nM, 0.01 nM, $1\times10^{-4}$ nM and $1\times10^{-6}$ nM. 100 μl of the dilutions were added to each well followed by addition of 900 μl cell culture media. Following incubation of the plates for 8 days, cells were fixed and stained for 30 minutes at room temperature using a solution of crystal violet/formaldehyde (0.4% crystal violet dissolved in milliQwater and 25% methanol, formaldehyde added once completely resuspended-to yield final concentration of 4%; all Sigma, St Louis, Mo.). Plates were then washed twice using tap water, drained and scanned on a LiCor Odyssey imaging system (LiCor, Lincoln, Nebr.) using scan intensity 1 in the 700 nm channel at 169 μm resolution, lowest quality and 3.0 mm focus offset. The images were exported using LiCor ImageStudio software.

Example 18: Cellular Activity of Anti-Her2 Amanitin ADCs in an In Vitro Pharmaco-Dynamic Assay Measuring Inhibition of RNA Transcription Alpha-amanitin is a potent and specific inhibitor of RNA polymerase II (Science. 1970 Oct. 23; 170(3956):447-9) and treatment of cells with alpha-amanitin results in inhibition of RNA polymerase II-dependent transcription. To evaluate the activity of anti-Her2 amanitin ADCs to inhibit RNA polymerase II, a microscopy-based in vitro assay was developed to measure nascent RNA transcripts following amanitin ADC treatment. Specifically, MDA-MB-231-HER2(+) cells were treated with a dilution series of anti-Her2-HC-E152C-S375C-1, anti-Her2-HC-E152C-S375C-2 or anti-Her2-HC-E152C-S375C-6 ADCs.

In vitro pharmacodynamics assay to measure inhibition of nascent RNA transcription: Cells in culture were trypsinized, counted and plated into a 96-well cell bind plate (Corning #354640 (Biocoat Plates), Corning, Tewksbury, Mass.) at 40,000 cells per well.

ADC stock solutions were prepared as 1 Ox stocks in 1.4 ml Matrix tubes (Thermo, #3790, Rockford, Ill.) and serially diluted 1:10 across 6 concentration points. Cells were treated with the ADCs and incubated for 24 h at 37 degrees Celsius. Following this incubation cells were stained using the Click-iT® RNA Alexa Fluor® 488 HCS Assay (Molecular Probes # C10327, Lot #1698441; Thermo Scientific, Rockford, Ill.; PNAS (2008) 105:15779-84) according to the manufacturer's instructions. Briefly, following 24 h treatment of cells with the ADCs, cells were incubated for 2 hours with 5-ethynyl uridine (EU) at 1 mM final concentration. Following this step all incubations were done protected from light. After EU incubation cells were fixed, permeabilized and incubated with the Click-IT reaction cocktail for 30 minutes at room temperature. Cells were then washed and stained using HCS Nuclear Mask Blue reagent for 15 minutes at room temperature, washed twice in PBS and kept in PBS onward. The plates were scanned on an InCell2000 imager (GE Healtcare Life Sciences, Marlborough, Mass.). Nine images per well were acquired using 1 Ox magnification and data were analyzed using the InCell Developer Toolbox software. The number of positive objects was determined using object based segmentation in the DAPI channel to count all nuclei. The FITC channel was used to quantify both number of objects and intensity corresponding to the RNA signal in treated versus non-treated cells. The mean object RNA intensity data were plotted using Tibco Spotfire (Tibco Software Inc, Palo Alto, Calif.) and $IC_{50}$ and maximal inhibition were derived from exporting the curve fit parameters of a logistical regression fit of the data.

Consistent with the cellular activity as read out by the in vitro cytotoxicity and colony formation assays, a concentration-dependent inhibition of nascent RNA transcript production following ADC treatment was observed. The $IC_{50}$ and max % RNA inhibition obtained are given in Table 8.

TABLE 8

Anti-Her2 amanitin ADC cellular activity summary: RNA transcription assay

| ADC Name[a] | $IC_{50}$ (nM) | max % RNA inhibition relative to untreated |
|---|---|---|
| anti-Her2-HC-E152C-S375C-1 | 0.0094 | 82 |
| anti-Her2-HC-E152C-S375C-2 | 0.0077 | 80 |
| anti-Her2-HC-E152C-S375C-6 | 0.029 | 78 |
| Untreated | — | — |

[a]Name consists of a description of the mutated antibody and a description of the compound(s) used in the chemical conjugation step.

Example 19: In Vivo Efficacy of Anti-Her2-Cys-mAb-Amanitin ADCs Against the N87 HER2-Positive Gastric Model in Nude Mice Xenograft models of human cancer have played an important role in the screening and evaluation of new antibody drug candidates (ADCs) in an in vivo setting. The NCI-N87 gastric model expresses approximately 250,000 Her2 receptors on the surface of each cell. Given the high expression of the Her2 receptor in this model, this is an effective setting to assess in vivo efficacy of anti-Her2 antibodies in both in vitro and in vivo assays. Therefore, the N87 xenograft model was used to assess the in vivo efficacy of anti-Her2-Cys-mAb-Amanitin ADCs of varying linker length, specifically anti-Her2-HC-E152C-S375C-1, anti-Her2-HC-E152C-S375C-2 and anti-Her2-HC-E152C-S375C-6.

Materials and Methods

For N87 gastric carcinoma xenograft mouse model, female nu/nu mice at 6-8 weeks of age (purchased from Charles River Laboratories) were used for implantation. N87 cells (obtained from ATCC, Catalog # CRL-5822) were grown in sterile conditions in a 37° C. incubator with 5% $CO_2$ for two weeks. Cells were grown in RPMI medium with 10% fetal bovine serum. Cells were passaged every 3-4 days with 0.05% Trypsin/EDTA. On the day of implantation, N87 cells were lifted (passage ×4) and re-suspended in RPMI1640 serum-free media at a concentration of $1\times10^6$ cells and 50% matrigel/100 μl.

N87 cells were implanted with a subcutaneous injection into the lower flank using a 28 gauge needle (100 μl injection volume). After implant, tumors were measured by caliper and mice weighed two times per week once tumors were palpable. Tumors then were measured twice a week in two dimensions. Caliper measurements were calculated using $(L\times W^2)/2$. Mice were fed with normal diet and housed in SPF animal facility in accordance with the Guide for Care and Use of Laboratory Animals and regulations of the Institutional Animal Care and Use Committee.

When xenograft tumors reached about 221 $mm^3$, mice were administered by intravenous route 2.5-10 mg/kg of ADC (anti-Her2-HC-E152C-S375C-2). Tumors were measured twice a week. Average tumor volumes were plotted using Prism 5 (GraphPad) software and stastical analysis was performed using SigmaPlot 12.0. An endpoint for efficacy studies was achieved when tumor size reached a volume of approximately 1500 $mm^3$. Following injection, mice were also closely monitored for signs of clinical deterioration. If for any reason mice showed any signs of morbidity, including respiratory distress, hunched posture, decreased activity, hind leg paralysis, tachypnea as a sign for pleural effusions, weight loss approaching 20% or 15% plus other signs, or if their ability to carry on normal activities (feeding, mobility), was impaired, mice were euthanized.

Figure 1:
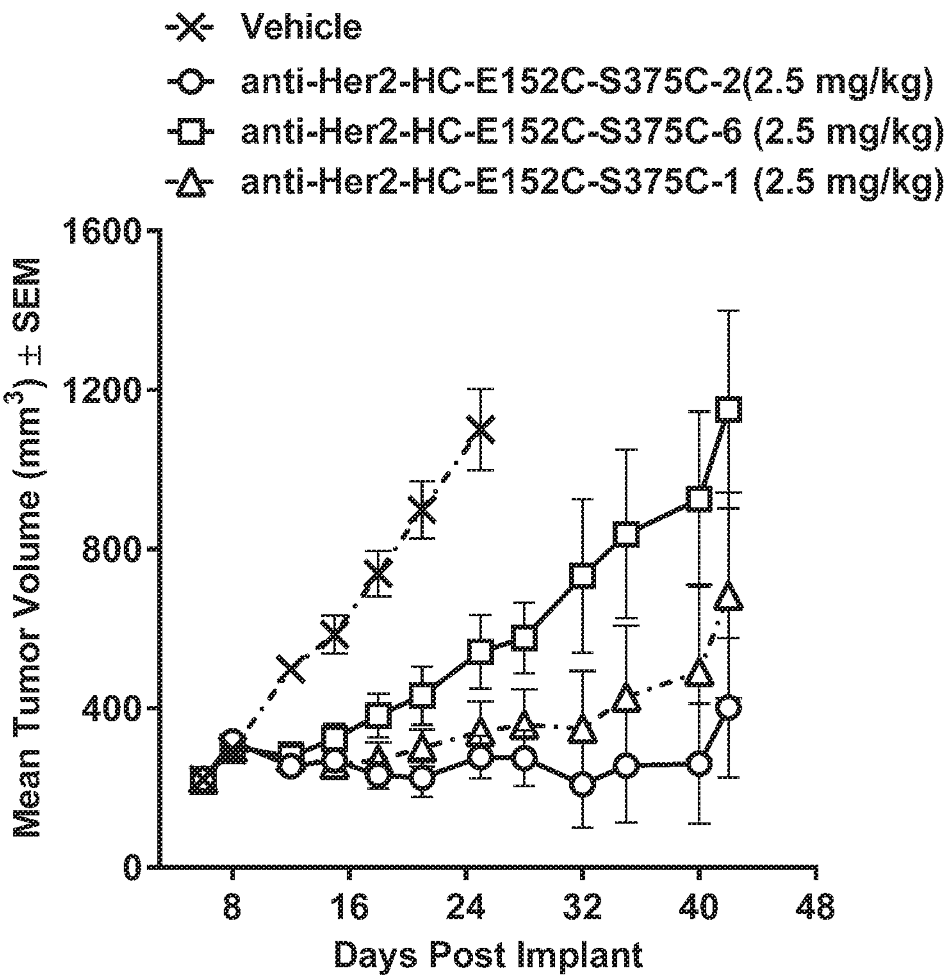
FIG. 1. Efficacy of anti-Her2-HC-E152C-S375C-1, anti-Her2-HC-E152C-S375C-2 and anti-Her2-HC-E152C-S375C-6 in the NCI-N87 gastric model.

Female nude mice were implanted subcutaneously with $5\times10^6$ N87 cells in a suspension containing 50% Matrigel™ (BD Biosciences) in Hank's balanced salt solution. The total injection volume containing cells in suspension was 200 μl/mouse. When tumors averaged ~221 $mm^3$ (6 days post implant) mice were randomized according to tumor volume (n=6/group) and were administered a single IV dose on Day 0 (day of randomization) of the following: PBS (phosphate buffered saline), anti-Her2-HC-E152C-S375C-1 (2.5 mg/kg), anti-Her2-HC-E152C-S375C-2 (2.5 mg/kg) or anti-HerR2-HC-E152C-S375C-6 (2.5 mg/kg). Doses were adjusted based on individual mouse body weight using a dose volume of 10 mL/kg. Tumor volumes and body weights were collected at least twice weekly. FIG. 1 shows the tumor volumes versus days post implant. The mean tumor volumes in the anti-Her2-HC-E152C-S375C-1, anti-Her2-HC-E152C-S375C-2 and the anti-Her2-HC-E152C-S375C-6 treated groups were significantly different from the vehicle on Day 25 as determined by One-Way ANOVA and Tukey method, $p<0.05$. % ΔT/ΔC at Day 25 for the anti-Her2-HC-E152C-S375C-1, anti-Her2-HC-E152C-S375C-2 and the anti-Her2-HC-E152C-S375C-6 treated groups were as follows: 13.8%, 6.4% and 36.5%, respectively. No tumor regression was observed in any group. All treatments were well tolerated and no significant body weight loss was observed in any group.

Example 20: Dose-Dependent In Vivo Efficacy of Anti-Her2-Cys-mAb-Amanitin ADCs Against the N87 HER2-Positive Gastric Model in Nude Mice Xenograft models of human cancer have played an important role in the screening and evaluation of new antibody drug candidates (ADCs) in an in vivo setting. The NCI-N87 gastric model expresses approximately 250,000 Her2 receptors on the surface of each cell. Given the high expression of the Her2 receptor in this model, this is an ideal setting to assess in vivo efficacy efficacy of anti-Her2 antibodies in both in vitro and in vivo assays. Therefore, the N87 xenograft model was use to assess the in vivo efficacy of anti-Her2-HC-E152C-S375C-2 in a dose-dependent manner.

Materials and Methods

For N87 gastric carcinoma xenograft mouse model, female nu/nu mice at 6-8 weeks of age (purchased from Charles River Laboratories) were used for implantation. N87 cells (obtained from ATCC, Catalog # CRL-5822) were grown in sterile conditions in a 37° C. incubator with 5% $CO_2$ for two weeks. Cells were grown in RPMI medium with 10% fetal bovine serum. Cells were passaged every 3-4 days with 0.05% Trypsin/EDTA. On the day of implantation, N87 cells were lifted (passage×4) and re-suspended in RPMI1640 serum-free media at a concentration of $1\times10^6$ cells and 50% matrigel/100 μl.

N87 cells were implanted with a subcutaneous injection into the lower flank using a 28 gauge needle (100 μl injection volume). After implant, tumors were measured by caliper and mice weighed two times per week once tumors were palpable. Tumors then were measured twice a week in two dimensions. Caliper measurements were calculated using $(L\times W^2)/2$. Mice were fed with normal diet and housed in SPF animal facility in accordance with the Guide for Care and Use of Laboratory Animals and regulations of the Institutional Animal Care and Use Committee.

When xenograft tumors reached about 215 $mm^3$, mice were administered by intravenous route 2.5-10 mg/kg of ADC (anti-Her2-HC-E152C-S375C-2). Tumors were measured twice a week. Average tumor volumes were plotted using Prism 5 (GraphPad) software and stastical analysis was performed using SigmaPlot 12.0. An endpoint for efficacy studies was achieved when tumor size reached a volume approximately 1500 $mm^3$. Following injection, mice were also closely monitored for signs of clinical deterioration. If for any reason mice showed any signs of morbidity, including respiratory distress, hunched posture, decreased activity, hind leg paralysis, tachypnea as a sign for pleural effusions, weight loss approaching 20% or 15% plus other signs, or if their ability to carry on normal activities (feeding, mobility), was impaired, mice were euthanized.

Results

Female nude mice were implanted subcutaneously with $4.5\times10^6$ N87 cells in a suspension containing 50% Matrigel™ (BD Biosciences) in Hank's balanced salt solution. The total injection volume containing cells in suspension was 100 μl/mouse. When tumors averaged ~215 $mm^3$, (5 days post implant) mice were randomized according to tumor volume into treatment groups (n=7/group) and administered with a single IV dose Day 1 (one day after randomization) of the following: PBS (phosphate buffered saline), anti-Her2-HC-E152C-S375C-2 (1.25, 3.13 or 6.25 mg/kg), or two doses of anti-Her2-HC-E152C-S375C-2 at 3.13 mg/kg administered on Day 1 and Day 12 post randomization. Doses were adjusted to individual mouse body weight using an IV dose volume of 10 mL/kg. Tumor volumes and body weights were collected at least twice weekly. FIG. 2 shows the tumor volumes versus days post implant.

The mean tumor volumes of all anti-Her2-HC-E152C-S375C-2 treated groups were significantly different from the vehicle control group on Day 25 as determined by One-Way ANOVA and Tukey method, $p<0.05$. A dose response effect was observed in the TBS-cys-mAb-2 treated groups when assessing % ΔT/ΔC at Day 25, with −2.8% (1.25 mg/kg), −4.2% (3.13 mg/kg), −19.9% (6.25 mg/kg), respectively. The multi-dose group of anti-Her2-HC-E152C-S375C-2 at 3.13 mg/kg did not lead to increased activity above that of a single dose of anti-Her2-HC-E152C-S375C-2 at 6.25 mg/kg, with −19.9% and −19.5%, respectively. Tumor regression was observed in each of the anti-Her2-HC-E152C-S375C-2 treated groups, including the multi-dose group, with tumor regressions as follows: −3.6% (1.25 mg/kg), −15.5% (3.13 mg/kg), −64.4% (6.25 mg/kg) and −69.6% (multi-dose), respectively. All treatments were well tolerated and no significant body weight loss was observed in any group.

We claim:

1. An immunoconjugate of Formula (B):

Formula (B)

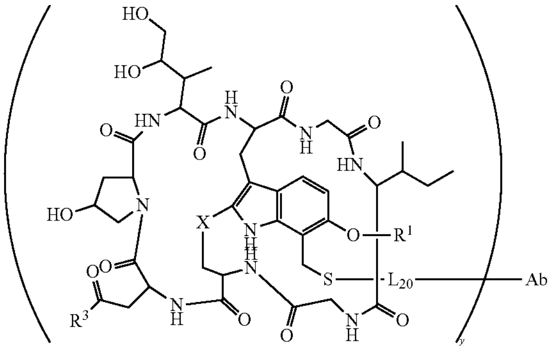

wherein:

X is S(═O), $S(═O)_2$ or S;

Ab is an anti-Her2 Ab;

y is an integer from 1 to 16;

$R^1$ is H, —$CH_3$ or —$CD_3$;

$R^3$ is —$NH_2$ or —OH;

$L_{20}$ is -$L_1R^{40}$;

$L_1$ is —$((CH_2)_mO)_n(CH_2)_mX_3L_4$- or —$((CH_2)_mO)_n(CH_2)_mX_4L_4$-;

$L_4$ is —$(CH_2)_m$— or —$(CH_2)_m$NHC(═O)$X_1X_2$C(═O)$(CH_2)_m$—;

$X_1$ is

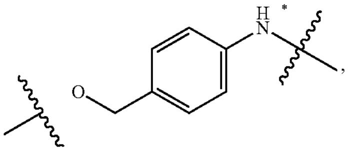

-continued

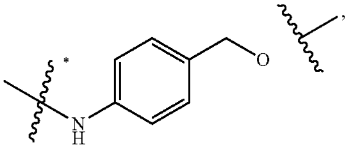

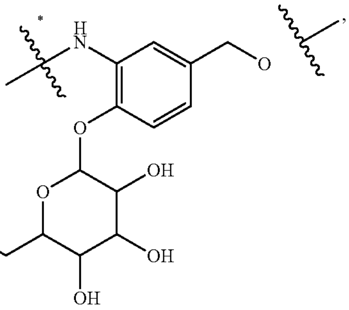

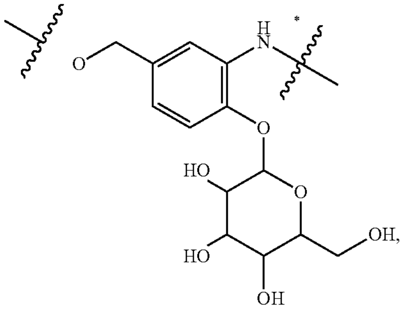

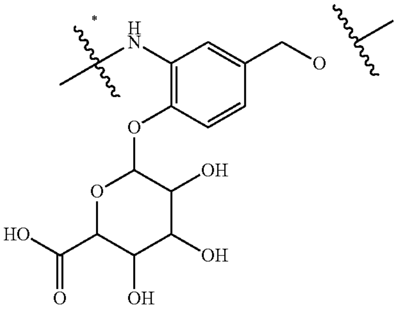

or

-continued
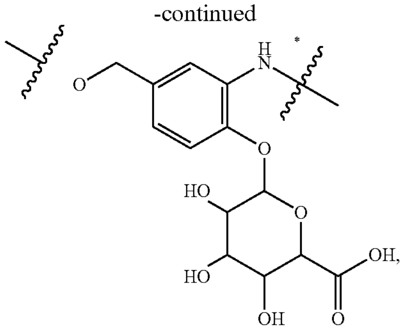
where the * indicated attachment point to $X_2$;
$X_2$ is
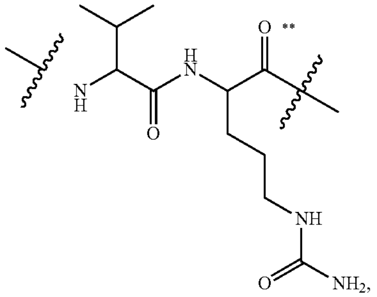
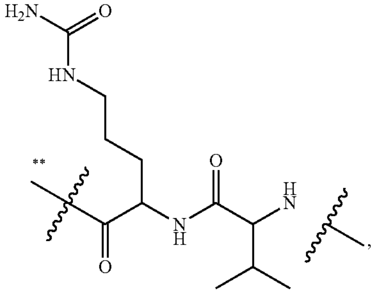
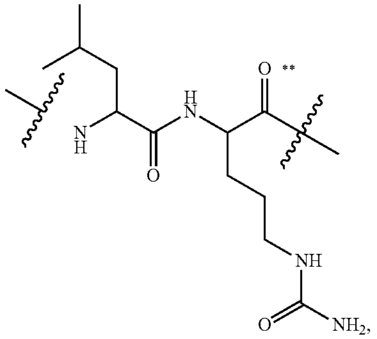
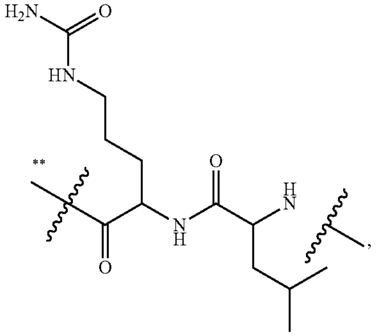
-continued
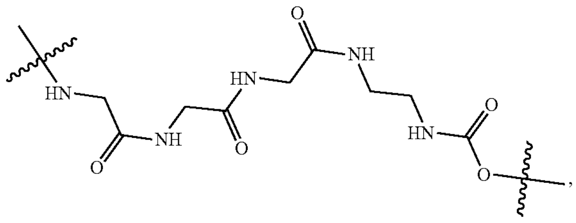
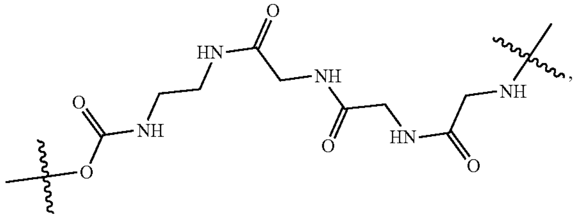
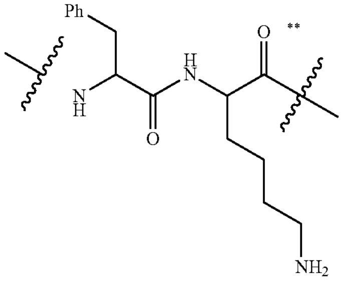
or
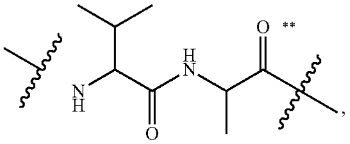
where the ** indicates attachment point to $X_1$;
$X_3$ is
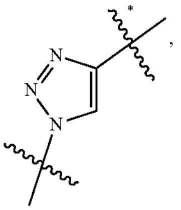
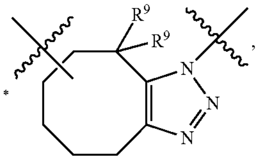
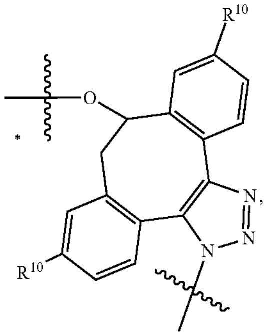

-continued
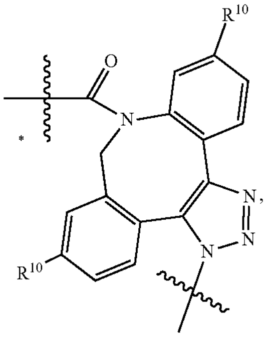
or
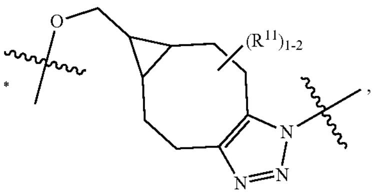
where the * indicates attachment point to $L_4$;
$X_4$ is
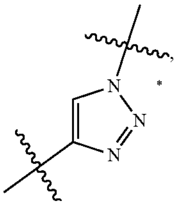
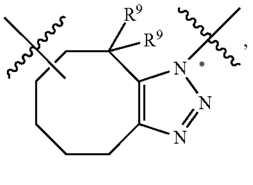
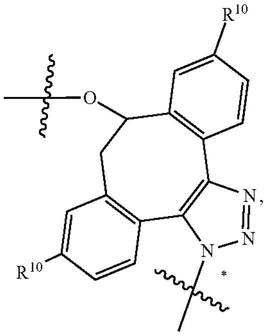
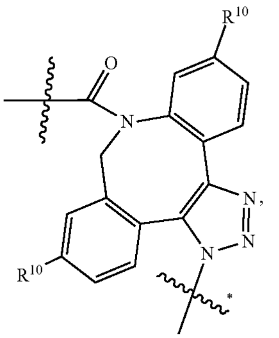
or
-continued
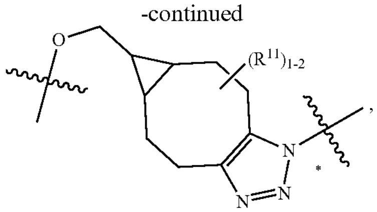
where the * indicates attachment point to $L_4$;
$R^{40}$ is
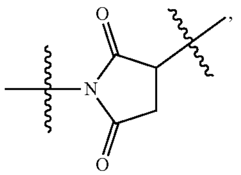
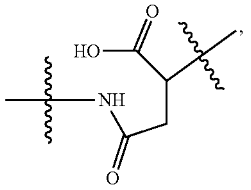
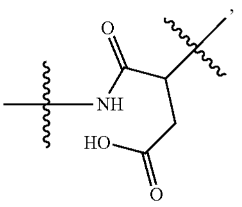
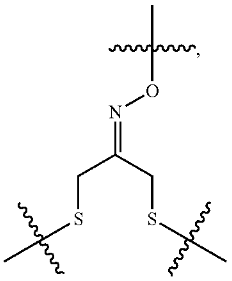
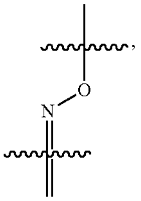
$-NR^5C(=O)CH_2-$, $-NHC(=O)CH_2-$, $-S(=O)_2CH_2CH_2-$, $-(CH_2)_2S(=O)_2CH_2CH_2-$, $-NR^5S(=O)_2CH_2CH_2$, $-NR^5C(=O)CH_2CH_2-$, $-NH-$, $-C(=O)-$, $-NHC(=O)-$, $-CH_2NHCH_2CH_2-$, $-NHCH_2CH_2-$, $-S-$,
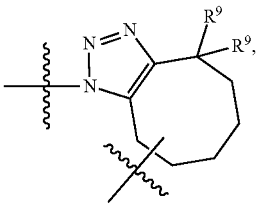
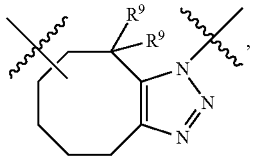
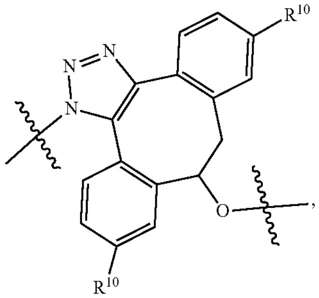

-continued

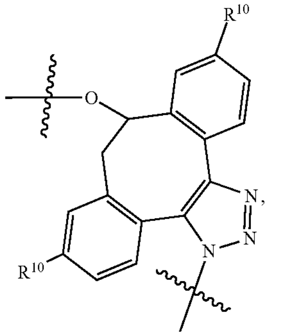

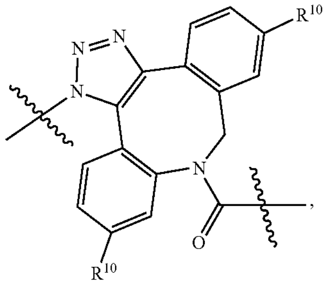

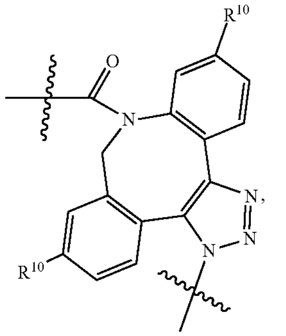

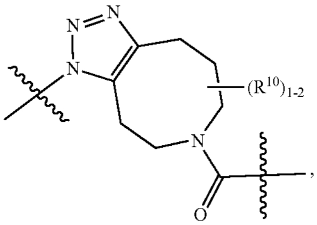

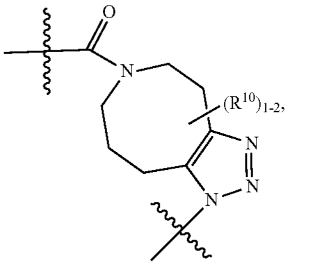

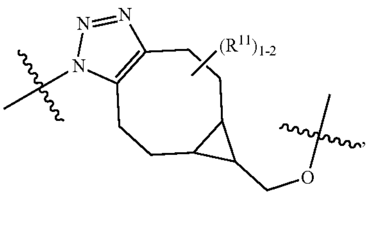

-continued

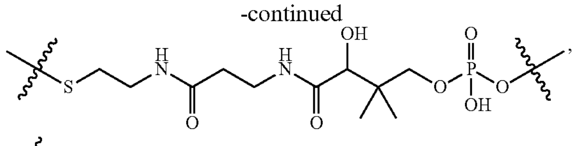

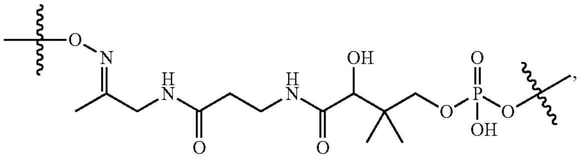

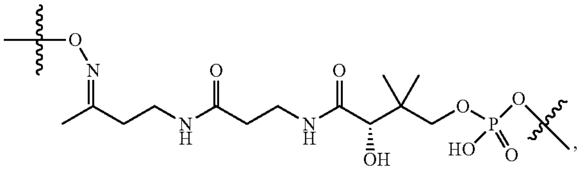

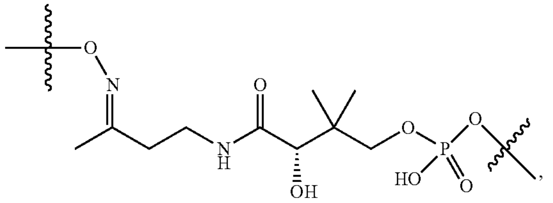

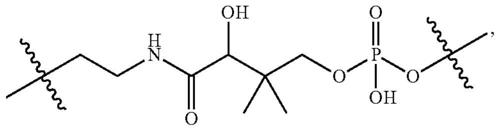

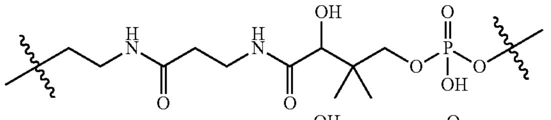

or

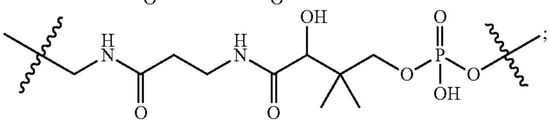

each $R^5$ is independently selected from H and $C_1$-$C_6$alkyl;

each $R^9$ is independently selected from H, $C_1$-$C_6$alkyl, F, Cl, and —OH;

each $R^{10}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{11}$ is independently selected from H, $C_{1-6}$alkyl, fluoro, benzyloxy substituted with —C(═O)OH, benzyl substituted with —C(═O)OH, $C_{1-4}$alkoxy substituted with —C(═O)OH and $C_{1-4}$alkyl substituted with —C(═O)OH;

each m is independently selected from 1, 2, 3, 4, 5, 6, 7, 8, 9 and 10, and each n is independently selected from 1,2, 3, 4, 5, 6, 7, 8, 9, 10, 11, 12, 13 and 14.

2. The immunoconjugate of claim 1, wherein the anti-Her2 Ab comprises a heavy chain comprising the amino acid sequence selected from SEQ ID NO:1 or SEQ ID NO:6.

3. The immunoconjugate of claim 2, wherein the anti-Her2 Ab comprises a light chain comprising the amino acid of SEQ ID NO:2.

4. The immunoconjugate of claim 3, wherein:

y is an integer from 1 to 16;

$R^1$ is H, —$CH_3$ or —$CD_3$;

$R^3$ is —$NH_2$ or —OH;

$L_{20}$ is -$L_1R^{40}$;

$L_1$ is $-((CH_2)_mO)_n(CH_2)_mX_3L_4$-;

$L_2$ is $-((CH_2)_mO)_n(CH_2)_m-$;

$L_3$ is $-((CH_2)_mO)_n(CH_2)_mX_3L_4$- or $-((CH_2)_mO)_n(CH_2)_m-$;

$L_4$ is $-(CH_2)_m-$ or $-((CH_2)_mNHC(=O)X_1X_2C(=O)(CH_2)_m-$;

$X_1$ is

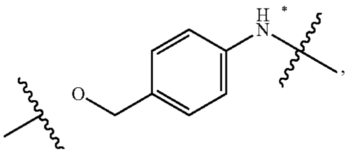

where the * indicates attachment point to $X_2$;

$X_2$ is

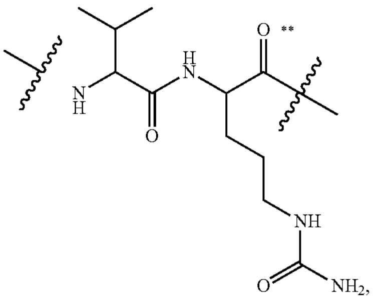

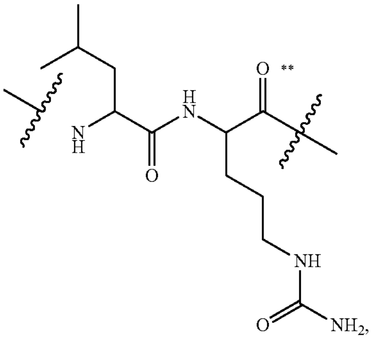

or

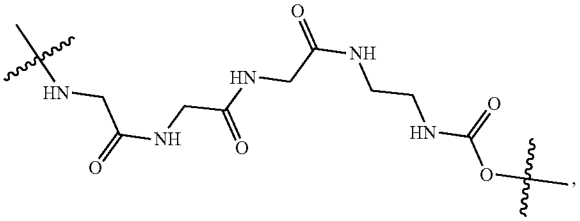

where the ** indicates attachment point to $X_1$;

$X_3$ is

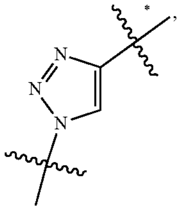 [SMILES: *c1cn(*)nn1]

where the * indicates attachment point to $L_4$;

$R^{40}$ is

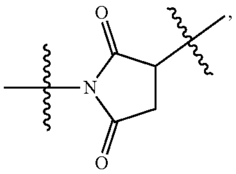

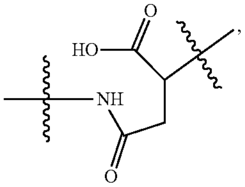

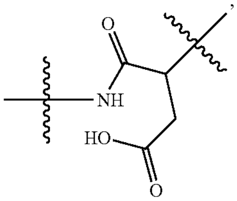

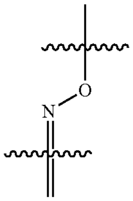

or

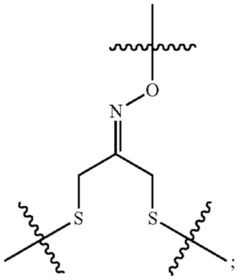

each m is independently selected from 1, 2, 3, 4, 5, 6, 7, 8, 9 and 10, and each n is independently selected from 1, 2, 3, 4, 5, 6, 7, 8, 9, 10, 11, 12, 13 and 14.

5. The immunoconjugate of claim 4, wherein:

wherein $L_{20}$ is

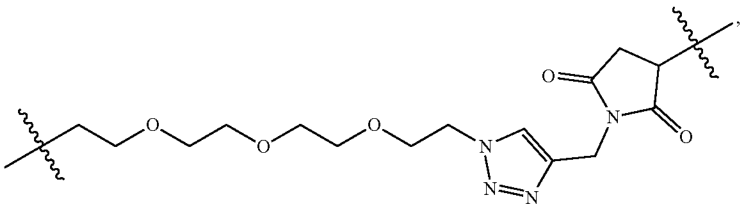

-continued
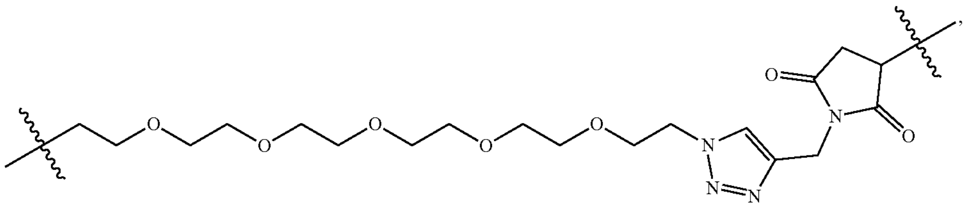
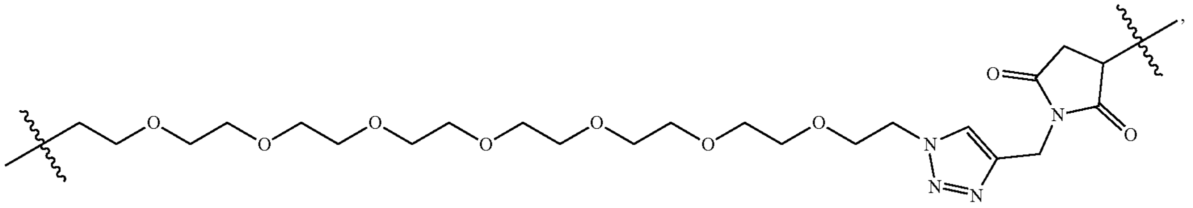
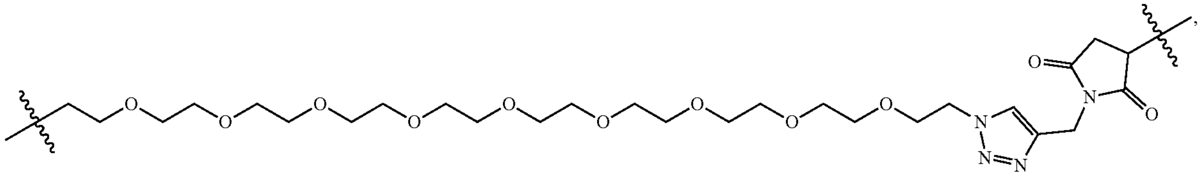
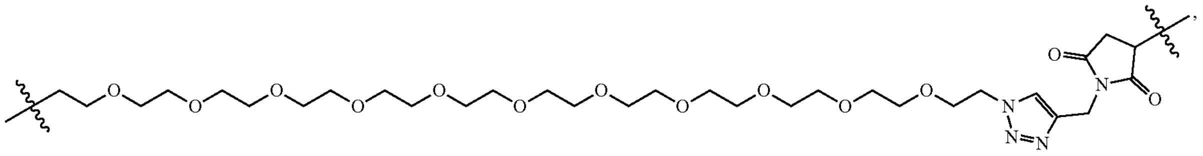
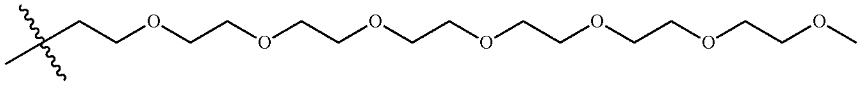
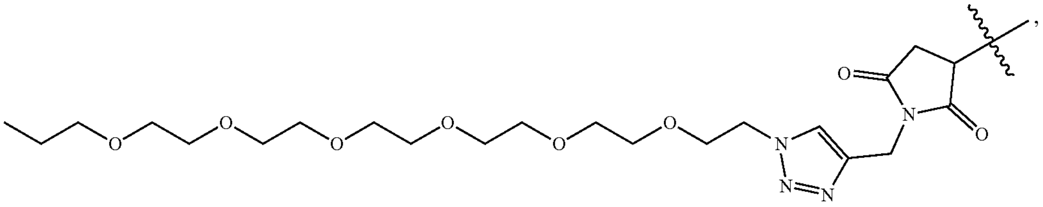
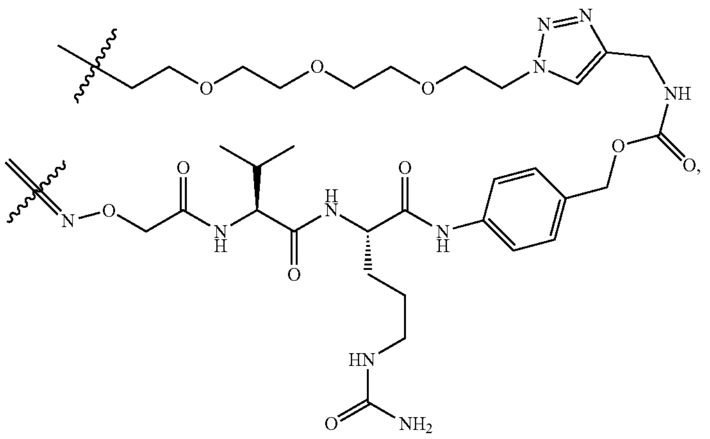

-continued
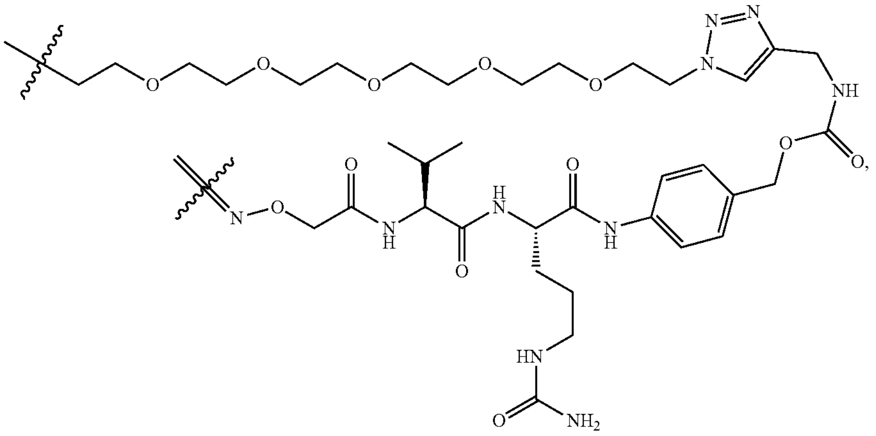
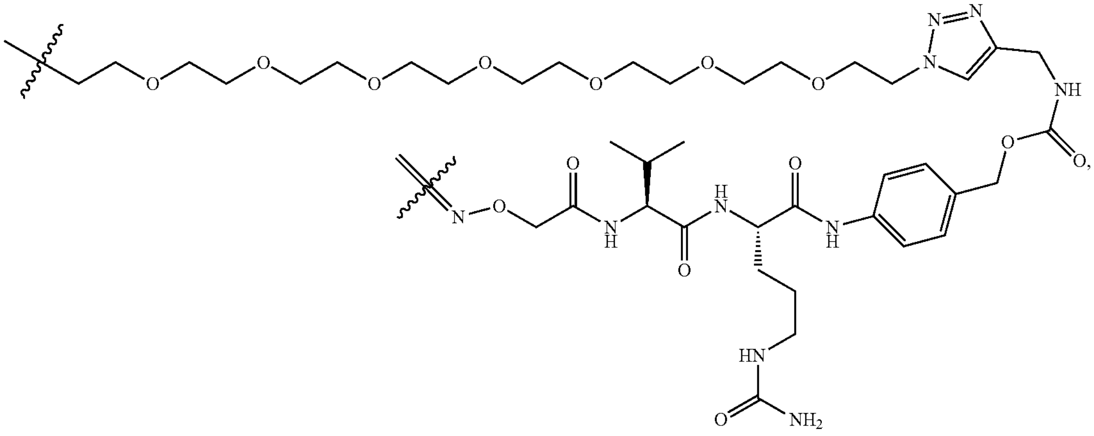
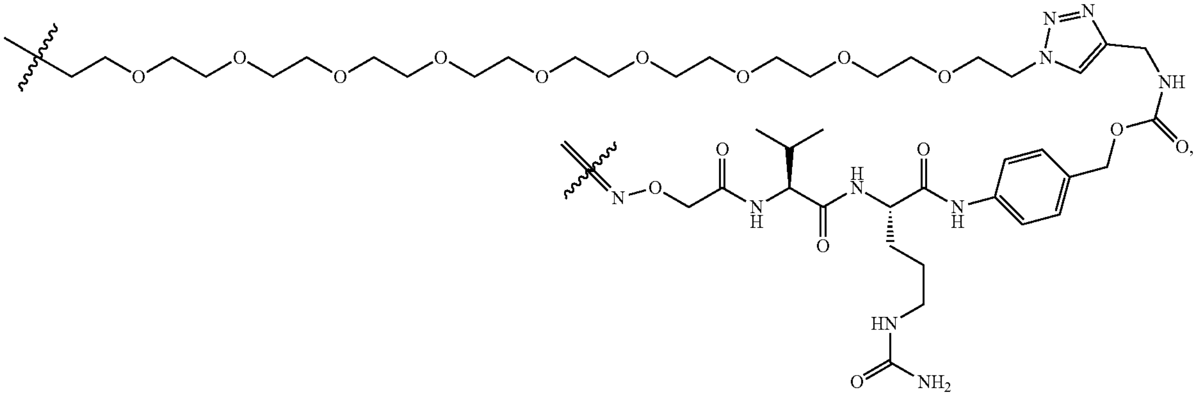
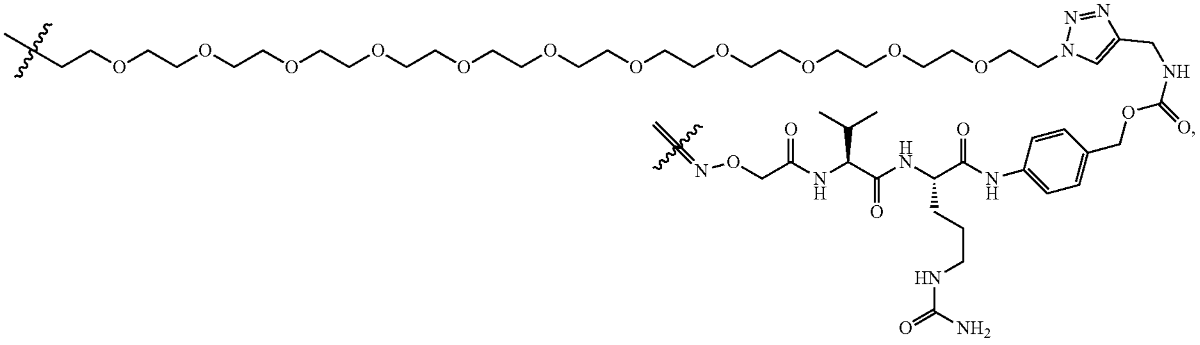
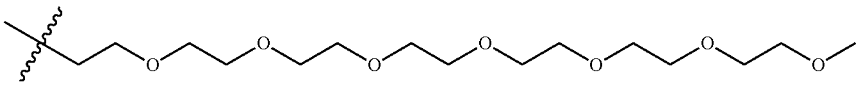

-continued
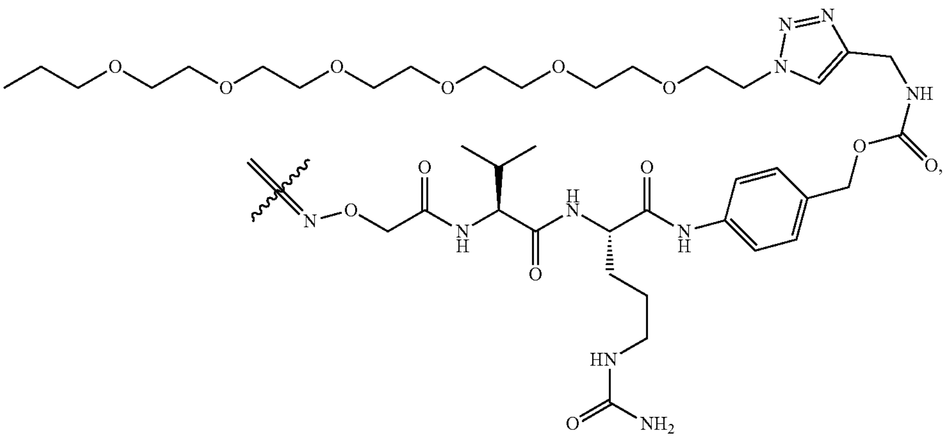
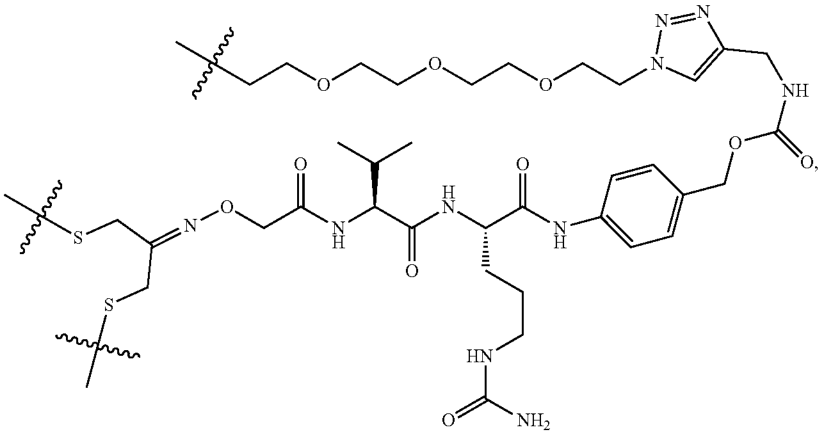
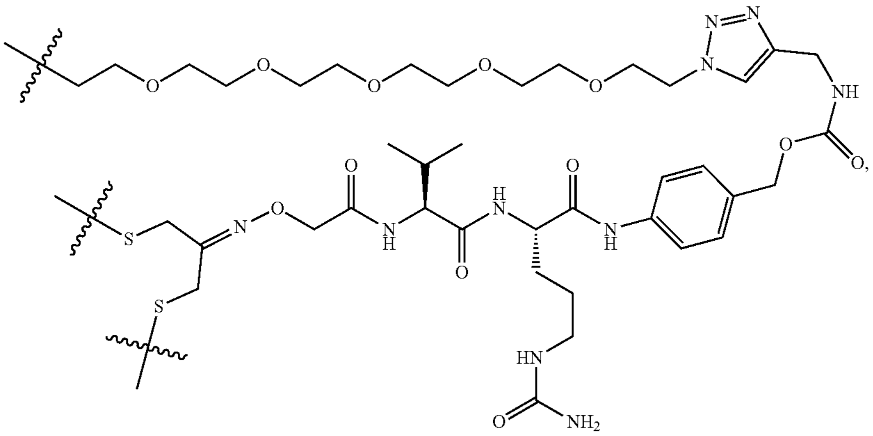

-continued
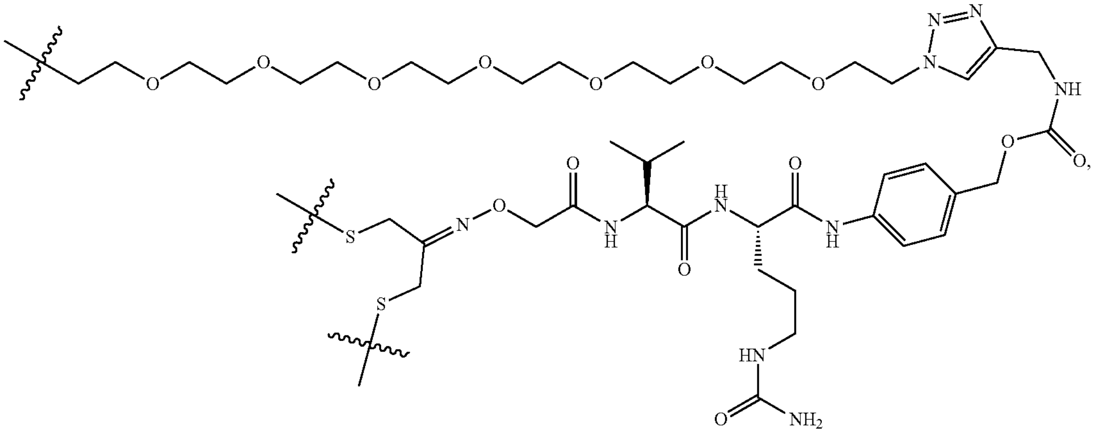
,
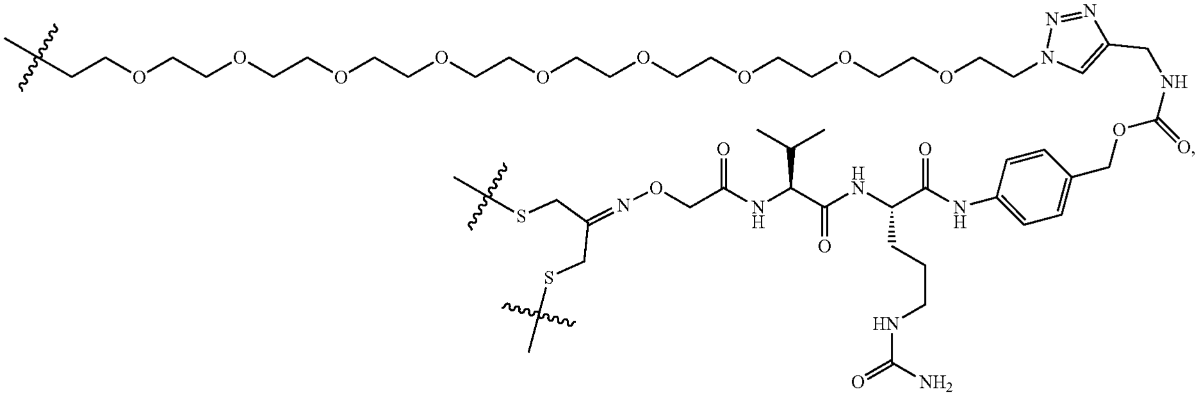
,
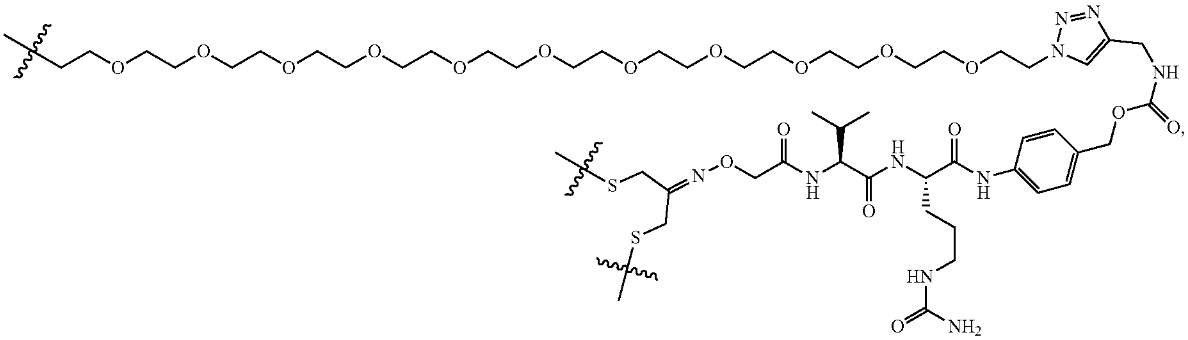
,
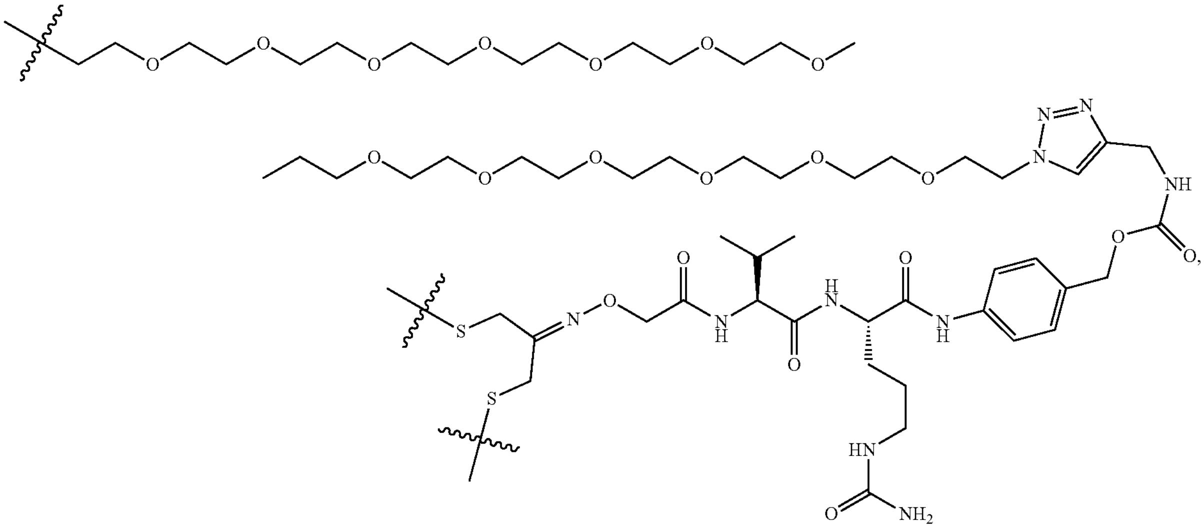
,

-continued
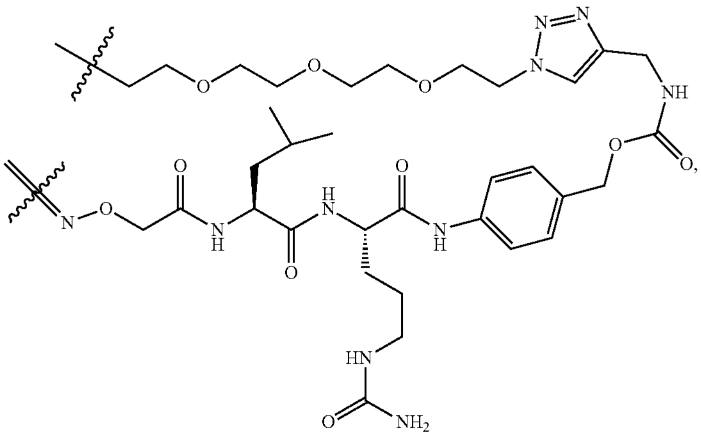
,
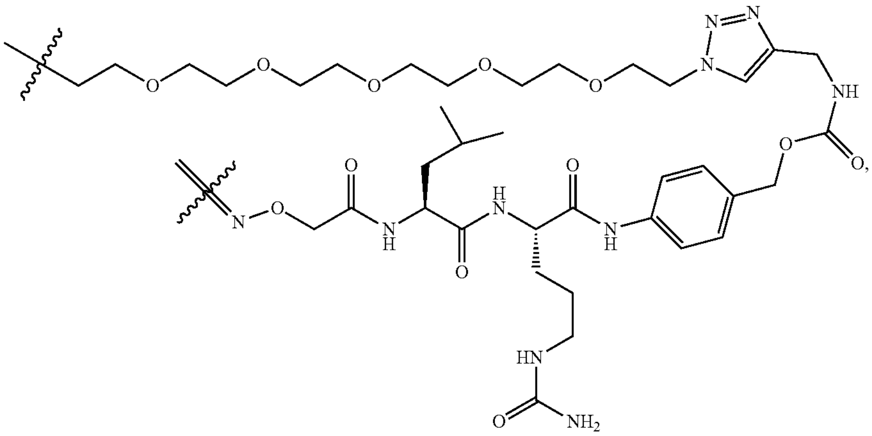
,
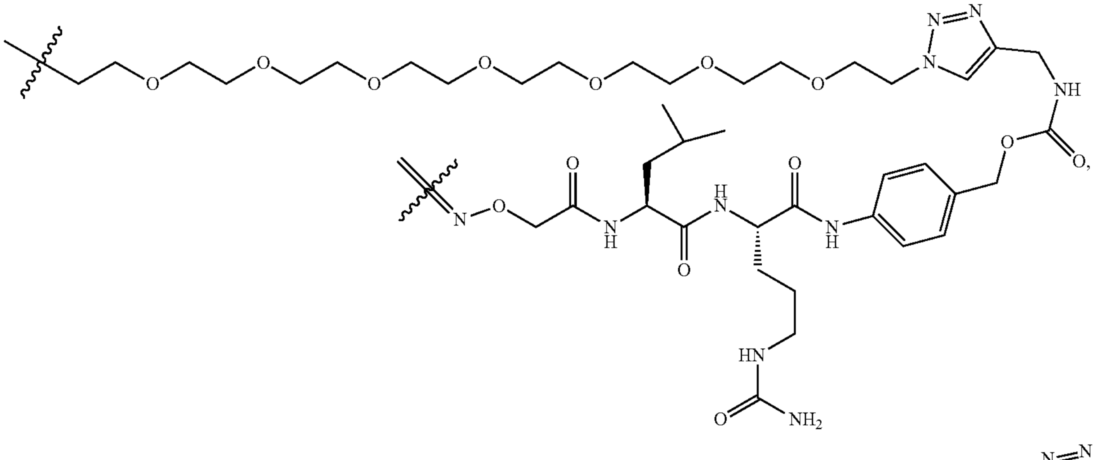
,
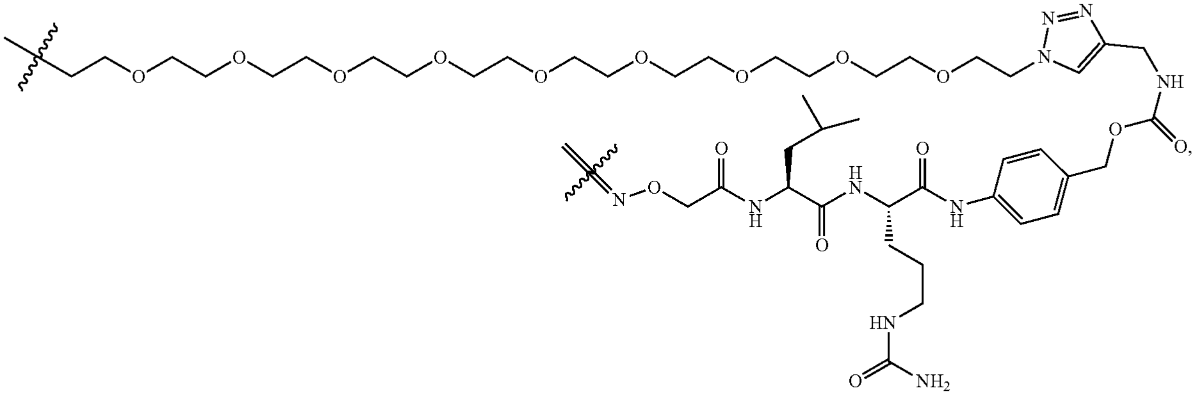
,

-continued
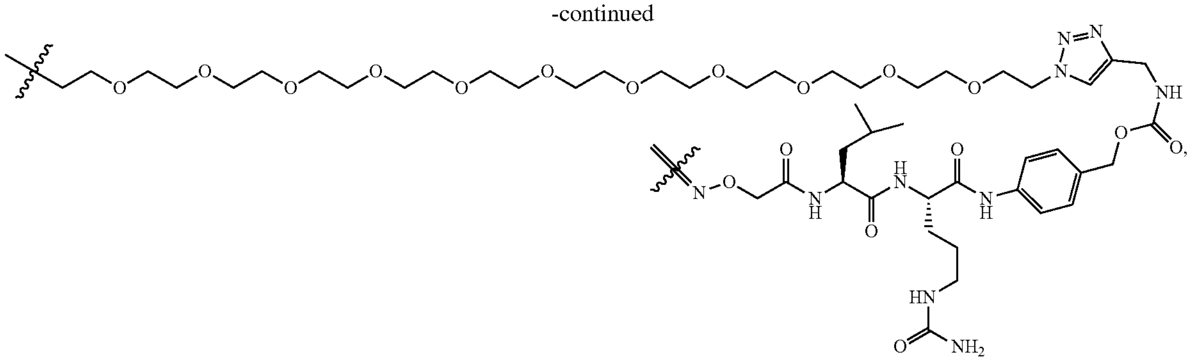
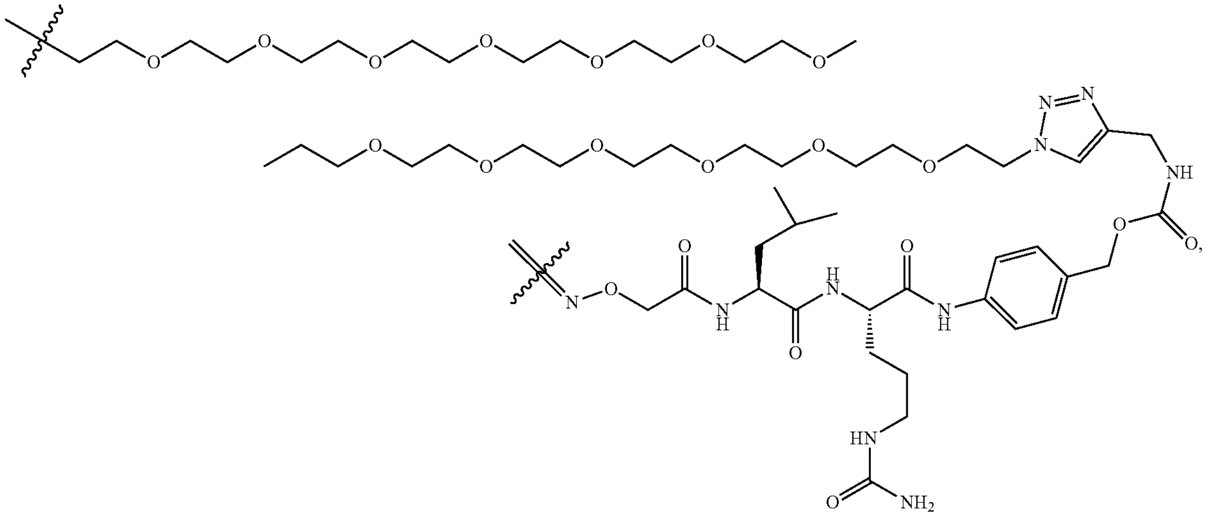
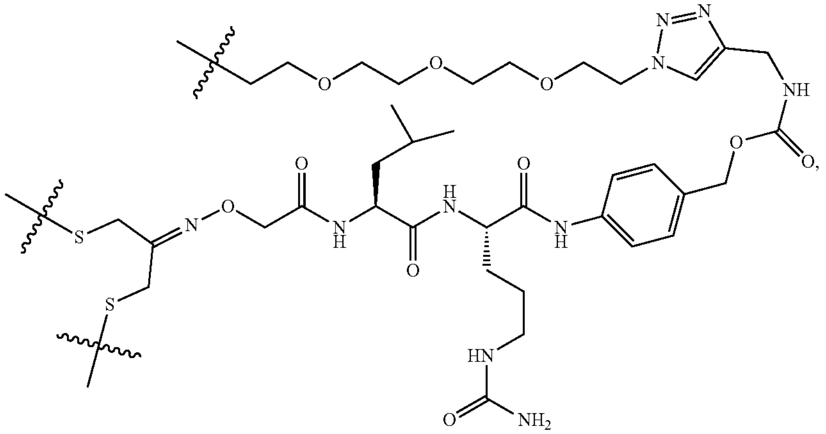
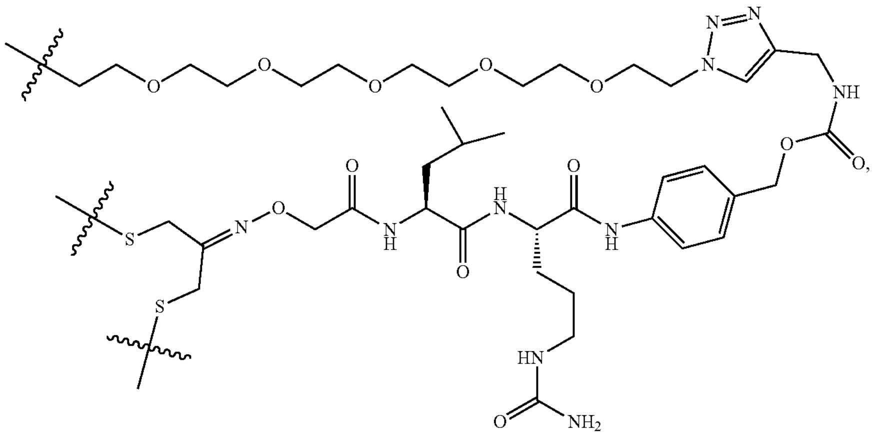

-continued
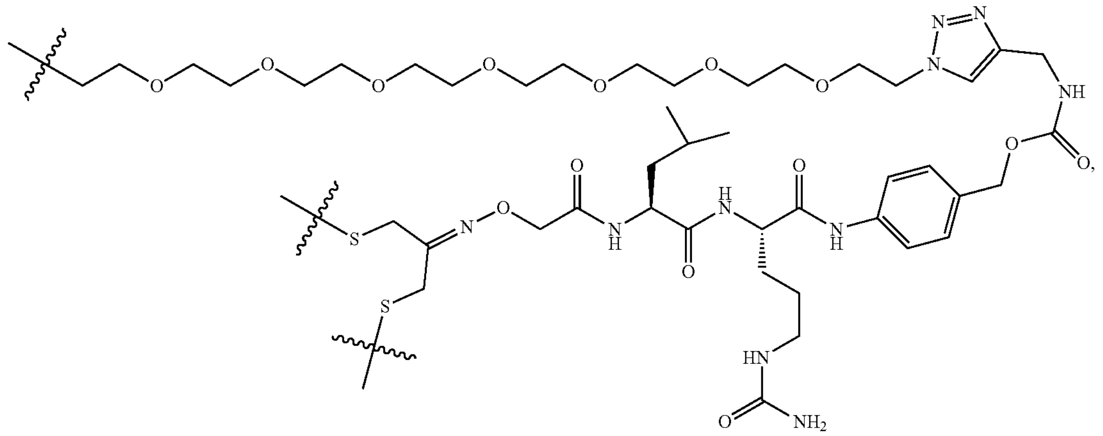
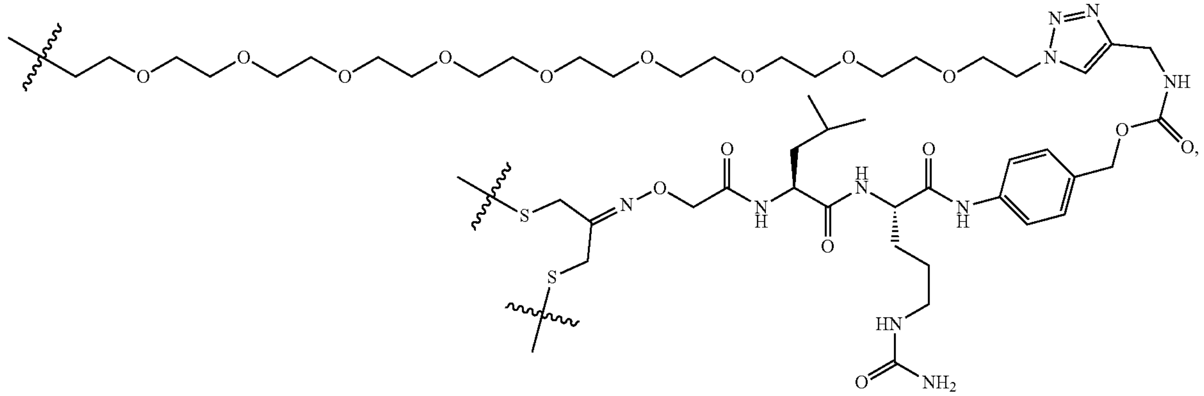
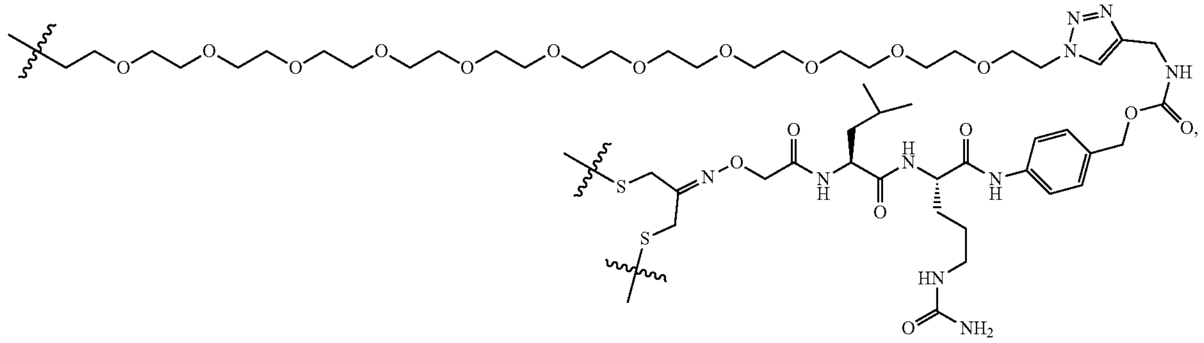
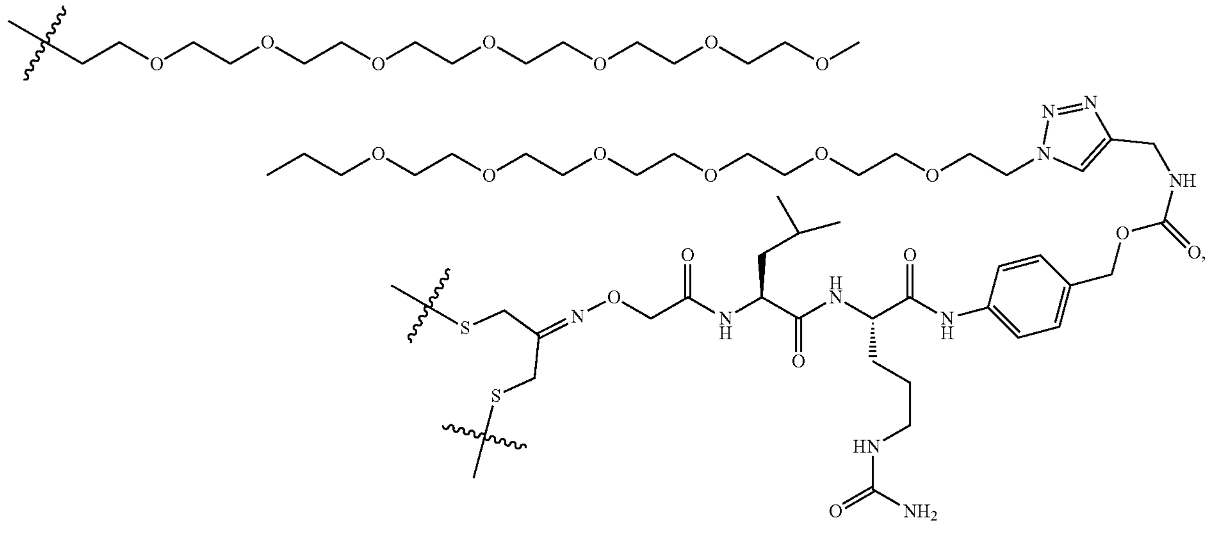

-continued
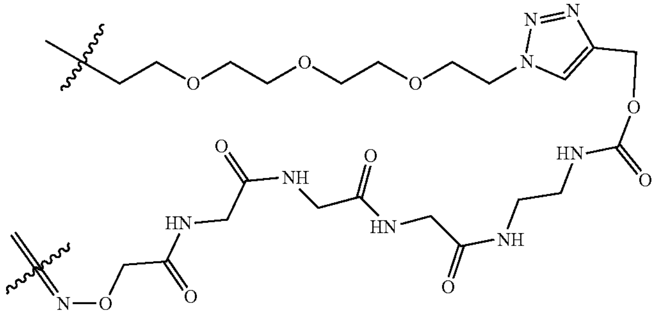
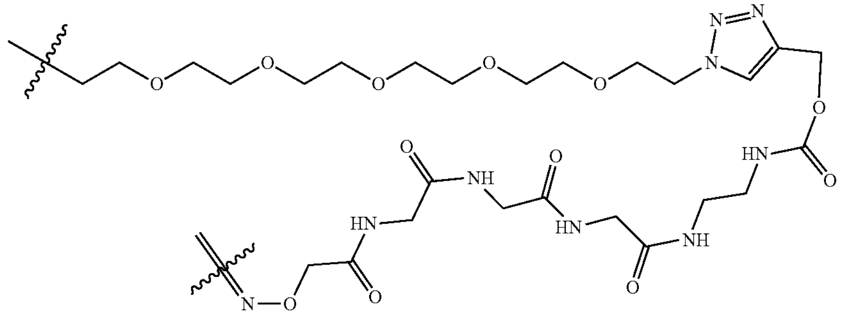
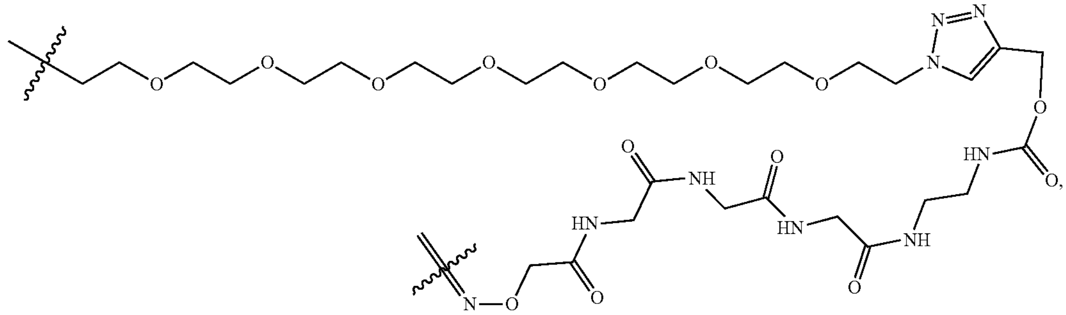
,
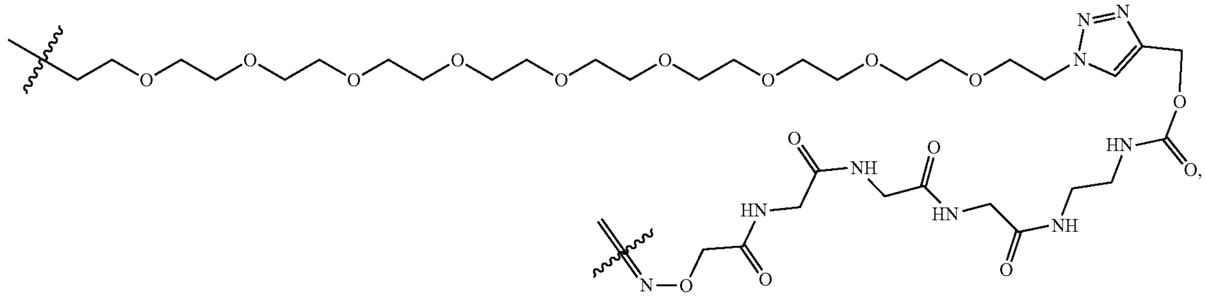
,
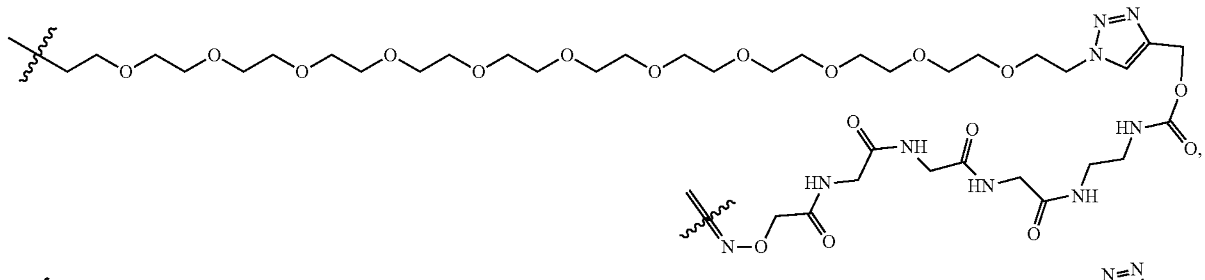
,
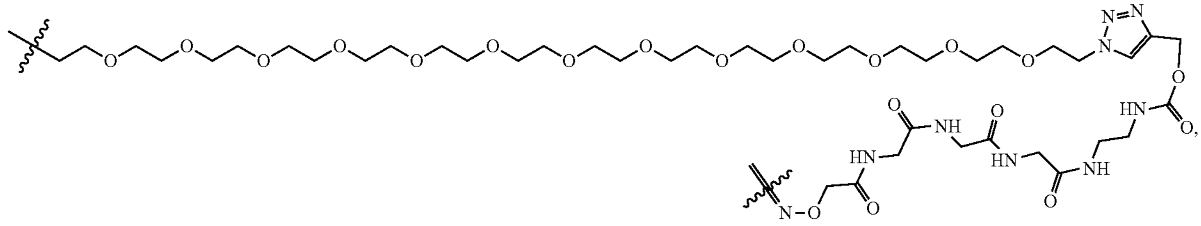
, -continued
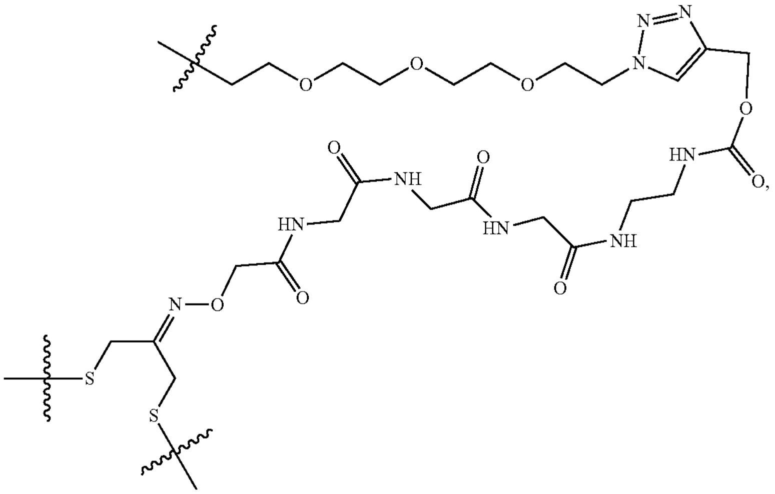
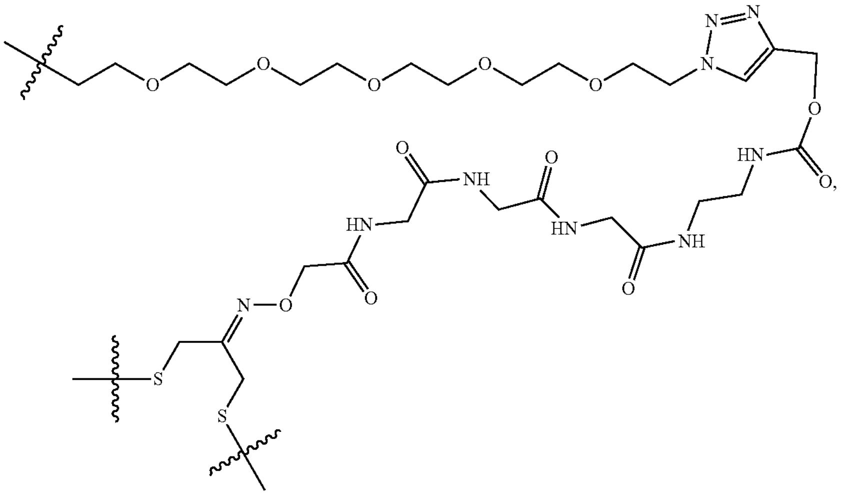
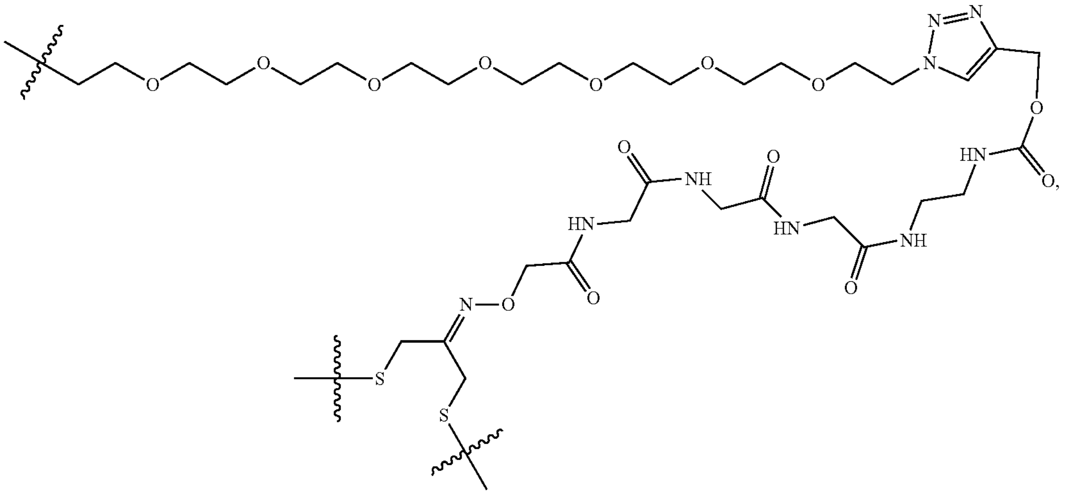

-continued
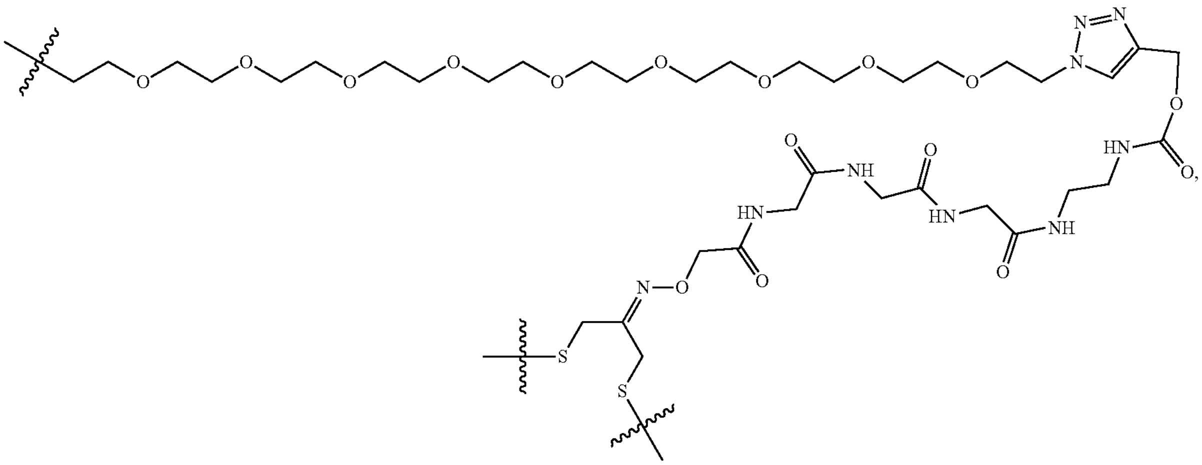
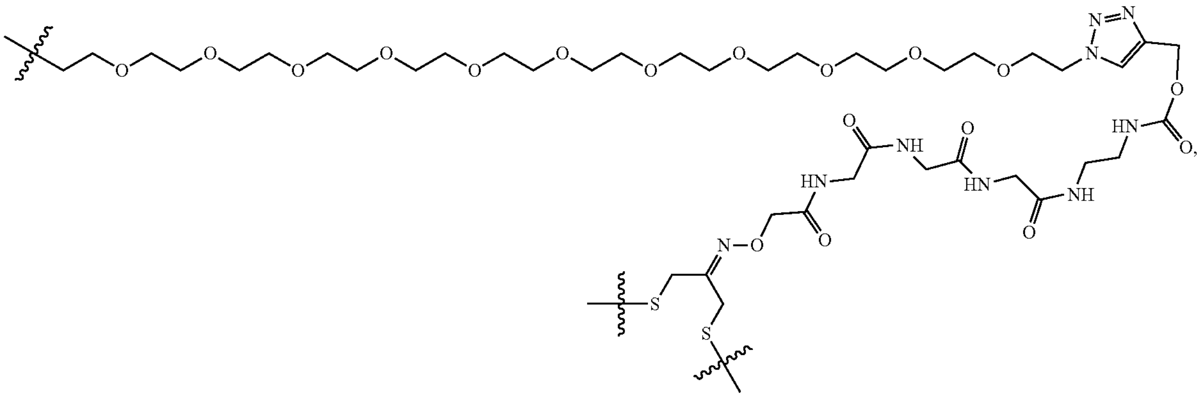
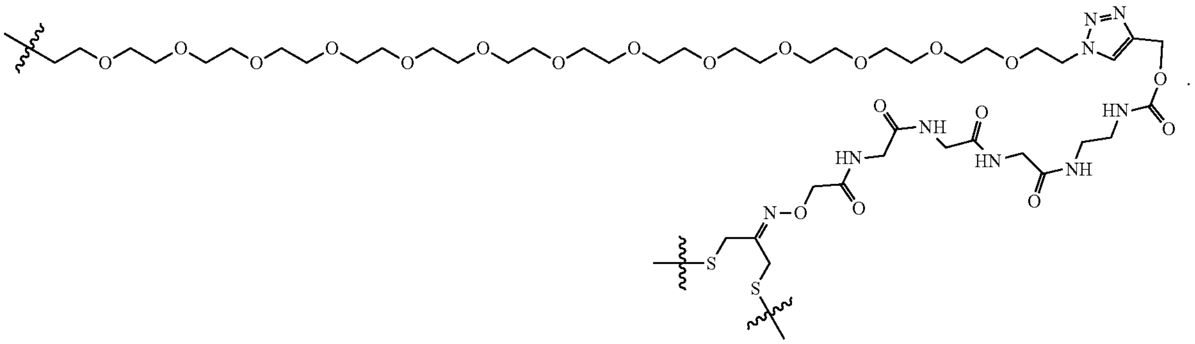 [SMILES: *CCOCCOCCOCCOCCOCCOCCOCCOCCOCCOCCOCCOCCOCCn1cc(COC(=O)NCCNC(=O)CNC(=O)CNC(=O)CNC(=O)CON=C(CS*)CS*)nn1]

6. The immunoconjugate of claim 5, wherein $R^1$ is —$CH_3$.
7. The immunoconjugate of claim 5, wherein $R^1$ is —$CD_3$.
8. The immunoconjugate of claim 5, wherein $R^1$ is H.
9. The immunoconjugate of claim 5, wherein $R^3$ is —$NH_2$.
10. The immunoconjugate of claim 5, wherein $R^3$ is —OH.
11. The immunoconjugate of claim 1 selected from:
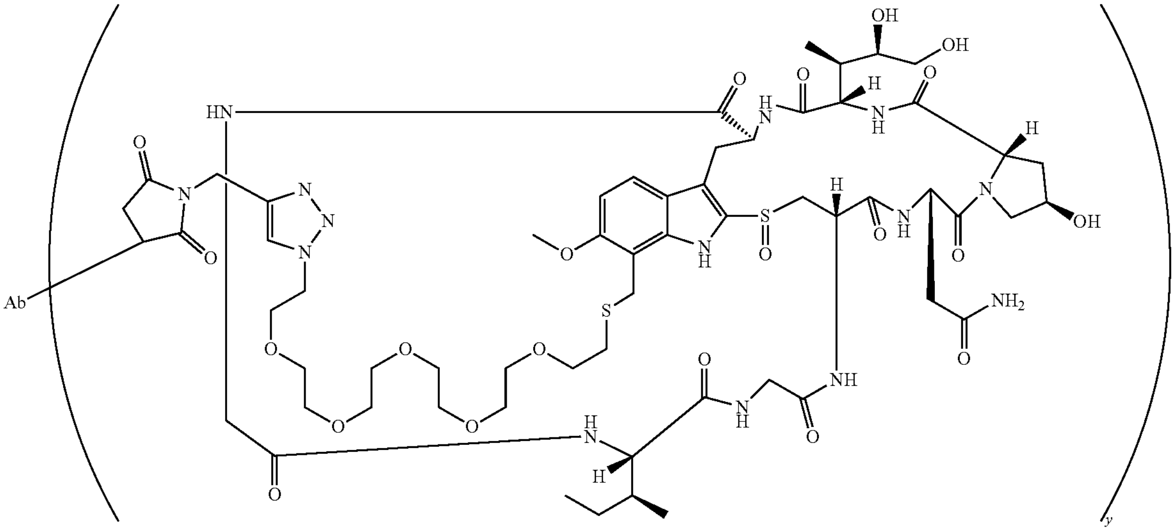
;
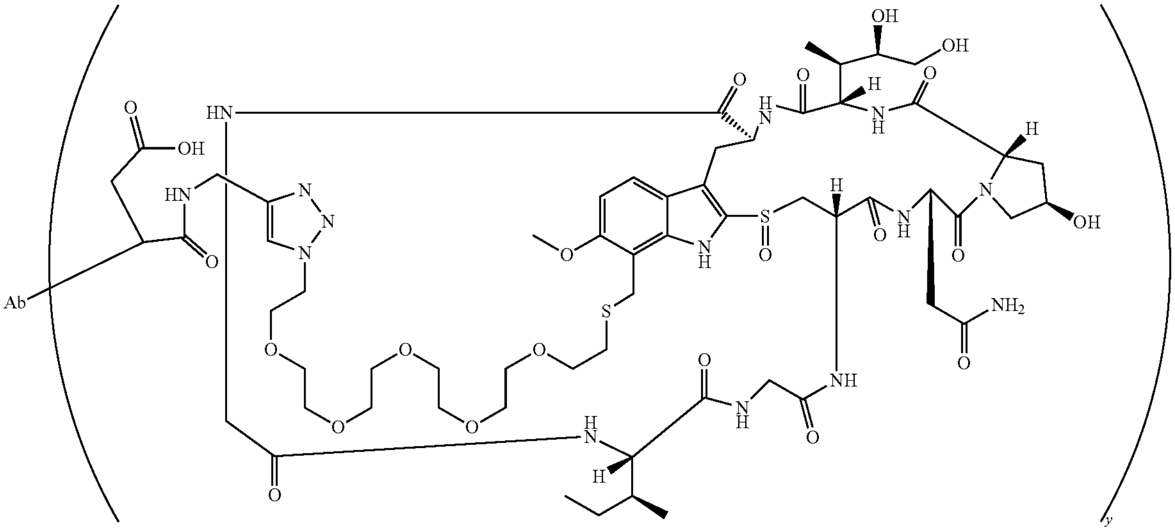
;

-continued
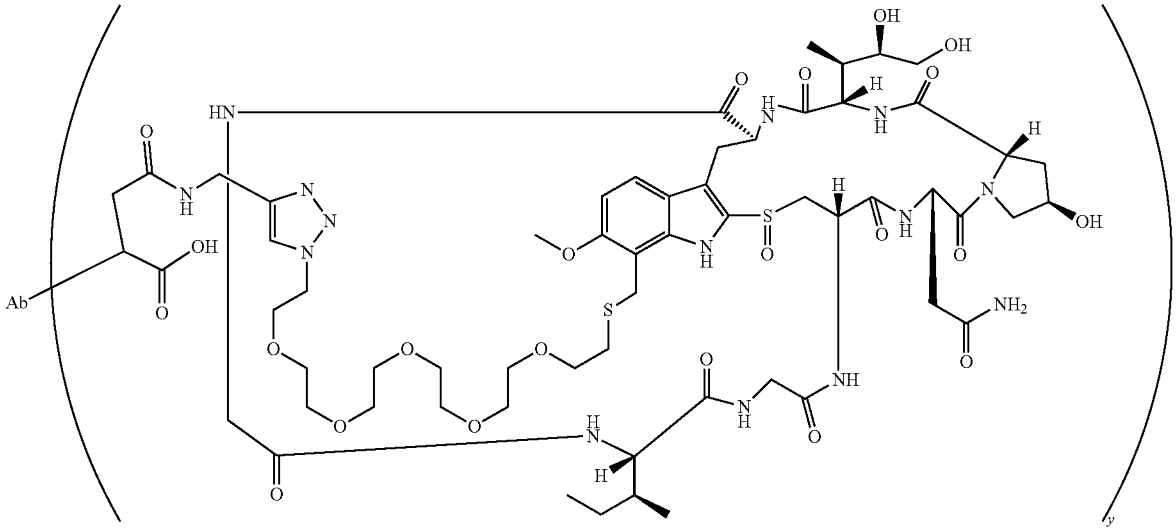
;
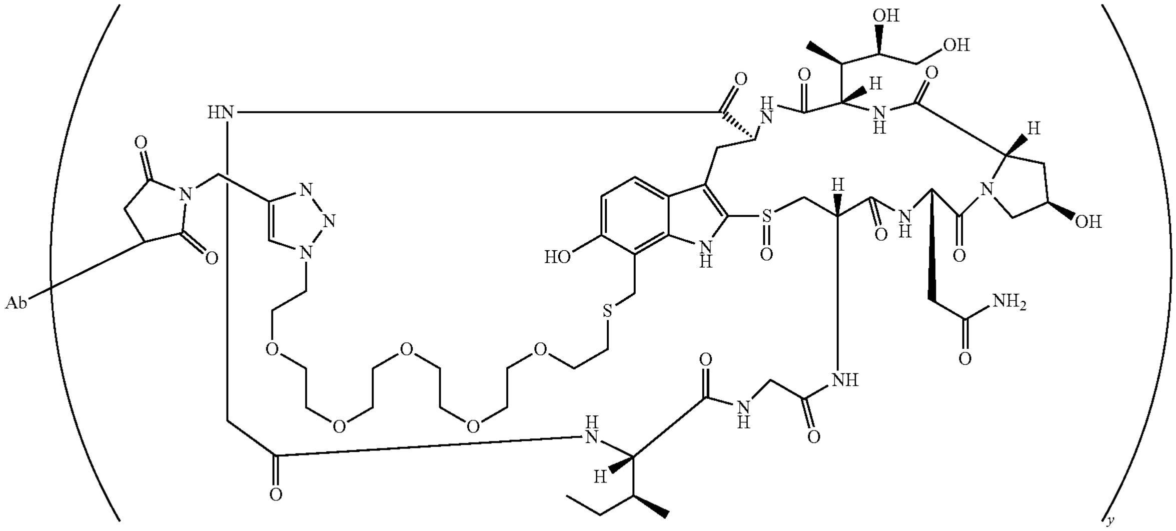
;
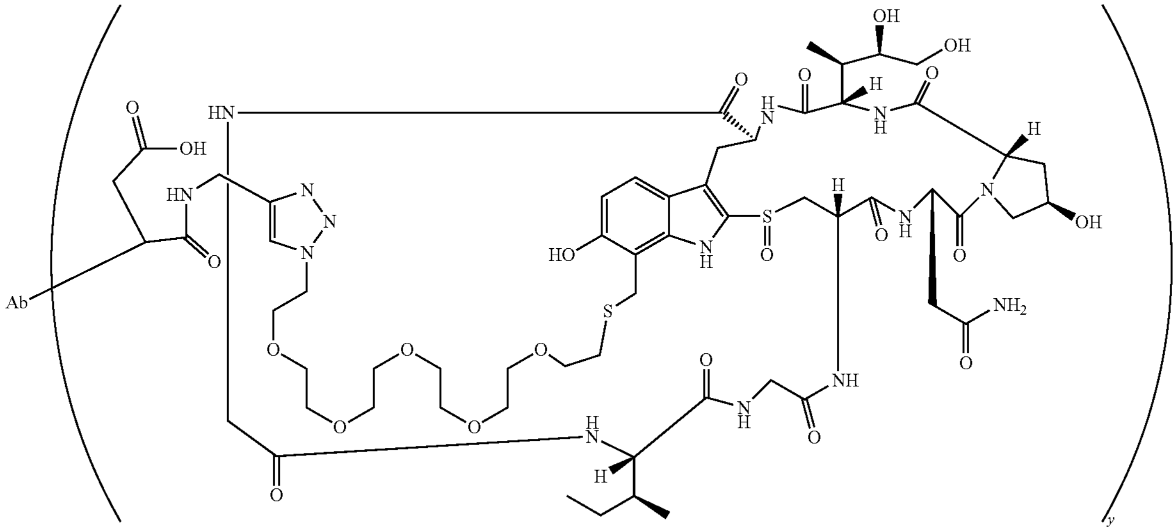
;

-continued
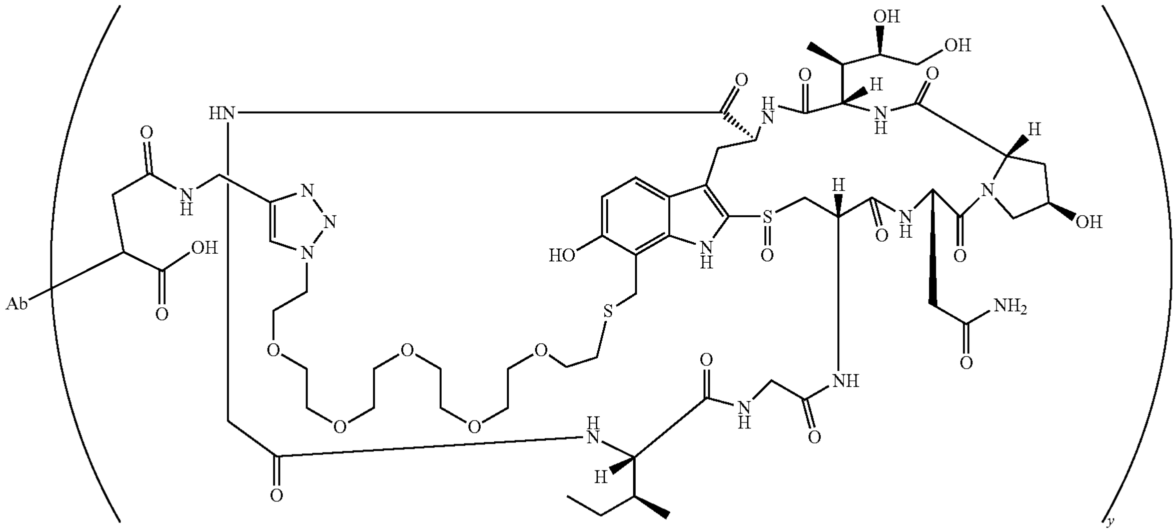
;
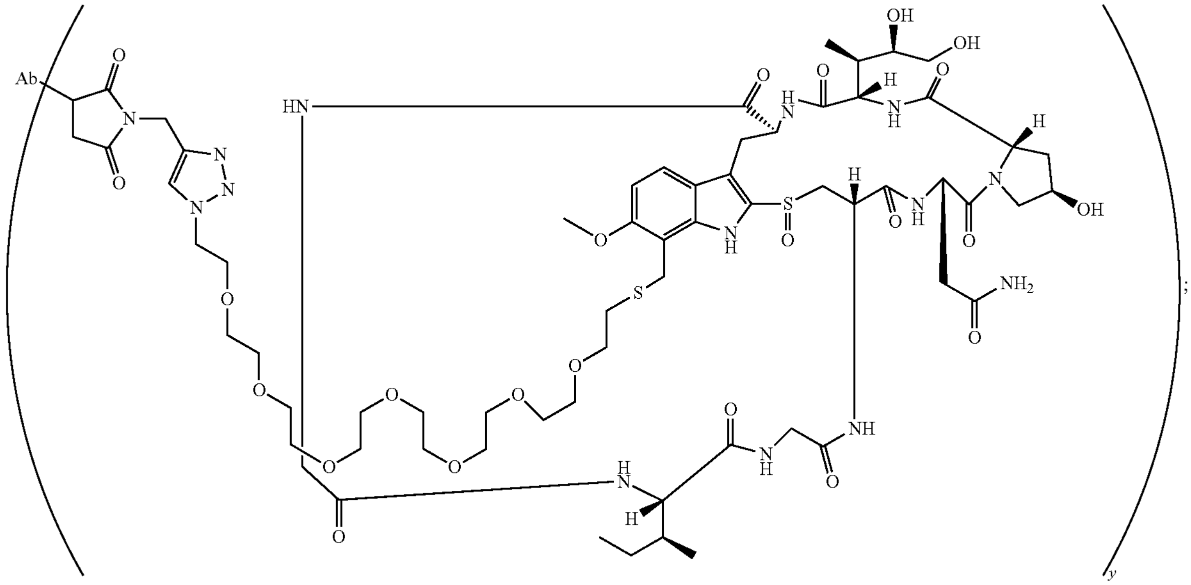
;
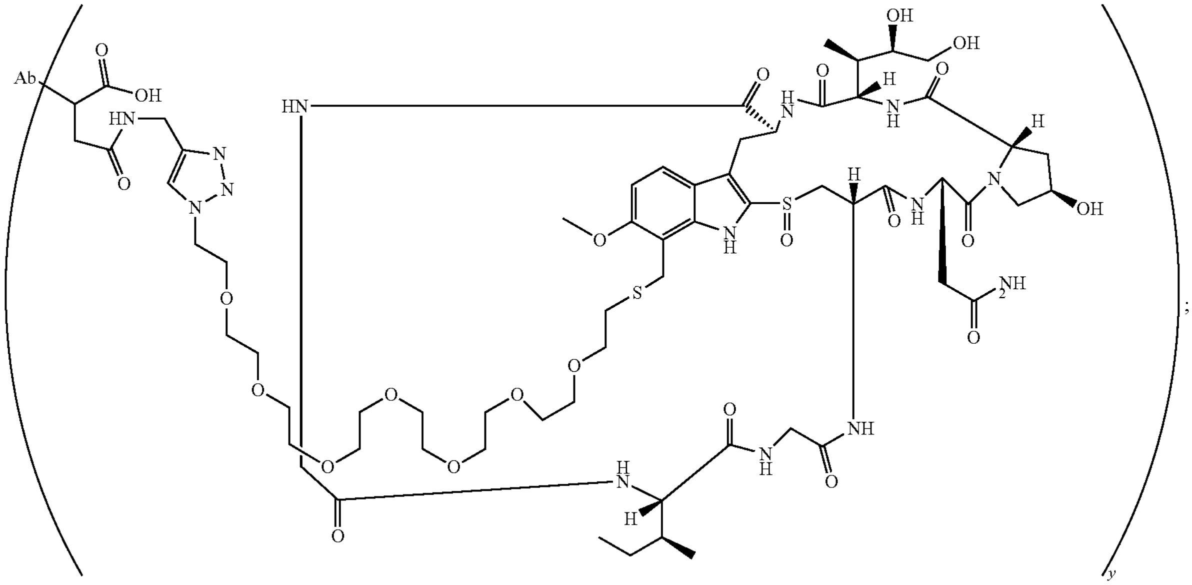
;

-continued
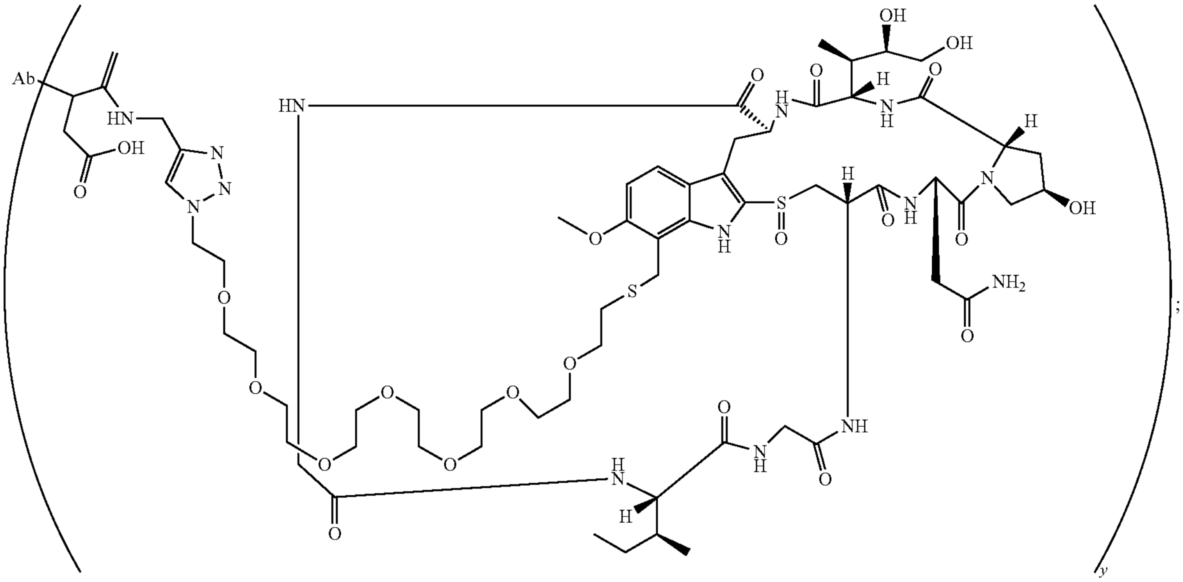
;
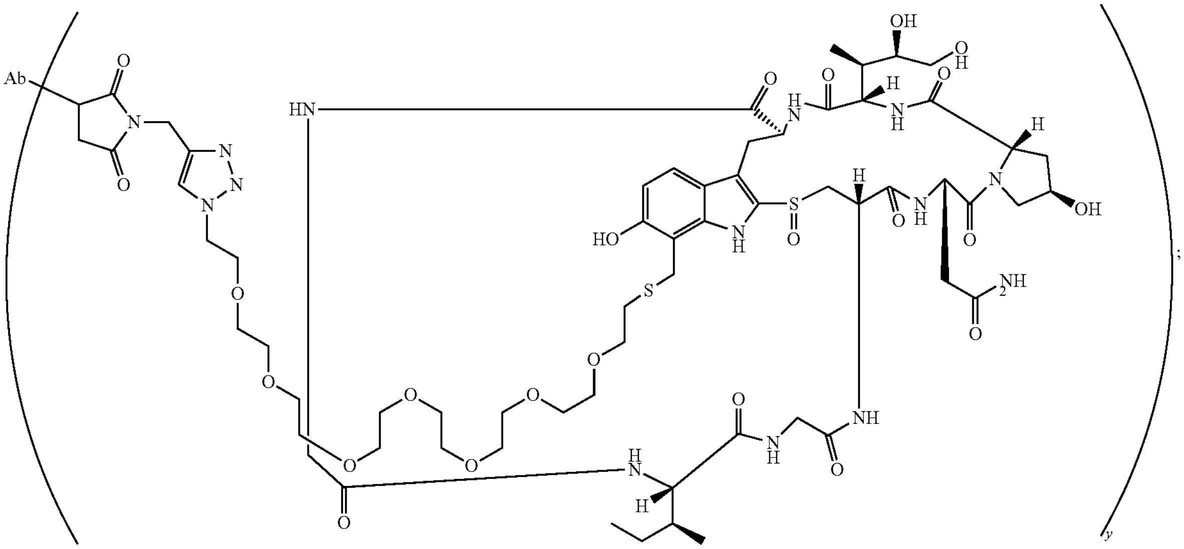
;
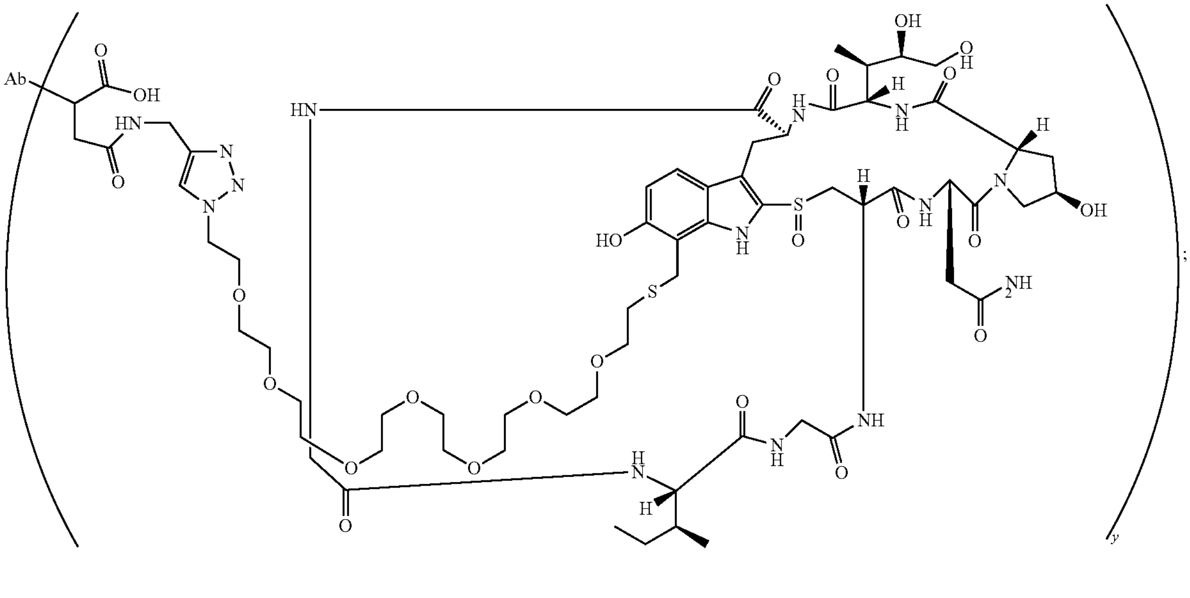
;

-continued
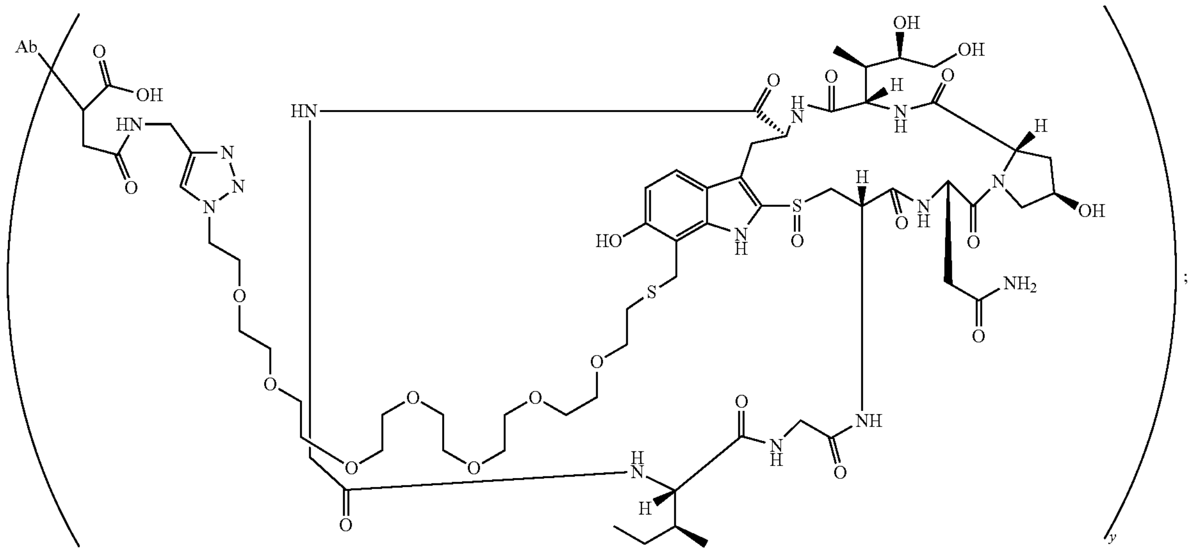
;
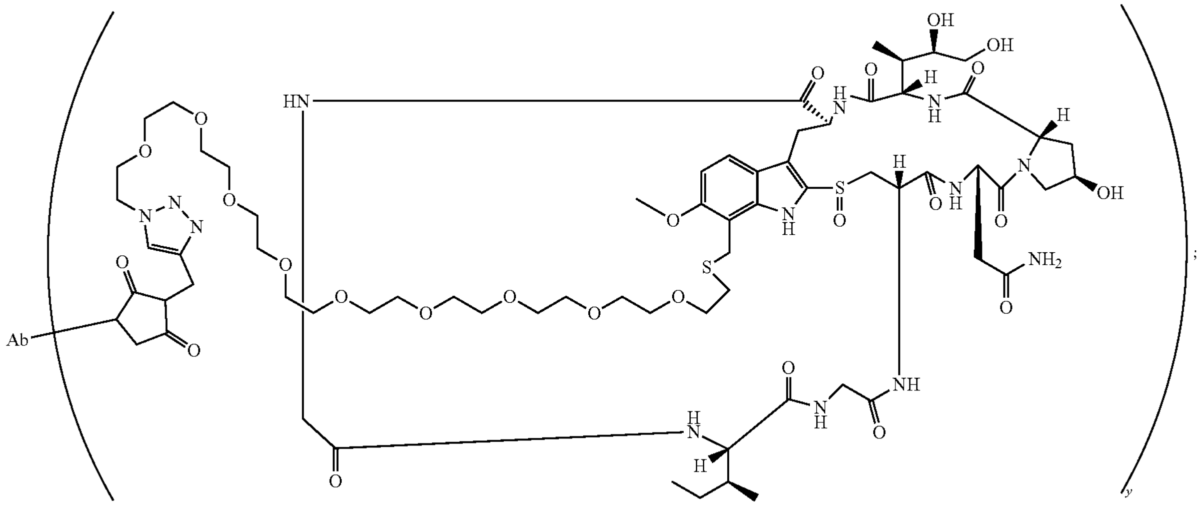
;
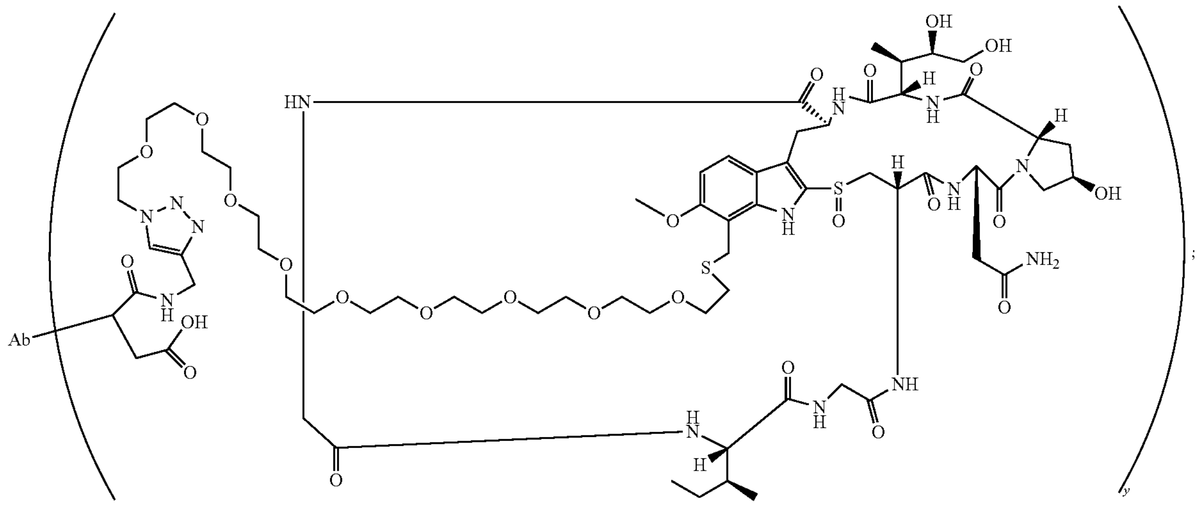
;

-continued
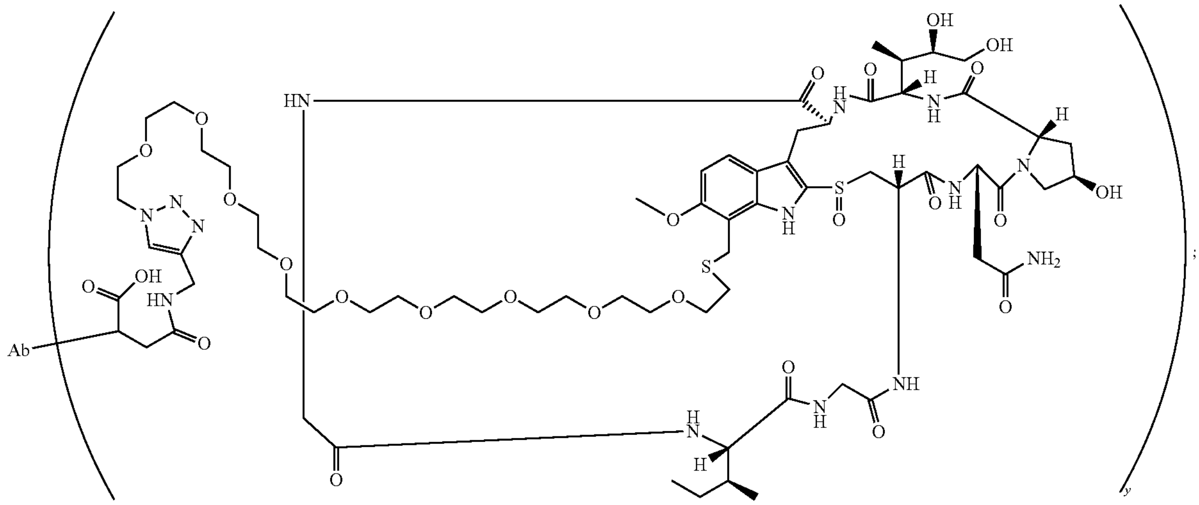
;
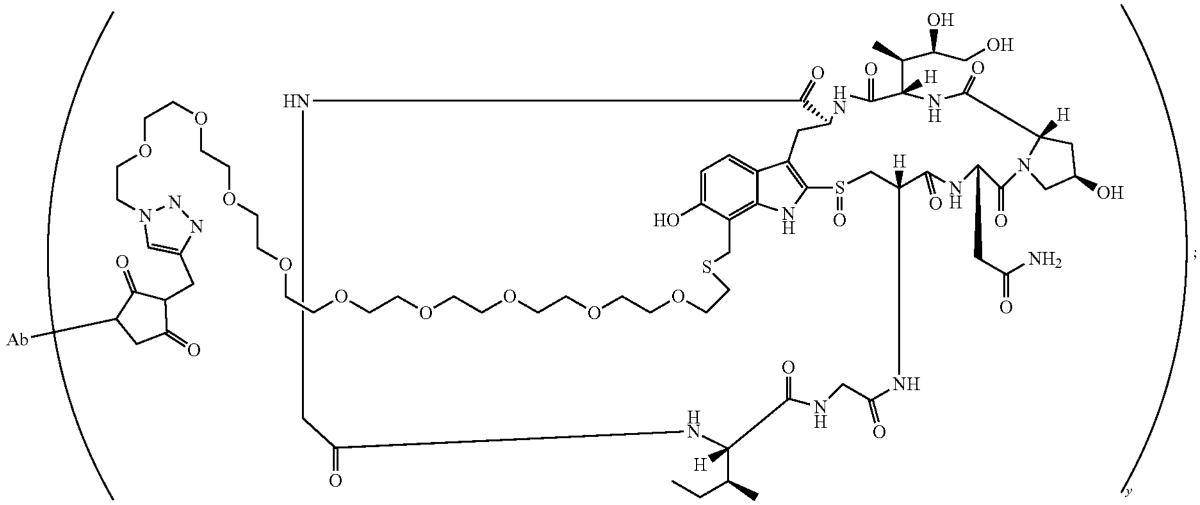
;
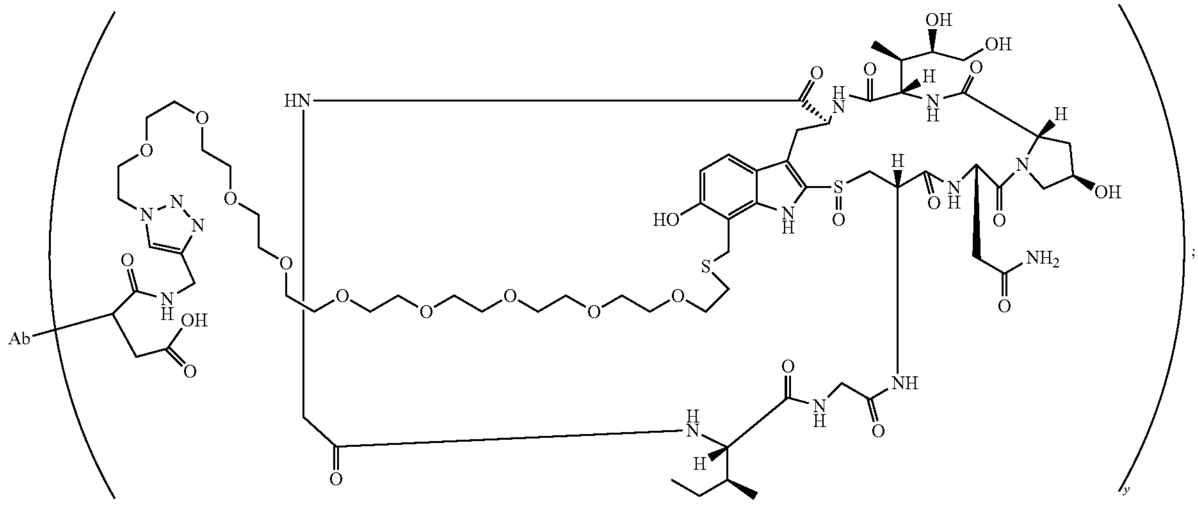
;

-continued
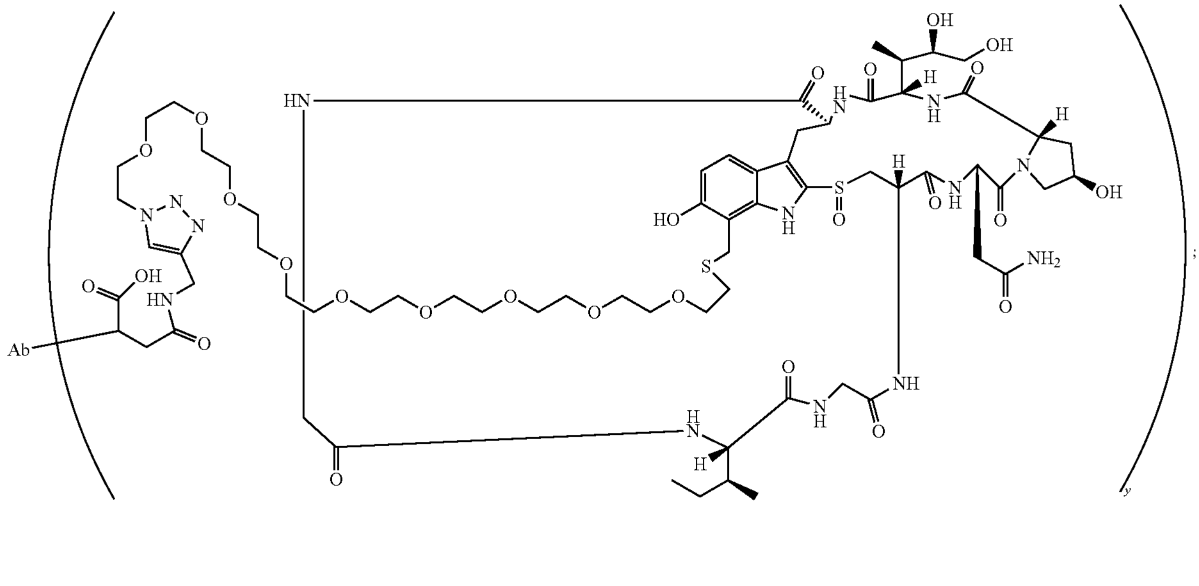
;
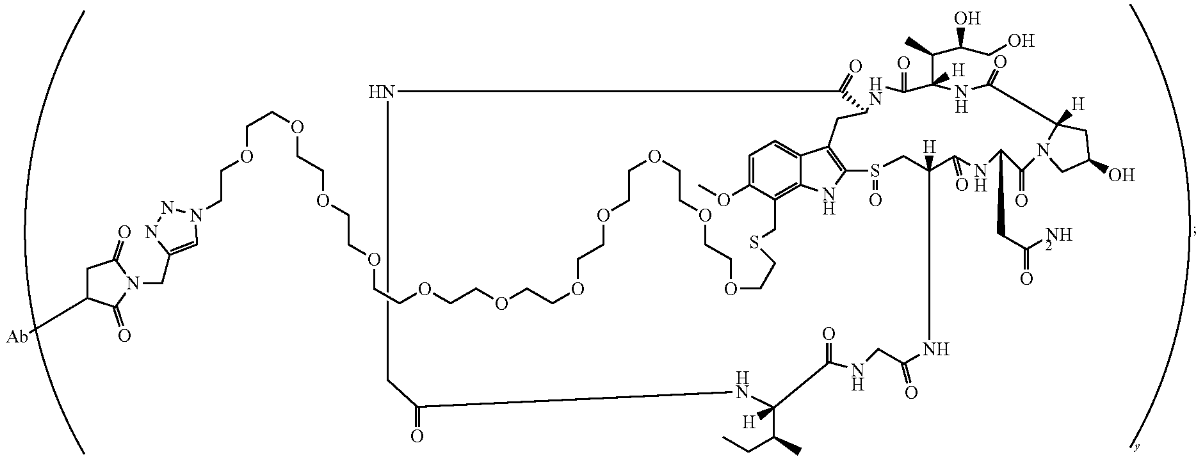
;
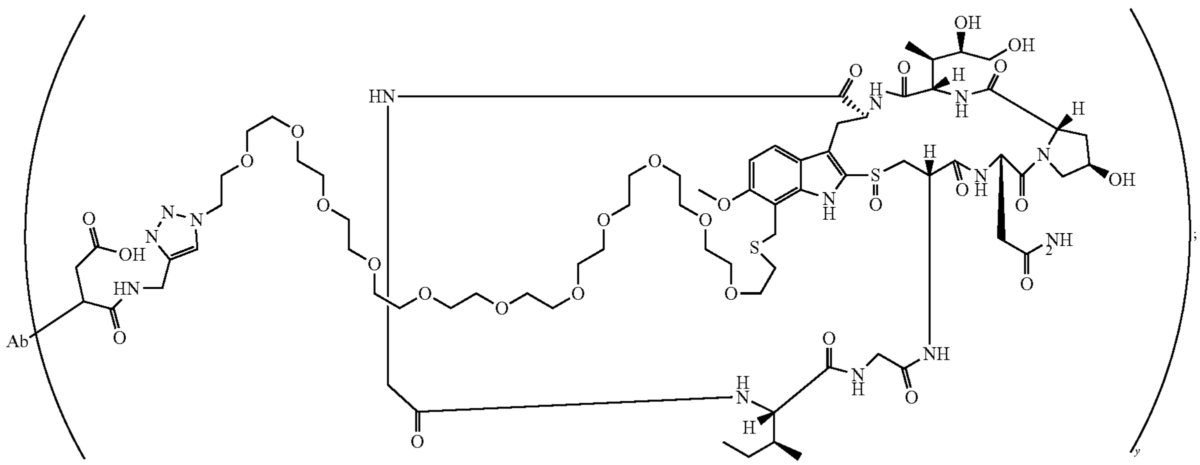
;

-continued
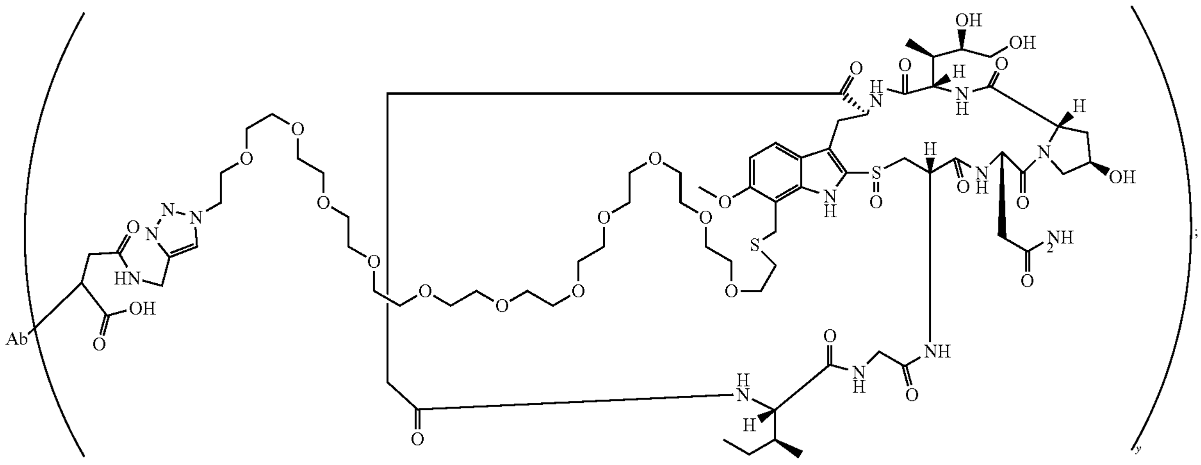
;
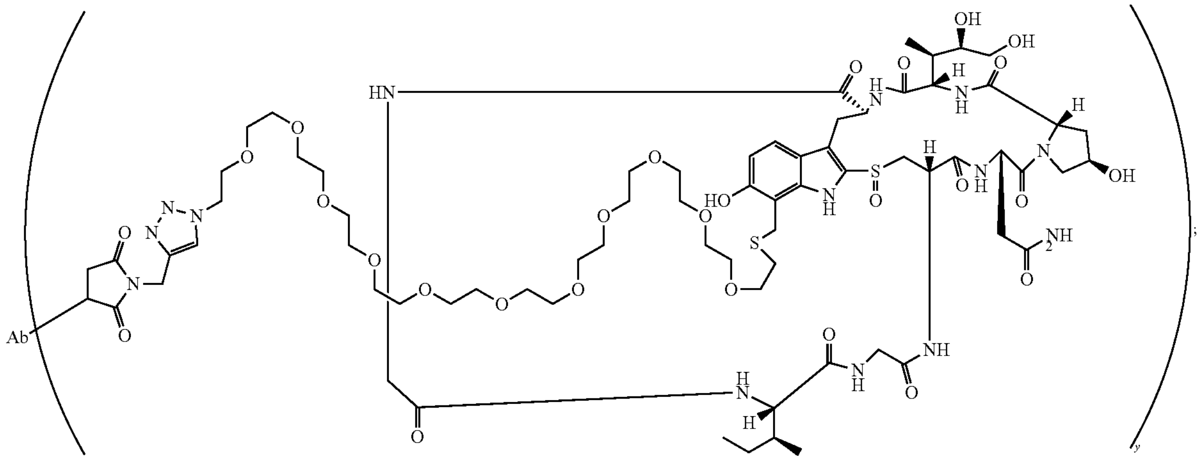
;
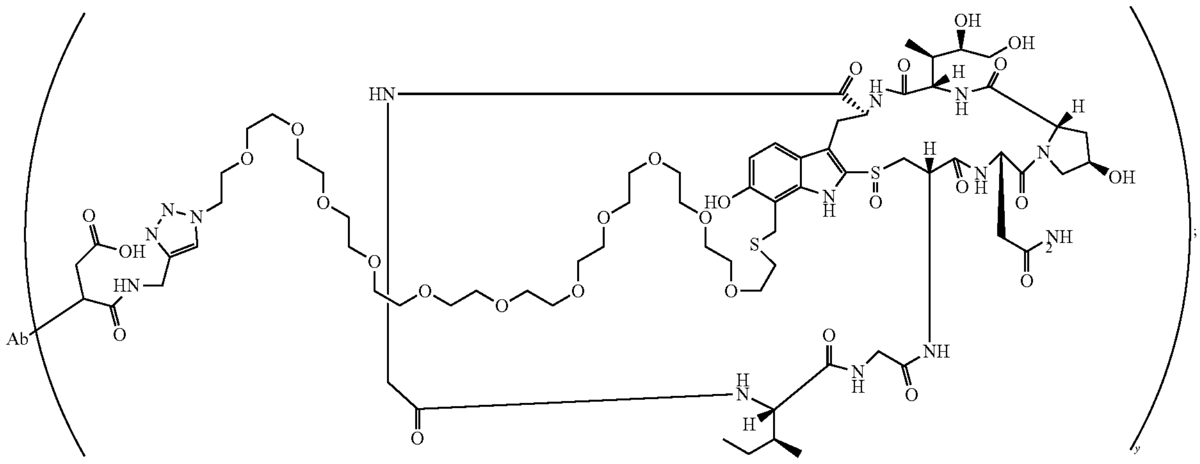
;

-continued
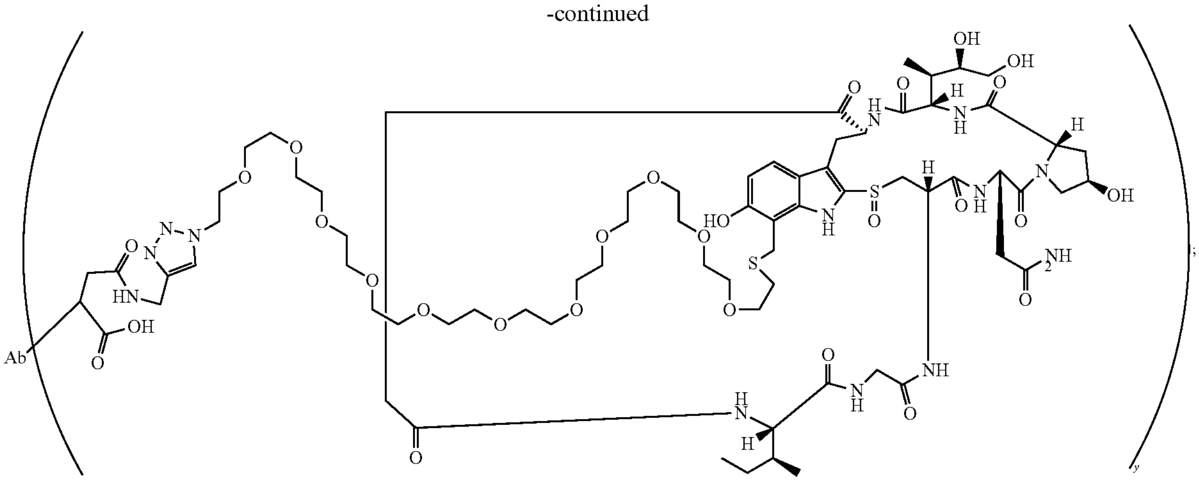
;
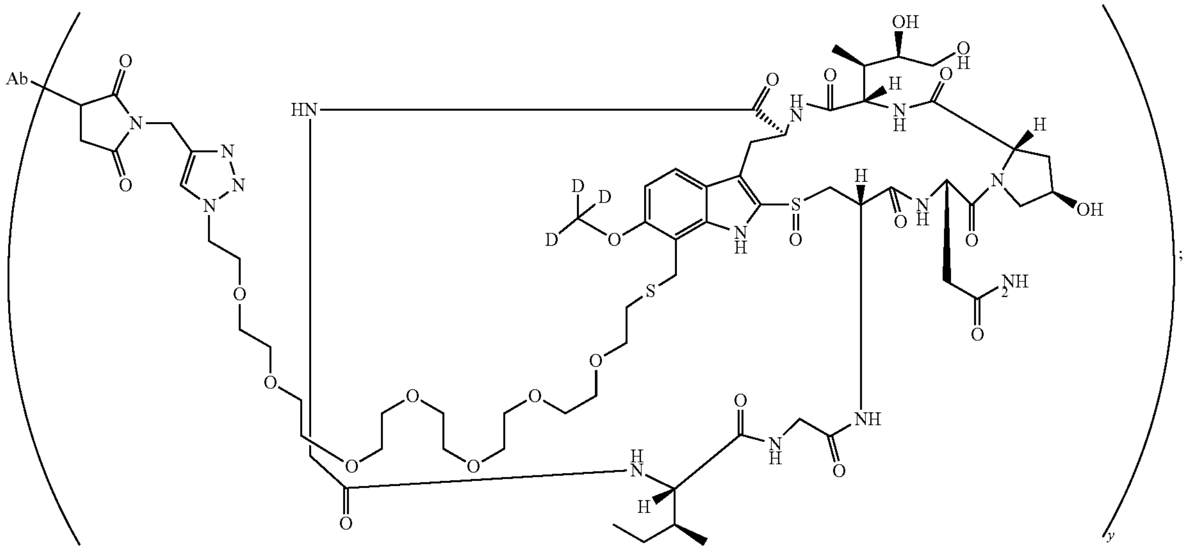
;
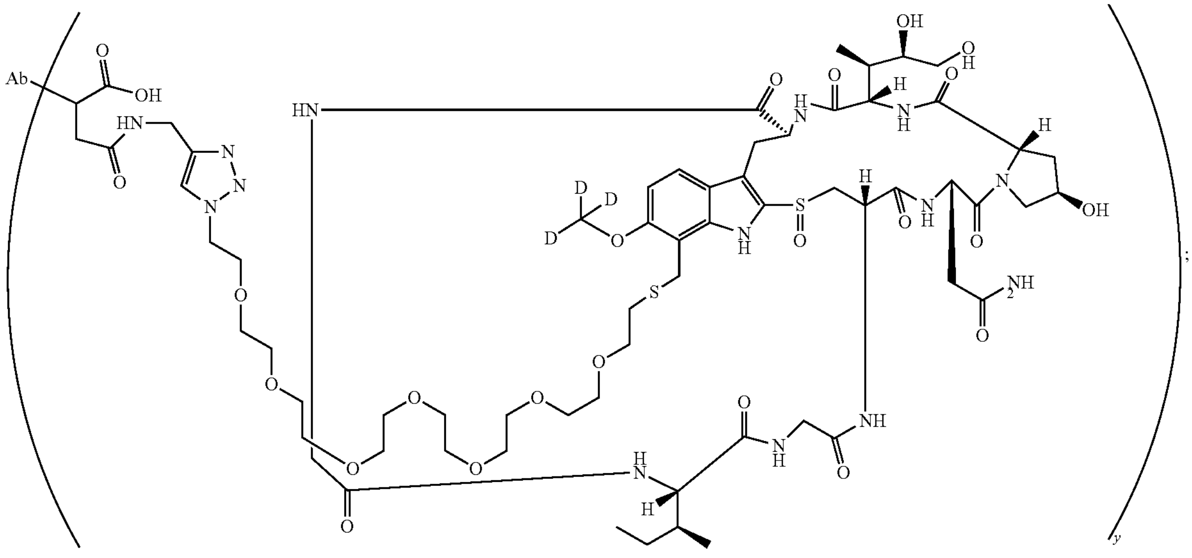
;

-continued
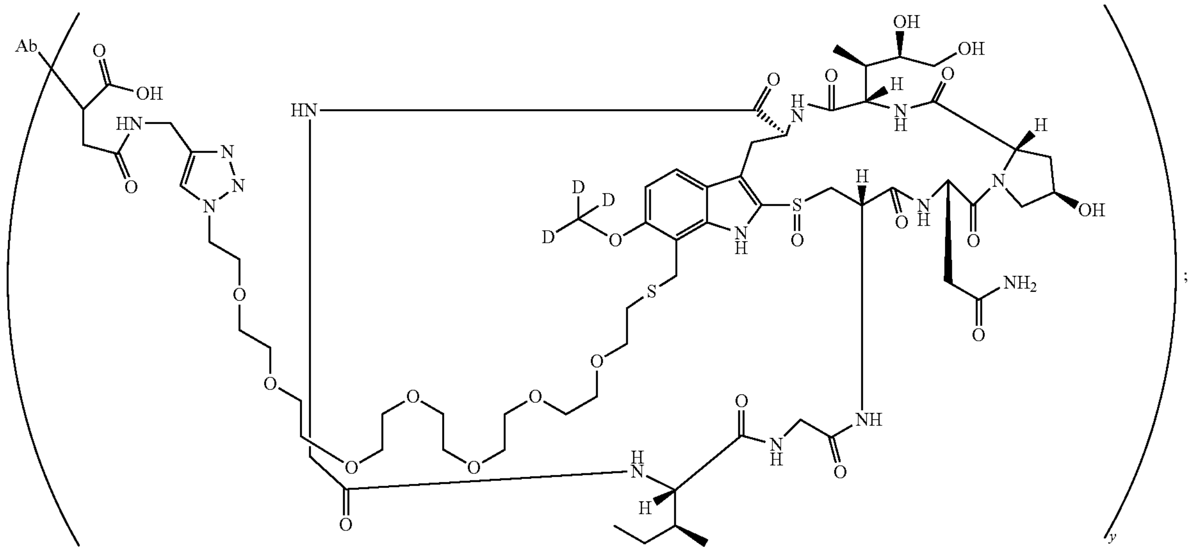
;
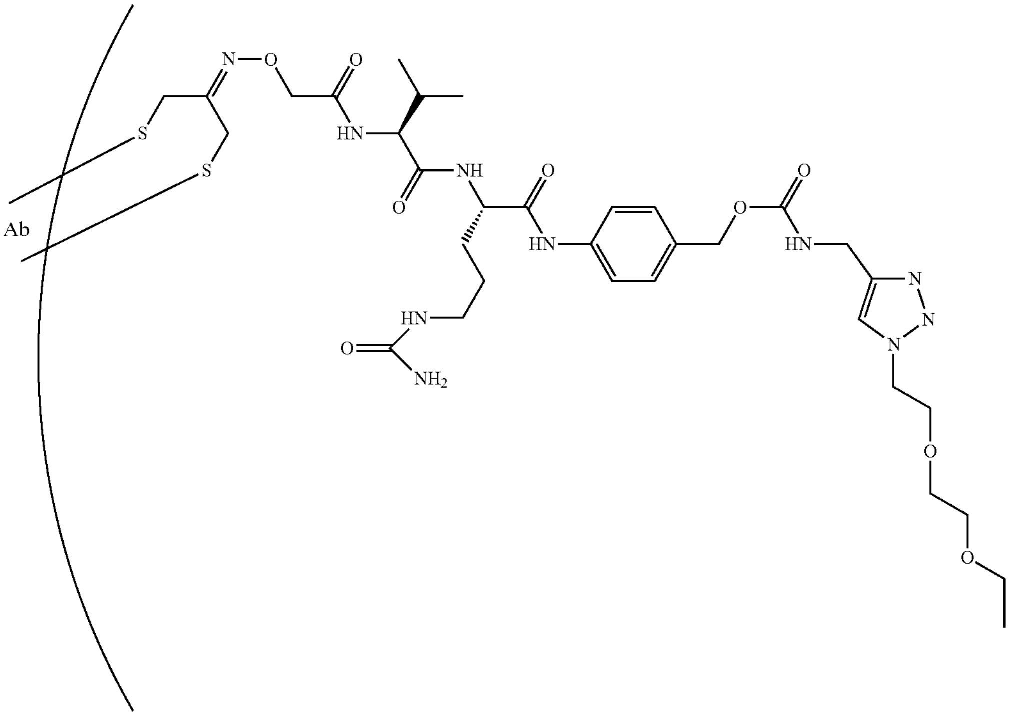

-continued
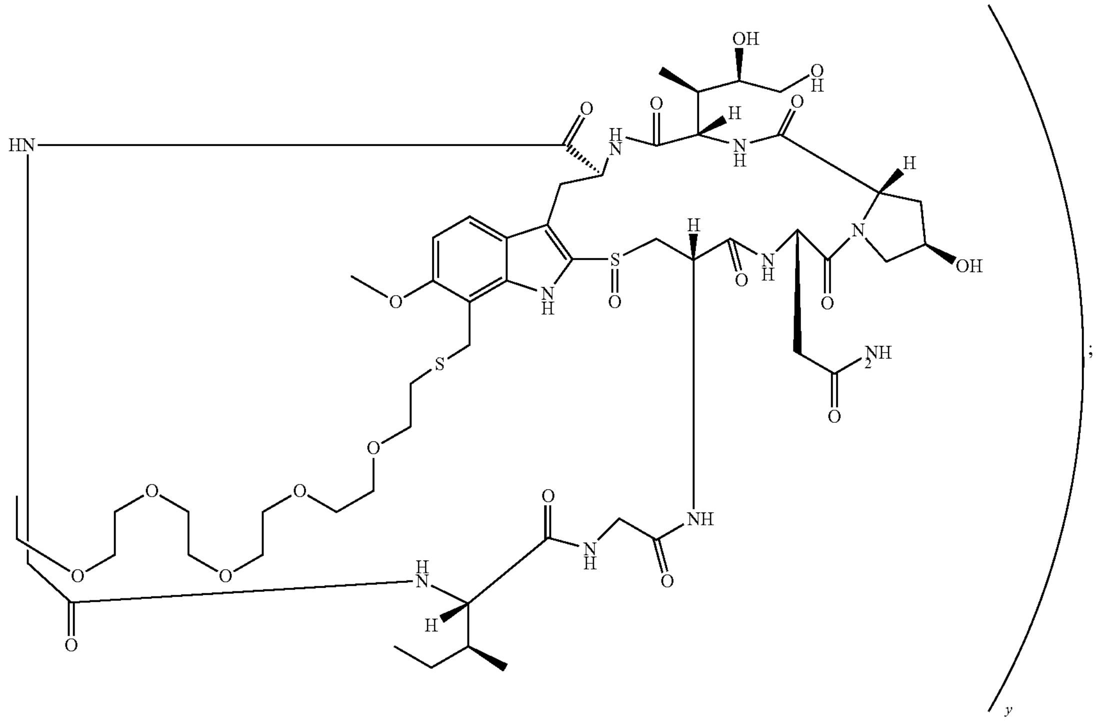
;
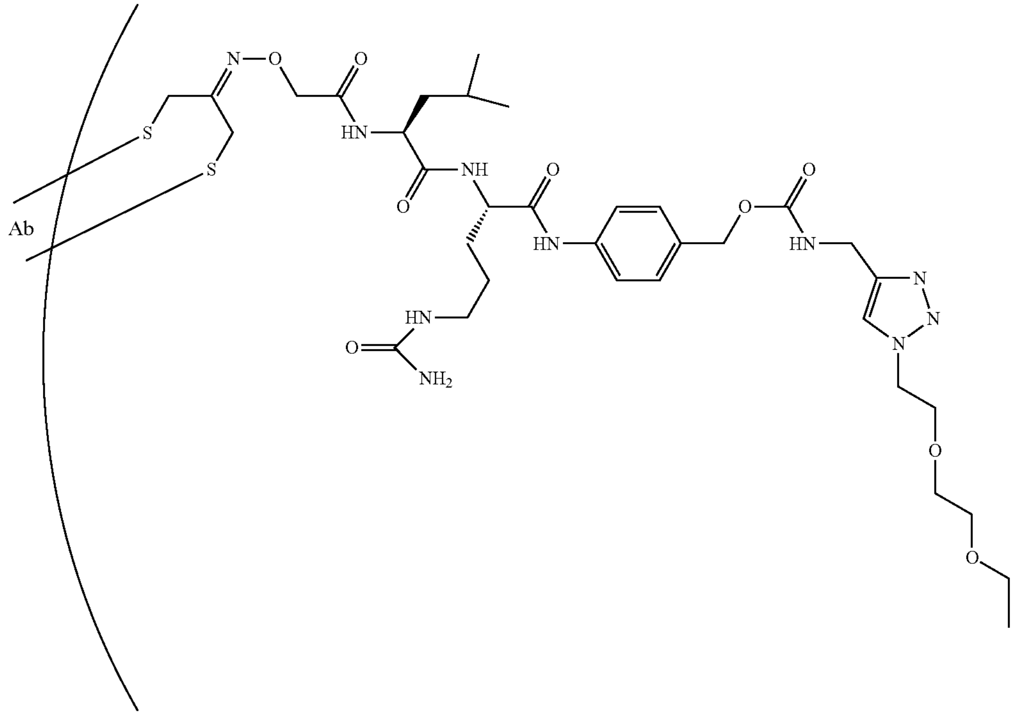

-continued
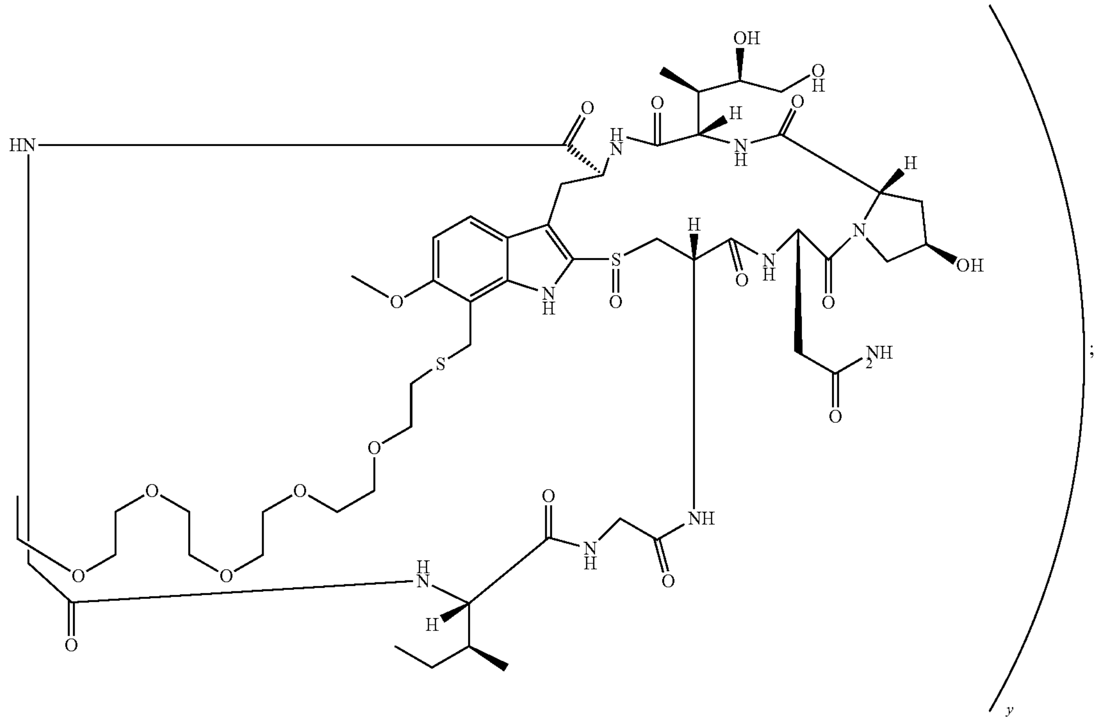
;
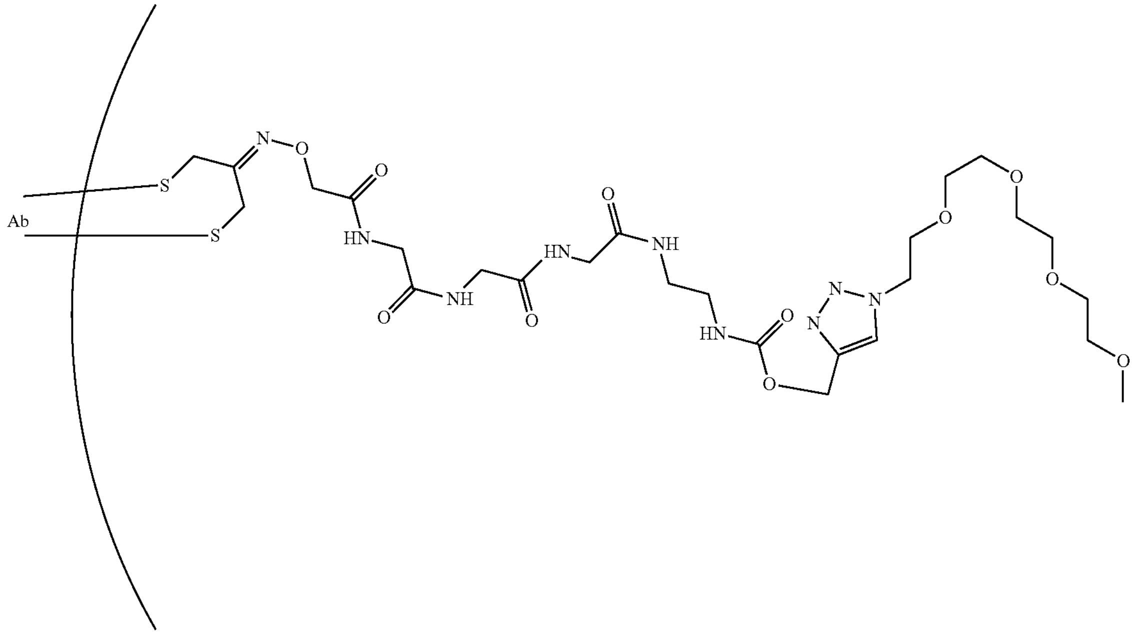

-continued
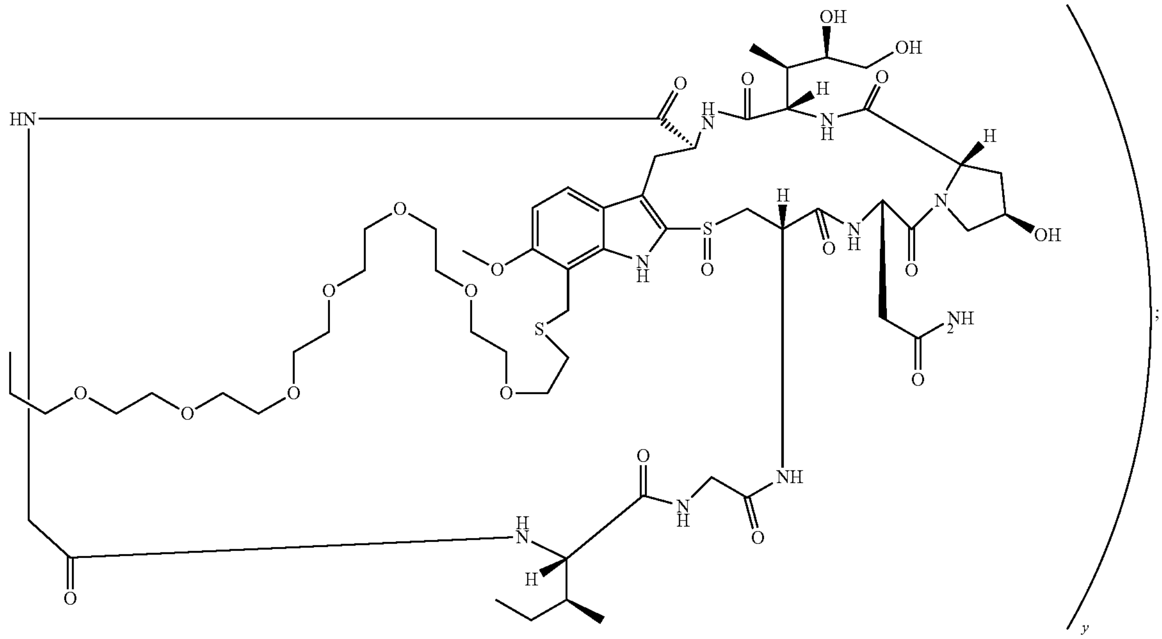
;
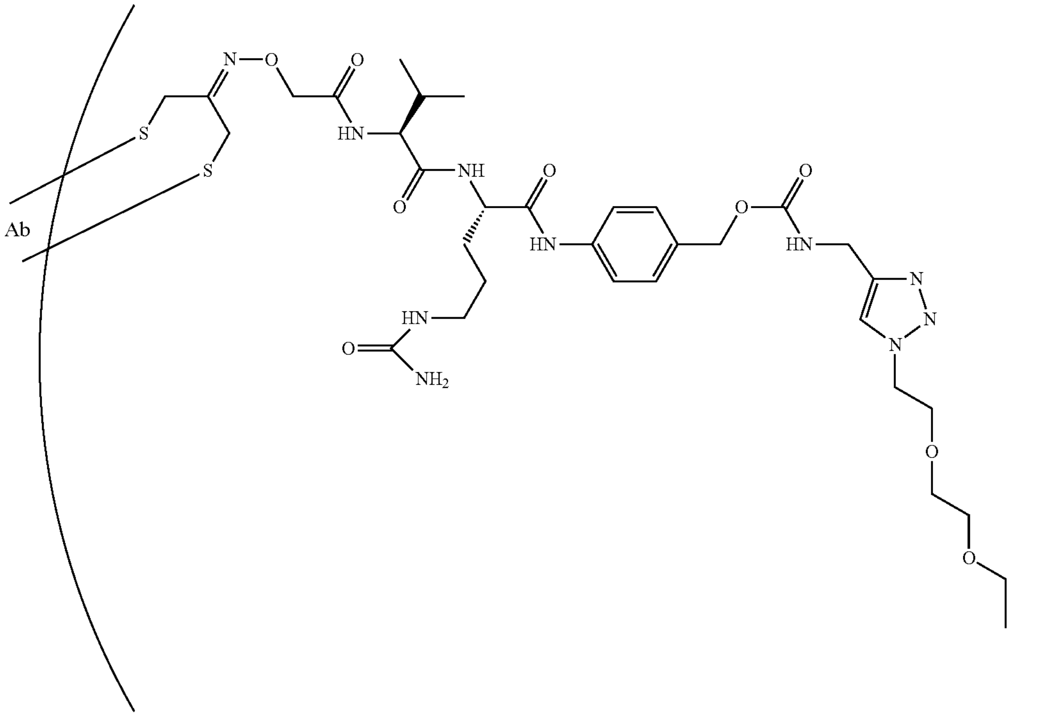

-continued
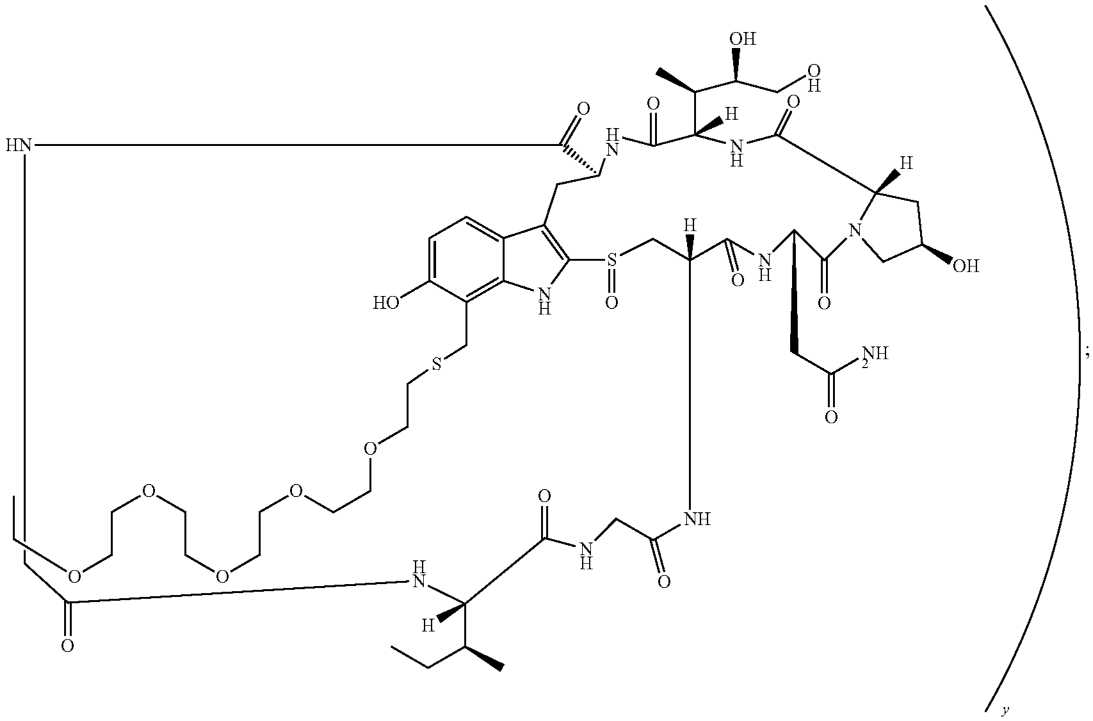
;
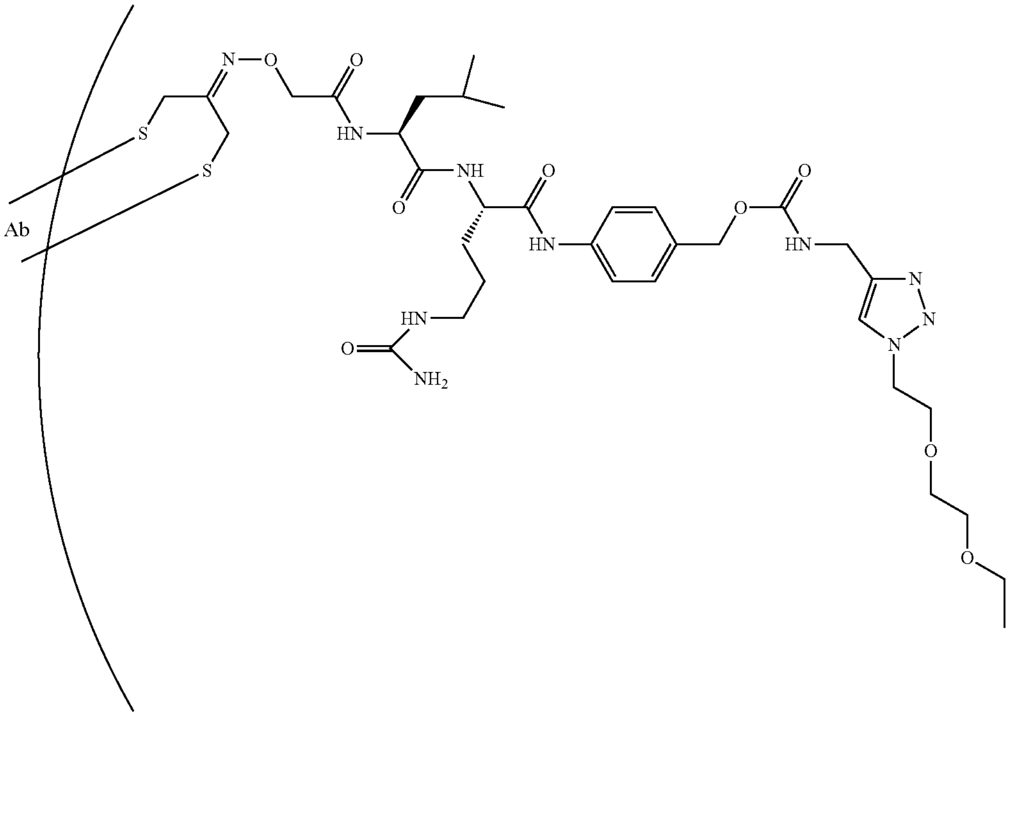

-continued
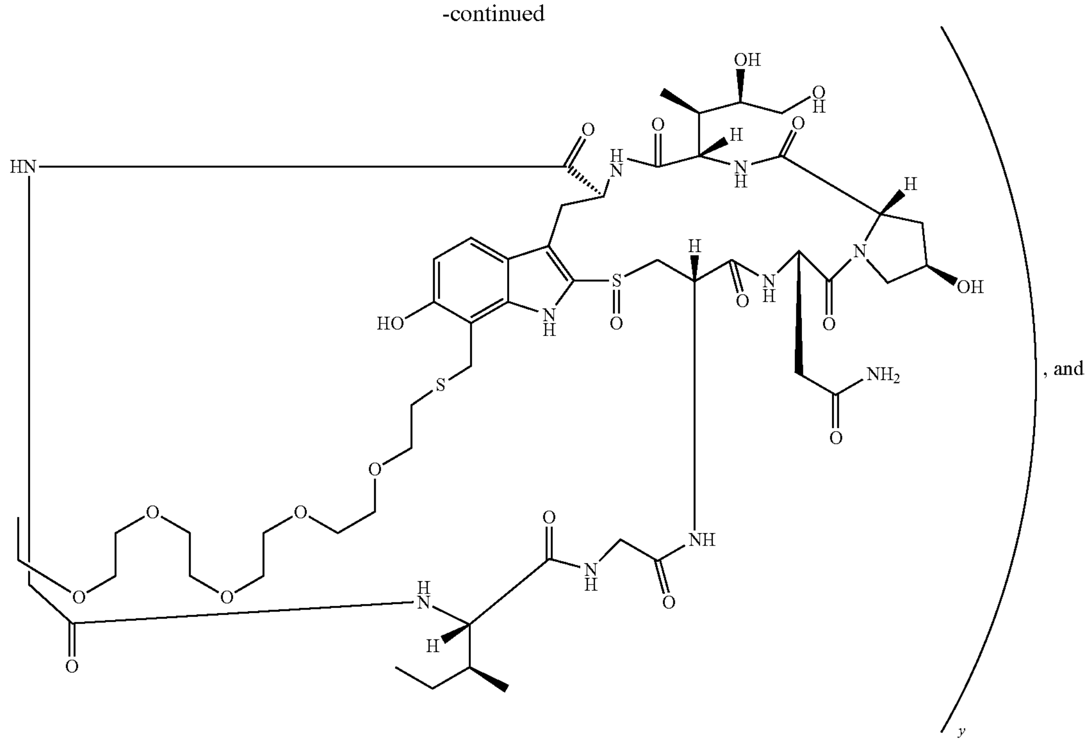
, and
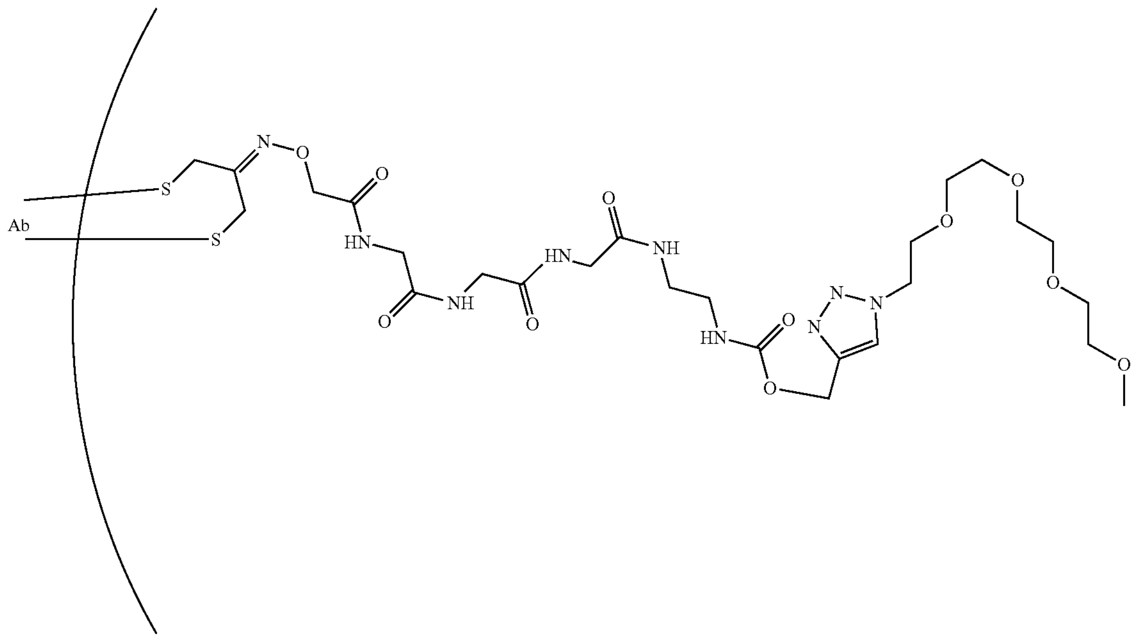

-continued

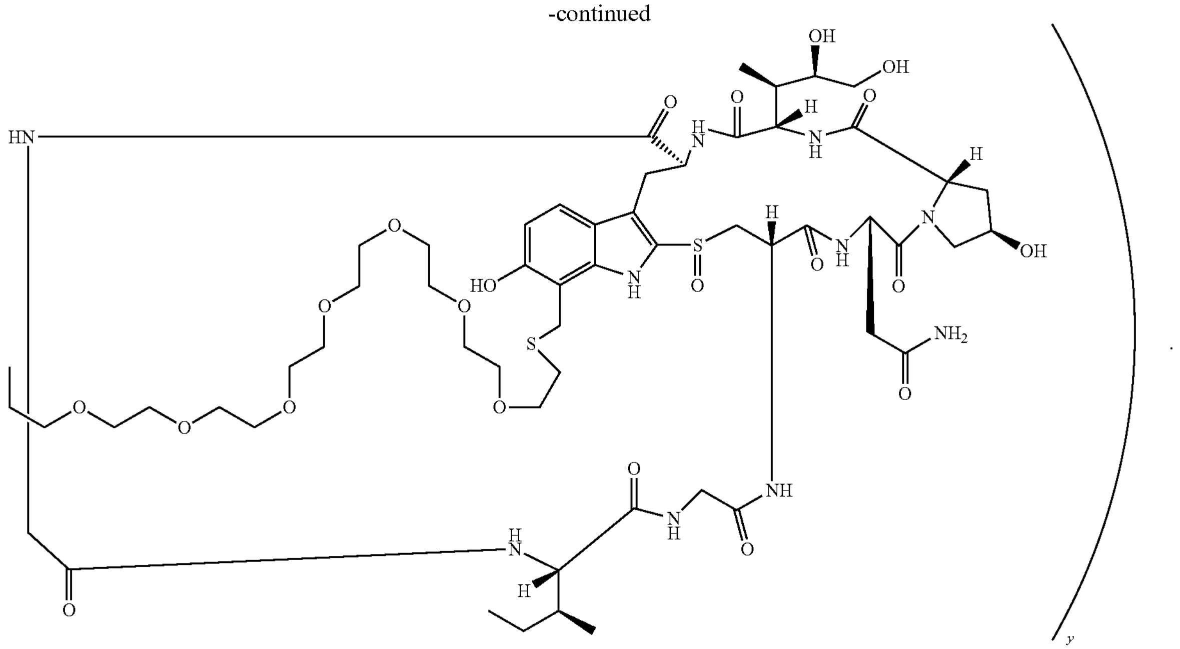

12. A pharmaceutical composition comprising an immunoconjugate of claim 1, and one or more pharmaceutically acceptable carriers.

13. A pharmaceutical composition comprising an immunoconjugate of claim 11, and one or more pharmaceutically acceptable carriers.

14. A combination comprising a therapeutically effective amount of an immunoconjugate of claim 1, and one or more therapeutically active co-agents.

15. A method of treating cancer comprising administering to a subject in need thereof a therapeutically effective amount of an immunoconjugate of claim 1.

* * * * *